US011046966B2

(12) United States Patent
Flasinski et al.

(10) Patent No.: US 11,046,966 B2
(45) Date of Patent: Jun. 29, 2021

(54) PLANT REGULATORY ELEMENTS AND USES THEREOF

(71) Applicant: Monsanto Technology LLC, St. Louis, MO (US)

(72) Inventors: Stanislaw Flasinski, Ballwin, MO (US); Barrett C. Foat, St. Louis, MO (US); Mohammed Oufattole, Wildwood, MO (US); Randall W. Shultz, St. Louis, MO (US); Xiaoping Wei, St. Louis, MO (US); Wei Wu, Chesterfield, MO (US); Shiaw-Pyng Yang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 35 days.

(21) Appl. No.: 16/549,573

(22) Filed: Aug. 23, 2019

(65) Prior Publication Data

US 2020/0056195 A1 Feb. 20, 2020

Related U.S. Application Data

(62) Division of application No. 15/802,843, filed on Nov. 3, 2017, now Pat. No. 10,550,401, which is a division of application No. 14/117,342, filed as application No. PCT/US2012/037561 on May 11, 2012, now Pat. No. 9,845,477.

(60) Provisional application No. 61/485,876, filed on May 13, 2011.

(51) Int. Cl.
*C12N 15/82* (2006.01)

(52) U.S. Cl.
CPC ................................ *C12N 15/8216* (2013.01)

(58) Field of Classification Search
None
See application file for complete search history.

(56) References Cited

U.S. PATENT DOCUMENTS

| | | | |
|---|---|---|---|
| 6,660,911 B2 * | 12/2003 | Fincher et al. ...... | C12N 9/1092 800/300 |
| 2004/0055039 A1 | 3/2004 | Hiroshi et al. | |
| 2007/0204367 A1 * | 8/2007 | Flasinski et al. .. | C12N 15/8231 800/278 |
| 2010/0058495 A1 | 3/2010 | Abbitt | |
| 2012/0084885 A1 | 4/2012 | Alexandrov et al. | |

FOREIGN PATENT DOCUMENTS

| | | |
|---|---|---|
| CN | 101880657 A | 11/2010 |
| CN | 101952435 A | 1/2011 |
| CN | 102016049 A | 4/2011 |
| JP | 2001-346580 A | 12/2001 |
| WO | WO 01/44457 | 6/2001 |
| WO | WO 01/44457 A2 * | 6/2001 |
| WO | WO 2005/098007 | 10/2005 |
| WO | WO 2006/039449 | 4/2006 |

OTHER PUBLICATIONS

Donald & Cashmore (1990) EMBO J 9:1717-26.*
Kim et al. (1994) Plant Mol Biol 24:105-17.*
Dolferus et al. (1994) Plant Physiol 105:1075-87.*
Liu et al. (2013) Nat Rev Genet 14:781-93.*
Cho & Cosgrove (2002) Plant Cell 14:3237-53.*
Potenza et al. (2004) In Vitro Cell Dev Biol Plant 40:1-22.*
Saha et al. (2007) In Silico Biol 7(1):7-19.*
Rose (2008) CurrTop Microbial Immunol, 326:277-90.*
Wang & Oard (2003) Plant Cell Rep 22:129-34.*
Joung & Kama (2006) Plant Cell Rep 25:1081-88.*
Hondred et al., "Use of Ubiquitin Fusions to Augment Protein Expression in Transgenic Plants," Plant Physiology 119:713-723, 1999.
Yuebing et al., "UBI1 intron-mediated enhancement of the expression of Bt cry1ah gene in transgenic maize (*Zea mays* L.)," Chinese Science Bulletin 53(20):3185-3180, 2008.
Clepet et al., "Analysis of expressed sequence tags generated from full-length enriched cDNA libraries of melon" BMC Genomics (2011), 12:252.
Callis et al., "Introns increase gene expression in cultured maize cells," *Genes Dev.* 1:1183-1200, 1987.
Chee et al., "Expression of a bean storage protein 'phaseolin minigene' in foreign plant tissues," *Gene* 41:47-57, 1986.
Cho et al., *Plant Cell* 14:3237-53 (2002).
Christiansen et al., "Maize polyubiquitin genes: structure, thermal perturbation of expression and transcript splicing, and promoter activity following transfer to protoplasts by electroporation," *Plant Mol. Biol.* 18:675-689, 1992.
Clancy et al., "Splicing of the maize *Sh1* first intron is essential for enhancement of gene expression, and a T-rich motif increases expression without affecting splicing," *Plant Physiol.* 130(2):918-929, 2002.
Dean et al., "Sequences downstream of translation start regulate quantitative expression of two petunia *rbcS* genes," *Plant Cell* 1(2):201-208, 1989.
Dolferus et al., *Plant Physiol.* 105:1075-87 (1994).
Donald & Cashmore, EMBO J. 9:1717-26 (1990).
International Preliminary Report on Patentability regarding PCT Application No. PCT/US2012/037561, dated Nov. 19, 2013.
International Search Report regarding PCT Application No. PCT/US2012/037561, dated Sep. 12, 2012.

(Continued)

*Primary Examiner* — Russell T Boggs
(74) *Attorney, Agent, or Firm* — Dentons US LLP; Amanda Carmany-Rampey

(57) ABSTRACT

The invention provides DNA molecules and constructs, including their nucleotide sequences, useful for modulating gene expression in plants and plant cells. Transgenic plants, plant cells, plant parts, seeds, and commodity products comprising the DNA molecules operably linked to heterologous transcribable polynucleotides are also provided, as are methods of their use.

16 Claims, 6 Drawing Sheets

Specification includes a Sequence Listing.

(56) References Cited

OTHER PUBLICATIONS

Jeon et al., "Tissue-preferential expression of a rice alpha-tubulin gene, OsTubA1, mediated by the first intron," *Plant Physiol.* 123(3):1005-1014, 2000.
Kim et al., Plant Mol. Biol. 24:105-17 (1994).
Kuhlemeier et al., "Upstream sequences determine the difference in transcript abundance of pea *rbcS* genes," *Mol. Gen. Genet.* 212:405-411, 1988.
Lasserre et al., "Differential activation of two ACC oxidase gene promoters from melon during plant development and in response to pathogen attack," *Mol. Gen. Genet.* 256(3):211-222, 1997.
Leon et al., "Transient gene expression in protoplasts of *Phaseolus vulgaris* isolated from a cell suspension culture," *Plant Physiol.* 95(3):968-972, 1991.
Li et al., Advanced genetic tools for plant biotechnology, *Nat Rev Genet* 14:781-93 (2013).
Logananthara, *Int. J. Bioinf. Res. Appl.* 2:36-51 (2006).
Mascarenhas et al., "Intron-mediated enhancement of heterologous gene expression in maize," *Plant Mol. Biol.* 15(6):913-920, 1990.
McElroy et al., "Isolation of an efficient actin promoter for use in rice transformation," *Plant Cell* 2(2):163-171, 1990.
Norris et al., "The intron of *Arabidopsis thaliana* polyubiquitin genes is conserved in location and is a quantitative determinant of chimeric gene expression," *Plant Mol. Biol.* 21(5):895-906, 1993.
Piechulla et al., Plant Mol. Biol. 38:655-62 (1998).
Potenza et al., *In Vitro Cell Dev. Biol. Plant* 40:1-22 (2004).
Rose et al., "Introns act post-transcriptionally to increase expression of the *Arabidopsis thaliana* tryptophan pathway gene PAT1," *Plant J.* 11(3):455-464, 1997.
Rose et al., "Intron-mediated enhancement of gene expression independent of unique sequences and splicing," *Plant Physiol.* 122(2):535-542, 2000.
Saha et al., *In Silico. Biol.* 7(1):7-19 (2007).
Sherf et al., "Dual-luciferase reporter assay: an advanced co-reporter technology integrating firefly and Renilla luciferase assays," *Promega Notes Magazine* No. 57, p. 2, 1996.
Sinibaldi et al., "Intron splicing and intron-mediated enhanced expression in monocots," *Prog. Nucleic Acid Res. Mol. Biol.* (42):229-257, 1992.
Vancanneyt et al., "Construction of an intron-containing marker gene: splicing of the intron in transgenic plants and its use in monitoring early events in Agrobacterium-mediated plant transformation," *Mol. Gen. Genet.* 220(2):245-250, 1990.
Vasil et al., "Increased gene expression by the first intron of maize *shrunken-1* locus in grass species," *Plant Physiol.* 91(4):1575-1579, 1989.
Welsch et al., Planta 216:523-34 (2003).
Xu et al., "Rice triosephosphate isomerase gene 5' sequence directs β-glucuronidase activity in transgenic tobacco but requires an intron for expression in rice," *Plant Physiol.* 106(2):459-467, 1994.
Yamagata et al., "TGTCACA motif is a novel cis-regulatory enhancer element involved in fruit-specific expression of the *cucumisin* gene," *J. Biol. Chem.* 227(13):11582-11590, 2002.
GenBank Accession No. HN314561, dated Nov. 24, 2010.
GenBank Accession No. JG468661, dated Mar. 16, 2011.
GenBank Accession No. HN298588, dated Nov. 24, 2010.
GenBank Accession No. JG469358, dated Mar. 16, 2011.
GenBank Accession No. HN327993, dated Nov. 24, 2010.
GenBank Accession No. JG467489, dated Mar. 16, 2011.
GenBank Accession No. HN319913, dated Nov. 24, 2010.
GenBank Accession No. JG480182, dated Mar. 16, 2011.
Office Action regarding Chilean Application No. 201601540, dated Jun. 14, 2017.
GenBank Accession No. LN713263, dated Mar. 5, 2015.
Office Action regarding Eurasian Application No. 201690416, dated Jul. 28, 2017.
GenBank Accession No. HN320890, dated Nov. 23, 2010.
USPTO Written Description Guidelines. (2008).
China Office Action and Search Report regarding China Application No. 201710186179.8, dated Nov. 7, 2019, 13 pages.
Australia Office Action regarding Australia Application No. 2019246918, dated Jan. 15, 2020, 7 pages.
GenBank Accession No. AM740200, Sep. 27, 2007.
GenBank Accession No. HN296636, Nov. 23, 2010.
Gonzalez-Ibeas et al., "Melogen: an EST database for melon functional genomics", BMC Genomics (2007), 8:306.
Gonzalez et al., "Genome-wide BAC-end sequencing of Cucumis melo using two BAC libraries", BMC Genomics (2010), 11:618.

* cited by examiner

```
P-CUCme.Ubq1-1:1:15 (SEQ ID NO: 2)    AGCTATATGTCATTAGAGAAGTCATAGCAAAGAGAAAAGTAACAGTATCAAAGGTTCAGA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    CAAAAGAAAATGCAGCAGATATGTTGACTAAAATAGTTACTAATGCTAAACTCGAGCACT
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    GCCTACAGTTGCTCAAGGTAATAGACTACTTAAAAGAATAGAATCAGAAGAAATAGTCAT
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    TGGTAGCAATAAAATTCAAGGTGGAGGATTGTTAAAAAGAAGAGTGAATTTTATTACTTA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    AAGAAAATCTCGGTGAAACTCGAAAGATCTCGATTCGAAACTCTATTGCTTAAGAACCTG
P-CUCme.Ubq1-1:1:16 (SEQ ID NO: 6)    ---------TCGGTGAAACTCGAAAGATCTCGATTCGAAACTCTATTGCTTAAGAACCTG
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    GTGAAGCTCGAGAGATCTTGATACAATCCCAGTGCCCTAACTCTTCAACAAGCTAAGCAA
P-CUCme.Ubq1-1:1:16 (SEQ ID NO: 6)    GTGAAGCTCGAGAGATCTTGATACAATCCCAGTGCCCTAACTCTTCAACAAGCTAAGCAA
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------
```

FIG. 1b

```
P-CUCme.Ubq1-1:1:15 (SEQ ID NO: 2)     GTTGTACTGTGGGGCTCAATCTCGGTTCAATCTCGACGCACCTGATGCTTTGTTCCCTGT
P-CUCme.Ubq1-1:1:16 (SEQ ID NO: 6)     GTTGTACTGTGGGGCTCAATCTCGGTTCAATCTCGACGCACCTGATGCTTTGTTCCCTGT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     CTACTCGATGAAGAAGCAATTACTTCTCAGGACAACTCGGTACCCCTAAATACAGATTTT
P-CUCme.Ubq1-1:1:16 (SEQ ID NO: 6)     CTACTCGATGAAGAAGCAATTACTTCTCAGGACAACTCGGTACCCCTAAATACAGATTTT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GAGCTTCGTGATCCTACAACTGAAATCAAATAGAAAAACTAATAAGTTAGTTAGAGTTTG
P-CUCme.Ubq1-1:1:16 (SEQ ID NO: 6)     GAGCTTCGTGATCCTACAACTGAAATCAAATAGAAAAACTAATAAGTTAGTTAGAGTTTG
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TTATATTTACTGCCATTAAATAACTCTGTAATGTAAATAATAAACCATTTAACTCAATAT
P-CUCme.Ubq1-1:1:16 (SEQ ID NO: 6)     TTATATTTACTGCCATTAAATAACTCTGTAATGTAAATAATAAACCATTTAACTCAATAT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GAAATATAGAATGAGAAAAAGAAAAAGAAAAAGTTAAAGAGAGAGAGGAAGAAAACTCAT
P-CUCme.Ubq1-1:1:16 (SEQ ID NO: 6)     GAAATATAGAATGAGAAAAAGAAAAAGAAAAAGTTAAAGAGAGAGAGGAAGAAAACTCAT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TTTCAAATTCTCTATACTTGTTTGATCCTTGAATAAGTTGAATAAAAGCTCTATGGCGGC
P-CUCme.Ubq1-1:1:16 (SEQ ID NO: 6)     TTTCAAATTCTCTATACTTGTTTGATCCTTGAATAAGTTGAATAAAAGCTCTATGGCGGC
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------
```

FIG. 1c

```
P-CUCme.Ubq1-1:1:15 (SEQ ID NO: 2)    TTCAAAGTGGATGTAGGCACTATTAGTCGAACCACAATAAATTTGTTATGTTCTTTTGCT
P-CUCme.Ubq1-1:1:16 (SEQ ID NO: 6)    TTCAAAGTGGATGTAGGCACTATTAGTCGAACCACAATAAATTTGTTATGTTCTTTTGCT
P-CUCme.Ubq1-1:1:17 (SEQ ID NO: 8)    ------------------------AGTCGAACCACAATAAATTTGTTATGTTCTTTTGCT
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATTCCTTGTAATCTCCATAAATATTTTCTTACTAAGCTCTAGAAATCTGCTTGTCAAGAG
P-CUCme.Ubq1-1:1:16 (SEQ ID NO: 6)    ATTCCTTGTAATCTCCATAAATATTTTCTTACTAAGCTCTAGAAATCTGCTTGTCAAGAG
P-CUCme.Ubq1-1:1:17 (SEQ ID NO: 8)    ATTCCTTGTAATCTCCATAAATATTTTCTTACTAAGCTCTAGAAATCTGCTTGTCAAGAG
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATTAGGTATCATTTATGCCTTTTATATTTCCTTTCGGTTGCATATCTTGAGCTAGTTAAG
P-CUCme.Ubq1-1:1:16 (SEQ ID NO: 6)    ATTAGGTATCATTTATGCCTTTTATATTTCCTTTCGGTTGCATATCTTGAGCTAGTTAAG
P-CUCme.Ubq1-1:1:17 (SEQ ID NO: 8)    ATTAGGTATCATTTATGCCTTTTATATTTCCTTTCGGTTGCATATCTTGAGCTAGTTAAG
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATCGAGAGGTTACTGTTGTTGAAACCGAGATTAGTATCTTTGGATTAACACGTGCCTACC
P-CUCme.Ubq1-1:1:16 (SEQ ID NO: 6)    ATCGAGAGGTTACTGTTGTTGAAACCGAGATTAGTATCTTTGGATTAACACGTGCCTACC
P-CUCme.Ubq1-1:1:17 (SEQ ID NO: 8)    ATCGAGAGGTTACTGTTGTTGAAACCGAGATTAGTATCTTTGGATTAACACGTGCCTACC
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    AAAATTTGAAATTTTGTATTTACCCCATTCATTGGATAATAAGCAATTCTTATAGTGTTA
P-CUCme.Ubq1-1:1:16 (SEQ ID NO: 6)    AAAATTTGAAATTTTGTATTTACCCCATTCATTGGATAATAAGCAATTCTTATAGTGTTA
P-CUCme.Ubq1-1:1:17 (SEQ ID NO: 8)    AAAATTTGAAATTTTGTATTTACCCCATTCATTGGATAATAAGCAATTCTTATAGTGTTA
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    TCAATTAAACTCCTATAAAGTGTAATAATTGAATCCATGAACTATTTTCATATGTAATCT
P-CUCme.Ubq1-1:1:16 (SEQ ID NO: 6)    TCAATTAAACTCCTATAAAGTGTAATAATTGAATCCATGAACTATTTTCATATGTAATCT
P-CUCme.Ubq1-1:1:17 (SEQ ID NO: 8)    TCAATTAAACTCCTATAAAGTGTAATAATTGAATCCATGAACTATTTTCATATGTAATCT
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------
```

FIG. 1d

```
P-CUCme.Ubq1-1:1:15 (SEQ ID NO: 2)     TAATAAAATGAATTTAGAAGTTTAATTAAAATAATATATTTTGTATGCTATTTTTCAAAG
P-CUCme.Ubq1-1:1:16 (SEQ ID NO: 6)     TAATAAAATGAATTTAGAAGTTTAATTAAAATAATATATTTTGTATGCTATTTTTCAAAG
P-CUCme.Ubq1-1:1:17 (SEQ ID NO: 8)     TAATAAAATGAATTTAGAAGTTTAATTAAAATAATATATTTTGTATGCTATTTTTCAAAG
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TTTGAAGAATGTGTTAATTGATACACATACAAAAAATCTAGGTTTTACATGAAAAACTAT
P-CUCme.Ubq1-1:1:16 (SEQ ID NO: 6)     TTTGAAGAATGTGTTAATTGATACACATACAAAAAATCTAGGTTTTACATGAAAAACTAT
P-CUCme.Ubq1-1:1:17 (SEQ ID NO: 8)     TTTGAAGAATGTGTTAATTGATACACATACAAAAAATCTAGGTTTTACATGAAAAACTAT
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GGAAGTGAAAGATAGCATCTAATATTTTATGACACAAAATGCAAACTAATATATAAAGGA
P-CUCme.Ubq1-1:1:16 (SEQ ID NO: 6)     GGAAGTGAAAGATAGCATCTAATATTTTATGACACAAAATGCAAACTAATATATAAAGGA
P-CUCme.Ubq1-1:1:17 (SEQ ID NO: 8)     GGAAGTGAAAGATAGCATCTAATATTTTATGACACAAAATGCAAACTAATATATAAAGGA
P-CUCme.Ubq1-1:1:18 (SEQ ID NO: 10)    -----------------------------TGACACAAAATGCAAACTAATATATAAAGGA
P-CUCme.Ubq1-1:1:19 (SEQ ID NO: 12)    ------------------------------------------------------------

P-CUCme.Ubq1-1:1:15 (SEQ ID NO: 2)     TTTAATTAATTTTTATAGGTTTCAAATTTGTTAGACTTGTCAAATACAAAATTTTATTGA
P-CUCme.Ubq1-1:1:16 (SEQ ID NO: 6)     TTTAATTAATTTTTATAGGTTTCAAATTTGTTAGACTTGTCAAATACAAAATTTTATTGA
P-CUCme.Ubq1-1:1:17 (SEQ ID NO: 8)     TTTAATTAATTTTTATAGGTTTCAAATTTGTTAGACTTGTCAAATACAAAATTTTATTGA
P-CUCme.Ubq1-1:1:18 (SEQ ID NO: 10)    TTTAATTAATTTTTATAGGTTTCAAATTTGTTAGACTTGTCAAATACAAAATTTTATTGA
P-CUCme.Ubq1-1:1:19 (SEQ ID NO: 12)    ------------------------------------------------------------

P-CUCme.Ubq1-1:1:15 (SEQ ID NO: 2)     ACCAAATACATACAAACATCAAAATTAAGAACAGAAAATCTAAATTCAAATGAAATTTAT
P-CUCme.Ubq1-1:1:16 (SEQ ID NO: 6)     ACCAAATACATACAAACATCAAAATTAAGAACAGAAAATCTAAATTCAAATGAAATTTAT
P-CUCme.Ubq1-1:1:17 (SEQ ID NO: 8)     ACCAAATACATACAAACATCAAAATTAAGAACAGAAAATCTAAATTCAAATGAAATTTAT
P-CUCme.Ubq1-1:1:18 (SEQ ID NO: 10)    ACCAAATACATACAAACATCAAAATTAAGAACAGAAAATCTAAATTCAAATGAAATTTAT
P-CUCme.Ubq1-1:1:19 (SEQ ID NO: 12)    ------------------------------------------------------------

P-CUCme.Ubq1-1:1:15 (SEQ ID NO: 2)     TAATAGAAAAATTAGAAAAAAGAAAAAGAAAATAAAAGGAATCGTATTGTTTTTTCCTTC
P-CUCme.Ubq1-1:1:16 (SEQ ID NO: 6)     TAATAGAAAAATTAGAAAAAAGAAAAAGAAAATAAAAGGAATCGTATTGTTTTTTCCTTC
P-CUCme.Ubq1-1:1:17 (SEQ ID NO: 8)     TAATAGAAAAATTAGAAAAAAGAAAAAGAAAATAAAAGGAATCGTATTGTTTTTTCCTTC
P-CUCme.Ubq1-1:1:18 (SEQ ID NO: 10)    TAATAGAAAAATTAGAAAAAAGAAAAAGAAAATAAAAGGAATCGTATTGTTTTTTCCTTC
P-CUCme.Ubq1-1:1:19 (SEQ ID NO: 12)    ------------------------------------------------------------
```

FIG. 1e

```
P-CUCme.Ubq1-1:1:15 (SEQ ID NO: 2)    CTTTTTCCCATTTGAGAGGTGAATAAAGCTAATTGAGCTGCTCTAACTTCCTAATCTTTA
P-CUCme.Ubq1-1:1:16 (SEQ ID NO: 6)    CTTTTTCCCATTTGAGAGGTGAATAAAGCTAATTGAGCTGCTCTAACTTCCTAATCTTTA
P-CUCme.Ubq1-1:1:17 (SEQ ID NO: 8)    CTTTTTCCCATTTGAGAGGTGAATAAAGCTAATTGAGCTGCTCTAACTTCCTAATCTTTA
P-CUCme.Ubq1-1:1:18 (SEQ ID NO: 10)   CTTTTTCCCATTTGAGAGGTGAATAAAGCTAATTGAGCTGCTCTAACTTCCTAATCTTTA
P-CUCme.Ubq1-1:1:19 (SEQ ID NO: 12)   ------------------------------------------------------------

P-CUCme.Ubq1-1:1:15 (SEQ ID NO: 2)    TGCTTTCCCCATAAAGCTTTCCCAACTGCGCGTAATCGTATAAATGGAAAATTGACCTTT
P-CUCme.Ubq1-1:1:16 (SEQ ID NO: 6)    TGCTTTCCCCATAAAGCTTTCCCAACTGCGCGTAATCGTATAAATGGAAAATTGACCTTT
P-CUCme.Ubq1-1:1:17 (SEQ ID NO: 8)    TGCTTTCCCCATAAAGCTTTCCCAACTGCGCGTAATCGTATAAATGGAAAATTGACCTTT
P-CUCme.Ubq1-1:1:18 (SEQ ID NO: 10)   TGCTTTCCCCATAAAGCTTTCCCAACTGCGCGTAATCGTATAAATGGAAAATTGACCTTT
P-CUCme.Ubq1-1:1:19 (SEQ ID NO: 12)   -----------------------------------TCGTATAAATGGAAAATTGACCTTT

P-CUCme.Ubq1-1:1:15 (SEQ ID NO: 2)    CCAACTAGATTCTTCCAGAACTAAACAATACGTAACACGCAAGTAATCAAAGACACGTTT
P-CUCme.Ubq1-1:1:16 (SEQ ID NO: 6)    CCAACTAGATTCTTCCAGAACTAAACAATACGTAACACGCAAGTAATCAAAGACACGTTT
P-CUCme.Ubq1-1:1:17 (SEQ ID NO: 8)    CCAACTAGATTCTTCCAGAACTAAACAATACGTAACACGCAAGTAATCAAAGACACGTTT
P-CUCme.Ubq1-1:1:18 (SEQ ID NO: 10)   CCAACTAGATTCTTCCAGAACTAAACAATACGTAACACGCAAGTAATCAAAGACACGTTT
P-CUCme.Ubq1-1:1:19 (SEQ ID NO: 12)   CCAACTAGATTCTTCCAGAACTAAACAATACGTAACACGCAAGTAATCAAAGACACGTTT

P-CUCme.Ubq1-1:1:15 (SEQ ID NO: 2)    CATTTTCCTATAGAATATTATAGTTATTCGTGATTAACGGAAGTCGGCAATTTTAGGTAT
P-CUCme.Ubq1-1:1:16 (SEQ ID NO: 6)    CATTTTCCTATAGAATATTATAGTTATTCGTGATTAACGGAAGTCGGCAATTTTAGGTAT
P-CUCme.Ubq1-1:1:17 (SEQ ID NO: 8)    CATTTTCCTATAGAATATTATAGTTATTCGTGATTAACGGAAGTCGGCAATTTTAGGTAT
P-CUCme.Ubq1-1:1:18 (SEQ ID NO: 10)   CATTTTCCTATAGAATATTATAGTTATTCGTGATTAACGGAAGTCGGCAATTTTAGGTAT
P-CUCme.Ubq1-1:1:19 (SEQ ID NO: 12)   CATTTTCCTATAGAATATTATAGTTATTCGTGATTAACGGAAGTCGGCAATTTTAGGTAT

P-CUCme.Ubq1-1:1:15 (SEQ ID NO: 2)    AAATACGTGAATTCTCGAGCGCTAATTT
P-CUCme.Ubq1-1:1:16 (SEQ ID NO: 6)    AAATACGTGAATTCTCGAGCGCTAATTT
P-CUCme.Ubq1-1:1:17 (SEQ ID NO: 8)    AAATACGTGAATTCTCGAGCGCTAATTT
P-CUCme.Ubq1-1:1:18 (SEQ ID NO: 10)   AAATACGTGAATTCTCGAGCGCTAATTT
P-CUCme.Ubq1-1:1:19 (SEQ ID NO: 12)   AAATACGTGAATTCTCGAGCGCTAATTT
```

FIG. 1f

SEQUENCE LISTING

<160> NUMBER OF SEQ ID NOS: 212

<210> SEQ ID NO 1
<211> LENGTH: 2611
<212> TYPE: DNA
<213> ORGANISM: Cucumis melo

<400> SEQUENCE: 1

```
atctgaaagg aacacctagc aaggggctac tctacaagca tactaagtct acaaagctag     60
agttgtatgg ttatgcagaa gacctggaca aaagaagatc actcgctgct tttactttta    120
tcctaagagg aaatgtgatt ttatggaagt ttaacctata gcctgtagtg gcactattca    180
caacaaaagt aaagtttata gccatgactg aagttgttaa agaagtcgtc tggctaaaag    240
gactacttga agaacttggc ttcttttaac agtcagtaaa catcatgtgt gatagttaaa    300
gtgcaataca cttgtctaaa aatctgcaat atcacgaaag aactaagcat attgatgtga    360
agctatatgt cattagagaa gtcatagcaa agagaaaagt aacagtatca aaggttcaga    420
caaaagaaaa tgcagcagat atgttgacta aaatagttac taatgctaaa ctcgagcact    480
gcctacagtt gctcaaggta atagactact taaaagaata gaatcagaag aaatagtcat    540
tggtagcaat aaaattcaag gtggaggatt gttaaaaaga agagtgaatt ttattactta    600
aagaaaatct cggtgaaact cgaaagatct cgattcgaaa ctctattgct taagaacctg    660
gtgaagctcg agagatcttg atacaatccc agtgccctaa ctcttcaaca agctaagcaa    720
gttgtactgt ggggctcaat ctcggttcaa tctcgacgca cctgatgctt tgttccctgt    780
ctactcgatg aagaagcaat tacttctcag gacaactcgg taccccctaaa tacagatttt    840
gagcttcgtg atcctacaac tgaaatcaaa tagaaaaact aataagttag ttagagtttg    900
ttatatttac tgccattaaa taactctgta atgtaaataa taaaccattt aactcaatat    960
gaaatataga atgagaaaaa gaaaaagaaa aagttaaaga gagagaggaa gaaaactcat   1020
tttcaaattc tctatacttg tttgatcctt gaataagttg aataaaagct ctatggcggc   1080
ttcaaagtgg atgtaggcac tattagtcga accacaataa atttgttatg ttcttttgct   1140
attccttgta atctccataa atattttctt actaagctct agaaatctgc ttgtcaagag   1200
attaggtatc atttatgcct tttatatttc ctttcggttg catatcttga gctagttaag   1260
atcgagaggt tactgttgtt gaaaccgaga ttagtatctt tggattaaca cgtgcctacc   1320
aaaatttgaa attttgtatt taccccattc attggataat aagcaattct tatagtgtta   1380
tcaattaaac tcctataaag tgtaataatt gaatccatga actattttca tatgtaatct   1440
taataaaatg aatttagaag tttaattaaa ataatatatt ttgtatgcta tttttcaaag   1500
tttgaagaat gtgttaattg atacacatac aaaaaatcta ggttttacat gaaaaactat   1560
ggaagtgaaa gatagcatct aatattttat gacacaaaat gcaaactaat atataaagga   1620
tttaattaat ttttataggt ttcaaatttg ttagacttgt caaatacaaa attttattga   1680
accaaataca tacaaacatc aaaattaaga acagaaaatc taaattcaaa tgaaatttat   1740
taatagaaaa attagaaaaa agaaaaagaa aataaaagga atcgtattgt tttttccttc   1800
ctttttccca tttgagaggt gaataaagct aattgagctg ctctaacttc ctaatcttta   1860
tgctttcccc ataaagcttt cccaactgcg cgtaatcgta taaatggaaa attgaccttt   1920
ccaactagat tcttccagaa ctaaacaata cgtaacacgc aagtaatcaa agacacgttt   1980
cattttccta tagaatatta tagttattcg tgattaacgg aagtcggcaa ttttaggtat   2040
aaatacgtga attctcgagc gctaattttc catacagact cgaaatactc taaactttct   2100
```

```
catcgcgctt tattcctatt tcgtaattcg ctcttcttca acctctcaag gttttcatct   2160

tttctctatc ttctgttttc agattgcatc ttttcccccct cctgttcgat taattgatgt   2220

ttgaattttc gagaaacgat ttgaagtctt tgttgtattt ttcatttctg ttcgttaggt   2280

aggtcgattt ttaatcgtga tgtccgacgt tgttcggatg attcacattt ggtttttgtc   2340

atcttctttc tatgttgtga ttatcatgat ttttatcttt ttttcttctc aagatttgta   2400

atttatcgat tccccatggt tcttggtttt ttatacatgt attgaatctg gttactagaa   2460

ttatgttctt cgacggacgt ctttcagatt taaattgcat tgtaggaaat atgatttgct   2520

atctgagtaa cgtttttcca gagtattctt gattgcgcga tctatcttca attgttaaat   2580

tgtttttgtt taattggggt catgacaggt g                                   2611
```

<210> SEQ ID NO 2
<211> LENGTH: 2068
<212> TYPE: DNA
<213> ORGANISM: Cucumis melo

<400> SEQUENCE: 2

```
atctgaaagg aacacctagc aaggggctac tctacaagca tactaagtct acaaagctag     60

agttgtatgg ttatgcagaa gacctggaca aaagaagatc actcgctgct tttactttta    120

tcctaagagg aaatgtgatt ttatggaagt ttaacctata gcctgtagtg gcactattca    180

caacaaaagt aaagtttata gccatgactg aagttgttaa agaagtcgtc tggctaaaag    240

gactacttga agaacttggc ttcttttaac agtcagtaaa catcatgtgt gatagttaaa    300

gtgcaataca cttgtctaaa aatctgcaat atcacgaaag aactaagcat attgatgtga    360

agctatatgt cattagagaa gtcatagcaa agagaaaagt aacagtatca aaggttcaga    420

caaaagaaaa tgcagcagat atgttgacta aaatagttac taatgctaaa ctcgagcact    480

gcctacagtt gctcaaggta atagactact taaaagaata gaatcagaag aaatagtcat    540

tggtagcaat aaaattcaag gtggaggatt gttaaaaaga agagtgaatt ttattactta    600

aagaaaatct cggtgaaact cgaaagatct cgattcgaaa ctctattgct taagaacctg    660

gtgaagctcg agagatcttg atacaatccc agtgccctaa ctcttcaaca agctaagcaa    720

gttgtactgt ggggctcaat ctcggttcaa tctcgacgca cctgatgctt tgttccctgt    780

ctactcgatg aagaagcaat tacttctcag gacaactcgg taccccctaaa tacagatttt    840

gagcttcgtg atcctacaac tgaaatcaaa tagaaaaact aataagttag ttagagtttg    900

ttatatttac tgccattaaa taactctgta atgtaaataa taaaccattt aactcaatat    960

gaaatataga atgagaaaaa gaaaaagaaa aagttaaaga gagagaggaa gaaaactcat   1020

tttcaaattc tctatacttg tttgatcctt gaataagttg aataaaagct ctatggcggc   1080

ttcaaagtgg atgtaggcac tattagtcga accacaataa atttgttatg ttcttttgct   1140

attccttgta atctccataa atattttctt actaagctct agaaatctgc ttgtcaagag   1200

attaggtatc atttatgcct tttatatttc ctttcggttg catatcttga gctagttaag   1260

atcgagaggt tactgttgtt gaaaccgaga ttagtatctt tggattaaca cgtgcctacc   1320

aaaatttgaa attttgtatt taccccattc attggataat aagcaattct tatagtgtta   1380

tcaattaaac tcctataaag tgtaataatt gaatccatga actattttca tatgtaatct   1440

taataaaatg aatttagaag tttaattaaa ataatatatt ttgtatgcta tttttcaaag   1500

tttgaagaat gtgttaattg atacacatac aaaaaatcta ggttttacat gaaaaactat   1560
```

ggaagtgaaa gatagcatct aatattttat gacacaaaat gcaaactaat atataaagga 1620
tttaattaat ttttataggt ttcaaatttg ttagacttgt caaatacaaa attttattga 1680
accaaataca tacaaacatc aaaattaaga acagaaaatc taaattcaaa tgaaatttat 1740
taatagaaaa attagaaaaa agaaaaagaa aataaaagga atcgtattgt tttttccttc 1800
ctttttccca tttgagaggt gaataaagct aattgagctg ctctaacttc ctaatcttta 1860
tgctttcccc ataaagcttt cccaactgcg cgtaatcgta taaatggaaa attgaccttt 1920
ccaactagat tcttccagaa ctaaacaata cgtaacacgc aagtaatcaa agacacgttt 1980
cattttccta tagaatatta tagttattcg tgattaacgg aagtcggcaa ttttaggtat 2040
aaatacgtga attctcgagc gctaattt 2068

<210> SEQ ID NO 3
<211> LENGTH: 82
<212> TYPE: DNA
<213> ORGANISM: Cucumis melo

<400> SEQUENCE: 3
tccatacaga ctcgaaatac tctaaacttt ctcatcgcgc tttattccta tttcgtaatt 60
cgctcttctt caacctctca ag 82

<210> SEQ ID NO 4
<211> LENGTH: 461
<212> TYPE: DNA
<213> ORGANISM: Cucumis melo

<400> SEQUENCE: 4
gttttcatct tttctctatc ttctgttttc agattgcatc ttttcccccct cctgttcgat 60 taattgatgt ttgaattttc gagaaacgat ttgaagtctt tgttgtattt ttcatttctg 120
ttcgttaggt aggtcgattt ttaatcgtga tgtccgacgt tgttcggatg attcacattt 180
ggtttttgtc atcttctttc tatgttgtga ttatcatgat ttttatcttt ttttcttctc 240
aagatttgta atttatcgat tccccatggt tcttggtttt ttatacatgt attgaatctg 300
gttactagaa ttatgttctt cgacggacgt ctttcagatt taaattgcat tgtaggaaat 360
atgatttgct atctgagtaa cgtttttcca gagtattctt gattgcgcga tctatcttca 420
attgttaaat tgtttttgtt taattggggt catgacaggt g 461

<210> SEQ ID NO 5
<211> LENGTH: 2002
<212> TYPE: DNA
<213> ORGANISM: Cucumis melo

<400> SEQUENCE: 5
tcggtgaaac tcgaaagatc tcgattcgaa actctattgc ttaagaacct ggtgaagctc 60
gagagatctt gatacaatcc cagtgcccta actcttcaac aagctaagca agttgtactg 120
tggggctcaa tctcggttca atctcgacgc acctgatgct ttgttccctg tctactcgat 180
gaagaagcaa ttacttctca ggacaactcg gtacccctaa atacagattt tgagcttcgt 240
gatcctacaa ctgaaatcaa atagaaaaac taataagtta gttagagttt gttatattta 300
ctgccattaa ataactctgt aatgtaaata ataaaccatt taactcaata tgaaatatag 360
aatgagaaaa agaaaaagaa aaagttaaag agagagagga agaaaactca ttttcaaatt 420
ctctatactt gtttgatcct tgaataagtt gaataaaagc tctatggcgg cttcaaagtg 480
gatgtaggca ctattagtcg aaccacaata aatttgttat gttcttttgc tattccttgt 540

```
aatctccata aatattttct tactaagctc tagaaatctg cttgtcaaga gattaggtat    600

catttatgcc ttttatattt cctttcggtt gcatatcttg agctagttaa gatcgagagg    660

ttactgttgt tgaaaccgag attagtatct ttggattaac acgtgcctac caaaatttga    720

aattttgtat ttaccccatt cattggataa taagcaattc ttatagtgtt atcaattaaa    780

ctcctataaa gtgtaataat tgaatccatg aactattttc atatgtaatc ttaataaaat    840

gaatttagaa gtttaattaa aataatatat tttgtatgct atttttcaaa gtttgaagaa    900

tgtgttaatt gatacacata caaaaaatct aggttttaca tgaaaaacta tggaagtgaa    960

agatagcatc taatatttta tgacacaaaa tgcaaactaa tatataaagg atttaattaa   1020

tttttatagg tttcaaattt gttagacttg tcaaatacaa aattttattg aaccaaatac   1080

atacaaacat caaaattaag aacagaaaat ctaaattcaa atgaaattta ttaatagaaa   1140

aattagaaaa aagaaaaaga aaataaaagg aatcgtattg tttttttcctt cctttttccc   1200

atttgagagg tgaataaagc taattgagct gctctaactt cctaatcttt atgctttccc   1260

cataaagctt tcccaactgc gcgtaatcgt ataaatggaa aattgacctt tccaactaga   1320

ttcttccaga actaaacaat acgtaacacg caagtaatca aagacacgtt tcattttcct   1380

atagaatatt atagttattc gtgattaacg gaagtcggca attttaggta taaatacgtg   1440

aattctcgag cgctaatttt ccatacagac tcgaaatact ctaaactttc tcatcgcgct   1500

ttattcctat ttcgtaattc gctcttcttc aacctctcaa ggttttcatc ttttctctat   1560

cttctgtttt cagattgcat cttttccccc tcctgttcga ttaattgatg tttgaatttt   1620

cgagaaacga tttgaagtct ttgttgtatt tttcatttct gttcgttagg taggtcgatt   1680

tttaatcgtg atgtccgacg ttgttcggat gattcacatt tggtttttgt catcttcttt   1740

ctatgttgtg attatcatga tttttatctt tttttcttct caagatttgt aatttatcga   1800

ttccccatgg ttcttggttt tttatacatg tattgaatct ggttactaga attatgttct   1860

tcgacggacg tctttcagat ttaaattgca ttgtaggaaa tatgatttgc tatctgagta   1920

acgtttttcc agagtattct tgattgcgcg atctatcttc aattgttaaa ttgtttttgt   1980

ttaattgggg tcatgacagg tg                                             2002
```

<210> SEQ ID NO 6
<211> LENGTH: 1459
<212> TYPE: DNA
<213> ORGANISM: Cucumis melo

<400> SEQUENCE: 6

```
tcggtgaaac tcgaaagatc tcgattcgaa actctattgc ttaagaacct ggtgaagctc     60

gagagatctt gatacaatcc cagtgcccta actcttcaac aagctaagca agttgtactg    120

tggggctcaa tctcggttca atctcgacgc acctgatgct ttgttccctg tctactcgat    180

gaagaagcaa ttacttctca ggacaactcg gtacccctaa atacagattt tgagcttcgt    240

gatcctacaa ctgaaatcaa atagaaaaac taataagtta gttagagttt gttatattta    300

ctgccattaa ataactctgt aatgtaaata ataaaccatt taactcaata tgaaatatag    360

aatgagaaaa agaaaaagaa aaagttaaag agagagagga agaaaactca ttttcaaatt    420

ctctatactt gtttgatcct tgaataagtt gaataaaagc tctatggcgg cttcaaagtg    480

gatgtaggca ctattagtcg aaccacaata aatttgttat gttcttttgc tattccttgt    540

aatctccata aatattttct tactaagctc tagaaatctg cttgtcaaga gattaggtat    600
```

```
catttatgcc ttttatattt cctttcggtt gcatatcttg agctagttaa gatcgagagg    660

ttactgttgt tgaaaccgag attagtatct ttggattaac acgtgcctac caaaatttga    720

aattttgtat ttaccccatt cattggataa taagcaattc ttatagtgtt atcaattaaa    780

ctcctataaa gtgtaataat tgaatccatg aactattttc atatgtaatc ttaataaaat    840

gaatttagaa gtttaattaa aataatatat tttgtatgct atttttcaaa gtttgaagaa    900

tgtgttaatt gatacacata caaaaaatct aggttttaca tgaaaaacta tggaagtgaa    960

agatagcatc taatatttta tgacacaaaa tgcaaactaa tatataaagg atttaattaa   1020

tttttatagg tttcaaattt gttagacttg tcaaatacaa aattttattg aaccaaatac   1080

atacaaacat caaaattaag aacagaaaat ctaaattcaa atgaaattta ttaatagaaa   1140

aattagaaaa aagaaaaaga aaataaaagg aatcgtattg ttttttcctt ccttttttccc   1200

atttgagagg tgaataaagc taattgagct gctctaactt cctaatcttt atgctttccc   1260

cataaagctt tcccaactgc gcgtaatcgt ataaatggaa aattgacctt tccaactaga   1320

ttcttccaga actaaacaat acgtaacacg caagtaatca aagacacgtt tcattttcct   1380

atagaatatt atagttattc gtgattaacg gaagtcggca attttaggta taaatacgtg   1440

aattctcgag cgctaattt                                                  1459
```

<210> SEQ ID NO 7
<211> LENGTH: 1507
<212> TYPE: DNA
<213> ORGANISM: Cucumis melo

<400> SEQUENCE: 7

```
agtcgaacca caataaattt gttatgttct tttgctattc cttgtaatct ccataaatat     60

tttcttacta agctctagaa atctgcttgt caagagatta ggtatcattt atgcctttta    120

tatttccttt cggttgcata tcttgagcta gttaagatcg agaggttact gttgttgaaa    180

ccgagattag tatctttgga ttaacacgtg cctaccaaaa tttgaaattt tgtatttacc    240

ccattcattg gataataagc aattcttata gtgttatcaa ttaaactcct ataaagtgta    300

ataattgaat ccatgaacta ttttcatatg taatcttaat aaaatgaatt tagaagttta    360

attaaaataa tatattttgt atgctatttt tcaaagtttg aagaatgtgt taattgatac    420

acatacaaaa aatctaggtt ttacatgaaa aactatggaa gtgaaagata gcatctaata    480

ttttatgaca caaaatgcaa actaatatat aaaggattta attaattttt ataggtttca    540

aatttgttag acttgtcaaa tacaaaattt tattgaacca aatacataca aacatcaaaa    600

ttaagaacag aaaatctaaa ttcaaatgaa atttattaat agaaaaatta gaaaaaagaa    660

aaagaaaata aaaggaatcg tattgttttt tccttccttt ttcccatttg agaggtgaat    720

aaagctaatt gagctgctct aacttcctaa tctttatgct ttccccataa agctttccca    780

actgcgcgta atcgtataaa tggaaaattg acctttccaa ctagattctt ccagaactaa    840

acaatacgta acacgcaagt aatcaaagac acgtttcatt ttcctataga atattatagt    900

tattcgtgat taacggaagt cggcaatttt aggtataaat acgtgaattc tcgagcgcta    960

attttccata cagactcgaa atactctaaa ctttctcatc gcgctttatt cctatttcgt   1020

aattcgctct tcttcaacct ctcaaggttt tcatcttttc tctatcttct gttttcagat   1080

tgcatctttt ccccctcctg ttcgattaat tgatgtttga attttcgaga aacgatttga   1140

agtctttgtt gtatttttca tttctgttcg ttaggtaggt cgatttttaa tcgtgatgtc   1200

cgacgttgtt cggatgattc acatttggtt tttgtcatct tctttctatg ttgtgattat   1260
```

```
catgatttt atctttttt cttctcaaga tttgtaattt atcgattccc catggttctt   1320

ggttttttat acatgtattg aatctggtta ctagaattat gttcttcgac ggacgtcttt   1380

cagatttaaa ttgcattgta ggaaatatga tttgctatct gagtaacgtt tttccagagt   1440

attcttgatt gcgcgatcta tcttcaattg ttaaattgtt tttgtttaat tggggtcatg   1500

acaggtg                                                             1507
```

<210> SEQ ID NO 8
<211> LENGTH: 964
<212> TYPE: DNA
<213> ORGANISM: Cucumis melo

<400> SEQUENCE: 8

```
agtcgaacca caataaattt gttatgttct tttgctattc cttgtaatct ccataaatat     60

tttcttacta agctctagaa atctgcttgt caagagatta ggtatcattt atgcctttta    120

tatttccttt cggttgcata tcttgagcta gttaagatcg agaggttact gttgttgaaa    180

ccgagattag tatctttgga ttaacacgtg cctaccaaaa tttgaaattt tgtatttacc    240

ccattcattg gataataagc aattcttata gtgttatcaa ttaaactcct ataaagtgta    300

ataattgaat ccatgaacta ttttcatatg taatcttaat aaaatgaatt tagaagttta    360

attaaaataa tatattttgt atgctatttt tcaaagtttg aagaatgtgt taattgatac    420

acatacaaaa aatctaggtt ttacatgaaa aactatggaa gtgaaagata gcatctaata    480

ttttatgaca caaaatgcaa actaatatat aaaggattta attaattttt ataggtttca    540

aatttgttag acttgtcaaa tacaaaattt tattgaacca aatacataca aacatcaaaa    600

ttaagaacag aaaatctaaa ttcaaatgaa atttattaat agaaaaatta gaaaaaagaa    660

aaagaaaata aaaggaatcg tattgttttt tccttccttt ttcccatttg agaggtgaat    720

aaagctaatt gagctgctct aacttcctaa tctttatgct ttccccataa agctttccca    780

actgcgcgta atcgtataaa tggaaaattg acctttccaa ctagattctt ccagaactaa    840

acaatacgta acacgcaagt aatcaaagac acgtttcatt ttcctataga atattatagt    900

tattcgtgat taacggaagt cggcaatttt aggtataaat acgtgaattc tcgagcgcta    960

attt                                                                964
```

<210> SEQ ID NO 9
<211> LENGTH: 1022
<212> TYPE: DNA
<213> ORGANISM: Cucumis melo

<400> SEQUENCE: 9

```
tgacacaaaa tgcaaactaa tatataaagg atttaattaa tttttatagg tttcaaattt     60

gttagacttg tcaaatacaa aattttattg aaccaaatac atacaaacat caaaattaag    120

aacagaaaat ctaaattcaa atgaaattta ttaatagaaa aattagaaaa aagaaaaaga    180

aaataaaagg aatcgtattg tttttttcctt cctttttccc atttgagagg tgaataaagc    240

taattgagct gctctaactt cctaatcttt atgctttccc cataaagctt tcccaactgc    300

gcgtaatcgt ataaatggaa aattgacctt tccaactaga ttcttccaga actaaacaat    360

acgtaacacg caagtaatca aagacacgtt tcattttcct atagaatatt atagttattc    420

gtgattaacg gaagtcggca attttaggta taaatacgtg aattctcgag cgctaatttt    480

ccatacagac tcgaaatact ctaaactttc tcatcgcgct ttattcctat ttcgtaattc    540
```

```
gctcttcttc aacctctcaa ggttttcatc ttttctctat cttctgtttt cagattgcat    600

cttttccccc tcctgttcga ttaattgatg tttgaatttt cgagaaacga tttgaagtct    660

ttgttgtatt tttcatttct gttcgttagg taggtcgatt tttaatcgtg atgtccgacg    720

ttgttcggat gattcacatt tggtttttgt catcttcttt ctatgttgtg attatcatga    780

tttttatctt tttttcttct caagatttgt aatttatcga ttccccatgg ttcttggttt    840

tttatacatg tattgaatct ggttactaga attatgttct tcgacggacg tctttcagat    900

ttaaattgca ttgtaggaaa tatgatttgc tatctgagta acgtttttcc agagtattct    960

tgattgcgcg atctatcttc aattgttaaa ttgtttttgt ttaattgggg tcatgacagg   1020

tg                                                                  1022


<210> SEQ ID NO 10
<211> LENGTH: 479
<212> TYPE: DNA
<213> ORGANISM: Cucumis melo

<400> SEQUENCE: 10

tgacacaaaa tgcaaactaa tatataaagg atttaattaa tttttatagg tttcaaattt     60

gttagacttg tcaaatacaa aattttattg aaccaaatac atacaaacat caaaattaag    120

aacagaaaat ctaaattcaa atgaaattta ttaatagaaa aattagaaaa aagaaaaaga    180

aaataaaagg aatcgtattg ttttttcctt cctttttccc atttgagagg tgaataaagc    240

taattgagct gctctaactt cctaatcttt atgctttccc cataaagctt tcccaactgc    300

gcgtaatcgt ataaatggaa aattgacctt tccaactaga ttcttccaga actaaacaat    360

acgtaacacg caagtaatca aagacacgtt tcattttcct atagaatatt atagttattc    420

gtgattaacg gaagtcggca attttaggta taaatacgtg aattctcgag cgctaattt     479


<210> SEQ ID NO 11
<211> LENGTH: 716
<212> TYPE: DNA
<213> ORGANISM: Cucumis melo

<400> SEQUENCE: 11

tcgtataaat ggaaaattga cctttccaac tagattcttc cagaactaaa caatacgtaa     60

cacgcaagta atcaaagaca cgtttcattt tcctatagaa tattatagtt attcgtgatt    120

aacggaagtc ggcaatttta ggtataaata cgtgaattct cgagcgctaa ttttccatac    180

agactcgaaa tactctaaac tttctcatcg cgctttattc ctatttcgta attcgctctt    240

cttcaacctc tcaaggtttt catcttttct ctatcttctg ttttcagatt gcatcttttc    300

ccccteetgt tcgattaatt gatgtttgaa ttttcgagaa acgatttgaa gtctttgttg    360

tatttttcat ttctgttcgt taggtaggtc gatttttaat cgtgatgtcc gacgttgttc    420

ggatgattca catttggttt ttgtcatctt ctttctatgt tgtgattatc atgattttta    480

tctttttttc ttctcaagat ttgtaattta tcgattcccc atggttcttg gtttttttata    540

catgtattga atctggttac tagaattatg ttcttcgacg gacgtctttc agatttaaat    600

tgcattgtag gaaatatgat ttgctatctg agtaacgttt ttccagagta ttcttgattg    660

cgcgatctat cttcaattgt taaattgttt ttgtttaatt ggggtcatga caggtg        716


<210> SEQ ID NO 12
<211> LENGTH: 173
<212> TYPE: DNA
<213> ORGANISM: Cucumis melo
```

<400> SEQUENCE: 12
tcgtataaat ggaaaattga cctttccaac tagattcttc cagaactaaa caatacgtaa 60
cacgcaagta atcaaagaca cgtttcattt tcctatagaa tattatagtt attcgtgatt 120
aacggaagtc ggcaatttta ggtataaata cgtgaattct cgagcgctaa ttt 173

<210> SEQ ID NO 13
<211> LENGTH: 2000
<212> TYPE: DNA
<213> ORGANISM: Cucumis melo

<400> SEQUENCE: 13
cttattcagc gctttcctgt aaaattaaag acttgatgag ggagaaaaag aaaaccggtt 60
cgcagcttca agaagacggc ttccgaataa gaatcagata ctcgatgatg gggaaacaat 120
aacaaagata tcaaaagaaa tcatgaaaca tagcataaga acgaaaaccc agaggtgaag 180
aacagtgccc aaacgcaact ttacccaaag aacatgtata aaacgtcttc cagacgttca 240
aaataagaaa gtggacaaaa tcaaagctac aaacgatctc caataactag atggaaaaca 300
ctaattgcac tagagatttt gaatgctttg ttgttgattt ataatcctcg acttccaaga 360
aaaagtaaca agtagaaatg aacgaatcag atccgcaatc gaagatctga aggcaagata 420
aggtaaggct aaagaaccat aggaaaacgg taaaaacgtc caaaacagtg tgagaaatat 480
cgcagattca aaggtccgaa ccctaagaac ggtgttatgc agctataaag gtgagaatca 540
aaaccctcta tccataacgt ggacggcgcg gttgaatcat tgtcttgttc cttgaaactg 600
aaggtatgcg agacatagaa ttcgatctca ctattatctt ctaatcaacg acgaagtaaa 660
gaagtgaaat ccagaacaaa gaatggagaa ttggaaatga caagaaaaac ggcagaggaa 720
agtggaaaag tgaaagcgga ctcacctaga tcaatgccct tggctggtcg agcttcagga 780
acctgtcgtc ggagagaaag agaaagagaa aagagcaaga gagagagaga gagagcacaa 840
ggagaagaga acgaggacaa tggaggcttt tgtttcgata ctccctgatc tggaattcta 900
taataacata actataaact tctctgggtt ggcccatcat cacgtatatt gggcttttag 960
cccaattatt tgttcactgc tcatgggccg gtgattttgg gctttcttct gggccttggt 1020
acataacaac ccagtatatg acgtattttc ggtgatagct attttcaaga acaccaactt 1080
ttttgttcaa caatgtggag atcaaataac agtatgtata tatacacaaa catatgctca 1140
tttatgaaaa atagaaagaa aaagaatgtt ggtaatttgt tacaaaatta taatttctct 1200
ctctttgttt gatttcatga acggtgtgtt ctatataaaa caatgaaata acataattat 1260
taaaatgatt cttaaaacat gatgatttca atattcatgg tttacatttg gtgggatgat 1320
tcgtttaatt attattgata atgtatagtt attgtgtgtc ccgttttctt tttctttggt 1380
ggaagaaaag aaaaaagtag gaaggcatgt aatattgcga tccttcacgg gacagatcca 1440
ttttccaatg tgatcgagta ctagttaggt ggagagtgga agaatcttcg tgcatgcata 1500
aatcaagtca caacttgcca atttggaaag aatcatgtta tattctacct ttactttcaa 1560
gtagggttaa gtgaattaga ccacaacgaa gcaatcaagt ccaaccaaac tcacttaggt 1620
caagcagttt agtgatatag acaggtcagt ggtcgttttt ttaatactaa gaaatgtcaa 1680
ttctatctag ttgactatta ttcatataga aggagaaaaa tgataactat gattgtccca 1740
caaacaacaa ctaccgatcg atctaaacca acaagtcgat gattggtgcc actttaaatt 1800
taaatctgac gccactcaat tgatgatcac ccctattcaa gcacacaaga acgcatgctc 1860
ttaaaacatt tggtaatatg attggaatta gtacaaaatg tttattcgat ctatacaaac 1920
aactcctttt taacacaaat gttttattgt actttcccgt gaaatggggt tagtaaaact 1980
atggagttaa taaaacataa 2000

<210> SEQ ID NO 14
<211> LENGTH: 2000
<212> TYPE: DNA
<213> ORGANISM: Cucumis melo

<400> SEQUENCE: 14
tataacaaaa tatgtgaaat tagccattat gtttgtcctt tcgttcttct tattcacttc 60
gttgcgattt ctttctatcg tctatcgtct ttcttctttt ttctgttgaa atttattttc 120
atcgtttttc ttctttttcc atcgtgaaaa aaatagtcaa atctaaatga tcgtgtataa 180
agaataaacg atcgtgtaga caaatctaaa tggtcgaata ttaagaaaat tgataggaaa 240
atttattcat tagaaaaatt ttagtaagaa aaattagaaa tgaaagggtt gaaccagaaa 300
gaaataaaag taatagacaa atgaaaattt taaataaaaa gaaatttggg atgggtgcat 360
ttactattta gtcttgagtt ttaattcttt tattacttta cataagatgt attaaattaa 420
agaggtaaga tagaattttt ttttaaaaaa aactatcatt agtaaattta acaaaagtga 480
catagcacca ttttcgttaa aagaataatt gttttatgta gtaaaattgg tagaaatatt 540
ttttaagtat agcaaaatat ctttgtcttt ttatatcttt cactgacaga taataataat 600
ttattaatat atcatttata tagtcccatt ttcggtaaat tttaatattt gaacataaaa 660
cactatttaa aataatgaaa aaaaacttta caaacttttt tatttttatt atatttgtaa 720
atatttctaa aaaattttac atttaaaata atattttcaa ggttaataca gaagaaaaaa 780
aacaaaaaaa gaggaaaagg caatttaaga agaatgacaa gaaaatcggg aggtggtgtg 840
gctaagagga agaagggacc ggttcttcaa gatccaacgc tccacattca atctcacttc 900
cttcttcaat tccgtcttct ccgtttcctc ctttatatgc ttctctcttt ccctcccttt 960
ctttctctcc ttcaatcaat caatcaatca atcaatcaat cctcccattc ccattacatt 1020
gccaaaaggt tctattctca ttctctacat ccatttccct ttctttcctt cttcttcctc 1080
tgtttcttct tcgtttcctt gattcatttc tctttgtacg ttccttcctt ccttctgcat 1140
tttgattatt ttcttttgtt ttacgtccgg aattgcaatg tggtttatct ttatttctgt 1200
ttttggacgt caagatgcct gttgttttta acattttgat ttgattcatc gttcatggcg 1260
taatcatgtc ttttggaatt gtttgaaatc caaggatcac attgatttca ctattgtttc 1320
atttgttctt ttttgttaat tttgtataat gaatcgtata ggggatcatt tttccattgg 1380
ttctcttgaa aatctttaag agttgcatta tgtatactaa gtctctctta tggcgtctgt 1440
ttgagtgaga attgataaaa gatccatggg aggaagaagt tttctttcat gaggcttggt 1500
tttattcagc tgtttcttct cgttgcaatt tgttgaagaa gggacatggg tatcttttac 1560
atcaaagtat aactaactat ataattcaat ttggttgata aagtagatac atgtaggagt 1620
caaccgattt gagtgtataa taatgttgtt atgtcccttg caacttaatg tagtgcatat 1680
ttgggagtga ttataaaatt gtataaatca ttttatgttt agaatcatct tgaaacacgt 1740
tttttagtat ttaaaaacta atttaatatt tagttttgca cttttaaatg aaatttttgt 1800
ttcactaata ttagttttga ttcattaaat gcatgctcca tcgtaatatt aaaagtaact 1860
agtgatttta accattttat aatcacatgt ctgtgatata gtgaagtgta cggctgcctt 1920
gttgagaatt gttacccttt agaagaaaca caggatgtat ttgatgttta acttgcattt 1980

```
tcttctggca ggcttagaaa                                              2000


<210> SEQ ID NO 15
<211> LENGTH: 1990
<212> TYPE: DNA
<213> ORGANISM: Cucumis melo

<400> SEQUENCE: 15

tatttgtaca atgaaaatat ttatttcttt tctcgattct ttaacaaaag ttcaaaatct    60

tttatcataa atacaaatat ttagtaattt aagtttagac taggtgtatc agatgtgcac   120

caagtgtata ttacgtgcat caagtatata tcaaatgtgt accaaacgta tatcacgtgt   180

atcaagtgtg tatcaagtgt ctatttgaag tcaagtgcat taagaatata tcacatgtgt   240

accaaatata tcaaaataaa tactgattga gcatcaagta tgtctattag tagtgtatca   300

agtgtattaa ttaagtttgt agcaaaggtg tatcatgatg tataacgtgt attatgtggg   360

ttggtttttt tttttttttg tcatttttgc aaaagtaatt aagtttgtgt tatgaaccta   420

atttttaaa tttcttttg tcacgtataa gagacttgaa aataggttta aaaggtctta     480

agggtatttt agtttgactt ttttaaaaag tatttatatg atatttaaaa attagaattt   540

tttagaaaga ataggagttt tataaattat tcttttaaga aaaattgcat cagatgacaa   600

aaaaaattta gaaataagca gcccataata actctttaaa tttgctatca gacgactatc   660

cgagggttat catcttttaa atttgctact tttacaattt agaaaatgta gtgacatgga   720

ccctattatc ataagatttt tttttgctat ttttgcaaac acatgttctt ttaaaatgac   780

ataattattt aaaataaaaa tataaagtta tttgatggat cttttgaacc tatttttaaa   840

agctaaagta ctaaaaagat acatattgaa aacttgaggt caaatgggct attattataa   900

atatgtggac taaaaatgta catttctaaa acttagagac taaatgcaca tatttaaaaa   960

agcatgtgaa ctaaaaaagt cgtttttcct aatatttttt tacaacaatg actaaattga  1020

acctcaaatt tgaagggtgg aaaaccatac taattattca ctaatgaact aaactcattt  1080

gatgatttca agacatatga ggttcattga gtagttgggt ttgaggggat gaaatgagtg  1140

gtggaagaaa gtttatgtaa cgacccaacg aaataggaag gtcatcccaa ggaagtcgca  1200

catccaatga gtaattacca caaaacaacc tctccttttt tctcaaattc ccttttaata  1260

aataatttga ttccccattc cttcctttct cccttggcag ccttctcctt ttttcaaagg  1320

tttttgtttt ttcttttctt ttttaaattt cattcctttg tttctctctt tctttcttca  1380

ttaacattct tcttatttcc tcattactga tcatctcctt ttcttggtat tattcttctt  1440

tcttttctca aagttttgtt tttcattgat gtagatgttt ttgtatcaat caatggaaat  1500

ttgagttttt cttatctcat tgtatcatca ttgagtgtgt gtttatgtta gggatccatt  1560

attaggatgg atgagaatca taatttcatt gctaatctat gaaccatgaa taaagaaatc  1620

taaatccaac atagaagata gaacatttgc attgtgttat gagtaaccag ctctgtcact  1680

tcaattggtt cttctacaca tttgatggca atggctttgt ttgatattcg tgatggcatc  1740

taagcattgg ttcttcctat gtttttcgtt ggctcttggt ttgatttgca attagtgaag  1800

agcatgtttg gaatgaatga gttgaaatca cctttaacat ttttaaaatc actttaaata  1860

ttaaattaat tttgagtgat aaaagtaatt ttaacaatga taaaattact ttcaaatgtg  1920

ggccgaatca aattgtctag aatgtttagg gttctccaac taatagcaat ttatccaaac  1980

agggtaaaaa                                                         1990
```

<210> SEQ ID NO 16
<211> LENGTH: 2005
<212> TYPE: DNA
<213> ORGANISM: Cucumis melo

<400> SEQUENCE: 16

```
ttgttagagg agttagcttt tcagggagtc ggttacaact tacaagacag acaaccatac     60
tgtacaatca atcactactg cctcaaagtc gaaaccattt aataccagtt gagcctcatt    120
gtgactgcat aattttgacc cctaccacga ggtaatttca gttcaaatca attgtatctc    180
tcttctggat atcagtcaag aatctcatgt tctcaagtta tagtacattg ataattactg    240
tgcattttta ttaatttatg agttaaaatc ctgctgatta attcaactaa aggaataaaa    300
tagttattgg catttggatg agaatagaat gtgaatccca tcattcatcg ctagattgga    360
ccgtaattat aagtgagagg gagaaacttc tgttgctatt cccttttat ttcttaattc    420
atttataaat tgtttttagg ccttttatat atatatattt ctaccatttt tacatttaaa    480
attcttttaa ctttattatg tatggactca aactaacaag ctttatttga taaaattgtt    540
caaactatta tattagtttt atatttgtaa accataaaac aaatccataa aattccacct    600
gcatcactca ctcatgttgt tgaatggtac gaaataaaca atacatgtga aagatgaaaa    660
taagaattgt tctcttatta aatctaaaat ctagattttc tttttagtac atttaacact    720
tcaatgaaag gtctaaaaca ttattgaatg acgtcacgaa ctattacaaa agattattcc    780
gatttatctc aaaaggggtc tatttcacta attttggtgt cccacatctg taaagagaat    840
tttcgtgata tgtgtagata tttaaatata attgaattcg atgaaagcaa agcaagaatc    900
gatatccgta gttattttga tatagatcgg tgataaataa aagacaatat gcataaagtt    960
tgtgggtaca gagtcggcta gttgcaatga ggggtatggc cccaagactt ttccccaacc   1020
ccaacggtca attaatcacc ccaatggggc atcgaatctt ccccaccatt ttccttttct   1080
tcgccgactc ttctacccat ctcttttgcc gactctttct cacaggtttg attaaatccc   1140
attcatattc agatacacta tttcaaaata actcgcaaat taatttgttt tttaaatatt   1200
ggtataataa taaaattaat tataaattgt gacctaaaaa gtactttgtg gaagagggga   1260
tatagtctgt ctaatatatt attgattaaa tatataatag aaccataaat gcaaaccact   1320
agaattgtta ataaaaatca acgctctttt aagtctttcc atagaaagaa aggcaaagac   1380
gcgcaacgtc tagaattttc tttataacgg aagctaactc tgttataacg gccgtccaca   1440
taatatggta gatttaaaat gacgtcagca tgtcgcttct aaatttgggt ccaaaggggg   1500
gattcattta tagggaaggg aaacggcaaa tgcaagcata gtgagtaaat acgtggcggc   1560
aaagtaatgg ataattctgc ctctgccgtg acgacattgc ccttccattt cactataaat   1620
acacctcctc tatccctcga tttcttcgca attgaatttc tcttctcatc tctgtcgtag   1680
caaaccaaat cgatttcttc aaaggtattt cttcctttcc tttttttttt tttttttttt   1740
tttttaaatc atgttgttca aactttgaga gatgaaatga ttaggggctt tcaaagtggt   1800
tttcgtttga tatgtttctt agatcgatag ggtttagaat cgagcatcct tgtaggtatc   1860
ctgaggtttg gtggttggat ctgcttaatt tttatgtggt tgcatggaaa attgggattt   1920
tttttttcta attacgtgat tctggaaata ttgatctgtg gttcagatgg aattgaatct   1980
gatctttctg ttttgttctg tatag                                         2005
```

<210> SEQ ID NO 17
<211> LENGTH: 2004

<212> TYPE: DNA
<213> ORGANISM: Cucumis melo

<400> SEQUENCE: 17

```
tagaaaaaaa ttgaagatct tcttaatgct aataataaaa gcatatataa aaaggcttca     60
tattacacaa gcatcttaaa accaaaccga acttgatttg aaattatccc actaattctg    120
tagatttcac caaagtcctt aacctttata ctaacatctg catttgactc tttcatttga    180
cctccaacat attctttctc attttccttc cattcaccac aaaaaccaac aaatacaaaa    240
aaccacaaat acatagaaaa ttaataaaaa aatcaaaatt tcgagatgaa atcattataa    300
actcatccga taactttgag atttgaaacc ttacactata taaagaaact catccgataa    360
ctttgaattc gcatcgaaat tacgtaagtg aagacgaaaa tgtaaatgat tagatgcgaa    420
taacaaaaaa aacataattt ctaaacgtaa aacactatat tcaccttatt atacttgatt    480
attttggaaa agtatgaaat ttgagtgtgg gagaggagcc aaagaattgg aaacttgtta    540
ttaggagtcg ttatgaaaca ttttcaacaa gccaatattc tttcacatac tataatgata    600
tacatagaaa taatacaata atatttttga aattgaggca tttttgtcgt aatttatcta    660
aaaatgtcag ggtagattca tcatgtatac aaatctctcg ctatcaaaac tatataaaaa    720
tcttgtgaat gatttcaatc gaaatggacc gagaaaaaac atcgtaacca cctctaaaat    780
cgataaattt gtttcaattt caaatcccta aaactaaagg tgctactttg tacaatttcc    840
cctgattagg gtgctaaagt taaaccctaa ataaaggtgt gtacgtttcc ggaagtttct    900
agaatcccca gcgaagttct ccaaatcgtg gcttgcagac caaggacccc cattaaaatt    960
cgtttcttcc tctaaacctc ctcccttaat tttggcattt tggtattttg gctcctataa   1020
attcaccccc tccttatccc taatcctttg tcttccaaat tttccttcaa agcctgcttt   1080
tcccatttcg tcgtgctttt tcttcatcta aaggtatatt tcagttctag ttttctttct   1140
ctgttgatct cttggatttg agggacgttt gaagttggct ttgtttaatt ctttgttatt   1200
caatctcttt ttttgttaga gttgttgttt aatcgtttcc cttgttgttt ttctcccttc   1260
tagttcgatt ttagaacgct ttttgtgggt tgattttaat ttctccgttt tcttacatct   1320
ttcacaaaga aacgattgaa atcgtgtttg tttttttttcc cacggcatac gttattagat   1380
cttgtagata atgatctcaa tctattgttt agtttttgca aataagaagt tggtttttta   1440
tctccaactt ttatatattc gattcgatga gatgttctac accgttagga tggaaccaag   1500
aagtgaggta agggtgtttg attgaaaaat tgaactgaga agttaaagtt ccttcctaac   1560
tttttaatgg attgtataat tcgttcaatt ccttgtcgtt ccatttttat ttctgtttcg   1620
tttttcgtgt tgctgcgtat cgcttccctt gttgttttcc tcccctattg attttgcgtt   1680
tcttggagtt tctctgtttt ctctcttcat ttttctacaa aaatcaattc tatttttatt   1740
cgttttcaat tcccgagctc cttggaatgt tatccttttc tcctgtgtaa ataagaaccc   1800
gtattcaatc ccagttcata gtttggcttt cccaaataag agcaaaaaga ttgtactgag   1860
aagttgaaga tttcaaaatt ttgtacatga tttcttctaa tttatcaatt tgattggact   1920
ttttgtatat agatttggtt cttgagctat ttatgttatg acgttttcat attgaggcca   1980
tgcgttgaat tggtttctta acag                                          2004
```

<210> SEQ ID NO 18
<211> LENGTH: 1935
<212> TYPE: DNA
<213> ORGANISM: Cucumis melo

<400> SEQUENCE: 18

```
tatacaaatg acaaaatatc gttgaagtcc aaaaaagatt tattgttggt aaatatcgtt     60
aaagttagta aatagatttt agagaaagga gatatagccc ttgtagtaga aacacacaca    120
caaattgaat tagatgtgtt taatgtttaa ttaaattaga tatgagtcaa cttatatcta    180
atataggaca ttattaaaca aataagaaat aagaaacatg aaacaagaaa aacaagaaat    240
agaaacaata tcaaacacat tcctatttct tgttctaaaa aaagaaaaaa catggtacaa    300
gaaataggaa acggaaaaga ggaaacaagg aacaaatgct accaaacggg cctaagtttc    360
taacaaaatg agctaggtgt agtttattgg tatagatagt gactttcaat tattttaaat    420
tttttatcc atacctccac gtctttagaa tctttcttat ttatatgtga tcttaattca    480
ttcatgtctc aatcttaaaa ttagaacatt acatgttcat catttttcc ttttgttact    540
gtgtttaatc tttcctaaca agacaaatag tttaacctta atccacacat tattataacc    600
aaattaaaat aatctacctt caaagaaaac attattataa tcttatatta accacaaatt    660
ataataccaa actctaacgc tccaacccaa cctaggaaga atgacaaggc tgtcataatt    720
tagttggttt ggcacgttgt tggaagttct caaaattatg gaaatattta tttccttctt    780
ctttatccat catcctcctt gggagggtga atttgtgtta aaaaagaata gaaactaaag    840
tctaagtggc aggacttaca ttatgtgtgt atgtggaagt aaaattgcag taacagttta    900
caaaaacaac tcatccatga ttcataacca acttaaatga atataatttt ttgcctaaag    960
attttaaatt aatatataag cggaagaatt aacctataac ttcaagttta acaacacaaa   1020
tattatatca tactgattaa ttattggaat gatgtttagg ctttaaacat aaagtattga   1080
gaggctaatt tgagtttaac tcactaaact atcattaccc tttcaaaata gatccaatca   1140
tccatttatt ataatactca atgaaataaa gcaaaagatg agtaaaataa ttcaccatga   1200
acattgataa ttaattttcc cactaagata aactactact cctcaaatct tcatatgtgt   1260
ttttcctttt tgagttgcac tcaaattttc atagttgaaa tttacccatc aaaacaacca   1320
acaatctttc aaattcaaca aacatttgac cttacaccct ttgatgccaa atccttaccc   1380
tctccctctt ccataaaaat tcttatataa accaccatca ctctcacttc tcaattcact   1440
ctcttctcta ctcccaatca cctgacttgc ctcttactcc accgccaggt tccgccccaa   1500
cttccccggt aagttccagt tcttcagatc tggttaccac atttgatttc ttgcttgtat   1560
ttgacgtggg aattttcata tcggcgtttt ttcgaactgg gttttgcttt atgatcatat   1620
tcttgtagta aaatgccatg aatctgttat ttgattccgt ttttttgga gatcggtcta   1680
gctttatggc catattctgg catttaaatg ccatgaatcc gtgatttggt tgaatttcac   1740
ttccgatcca atgtttatgc tgatattgac atctttgcat tcaatgcaga ggagttttgt   1800
ttcgatttat tactgatctc atcacactga tcttgaattt tttatacttt tatgtgtgtg   1860
tgtgtatttt ctttaatatc tatgccaatt gaactatgtg gttaacttca gagtgttctt   1920
gtgggcagtg agaag                                                    1935
```

<210> SEQ ID NO 19
<211> LENGTH: 1606
<212> TYPE: DNA
<213> ORGANISM: Cucumis melo

<400> SEQUENCE: 19

```
atatattgta tcgattcttt agttgctcta tgtttttgtt tgcttcattt gtcgattaaa     60
ctgtaaaatt aatttctttg acaaggaaaa agatataatt taattctata atttattaca    120
```

```
atctaatcca tatggtttaa taaaacactg aaaattgttt atgaaaattt tatcgaacta    180
caagaactat taataaagtt tttttaaacc gtaaattgaa tgaattttct ccacggtgta    240
aatttgaaaa cattaattaa ttaattaatt aattttaatt tcaaggtttt ttctgaccca    300
tgaacctatt ttatgatata agttgttcag gggttgcaat agtaaccaaa taaagttgat    360
cagaaaaggt taacaactca tgaaaacttc caaatgcatt tgtgtttcaa ttattttctt    420
aaccctcttt ttttggtaat tttagtttaa aaagtgagtc ggttgatcat tattgttctt    480
taatttcttg ggagaaaaat attaatgttg attatggtga tgagttaagt ccaattcttc    540
atcaaatcat accaaattag gaacaaaaaa aacatcaatt ttaaggtgca aatccatttc    600
taatggctaa aatgtcaagc atcccaccaa accaacaatc tctaaaccca tttttactcc    660
actaatctaa tgtttaataa taatcaacaa ggttttgctc attccttttt tagttaataa    720
tcatttaaca ccaaagctca aaagtaccca cccaatggat caaaatcgag aatatatagc    780
atttaaggat ataaagacta gagataataa taacctagct tagagcttaa agggatacac    840
tagccatcaa gtcaatttgg tagacaatct aaaaacaaat aattcgatga aaataaagtt    900
gtatttttgt gttttcaaac atgttttaag acgaaggttt ttgataaatt tgatctcaat    960
aggtaaacaa tggtaattac tcgattataa ttactcacta aataccaaat cgaatataaa   1020
ttattactaa ttaattatga acatgtttta cattttaaaa aatgaataat ttttttttta   1080
gaatttgtgt tattgaaaat aattttcaaa acaatattga atgaatctta agtgaaatca   1140
atgtattaaa agaacataaa acataatcta gatggtctat cgaacaagct agaaaatatc   1200
ttccataaat ccaatgatta agacaggcag gcaggcatga agataagagg attggattaa   1260
ttggtgattt taagttatga ataaagacac aagaactagc agctctcctc ttcttgtcac   1320
cttcctttgt catccagctc acacaactcc aacttggaat ttgacaggtc tctcttcact   1380
catacattcc cacatgaaat tattaattga atcttcaaca ttgtctttga ttcttcagct   1440
gcactgtcct tttccaccat ttttttcttc aagataaaga ctaataaact ccttatatat   1500
tcctctcttc ccattcacct gtgcatactc acaaagcaac tgccatttcc ttcttgttta   1560
tctctgtttt tttcttacac atttgttgaa ctttccctct gaaaaa                  1606
```

<210> SEQ ID NO 20
<211> LENGTH: 1487
<212> TYPE: DNA
<213> ORGANISM: Cucumis melo

<400> SEQUENCE: 20

```
taatgaattt gtatttgtta gtggattgag tttatatgat attaattttg acccaaacag     60
ttgagtacgt aattaatgtg gcttgcattg aaagtgatat gggcatatag tatgtgtaga    120
atgtagctga cacaacacat taacaaaacc caattttaac tttttctttt tctttttctt    180
ttaattttat atggatcaga tcacatgtca ttttccatta caactcactc tctaccaatc    240
atcccatccc ataggccata ccccataaca tccctttcta aaatatctaaa tcatctccct    300
aaattattac atttttttttc tctcaaatat aactattcaa ttcataaata ttattctttt    360
tttagctctt attatttcaa ttatgatttt aaatattcct tttcaattta cgacctttta    420
tttaccatat caacatttta attctactca attaaagatc attataatga aatttcaggt    480
ataacaaaat aaataggtgt gatataatga tggactacta atttcactaa tttcgtcatc    540
tgaaataagg acaagttcca actatcacta ttgtgaaaac ctcataactc ctaaaagtgt    600
```

```
taaaattgga ccctcaagtt tataataatt ttgcaaattg aatcccaaaa ttaaataatc    660
agtataattt atacgttttg agagtcaaat ttaatatttg aataagcttg aatacttaac    720
ttctaatttt gaaaatttaa aaatgcaact gcgagagtaa cttttgcaat tagccgtcga    780
aacaattaat tatattggtt aatttatgtc tcattctctt ttgatgacca taaagataaa    840
cccatttata atataaatat caagcaaagc taaaacaaaa tctttttttt ttcaaattag    900
atctaaatat gaataaaagc agaactttct agaagtacaa atttgattat ttttcttgag    960
ataaaatttt cgctatgaac ctttttataa taggaaaaag agaaaaagga tggttttata   1020
taaatgtatg ataaaaaggt aataatatcc attgtaatag taaaaaagaa aaaaagaaaa   1080
aaagaaaaag caattttctt tttcatgatt aggaaatata aaaacaaaaa ttggctccca   1140
attgacatct ttaatcttct ttttcttttt cttagaaaat aaaattagtg agagaaggaa   1200
aaaaacgaag ggttgagaga tagagagaga aaaaattgat ttttaattta gtttattttc   1260
ctttttttgga gcacaaaata aatagataaa taaaatatta gtttgcaaaa aagcccctcg   1320
agtttatctt atttgctcaa aaaagcaagg ataaatacct cccgacatcc ctgtttatcc   1380
ctctcagttt cataattcca ttggttcgat aagaaaacaa ttctcccaat attcccgctg   1440
tagatctcgt cgattttccg tttgtttccc gggaagatca atcaaag                 1487
```

<210> SEQ ID NO 21
<211> LENGTH: 1448
<212> TYPE: DNA
<213> ORGANISM: Cucumis melo

<400> SEQUENCE: 21

```
ggtgtcttgt tgtaaggaaa tggaaagaaa agagaaaggc tcttgttgtt gtccttgttc     60
tgtgtatcga tgaaaatgga tcgacgcgaa gaagatgaag gacgagagtg gggattataa    120
gacagagaaa ctccgaaatt tgagggctaa tatggtaata acaaatggcg ggatactttc    180
aatggacgtg gacccattgc ttctttaact caccgtctga tctttatttt acggtcatga    240
tttccctctt tccccaatat ttttgggagg gaaaaccaac tttgtttttg taattttaat    300
catttttcct caaatcgtaa aaaaaaaatt atagattttt tcaaaaatag aaaaaattca    360
tataagaaaa ccaagataaa atattttgaa aaatatccta ttttttactt cttaaaaata    420
attcataaaa gaattattat aaatattaaa aaatatcagt accactatag acaactattt    480
atatagcaca tatagatata tttgttggtt tttctattta gtatttgaaa acaactccaa    540
aaacaataca tttcaatata cctacgaagc atacaaatat aattattaat tttaataagt    600
tcaaaaatat ctaatggcat ccttatttaa tcaatttttt catcgacgtt atacacggta    660
aggatgtcct aatccttgac cattgaaaga cgtttgtttt gataattata tcttttgata    720
tatacaaaca tttatctcat gattagaata gtcacctttt tatttgattt aacgattata    780
cataatattt gaaaattttt aaatccatca acacaatcaa accaaaaatt tcctaactac    840
ataatctaca agagatttac catcttcttt aaacaattgg tcattacgtt tgttaatgtt    900
taaaattaaa tgcaaccata ttgggtgtaa aagccaaaca ttgatttgat tattaaagtt    960
ttttctatat agacttgatg tgtaaaccta ataaccaact tgagctaaat aactttaatt   1020
tctaaaattc attaaactgt cctcatccaa attataatat caaagatttt tgaaatattt   1080
aaaaattccg aacatgggaa ctactggaac ttggcaataa attcaagcaa gaaagaggaa   1140
aacgatataa tcaaacaatt aaaaaacaac agaaatttat ttaatcaaag gaataatctc   1200
atcttttatt tattgggttt tacttttaat actgtgagtg atgattggaa cattaattaa   1260
```

```
catttaagac attaatttgc aacaatcaat caaaattgta taaatccact tgttttgatt   1320

tatttgaacc atcacttttt tttttatata tatatataat atgggagtga aagatcaaac   1380

gtataatcat gaaatgaaag atgggatatc attgaactta attaaatatc attgaactgc   1440

aatttttt                                                            1448
```

<210> SEQ ID NO 22
<211> LENGTH: 1235
<212> TYPE: DNA
<213> ORGANISM: Cucumis melo

<400> SEQUENCE: 22

```
aaattttaat aattaaaatg aacaattttt caagagtaat agagtttgag agatgtcaga     60

gaagtttgag gaagaagata acaagtggga gaagagaata agtttgttgt gtgaaagaga    120

aggggaaatt tcattcaagg gtatattgaa ctttttactc aaattttgta agtctatttt    180

ttccgatcaa tcctaaaatc acacacaccc ttaaaaaatg gattatattt ggcaattttc    240

catgataaac tcatttttaa tttagagtta tttttcaac gagatattaa cagttttagt     300

tcatatacta attgtaagaa tagtttcttt taagttgaat agaatttttg aaacttttaa    360

tagttcaaaa ggtatttttg aaacaaaata agaatgtttt tgaacttttt ataaaaagaa    420

ttgagatttt tttgaaattt ttgataaaga gaaaagaaaa gaagaaagaa aaaagaaaaa    480

caagtttgta gaactccgtg ggaaaatcgt cgagggccct gtgaaggaat tttgaaatta    540

taatgagggt attttcgtca acaagggaat ttagacatcg tatataagca tcctcaaacc    600

ctataattaa gcccttcaat ccaattgcca ttctccatct ctcgccgcaa gggtttaaga    660

gcagcttctc tcctcaggtt ggggtttccc cctatcttct tcattcttcc tcttctcgat    720

ttctttcttc tatttgctcg atagtctctt atttcttgag cttttgctgt ttttctcctg    780

tacatcctaa catgaattat aacttggttt tgattttgtc ttttacttct gtattaaaca    840

acttttctta cccttttatt cttctcttct tcttcgtgtc cctgcccttt tgtttttatg    900

ctaattttat gtttctgttt atcaatctat cgaggcgtga cctgtcgttc ttccaatagc    960

gtagatctgc acttaatcta ttctagctga ttggattggt cgtttttcgt ttttttaatt   1020

tattttctct gttctagttc cgataaattt ttttatatat aattaacaag ttctccagcc   1080

aaaagggtta atattgcgtt ggatatttta atttttacgt tatttagatg tgtgaatcta   1140

ataaaattag ggttattcat aaatttcagt aatgatattt tggttatctg ttcttgctgt   1200

tcctgtttcg cagttctttt acctaatatt caagc                              1235
```

<210> SEQ ID NO 23
<211> LENGTH: 2003
<212> TYPE: DNA
<213> ORGANISM: Cucumis melo

<400> SEQUENCE: 23

```
ctagacattt ttgtctaacc tttcaaatgt tttgttttaa tcttccctct cccaaatagt     60

gaaggacatc cagtgtcaac cgtgaacgca tactgtgtca ttcatgaaac aaatcttttt    120

tgtagtgggc attgtcagca tacatagcat gtagaagcta tagacagatg ttgctttgag    180

ttgtatttag ttctctttaa aggaactttg tacaaagtac tgaatgtact ctgttatttg    240

aaatatcaat gaagtcctct taattctttt gagttcccat tccacgttta agttgttagt    300

tgtattcatt ttcgcttact aggtgttctg catgtatctc acagagagac tcacgtgaaa    360
```

```
tgtttaggcg gtcacatccc taatgacttt tgaaggggtg tgacacgatc atttgaatat    420

atcacttatc taatagtgac agtggtctat atctttgtct atctgtatag atcattggtt    480

gtttagatat tggtacacta ttgtgtagtg aaaaaagaag aagaagaaga aaaatataat    540

acttgataat gagaaaagaa taagaaaaaa tattgtcttt atgaaagatg aaaaaatgat    600

gctgaagacg agaaatgacg gaaaaggaat aaattctaga tgaagagatg aagaaattct    660

agaagaacaa atctagaatt tataaatggg ataacaataa agataaatgg gataacaaag    720

aaaaaaaatc aagaaattac ctaaatgttt caatcttgct acgccttaat tagaaaaaga    780

aaagaaacaa aaaagaaaat gcacaaaaat atctatatat atatacacac acaagcacaa    840

gaaaaaaatg aatattggaa aaagacgaaa atgcattatt ttttatttgc gttagcgagt    900

tgttgtgatt ttgtgagcaa gaaaaggata tgcaggagaa ttaagataaa taaggaagat    960

tgaatagaga ttaaaagaga aatatgggaa tagagtgggg atgaaaggtt taaagatagg   1020

gagggaggga gcgagagaga ggagaaacaa acataccttg agaaagggag aatgagagag   1080

ataataaata aatacggtga tttggaactc ataaaaagat taaaaaaaaa aaccttagag   1140

taaagacttt tccatgcatt tcgagaaaat ggaaaagaat attctattct atttgcttgg   1200

acaccaagtt cctttttgtc gcatgcatac gtctatttat ttctgcttgc ttgcataggc   1260

agtttttgtc caaggaaatt cagcaaaggc ggtatcaatt tcgtcaactt agaatccact   1320

cagtactatt tgaagttcct cactaccaat ttgcaccatc caatctcttc tctctccaac   1380

ttcctgccag ggcttaacct ctcttaattc cttatcctta cttgttacct tacctggttc   1440

cactcttcac gtctctctat tctatattgt tttttttca ttcataattt tgttactctc   1500

ttctctgtcc cctttgtctt ggattttatc tctccatata ttcattggaa taatttaagt   1560

tctttgtaga ttttatgaaa ttaccaattt aatttttcaa acagtttttg gatttgttta   1620

atttctcctt ctctaaatcg cgttgacttt atgttatttc gcccttgctc tgtttctct   1680

gatcataaag tatgtacttg attttatggt gaatgctttc ttgatttaac aaccctggtg   1740

ctgaaatctt ttttaaatcc tacttttgtt gttttacata tgttcttact ctaaaatgag   1800

cgacttattt ccttttattc ttccttcttg attaaggatt taatcgttga agtatgctta   1860

tattgtggaa atttggtttt aattgatcat acgagctagt attactagct tctcggtttc   1920

tttggatgag ttatatgcat atgatgattt caattccaat ttttattttg caacagattg   1980

ttttttgtgg ctgaaattca agt                                           2003
```

<210> SEQ ID NO 24
<211> LENGTH: 2015
<212> TYPE: DNA
<213> ORGANISM: Cucumis melo

<400> SEQUENCE: 24

```
gatcagagta gcagttgagc aaacccaaac caaacccttt atctatacaa tcctctcaaa     60

ataaaattat tgtttaatta ttcccatatc tattatcatt tttccataat tgcattgaga    120

gaaaaaaaaa aaattctagg agacctaaat acaacaacaa ctatttaata atagccccat    180

gtcacattaa ataaaactaa caaaaagttt aatacgtcaa gaaacgatac ttgtggatat    240

tgaggcatgg gtccctcctt ctttgtatat tcaaatctgt ggtctgccat cagataaggc    300

ctttaccata taataagttt tcaaaaaagt aagcaccact tgctgctttt ttaatttaat    360

tatatttaat ctaattattg aaacttatag ttgttttcta tccttattct tttcttctct    420

tcaaacaccc tcctattaat ttaaaataac caaacaacct ttttctttac atagacaaac    480
```

```
ttaattagat taaatataac ttgtaattag attaataata tagtttaaaa agaattttat    540
tttaagtaga attattagta aaaatgaatt ttgtggatag atacttggaa tttaagagaa    600
agttaaaaga gagaaaaata tgaaaaggaa ttaaatgatt aaagttgaat gtaagaaatc    660
aataaacata aattccatgt attaaatttt tgtcggtgtg tgaataaata aatatctatt    720
actattagat tacccagctt tgtttataaa aagaaaaaga aaaagttttt aaaatattgg    780
aaaatttgt ataattattg aagaaattgc gtggtctttg caatttgggc atcgttctta    840
tcgcttccaa tgaaggggcc gtttacctcc accactattt ccaacttgtt tttgtaccat    900
tctctatatt tctttgacac ctatattaca cgtgtcttta atccattgga ccttcgtcct    960
actatatttt tacccgaaat gacgaatctg tccttctcat ccacctataa attcacctct   1020
ccggctcctt ccctttcatt cagttttcct ctattcttct ctctatacgt catattcatt   1080
tcttccaagg ttcgtcctcc ttttatcttt cttctttctt tcactttttt tcgctttttt   1140
cttttctttc ggtttttgtt cttttaattt cattcgtttc tttttgttat atggtatgtg   1200
gtatttgttg aattgagatg ttttagggtt tcgatttagg ttttatttct tatcctactt   1260
aagggctatt gtgattttgg agaaaggagt tcttatttgt tttttttttt ttccttttc   1320
ttatctggca gatgcaaatc ttcgttaaaa ccctaaccgg taagacaatc acccttgagg   1380
ttgagtcgtc tgatacgatc gacaacgtca aggccaagat ccaggacaag gaagggattc   1440
ccccggatca gcaacgtctc atcttcgccg gtaaacaact cgaggatggc cgtaccttgg   1500
ccgactacaa catccagaag gagtccaccc tccaccttgt cctccgtctt cgtggtggca   1560
tgcagatttt cgtgaagacc ctgaccggaa agaccatcac ccttgaggtt gagtcgtctg   1620
acaccattga caacgtgaag gccaagatcc aggacaaaga aggcattccc ccagaccaac   1680
agcgtcttat cttcgctgga aagcaactcg aggatggccg cactttggcc gactacaaca   1740
tccagaagga gtctaccctc cacttggtcc tccgtcttcg tggtggtatg caaattttcg   1800
ttaagaccct gacgggtaaa accatcaccc tcgaggtcga atcctctgat accatcgata   1860
acgtcaaggc aaagatccag gacaaggagg gaattccccc agaccaacaa agactcatct   1920
ttgctggtaa gcaattagag gacggccgta cccttgccga ttacaacatc cagaaggagt   1980
ccaccctcca ccttgtgttg cgtcttcgtg gtggt                              2015
```

```
<210> SEQ ID NO 25
<211> LENGTH: 2006
<212> TYPE: DNA
<213> ORGANISM: Cucumis melo

<400> SEQUENCE: 25

accaccacga agacgcaaca caaggtggag ggtggactcc ttctggatgt tgtaatcggc     60
aagggtacgg ccgtcctcta attgcttacc agcaaagatg agtctttgtt ggtctggggg    120
aattccctcc ttgtcctgga tctttgcctt gacgttatcg atggtatcag aggattcgac    180
ctcgagggtg atggttttac ccgtcagggt cttaacgaaa atttgcatac caccacgaag    240
acggaggacc aagtggaggg tagactcctt ctggatgttg tagtcggcca aagtgcggcc    300
atcctcgagt tgctttccag cgaagataag acgctgttgg tctgggggaa tgccttcttt    360
gtcctggatc ttggccttca cgttgtcaat ggtgtcagac gactcaacct caagggtgat    420
ggtctttccg gtcagggtct tcacgaaaat ctgcatgcca ccacgaagac gcaacacaag    480
gtggagggtg gactccttct ggatgttgta atcggcaagg gtacggccgt cctctaattg    540
```

```
cttaccagca aagatgagtc tttgttggtc tgggggaatt ccctccttgt cctggatctt    600

tgccttgacg ttatcgatgg tatcagagga ttcgacctcg agggtgatgg ttttacccgt    660

cagggtctta acgaaatttg cataccacca cgaagacgga ggaccaagtg gagggtagac    720

tccttctgga tgttgtagtc ggccaaagtg cggccatcct cgagttgctt ttccagcgaa    780

gataagacgc tgtttggtct gggggaatgc ctttctttgt cctgggatct tggccttaaa    840

agaacaaaaa ccgaaagaaa agaaaaaagc gaaaaaaagt gaaagaaaga agaaagataa    900

aaggaggacg aaccttggaa gaaatgaata tgacgtatag agagaagaat agaggaaaac    960

tgaatgaaag ggaaggagcc ggagaggtga atttataggt ggatgagaag gacagattcg   1020

tcatttcggg taaaaatata gtaggacgaa ggtccaatgg attaaagaca cgtgtaatat   1080

aggtgtcaaa gaaatataga gaatggtaca aaaacaagtt ggaaatagtg gtggaggtaa   1140

acggcccctt caattggaaa gcgataagaa cgatgcccaa aattgcaaaa gacccacgca   1200

atttcttcaa taattataca aaattttccc aatattaaaa acttttcttt ttctttttat   1260

aaacaaagct gggtaatcta atagtaatag atatttattt attcacacac cgacaaaaat   1320

ttaatacatg gaatttatgt ttattgattt cttacattca actttaatca tttaattcct   1380

tttcatattt ttctctcttt taactttctc ttaaattcca agtatctatc cacaaaattc   1440

atttttacta ataattctac ttaaaataaa attcttttta aactatatta ttaatctaat   1500

tacaagttat atttaatcta attaagtttg tctatgtaaa gaaaaaggtt gtttggttat   1560

tttaaattaa taggagggtg tttgaagaga agaaaagaat aaggatagaa aacaactata   1620

agtttcaata attagattaa atataattaa attaaaaaag cagcaagtgg tgcttacttt   1680

tttgaaaact tattatatgg taaaggcctt atctgatggc agaccacaga tttgaatata   1740

caaagaagga gggacccatg cctcaatatc cacaagtatc ggtttcttga cgtattaaac   1800

tttttgttag ttttatttaa tgtgacatgg ggctattatt aaatagttgt tgttgtattt   1860

aggtctccta gaattttttt tttttctctc aatgcaatta tggaaaaatg ataatagata   1920

tgggaataat taaacaataa ttttattttg agaggattgt atagataaag ggtttggttt   1980

gggtttgctc aactgctact ctgatc                                        2006
```

<210> SEQ ID NO 26
<211> LENGTH: 2017
<212> TYPE: DNA
<213> ORGANISM: Cucumis melo

<400> SEQUENCE: 26

```
atggataagg cagagcttac cactaacctt ctaagatatt ttcgtcgctc ggcatttatt     60

cttggaggga accacaccaa ctccaaaata cccatgaaac ataggaaaaa atggttcata    120

gtctaagttt ccatttcgat tcggtttggt tcggtctttt attttaaaaa caataaatat    180

aaacctacta atttgatgat gacaagttta ctaatgttaa gtaagaattc atcaataacct   240

aagaatttgc aagtttttct taagtttgat ggtaaggatt tcgtaatcct tgaaatacaa    300

caattgtata gaaatgaagc gttgcatttt taacgtctat ataggaacac tattttactc    360

caatcaagtt gtaatttgat agataatagt ttgtataact taatgatgaa gagctttttt    420

ttttatatat aatttttatt aatacgtata gttcaaaatt ggaattagct atcactaaca    480

cgtgcttgcg atagaaacaa caataaattc aattagtgtc gcatgtattt catatggtat    540

tgatgacata agagtagttt gatacgatgg gttacatgga gtgacatgat aattgtatta    600

aatttcaata gttatgatct caagtttggg ttgtgtctca ctttgagctt tttgagaaat    660
```

```
tggcctcaag actcgcctaa tttaatgttg cttcaagcta tagatgctta catcgtgtgt    720
atgaaacata ttgcactttg atgcttaaag ttaatatagt gagtaactaa ccagatatta    780
cacgctactc ttttaaaatg gtcaaataag aacatttatt agtatgtgat ataacacgta    840
ccctccaatt acatacaata attgatcaac ccaaatcttg aggtatttaa taataacaaa    900
tacaaaatag atggattata tatctgaata gctaaagaat aaagaatatg tgttatgttg    960
tagttacata gtacaataag tcctctcaaa attagaatgg tataataaaa aataagaggt   1020
acattcttaa agaaaatgtt atcaaaactg ttgcatcata ggcattttgg caggaagaat   1080
agtggaagaa aattcttaaa cctaaattct atcgatatta aatagatttt ataagggata   1140
attgcaaatg tagcaattat atttaaaata attaagtata tagcaacatt ttaaaaaaat   1200
ggcaaatata gcaaaatttg tcaaaatcta tcgatgaccg atagatcatg taagtctatc   1260
actgataaac cataggagtt tatcaacgat agaagtctat caccgataaa ttttgttata   1320
tttataattt ttttaaaata ttgctacata gttaataatt attctaaaaa ttgctattac   1380
caccggtttt taaataggac ctaaatttaa ggtatttgac ataaattttg atgaaccaaa   1440
ctagcccaaa tcaaagaagt ttgggcccaa agcccaacga atccacaaca aacaaagccc   1500
acacaacact tcatgaaaat gattttttca aattttagaa aaaggttata aaatataaaa   1560
aaaataatca aactatccct ggtagctaag tagttattat tatttttatg gatacgaatt   1620
gagtagtatt tattttaaaa taggataatt gatcttagtt tcacttgtga tgaactattt   1680
cactttatta tttgtttgta attcaataaa attagggttt gattgtcaat gataattatt   1740
acaacctcaa tattatactc agtaaagaaa aataaaaatt taaaattgag aaattaatac   1800
caattttttt tgtgaaataa aaggaaaagt aagtaaatat tataaaattt tggacttgga   1860
aattaaaatg cattaataat aatatttagt attattgaat taaaatggac accggaaacc   1920
ctaaaagagg gagtggccac ctataaaagg gaagcactca tctcacccaa acccttgtta   1980
ttcccaattg gccgtgcggc aaagaagcct ctcaacc                            2017
```

<210> SEQ ID NO 27
<211> LENGTH: 1353
<212> TYPE: DNA
<213> ORGANISM: Cucumis melo

<400> SEQUENCE: 27

```
tgagggtcaa aggaggagga agaacaagaa gtaaatgaag tggagtcatg ggaaaaggaa     60
aacaaatgtg agaaaagaaa gaaagccaga gagggaacat aaaattatta gtcagaatta    120
caacagaaaa tttctgaaga attgagtttg tatgcagcaa taatatattg aacaaataag    180
gagagaagga ggaggggaaa ttcaataaac agcagaggaa gaagaatggc gaaaacccaa    240
tatctaaaac tagttaattc aacaagaagc aacacaatca tttcattaaa aaaagaaaag    300
gtaaagagaa attcccagat tcgttactct agattggtcc aatggagtgg aaagggatgc    360
aatgaaatca gtaatagaaa agaaaagagt taaagtagta ttggtaggta ccgattaaaa    420
atggaaggcg tcggaaggaa acggagagtt caataaaagg aagattcttt gcttcctccg    480
gccatttgat gagaaacaaa aactccgcac ctccaagttc cttccggggg aaggagaaga    540
ctcttctatt ctggggtaca caccctccct tcctgctaca gaatcaaatc taaattattt    600
tggattggaa tggcatggga ttggtctaac ttccaatttc tcgacacaca accccaatct    660
acccgccacc tgtacccagt tttcccaaaa cgcaactcac attgcaattg caattcttgt    720
```

```
ctttaataaa tacaaattga tttttctttt tcttttttttt ttttttttaat aacgattaac    780

cctaaaaaaa ataaagaaaa gaaagccgat cctaaaagta gaattacttt ttttttgttt    840

ttcaaggttc acgtctgtgt ttgcatagac gtgttgtagt cggtgggtgt gtaaattaga    900

gtttgttttt ctcatctctt gttcttttta acgaaatttc aaagatacaa aagcataatg    960

aagaaaagta tacaaagcaa cgtaaactta gcattttgca catgatacaa atttagtcaa   1020

actcaaaccc tggacaacct agcactctct tgggcacgtg gtagatttat gtgaatttcc   1080

ctatttttct tttgaactca caaatgggca aataataata ataaaattta ttgttgattt   1140

ttcttatatt tcaatttatt acctctagtt ttaacctaaa gtttagatgt atataattat   1200

aaatgagcgg tgaaacgggc actgattgat gaatatattg ggccttgggt tggcccaaca   1260

aacctaatgc ccaaatataa aactttggca accatagtta accctaatct gtcaatctac   1320

tctcctcgac tcggtaaacc tgcgactccc aca                                 1353
```

<210> SEQ ID NO 28
<211> LENGTH: 2005
<212> TYPE: DNA
<213> ORGANISM: Cucumis melo

<400> SEQUENCE: 28

```
cagtgtgctg gaattcgccc ttatccaagg agattaatgt cgagagatta ttatcgaggt     60

ttgaatttat tttgtccaat catatgattc caagagctga ccatcaattc aacagaacat    120

gaaccggaac ctcataccta ttgtaatggt tcacagcatc ctaatacaga acatgaaccg    180

aaacctctta cccattgtaa tggttcacag catctttata cgtattatag gtagtaccat    240

tgaagatgca tttaaatgct gtccatgctc tgttctctaa aaagttggac ttggacttgg    300

acgtcagctg aaagtatgaa atgcactgta gccaacgaag ctatgttttc aggcttcaac    360

atggttttag gaaagtggag gctctttggt tgaagggttg aatgaatgct tttctaattc    420

cagcatgatc ttcaaatttc gacacaaaaa gcttaagtat tttgttccgt tattctttta    480

atccttgtat tgttatatat tcttttctct gaactgaatg tacgatgatt gcaggggtcg    540

agagcaagtc cgatataatg aaacacgtaa ggacgtgatt gaatgaaaaa ctatgagcag    600

agatacaaag tctaacttac gggatgaacg atgagaggtt tgaccaagag ctgtgacgcc    660

tgtatatttc aacaaaagtt gatgactaac atcacatgtc agagtaatca aagaaatgca    720

gccgcacata tatatatcta tatatatatc gtttagtttt tttttttttt tttttatttt    780

ttttttatc taattatatt ttaattctat tttcctctgc cctcctcccc ctcctcttcc    840

cccacccttc ttctgcacat agtagccaag gattgatcgg tttcttttga ttcgggggga    900

aaatgttgta caatttttgc ttccatagaa gcttgaaagt tttgcagatt atgttgtaaa    960

attacccttg tgtactcaca ctagttcttc tcgtggaaac ttatattaca atggttgagt   1020

tttaaggggc atattcacac tggtaactac cattttctaa tttatgaatg ccgagtttct   1080

ctccatgaaa gacctttcaa atgccctttc ctccgcggtg cgtttgttgt tgtaaatgtg   1140

cagtgtcgtt ggatacacga ttgtgtgaaa gggaaaaggg aatacgatta actcttaaat   1200

tcaaccccta tctccatcag tatcaatcac atttcagcaa ctagctcttg aataacattg   1260

agattcttgt ttaatccacg tactactact actattacta ctatttgaca gccgatatct   1320

caaataacat ccatatttat caaattggta ttttaaggac ttttaatttc ttcgtacata   1380

tttcattata atttaactac tctgaccatc attgaaaatt tcacaaagaa gacattttaa   1440

attgaattga gttgaattaa gttgatataa tggttgaacg ttggatttaa tttataattt   1500
```

```
agtggtgtat gggtccattg taataattct taaaaaaaat atcatattct gaattctaaa   1560
gaaccatcta agaccaaaac taaggggtca ccaatgagta tggtaaagtc aacaaagttt   1620
gtctactttt cttatcctta tcatcaagag tgcaatatga tatcaaagat aaattgtacg   1680
tgggcgtcat ccattgggta agaccaagaa gcaaaatatc atagagaagt tgttttagta   1740
gccataggaa ggaaggaagc aaaataataa tatagatttg aaattgtgga tgataaactg   1800
ccaaatggga attcaaaata aactaaataa ataaaataaa aagagaaatc ttgggagttt   1860
ccattttagc caatgaggaa acagatagag atctcatcaa gataaggacc ctattctctt   1920
cttcatctat aaaacaaaaa caaatcaaac cctcatttca ctcattcaaa acaaaaagta   1980
ctccaaagtc aaactaacaa atacg                                        2005
```

<210> SEQ ID NO 29
<211> LENGTH: 1445
<212> TYPE: DNA
<213> ORGANISM: Cucumis melo

<400> SEQUENCE: 29

```
tcccttcagc cacttaacac ttaaaaatct taggaaactc cattggctcc tctttctcca     60
atgaaatttt gacatctgtg ttgttgatag ctcctatatc ctttgagaat ttgatataca    120
cctgtcattt gctgatttgt ggataactgt tagccttttg atattgatac gttccttttt    180
tatgaatttt tgtaaatcca ttcaatttta atgctgtcgt aaatgaaaag ccctttcatt    240
aatgttgttt atatacatat tttaaaatta attcaataac aagtttagtt ctgttagctt    300
ctaggtttgt atctatttta tctattaaag gtatgtttgg gcttcaggtt ggaatggagt    360
agaattgaat gggttgggga gtaaattttc cattcaacaa gttcaatttc aaaatggcta    420
ataagttttg aactcaattt tattttcaat aaattcctta attttttgtt ccttgtttgt    480
aaactattga cttattcgat atattttaaa attgaggtat tttaaaaaaa taatacaata    540
ttaaaattat ttataaaata taacaaaatt tatgtatagt ttatttgaaa attttactat    600
agtttcattt ttatattatt cctaaccatt tccatttaaa attatttcaa ttatttcttt    660
tattaatata attgaaattt catggattta ttagacacat gatttgaaat tttatgggtt    720
tattaagtat tttctaacac aaaatcgctt ccgcatcgtt ttcaattcat tcagtaatag    780
aagtaatttt ttaaaagaac caaatttgcc aaattttgag ttccataagg actctgaaaa    840
ctcattatgt ctattactct tcactaattg tagagactta aattcaagat aagagacact    900
aattgatgat aattgcccaa aaaataaaaa taaaaatgtt tcttccccat cctcaacctc    960
catgaattca cagagcccaa agattaatta ttgggcccca attcctactc atatatacct   1020
tacagtccct caaagaaatc ttaggaagta atcaatttct gtttattcaa gatgtagcct   1080
cccaaaagaa aaatacatca catcaaattc aaacaaaaat atctacagct agcaaaacct   1140
caaaccgtta aaatttcaag ccacataaat gaaattttca tctgaaaaaa ggacaatcta   1200
tctagacgtt agatttcagc cctaatatga atctgaagca tttggtggac gagaaagagc   1260
catgtaggaa tgcatcaaac aaaggaaaaa tctttgaact ccaatgggat tgaagataca   1320
gataccaatg gataagaatc tgttctcttt gcccactatt taaactcacc aaacccacca   1380
gtatcttcct caccacaaaa tacattccac cgttgatcac aagccttatt ccaccacctc   1440
caaca                                                              1445
```

<210> SEQ ID NO 30

<211> LENGTH: 1282
<212> TYPE: DNA
<213> ORGANISM: Cucumis melo

<400> SEQUENCE: 30

```
tgcaattaag aataagctaa tcttaatgaa gaaaagaaaa tgttctttgt atttgataaa     60

tggtggcgtt ttgggggact ttatatgctt tttttttccc atgagattgg ttatcttcat    120

ttccgtcatg atgtcgccaa gtggcgcttc attgatgata tcttaaaatc tataatgatc    180

atcctctttg ccaatggtgt ggtgacacgt ggaaggactc tccatcttct aaaagattct    240

tcaaataaaa ataaataaat aaagaaaaaa cttgtaagaa gatacatatg tacattttta    300

tatgaaatta atatgagaaa taatcgactt tacagtgact tgatcaaact ttcttatttg    360

tttcatatgt taggttaaat tactaatcaa ttcacgtact ttactagatg agatttcacg    420

tactttactc attgagtcca acggttgatt aacttatttc aagaaaattg attcattcaa    480

ggatgtttcc aactctcata taatttccat gttgttccac ttctatcaag tacaatccta    540

tcgaacacaa gtttgtttaa ctgaagttca ataatcgaga tcaagatagg ccttattatt    600

tcttctagag gttcaagtga tcaatcaaaa aaggtttatc acatgattca ttccaattca    660

actaagctaa taagtggtgt tgcatgatag agtatcggac tagctcgaac ccctatcaat    720

atgataaatg tctatgtata taaataggta cttaacccaa cgaacaatgt gtcttacgtg    780

agaaagcttt tttctaatat acataaaaag cttgcatgac tttttgatga attgtgtttt    840

gataaaacat atttgtgagt atattatctt tataaattta agttataaca acaatgtata    900

ggtgtgagta tgcttttaaa cttaataaaa aaattagaaa aaattacctt tttagtatga    960

aagttttaat gatatatcaa tttgtgtctt tatgatcaaa atgtatactt ttagtctcaa   1020

atgtttataa gaattaactc cttaataatt atcctaaaca atcatgttca aacttggatt   1080

cttattgaca catatttcat tttaatctaa gtttagaaat gaagataatt aggataagga   1140

tctttagctt atgatatctt atccaatatc ttaaataaat cttcaacacc aagaaatttc   1200

cctattgcgg atatttcaat atcgaatgcc ttggagtatc aaaggcattg gataacaagt   1260

gggacataat tgcgataaaa aa                                            1282
```

<210> SEQ ID NO 31
<211> LENGTH: 2002
<212> TYPE: DNA
<213> ORGANISM: Cucumis melo

<400> SEQUENCE: 31

```
ccgtagattg aacttatggc ttcggtcagt tattgagatt ttaattctct ttaacattag     60

gctaatccat gagtttacgt gtgctaacat gttaatatga aaagtatagt agaaaagtaa    120

aataatataa ataaataaat tggattgttt tgaaaagttg aaagattaga atatacataa    180

gattctgaaa tatctcaaat ttttgaccca gcaaactgaa attagccaaa gtaggttgtg    240

ttgtaaataa ttatacttta tattgttctt tttgtataag cttttatgtg tcaatgacaa    300

ttttaacagc taaataattt aaacagaata ttgccaagat gggtggctac aaaaataatt    360

gtaaatagaa cccaataata attagtttaa tcaattatgt ttttattaac ttgtaaatta    420

aatttacact gaaaagttga aagagtttgg aaaatatttt atttgaataa atcaaacaat    480

tgaatactaa tttgcgtaaa atacgtagtt taaaatatat atatatgtat atatatatat    540

atagtgtaat tttcaagtaa taaataaaat gaaaattaaa ggtttaaaaa taagctaatg    600

ggtgcttaaa gtatctacgg aaacgagatt gcattcgact cacgtacgac atgaaaaaga    660
```

```
tataaatgaa ttttacatta aaactattaa attgcacata tgattgtcca acaagtaaga    720

agaatcacaa tcaaagtaaa aagaatcaca atcaaaagag aatgtatcta atggatgatg    780

acaatttact taagatttaa gaattaatct aaaaatttag agagaggggt aaagatatca    840

acttttattt accagaacta aaaattatcc ttaggcctca attgctttag taatggatat    900

atatatatat atatacacat ctacctaaca aagctttaat aatagtaata ataaaaattt    960

aaataataaa taaaagaaat cgaccaatat aaaaacatat aaaaaatgta tagttaaaaa   1020

gaaagagaga aagagagaaa gagagaagag tacatgcaag agatttgatt tggaaggagc   1080

acataatagg acaagagaag ggtaattttg gaatttgggt caattattct tagtccaagg   1140

gttacactac aaaaacctaa cagccttcac aaatttttcc ctctttcgct cgcttcgctt   1200

tgcccaaaca ctcgcctcca actccacgga tcagatccga agagtttggc aaaccctagc   1260

ttcctctctt caatctccat ctttttcttc tctaacaatc cacaggtttg tttttcattc   1320

ctttctcttt cgattttgcc ttcctcttct acttattcga ctgcacgaat atggttgtat   1380

gtatgtttcc gccctctttt catatccctt tttgttcctt tagccttgaa ctactctggg   1440

ttttcttttc ttttttact tttttctatt attgtatatc tcaagatttg acgctaatct   1500

ggtctgtggt tgtgggttga gttcgttttt attcgtttgt ttgtttgttt gtttatggcc   1560

atggcttgta attgcttctg taatctacgt gaatctgttt ttgctttgga acgtttttgt   1620

tgttcaactc atacgagaat cgtcgtctat agttgggttg ggtttttttt ttcagtagca   1680

tcttgctttg ggaaaaggtt aatgcggtgt cttttttttt tttttggaga aaaaaagtta   1740

ttagacatcc ctcaactcct tttcctacat tgagacagaa gtttaatgct tgttttcctc   1800

tttatctgga ttgcaagttt ggcttttctg ttacagattt cctttctcag gatagctttg   1860

aacagatttg taatgttgtt ctgtttattc cttggtgggg ttgataaaat ggttatgatt   1920

ttttgtttgt tggcggcata attctggata tttttatctg tttggtctgt gttcatattt   1980

gcattgtttt ccacttacag ct                                            2002
```

<210> SEQ ID NO 32
<211> LENGTH: 2003
<212> TYPE: DNA
<213> ORGANISM: Cucumis melo

<400> SEQUENCE: 32

```
tggatcgacc atgacattca aaaaccttta agatatggat cttataaaat aaatgtaaag     60

ggtaaacaat tcttccttgc ttaacccaag ctatatattt tatgcactaa tttaggtatt    120

agagtatatt cagctgaaca ccacctacca atgctagtac tttaatcagt caattctaac    180

ttcgataata tatctcaacc aaattagtga aaaagagtcg taaatgaaaa actatgtacc    240

aagatattct atttgttttt tttatgttta aatatctcaa agataatacc taaaacgttt    300

tctcctcgta caaagattcc tcatttactt tttattgtcg taaactctaa tacaataaac    360

taaaacaagt acaaatacac tagctttaga aatctacttt ttattgaaac caaaaccaat    420

aattcaacat ttcattttca ccgacaaacc tttgtaaaca attgaagtaa tttttgttgg    480

tactatgaat agtaacatca agtcttcaag tgcatcatat caaccaagac atgttcttaa    540

aagcgacact aaaagattta aaaccaaaag catttatgaa atccgaactt aatcaaatcc    600

taaatatttt tcacttaaaa aaaaaaaaat aggaagaaaa attgacataa atgggatatt    660

ttcgttttca aactggcaag ccagcatgca ccacgttgtt gacgtgtcct tccacgtcgg    720
```

```
aaaaaaaaat attaccacag taaaaagaga ataaaatgaa agtcgttgac tctcccttag    780

tcggaggaag cgcgtgaagc tgaagccgga ttagaaatcg gcaataaccc cgacacgtca    840

tcgaaatgct agtatcaaat attgtccgtt ggatcttcct tcaccaactc tatttgaacg    900

gccacgatct tccaggtcca acggttcgga agaatctttt cgaaattcca tggctagtcc    960

ctacactcct ccctattggc tccctagggc atcccgaccg gttattccgg ttgccgggaa   1020

ggtggctgga cgctataaat acccgctttg ttcatctcgt agtccttgta ccgttgagct   1080

tcgccttcta atagagctct ggttcggttg gcgtattagc tcgaattctt tctctcttcc   1140

agatctacgc tgccgatttc atcaggtttg cgagctctgt tccaccattt ttcttttcct   1200

gaagctttga gcatgcttgt gattcttcat ttcctcattt ctttgatggt ttatgaaaga   1260

atttagggga attttctctt tttgtattct agtggtactg gtagatttgt ttgaagtttg   1320

tttctcttct tctgagaagt gaattcttcc agatctgaca gttgcttttg atttttttctt  1380

tgggaattag tgaatgatac ttcgatactg ttttttgctc tctgagattc tggatctcgg   1440

gccttggggt tttctattgt cttttggtag ctatgtttcg tttgtcagct tgtatttgtc   1500

attgttgaat ggttcgatcc ggtttgtaaa taaaataaat tttgtaggcg cacttgtttt   1560

ccacggtttt cgtgttacgg tttcatgatt ccctagatct ctggttagaa ctaagttttt   1620

tgtcggtaat tggatttggt aagggactgt tactgtggtt gaattgtaga tccagtcatc   1680

ttctacatga gtgtagggtt ccttagggca gatcttgtgt tttataattt taattttgtt   1740

gtttccctga ttttgaacct gtttggttgt tcagattcgt cgagtcattt ccattcatta   1800

aaagtttcta taattttatt tgaatcttct gaatctgtgc ttgtattacc cagatttcta   1860

taaacctatc ttgatttcaa gtgtgctatg tggtaactgt tgatattttc aagcttaagc   1920

aatactgatg tgactaaaac ttaactaatg aactgaatgt tttttgtaca cgaactaata   1980

tggtgttttg ttatgtttca gag                                           2003
```

<210> SEQ ID NO 33
<211> LENGTH: 1372
<212> TYPE: DNA
<213> ORGANISM: Cucumis melo

<400> SEQUENCE: 33

```
aaataaaacg cggagacaaa cttggacttc cattcccttc ttcttccttt ttcttgtagg     60

aattcttctt tcttccttat aaaattctcg gaccctttt ttttcctttt taattttatt     120

tttccttctg tagttcgttt cttgatttag attttcgaca aaggtacctt ttacaggttt    180

gttccttctc ttcatcgttt actccgattg atgcatttcc tctattttca cttttggatt    240

ggaattatta cgatctatgt tcaatatcgt ttgatccatt ccctagatgg aaattatgtc    300

tctgtaatta tacatagtgt ttgatttgtt tgggaaattt tgtttctttg tgataatgtc    360

ttcatcgatt tgatgatgta tttgtttttt tttttttggt ggaatcgata tgatttatga    420

tttgggtgtt tttttgcttt tgagaattat gatttgatca gagtttttct tattatttct    480

gttgttttgt ttcatttcct gccgttttta aagatgtgtt tagattctgg ttgtttttgt    540

ccttttgatt atgtttttat ttttcatgta gttggaaatc aataggattt cagataattc    600

atttggttgc atagggattt gaggattgga agttcggcac tctataactt tgcagtgaat    660

gatttgggtg aagtttttcc tcttgtttgt gctttcatgc ttcagttgcc tcaaccaata    720

tcgcttttttg gaagtcttga aaatctgtag ctttgagctt gtgtttagtt cgcaactgaa   780

gcttcaagga aaaagtaatt tctttcgatt ttcgtaaaag gggggaaaaa ggaagtaatt    840
```

```
ctactaaaat tttctcctat gaactcgtag gtcacatagt tgttatttgg tcagttgaca    900

ctctagacta tcttgttacc attccacata actcaaaggt tttaagaata aactcaatat    960

gggaatggtt tcattaggat tgcagagtca ggaacaagag aggttgcttt gcacaagtta   1020

catactttct attcttaggg agaaaagcca gttgtcattg ttcagggaga agattaattt   1080

ggttggaaag atttattgtc cttctgtctt taggttgtca ttggtttgtt ataattaaag   1140

tttcttgttt cctagaaaat agaagttttt ccctatgagt aatgttatac ttcattgtct   1200

tttattttgt gacaagcaaa cagtgattta ttggatgaac tacagttaaa ttctgaatcc   1260

attaattttt ctgaaatcca ttgtgattag aatcatgcaa tgccaactga agaaattttc   1320

accaattatt aaatgaatat gtttatttgc agggtgtttt aaatagatca ag           1372
```

<210> SEQ ID NO 34
<211> LENGTH: 1122
<212> TYPE: DNA
<213> ORGANISM: Cucumis melo

<400> SEQUENCE: 34

```
atatatttat tgctagggtt ttccggttcc tgtttgctcc actatttcag ccgcctaggg     60

ttgaaacaac tcattcctcc gatttcagga ttactatctt cctcctcgac cttctccggt    120

aatactttct cttcacaccc cttttgttgt ttgtgatttt taacttcctt tggattgaaa    180

tgcgagatct gtgtgtttct accactcttc tttcttaact tttcgatagt attgcatgtt    240

ccttacttat ggagaggata atgtgtactt agggatatca attttcgttc acagtattca    300

atattcatga cttactgagg tgtgaggagt tttcatttca tagaccgact gatgctatga    360

tctcaagccg agtttgaccc ctgtttttct ttttatattc tttttcttat ttttgtgtca    420

atatattagg tgatcaatga catcctaatc tattattagt gaattgagta ataagaagta    480

aagtcttgtt tatccaattt tttggtttgg atttattact attttgttgg aatgcttgaa    540

tgaattctaa tggagtccgt agaaatttgt ttcaggcgtg cgccttttct tctcactaaa    600

tttttcatta ggaatgggtg tatttatttt caggagaatt tgtcgattgg cgatagttgt    660

cttgttcttt ttcatttcct ttataaattc tttatggaaa aaatgtattt gctgcaacct    720

ctgtcttatt accccctattt gaatcaatag agttcctgat ccttcctacg atgtggtttc    780

tggggatttc tctctgggtt cgtgtgatag atgggtgacc gagggaacac cctttattgg    840

aaatgctcct attcttcaga gtcggtttct cattttctca cctttacgct ttgctgctgc    900

tctcattgac agtcgaaccg ttttggaatt cgtgatattg tgtgtatttt ggggatgaaa    960

gttttcttta ataagactag tgacagttca ttattgattg tggagaaatt tatgaccatc   1020

taattttaat ttgaacaagg gaggatgaaa atgattgggc gcattgcatg ttttatccaa   1080

ctagtactca ttttttcttt gttctgatat tcttcaggaa ca                      1122
```

<210> SEQ ID NO 35
<211> LENGTH: 2017
<212> TYPE: DNA
<213> ORGANISM: Cucumis melo

<400> SEQUENCE: 35

```
actattggag acgacgaagg aaaactctaa tgtgagctta gaattgaaga tggtgaacaa     60

ttgggagtct tttttaaaaa tctttcgtcg gtatattgaa atttcctttt acactcaaat    120

aacccccctt ttcacgcgtt caacgtcttc aaaccttcct ttttcaatta ttttttcgtt    180
```

```
tacattaatg acatttaggt aataagataa attagtggat tcttttgtga aaaatgttag    240
cccatttaag acttttatga aatatattag aaaaaaatca tatagcaatt tatattattc    300
tagttaaaag cccataatag aaactaaccc aacctaaagt aacgtaaaca ttcaataaga    360
gagacaaatt ttaaaataat ttctaattaa aaaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccctactac ggtaagtcga ccttactgct ttcggcttct    600
agtttttca atcctgtcat tagtcctttg gagttcttct gtacatttat gacgttttcg    660
gctcgtgttt tgtttcgcct gtatgtagtg ggtttttcga gttttgtttt tactttttt    720
tatacttgca ggaattagtt gaaatctatg tacttcatgc cttggataat actcttgatc    780
tgttgtgtta ttcaaaaatg aattgtttta agatggtatt tgagaatggt catgtgagtt    840
ttgcctactt ggttattaaa atgaattgtt ttaggatggt atttgagaat ggtcttctgg    900
gtatttggtt ggaacctttg tgctctgcta tgaattaggg tgttctcccc gtttttttt    960
ttttttttct tttggttatt aatatatctt ttatgactac ttattcatat atgatatctt   1020
ttactcgtaa attttgactc atttgaaagt tttatcctta gtcctttctc attcagggtg   1080
taaaggtatg ttgttagggt taaaatagcc tatgcaggaa agttctgtat ttgttctaat   1140
tattgcattt gtgtgcattt gtatctagtt tatttcttgc tgagagtatg cttcattttt   1200
tagtacacat cacttgtgcc actttattat agttgcacat ttttgtttat ggagaggatg   1260
aatagcattt agggatgtca atttttttatt gagaaaaccc tctctcctac ttaagcttgg   1320
ggaatttttg ttctaaatgt ggtaaacata atacttcttc ttattttaat ttgaatggaa   1380
ggggaagacg aatactaata ttttcaacga accttcacaa ctttttttc ttatttagga   1440
agccatgttt ttcaaaattg tactgtgtga tccacatatt tatcgattat tagtgaatcg   1500
aataataatt agagttttat tggtataatt ttgaagttca gacttattac atttgtggaa   1560
agtttggtta caattttcaa ttttattgga atcctaagaa ctttgtgtta acatatattg   1620
agttttcttc tcttttttt tactcattaa gttctctatt aggaatgttt ggttcaatgt   1680
cacatagtcg atagctaaga ccagtgaccc acaaagctat gattgaacga aaaacaagcc   1740
tttcacatct tggtaggaat ttgttatttc tcaatagatt tacagagctg tttcatgtga   1800
tcacaatttt tttctatttt tctgaagttc tctattagga atgggctatc tggttagttg   1860
cttttgagag aacatgtgga ttggtgttgc tcggtttcct tgcctttgta attttgtcct   1920
tggaaaaagc aaaatgatta ggtatcctga tatgcataac atgtttaagc caactagttc   1980
tcactttttt agtgcaaata attgatcttc aggaatc                            2017
```

<210> SEQ ID NO 36
<211> LENGTH: 2000
<212> TYPE: DNA
<213> ORGANISM: Cucumis melo

<400> SEQUENCE: 36

```
aagttgttga ggctttcaat ccaaccaaat aattgtttcg ttttccacta caatttccta     60
gtactaaggt agcaatggat cgatccatag agaaccattt gatttttcac taaaatcaat    120
ggttgctaag taaccaaggg aggattggtt gaattgattc ctaatttcac ttcaataatt    180
aaagcaatgg caataaaaca aaaattggaa gattgttgaa ttaaatttag caatgagata    240
aatacctagg ccaagactta cgtaggttac tttagattca caactcaatt attgattcat    300
```

```
aatgatatta gattccttgc aacatatgaa caaaatctta gttgaccacg tctagagaag    360
ctaatgtgat gttctataaa tcaaatcaat ccttatgtct agattaaaag catcctagag    420
atgaaaatca attggcatta aggtttgagg ctaaagctaa gtcgatcaaa caatttggag    480
ttgtctaatt gattgttcga tgtgatacaa ttctaaacta gttagataaa cgtaattaga    540
atggaattgt caattcaata aatgattcta acttagctta tgttatcttg cagtctaaaa    600
ataacaatta catattagat ctagatctat aacaattaat taaacatgct tggaaaatcg    660
ccaatatttc cgaacacact caatcaaaga aataagtcca aggaaagaat tcattaaatc    720
ttaagattca caggatgaaa atgttcataa catcacacaa gtgtgtgaat caaaagataa    780
gactagaatc tcgagataat agtaccttag ctatgataca tcctcgaaaa catccaacaa    840
aatcaatgaa agtcttgagt caattcgtct agtaaaatac gaagagttca agagaaaatg    900
cctaaaattt agtgccaaaa attgtgtaaa aagtgttggc ggctagggta ataatgcaaa    960
attaagtcac agcaccgcaa caacgtgcaa aacacatgtg ctatactctc gaaaaactct   1020
atagcatcgc agtcaacacg ataccgctac acaacacgtt gtagggctga ggtgtttgca   1080
tgaaattaga ccattctacc ttacagcatc gtgccttctt cgttccattt caattttctt   1140
gccccagttg acacactaaa cctccaatta atctcgttta atataaaaga taattatgat   1200
tttctttatc tacgaacaac attattgtga aaagatataa ggatgatata tcacaatttt   1260
tagggaaaaa aggaaaatat attggcattt attatctcta tcaaatagat gattttacaa   1320
ttatatgtta agatgtttta atccttgcta atgtgaatat ttattttatt tttgttcaca   1380
tgaaacaatg gtattttgta cactccaagt acaatagttt ctttaaaaaa atttaaaatg   1440
atacgtaaat tatctaaatt gacatcttaa ctaagcaaac aaaaatagtt gtttgaaaac   1500
tagacttatt tagtttacaa aaacatgcac cagatatcct cacttaatca ctagctctac   1560
acccaaaata tagactaaat aacttcacat ataatataca aatttaccaa actcaattcg   1620
gcatctcaat tggcgaaaga tctttttaac ccaaaagaag acgttggggc attaactttt   1680
caaaatgaac tttggcttca tagtaggaaa ttgggagtga aacatgaggc tgaaaaaggg   1740
ctaacaaaga gagcgatcgt ccacgtggtt ggcagtcaag aggtctttat agaagaggat   1800
gaagaacttg tttcccattg gtccgaaatc tatccaacac cctcctatta gatttccctt   1860
ccagattctc atcttcatga ttcctacttg gctccattta aacccacaat tcaattcaca   1920
atatctccca cacatcctct tcttcatcat atcataaaac acagtccgtt acatacctga   1980
aatcttccat ctcaaaaacc                                                2000
```

<210> SEQ ID NO 37
<211> LENGTH: 1760
<212> TYPE: DNA
<213> ORGANISM: Cucumis melo
<220> FEATURE:
<221> NAME/KEY: misc_feature
<222> LOCATION: (1)..(1760)
<223> OTHER INFORMATION: n=g, a, t or c.
<220> FEATURE:
<221> NAME/KEY: unsure
<222> LOCATION: (1)..(1760)
<223> OTHER INFORMATION: unsure at all n locations

<400> SEQUENCE: 37

```
ataatgaata gcaaactacg taagttaagt tttggttact caaatttaaa cgacgtaaaa     60
aaaagaagaa gaaaagaaaa aatacgatgg aaagaaatca cagagaaaaa aagaaaggaa    120
```

```
aaaaagaaag acgatggaaa gattaaacga cgtatagaaa gaagaagaaa agaagaaann    180

nnnnnnnnnn nnnnngcagc gaaaaaaaaa gaggaaaaca ataaagatga caaaagaaat    240

cggagcgaag agaagaaaaa gatggaagaa taaacttgaa ttggacaaat tttatggact    300

ttttacatag acactaattt ggtttttttg ttagcttcct acaaattttc ctcttttatt    360

ttatttttgt aaaagtaaat aaatatgtgt cattagtcta attttttgaa cttattttgg    420

gagagataga ggaagacttt aaaaaattat tattactctc cattttaatt ttgagaagag    480

attgtgttgt accattcctc ttattgcttc caatttcttt gagggcagcc ctagcctttg    540

tacaacgcaa gcttcctgta gtatctctat ctctctctct ccctcttccg acggtgatct    600

cttttctctc tctcacattc atcacccgcc gccgccggta gcttctcttt ctctgacgcc    660

accgccgccg gtaatctctc actcgtcgct ctcaacacag agaaatttct gattgagcat    720

caccaggtcc ggcaactaac attccttgct tctgcatctc tttttcttca atttctggta    780

tagttttgat ggatggattg tgtgtattca atcatttatt gtgttttgat ggatgaaccc    840

gtttattatt ctttttttatg acttcaagta attgcaactg ggtacttcta tctgcaactt    900

cttggctgaa gtaattttta gttaagtgca aacggacggg ctgggaccga gccaatctaa    960

cgcttatttt atcgaatttt gaggagttgg ttttgtttgg gtttatagct taggaagggt   1020

ttttggtttc gaagaaccta ccatttgaag ggttgggtct aaaatgtcgc ttaattcgac   1080

ccaatatgac tctgaatgtt aaatattgaa tagaaaagaa atgaaatact atccctaacc   1140

tgtctgccaa tttcgtgcaa aaaagcctaa tagccagttt tttctcgccg gcagtacatt   1200

cgccttcccc ttccaagcgc tacggactgt tgctcaatct ccagaatctc tcaattcgca   1260

gggggcaagt tctttccatc aatcatttta tgtatttttg cttctgccct agatcgttca   1320

tctaaagttc tttacctttt tcttctgttt tgtttttttgg tgtataactt atttgatggt   1380

gatggattat gattcagtat cattttctta ttttatatca gcaacaaatt tggatttgaa   1440

atcatttttt aaataccttt tgatgttaag ggtttaggct tattattatg attcagagtc   1500

attttctacg tgttaaatta gtttactttc caagtatgca gttatgttca agcagttatg   1560

cagtcatttt ctgatgtggg agatagtgct gttttcctta aatgttttct atttaaacca   1620

ttgtgcgctt ggttggtggc cgtgcagata attgcatttc tttttttgga ttggggcagg   1680

ttggttactc tctggtttaa ctttcacaaa gaaccaagac agacatccgt aacttgtttg   1740

cataaagaca ttcaaccaag                                                1760
```

<210> SEQ ID NO 38
<211> LENGTH: 1767
<212> TYPE: DNA
<213> ORGANISM: Cucumis melo
<220> FEATURE:
<221> NAME/KEY: misc_feature
<222> LOCATION: (1)..(1767)
<223> OTHER INFORMATION: n=g, a, t or c.
<220> FEATURE:
<221> NAME/KEY: unsure
<222> LOCATION: (1)..(1767)
<223> OTHER INFORMATION: unsure at all n locations

<400> SEQUENCE: 38

```
aatataaata aatctcatta ctctttatga gctagaaagg atgcctaatg gacctacaga     60

ctagaagcta caacgatatg agattaattg gctaaactca ttaaccacat tatgatatat    120

ttgttaactg tgtgtacact ccactaaaga ctcgcagctg aactcttctc actgtagata    180

tatttatgtg tccacggata tagaccaata ccaataagtt agtccttcac aagtgttcat    240
```

```
aacactagct gggtcaaatt actgttttcc ccttgggtta cttctagtcc ttaaatacca    300
atgctcctct aatgaacaac ctgtttaatg tccaaccact aaacagaatc ctttctcatg    360
ccatagagag ggtaagacct tcaagtcctg gatacaccat ttaaaggagc gcttatctat    420
ttaccataaa gtcaagaagg agtgaattcc atcttnnnng attatgttcc cagctcccca    480
cccggttttg tcctcaaaat gataaatata ttgagttgac aatctgacca ctctcacccg    540
tacaaatcaa aagacaatcc ctcgcgaata ggagttcata atatactcat aattaagact    600
aagttatcca tgtcattcta atgaaataga aacccaacta gttaatggag ttacatcttg    660
tggttactat ttcgtggtcg ggtcttatgc aaactcatta catacgatac cctcactcgc    720
atgtcgctta cttgaacatg ttgaataaat gcatttatat tagatacaaa gtaagtcgta    780
tccatagtgt taccaggata agttacctag ccttaaccct atactataga cnnnttaagc    840
tgatcttgaa cattgtttcc tgtatgtctc tacatactgt tcaagactca tcaaacaact    900
caagatgtta atttattgga tttaggttat taagataaaa cgaataatat aattaataac    960
acttcttgaa attataataa tataacactt tattaataac taccaatgaa ttatatttac   1020
tatatacgag ttttaagaca taaaatccaa tataagggtg tatgaactgt taaagatgat   1080
gtgctattct tgttggatat tataggaggt atttagtgga ttatttgtga aagaataagg   1140
aggtacttat gggaagactg ctggaggtta gggaggatct ttgaaaatta ggaagtaggg   1200
atcaacaaaa aaaacgaaag ggaaagctta aagcttaaaa aagaaacgaa ataaagaaaa   1260
atgatttaga ccagcatact aaaatggcaa tgtaatctga ggctaatgta tcaattgaga   1320
actttgtagt cataatgatt aatcccaaac aaattagttt tcaagaaatc aaccccaaat   1380
aaaatgactt aaatattgaa gagtttaaat ggtctaaaat tattgttact gttttttatt   1440
tttggaaaag agacgaaaaa ggaaaaataa gaaacgccca ccgtggggct cgaacccacg   1500
accacaaggt taagagcctt gcgctctacc gactgagcta gacgggcttg gtgtccaaaa   1560
atccaataat attgaaaata ccatatagtt taatgaactg ggcaattgga ataggcccaa   1620
tatattagat atagcgaccc aattgttagg cgtgtcttct tccaaaaatt ggaggcaaaa   1680
cacaaaccct agcatccgct tctgctcctt tatcgtttct ctcggcgatc aattttcacg   1740
gagctaggtt taatcaagct tcaagca                                       1767
```

<210> SEQ ID NO 39
<211> LENGTH: 2000
<212> TYPE: DNA
<213> ORGANISM: Cucumis melo

<400> SEQUENCE: 39

```
tttaaataaa aataaaaacc atctctttat tttaagtagt taaatgattg tcgtttacta     60
aattaactct agcctatttt aagacggtct ggtcaaaaaa tcgattacga ccgaccaata    120
ttcatctaac ggtcttatta tttttaaaag atatagaaat gtatctcgtt aataaagcca    180
cgacggtctt tttctaataa aaattcaact aaaccatata acaaaattat tgtaccatga    240
aaaacacttt catacataat gcaaaacaac aatagcaaaa aaccaaagag gaaggggaca    300
atttggggaa aagtaatctc aaatttccct ttttgacttt gttctaaatt agtttattga    360
aataaaatct actaatttcc catttccaaa ttaaaatgct taatctttgt ctcattagca    420
ttgctagaac aaattgtctt ctcaaaataa aaataaaaat acaatatcaa ctatttatac    480
ttaattatct aacatttctc caacataaaa agagttatat atatatccta ttttgttctc    540
```

```
taatttttcc tctttttttg gtaattaatt ataatattgt cctaacatat tatattagat    600
agcttcgaca aaccgttgct taaaaaaaga aaagagaaat ccaacctaac tcaatccgaa    660
aatatacaaa gtacaaaata attataataa ggtagatggt atatgcatca atgaaataat    720
attgtcaact ttcctcgatg atgatggtaa taataataat aattttatat ttattaggcg    780
taatattttc ctcaatttta gtgtttgtat atactttcat atgtttaatt taagttttaa    840
aatttagtcc ctcaattaac ttgaaattaa ttaaagaatg tgaaaatgtt aatgggtgaa    900
ataaataatt tagagaaaaa ccaaaataaa ttagaggtag ggagtaattt tagaagttca    960
aaaaaaaaaa aaaaataaat tagatgtttg aaagtacaga tttgtttaaa tatgaaccaa   1020
cttcgaatag tctttccatt ttttcttata aaaagtcttt ctgatgtgga tactagttag   1080
agtatcctat caactcatcg atccaaagaa catactttca atcgtaagtc gtccattcta   1140
cttcgatcta aaatgatgct aggtttgctt caccttcacc cttcacaaag acaagtgcag   1200
gtgtgcttcg ctctatcaca tgattttgat tatgtcttca agaacttcac agcggtttta   1260
aaaaaacaag aaagaaaaga gtgagagtgt ttttatgtca gaaacatatg cccaagctta   1320
tgaaacttgt tgatcttgta gcgattgaat aacaaatgga aagtatctca tacaatttct   1380
ctatttttca cttttatcga agaactttgt ctcactaact cgtaatctaa aatacaaact   1440
cttcgactct aatatattaa ctccaaactt catttttcac atctatggaa cagataaagg   1500
tctaattttt taaaaatatg atgggaatta aagtatagta aagagattag cttcatcaat   1560
gggcttggat tggagtccaa agggttagcc caaacccaaa acatagtaaa tccaagccct   1620
ggaacaatga atagcacgga aagtttgtgc tgccggagga gcgtattgga aatgaagggt   1680
ttaggatagt tatggagcag aaaacgacac cgcatcatta aggacggatt tgggatttta   1740
agaatatatt agggacagaa taggaatttg aaaagtagcc ctagccactc aatttggtaa   1800
cagtagcaca aaaattggag gatacctaag gtaagcgaca tggggtaata cacagaattg   1860
tggctatggc agaattggat agaactccca tttgaggctc tcttttctct taccatttct   1920
acaagataac actactcttc ttcactctcc aaaaccccat cttcttcttc ttctcttagg   1980
ttcctctctc ccttcctcca                                               2000
```

<210> SEQ ID NO 40
<211> LENGTH: 2000
<212> TYPE: DNA
<213> ORGANISM: Cucumis melo

<400> SEQUENCE: 40

```
aattggaacc tgctgatatg aaatgcataa gagaactgaa cctatcagta tcatgcgaaa     60
cctgcagcat agacatacta ccgtgatgtt tcaatttttc aagcaaacaa aatatccaaa    120
aacacacaaa atagaggaaa ataaggcgaa attacaaacc tctctaggat tttcaagatc    180
ttccatattc ctctcagatc cgggtgtaaa gacaaccagt tcgaagttcc aaagctgttg    240
caatactact tgtctaaacg tcatagcaag tatatttttg gacgaggtac ttgaatggaa    300
atcttgagcg agagactttc tgagcttcgt ggccttttcc ttgacttctc tggcaggtaa    360
aaactgttaa cacagtcaac ttaggaatga caaatacaat cggatagcta aattttatct    420
aacgacaata ttccagagag gggagagaga cacattgttt tataacaaga ctcccaattt    480
catgagatga caacatcgca cgacagtcaa acaaaattct aagagaacat caaataatac    540
tagaaacgga catattagtg aaggagctct taaaggtagc cttgaaccag agatgggaac    600
gccatcaaat caatctcatt catcaatcat ggagttaatt gttccgatgg tggaattcaa    660
```

```
aatcggtcat agatttttat tttaagaata aaaattaaaa tggaggctcc tgaagctaac    720

atgccaggtg caaaagtttg ggagaacgcg ttcacgtcaa cattcgaatt cagtctcata    780

aatggaaatt gtagcaatga cgaaaaatat tcatagttgt tagtcacgga aatcggttcc    840

ataatacacc accgtcgaat gcgagctaaa acgagcacca aattacgcag tcaggttaaa    900

aaataactaa ccagccgggt cgagacagtg ctgtgttcat cagaaattcc cggaaataca    960

gtctccacaa ccattgcagg catcccagaa tcaaggtgct cagtggcggt ttcaccgcca   1020

tcagccgcag ccgcagtaac agactgccgg aaatcgacgc ctccgaccag agaaagccga   1080

gacaagtcat tctcgtacgt ccggacacag ggaagaatct tctcatcgga ctccagcaca   1140

gcttgaagaa cctcttcctc ggtcgtcgga attggcctcc cagcagagca agagaaggta   1200

gaaaagcaat gccttgagtt tttcagaaca attttgggag tataaattaa gggtatagca   1260

aacagttggc gagctggtat agcctgtata ggagaataat ggataaaaga caaactcaac   1320

gccattggag aaatggccat aaacctctga gcgagtgcta gggttttcgt tttatagtgc   1380

tactagctgt gcgtcgccgg agaagcgatg tctcgtgccc acatcttttt ccctccattt   1440

cttttcgggg ttatttctct atataccctc ccaaaatatt acaattaaaa cagttccatt   1500

ttgttttaaa aaaataataa aaatttattt ctcaataatt ttttttgaaa attgaccgtc   1560

aatttcgtac aatctacttt taaagaaatg attacttcat ggatggtttc taaagggaat   1620

ccaaaattta aaagtttaat taatttagat tatgttttat ataacattga ttaaatgaaa   1680

tatgaaataa ggtgtaagtt gatattagcc ctaatatcaa agatgagggt aaaagtaaaa   1740

taatagtgaa aagatatcca actgattctt gggtaccggt tcgggtaggg tttgggggaa   1800

tccggttggc gttttttgag cacagagaga tgtaaacggg acgggaagaa ataaaggcca   1860

acacaactat aaattctcct ctcggcggaa aggcggagca gcgtccaact tcgcctttca   1920

caaaatttac taagaggggg cttccattct acgtcgattc tgctcctctt ctactttttc   1980

ccttctgctt tttgtcgacg                                               2000
```

<210> SEQ ID NO 41
<211> LENGTH: 2000
<212> TYPE: DNA
<213> ORGANISM: Cucumis melo

<400> SEQUENCE: 41

```
ggtctcagac ccataggaat agatcattta ttgccttatg aattagttta tgagtacata     60

ataattgtca accgtataca aatcaacatg aaagaatata atgttgtaca tagtcattcc    120

aagtttacta atattatatt ttaggagtgt tctacaccga acctgtcaca tgtacactgg    180

gtatgctacc cctgaattca atatcataaa gcaactttaa ttgtcaagca ttctcttgac    240

catttgtgac ccatttgctc ctactttttc aatcaataac tatcacaaaa agctagatac    300

cacatgtgat aaactcactg aaatcaggta tatggttacc tgtgcttggt cagcactcaa    360

tcagattcga aggcctagtc tttgtatttc ccccctctg cacactacaa atagtcctcc    420

acgtaaagac ccataacaaa acgcaaacca agtacagaaa atctagccga aatccagacc    480

actcaaacat aacaaatctt ctggtaagtt tgaataaaat ataaaactaa cctaatttaa    540

tcaaataata caataaaatg gaagcaacta acataacata tctaaatatg atcacgtagt    600

aggaaaaaaa aaaacattcc aaaactatta acaatcattc ttaatggtat gggtcaatcc    660

ccattattta ggactataac aagaattcct catacctaat gccacatcct atgtccaacc    720
```

```
ctcgagatta cctcgtgagt aatcaatctt attcatcctt atttcaaatt atgtgaaatt    780
tctcatcagg ttgatcatat tgactttcaa tacaacttat gattaatctt tcccttgata    840
taatttcgta tgaaaaggaa gttgacatta tgtgattttc tcataaggta aaccaagtaa    900
acttgacatg acgtcttaac aagtcttggt ttctaagtgt aatttactgc agaaaaaatc    960
ctaaattcta tgacttttcc tatgagattg accaaatcaa ctttacgaga aatcttggga   1020
agccatacct acaaagtctt cccccaagaa attacaattt ctagtaaaga ttgttgaaat   1080
ttaccctcca atttttccgt gaaatttgac aaacttgtaa gaatatcaaa tttgggttgg   1140
atattgacat tccaaaataa gtagttttaa aaaggattta tccaacaata atagaagaaa   1200
aaagatagga aataacatac ccacgtaaat ggaatgtaaa tatttatata ttaggtgtct   1260
tgaacgaccg tcaaacgaaa ataaattgtt catccgaagt tgaaactctt taagtgtaca   1320
tttatctttt cgtaagaata aaatgtaaaa ttaacgtgtg aaaggttggg ttaaataagt   1380
tatgtagaga taatattgaa gatgatagaa taatcacgat cgatgaatta gtatagtccc   1440
agagcggatt taaacctctc tcactttcat gctttctata tatatcaaaa taatttcaag   1500
tagttggttt agtcgtaaaa aagtcaacca atctctttta gataaacctt gagttattaa   1560
aaaattagat caaagataat cgttgaaatt gaaattttaa gagtataatt ataacaaatt   1620
ggaaagttct aaagtagttt ttgcaatatt ctccatcaaa atagagtaga aaaatatttt   1680
agtaattttc ttatcttaat tttagttttg taatagttat taggatggtc ctaagttctc   1740
aatccgcttt tagtccataa aaagaaagaa gagagagaaa aaaagtcccc gatccgcgac   1800
acataccaat ccaaccaatt atgcacaatc catgtgatat cgaacggtca caagaataaa   1860
tgctttctac acacggatca ccatccaacg gcttttcctt ccatctcatc ctctatataa   1920
tctaccaact ctgtcatctt cgacacactt caattatctc agcttttatt tcatcggatt   1980
ttccatcaaa caaggcaaca                                                2000
```

<210> SEQ ID NO 42
<211> LENGTH: 2000
<212> TYPE: DNA
<213> ORGANISM: Cucumis melo

<400> SEQUENCE: 42

```
actccattat ttggtttgat taaagcttcc atctgattaa taaataataa taattataaa     60
ataaaaaaaa gcgagagttc cattaagtaa tattatctac cgaaagagag caactatcac    120
ctcaaacttc aaaaagataa aatagagacg aaacttgacc aagtcaaaca caaaccacaa    180
acaaccgatc tgacagaaag tttgccagaa tcttcaatgt acacgcgaag ataaacaaat    240
aattaaatct cgttcgtctg gataacataa cacagcaaat gaattttttt aatacatatt    300
ttaaaaaaga aatttaaaat tggtagattt tataaatcat ttccaaaggg tttttcttgt    360
tttaaaatgt ttttttgttt aaaataggca gttcatcacc acttgagaag atccaaactg    420
ggcggcaccg gttctgcgac gcttgagggc cgtctccgac tcttcgccgt aggaggccga    480
tttacgcaaa gaataaccgg acaatgttgg acagttttga cgagaagtta aaccgagtaa    540
gggcttatgc ttcttctcaa tgcgctcgtc gtcgtcgtcg gcgacggcgg cagcggtgat    600
ggggacttgc tctgttgcgg ggtgaacatt gggattccga caagaaggtg ggttcttagg    660
gttggaggga aagtggaaag cgttatgggg ttcttgatgc tgttcctgca acttttgctg    720
tttgaggaag cgcttttgga gatctaaaag agaagggcga cccttttttct tcttcttctt    780
catggtggat ttagaaacct cgcccattgt tcttcttccc tttctcgcag gaacgaagcg    840
```

cagggaggtt aattgatttc agttttcacg gcggagggtg caggatttct aggcacgtgc 900
gaatcgcatg accctatcac gtgcgaatca gtgacggtat aacgtgcatg caaaggaata 960
gaaacacaaa ccgctcttac aattataaaa ctctaaacta aactacgaac gcatctcata 1020
atgggcccac tccatcatcc tatgggcctt ttgaatttta tgtatactat tttttttttt 1080
tttttttttt tctttaatca caatcaattt ttctggtatt tttttaaata ttcaacaaac 1140
tttttgtttt aatgttgtgt atatctaatt aatttagttt tattggatgt cattttttct 1200
atttttgaaa aaactcttaa aaaaaatata aacaaaaaaa gaatggaaaa agaatatcaa 1260
acaaagagag gagagagcaa ccatacctaa aaagtttgaa agtaaaattg aaaaaaagaa 1320
tatacattga gggcagtgtt gaaaatgaaa ttaatgaaaa aggaaagggt acgtaacaat 1380
aaattacatt ttcttgcagg cttaaacgaa ggcccatata tgaaaaggga agcttcgatt 1440
tgggttcagt tatgcgggcc tggggttggt attgggctta attttataaa gaaggcccaa 1500
atgttggaaa gacgggcttt gagagagggt gttcggcttt tgcccgaggg gggtggggga 1560
gtggcaccgc caagcgaaga caacgaatat taggagagaa aacacaaaga ggcggagaga 1620
tggaagagaa tgaggtggac caatgagata agagtgcgca gattattgag gtggcaataa 1680
atttagaatc ccgcctaaat cccagctttc atttcatgcg caattgaatt tcaatttgcc 1740
attcccctcc atagggactt aattatcccc tttttttac tctcataact ccctctcttc 1800
ccaccacgtt cgcttcttcc tccccttcc tcttcaaacc ctaaacctaa cctaacctaa 1860
cctccttccc caacttcttc cgtcggtacg tttcatccat ctcctcccac ttttcatctt 1920
tttttccttc taatttcatc tcttttcttt gtttttcctt ccaattgttg ctgatcccat 1980
actatactgc aggattcgaa 2000

<210> SEQ ID NO 43
<211> LENGTH: 1115
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(1115)
<223> OTHER INFORMATION: unsure at all n locations

<400> SEQUENCE: 43
aaagaaatca aagcgaaaaa acgaggagga aaagaagaaa aacgannnnn nnnnnnnnnn 60
acataaataa agaatagaaa aataaggaag atgaggaaag aaatcgcaga aaagaaaaag 120
agaaaagaat aaagacaaaa ttgcagggaa agatggagaa gatgaaataa taggaagaag 180
acgaatcgcg agaagaaaat aaagatgaga gggcaaacct gaaatattta aaaaattgct 240
aactttatgg gttttgttac acgggccgta aatagttttg ttacatttat gtaaatttac 300
aatcaattaa ttatacaatt aatcaaattt ccacaaatac aataattgga tattttccca 360
aaatatctaa taagtttcaa tttctaccca tcaaatattt caaccattat taacaccaaa 420
aaattcaaag attaaactta agataattac aaanaaatta ccttaaattt ggggcattac 480
acatttacat tgaactatac aattgtttac cataatcaaa acgatcgttt ttttatgatc 540
gacatgataa tttcctatga tcaacacgat tttttatcat atcaacacct tcatttaaat 600
ttgaagtttt tttcccatcg ttaaaaagaa gtacacgatc ttttagaaga agattacttg 660

```
cgcgggctga ttaatcgtct gttgactgtg acatttttta tatttttcat catgagcctg    720
tatgtctttt ttgtttttat aattgtttta catcgtgtaa atagtttgcc gattagttat    780
atttgttaga aaacactttt tcaaatgtcg aaaatttgat tttgatttat taaaacttta    840
gtaaaggata gtgtttatta cgtatagaat cccaaatttt cacaataatt tttcaaaagt    900
aatccaaaag aaaaaagcaa caataataaa aggctcaaag cgacgtcgtt tagggcaaca    960
gctggggaga agaggacgat ctgaaaaatc atttcttgag cgaagggaaa aggagctcta   1020
ctaaagcagt cgaaaaaaga aaactcaaac ctcgctgcga ctctcgacat tgattctgtt   1080
ttcaattcat tttgccaaag ttaatcgatc cgaac                              1115
```

<210> SEQ ID NO 44
<211> LENGTH: 2000
<212> TYPE: DNA
<213> ORGANISM: Cucumis melo

<400> SEQUENCE: 44

```
tatagtttgt aacaatctac tctatgttct ttcaattttg atacatttga atcttaaact     60
ttattgagtt acacaatata gtccttgtat tttaaaattt ataatgactc tatttatatt    120
aatattatag aaatttttgt taaggtttaa taaaaatttt tctgtataaa taaatcgaac    180
acgaagtcta tatttagact gcaatatagt aaaacctgac atctaagttt ggtgaatttt    240
gttttgcttt aaaaactaaa ctattacaat tttaaaaata ttttaattta gttaatgcac    300
attaacttta cggagtaaat ttttacaaga ttgaatatac atagattaaa tagttataaa    360
accaaagatt agagtaaaaa catttaaata gaaagaacta agattttttt aaaacgaaaa    420
tgatactaga tacatatata tgtatctata ttataattac tcattttaac atatagtttt    480
gaaagaacaa agattagttg catgtgttga ttgtttttaa gaaggaaata atttttgaat    540
ggaaaatttt caaaagtttt aaatttgaca ataaactcat atttaaagtg tactacaaat    600
tttaactttt ggttaaactc cttgtttagt tcaatcatgt aataaattct cattccaaga    660
atcgttttag aaaattttat tgtgcattta ataaaatata gaacatatat ggcatataaa    720
aattgattac ttttttcttt ttttgggacg aaaaacacat tagatataat cttttttgaa    780
agtttatgaa ctttaaaaat gggttatttt atacggtggt caactttatt ttattgaaat    840
tattgagttt ataaagattg ttatatcatt ttcttcttct ctttcactag aatacaatca    900
aacctatcaa actctctatg acttatttag aattcttttt gttatatttt tgaaattaat    960
aaatgaaaag cttagagtct aaattataac aattaaaatt gaaaattttg caataatttt   1020
atttttagca aaatgacgtt tggtttttgg ggattgggaa tggatcgata ctatcccgat   1080
tccggacaaa gaaaccgacc cgagattcga atttttttcca ttcccaaaca gagcacttaa   1140
aatttaagca acgttataac ggcgtcaccg aactaaacgg aaaaatatga agaaaattag   1200
aaaaagaaaa acggaacagt caaacgttac ttcacgtcaa tggcaatatt catttttttt   1260
tttgtttaaa taattgaatt taattaattt ggtttataaa aatagagtcc tcatatatcg   1320
cgaatgcgca tttgatcgtg aaggacagct tctcccttgt gttcaagaga gagagatcta   1380
tcattcttat ttggggccga tctctctatt ctcctctctt ctattccgta agtttttctc   1440
attcattctc ctctctcatt tctctccgag atctgtttac aatccttttg attttcattt   1500
ttcctgcttc gatctgtgct cctggtgatt ccccttttcct gttttatctt ttgttgatct   1560
tggaattgat tgttcttttg tgggttttca ttgatttgta ttttctgatc tgggtttctg   1620
ttttctcgcc ttgatgtttt gtatttggat ctgatctgac gtacccttttt tttttttttt   1680
```

```
tatttgaatt gcttttccaa tgtttatacc tggattttta ttgatgcatg ggtttaaccg   1740

attggttgga tgcgttttct ttgtgctgga tctaggtgtc cttgttttta atttgaattg   1800

tgggtaaaaa tggcattatt gtaatgtgtt tggagtttga ttttgaatct tggctagttg   1860

atttttgaat tacaaagatc ggatcctctt ctttttttggg ttgtcttaag atttttggct   1920

ggtttaagta tttgatgtcg ttgtatttta aggggtaact gatgccggct tgttgtgttt   1980

gtattcagtt tacttgaaaa                                                2000


<210> SEQ ID NO 45
<211> LENGTH: 2000
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 45

attatctaaa cattaactgc aactaataca gattacagta aatttgaatt atgatgttat     60

ctagagtcat ttgtcttcaa tgatattgac tcagattcaa actttatgaa aatgttaccc    120

tggaaaatat tctaccgcaa aatttcaatc caaagttaaa ggttgaataa tttagaagtt    180

ttctgcgact tccacccact tattatttag aagacctgaa atcaaaatga tagaagatga    240

atataaatat atttttttgc tttaaaattt ataaatcaaa catttgacct agtaattgat    300

aatacataat attatgtgac tcgtaagtaa aaaagaaatt gaaataatat atatatacgg    360

agatcgcaaa aaataaaaat gaaagtaata taaagtaaac gcaaagtaag aaagcaagca    420

ttttcaagta agattgaaac ccccgtccct gggggctcca agataacacg ggtgcccaat    480

tacccggtac acgacttttg ttgaacaaca ttgaataatt agcccaaatg aaaatatttg    540

tcgacatatc tttcttataa tatgtaaatt agataccaac acaaacactt gtaacaatat    600

cctaactaac ttggttttaa atatatatat atatattatt ttttttcta tttatttatt    660

tnnnnnnnnn nnnnnnnnnn nnnnnnnnta gataccaata tttagtggcg ggtccataaa    720

ttttatatag ggttattata taataaacac taaaaattta gatattatta ttttcaaagt    780

taggccacaa gtaaaagtgg ggatataatt attatactat aaccatattt tggtaaaatt    840

aagtattaaa tatactttaa aattaatatt aaaatataaa aatcgataat gtgtgggata    900

aatttatgga tgtaaatatc aatgttttaa tgttcaaata aataaatagt aaatagaaac    960

aaaacaagaa gtcagtcttt actactaatc gggactaaaa tttgaatttg atttaaaatt   1020

taaaacttaa ataggactaa aaatgttagg acaaaatagt aacaaacacg aaatttaggc   1080

aaagaaatat aattttattt atttattatc atttttttta tatatataat tgaaaattga   1140

ttactaaaaa aaacaaagaa cggtaaaacc ctagattaaa atcaaaatag aaannnnnaa   1200

cccgaaagga gaattttgat ttccagagct aaacataaca cgatccaaac ccataaatcc   1260

cgcatcgagt ggaaccgata tcttctcccc ttcgaagttc caactctccg tttccgtctt   1320

tcttttcgat tctccttcaa accctctttt cttcgtcttc ttcaaatctc tacatttcaa   1380

aatcttcgct aatctcttct tccccttctc ttccgatctg accgtgaccc cattcgaagc   1440

ttcttctttc accaagcttt ctctccgcta tcaactttaa ctttcgtcct gtattcctta   1500
```

```
gccttccctt gcttttgcag tctccgccac cgaacaattc ctatcccgag ataatcccac   1560

ttttgggtcg tgtttctcac ttattcaaat cgctggttct ttgattttgg gcttatttca   1620

ctctgcatct gctgcgactt ggaggttata acatctctct ctcggtcttg ttaggtatga   1680

aggatttgag atattttcta atctatctga actgggtttt ctttcgcttc cgtttatgag   1740

atgtaatttg ttgttctggg aagttttcag atcctttcta atgggcttct ttaatttaat   1800

ttaaagcttc tttgtttgta cgagatgtca agtcttaatt tctagcaata tcagtatctg   1860

ggttggtggt atttaggatg atcaagtctt ttgttattta atggatgaga acaattattg   1920

tcattgttat tattattttt tggaaaaaaa atcaatgggt tttcactggt tttgttgatc   1980

tttttagata attgaagttc                                               2000
```

<210> SEQ ID NO 46
<211> LENGTH: 2000
<212> TYPE: DNA
<213> ORGANISM: Cucumis melo

<400> SEQUENCE: 46

```
cttctcgatc gcagcaattc aacttcataa acaagtccaa gaacgaagag tttgattccc     60

ctaatttaac ttaattttct ggtgaaaatg gaccatactt ttaattacat attattttgg    120

ttattgcctt ttaaatggtc tattttaatc tctaattttt tttattaaac aatgatggtg    180

aatcttttct aaaagaaaga aaaaacttct ttacaaacta tccaactcta ataacaacac    240

taattataaa ctagtctact acctttatta taacagcaat taaaagaaaa aatcgtattc    300

actgacaaaa attcgttctt ttgaatgctt atcgaatgtt ttaatttttt taaaaaaata    360

tataaatatt tgtaagggaa ggatcagaat taaaactctc tcccctcaat gaaattgaat    420

tatttgtttt tcttgttttt ctttttttaa aataaaccta tggatttagt tggtcggtcg    480

aattaaaatc gtgaggtcgc acacgcggtg tcttgtggat tcaaaattat gattatttcc    540

atcacccctt ggctttttcg ctccattcgg ccatgcctta caaatttcgc tccactccca    600

ttcttctctt cctctcctct ttcaactgca ttgaggccga tcctttaggt aaatggttct    660

ctcccatttc atctctaatt cctctgtttc tttttatttt acttgttctt tttccagccg    720

gatcctccat ttctgtggtg aaactgaatt gttcttatcg atttcttgtt tgaattctgt    780

ttttctctgt ttgtgtctgt gtgtgttttt aatttgtttt ggcatgttga agtttaaaga    840

taccaaaagt tgcgcttcac tactttccag tttcgatggt agctgctagt tgtaacgctt    900

acgttcttgg ttttttagtt aaaatttttt tgcttcttgt tgtttactgt ttagcaaaaa    960

gcatggggaa tactaccaaa gtcccgaact taatagatag atgatcatgt gctaagaagt   1020

gcgatacttt ccgtagctga tacgtgacac agtgtctgac atttgtttga cacatattag   1080

aaacttgtta gtataacata tgtgttaaac aggcatagaa cacctgttgt actaaaaaaa   1140

atatttgtat gataataata ataactttga agtgtaaaat atatccagct aagtttttc   1200

aagtatacaa gtgcattaac tcatttcctc ttgattttct tttggtataa aaattatata   1260

tattttgaaa accgtatact ttaataaatg tatccttgtg cattatgtcc tagattttta   1320

gaatatggtg tgttgttgtg tctatatcgt gtcgtatcaa tatctcgtat tcgtatctgt   1380

gtttgttaga tcatatgtat aagcgaggac agctatttct gatgttacaa gaccttcttc   1440

aaattttaca ggaaatcatt caatttgaaa attcaagatt acaaatgcaa tctaaaccaa   1500

acttcaagaa caaaaagtgt tatttgttaa tatccttgcg acctcaccca aagtatctat   1560

tacaaacttc agaaaaaact tcataataag ggttgggttg aaaaaaaaca tgaagaagtc   1620
```

```
ccaccccaac ctaactctaa aaagcataaa aaattcaacc caacccaaac cttacaattt   1680

gggttgggta gtccgtgttg ttcgggttgt cgggttattt gaactcctag ttttagctaa   1740

gtgtaaactt atttaaggat gttgaaggtt agcattgatc tttctctctc aaatttggtc   1800

aagaggaatt attttttgag tcattcatat agttccattt tgcttttgag catttgaatt   1860

gtttgttaac tacttctttg attaatatat tcgaaagtga aatttccttg gtttacttta   1920

ttgatcagtg tcccatttta ccagttattt cagttctcct aataaccttc attggacttg   1980

agttcggtta acacaaaaca                                                2000
```

<210> SEQ ID NO 47
<211> LENGTH: 2000
<212> TYPE: DNA
<213> ORGANISM: Cucumis melo

<400> SEQUENCE: 47

```
aatgtatcgt gggcatttat tatgacaata gtgtaaaaat gttgttaaca tatctgtgta     60

ttgtcgatga tgtagatcta ctacgccaat agttatagtt tccatcggta tatctatgaa    120

atgtcaacgc cttaaaatag ttgcatgggc atagacttgt ttttttagaa aaatatgttt    180

tatatttgta tttttttcac taacatcctt ttggttttgt atctaaacac aactcaaaat    240

atatcaaata ctgaaattca tttcctaaaa aagttacaat tgtttcaaat ataagtcacc    300

tgaatgaagt tcttaaaaca caaagaattg ttccttacaa aattaacata agcaaaatag    360

taagatcgtc caaaataaca aacattacat aaactttaga ccaacttcta atttgtttgc    420

caggaagtga tctccattga aagtttgtct taaaaaacaa ataaaaagaa aataatagaa    480

acatattcaa taaactagta cattttgcac cttacatata tatacaaaaa ctttacctac    540

tttaatttct tgaaaatcta aattttgaat taagaacttt tcttacaacg ccaaaacaat    600

aataacttat aaatcttagt gatggaataa taagttataa ttcattggtt gattgtatca    660

ttaaccattt ctttcttttg gtgtgagaaa cttatccaac taaaaatatt cacaatagta    720

gggcgggttt gtcgtggctt tgtctgaatt tctacaacat gtgtaaatat tttcaactgt    780

tttatcctct aagacaattt tcctaaaaac aatcatgttg ttcacacgag atttccaagg    840

aaatttaatt caaggagttg aacttgtatt tatgttgatt tgatgcctat gcttaatttt    900

aagatttgag aaagcacgtt atatttgtaa agttggagta ttggaagaaa agtttgtatt    960

ttcaaaagaa cctcaatatt cgagatcgac ggttggcttc aaaagttagg aagtctttga   1020

ctcataggag aatcctatct agactttatg caatataaag agagttctgt tttatggact   1080

tagttggata aataattaat ttgattcaac ggtcataatg aaaacatgtg acatcattat   1140

aattaaccaa tttatatctt taatacacat atcaactttt aaatagttct aaattcaatt   1200

atttgtattt atcatcatta attaaataaa taatgtgaca atttgtgatt gatccaaaaa   1260

tttcatattc aatctatact atattagtta agcttaaaat tttactaaat gcttaaagtt   1320

ttggattatc gagcttccta ccaaacaaaa gcctctattg cacatttaaa atatagaata   1380

gtaggtttat ataatatgaa agattgactc ttaagaccat actctatgac ctaatgaaat   1440

cgacatttat gtaattgata attaataatt aataaaaaaa gtgtgacaaa aaagtggaca   1500

taataaaaga aaggaaattg tgaagcatta gcatccgaat ttcgaagaaa acaaagggcg   1560

ccctcagatc aaagaggaca tactataaag tctccacgct atttcaagaa ttggcgtgat   1620

tctcaagcga catttccgta attcaccaca aaaattaaaa acaaaaaaga actcacagat   1680
```

```
tctgatttga cttttgaaac cccaaccccc atcatctccc aatttaattt tccctcgata   1740

tttatccaaa ttcagaaaca taatcttgac aattttatgc tccattcttc caatctcagc   1800

cgtacgtttc attcaaactc caattctccc ccactgcgcc ttccactacc tttttccttt   1860

ctattaaagt gtcctcacaa actcacctcc tctctctgtt tctgtctgcg gtaggatcgc   1920

cgactccgga tttacatttc aggggtcgaa gatttgttct ggggtttctt taatttcttt   1980

atatatatac acacacaatc                                               2000


<210> SEQ ID NO 48
<211> LENGTH: 2000
<212> TYPE: DNA
<213> ORGANISM: Cucumis melo

<400> SEQUENCE: 48

gccaaggaaa atgaattgtc taagaagaag aaagaaaaga aagaacattt tttgcaaggc     60

tacaaatcaa aacttaaatt atccacgtga cacaacaagt tcagagagga aagaaccctc    120

taaaactccc atataccttg gcaataacca tgacaatagc aataaataaa caagtccatg    180

acataaaata aatattgttt tcattaaatc tcaataattc atatgtagtc cgctccgatt    240

atgccacagt catatatcaa gttcagtatt ttaacaattc aagtagacat acataaagct    300

actatggaaa acataaacaa gaatggaaga aggagggtta aggaaacctt tatccctgat    360

ggagtttcag taaaactgag cttgtaggta ttagtacgaa agctgtgaaa tgaacaacct    420

tggccaggta attgaggcac cccaagattt cctttatcaa cactatcaaa gaaagtaaag    480

aaagttatca cttcaaaacc caactcccaa aagcagctca tcattttcca gtaagttaat    540

actttgaaag atcaaaatca aatctacaat caaattagac ttcttaatag ttattgccac    600

gaaccatgca tttgtcacgt tattaagact atggtttgca ataatctcct atctggttgg    660

atcactactt atactaggca cagcataaac taaagtagtt tcccagagaa ggaagaaaca    720

tgaacctggt tgggtccatc ttggcagtaa aggatttaag ggagaagagc aaaccaaaca    780

taagtttatg gtcttgctgg ggattcaatg tccggagagg ccgattccac tccctgtaga    840

acaagcaaac tccattccta ttgaaaatat acatcatatg cacattgttt ccagtcgctg    900

tcggtaccgg aggcgaggga ctaatttctg acccaccaaa gaactgcatg gtttctggaa    960

taaactaaac taaatcaaat caattgtcat ataaaatgat ctacgaatct aagattctaa   1020

caaacccaac atttcactca actctacaat cagtaaccta gcaaagcaac taataattca   1080

atcattccta ataattcatt gaggttaaaa ataaaatagc gaattgtcaa caggtaaaat   1140

ctaacccgac ccaaatcagg aatcactaaa gcaagaagct gtatgactcg atcaaaaata   1200

acccagatgc atttcccttt ggcctctcta cagaaccact caatatagtt agaaacaaat   1260

ctagtgtaaa attgggagtc ctattcatac ataattccaa ggaaaatgga ttttacttat   1320

gcatcgtata agagactgtg agcaggggaa aatggagaga taatcaccaa tgagctggat   1380

ggtgacagat tcaagaagaa gcatcaaaat caaacaacgg agagcagaaa gatacctcaa   1440

agagcagaga ctgcaaagta aaggaagcga tcaattcaac gacgaagctc ttgattcgtc   1500

aggcaatgat tgccggcgac aacaacgtca gcagatcgga gccttacggc accggagacc   1560

cctccgacaa ggacagagtg aacgaacgtc gtttgtgaac ggtgtaagca aatcgatctc   1620

tcggagtcca actccaaagt actgtttcga tatgcattaa tacatttgat ttttgttata   1680

tcaaaaataa atattatatt aaaatttata aacattaaca aaaaaaaatt aatttcacat   1740

aatttaaagg accatttggt aatatataca aaattgcaaa aatcaaattg ggcctatttt   1800
```

gttgttattg gaggcccaag atgggtggtg ataaatatgg gcctccaaaa gaataagcaa 1860
aaaaccctaa tttcctctct tcctctcttt cccaatacta taaatcttca ccattttcct 1920
gattagggtt tttgttcgtt cttggccgtc cccttcatcg ttcccagaga gagggagaga 1980
gtaagttgca atagtaaaac 2000

<210> SEQ ID NO 49
<211> LENGTH: 2000
<212> TYPE: DNA
<213> ORGANISM: Cucumis melo

<400> SEQUENCE: 49
aattagcaaa ttgtatgtaa caacgtcatg aagaggcatt tcatcgaaca atttaatagc 60
agagtcaaga tggcccagtt ttataagttt attgatttct cgattcttaa ggtaaatgag 120
atcgcgagca tggaaatgca gacccaaacg agaatatggg tgtggtaaat ggaccggtga 180
tgttgtggct acaaattcgg attttacagc agtaatagtt ctgacgaagg aagcgaattt 240
agtgaccttt cgcatcacag tttaagctta tcagagacct gaacaagggc tctagctcta 300
caacttagaa aggtttgata tggtccgtga tcgggaggga ccgaataaca ggcgcttaaa 360
ttgttgttca taaagaagag gattgtcgtt gatgtatttt aaccaagaga tgattagtta 420
tccacatcca cagagagaac agaagacggc tttctaaatc tacaccgata aaaataaccc 480
taccactttg tttctttaga aaagggtcac attctttaaa aacattagcg tcgaggatta 540
atagggtata ttgactaatg ctctgtttgg atttcgagaa ataccaattt acaattgatt 600
tcaaattaat tatgttttgt tgttgcacga aagataaaaa gaatttaaaa ttcaaaagga 660
tctcaaatct tatttttaac ttaaaaactt ttatgaccca aacggtttat gtatgattta 720
aaagtagaat acctctgtga attcttaatt tttttttctt tccaattacc acataaatat 780
gaaattttaa atacatttat tttaaatttt atatccgaaa caaaataata atttaaaact 840
atttctcata tatgaagtgt gattcgatct aaattataaa ataataaaaa tttacatcta 900
gttttgatta tttttttttcg ttagatacta aattgttaag aaaataacat ttttaatcca 960
aagttttgaa gaatatatga cttttaaaat ggtatttatc tttttagtgt ctgattttta 1020
aaaaatggat ttcaaaagtt catcaaatag cattgtattt ttattttaaa taattttgac 1080
atttaaaatt agagtaatgg tttataaaag acacttgatc tctaaaacta ttttcttaga 1140
tataaatacg tatgattatt tttaaaaatc aatcaaaata ggtaaattgt aaaaaaaaaa 1200
aaaaatcaca tgaatagtag ttgtaattat gctctcaaac tttcggttat gaaaaataaa 1260
cattttaact tttagacgtg tcaaagttga gtcaagttgg accttcaaag ttatgtagtt 1320
atataaattg taatatatgt ataagcttgt ggattcaatt ttatcattta tgggtccaat 1380
ctctacaatt atcgtaagtc tatgggtcaa ttgtaacaca tgtggagttt aagagctcaa 1440
ttttggacgt ggatgtgttt tgcaaccaac tccacacctt aaaaaggtgt ttttttttaa 1500
tttatcaaaa aacaagaatt tagaatcttt aagtttatct ttaaaaatca acggacattt 1560
tgaaaaccaa ttgaaactac tgttataaac ctaacaacta aaagtatatt ttttaagacc 1620
gaaagcataa atccataaaa aaaaaatcca gaactgaaaa tgtaactttt atagttgaaa 1680
atttagctaa attatacata ttaaaattca aggaccatat aaaattaaag tacctgatta 1740
aataataacg aattaatgtt tggtattttt aacctacatt agaaaaaaaa aacaaaagaa 1800
aaacggcata ctatttgtca agcgtccgat gggaagaaaa tccaacggtg agtgttagta 1860

```
ttgaaatacg cagttctcgt gaatgagcct ggcttagatt tgggaacaag agccaacccc   1920

tttcgaccga gaagccgtcg tcttcaccat attcgcctca accattcgat agccacgttt   1980

gaagaagaat taggattgcc                                                2000
```

<210> SEQ ID NO 50
<211> LENGTH: 2000
<212> TYPE: DNA
<213> ORGANISM: Cucumis melo

<400> SEQUENCE: 50

```
agccaatggt tcaattaaca gctctagttc tagcatggct accgctggta acctttctat     60

gactagagac gtcttggagg tggagggtag ggcacgagga ttgaaaggtg agggtttggt    120

gaaaactcaa gcctttcaaa ttcaagaaag catgcttgac ctagtagcat ctggtgatct    180

tggggaattt gcaatggata ctcataccct tagtcggcat tcgtctcttg gttctgctgg    240

tatatatttt tttctcttgt tttctagtga tatttttcttt tatcaatttc cattatgaag   300

atggaatctt atgttctatt ttttcatttg gaatgtaggc tttcacaatg aaaaaattgc    360

taatacgttt ccagaagagg ttgctaaaga cccgtaagtt cttatttctt aacaatttcc    420

tcagtttaac aagttttatt tactaacata tccttagttg tataaatatg aatctattat    480

attaactatt tcatttatct atcttttaac agggtgacca ttcacaacaa agataatact    540

tcattgaaac gccctcctgt ctcacgcact tcggcatccc aggatggatt gtctgtcctg    600

attcctgatc cggttgttag aggaaagaac tcagatggta aataataagt gatccattct    660

gttatcttct ttattcattt tcaattttgt attttgtata tatttatata atattttaga    720

aagataaaag atccatcctg aaactttgtt tcaggtggaa gaccggaccc aactagtatc    780

ttggtgaacc aagaaaacat ggcagccatg aagaaagaga tgcgtttccg gcgctcttct    840

tcttgtagtg acagcgacgt gtcagagact tcttttattg atatgctgaa gaagacagct    900

ccacaagaat cccatttgac aacggcggga gttccagagc catctgatgg aatgcaggga    960

gggaaaggtg ggaaaaagaa agggaagaag gggagacaga tagatcccgc actactcgga   1020

ttcaaagtca ccagcaaccg aattatgatg ggtgaaatcc aacgcttaga cgattgatcc   1080

attaggcaag atatagaaca gaaattgatt tttttttttt tttttccaat catttttgta   1140

gattgtgcag ttatttgttt tcgtgtttgt ttaaccctct tgtaagttgt tgtatatagg   1200

tttcttagag ttgtcagctg cgttgaaaca tgtggccggt atatgtattc caattctttt   1260

ctttttttccc gcagttgtaa atgatcaaat ttgagttggt caaattacca aacctttgta  1320

caggaacttc gaagagagtt gaaattttat tctttttctt ttttgttctt ttatagagtt   1380

cgagattatt tgtatgaata taatcaaaag caaagcatgt aaaaataaaa tgatttgaaa   1440

gggaggtttt ctatcccatt caatgtgacg aatccaacac ttaaagtaaa tttgaaaact   1500

gtctaattta tatgtatgga atgtaatgct cttcaagaaa ttatcttatc ttctaatatt   1560

taatgggatt cacataaata tgaaatttca acgtttttct tttccttttt gttgtgagat   1620

taaggatact agataataac cgacctcaac cttttaggcc aagaggtctg gagtctttat   1680

acttgaaaaa agtttacaca tattctaaaa gattaaaagg ttaattgttt ggtaaaacat   1740

taatgatgac gatacttaag gtttcattaa aaaaatattt ggaacaattt gtttataatt   1800

taataaaatt gtaactttga acattttgaa ttacattttg tttttccatt tttacggtcc   1860

tcgaactcat cgatactcac aatggagaaa aatatcacaa tgccgaaaat acccttcttg   1920

ttcccttctt atacaaaagc aacactattg gccttatcaa cggagcagca gctactctcc   1980
```

```
tttagcacaa atctccatcc                                             2000


<210> SEQ ID NO 51
<211> LENGTH: 2000
<212> TYPE: DNA
<213> ORGANISM: Cucumis melo

<400> SEQUENCE: 51

tggtgtaccc acttggtttt ttctcttttt ttcttttagc tttttgctcc taaatttctt     60

gccttagttt tcaaaagctt gtttttattt ttgaaattta accaagtgaa tagaaaaaaa    120

aaagagaaaa caaaagcttt taaaagcttg tttttatttt tgaaatttaa ctaagtgaat    180

aggaaaaaaa gaaaaaagct tataaaattt gacgaaattt gctgtatttt gtacatttta    240

ctatttttct attttaaaaa atgtgtctga acgaaaaact tatattatga gatttaattt    300

tcaaaataaa attataccaa acagacttta gaattgtcaa tcaaatttga caatgattag    360

gtgcattttt taaagttatc ctaaagtttt tttttttttc gtagtcttgc ccttgctttt    420

atcgttaaca aataaaattt tccttatata tatatacaca tttaactact caaggtctgt    480

attttttcca cctgatttat ttaatatttt tttttttgc agaaaatcta tttgtatttt     540

aggggaaaca aatgagtgaa gagatcatca agcaacggtt gcgatgttgc agcggaaaaa    600

tctttggttt gtcatttctt gtgatggggg tttatagggt agtatggtta ttgtatttta    660

ggatgttgat ttttatttta atgagccaag agagagatgt ggattctaaa attgatgatt    720

gatattattg atgtgatata aatatataat tttgtgcgaa aattgctatt ttattttctg    780

tatgctcatt cagatcacac aataatattt gatgtagctt tacttattga caaaatatag    840

gttttaatct tgtgctcata caaacaacag ctatgggtga aattattttc tgattttatt    900

tggcaaagat gatgtcagca ttgtgtaaat ttaatgtgaa ttacacttct gatttcttcc    960

caatgtgccc tctcaaatat tggcaccaag ccatttaatt gtaaatacgg aaaggtcata   1020

aatttccatg caagatttat ttcatgttta aaatgattgt gtgaaacaaa atgaaaaaca   1080

agaaattctt acctccaacc tcaaagtagt cgatatgtca aggttcaata tcaattttaa   1140

atatccatga atagctttga tatcttttat aaatgcttgt aatatatata tactaatagc   1200

aatgtctata agttagtttt gagagtaata cttgttatag ataacaatgt tactctattt   1260

accactctac tattgaaagc ttctttttct tccatttatg aattaataac ggtcaagatc   1320

caattgcatg agttactttt aattaattac aatctaaaat gttaatataa gtctaaaatt   1380

gtccaatata tgtgattttt tttttctctc tcaaaccttc ccttcttttc attgaacttg   1440

tggttcaaat ttgatggagg acactgggaa acagcacaat tcaaagagcc aaagattgag   1500

taattttttg atttcagagt tttcatctct tcttcattct acacctttca cttctcatcc   1560

acaactatcc aatcaaccat tgccacgtgg catcaaaaat atccaaaact gaatgagatc   1620

caccacaaag ttcctctcat cactgtttgt catcaactca tcaagaactt catcatcaat   1680

cagaaatcca acatttcaac ttctcttagg aaatgacatt tttaccagtc tccaatgtca   1740

aaaactcaca caaaatccct ctttccaatc taaattttac aaagataaca ggggtaattg   1800

aagaaactta gcagtaagtt aacatattat agctttcatc aacccaagtt tttttggttc   1860

ctttctaaac tgtagtttgt tttcttgatc cattctaaat atttcctctg catgaaaaga   1920

agaaaggaaa agtgaaggcg aaacctgttt tatgcttcag aaaaccaatt cagagtaacc   1980

aaagatctga acttcagacc                                             2000
```

<210> SEQ ID NO 52
<211> LENGTH: 2000
<212> TYPE: DNA
<213> ORGANISM: Cucumis melo

<400> SEQUENCE: 52
cgctcaaatt actaacatcc ttctctttct tgttcccatt cgactagaga gacactatct 60
tatccacctc agttggctgg gtgaaatcat tgaaactaac ggttgattgt ccagattgtt 120
aaactaccct atgttttatc atcttggtta catttatagg attgtcagaa taataattcc 180
ttttgaaatc atattctaat tggcacagga ctaaaataat gcctttctta agctgtaata 240
attagaatct aaacagtgaa gttagtaact gattgatgac atttccacga ttttcattta 300
tatcctgtgc agctattctg acatcacaaa acatttcttg attttcattt ttacttgtca 360
tccatcagtc aggacgatat cggcgcgctt gttgacgacc ttgtcctaaa tacaaagagg 420
cttatccgag ctacttcaag ggagattgac aagtggaaaa gatgaaatta ctcatttgtt 480
attacattgt acaagtgatc tattaggaag aaccacaatc aaaactgaag aaaaaagaaa 540
cgtgctggct gtctacgtgg cttttagagg tagaatttat gtacaattgt ttagaaagat 600
gtatttaatt gctctaaatc tcatatgcat tggattttga gcaatcttaa aatgccgaat 660
acttaatgta ttatcgtagg ggtccctaga tggcagattt atcatgtcca ttctccagaa 720
agaaagaaaa aaaccctttt tattatactt gttcatttta agctttttct ggttgattat 780
aatgtcagta atttaaaaaa aaaaaaaaat tactgtgtat tggcatcggt tatatgttat 840
atacaaccct agttaaaagg taaagttttg ttcattcggt cattagtcat tcctatacga 900
acgtcacatt gtgctttata atttcaatag gttaaaagta ttcaatatag ttttttaagt 960
tacctagtag aggtgatcat tggttgatcg gaatcggttt tttgacaaaa ccgccactga 1020
accgatcata gtcggtttag taaatgttca aatcgacctt gacatcgatg agtaaagatc 1080
ggtcggtcgg tttttgtcgg atgggccggt ttaacacttg gaaatactat tttgaaattt 1140
ttcgaaatta atccctcttg ttttcctacc gaccgatttt gggtttggtc ggtcagttcg 1200
attttttcgg cctatcttac tcactcttat tacctaggga ttgaatttca ttttatcctt 1260
agttttaggg ttcttttttt atacttttga aatatttatg tcgatgtcta gagtttaaaa 1320
ataacacttg aaattataat ataatttttt ataattgtta gctataattt tacgtccaaa 1380
tatcaactca ctcgcaactt gtttaatcaa ccaataatat gtgtctggaa tagtaagtat 1440
ataacttgtg gaaaatgact ttaaaagact tttttaaagt atttatttaa tgccaaaata 1500
tctatattta tgtttataca ttaacataca tatccaaagt tacatattag atttgttaaa 1560
taattcaaaa tgagctaaag aaaaaaagaa gttccatata ccaaaataaa atataaaaag 1620
ttgaagacta aaatagagat tttgaaacaa ggtaagttag atttacaaat tgcaatatgg 1680
gagaccaaac caccacataa caaaaatccc aatgtccaaa tggcgcaatt ttgtttagga 1740
tagctcacgt tatccaaatc actcaatcgg agagaccaac ttaaaggcca catctgccac 1800
gtcaccatac tccaccaatc acaacacagc attggatttc tcagcttatg agaccaatca 1860
caaacctgaa tccgacgtgg catgtccaca tccaccagta ccaaccatat agcttctacg 1920
ttctccacat ctaatcttca ccatttacac aatattcttc attcttcttt cctcccttca 1980
atccttcatc ctctccgccc 2000

<210> SEQ ID NO 53
<211> LENGTH: 2000

<212> TYPE: DNA
<213> ORGANISM: Cucumis melo

<400> SEQUENCE: 53

```
aattctaaca actccggaac caaataattt agcatggatt gaaatataaa tcttcttgac     60
ttgcaaaaaa atcattgtaa tggtcttatg ttggttatag ttagggtatc gaaacgccat    120
acaggaatat gggattaaag ttaacttttg ttcatcaatt tcagcttatg aacttctaaa    180
atatcaattt tacctttgaa cttatatgtt attacccctt tcgattgtgg tatgttaatt    240
aatatctgaa tctcagtcct tatgaaactt ttttatactg tcacaaacat atgaagtttt    300
attgtaagtt cttagaaatc atctaaaaag agtagtttgt tggactattt attttatttt    360
ttcttattaa gttgttttca cgccatttca gtaaaataac tatagtgaat agagaatcaa    420
acttctaatc ttaagttaag gtagtagggt atatgctaat tcaataagat aatccgtgat    480
gcttgacatc tgacttaatt gttataagtt ttaaattttt tattgtaata tttaaaatac    540
tagtttttgg tttctaataa agaaataatt gaacaattac aaatatttat acaaaattaa    600
actagaatat atgatcattt tccttcgtgt tagaaaaagg gaaatatatg tgtgtattta    660
tacatattag atattgtttt actatattcc attttcctca cgggaaatgg aggattgagt    720
gggagataaa cattgtcccc aagagaattg ggaatggaaa tgcaaatgac atggccctcc    780
acaaaattgt tcgcctaaaa atgggctttc tcacttctca ctccgcaaga aaaatatcgt    840
ttcccttcga attattcggg cggcaagatc tcaaaaccac atgtttttct ttctttattt    900
ttcaagccta cattatttat aaaaatataa cttaagcaga gaattatgta aattcaagtc    960
catttttcgc ttcacttagc taaatcatta acaaatctgt aattttgttc ataaattagc   1020
tcaccaatta tgttttagcc cactaaggcc cattagacat ttttattaga aaaacatgaa   1080
ccgttggatc aagatgtgtg ttttcttttc tttttctttt tatttttttt gggttttggt   1140
ggggttttgg tggatcatgg tggatcaatt cgtagcttta gcaacctatt attatatgga   1200
gggaaagggc gtattaatct gttagcgccg tccgggagtt tagctttctt ccccgagcct   1260
cggtcttatc ccctaactcc aaaaccctag cccaaaggta atccactcct tccccctccg   1320
ctcttcatct ttttctattc atcatcttta atctgttctc ccttttggtt cttagattct   1380
tcttttgttg gattctttta atctttactc atggttggcc ttgtaagttt agacgacgtt   1440
tttatacatt ggttaatcct gcttctctat ctattcgcac gctagggttt tcctattgtt   1500
ttctattctg ctctacttct gcaaggttgt gttcttcttc gttcaggtcc cttttttttaa   1560
ccgaaattaa attaatgcaa attcgtttgt gcttctaatt aggaagcctt ttggaacatc   1620
tcgacatttt gattgctgca tttcatttcg ggtatatttc tatgattgaa ggatgtgggt   1680
ctgttcactg catggtcatt acttatgcag ctatgcttat cgagtccatt atgtttgtgc   1740
aatctgtttc cggattcata attttttagt aattgatcag tagatgaaaa aagatattgt   1800
aatattcctt gagtgttgca ccagtcttgg tgggtatctg ctcctgctct ttgcttgtgg   1860
attttacttt tattatatct gtattattcg aaatgttctg ttcttgttat aacttatacc   1920
cgaagatgtg ttcctccccg cgtctagcgt tgtgggttac ttatgatgga catggttttg   1980
attctgtttg gtttgtgcag                                               2000
```

<210> SEQ ID NO 54
<211> LENGTH: 1547
<212> TYPE: DNA
<213> ORGANISM: Cucumis melo
<220> FEATURE:

```
<221> NAME/KEY: misc_feature
<222> LOCATION: (1)..(1547)
<223> OTHER INFORMATION: n=g, a, t or c.
<220> FEATURE:
<221> NAME/KEY: unsure
<222> LOCATION: (1)..(1547)
<223> OTHER INFORMATION: unsure at all n locations

<400> SEQUENCE: 54

ataatgtgtt gatgttgatg atcatgcatg gtatattaat ctcatgatta aagacgttaa      60

gattaatatt cattccatgt ttatgatggg tgttcttagg gttgtaccca tatgggtgtc     120

cctcgggatc accacctttt ttatgactgt atggttctac gagaccacca gtctgtcatg     180

atatgtttat gaatggtacg acggggtcac ttacagccca attgcttaag tgttccttcg     240

ggttcactga agacctattt ttcctaggtt ttcctttgac ttcagcaaaa atcagttttg     300

tcctaggtgt tcctcgagtt cactgaagac tagttttgtc ctaagtgttc ctttaggttt     360

atcgaagatc agatgtgttc ctacagaatc attagattgc aagtgttcgg gaacacatcg     420

gtttaggggt acttctttac atgaacccta atggaaaatt aacagacatc tagcggaatt     480

agtagttggt cccttactga gtatatattt atactcactc tttttatgtt taatatttca     540

ggcaaaggtt aaggtagagg aaagttgacg agtgatagaa aaggatctgt gacatgtcat     600

atggggactc agtttcgttt ctgcttctat gtatcagtgt ttcagtattt tgtttnntaa     660

tgaaaattta gtcttcctct attcaagaaa gtgtctcttg ttattgttta tttttagtaa     720

tgatttcaac ttagtataaa tagttggatc attacaaata atatattggt gatatacttt     780

gtaatgatac attgagttat attattcata tgtttaatat acaaaactgc aatattaaaa     840

aatgaaaatc acgtaataag tatatcaaca aaataataca tatattacaa gcacgtcaca     900

acactaatat acaaaactaa tataaagtaa gatcaaagca aaaccaacgt aaaaaataaa     960

acaaaatcat ttgaaattaa atttaactca aaatacacat cgaagaaagt ggagaaaaat    1020

cacaatagag ttaaattact ttgattaata accattatat ttcatattga aaataatatg    1080

tcattagtat tttaaaatca agattaagat aggaagaatg aattgctctt ttcgtataaa    1140

aagggatgat tggggcctta cgaaaggaga aaaatacata tgttatcgaa aaaacaaatt    1200

atttttcttg taagagagaa tgattatatc cttaaaaaaa tgaaagaaag aaacaatcat    1260

ggcattaaaa aggaaaataa ataaattatt aaagggcagt tcgataataa taacaaattc    1320

aacgagagta ttaaaagaaa atgagaattt gcaaaattta aacaaatgtg tatattaagt    1380

acagccaatg caattttcaa attttaattt atttggttta cccaaaattc aatttctaaa    1440

ttgagaggag gatatagtaa attcacacgc attatcccct tcgagtttca tcatctcacc    1500

cattcttgca tacagtgcag ttacaattcc ttcattctgg atagaca                  1547


<210> SEQ ID NO 55
<211> LENGTH: 2000
<212> TYPE: DNA
<213> ORGANISM: Cucumis melo

<400> SEQUENCE: 55

aaacacttat catgttatgt atcccacatc gaaaagataa aagagacttc atgatcttta      60

catgatatat gagttactcc ttcgactacc attggttttg gagatggatt caacccaata     120

atatgaatct gacccaacaa tggtcaactc aaagagacac catcttgaga tacatgttgt     180

gtacccatat tagatgaatg actatacctc gcaatattta taacatacat gaattacttc     240

tcttactgta atttggtttt gacgtggagc ccatgattat ctaattaacc ataactggta     300
```

```
tatgatatat tagtaggtaa cccgaagagg ttctaagata aacacagaat tcaatagaat    360
cagagccttt ccaatgatat ggctttagat gggaatgatt tgaagtataa tcattctacc    420
acacccttta tatttgtctg tcaccagaaa tctcatcttt tcttgaggta ttattcactc    480
gaaaagaggg aggcattttt gggttaccca tctaatgcac gatgaactaa gggaggtcaa    540
gttctgggaa tacagctagg caaccttcac agtggataca ttcgaacaaa tgataaatgt    600
gaaaatgaat catttcatga gtgtgactaa cccaatcatt cctccttcta tatctttgaa    660
tcccacagtg agtcagagta aaagttccag caacaagtcc tacaacccaa attctttagc    720
tatttcttcc accagaacaa aaccaagcaa aaaatcagcc acaaacacag ctcaacaatc    780
tataaaggcc aaaatactaa gacagtcacc attaccacat tgaaagccgt attttccaac    840
agactttgcc tgcaaaatag atcacaaaga cacgatttca cattggacag acgccacagc    900
tccacaatct caatttcaat caaataaaag taaatcaaag ctaaatagca agtgtatggt    960
accacgaaag cagcatggct gacgccactg aggcctgtaa gagagaaaac aaaataagtg   1020
tagaagataa agtgaaatag aaaaatcaat cgataagata gattttcaga ttaccatttt   1080
tacgggaatt gtacggaccc aaacacaaac cccatagagc gccggcctga agatgaacag   1140
gggcaggaaa ttcagaggaa gaaattaaag aaaatgaatc atagtttgag aaattattcg   1200
taaagtttac cgttccgacg cgaatgctgg attcgacggc gagggaagaa caaggaacga   1260
cgccgttgag ttcgtcttcc atcttccaat tctcaatttc cttcggaggt ccgtatgctg   1320
agagctctgt gtctaccaag ttccaaccat actacgtcgt tttggatttt tatttttatt   1380
ttctttcctc tcttttgcca aaaaagaaaa aaatagtatt ccaacctaaa acctcaaaat   1440
aacatatttg ttgtacaaat tataattagt aaacatttgt cattgtgagc ttggtatgta   1500
atattaacac gaactttatc gctaataatt tagacgttaa tgaataattt gagcattgcc   1560
ttcttatatt gttattgtgt ttataatagg attgcttaca atgtaaccta gtatgttgtt   1620
gagctcgtta actttttttgt ttttcttgaa tattcaaagt taaaaaattg tacaagtttt   1680
tggtgacgtt ttcttactac attatcggga tgaagatcaa atatagctta gattagagaa   1740
gataatcatg ttgatttatc gttaaacttt gactacaaaa tccgtttaat tttttttgg   1800
atgaattagt tatacaattt aaacttaaaa ggggtgaatg aagaaagagg atagttttac   1860
aaattcgaag tgaaatgagt tatttctgct taaagaaaac aaatctcctt cgtgctttaa   1920
aacacaaact caaaacccta aattcagcgc cgattcttca atacatctct gcaggaagtt   1980
agggcaaagc agaagcaaaa                                                2000
```

<210> SEQ ID NO 56
<211> LENGTH: 2000
<212> TYPE: DNA
<213> ORGANISM: Cucumis melo

<400> SEQUENCE: 56

```
acttccaaaa atcagcctca tgggatattt aaagaaaacg taaattaaaa ttagcatcat     60
ttcatattga acaaactaca aaaattaact ctaaaagatg atggtaacta caactaaacc    120
ttcaattttt cattgtaaaa atcgaactct taaacttgtt caaatattaa aatttgaccc    180
tcaaacttaa aagagctaaa aaaagacctt caaatagtaa aagtagaact ctcaagctta    240
tagaattatt acggttatga ttatagccat agatgattca atcgattttc ctccaagatg    300
atggagtata attcttcaaa tctagctgct tagatgttat cacgataatg aaatcatatg    360
```

```
ggaactcaac aaaaagaaag cacttaatgt tgaaagacat tattctttgg gtgttgagtt    420
gggcgaactt gatttttatt attaatccgc aaaggacctt ttgagtaagt tgtggcaatc    480
tttattggag tgctaagatt tgttattcga aatttcttgt tttgatattt ttccaactaa    540
aactaatttt tttaagaaat gcaccttcaa ctgatttcat gcgtgtcctt ttgcaagact    600
cgcatgggac ataacacatc atcttatatg gcaaggccta tgtgtcagtg gagatttgac    660
gtcaatttct ttccactgag agtcgtcctc tttgtgatgg cagaactttg gagagtcatc    720
aaaattggtt ctttgaaaat gtttcttatt ttgatttttt tttttgaaag aaatgagagg    780
aataagatat ttttacgagg actctactag tgggtcaatt tgcccgcata tggatatgca    840
taagagtcct tttggagaga aagggtatga tggaaagaca ttgcaaaggc ccgtccacta    900
actttctatt atacaattag gtggaagcca cccatagcaa tgtcttggtt gaacactgat    960
attacttgaa accatgcatt taagatgtga aatctcgact agatgcttta ggaatttgga   1020
ttgtgtctgt tttgttgaat tcaagttcat tcctaaatac catgaagtta agatccttga   1080
agcaatgaag accatttatt tagatcctta attcaaatct ctttactaaa gatgattgtt   1140
tataaatgat caatttgttg aatgatgttc tacttgatat ctctaaagca tctcttttcg   1200
gtgagaagcc cacaacttga atagtattcc ataaatcatc tatttttagt ttctatcatg   1260
ttctttaaca tcaaaacatt ttagcgcact ctcttataac taagacttag aaaaacacga   1320
atcttccttt cttacgatat atatcctaaa tggttttcta tatttgtgcc ttacaatata   1380
atcaattctt tttctatttg atattgtcat aaaataatac tgataacata gtttttatgt   1440
tttattaaca cctaacaaga aatatggaag acgttaatat atcttcaatg tcgatattga   1500
atcattttat ttatgaatat atccacgcgt caaaaaatat tttaatcatt aacttctagg   1560
actaaattca aacattcttg gaaccataga caaaagaaca aaatttgcaa cctcaacaaa   1620
caaaatttta tctttacatt tgcggctaca attcacaaat tcccaaacca tgatagaaag   1680
gccccaatct cccacgtgat aaacacacat atggcacgtg accaaatcaa aatcatccac   1740
atgatgaaaa cttaatggac agctcggatc ccaacaccca ataaaaagca gccatgaagc   1800
tgacgtggca gatttccccg aaaacctttt aaataataaa caataaaaaa atatatacat   1860
aaccgttggc aacgttttc cctccacaca ttttcccatt gccttatctt tctttccctc    1920
caaacagcga gggaagaaga atccaatcat cttcttccaa taatttctaa aacgaaattc   1980
tgctcgattt tccctctcca                                               2000
```

<210> SEQ ID NO 57
<211> LENGTH: 2000
<212> TYPE: DNA
<213> ORGANISM: Cucumis melo

<400> SEQUENCE: 57

```
tgggtaacat tatgagtttt attataattt aaatgaagat caaactttaa gttgtagggt     60
caccatagga ataaaatata atcaataagt tagggcccct tagtcccacc tcgtaaagga    120
gttctgtcat acatatacat tatgatatta attctatctc catgagtcat acatgtgatt    180
ttagtacttg taattttcat tctttttcct attataattc attcaagtac tgtcaatatg    240
gttaggtatt gaaattaatt atagactcag atatcatctt cattaatgga aatggaatgt    300
tatattctac ctctcatttt tacacgttga tgataaatta gaagaaaaaa aattattatt    360
tatattgttt taattgtgag atattagttc aaaatgtaat taataaaatg atacgtgtct    420
tataataaaa ttaaacaagt ataattaaat ataaaacaac atacacactc tttaactaaa    480
```

```
agacacaact cacctaatgc tcgacttaaa atcactttgt gtcgtaactt aaccatcaaa    540

gcatgttagg gtaaacacaa taaagatgat ttttgagtta tgcatgtcat ataatgtcac    600

ttccaatttg acttatcttg cttgcttgat tcatgtatat aaacaaaaac atgaaaagta    660

gtgtaaggat accaattacc tactgatttt ttttaaaagt agtttgtcta agacgtgtta    720

aattactaac ttagtcacat ttgagtttta gttctaactt attaaacata aagtaggtat    780

ctcccttact catgtgtgtt tcgataatgt caaattccaa tgtttgatta accaaattgg    840

gtaatttaac ataaatattc ataatataat atttttatg gaataccgac atctaaaaag    900

aaatcaaaat gaatattatt aggaggtgag tttttaagag agaggaaaat aataaaatat    960

ggcatcaaca agaacaataa taataagaat agaaatccga caaaggaaga agtggatgcg   1020

tgttagtact attgacattg gcatatgaac ggttgggttg ggcctcaaat aatttgcatt   1080

tctaacttcc aaacacctaa ttcctttttt tttatccata cttgcaaata tatatttata   1140

tatattcaac aagtagttta atttatttga tataccactt taagttttaa attgatggta   1200

gtgtataaat aaataattta ggattaagca tgtctatgaa ccttttgaaa tttgatggag   1260

tatatataaa acagaatact catgggttca ttataaaaat ctaatagtaa atgtattttt   1320

tatttcattt aaacatttc aaacttttaa aaattaaaat tatcttaaaa aacacgtgtg   1380

gtttcgaacc atatggttaa aaatattgag gttctctatt ttgcaaaaaa tttggaaacc   1440

ttcatggaag ttgatataaa ttgttgtaat tagttagtat tttttcttta tttgtggctt   1500

aatcatgcta tgattgatca ttttatcatc atttctataa tgtaaaacaa tatatttgat   1560

gtgtattgta aattttatg caagagtaga aaattaataa aaaaaaaaga gagaaaaata   1620

attataaagt aatataaagc tattaacatt ttaagaaaaa taatagtgaa aatgaaagtt   1680

tcggacaata attcaataaa gaaatttgta gatttcgatt aaaatttcca aaattaagat   1740

tttcattaac acgtgtgcct cgcaaccgtc tcctacgtta tcccgtaagt agcccaatct   1800

atcccattct tacacaagcc gtcggcccaa attgattgta ggccatcggc ccactcaaca   1860

cccacaaacc ctagcccctt gctcctcctc ctcctctttt cacggctgct cactccctct   1920

ctttttacac cttctccttc tccttctccg tccctcttcc cttttctgct actatcttca   1980

gcacttgctg agcttcaacc                                                2000
```

```
<210> SEQ ID NO 58
<211> LENGTH: 1591
<212> TYPE: DNA
<213> ORGANISM: Cucumis melo
<220> FEATURE:
<221> NAME/KEY: misc_feature
<222> LOCATION: (1)..(1591)
<223> OTHER INFORMATION: n=g, a, t or c.
<220> FEATURE:
<221> NAME/KEY: unsure
<222> LOCATION: (1)..(1591)
<223> OTHER INFORMATION: unsure at all n locations

<400> SEQUENCE: 58

aatgttgatt taccettgct ttgtttgaat ttcgtcctcg tggacttgac ctttggtctg     60

cttcgtatag gactatttac ggctgccctc atagtccaag tccttgtccg ccttacccta    120

tactctctat ctctagacaa tgtgaagcgg gcccttctat aatattgggc cttgaagttt    180

tgggctttgg atctgccgaa ttgtgttggg tttctctccc aatttatttc atttctttat    240

tcaaataatt ataaatatgg aattttattt tatttaaaat ataaaagtta aaattgaacg    300
```

```
aatccaaaaa taatggaatc aaatcgacgt tttaacatat ttttcaatta tgtttttaca    360
ttcattttcg tcctacaaaa atattcccac ctttatttcc tcgatatcgg aggtcacttt    420
gtatgtttca ttcgggtgat gtgatataga tcgagtttct atgcttgatt gactatggaa    480
atatatttta agaagatgtt ataaaagtaa aataaatgtt ttgattgtgg atataattat    540
attttaaaca agatgaggaa taattagatc cgaaccaata atcttgagtc aagagtgtac    600
attgaaagtc gtatattaaa taatggttga gtttataata atattgatag attgcagtta    660
accatatttt ctcaagttgt tgaccaaagt acttatttta taaacagttt agggaatgtt    720
tatgaagttt tgccaagtgt tttgaaccta tatgagtatt gacttaattg gtatataagt    780
gcattaacaa tcaagaggta tttaatttga atcgtcctac ccctatcatg ccaacaaaac    840
aattatatgt ttgtcatatt ttattgaaag tgttttcagc gcaatttagt ttgatttgcg    900
tacaaaacat gtctacacgt atcgagttag tagtaatggt tgctagttaa gactgtgaac    960
taaaacttta aatttacatt aaaaanaaaa acattatggt cgtttggtcc tcatatgtga   1020
ttgatagata ttgattaatg agtatttgtg gttgttgcca acaataaaga tgtagacaag   1080
tgaactatgt tggttgtcaa atcttgtttg tatttgttat gtgtggtttt caccaccaat   1140
gttgtagagt gtcagatcca gaatagcttg atcatttttc atatatatct acagactcaa   1200
ttagtagata aaaactataa gactttgact tatttctctt aaaatgtctc ctcgttctgt   1260
acaatcctca acaacgtttg gtgactttaa aacatcacaa gaatctaaga agaatgatga   1320
attagatgca atgcaaagat ttggacctta attttgttac tttaaacttt atatccgaac   1380
attggaagag gcaagcaaaa agcgcgcttt agaatcgcgg tttctttggg ccgagtgggt   1440
tgctcataac agcggaggtt tgcttttctg ccaagaaaac ccctcaaaga aaaagggctt   1500
aataagcagc tgctccattt ctaagtgggt ttagccttta gcacggaagc gccaattcga   1560
ttcaactctg atacactgca aaaattccgc c                                  1591
```

<210> SEQ ID NO 59
<211> LENGTH: 2000
<212> TYPE: DNA
<213> ORGANISM: Cucumis melo

<400> SEQUENCE: 59

```
aaagaatgga gcaagctgat attgctaagc aaaagcttct gcatgattgt gaagttcttc     60
accaccgcct tcaagattct actgtcgact ttttcattga gcaggaaaat aaactaattt    120
tggaaactgc ttcgacagct gacgacgcaa tagatctgtt ggcaacatct gataatcaca    180
ttaaccttct tttagcagag gtacttgcgt ttgtttccat tgaaatgcat ttgcatattg    240
aacttcttca tcctgaatgg cacaagtttt tgtccataca aacaggcaaa gcttctggct    300
catgatgcta acaacagcga tgacactgct ggatcagccc gtccaaatgg aactgataaa    360
ggggcagctg accaagtatt aagtaacata ctagcaaata tgcttgtcga aaatgcccga    420
ttaaggatgc agatgaacgc cgtcatcccgc tgtgttctaa atgcaaatgg gacaagtgag    480
aaagatgaag atgaatctct caaggaagaa ctgttctaag caagttttta gaggaagaga    540
ttcctgaatg cacatataca atgaccttat actgtcgtgg caagaaatgg gagagctgta    600
gattttgaat aaatgcaaca gatgttgccc attaatttgc aagtcctgac aaatttggtt    660
gtcggaggtg tagaaatgat gtatcaatta aatatttaac aaagtgcctt ttggcttggc    720
taatcatggg catttgaaga ctttgcactt ggtaagagct caaacaaaat ctgggtggct    780
aaatttagtg ttgattaaat ggaatttcac tgatattcat gatctgtctc ttcttccttc    840
```

```
attgatatat tatcttctca gtaaactcct gggcctgatg cagaattgct tttaaccatc    900

tgcatacaga gaagaagtaa aaactagctc acgtggataa agggaaattt ctactgacat    960

gttggcatta gaagaaaatt ttgaaagagt tctattacca taacatcatc tacttccgtg   1020

tattattgaa actattattt ctcttacccg gagatattaa attaataaat ttctatttac   1080

attttgaaga tgctcgtgat tattgataaa aatgatgaat cattattttg attacgttac   1140

aaaaaagtca aagagagtaa caaagctatc aacaaaatat tagtaatata tacaaaaaaa   1200

gtgtaaattt aatattaaca ctgagaaata tacacttaag ctaatgggtt aaaatattta   1260

tccattgaat taaatatggt ttttctgtat ttgtgatatt ccaataaata tgaagctgtt   1320

atactgtcaa attcatattc tgcctataca atcaatttca agtcactcaa ttttgcaaaa   1380

ccatatcata ttgagttcaa ataaaatttc atatctatat acataacgaa aatgttatgt   1440

ttttgctttt aatgttttgg gtatctttct aagctacaag aaaatgtaaa aatgataata   1500

agaaatagat tatattaaaa ttattttaca aatcaaattg cggggatagc tcagttggga   1560

gagcgtcaga ctgaagatct gaaggtcgcg tgttcgatcc acgctcaccg caaatttttt   1620

tcttcttttt tttcccttgt gtatcatttt aaatgggctg ttcttacttt gaactgcgga   1680

agcccatgaa agctaggccc aatttagaaa ccgaccatct caagggtcgg ttcgtcattt   1740

atcaagatcc gataacccga ttcgctccat tttagtctct gctctttcat ctccctcacc   1800

cattctcgct tccactgagc gggcaaggga gcttaacccc tcaaagccct agaaaccgcc   1860

attggagaag ctccactagc ttcttcttct atcagcgaac gtattttcgt cttgtataga   1920

cctttcatct ctggaaccga tcggaagttt ggagtttctt ggtctcagtt tgtagattag   1980

ttttatcttg gcgtctcaat                                               2000
```

```
<210> SEQ ID NO 60
<211> LENGTH: 2000
<212> TYPE: DNA
<213> ORGANISM: Cucumis melo

<400> SEQUENCE: 60
```

```
gtgcatttaa aataatctag ttgcatgttc taggttcgat ttattatttg gggatttagt     60

tgtgtctgta tgattgaaaa aattaatgtt gatcttgtaa cacaattgtt tttccctcga    120

tgatttgaga ttatttcaac aatttagatc caatgtttaa aaagccacct tggcatcttg    180

ccttcctcat tcgcaacctg cctccagttg aagcctcgag gctcaaagcc cagtgcccta    240

ggacttcttt attaatttta cttaaaaata aagtttgtat ccctaaatgc ataaaatacc    300

cttgtgttta aggctttctg tttcttcgcg tttcacgtca ggtcagacca tgctcagcta    360

tttttccacc attcttcttc ttctctccca aagtctatca agtattttat ttccacacat    420

atattcacct acgccaattt ctttttaaaa ttttatagat atatacagtg cacctcacga    480

aaacaaagtt tgcacttctt cagttttttg tttcgcctca cacttaagct acaaaaggtt    540

attacgtttt agtaacccac tactcagctt taaaaacact atttgtatca tatgacgtcg    600

cccttatgga ataatttcac ttgattatcg ggttgtttca taaacaatct tactctgttg    660

tacctttgac aggcctggag agcatgcaac tcctctcttg cttgagtttg agtaacaata    720

aaatcggaaa ttttactgca ttggagcctc tgagactgat aaaattctta aaagttttgg    780

atatatcgta caacgagata ggttcgcatt cgatcgacac aaccagatat ctcttctcat    840

ctccactgtc gcattccgaa gaaattgatt tgagcagtga tgaaatggca acaaatttta    900
```

ctgatatggc aagttactgg gaagcatatt ttctattcaa agatataagc ttgatgcaat 960
tggatataga aggaaacaca atatctagtg aaagtttcaa agcatttctg gtaaagattc 1020
ttcccaaact ccactggctt gatgggaaac gggtacaata gatatggctt aatttatcta 1080
catccaatcc tctgtccatt gtggttgttc atcccctgaa tgtaaaaagg tacgctacga 1140
actagcattg atcctaaatt gaagacattg gttttgattt cttcccaatg caaggttaag 1200
aactaaggat ttgatattgc atccaataag cataggttat ttaagatttt ggtgatagtg 1260
aaaattaggt gacatgtctc gaaagcttaa agggatacat gaggtatgga gatggagatg 1320
gatgtggtta caacatggaa atgaatacgg tgcccagttt tttggactgc tctaaatcaa 1380
attttatcat atacattatg atactgtgtg ccaattgtat ttaaaaaggt actgaacttt 1440
acatttttgt tgtcccaaat tttgaaggat tgtagtttta ataattctta taataactat 1500
caatgttaat taaaaacttc agtatattta caatttttct aaaaatgttt gctatacgtt 1560
tagttattat cttgatcaat tgccccaaga gaaaaattac cctggactat ttcccaaaaa 1620
catcttctag tcgtccatca gctatagttt caaatctgtg tgggcccagt cggcccagtt 1680
cattgggcct gagaatagag atcatgaacc ggacggccca aaccttttc aggccccagc 1740 caagcctggc ctacaaactt ctaacctaaa accttatccg ttgaagcaat ccaataaaac 1800
aaagccacgt aagcacccag gatctaaaaa tgtatccaaa tccaccaatc tgaggccaca 1860
aatttagcct ctgtggctga atggatgtcg aattacaaga atctctcgat ttcttcctct 1920
taaatccatt taccctcaa acaaataaac acaaaataaa gaaaaggaga agaaacaatt 1980
gtcgtaatta gcagcaagaa 2000

<210> SEQ ID NO 61
<211> LENGTH: 2000
<212> TYPE: DNA
<213> ORGANISM: Cucumis melo

<400> SEQUENCE: 61
acctagaact tctaaacgat aatctcggaa aaaaaattgg aacaaatcat aataatgaca 60
attaagaagc aagaaccgtt gacaaaagca agatttagag ggagtaaatt tgcatggttt 120
ggtgatgatt atttagttga atttagccta ctcttaggaa gtatccaata atcatacgca 180
aatttcacgt agcatatgaa gcaagtgcat cataataccg cataacctgc ggggttttgt 240
catctcgatt aaacacaatg tgaacatgat gatgtctatg tgtttccagc ttttgttcta 300
atgatgatag acgatagtgt ggtatagttc atatccttga tttaattgtt tccatgtata 360
ctatcgaatt tttaatatat aattaatgta tgaaatcaaa tatcaaataa tgattgtgat 420
ttaatggaat aagatcatgt ctaaaattgg taatagtaat aacgaagaag gaagagaata 480
ataaactacg atttcttgtg aatctcctag ataaattagg ataaaaacta cgagtaagaa 540
tagaataatt atactatata aaataggagt tacaaatttt gtttcttaaa ataccaagct 600
ctgttacaag aaaaaacttt aggtattata tcttcaacat tttgttaatt tgttagagat 660
tttaggatag tttgtcaact atgggtcttc taagaaactt ggtcatcaag caaatctaat 720
gactcgaatt gtccttgatc gatgtgaaag atccaatgac ttcgaattat ctttatgcaa 780
tgtgtaagat ctaattgtca taaattgatc tcatgtgcaa agtgtaagat ccaatgatcc 840
aaaattgtct ccaacaactt cttgaacaat aagataactc tttgaagaat cttgaatatt 900
aattttgaca tagatagatt gatcttgaat attaggaaat aaggaaattt tcttatgtac 960
atgcctgaac tccttcaaca tagcattttg aatcatatct cttctctagt aacttgtata 1020

```
gttgcaatat attttgcttc tgttgttgat atatcaacac tgattgaagt tttgaaaccc   1080

aacatatagc tctagtggca agagttaaga catatatgtg gtgaatttac ttctatcaag   1140

atcacaatct aagcagatat actttgaaaa taaagttaga ttatccatta tacaatgtaa   1200

tatttacgga ccatttaact cgcttagaaa ttagagttat tttgcaaact ttattgacaa   1260

atatcttcaa aaatttcata caccgtatag acactatcat aagatgttaa agaaaaaaaa   1320

aaggtgaatt ttccatacaa ttaaaaaaaa tcttaaacta taaaggtggt ttcgatacct   1380

ttaaactttg aaaagtttca ttttaattct cgcacttatt gttttaaaac aaacttagta   1440

aaattttcgt ataaatttag aaagaaattt tatatttaca ggtggggaaa attctaaaca   1500

catagatgaa gataaataaa aacacgatca actataaact atacctatta ttaccttcat   1560

ccttaacacc atgcactcaa atattcatta attctctata ttttttcta tcttagcctc   1620

aaaatttact ttcatcctaa acttcgagcc ctcaaatttg cgttatttca ttcacgatat   1680

tccttttta cgttctttca tttatggtat tcttctttac gttcttctat ttacgatatt   1740

cttcttgctt ttatagtgtt ttagatttgt tcataaacaa cgtataaatt gaaaacttta   1800

taaatttagg gcattaaggt ataattgaaa ttaaaaccat atttatagtc attaaccaca   1860

gtattattta tcctttattt attaaaaaaa aaatctactt ttagttttaa atttaggcat   1920

tttacgcaaa gctaattacg acataaaaca ccaaaaggag accccgttcg atcttcacat   1980

cttctcggcc agaaacgacc                                                 2000
```

<210> SEQ ID NO 62
<211> LENGTH: 2000
<212> TYPE: DNA
<213> ORGANISM: Cucumis melo

<400> SEQUENCE: 62

```
gcaatggcgg aaataacgta gcagagggca caaacaacga agaggagctt cgttcttcgg     60

tgcgccatct gggaaagtga gaaatggtgg acgaaacaca aacgggggaa tcggattgga    120

tctctcagaa aagaaatggt tggattcgat cacagatcaa tgaagcacat tactcggttt    180

ttcaagaaga ttacaagaac ttgcttcttg aaacctctct tcttctgttt gaaatttttg    240

ggcgtagaat tgaggaccgg agcagtcgcc tgaatttggt cgtcgaatcg attccacgga    300

aacaaaaata tgaagaaacc aaatgaatga cttagcccac tcactacgct tggcgacgtg    360

ttcttcttac gaacggacca atcaaatgcg agcctgatga atatgggcca atcatattat    420

gccacgtaag actttacttt tgcccctgac ctatgggaag aaaattgtgg tcttttctta    480

tgtcaataga agaaaaataa aattatatga aagtcttaaa aggaaaaaaa caaaccatgt    540

taatattact gtttaaaacc ataacacaaa atcaattatt gtttatgttt tgagactccc    600

ttatggtgtt tgctagatag tgtggatttt gtttttgaaa attgtttttg aattttgtta    660

ttcttaagtt tttttatccg aaaatttcat tctagaaaac aaaattatat aaaaccattt    720

taaaacataa tatatcgtgt tatagttttt taatgtaacg ggattacacg gcctattatc    780

aattatataa taagatagat taaataaaca aaaatgattt atatggcttt tttaaaaata    840

aaatttaatc tctaccgctt ataactataa ttaagtcatt ttggtttaat aaaatcatat    900

tatatagtct cactcgtatg tattatttac aaaagatgtc gactttttat caaattatag    960

actaaactat aattttcttc gaggctaaaa ttataattta accaaattta taaatgtaaa   1020

atgtatttat aaataaacga ataatagctt gtcgtcaact atattttagt ggataagtaa   1080
```

```
gattagtttt atgatttata aatatatagt ataaaacaca tttaaacatg ttttgttcat   1140
tgcgtttggt tgatatttaa acctagtaac gaaaaagtat taggtattac attaaattag   1200
catccaccta caatgttaaa tttttaagtc agttaataat ttaagagact ctcttcaaca   1260
ttgacttcat gcaacataaa atggtagaaa ttttcacacc attgtttatc gacattacta   1320
cgtaggagaa tggcaaaact ttcttatatg tatgtgtgct tttagatgtg tctttacatc   1380
ccttatcaaa acgaaaacct aattctaacc aaatcaaacc aacccgggtt gttgggttat   1440
tcttacaagc catttgttgg attaaaaaac caaaatagag gatgttcggt tcaagcattt   1500
taaagttttg ggctatttag ttcgaccact ggtttgttca aagtcgggtc ggaccaaacc   1560
gtgagcgatg taaacaacaa aggtctaaat tgggccggga tcagatgggc tgaagatcca   1620
cgattctggt ttccaaccca aggcccaatg aattacaaca aaaaagcgta ctcaggaaat   1680
ccgaatctgg atctcaacgt actctaacct ctcacagttc gccacgtcaa gaaaacacgt   1740
caatacttta ggcgaaaatc aagtgaagaa ttccccacaa taaggaatcg tatatccacg   1800
aaactatcca atcagcttac gccatcggaa gattcggaac aaagcaacag ttcaatggta   1860
tatcataggg tgagaataag tcggttccgc agactagtat ttcttagtca aactttacct   1920
gcttcaatcg gccgccgatt tcccgatatt tacaacattt agttccgatt tttccctcga   1980
agctctgaag tatcgtaaaa                                                2000
```

<210> SEQ ID NO 63
<211> LENGTH: 2000
<212> TYPE: DNA
<213> ORGANISM: Cucumis melo

<400> SEQUENCE: 63

```
gatcaacctt gaaattttcc cacatactgt gttgtaaagt tgtccccaat ttcattcaca     60
aattacctac ttgaggaatc ggcagtaaga agagatcata atgtattttt gctactacac    120
tcgcaagtct aatcagagga tttgattaca atatcttgct gctgtaatag attcgttcat    180
aaattaatcc agattgaaaa gtcaagcttt acttcatttt catcgacaat gtagaaattt    240
tgtttataac tttgtactat tgaatctatt gctcctcgat ttgccccctt ggtacgatat    300
caagccatta tttttccaac tcttactcgc aacttcaacg catgaacttg accagcttca    360
acctataatc ttatgcatgt ttttaatgat taaagctgaa atagattgtg aaacgtacct    420
tattctcact accgctgcca aagccaacca agcttccacg ggtacccata aggtccacaa    480
tcatggcact cttggatgac atgtattggt tcctactgtc tcttccgggt tctcttatta    540
atggccccga aagcaacctc tcccggcatt ctcgaaattc ggctcactaa tattctttag    600
ctactaaaac acatgtcctc aaatttctca tttaaatgtg atctgagaaa gtcattcgac    660
ccattttagt ttaaataagc atcaagtcaa aaaccattta acgtgggctt aaaaatttac    720
agcagcgcag cgtacactaa agtttatgaa cgatgaaagt gggtggcaga agaaagcaag    780
aagtccgaga gacatgccaa aaagagtaaa agtcatttgt tggggccttg acagcaaggt    840
tccatatgca tcggtccatt gcagcatggc ggctcaaaat taaattttca cccttgcttt    900
tgcttctcta acctaccctt ctacgcatcg tgtctatctt ccttcacact cattttgtgg    960
taagctttaa cgcaacattt tcttaatgta atttaagctt ggcccaccaa tccctttgaa   1020
aagtttcctc tagatggtgc gtgtcaattt caaattaaca atttgaactt atagttctaa   1080
cccccatatt gtctgccctt tttctcttct tcttcttctt cttctagttt tgttctggtt   1140
taatcttttt cggttttctc tgtgcagggt agtagctttt aagcttagtg attttctctt   1200
```

```
gttaacaact ctaagcagtg aattgttaga gacctattat ttcatataaa tactagatga   1260

cttcgactca ttgattaggc tggaagctgt caaaattaaa gagtttgaca aatacccact   1320

aatttggtaa ccaagagcca gcaggaacat ttgtatttat tgagacaagt gaaagtttgt   1380

tattttcttt actcaaaatc tctctttaat tttatagata tagacattac ttggataaga   1440

aagggagttc accggccgga ggttttcctt caaatttaac agtgactgag gtctctttca   1500

gctttgtttt tttggtgtta ttactgtttg ctcaatcctt tgaacgagtg gtgtaacttg   1560

ttaaatgccc acaaattcat gggacgcaat cctttaggag aaaggttggc cactagttat   1620

tggtggttac cgtggctctt agcaacttag catcagaatt tgtcttgaac ttctagtcgt   1680

tgaaaattct cttcatacaa agctaagtct gcttatttgt aggatccata aacatgagat   1740

gataagggtg atgggcctaa gaatgcttga tggaaacatg gtcattggac ttgcttatta   1800

attgaaaaaa ccagccccgt ctctggttag aaccctcatt aggattgtat tgtttcaatt   1860

ctttcagctt gttctggatt ttaaaggctc caatggtttg agatgatagt catggaggtg   1920

ggaaggaatg gacaatacag ttttgaagaa ctgggttatc tcaaatggga aggtgaaatg   1980

tttatgtcag tatttgcttg                                                2000
```

<210> SEQ ID NO 64
<211> LENGTH: 2000
<212> TYPE: DNA
<213> ORGANISM: Cucumis melo

<400> SEQUENCE: 64

```
atcttcaccg ttaaatcgcc gtggttgtta gcggcggcga ggagagagag tgctctttct     60

ctgagaactc ctgccatagt agacctaaag gaagaaagtg gtagtgaaac aaggaatggt    120

gaggagggtg agaattgagg aagtggttag ggctttgaag gaacggggaa ttttatttcc    180

gggaagggaa acaacagggg agaacacagc cggagcggtg tggttgtgag aaaatttaag    240

caagcagatg agacgacggc ctggcgccga ggacaggcat atgaatatca cgtggctatg    300

gctatgggaa attgaacgta ggccctttct cattcttata ccaatcttca tttttctatt    360

ttctagggtt tcttttcttt ctttttttctt tttcctttt cacattttta tatgtcattg    420

aatttcgaag tttggagtta atatgttgga gtcgtgtatc tatttagctt catgggttat    480

aacattattt tggatgatgt atgatattta atctcaattt aagaaggaaa cgagtaacca    540

aaaaatctta taatgaggtt tgtccatctt ttatgtatta ttctccactt atcacatttg    600

tttgaaataa ataaataaat aaatgttgtg tcacctcaaa cacaaccata tggttcaaat    660

tgaaatttaa cacttgatgg tccctatgtt ccatacgacc taacaaggtc atcttttgat    720

tgtgaggttc atccaacata aagttgttat aaactaagaa tatttcactt atgagtgttt    780

atgtgcacgt tgttggtata ggccataatt ttcaatcatt taaaactttt attaaccatg    840

atttcacatt atcttgatct ctcccattcg aatatgattt tggttcatct atattcccct    900

tataaactca acgttacgtg cctaccagtt ttcgcttggc tcatccccaa cccatatctt    960

actgtggaat gttttttctc tgataccatt tgtattgttt cacaccttcg aatcatattt   1020

tagaatgttg atacagtacc taatgcatgt gatattcccc tccatttgtt gtgacatggc   1080

agcatttgtt cttacttgtg tttgaattgt tttctaagag aaaaaaatga tatctccaca   1140

aaccaacgca catcatttta gcatatcatg tgtctcattc acgtggttct taaaaaaaaa   1200

tcaggacatt atccaataag acgtggtcaa gggatgaacc aaatgaaaat taaaagggca   1260
```

```
tgtaatggcc gagttcatga atgcgtcata aatgaatcaa tatcacacta aaataagacc   1320

gatcacaagg gtgtgaaagc atagttaaca ataatataaa aaaaactaaa agctcatatc   1380

tatgccaaca acatacacat tattttcgat tgcttaatcg tatgaacttt aaagttaaac   1440

gtgtttattt taaagttaaa cgtgcttatc ttaaaacaat cttatgttgg acgacctcca   1500

caattttttc cattacgcat gtgagaaaca cattgaaagg actcgaatta gcatgtagag   1560

aatggtgtag cccccattct ataaaagcaa ctcaagatct gaacatgcat tgaaatttca   1620

ctcttcattc ctgacacata cataaagaga agcaagtacg agaatcatcc tctacttttt   1680

attcacaagt tttaagtcaa atttcaactt gatttgtatg tttcaaaacg acacacctac   1740

tcatttaatc ttgagcgtta cttcaattgt ttttatgttt caaaatgtta aaaaagaaaa   1800

aaaaaaaaag ttcaatagtt ttgtaaattg caaaaaaaga gaattacgag tatgcccctg   1860

tacatttaga agaagcgtaa ggtccatatg ggaatcagaa caatcaatcg acggccacat   1920

ctcacgagac ataaacaggg ggagttggag gaatcgacgg agatcggaat ctggtttagg   1980

gttttagcaa aagaagaaca                                               2000


<210> SEQ ID NO 65
<211> LENGTH: 2000
<212> TYPE: DNA
<213> ORGANISM: Cucumis melo

<400> SEQUENCE: 65

aactcagtga atacgataag aaatttaatt gaagttaaca aactcaaact taaatatttt     60

ttaacacgga caatttaaaa ccaaattcat agtctccttg tatagtgttt agagtgtgtc    120

gcttcattaa acctttctat cgtggaacaa atctcttcta atattttgtc aaaaacctat    180

catcacccaa aatatcatga taattatttg atgaggatca aggcttagag aggaacaagg    240

gaacttttca caagggtgga gagatttagc tattaggttt aactcgttgc ttctaatggt    300

ggatgaataa cgacaaattt taaacaatga acgttatcac gttgaaacta tctacttctc    360

tcaacctact actttatcat aaggtttgaa aagttctatc gaaaatttta aatacataaa    420

acataaaaag gaaaattttc attggagaat tttccatata tgtttaccca caaaactaag    480

gctaattaaa aagctaacct taagactaag gctaaaatgg tatcttatgc tacatttttc    540

agttgctatg ttttgaagca aaagctaatt atttgctaat aatgagatag gcatgtgggt    600

gagtgatgag cttagcctgg cctgcctttg tgtttcttct tattctctta aatatcattg    660

ttcaatcaaa atagttttgt taaatttagc ccatcctcac ttcaacctct tatatttgga    720

ttggccttct ttgtttttttg ggcttttgat atttgatgta atggacttca atcatttata    780

gaagccttac cctacagaaa caaacaaaca aaaagaggaa aaaaaaaatg gtgagttggt    840

taataacaac tttctaactc aaccaatata tggtgtgtgt atatatatat atatatcgaa    900

tacaaaatat gaatatgata tgaccacata aaattgttga aagggttgaa aattagtgaa    960

ttggactttt aaattttgta gtgtagtggt ttacctatga tgctcgtaat gttatttaat   1020

tttaaatgtg tttttttttt ttacaaaaaa aagtctcgcg gtgcaagttc aataagttga   1080

tttaaaaaca aatccatcaa aataatgttc gcttgatatg atcgagtata gagccgaatg   1140

tgtatcaaac ataaattcaa actttaatag agtgaaaaat aaatgctacg caaacaaagt   1200

ttttgtatta gcttcttaaa tgtacatata tacttttccg attcaaacac ctccaaaata   1260

aaactcaaaa gttaaaattt agactcagaa aatgagagaa aaagaaaact aaaaacgaat   1320

tctaaagata agcattttca aatataggaa aatgaacaat aaatatttac aaaatagaag   1380
```

```
aattgtaaaa aacgacaaat tgacataata cttacaaaac ataacaaaat ttcagattct   1440

atcaatgaca tacactgata tatctttatt agtcatagaa agtctatcat ttataaaatc   1500

caaatttttg ttatatattg taaatattta aatttgtttt accatattta aaaattttag   1560

atttatcacc aacaaataac catagatttc aaattttgct ataaatattt ttaaccgttt   1620

atttaccata atttttctat tataaaaaca aaaaaaacaa aaaacagata aaagcgaaga   1680

aaaagtaaga gagcagaaat attttttgat ttaggtttca tttggtaaaa aattgttatt   1740

aaaaaataca aactaatggg aaacaataat aataatttaa ttttttaaa atctaaaaag   1800

aaaatagttg acaacaataa tttaataatt taatacacaa gccagtgtta ttaatctctt   1860

tttttctaac aacgcctttc acgagacatc ctctcaatcc tcgacatcca gtggaaaaac   1920

agtatccctc aaccctcagc tttccccaac cgccctccgt cgttcttctg atcgtcgcca   1980

ccctactccg tcatcggaaa                                                2000
```

```
<210> SEQ ID NO 66
<211> LENGTH: 2000
<212> TYPE: DNA
<213> ORGANISM: Cucumis melo

<400> SEQUENCE: 66

catatattta ttatgttcca cttgataacc attttgtttt tgaaaattaa gtttaaagac     60

gacactaatt ccatcttcaa ctttcttctt ttgttatcaa cattcgacca atagtccaga    120

aaaccaatta agttgttgaa aactaaaaaa aaaaaaaatt cttataaagt tgtttttttt    180

ttaaatttgg ttaaaaattt taatcattat acttaaaaaa tatatacacg aatcatagta    240

gaaaattgaa aacaaataaa cttaattcca aatctacttt aaaggctcac tatctgtcaa    300

gaggctttgg tatagttgtc tgtactgatt aagtgtgaga gttcttttaa tatttgtagc    360

tgaccaataa attctttcct ttctttctaa ttttgcttta actccctatc ctattcatac    420

acaataaata tacaccatat tctaattgac aatattgttt ggatttgttt gttttcttta    480

cggtaggcaa gaagttgcct agttgttgtc tgacctcaaa accctttgtt gataagagca    540

aacaaagtct agttttccaa aaaaaaaatc accaactcaa ccaaatcttg agccttttac    600

taatttccat cccaaactaa tatctaatca gtgcttacat gtttgagcct tcaactcaat    660

ttaacatcaa aacatcttgc aaccacacct tgacatgagt atgaaaacaa tataggagag    720

aactttagta ttacattgag ttccattatc attgtacatt ctcaaccaac gaaaccaacc    780

caaaacaaaa tagtttttg taacatatga gattaggtat cgtcctagtt aatgatttta    840

caaagttata tgagtattca tttgttgata tagtttgacc ggatcggaca gttggctaca    900

atggtatatt tctataaact aaggtataca atttttcatg tatgttgttt gatattgttt    960

tattattggc acatgtcttt tgtgtccaat agtaataaca aggttgtttc ttatctaaat   1020

aaaataaact cttgccagat aattgaagtt agacttttaa tcaaaacgta atattaaatg   1080

gggatgagaa ataattgatt attaggtaaa cctaacaata aaatctttaa attgtgttag   1140

aatcatttag ttagtcgagt tctacactaa aaaaaattaa aaacactaaa atcatttata   1200

aataaaatat tcaatatctt caaaatgtac taaaacattg aagctcataa aactaatcat   1260

ttttcttttg attaaatttc tctctcatat taccaagaaa cctaagataa cattaccaac   1320

gattcatacc aaaaaaattt attatcattg aacatatctc aaactagtgt attcaataat   1380

ggttagagta gtagttatat taaggtgcca tgagtttgat atttttcttt tttgcctaaa   1440
```

```
ttaggttaag ccgtagctag cttgaacaat gctaaagatc ttcttaagag tttcgtagtt   1500

taacgtttat atgataaatt ttattacatc cgaacttgat atttaatttt tgtggctctt   1560

atctgtgttt agtttttctt attctctttt aacttgtagt aatcaaatga aagccatttg   1620

caaatgagga caaatgcatc tgcaagatat atattagcca atctcttgat atttttatgc   1680

tctatgagac aatatattct gccatttgcc catcaaatgg ccataatttc tcaagatttt   1740

tccatttcga gtttgtttca atcttctact ccttttgttt ttcctttgtt caatttttttg  1800

gacctttgat gaaatatctt cataactcct atgacgtggg caccatccat tggttgtcat   1860

ttgataagaa atatgtgtca atggcacaat tcccattcca tttatatatt atatagttcc   1920

taaagccata tccccatgat ttatatcctt cttcaagctc acaattgaac tttaacatta   1980

cttcttccct acacaaagat                                                2000
```

<210> SEQ ID NO 67
<211> LENGTH: 2000
<212> TYPE: DNA
<213> ORGANISM: Cucumis melo

<400> SEQUENCE: 67

```
aaataatttg tggattttat catattatgt accttagact ttgtaaggtt tataacacaa     60

gatgtggaga aatcccatga tgaacatgga cgttattata tcctttgaaa ctaaaaacaa    120

aggaaaaaaa gacaaatggc tgagtataag aaaaagagaa gaaacaacca aaaagctaaa    180

atgtcatgct ctcatatgta acatatttga attgggattg atttcaagat gtattttaaa    240

ataatttaac acacgataaa ataattctaa caaactcaaa attactctta aacatttact    300

tgatatcttc gacataatga cttttgtttt aatacaactc aaaacataat taaggttggt    360

tttaaatgac aacaaacgaa aaactcgatt ctaatttcaa tactagtctt tgaaagccct    420

aaggagcgtg gttttgaatt gtatagcaag gtttcgaaaa ttttaatcat caaacaatag    480

gtatatttac ctgttcctca agtacagtta attcatagct acttgtcgtg cttcctacga    540

caacattgta agacttgcca cacactaatt gaagccgttg ttgaaggtag ttttccatgt    600

atagcttgaa tcgacggatg accaaagagg ttgaagaagg tttgaaaaat aggggaaggg    660

atatacaaag tttgagagtg agagagggag agaaatagaa atagaagaga ctgaaaaatg    720

taaaagaaag gatgaaaaaa tgtggggtaa acgcaaattg gatttttata gtagtatttt    780

gaaaatgcta tagaaaggct atgtatagta gtgcttccaa agttctatat gaatgagaca    840

aatcaaaata tatttttttt gattaattaa ccccaaaaag actcataaaa aaatcttata    900

aatcccacta agatattgca tgttatatgt agtaaaattt atcgttcaaa taaaccttaa    960

acataattca aacgaagaaa gtaaaaattt gaatttctta tcttacatca ttcaaccaaa   1020

caatttccat ataagagatt aaacttctaa ctttaagaga gagatatcca gcatatgcaa   1080

cctaaaccaa cagtgacttt gctatatatt tgcacaaaat gtgggggaca aagttgtaat   1140

ttcggaatat caatgattaa agaaaaggta aaatttaaaa ttcggaagct tgacgtggca   1200

acacggaatg gtgatgatat ttccaactcc tcgcgacttt tagaagttgg cctcaccaac   1260

cgcatatccg cccctttgcc acgtgtcaga ctacaacaac ttccaacaat ttcctttaag   1320

aacaccaaat tatatcaata aatatttaac ttaaattaag aatatatttg ttacaatttt   1380

cctactgagt tagatagata gacagacttg tcaattaact aataagtcca aagtcaattt   1440

actcaacata gatacaattc taatttgagt gtgaaataca tattcaaatc aaaattatta   1500

ttaagaggaa aaactgattt gctttctcaa tttaaaatat aatattttga aaaagaaaca   1560
```

```
cacatgtatt atggttttca atatatttac tttcttagtc acctaatctc aaactaattt   1620

ttgaagaaat taaatatata tattatcatt tttattttct tggttatgat attggtatag   1680

aatcaacaaa actacaagtg tcctctcctc tgctatcgat ggggattaga ctctaaactt   1740

gtttagcgat tagtaattat atattagaaa aagtttatgt taatgtggac ccgacaatct   1800

caccaatagg ctcttcactt caccaacccc cgacccattc cctctaataa ttcgacacgg   1860

ctcatccccg gttcgaaccg ggccgacgtc ttcctattta acacacctcc atttcctctt   1920

ccctccgcaa cacaaacaga gacctcaccg gaaaatcaag ttaaagcaaa accaaagaga   1980

agcttcatca ctctccggaa                                               2000
```

<210> SEQ ID NO 68
<211> LENGTH: 2000
<212> TYPE: DNA
<213> ORGANISM: Cucumis melo

<400> SEQUENCE: 68

```
taatagttgc aggtcttgtt taaaatacta atctaggtgt gtaaaacata gaaagtttaa     60

tgtggaattt cttatgagaa cgattaaggc tggtgaatct cgcttggtta aatttgaagt    120

agtttcactt cgatggagac tagacgttta ggcattcgta atttcagaga caacataacg    180

aggctacgtt gggaaaatag ttatgtcatt ttatcataac tgcatacttt gtggtaagga    240

tcatactgat tagtaagtac ggtttccact ctatagtgtt tgagtcaact tctgtgcccc    300

tttactaatc tcacgagaga atccgcctgg tcctgtaaca tttgggtgtc aaagaaactt    360

gtaggaaaga ttccgaccac catggattga atcataagtc aagggccatt agtaaaaacc    420

tctaacttgc tcttgcttta aattttcctc tattctcctt attcgttaag cattgggtgt    480

gggtgctata ctaacttttg tgggttgtta atggcctttg tttctgtaga tagtaaggac    540

ttctactgta aacttgcttt ttgtttgcac tttctcactc tttcattttg ttaaaaaata    600

taagacaaca taacagagcg acagagagaa agagagacta accatagcaa ctggagctcc    660

ttgtgaaatt tatccaattc ctcagaagta gacaatatag gcttctttac agcaactttt    720

ctaccatcca accttccttc atacacagta ctctcggccc ctgcatcacc attcgataaa    780

aatccaatat gtcaacagaa cctctcaggc aattgaaccg gaataaatta gtgcagcgtt    840

gagtgcttac ctcgggcaat tggagagagc agcgtgaatg cggaaggttg aagatgaaga    900

ggaatcgaat tgctggagca gcagccctga tgcaggtgtt cggatccata attcccaaat    960

ccatatccgt tttcgtgaag aaatgttgag gaaaaattca ttatgcgttc agtttatacc   1020

attggagagt gggaaagttc gtattgtttt gctaatttcg tcgattctca ggtcttggag   1080

taaaaacgtt gtacccgcca cttcccattg ggccattgtc caatattgtt tgggttgggc   1140

gggtggatga cccaaatttt ggggaagata tgagatttgt ccaactctgt tatcaaatat   1200

gaccaaatga acaaaatatt gacttttttt tttctatatt tttttgaatg aagtataagt   1260

agttgtttta ttttgtttat tttaactcaa aattaccaaa tttggatttc acaaacataa   1320

aatagatttt atacttttta taattcaatc gaaagttgat cgtatatgaa aagaacaatg   1380

aataaagaaa gaaatgtaaa atttatatca acttaattaa aacctcgcaa tacaaaaatc   1440

gagtgaaata gagggtggag gatgagagga agagggagaa gacatccata ccctccatgg   1500

acatgggtag atgtatgggt tgggttgggt tgggttgaat tgggtcaacc catccactcg   1560

gttcatatag acagcattcg ttttataatt tatccaaaat aaaatataat taaaagaaga   1620
```

```
aaataaaaga aaaacgaaat ctccaattcg cgtaggaaat taaaaaggaa gagttaattc   1680

aattcgattc tctcccatct tcatcataat tttgcgaaag gatcgtaagt tgtatacttc   1740

tctccttgct gcttttcgaa tcgggataag aatattttct ttttgtcttc cccattccta   1800

ctcttcaaaa ttctctgcat tttctaccca tcacttttac ttcaaccatt tttgttgttg   1860

ggagttccat attttgattt cctctacaac gcctaaactc ttcttcttct tcttcttctt   1920

cttcttcttg gagtgatttt tcagttcaat tttggggatt tcatctattt ctttgatctg   1980

cagcgttgct ggaagttgcg                                               2000
```

<210> SEQ ID NO 69
<211> LENGTH: 2000
<212> TYPE: DNA
<213> ORGANISM: Cucumis melo

<400> SEQUENCE: 69

```
agtttattct gttgtagcaa ttcaaagcag tgtgatccag atgagtacat atttggtagt     60

agactcaatt atcattttat ggttgaaaac cacatcctct tctgtcattg ttcatattat    120

tacgaggaaa aaagccacgt cctctttcaa aatttcttcc acaaactctt tcttaaaagg    180

aggaattaga gtttgaaaga ctaattagat cgagaattat tcatattcag attggtacct    240

aattgagtag caaccatcgc agtaggttga agagaaaggt cctcttgttt acgatgtttt    300

gcaagagcaa attcttcaaa tttcaagaga gtatgaagtt cttcaaagat tactgattgt    360

gaacgagtgc gcatagagat gtgaaaatat tgtattcatc tagaaatcaa atgagagtat    420

agatcaacaa atcttcatcg tttactattg aaacacacat ttgcaagttt atctttgatt    480

tttttgcccc tcctcatgta tgaattaata gattcatcaa cttctttgaa atcgattgaa    540

gattagtttt gagattaaca atatttgatc gtaaatttga gtagtgattt tcaagtgcga    600

cccagacttc ctttgatgaa gtacaaccaa caattagggt ttttacagac atagtagcac    660

tgatcaaggt cataaaagct tgatctttag caatttaatc tttatatata aaagattcaa    720

cattgtcgtc gattgatttt gtattgtaga tgaactagtg gtcgaagaaa tcaaaatcga    780

ttttgaaatc aaaatcgatt ttgctagagc tgtacttatg tcatcaacaa atccatataa    840

atccatatag cttgtgtgct ctcaaaatag tggagaattg gaatttctaa gaaacataat    900

ttgttgattc gagtctgata aatatgaggt acatatattt gtgaggaaga tcaaaaaatt    960

gatttctttt gttcaagaag actcagcgga agccattgat ggagagaaca aaaatcggag   1020

gggatggtta atcatgggtc tttgatctgc tctaatacca tgtgatcttt accaagttgt   1080

gaaaaaataa tctctcattt tctcattaat ttacaataat agaatatggg tatctattac   1140

aacccaattt acagaggaaa tactagctga ttacaacaga atcagtgcca aatcaattat   1200

taaaactaat actcaacact aattaccaaa gaattagtgg ttttttttacc acgaatttat   1260

ggggtaaaaa aagtgaactt ttaccaaatt agtaaaataa aaaaagaaag aaaaaaaaac   1320

gtaatattca aatggatggt gaggcatgaa gaagagtagc ctaaagtaca tgaagagcta   1380

aaagacttat tatcttccat tggtcccatt gaagaccaca aagaaaatat cagtcctttt   1440

tctctttaga gacacaaacc caaagtagaa agaatctttc acaagaatta ggaatttaat   1500

gcaatttttc tttttaaaaa aaatctccaa ttttctatct cattatccac cctttccact   1560

ctaaacttca ctacaatttg atgaaatctg tttccaccaa tcagattgca ccaaattcca   1620

tcaaaaacgc cccatcagat aattatggat gtcttcttct tcctctcttc tttcgtggct   1680

gaaattgaag ctcaactcaa aaatacattt cattttcaaa attccctgat gacccaattc   1740
```

```
gccacgtgtc ccttccactc accactaccc acacaaaaca actgcttctc ttcctcttcc   1800

tcttcttctc cattaaattc ccagacccat ccctctgcaa cttcgaatgc aacagaaaga   1860

aaacggacca aaaatccctt gaggaatttc tcatttttga agcataattc aaagattaaa   1920

cccgtattaa ccctcttcat cttaccagag gtttgattta ttgatcgaat tgttttattg   1980

gtttttttc aaggtcacca                                                 2000
```

<210> SEQ ID NO 70
<211> LENGTH: 2000
<212> TYPE: DNA
<213> ORGANISM: Cucumis melo

<400> SEQUENCE: 70

```
gcatcttatg gatgtagtca caacatattt atatggattt tctgataatg atatttatat     60

gaaagtccca aaaggattta agatacctaa aacatataaa tcaaattccc ataaactatg    120

ttcaataaag ttacagagat cattgtatgg attgaaaaaa tcatgacgaa tgtgatacaa    180

tcgcctgagt gaatatttag ttaaaaaaat aatatcaata taattcaata tgtccatgcg    240

tttttataaa gaaatcaccg tcaggatttg ctattataac tgtatatgtt gatgatttaa    300

atataattga aattttgaag agttttcaaa ggcaatagaa tattaagaaa gaatttgaga    360

tgaaagatct cagaaaaata aaattttgtc ttgattttca aatcgagcat ctagtaaaag    420

ggatatttgt tcatcaatta acttatacag agaaaatttt aaaaagattt tatatagata    480

aaacacattc attgaacatt ctaatgcaag ttcattcatt aaatgtgaag aaagatattt    540

ttcgacgtcg agatgataat gaagaactcc ttagtccaga agtaccatac cttaatacaa    600

ttggtgcact tattttgtca ataatcaaga ccagatattg cattttctat aaatttatta    660

gctagattca gttctccaac aaaacaacat tggaatgaag ttaaacatat acttcgttat    720

tttcgaggaa caattaatat aagattattt tattcaaata aatcaaattt taacctagtt    780

agttttgcat attcttgatt tttatctgat ccacataaat ctagatctca aacaggttat    840

ctattcacat gtggaggaac tgctatatct taacgatcag tgaaacaaat taccataaca    900

gtcaactctt caaaccgtgc tgaaattctt acaattcttg aggcattcat gaggctagcg    960

gagaatgaat atggttaagg tcgatgactc aacacattcg aaaattatgt ggtttgtctt   1020

ctagtaaact ccttccaaca acattatacg aagacaacac aacttgtata gctcaaataa   1080

aatgaggtta tattaaaagt gatagaacaa aacacatctc accgaagttt ttctatactc   1140

atgatcttga agaaaatggt gacatcacag tacaaaaaat ttgttcaaaa gataatttgg   1200

tagatttatt tacaaaatta ttacctactg caacctttga aaaattggtg cacaacattg   1260

gaacgcgacg acttagatat ctcaagtaat gttacatctt acttgccaag ttaactatac   1320

atagtgacat ttggtggagt tgtaagaaac actaatattg gagaaaaatc gaaagaaatt   1380

ggaaaatatg gagaattgaa ttttttttag atttttctta ttttctaatt ttaggtttcc   1440

gtattctgat tatgcctcat tttcacaaca ttaataactt taataagatg atttcttggg   1500

ttaagggaaa aaatcatttt tttagagttg cacgtacaaa aatattatca taacatatcg   1560

attataataa accaattcac cgtcaaccta acctaggtag agtttgagtt aaatgttaaa   1620

agaatatcca cccctcaaca ttgtaatccc aactaataaa tcagcaacct aaagtttttt   1680

ttaaaaaact aaaaagaaga gcaatatatt ttttttacta ttattttttt aaagagtgga   1740

tttatttatt aaattaaaaa atgaaaagaa gaaaatttgt tagtttgggt aatccgaaaa   1800
```

```
cccgattatt tgggcccgag aaaccgacgt tttgtttatt gttcctcacg gcaataagta   1860

atggcgtgaa tcgaccgcgt gcgcttcaag ctatctagac atttttatat cctccgatta   1920

gaaaccctaa ttcagattct ccgtattacc caccctggaa catctttgaa acgcgaaaag   1980

gtgacccgaa gaaacttgaa                                                2000
```

<210> SEQ ID NO 71
<211> LENGTH: 2000
<212> TYPE: DNA
<213> ORGANISM: Cucumis melo

<400> SEQUENCE: 71

```
taataaagtc gatgatatga attaattaga cggatgggtt atactatagt tattttattg     60

tcttttatag agaatttaac attggtagcg gggaaaatcc gatagatatt ggtgaagagg    120

aattcgttgg tggatgtaaa ggaaagttag tttcgccttg gcacaacgaa gggtttgaat    180

ggaaaatcat gataagttcg actgcctgtt caactaaacg aaagatacca agtcaaacct    240

tagttttctt taaggattta tgatcttagt agtgtatcta tttaaagatt caaaggtatc    300

aatagactat ttatttcaat cgttgtgttg aaatctagga gtatatttaa cgattaactt    360

aaaagatttt gctatcttgt tttgtgtttt tcattttttt gggaaaacct agtgtctttt    420

tattttattt gatacaataa gtattataaa aatgactaga atgactatat acttgatcat    480

tattttgaca tatttgcaat atattaaaaa tgactactta ttttaattac cttcatggtc    540

ttttttttaat ttatgaaggg gtgggctcgt gtggcagatg aggcctgtca taattagcct    600

taccttaaat aattgggccg gttctttggg aaatatcggc ccaacctaac ttttcatggg    660

ctcaaatgat gctttatcta atacccatac tttccattac ctttgtatat tgaattagaa    720

tgatagaaaa acatactaca cagttgagtt aggatataaa taaatgcatt gaactatgta    780

ttacatagtt gagaaaaatg agaatgaagt tttgtctttt gaatatatat tctgtgaaag    840

ttagatgtat atagaaatga tgatacttcg gcgtttgttg aagattgagt ggggtgtcaa    900

cctaatcata gttggtttaa gaaaagtttt aattataaga taaccgtttt aagtgactta    960

tgccatattt tgattgcagg ttcacaatga aatgttttaa tttggtgatt agactttgac   1020

aatgtggtaa tttatgttaa gtgagttgtt gtctcgttta ccttgatcat ttgtctctac   1080

tcatttctca ttttgtttca tcccttgtta tatggcatcc attgttgttg tatttgtcat   1140

tgttcacatt cgatgcttaa ctaggtaaga acaacatttt cattttagaa ttggaacgat   1200

agaaattcat aagttttatt tttgaggcac ttggttcatt ttaatcatag aacattagtc   1260

cacaatcgtt tggaataaat ttacactcta tctagatatg gaactcttga caacctctac   1320

caaggaagga tgaaaagcaa aaaaagagta gaaaaacgaa agtagacact ataacaagcc   1380

aattagccca ttgacaaata ttaccacgtt attaaagttc attttaatca tcgtgtcaat   1440

tatcaacctt ataggtcaaa taccatttat aattattttc aaattcaatt aatgaaacaa   1500

gactcaaaaa accaaacaaa tatccaaacc caatatttga gtttagaata taataatttc   1560

atagttagac ttggagacag atttgtacgt atatgttaaa ttaaaaattt aatcaaagta   1620

taaataaatg atttggagtg gcaagaaaat attggccaaa atttcataag aaaaaggaag   1680

aaaataaaaa ggtgtattgg ctaacaaaaa cccaattcca tggggaggag aaaatttgag   1740

tcctcaaaaa aggatttcag atagggaacc aaccaatcaa aacgaaggac gtctccacgt   1800

gtcgctacaa gaggccatct ttccaaaatg agatcgcgga taaacaagcc ttttctgagc   1860

atagaaaaat ggcgaatttt aacaaaaaga aaaatctcag taaagtcatc agctacagct   1920
```

gctctttgac ggccacttga ttcactattt ccctctcttt ccggcgctga ttctagtgtg 1980
gttgaacttt ctgcaaagaa 2000

<210> SEQ ID NO 72
<211> LENGTH: 2000
<212> TYPE: DNA
<213> ORGANISM: Cucumis melo

<400> SEQUENCE: 72
attacttgaa cttaatccac atttatgtct ttatataaag ttcgaatact cataatatag 60
ccaagaaacc ttgtttattg gattttgagt tttatcataa gcaaatctct tatccaataa 120
caaattatta aacaacactt caacaataac tttattcaac aatatattag tttaacattc 180
acaaatcacg agtattagaa cataaaacgc aacaaagaat ggactaaggt actatattct 240
aacttaggtt gtttaggatt tccatatgtc aatgcttttg tgatttttga actagatttt 300
cttgttagat taattcaatt ctatttttaa atggcttaat atcttatttt cggatgcttg 360
gggattgcta gactaccgct ttgttgaagc aataagttaa atttgtttgt tacaggtatt 420
gatcaatcta acatagaatt gaatttgtat gaatatttag ttagacgctt gaaaactaat 480
tattctacca atgagccgta gatcttaatg caattgttat taatttgaac tttgtatgct 540
tctcatcgat taaatttata tcaagtagtt aattaggaca aatctattgg ctttttcatt 600
taattttgtt aagtaaaagc aacttagaat tttgaaaatg atgaacccat gatccaatac 660
attgaaagag aattttgttt aactcaaact aggattcttc tcacattgat ttcgtataat 720
ttaacttttt caatttatat caatcccccc agggtgaaaa aaatttgttt gaagaattca 780
tgtgctttct aaatctgatc tagacttgcc actaaaatta acttttgata tgtaatttgg 840
ttaaatattt gattcggatt tcgacgacaa acaattgatc aatgtggtat taaattctga 900
tctccatgta agaaatttac acattttcat aagttcaatg ttgacacaaa gagagtaaga 960
gcattttaaa aaaaaagata cttttaatct tttctaaaaa aacaccaaaa tgccattatg 1020
taaatgtaac ctaaataata aacatttaaa cttagaattc atgcaattag gctttgtatg 1080
ggacattgaa ttgattatta aaatcagtag ttatagaccg tgagttataa tggtttgtat 1140
tagaagcata aattatttta attttgatcg taatagcatg tatttgagat ataaattaat 1200
ttagtttggg tggcaaatag taaacagtaa agcaaaatat aaaaaaatga atttaaaata 1260
gtaagatttg taacaaatga ttaatactat aacaaacgtg gttttaaaat aacgttgatc 1320
gtagctaatt gaacattatt tattgtaaaa ttgagtgttt ttaatatttg gagcctcaaa 1380
cttcgggtgg atcaccacaa tataatcata ttcaaattta aaattttatt tttttatta 1440 attataaata ttgattgtta atagatgctc attatgggcc atctgtcact ccctccgtgc 1500
atatcctacc tgaaacatca tatatcttaa acaatgtcca ttgccatgtg tcactatttt 1560
tacatcccat ccacttgaca aatatgttga agatgcctac tttttaggg atcatgtaat 1620 ctatctcatg cttgtcaaat tgttcgataa tagtgttaca aaaaatttag taattattat 1680
tattatattt cttcgatatt tatgcttcat atgccattgt gctctccatt tttaccatac 1740
ttaaaaaaat ttcttattat aaattttttc aaaaaaaaat ttactatata gtcatcatct 1800
ttattaaaat taaaattgag aacctgatat ttttgatatt aataatttaa aatttgaatt 1860
aatccacttt aaaattatta ataatttatt cgaatttggg ccttaaggaa gagatacgga 1920
aacaaaccct agatcccatc tatatataaa tcgccacaaa accctacctt tctctcagtt 1980
tctcgtttta gccggcaaaa 2000

<210> SEQ ID NO 73
<211> LENGTH: 2000
<212> TYPE: DNA
<213> ORGANISM: Cucumis melo

<400> SEQUENCE: 73
tgaaaaacta aattaaattg tccttacatg tgtataaaag aaaccttcgg acatttgatc 60
tgagaactat gttaaataat aagatccaaa aaactgaacc ccaacatctt cgaaatcgat 120
ttgatttcaa ttcttaagat aagctacatt caagttacct agatgatcta agaaactaat 180
gattggacaa agttagaaac tcccaataaa ccaatgatct tcaaagcact ctacgatcaa 240
gacagattaa tttttagttt gaatgctttg aacactcgtg cattctatca caagaacaaa 300
aattatacgt tttagaattt tcaaatatca ttcatcccaa tttttatttt aaacgtgaaa 360
attacaactc tatttatact aattaaaata ttaattaaca tgttacaata tttaatttta 420
tgtcatttca actaatgtaa taaataaaaa caaataagac aacgtaaata cacaatttca 480
taaacattta atttcacgac ttttaagttt tctaaataaa ttttcaactt tttcatttga 540
tttaattatg atttctcgga tcatatctat atatatatat atatatgaag ctgagtttta 600
gaaattgtaa attcaaattt ctttaaatgg tacaaattca attagtaaga ggaaaaacag 660
ctaattaaat aatgtgtgat gccccactcc ctaaaacagt gggtttggat cgattaatca 720
actaaaactg accacaaaac aatattcttc tacaacccca ttgatttttt taatcattaa 780
gtgccgattc aaagaaacaa taaacaaaag aagttgaaaa gattgagact tttaaattaa 840
atctgcaaga ttctctccaa actcatgttg tattcaagtg tttaaagctt aaaatatcag 900
taattatgtg ttatttaacg gtgaaaccaa tcaaatcaag caagattctt caatattcaa 960
ttccaaatcc tcaagtttcc atgaaaactt cataacgcct ttatccctcg aaagccaaaa 1020
ttcaatttcc tccattcatc ttgcagccct atctactttc caaaagccaa caaataccct 1080
tttaagcagt agccttttgt ttggttgtag taggatcttt gtttctcttc cattttaaca 1140
caagccacag gagaatctct atctctatcc tgcaaccttc atccccacat tgttcttcct 1200
ccattatcgg aaaaacccag tacagggttt gctttccggc cactatccgg ttgttctttg 1260
taagtttttt gggttttcat tatctgggtt tgtggctgct tgtggattca gggtaatgtg 1320
gccatgtttt atagtccaca gccttttttt cttcttttga catgggatta tttctgattc 1380
tatttgtcta ttgttacttt gtgctttttc tggtttgttc ttgtggtcat catttcttat 1440
gcttggaagt tcgaacatga atcaattcaa caactaagtt gagagtgttc gactctctca 1500
tctcattgac cctgatggta tatcttggct tggaagttag aacatgaatc aattgaacag 1560
cttacttgag actcgagagt gttcaactct ttcatctcat tgaccctgat gatatatctt 1620
ggctttggag ttatgaacta tgagagcttg gaggatgaac taaaaagaag ggactatttt 1680
ttgagatgga tatttagttt tagtaattta gcttttttttt tttagtacat agtacattaa 1740
ctttgttcgc gaggaaatag tggtcttgtt gacgagcatt tcttaaacaa tgtagttttt 1800
gtctcatctc tttaaaagtt tatggagggg caaacaagtg agatcaatag ttatagtatt 1860
tcaatctata actttggaac agctgatttt taacttttcc tttgtctttt ttttattata 1920
gaacacatta gagtgcgtta gattcttcag ttctgagatt ttgatctttg agtgctctct 1980
tttagcagta gaggcaaaca 2000

<210> SEQ ID NO 74
<211> LENGTH: 2000
<212> TYPE: DNA
<213> ORGANISM: Cucumis melo

<400> SEQUENCE: 74

```
actttcagta gattttatct cataaaagag tcataaagat aattagtaat gaataaagct     60
ttgtttgaag aaatgtttca ttgcaactga tatttgtcat tgatgtacaa atggctttgt    120
aactctccac tttttctaat ctaaccattt acatacaaaa tatctacgat acactaaaat    180
gaataaagaa attttttttg tcaaaaactg tggggagaat tgctccttgt tctcaaatca    240
ttcatgaact ttgcaattta gaagtaacat caatgaaggc ttcttccttg cagggaattc    300
tcaaacctcc agttgggtgg ctgaatccaa actcttcttc agccttgttg agcaagtcta    360
tgaatgaagg ctgactcaag tacgatattg gaacgaaaaa ccgctttctg tcggtttctc    420
ccacgtacac tggaatgtgg cctttgggaa caatggactg acatcttgct gagacagact    480
gcatcttgag aacttgcttg gcagcggaaa gaagaaccga aggcaaacga attcccatgg    540
ctaaattgga ttgaatcttt ttggaagtgg taaacttcaa tgcttgaatg agaatatgtg    600
aaagatttga agttggagat tagttgtttg tttagagtct atatatagaa tgagaaaaga    660
gaaggtattg tgacatatga atagaagatg ggaaaccaag aaagttgggt tcatcaatgg    720
ctcacatggg ttgctccatt ggttaaggta cattcatttt ctcattggca ccaatttctg    780
gtaagatggc cccatatgtc ataatacgtg aagtcatatt gatctaaaca aaatgggaca    840
caaaaattgt aactatttca attagcatta aaatcatgtc aagaaaacta cattaaatat    900
agatatatta gttaatgatg taataatagt ttcatgtgag atcaaactac gattttttt     960
tataaataat gttactttta aaaaaatgtc aaaaatatgg tagaagaaaa gctattacaa   1020
aaagttaagt catctactcg gttcataatg cgttatcgtg gatcgggtac acgacaaggc   1080
aatgaagaca tagacccagt ctatgacttc gatgtaaaat gtgggttttt cctaattact   1140
cgtaaaaaaa tatttttgaa aacttttctt tttaacaaac ttaaattttg gttaattata   1200
tatataaata ccatctttac tttcttatta tccaaaacaa tttaccatat ataattatat   1260
ttattcaata aataataata taaaatattt agataaacaa aatcaattat ttcaatctta   1320
tatattttaa atatacacta agctaattta aatttacatt ctgaaaattt taattatatt   1380
tctatctaat ttaagatttt aattatattt ctatttaatt taaaatttta atggaaaatt   1440
aaattgtaaa taagaataag agtacaaact tactattttt atttcatttt taatttataa   1500
acttcatctc ttttttcata tatttttaag aaatccaacc ttatatttcg aaatttattt   1560
aaaaaaatta taaaattttt taaactatat ataaataaaa attgtaattt ttgaaataat   1620
ttattaattc ttacaacaaa cttataataa taacaataat aataataata atgagggtac   1680
tcgattctca aaaaaaccga accgatcaaa caacgttaga tcaccaacac agaagtaggg   1740
tttttcatcg gcacataaaa accctcactt cttcttcata aaaaccctca cttcttcttg   1800
acctaattcg cgccgttgat ctccggttcg atcggtttct acgctgtaat ctcaagctat   1860
ctcctacctt atccttccct ctctttttct tcttcttctt cgtatatgca tatcttcaaa   1920
tttgctgctt tttttgtctg attattcatc tgggtttgtt tgcaacagga aggaggaaga   1980
atttcaaatc aagaagaaaa                                                2000
```

<210> SEQ ID NO 75
<211> LENGTH: 2000
<212> TYPE: DNA

<213> ORGANISM: Cucumis melo

<400> SEQUENCE: 75

```
tttattaatc tgaatcattc tgtttcttct gagagtttta ttccttttaa gattctaatt     60
ttattttgga tagttgaatt ttggtgtgct ctctttgccc cttctttatt atacattcct    120
ttatcttaaa aaagccaaaa agttaaaaaa caaaaactaa tcaaaattgt aacatttaca    180
attttatgag catgacattt aaaatatcga ttttgaagtt aagacgttgt attctcacca    240
tcggttttta tctcttccca ttccattaga gtgataggct ttatctttca tcactgtcaa    300
aattcatcca acgtccaaga tctcttctgc aaagagttac ccacaattct ctcagactca    360
ttggcccacc ggataccgag tggatggata gaacctccaa gattgcgaga gcaaaagctc    420
agccaaaact tgcacaaact cacccatggc ttccctctct tgtactacct ccattaatct    480
caccccaaga tccttcaatt ctcgccccca ttcaaattag cttcccattt tcttggtctt    540
cagtccaacc ttcgatggct ctcacccctc tccattggac cctccaatgg gtctagagca    600
acttgctggt tcaatttaag gcaaaatgcc gagggtgcag gcatttatgg cagccagtcc    660
cgagatgatt tcaacagaga tgatgttgag caggttcttt tactaatttc tctcttcttt    720
ctttgtattt tgttttgtga ctttgattgt tgaagagtgg tgtcttttgt ttaattgctg    780
gtttgggctg attcttatgg gtttggagtt gaaattgttc ttaccctctg gctgttctgt    840
tttcttttaa gtattgtgaa ttttcaatgg ctcctttagt gaagatagat gaagaaattt    900
aaattagtaa tttttcgtac cgatgactct cttccagtgg tgttaatgtc aaactaacct    960
tttctttacg tcataaagca cttaatcggt tggaactcag tagacgtctc actcatgttt   1020
gtagccctaa cctaatgcca tggcaatcga aatttatatc gtatccctat tgcgattatt   1080
aaacatcacc ataggtgaga cattcctaac gtgatatact gagttctaga tggttaagtg   1140
ctctgacatt tcacattaac gcctcatccg cactggttag tcgaaagaag aaggtgtttc   1200
tgttatgaga ttgtgagaaa ggacctcctt aaacattata accaacctca taacttgtgc   1260
atttgtgtat caaactctgc tttcacataa agaaactaaa acaaggtatc acattgccgt   1320
tatgaaaagt gcatagaact tcctgcttcc ctcaaacaaa acttgcaaat attactgatt   1380
ggccttagcc tttaggtaag ggaagaatca aaagtattcc ttcatccttc tgctttaaaa   1440
atgtgctaaa tgacgttgtc catagtttaa aaactcgacc aaatcgcatt tgtcttacag   1500
tctctcaacc ctttttaagc actctcagag tcaatccaaa tagattccta gttcctaata   1560
tgtaacaaga agagtgatac tatgaaaacc cacaaaaaac ccacaaacat gtgacttgag   1620
ttaagatgac tcccaatccc actgtatcaa gcttttcaaa tagaggaatc acgatgagat   1680
gaacaataat atcccaacgt gctgctatcc caaattagat acagaagtct acttgtggtg   1740
ttcttaatcc aataattcat tatgaaattc ttatataatt tcttaatgag tatcttagaa   1800
ttaatgttac aacttatctc ttattctata tgatagaatc ttaacataag tattcatatt   1860
aagagcaaga ttatgttgat acttctcgaa tcataccaaa aacttggaac catgacatta   1920
acttcattcg tggaaacaag ttttgaagga aaaagaagga ttgacaaatg aacgttatgg   1980
ttgtgcagta ttttaactac                                               2000
```

<210> SEQ ID NO 76
<211> LENGTH: 2000
<212> TYPE: DNA
<213> ORGANISM: Cucumis melo

<400> SEQUENCE: 76

```
atctaaaact gcatttttta ctacatacag attcaccttt aggtgctggg gcttccccta     60

tttcatttta tcaatgaaat gtttcttatc tagaaataaa aagaactaca tacagattca    120

caccactgca gaaaggtcaa ataaaacatt catcataatt caaggtaagt aagcataatt    180

ttgtgaaact tatgtgatgc acttaatata tgaacgattg ccccttgttc tctcaaagtc    240

agatcttctt tttcctaaca attgaagaaa gtggaaataa gttaattacc acggccacgc    300

aataatctcc tgatggcctc caatgaaccc cccaaacata atgctgtagg gaatgtcttc    360

ttgcaatcct tcaagacgca caatgtgaga catgcaaaat attaaaaagt gacatcttca    420

aatatagcaa aagaaatcaa aatatttaca aaaaatatag caaagtttca tattttatca    480

attatacaca ctgatcgaca tattttgtaa atattttcaa tagttttgac atctacaata    540

attagttgag attttgtagt caacaggatc cagatttgtg tgttgaaagt tgaaacccat    600

gataagataa aatcccggtt aaatatttca ttttcattct taagtttttg aaaaaggaat    660

agcttggtaa gctacattcc gcatggtaaa caagcataca acttttgttt caaagaacca    720

acaagtacta caaacaaaag agtaattgat ttaatccaag ttaacaatga caaattggta    780

atatttatag gatattagtg agataataca atcaagttcc aaaagatgtt atatttacaa    840

ctatgagcat tcatcttgtt actaccacca agaaaaagta gcggttttcc aatctctgtc    900

aagtatccat ttgagttatg atttcatatt caagactgtc acaaaaattt cattaaaagg    960

tgcaagtgca acatttcctt aagaaaagga taactgagag atcaatgact ggaattcaca   1020

agttaaaatg aacacaactt cagaacatca caagctaata cctccaaacg gtccaataag   1080

ttttctgcaa cactgtcaac aagcgaatcc tttgggcgca tcaaccaagc agctcggtcc   1140

cgctgttacc aagaaacagc aatttcagca agaacaaaat atagaaatcc tccaagaaaa   1200

ataaacaaac aaataagttc gaaggcacca catatcagaa agcttatgga ggagtacatg   1260

tagtacaaac gctcttgcca tttagtttta cttgttaaaa gtgatttgct cagaataaac   1320

ataaccaaag cagaatccga acatatgaac caatgaatta ataaacccca tcacagaaag   1380

acaagtaata ctcccagaat tgtactctat acagacgacc actacaattt agccacacaa   1440

tatcaccatg ttctctccaa atatatttaa aaaaaaaaaa aaaaaccctc ctattgttgc   1500

ggttaacaca aatagatcaa aaagaagaaa gaaaaaacta aaaggagaca aaggtgttaa   1560

atttggttta cctgtttacg cttaagatca cgatcaaaaa ccttaacctt tgagctgtgc   1620

attccatcac cgattcttcc gtcataatta tcatcaccag tagagaaaga acaacaagga   1680

attgaatttg gaaaatctcg ccatcttgca cttctcaaca ctgagaacga tcttatgatc   1740

gtagacggcg acagccctct catttcacag tcaccgattg aacctcgccg gagagacgga   1800

gggaaatttt gtaaattttt aatgggcctg ggccgtaaag tcgtgtccaa acactcctta   1860

aacggaccaa aaccggcgta gaaatgaaac tatccagata agggacgtgc tatacattta   1920

tccaaacgag gtctcttatc gtatcttgta caagttcgtt gcttttcacg gctgtctcta   1980

gaattttggg ttgggcgaaa                                               2000
```

```
<210> SEQ ID NO 77
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
```

<221> NAME/KEY: unsure
<222> LOCATION: (1)..(2000)
<223> OTHER INFORMATION: unsure at all n locations

<400> SEQUENCE: 77

```
aaacctactc tgtaaatgaa ggtttacatc tcttaaggca gtaccatttc tgccattact     60
tctaccattc ccacgaaacc acctcttttc tctttcattc tccccgtcag gtatgcattt    120
ctcatctcta agtccgccca ctgttttccg actgattttt cgatttttaa ttagtgagtc    180
ggttttattg tttcttattc taagctttct tttactcttt atatttttag atatttaatt    240
tcggatccat tcttcccatc atgcccaatc caaagactgt cgaaagtttt gattgttggt    300
aatgggacat taggtctggg gtttctgttt ttcttatcct ataaattggt tatccttcgt    360
ttcctctatt ttgactttat tccgtagtta ggttagaaga agaaactact gaataatgtt    420
tactatacaa acacctcaaa atagccaagc ctgtcgaaac acatttagct gataagctag    480
ggatgaagag atcaagagat ggttagctca gctgtattgc atctcatggg ggacgggtga    540
aacgaaccag agaagtaata tacacgtttt ttttttaaaa aaaaaaccga ataatttacc    600
tgttcttgct acaattacac cgataagttt tcaacttgag caattacacc gtctaatttg    660
cattgctgaa gaaattggtc tgttccatta ccactgttga ttaaaaagtt ctacttgtca    720
gcacagcatg tccatgtgcc cagatagttc ttgatctttg gaaaaagtgc tatgtttgca    780
tgcttcggta agatgtgagg ttaaaatgag gaggacataa tgttggcata gggaggtcaa    840
aatgtgttaa ttgagagaaa aaatgtggtg gatattggag aggagacatg gaagtagaga    900
gaaagagatg aggagggagg ggtgaaggta aagggaaata gacatacaga aataaagaac    960
tgtgcgagta atgtgttgcg ataagtgaaa gagagaaagc aagagaaaca gtggtagaaa   1020
attgaagtat agagagagat gtagagaggg aaaatatgga gaactacaag ataaaatatc   1080
tttattcttt ctctatctaa gtatttatct ctttagaagt tatctctctt tgtttctgag   1140
tttaccccta gtattttctt ttttctttct caagcccttc ctctctaaca caatttctct   1200
ctctctcttc tccctctctc tctgtatctg gctgtggcac tttttttgac ctcttccttt   1260
ctgtctttat ctcctttgaa gacattttga ttttcctaca cccctcaatt ggtcttctac   1320
tcaaactcat ctacttgtta ttatattaaa tgcatgaaat cctaatattt taggaagctg   1380
gagactcatt gtgcgtgcat ctgcttgctt gtagaaagtt ttaaattgaa aggcaagccg   1440
aaggggccta attattcagg ccaggacaat gatgttggtt ttagtttttt gtttttgaaa   1500
nnnnnnnnnn nnnnnnnnnn nnnnnnnnnn nnnnnnnnnn nnnnttttga aactaatttt   1560
tttcttagtt ttcaagactt ggcttggcat ttaaaaacat tggtagaaaa tggataacaa   1620
aaccaagaaa cttacatgtg gaagtagtat tttataaagct tacttatgtg tggaagtagt   1680
gtttagaagc ttaattttta aaagtctata accatatggt catcagtaga gtctcatgca   1740
acttatgttg tgacagtggt gtaattgttc taattaaaaa ttttcgggta caaatgtaaa   1800
aaacattatc gaacagtggt ggtttgtgaa atatgcatta actttttgaa aatttgatgt   1860
gtcatcatat tcattccatg ccgtgccttg tttccctccc agctccttat ccatgctaat   1920
tagattcaga ccattatccc tttggaacag ctatgcttaa ctctgttctt ttctccctct   1980
gtacaacagt atatcaaaaa                                                2000
```

<210> SEQ ID NO 78
<211> LENGTH: 2000
<212> TYPE: DNA
<213> ORGANISM: Cucumis melo

<400> SEQUENCE: 78

```
tagcttgtta attcttgtgt tgaagacgtg tttcaacaaa tctgatgggg tattcatctt     60
aagtgtccac tgaagaatgg gggttctgtg gcagatctgt atgttatgta gtgaaaacaa    120
atctgtaaag ttttttttta cttcgaattt aacgttgctt aagcttctgt gtacagtttt    180
atcactgcct cgaggttatg attattattg gattaaatta caatttagtt tacgtttacc    240
ttggaactgt gtatttcttt tgattgctca acttttctcg gggatttttc aagaattgta    300
tttttaaaat tttaatttat ttggaacatt aagaagttgg ttatttacag atgagatata    360
acactgtgat tggggtggaa aataaacaca gcttcaaaca cggagtgaga tatagttaat    420
tacattacat agtactagag attatataaa tcactccact cacatgagtt ttcatcttaa    480
aagattggaa tttacatctt aacagatgca atcttttaat gtagagttct taacgtgttc    540
tcttacggtt gtatcttttc gttttcatta ttctttggtc aaatcaaaat tagactttat    600
agtttttaat gaaatattgg acacactacg attcatcaaa gtaacccatg atcttataaa    660
gttgtgaaat gtatgtatat tgtctttgat caaactttac gtttaattat atcttgaatt    720
tataattttg tatttaagag atgaatgaat tttagaaaat tctaaagttc ctaggccaaa    780
gttgttatag aagggtaaag aatgctttaa atcatttatt ccataatcat tagttttata    840
atttttattc ttcgtaacta ttttttaaca aaaaaaaaaa aagttatgca tctcttaaat    900
actatctttt aaaagggaaa ttttcataaa taaataaaaa aagacgatag tatacacata    960
aaaaaaactc aaatgattta tagagagttt gatgaatttt gctggattta taaatagttt   1020
agaaaaataa gtattaacct aaaattttgc ctatatctca atggccttct atgtctatgt   1080
tatttcttaa ctaaaatcga aaggatatag gcttatggat tggcttaagc taaaaaatgt   1140
cggtccaaat agttgagatg tcaaacctta aaagtactac gattatgtga ttttcacatg   1200
acatagtgtt ctatggtcaa attttatagc gtacttattc caatccatca ctttttatag   1260
aactaaaatt catagttcct attttaatat atatatatat attaaaaaca cacattaaat   1320
gatgatttta tctcttctag gttgattgaa aattactaac taaaaaacac ggtgcctcaa   1380
acctccaacg taaatacgat ttctaagaac tgtgtttttt gtaaacgcca agtgactgat   1440
taaatctctc cattctctgt ttacttctat ttggggttat ttatgctaaa ggatattatt   1500
cattcaatag aataaatgtg agatagtcga gttatattca tagatgttac aatgaggtga   1560
ttcattcctt tgtcaaacaa tgctttctcg actcgtattt tactgtattg gatcgaaatc   1620
cttcttactc gcatggtttg ccttcgttga ttagttttgg tatgaattga tgctttgttt   1680
aagggggaaa atgaaaatgg ttcaattgga ggacaattgt ccaaatttcg ggacattatg   1740
ggttaaacac aaagaagaag tccaacagtg taattttgtt aaagattgcg ttacatttcc   1800
gaaatataaa tgagggtatt ttggggaaag gaaatcaata taggccttgg ccgggtgaga   1860
tgcgaaaaag tctcaaaact gagtgagaag cgtttgagct gggctcgcag ctattgaaaa   1920
agagagaaca aaccctttcg tcgctcttat tttcttcctt tgatctgaaa tttcctgttc   1980
cgatctcgct ttaggacgca                                                2000
```

<210> SEQ ID NO 79
<211> LENGTH: 2000
<212> TYPE: DNA
<213> ORGANISM: Cucumis melo

<400> SEQUENCE: 79

```
aattcattcg ggattgttat gaggtaataa aaaatatctg agtgcgaaca tgataattgg      60
taaagtgaaa aaatgttcag ctattctgtt ctagatacag ggatggaagt gggaacaatg     120
ccaccttgct tattgacaat aaaatgagga gtggcaatat tttgtttctg aataaatatt     180
cactagcata acatattagt gatgattcaa actaaagtgc actaggtcac tagtttcttg     240
attcatcgtg tttggtagta atggtaggta ttgtatctta tagtattgga caaagcttta     300
ccgaccataa attgtggata atgtgcagag aagaattggc agttgaacgt tcctggatat     360
tcaagtgatg agtggaagaa tcacaacaaa aatgtaagaa aattatatta ccctctctaa     420
aacatcattc tattctcctc cctaaaaaat cattctgttt caatttaact ttcaaaattt     480
tgttttagtt taaccatatt gagttttttt tctttttaa ttatcgtagt tatcatcaag      540
tgatgtccac aagaaacgtt tggacatggt aagttggact tatctcttca agtgtttgct     600
ccatttcttc ttttatcatt tgtctcaaat tttctcttct ggggtttcat cagatacgcc     660
tattgaagga agcctcctgt gtcgaaacaa atgtaaacag ccctaaagag atggtacgac     720
aaggggttgg aatgtcaatt ggtcccaaca ctctaacaag gccttcaccg agttcagaac     780
aactattatc acaaacgtct ggttcacagt tgctgcagca aatgatgagg ttttagtgta     840
ttaactacgt ttgaaactaa tgcttggtag agatcccaac tacttggtga ataaccaacc     900
ccagtgtcag ttcagggata caacaaataa aatgagattt agaggatgcc atatcagagg     960
gaacctggac tggacatctg tgtggagtgg agtgtgatga tttttagtga tacgtctttc    1020
ggaatcaatt tttttaggct gtataatatg aagttgcatt atctggaaca cgggcgtaat    1080
gttaattgta caaaatattt ggcaggtcat attagtatag gccttaagta ttgttgttgt    1140
ctaccatgaa ggacattttc caatttatga ttgataatct ttacttacaa tctcgagtca    1200
tatgaagttt gttgatcagg atcatagcac aattattaca aaaatgaaat agaagatatg    1260
atttttcacc ccccccccac cccccccccc cccccccctc ccattcccat cccccctttt    1320
aaactgttac attacaactt gttaactgtt gattttccag atgagagaaa gggcctactt    1380
gtcttgtaca gaaaattcat ccatgacgat aaatgcagat gacctgaacc aaacgtgaca    1440
gtaggggttt cttctatgcc acaaagctcc aagccattca tggtgcgcat gtggtacaga    1500
gaggcttgat ggagcctctt caccttggtc cttagctatc taaaaattgg cttcttatgc    1560
tgatatatct cttcccatgt gcatttggtc cactccactt tcttcgtcga atatccttgg    1620
gttaatcctg aatggtaagc acaacattct tgctaattaa tccctctttt tatcctactt    1680
gccaactgta caagatgagc agaagaagaa ttgcccaatc atgaggtcat taactgcaaa    1740
aaagagaatt tatttctttc tttgagaatc tgatcttctt gagagttcat tgacagccac    1800
atgcatcaca aaatgaaatg ctgtgtggcc ctcattcatt cattcatcaa tcttcctatc    1860
ctgccatttg agtgaatgtt actccaactt gcaggaagct aaattagtac ttttttatat    1920
aaaccctatg aaactcatca agaaaccaca ccatcccaaa aaggaaacga gtgaacaact    1980
agacaactca ccccgaaaaa                                                2000
```

```
<210> SEQ ID NO 80
<211> LENGTH: 2000
<212> TYPE: DNA
<213> ORGANISM: Cucumis melo

<400> SEQUENCE: 80

cagcgatctt cgtagaaact aattcaatgc tagctcatta tttgactttt ctcaggcaag      60
gctccgcgag gaagagaaaa ggtccaattt caggaaccaa gggcatggac aggttccggt     120
```

```
cagaagaagc tttttacgta aaccctttgc cagattgttt atgtcaagga gaattaccaa    180
atggaagtac gacttccatt ttcagatagt tcagtagaac atcaaagata aaatgctctt    240
agagagctca atgtatatgc aggcgaccac tcaacgtgtc accagctttg tacatccaat    300
aagccagcta cgatggaacg acggagtgtt tataacctga gttttggtag ttggcggagg    360
cggtgatggt ggtatagaag gaaggtcgag ggatggcaaa ccctttacgc caagtagtgg    420
aagggagtag ttggagatga acacattttg agaagtttcc aagatcactc catttggggg    480
agaggggatg ttggttattt agcacaattg ttttcatgtt ttagtaattt tatccaataa    540
tgagcgaggc attgaagcaa ttaaatttat ttttaatgat tttttcaccc ttccataggc    600
tttttctttt ttcttttcct tttagtttgc aaactttagc tccttttatc ggctgtcgaa    660
ctcatttttg aagttattga atgaaacaca gtttgggctg tgtcagatgg gtggtgaaat    720
tttatacatt ataattacta cataaaatga aatcatattg taattttcta tctatgccac    780
aatttttttt tattgcatca tgaggattaa attgtacgag tccaaatttg tacagtcatg    840
tttttaaagc tttcgagcat tgttactaat gcatggaaag gatcgattat caagtatcct    900
cccaacttca tgaaagttat tatttgtctt ctaaatttgt tttagaaaat gtttaattaa    960
ttatttgaga agaaagttta actaaatcct attggtttcc tctaaggttg tcatacttat   1020
ccaataacaa ttacgtttaa aatcaaaatt attctaatgg tataagacta atgttttaaa   1080
agcataaaat tgatgaggaa ggattggaag taatactatt tattttgaag gtaaacattc   1140
ttgaatgtct gtcctaaaat cactaatgtt ttcttagttt gagactttga gtcgttgaac   1200
ctctccatct ttataaaata taatacgagt ccttcacaat aacttaaaat atatactaaa   1260
tcctaattaa tgaaaaataa ataaataaaa ggtacaaaat cattaaagcc taaaaatcta   1320
ttactccttt aaaacttttc aagggtccct acaaccaatg agaaactacc acgtcatttt   1380
cacaatccgt tcagtgttta gaaaagtcaa atcgcaccgt ccatttatcc actcgtacca   1440
agtacggtag gaatctatct accgtccgat taagcacaaa gaagcacagt aaatgtcaat   1500
cgtgtccatc cgccgccata ccgcacatcc ttcgtccgac cggaaggccc tatataaagt   1560
cctttggttt tccgaatttc tacttcattc gcttttgaaa gatttcccaa tctcttcgtc   1620
ggccaaaatt ctctctcgct tctcaaccct tcttcggctt tttcatccag gtttgtttct   1680
cttctctttt ttcttccttt gttgttcttg gaatatgttt aatttcattt gtttttccat   1740
tcaatttcat gctagatttt acgattaggt tgattttctg ttcgtagatt gtaattgatg   1800
gttagggtta gctttttctc ccattccttc tggaatctgt ttcttgacct tcgaacttcg   1860
ttgataaatc tttagaaaca tttacataac caaacaataa ttgaacaact cgtgttgtta   1920
tgcctatata atagcggtta ggaaactgga aacgccctta taattgaaat cgccttagaa   1980
atttgttttg attcatacag                                               2000
```

<210> SEQ ID NO 81
<211> LENGTH: 2000
<212> TYPE: DNA
<213> ORGANISM: Cucumis melo

<400> SEQUENCE: 81

```
tgtaatgact aaacatacta tagcctattt ggaccgggtc gaaaatccaa attaaccaat     60
ctcccctcag cctcacacca aggataaatc atgtcaacct tctccatttg acatgctagc    120
tggacaaaga gaaatactaa ctcaaattcc atataaatat atctttacga ctccttatca    180
```

```
ggtaatttag actcaacaat tagtaataaa tttagtataa tgaatgatag tttccataga    240
tcaattatat catttattga tttgctagat ctagagtgaa cttattgact aatataccaa    300
atataaaata tatcaatgaa cttacccacc aaacataaaa atgtaatatt tatatctaca    360
tgaattttac aataaaaagt gtatcatata aaatacttat atacataaac cctattatat    420
atatatatat ataaaaggaa ggtaagatgg aaaaaattgg aagagaataa tttgacctaa    480
aaaaatcgaa agagaaaaga gtatttaata tataaataaa aagaaaaaga gagaaagaaa    540
aaaatcttgt tcgtcgactc ctcaaaaacc ccagcgtgta gcggttgtga gagaaggaga    600
gctcgtttcc atcacgataa aaccttatct ttctccattc ttctatcttc tcttccggag    660
ctctctccat ttctcagccg ctccccacaa tttcctctaa acacacacat acacgactat    720
ttttccattc aaattccttc acttcgtttt ccattttcct tttctttacc ccacccactc    780
acccacctct cgtcgatgga ctccatggac ttggcccaac aaccgtcgca acagaattca    840
gtctcctcag gttcttcttc cacttcctcc tcctctttta cgtcttctac cgttgattcc    900
catgtcgata ctccctctct cgatgaacct gagatggggg ttgctgaaat taaaactagt    960
gtagttgccg atgggggtgg tagtgatggt gctggttccg aaactgaagg gtttttgagt   1020
ggggaggagg aatttgagtc tgcttcagat agaccaattg tgggttatcc agaggaagag   1080
tccatcggga agtccgccca aggggctgat actggtactt cttttgtggg ttattctcaa   1140
ctttctgctc cggttagtgt taggccaatt gcgaaggttt ctgttgatag tgacgttgag   1200
gaggaggatg aggaggagga ggaggaggag gatgaccttc aggtggatga gaacttgagg   1260
ggaaaggagg aaattgagga taaagtgggt ggagaagatg tttttgttga gagtaagaag   1320
gggaaggaag ttgaggttcc agtggaaaag gaggagacta ttgttgtatc tgatggaaac   1380
aagaatttgg atgatgtggt gaatgatgat gatgatgcca gtcaagtgca ggaaagaaca   1440
attgagttgt cggggaactc aaaagagggc aatgtgcctg aaagcttagt agctgaagat   1500
gttggctctg tgcccgagga atctgttgat ggtgggaagc aggtgtcaga aggggatgaa   1560
ttgaatgatg tgacagttaa acagtcacaa aatgaggctt cagatggaaa aaagaagcag   1620
agttggataa agaaactctg gcgtctggga agcaggctgg taaagggatt gacttgagtg   1680
agaaggtggt tgctgaggat gtagagcaat tgaaagaaca ggaaacacct ggttcttctt   1740
ctgacgagaa agctgttttg ggagaccaag caagctctaa gcttgtgaaa ctagcagatg   1800
aaaaacaaga agaggagacc tctgcggctg agaagcaggt agatgtggag gtcaaattga   1860
atgacacggt ggctgctgct gaagatggag agcagttaaa aaatttagaa actgattctc   1920
ctgttgacga caaaattgtt ctagctgatg acgaaaactc taaggtttta gaaccagcag   1980
atggaggaca agaagcagaa                                               2000
```

<210> SEQ ID NO 82
<211> LENGTH: 1072
<212> TYPE: DNA
<213> ORGANISM: Cucumis melo

<400> SEQUENCE: 82

```
tttaatatgg tatcagagca aatggtccag agaggtcttg tgttcaagcc cctgcattta     60
cgtttccttc ccaattaaaa ttgtttccac ttgttgggct tttcaaatat ttcaagccca    120
caagtgaggg ggagtgttag tgtatataat taaatttgcc ttcttcaacc actagctgaa    180
gtttgtgggt gaattggtgg tttaatagta actatatcat gcaattagct tttttgagtt    240
caacaatatc tgtggtggag atttgaaatc gagattatga tgccttaacc atgtgaacta    300
```

```
tgcttaggtt gacaactata tcatgcaact atcgaaaaca tcatctctaa tttataggtc    360
tttttaaca tagttgaagt ttcaatattc tatatgaaca cagctggcta tttaaattac    420
catattgaaa agcagcactt gaaatgcttc taaaaattaa tgccaattag aagtgtttat    480
gattctaatt ggttaacatt actgaacaca gattagttat agttattgaa agaataaaaa    540
ttgtaaaatg ccgaactaat accaaatgga tgggtagtct gcaaatttta ccaaatggta    600
ctacagctgg tgatgaactt agaaggggta aaggtatagt gtaactgtct aagttaatgc    660
cataaaggta tagtgtaact gtctaagtta atgccattag cagatcaagt ccgttgtatt    720
atgtactgaa cacatttttt aatcgtatag ttctaaatcc tataatctgt cgaccaagtt    780
ttaggtttgt taggctgaaa gttcatgcaa atctaggtgc ttttttgtac taattgtttg    840
agattcagaa attgtatctc aatgttctcc atgattatgt gcgtgtattt gcaaacagct    900
ctttggtttt ttcttcttct tctgacaagg atagtcaaat caattacagg acataatttc    960
aagatttaag gagagaaagc aagggaaaga ttcacgggag tggactgagt ttccaagcag   1020
agttgcagtg caattaaatg atactcatcc aacccttgca attcctgaac tg           1072
```

```
<210> SEQ ID NO 83
<211> LENGTH: 1730
<212> TYPE: DNA
<213> ORGANISM: Cucumis melo

<400> SEQUENCE: 83

gttcaactcc acaagtcaaa tttttttgga aatctcgtgt gaacacttgt gaaacacttt     60
atttttatat taaaagaaac aagaagattt aagatgagaa tcccgtattt gtttggttga    120
aggacaatga aattggtaaa tatatcccat cgaaaaataa tcaaatctag acacaaaaat    180
ttaaagttaa aacttactta ataatcagct ggagcatagt ttaatttgaa tgaaaataaa    240
aatcctaaac tagagaagtt tcttatggta ttgaaaggcc agtttagaaa gcccaatagc    300
gtgggttttt cttggaccca tgtgtatgtc tcactcatga aattaaatta attggcctcc    360
acattcacct ctctcctccc aattcccata actcaatttt agacctctta aatgaaacat    420
atcatatttt cataaacttc ttttttacgt tacttatgag attaaaagac tttaaataaa    480
gtgtcaattt atattatagt agatgagatg gagtgtgtgt ctttgtgccc tccttggggc    540
ccaaggacta agtaaggatg aaagggcaaa gaaatacaaa atagaagaga gtagaaagaa    600
aatgaaatgg aatatatagt aagggttatc gtttatggtt attatgaggg aagggctgaa    660
attgataatg aacctatcct tatcttccct tcttcacctc tcattttgct tgaaattaca    720
aatgactttt ttttcaatta ttttgtgtgt acatccaaat gtggtatgca catatgggcc    780
tcccattaac ttgtgatcca aattaattct tttgcaacct aagttgaaat taaacacttt    840
tacctctctt tttttcccta acaattttac tttcattgtt agatggttga ttatcttgac    900
atgtaacaaa aagttctctc atgtcaagat agaaaaatcg aatatttgat tttgagattg    960
ataatattat aatatcagtt gagctatact cattttaact atcagtaaag cttcattaac   1020
atattttttta tttagtaaac taagattaat ataaatagaa tcttactttc attatatact   1080
ttgacgagac ttaaaaccta tttagcgcat gatttttaaa agttggtagg attttaaccc   1140
ttgaaaaatt ggtcattcgg gaatcaaaac attagtttcc ctttgagcat ttatttttaa   1200
agcacttcaa aagctaaatt agtagcatta aaaaaaaaag tcaaatagta tatatatata   1260
ccaaaacttt gtttttcaaa actatatttt aaaccaacat tctttttttt ttattattta   1320
```

```
ttactaatta agtgcagatt atagtggttc tcttttgtag ttggatcaaa tatttcattc   1380

ttttttgaca ataacaaaag ttaaaatact cattaaatgc taaaaacttc catactaaca   1440

ttattgaacc attaaatata tgagcaacga aagtataggt aagaatttat attgttgttg   1500

tttagtttgg aaatagaaaa tggaccaatg ggtgagcttg gtttaagtta gggttcttgt   1560

ggttggatga taatgaaata aaatggccaa aattttaatg gagaagaaga tccctttaag   1620

ttcaaccact aatggagtct tttaggatca attcacaacc cctttctcct tctgccacgt   1680

gtcatctcag ctaatctcaa ctgtgtggtt gttgagaaat tttgaaactc              1730
```

<210> SEQ ID NO 84
<211> LENGTH: 2000
<212> TYPE: DNA
<213> ORGANISM: Cucumis melo

<400> SEQUENCE: 84

```
aactagacta gcgagtgcac aaccaaatta caaaatcctt aacagagaca accatctatc     60

tcctttaaag caacaataac atcaaccgaa ttagaatcca caatcagtaa agacgatgcc    120

gacaccaatg accaaaaccg atcaaatata gcttattacg gaccattact tcaacagtta    180

catcaacaaa aaaaaaaaat taaacattgc taataaaatc tgaaaatgag gaaaaagaga    240

ttaaaagttt tgaagataga aagaataaat ctgaaatgtt ctaatttgat atataagaaa    300

tatgaggtaa tatgacgaaa gcattttgat agttttcacc aactcccttt gtgaaaggat    360

acatccaacc aattttacaa tttctgttca aattttgtcc acctaccctt ctcttctgcc    420

ccccaaggct gctttctttc ttttattatt tgctaaatta ccaaaaacta ttttcgaatt    480

aaaccatcta tttcaattat atacgtcatt cgaattttaa cttaattaac attagtatat    540

gtttcggatc aaggatagtg gtataaatca tcctaatttc aatttgtatt tagaaaagtt    600

caattatact taaaacttct aaaaatttta tattttaaat ttggatataa attaaattta    660

agatttatgg aaggtaaata attagagcaa aacaaacttc aaactatatg gaaaatagaa    720

aaggaatatt ttagccaaac aaaaacactt attatattta ttttgttttt tgtttttttt    780

aatttaacaa tttttttttt tattggttga atgtgtttct ccactggtga gtctccaact    840

ttgacctgca aagggtctat atagcgagtt tcacgagcac ctaaccaata tctgtgtaat    900

aattcccatt tttctttcat acccacttca tttgatcatc tttttcacaa ccccggatct    960

ctaattcttg ggaatttgcc tctttctcga tccatttcca ccgtaattga aaaatattca   1020

ggtttgattt cttctgggtt ttcattcaac tgtctaactt cattatgccc tttatgtgtt   1080

tgttgaaagc cccccaccca ccatcgttca atgcggtttc tttacctttt gttcggtttc   1140

aacgatgatt tagaagttat agatggatgc taattgtttc gttgttggtt tgatccactg   1200

atctgccttt gattggcata aaaggagatt ctagatcttg ttttgatgtt gtgatttatg   1260

gatattattg ttatagtcgt ggaagttttt cttgtcgttc tgcggtatat ggttgtttta   1320

ttttttgagt ggtaaattga gcagattgtg aacttttggg ttttatggtg aaagcatgaa   1380

ttagtaaatg tagagctgct gaaacaaaat ggaggtttgc tagacctctt tgtgaattct   1440

taatggtcag cctccatctt aagaggctaa gtccaaaaat ttaaggcagt cttttgttat   1500

tgttacaaag gacaagaaat aacagaggag ttattttaat tgaatcaagt tggaaagaag   1560

tactacttca tgcttctttc aaaagcaggt caaagtgctt taaagtcttc ttatttattt   1620

attttttcct gaatcaattt aaactaatga tagaaagaag tgttttttaa tgggttatta   1680

taagtaacat caatttttaa ccattccaaa agttacatca aattcatcat agtgtgagtt   1740
```

```
tacgaatttt ggaagttgta attttaagtt aatacttctt ttaaggaaat gtacactttg   1800
catgttgtgt tcataagggg tatttctttg acaaacgcag caaccacccc ttaatgaaaa   1860
ctacaccacg gtggttggtt ttttcttgtt attttttttac ttggaattta caataagttg   1920
ttatattcgg atatatggca aagcagatat ctgtttttat ccgaaacctc ataaatcttg   1980
aatgtgcagc aggtaaaaac                                               2000

<210> SEQ ID NO 85
<211> LENGTH: 1020
<212> TYPE: DNA
<213> ORGANISM: Cucumis melo

<400> SEQUENCE: 85

tcattgatga agaaggaaac tttaagccaa ttcgacaact tatccattca acaactttcc     60
accttcagac attcagattc aactataata taacataaat tgatagtcaa gtctttttttg   120
agacaaccat aaatcatctt agcttcgaga actgtcactt ccttaaattg gtgaatatat    180
cacattccat ccattcaaaa ctttgttttc gaacttttac tgtagttatg aatcaataaa    240
ttgggagaga tattgtttaa aaagagagag catatttgtt tctattattt actctctcct    300
aagagagggt taattagtct ataaatgatc tattcttctc gtccattgaa attttgttat    360
cctaaattta tgaatacttc tacccaaaat aaagactttt ttttttgaaa agtgtcaaaa    420
aaacataaag aaattgacaa aacattcatt tttagtggat ttttacggac gtaaatagtt    480
tgttttgttt cttttaataa tacaattttt ttactttaaa aaatattttt gttataaaac    540
caccgtattt ttattcaatt ttaataaata aataaatgaa agaatataaa aaagaggaag    600
gaaaaagaag ccaacgaacc aacggttgcc acgtatcaaa ggtctaaagt gcgcaaaacg    660
aggccttcgg aaaccaaaat gcgtggcttc aattggagca agtaaacatg gaaaccacgt    720
ccattgtaac gcttcctgat ctcttcttta caaccgttgg attcgagtac tttttctcaa    780
cgattaacga ctgagtggac ctccacttgc ttctgttcca cgcgcgtggg attgacgtgt    840
ggtccacgca actcttctcg ataggatcat tcgagaacat cctttactta aaccgcctct    900
ctctgcctca atttctcgtc acttccttct ccttctttac cctttccact gcggctgatt    960
cttcttcgcc ttttattctc tcgtacgccg ccatattctt cacttctttt tccggcgaca   1020

<210> SEQ ID NO 86
<211> LENGTH: 2000
<212> TYPE: DNA
<213> ORGANISM: Cucumis melo

<400> SEQUENCE: 86

aaatcatctt ctcccatttg catgtgttaa cgcctaatgt agtacattta ccatgattcc     60
tagaataaga ccgattttac caacgagaag ttgctttcaa cttgctacaa tatacataac    120
atttctttgg tacgttattg atgagaagag gtataaagca tttcacagta ttctctcagc    180
aactcattag tttaaaaaaa aattaaagga atatttgaat atcgggggat gaattaagta    240
tagcctcaca atttgccagc tccttctcct tagcggctgc caacctccga agctttgcag    300
cctgtgcaaa tgtagacggt ctacaagaac ataaaagcaa atgaatacga tccccatgac    360
agccataaca gttgcaaaca atcatataga atgaatgatt tgagcctttt ttttttgtaa    420
gatgatttga gccgaattaa cagtgtctaa tgctgaatcg agctggaaaa tactacttac    480
tgagataagg tgctagcctc cctcagaagt tgctttattg atttgcgcaa ctccaattcc    540
```

```
acctggctgt tggaacctcc ctgaaaagta cacgcatgat ggaaacatga ttgtttcaaa    600

acaaacaagt tgacaagatt gaacggataa caattataac atagcaaatt cccagacatt    660

aaaactgaaa atgtcaatag atctccacat taaatgcatc acgtccctaa actaatcaaa    720

tcaaatgtct tcaatccaat atcgtaaact taacgaagca cagttaggca tattgcattc    780

tcaagtctgt caacgaaata ctgaaacgcg ctacagccca aacctcaaaa ttttcaacta    840

taaataacaa gctttgaatt gaaaaacaaa cggaatgata gaaaatacaa acacgaaaaa    900

attccgacgg gaaaaagaaa atcaaacgaa aaggcgaacc ttcttcaggt gctccagcca    960

tctagcgaga aactgaaaac cgataacgat aaagaaaata aatggagcgg caatggagct   1020

tccatgctct acgattcctt ccgcttccat ttccatttcc agaggacttt tctgccacaa   1080

cggtgaatta atcaaacaaa gaaactccgt tcatcgtcgc aattcgacgg aggttattct   1140

ggaagaagtt gagatcgtaa ttgggctacg aatatcatca aaggggcttc aataaaaggt   1200

ctctcaaaac ccaaggccca aaaaaacgaa aagcccagcc caattagtgg agaatcaaaa   1260

cgctgcgttg tagatacaaa tatcttagga aagggaacca agttacgaaa ataccccctga  1320

gtagtgagat caatgattac ctcaacgacg cgttaatcgt tttatcacgt ttattgtgat   1380

aagttccgca ctaaggaagg gacgagttgt aggaagggag gggtaaactg gtgatttcgc   1440

attcaaacaa cgggctttaa ctcacgtgtc cggatctgtt gagagggaac aattcacagc   1500

gaggaaattg caaataacac acaaaggaaa cacaaaagag cggaaagcaa atgtgaagag   1560

acgaagagta gccaatgaga aaaaaggacg aggatcgatg acatggcaaa agatttttga   1620

aatcccgcct aaacccggag tttcaattga tatcgcgatt tatctctccc tctctttaac   1680

gaaaccgact cccttcatat ccctctctct cgctccctct tcacttcaaa gggcttttcc   1740

ttctttccac ataaacacac gcactcgaag ccaatctcaa aaccgcatca cacgaaccaa   1800

actaagccta acccaatttt ttctcctcat atttcactct cacactcttt ccttatcttc   1860

ttcttccccc aaaccctaga gttttacagg taaactccca atctctccgc cgctccctcg   1920

ctcgattctc cttcgtttct ccgccttttt tcttataatc attacctgtt ttctccttcc   1980

ctctatctgc aggattcatc                                               2000
```

<210> SEQ ID NO 87
<211> LENGTH: 2000
<212> TYPE: DNA
<213> ORGANISM: Cucumis melo

<400> SEQUENCE: 87

```
gtgtagagtg agtgacggtg gccgacagtt cgtaacattt agttgttagt gagagacggt     60

gagacgtttg gtaacaaact ttgtttttag ttcaatcatt gctttgtttt ctctttcttt    120

tccttaatgt ctaatgtttt catcttcctt tctttatttc ttacccaatt tccgaatcaa    180

attttaattt ctaaaaaagt atttaaaaaa aaaaaaaaaa ttagtcgctt tattcgagaa    240

tttcataatc aacctaattt tcaaaattaa tcatcaatct ggaaactttt ttattttttt    300

tctcctttgg attatcctgt atgaaagtca acatactttg cactccttga gaatattttt    360

agtggtgttt ttttttctc ttaataaata aaaaagttta catctataat aatcaagatt    420

ccttggcagg tgtcactgtc aaaataattc ctatttgttg aagttgaaaa taatttaact    480

ataaacttta tttgaacgtc aaaaaaagaa aaaaaaaaga tatatgaatt cacccattcc    540

ataatttaac tatataactt tatttgaatg ttgaaaaaga aaaaaatgaa gacaaagcaa    600

attcacctgt tgccattacg acaaaatttc aaatgcgttt tattttgttt ttatgtccac    660
```

```
aagattctct atttgtattc tgcgaaatta aagtcacggg cttcgcacgt gtgtgattaa    720
tagtatttgt aaaagggcat gtagtcgaac aggatgggaa ttaaaggaga ttatgaatgg    780
gttgggtcgg gaaggcccat ttctataatg aattgatggg ccgtcaagga catttgtcta    840
cataaagggc atggaccatg aagttaagcc cacttcctaa acgagttcct tagtgtgtct    900
acattcatat ttaaatcatc tttaattcag aattttcacc atcatcaaat aatgtcttat    960
aaacctccca ttttatagtt taattatgga ttctaataaa aaatctctaa cttcaaagtg   1020
gataattttt tttttttttt aagttgaacc atgttcattc atttaattac atggaataaa   1080
aataacgtaa tttaggttaa aagttgagag gataagatga agttgaaaaa ttacaacaag   1140
ttaagaaggg aatatgaaga agaagaattc aaaattgaga acataataaa ggaattaggt   1200
ccaaagctgt aaagactagg agaaacgagt agagaaggga aggactcgtt tttcaaagaa   1260
aagaaaagtg tggaaaagga aaaaggttca ttaggggtgg tgaggaaatg gatggatatg   1320
gaatgatgat gatgagaaag aacagcacgg gaagtttccg agtagttgcc ttttgcatat   1380
accaacaagt tatctaataa aatgttttga ttaattacat taatttattc aattgattta   1440
tcggaaattt ccatactctt cacgtgatat gcacgtggtc ttcccatgtt ctaatatttt   1500
ttgtttttga aaatttgaat tcctactctg ttttgttatt ctgctcattt aactactcaa   1560
atattttagt ttgtagatat aactttgtaa atttttatta taacattttg taaatatttt   1620
aaattgtgcc catagattat gagtagataa atttacgaat taaaaaaagt ttaattctca   1680
cttcaattta attttttttt attattatcc aaatctattt gtcgcagtgg ggaaaacggg   1740
gacgtacggc cgattggagt ccaattagtg gatgtgaaac gtggacggta gagatgcaat   1800
atgaagctgg acatcaactt tgcgaaggaa ttgttccttc tttccctctg acgcttgtcc   1860
cgttattgct cgttttaaag caattcgagc tccgcgttgt ctcttccctc acgttttcct   1920
ttcaatccca ctgctcctcc tttcaccaat aaaacaaaaa cgcctcaaag aagaagaagc   1980
aacgaccaga aacctcaaaa                                                2000
```

<210> SEQ ID NO 88
<211> LENGTH: 2000
<212> TYPE: DNA
<213> ORGANISM: Cucumis melo

<400> SEQUENCE: 88

```
gttcgagcat gtgaatgtct tctgttgttt gatgttagaa ggaaagagat gggttaggga     60
gttcctgttg atgtctagta ggttcttttt tttttctctt gtgcaatgta acatagtaac    120
ttcgctgcaa agcagctctt atccttagaa tacgaaaatc ttctgttttt tgttatgttt    180
ctaactttat cccttcttga ttttaacttt tgagttaaat tccatctctc tgactttgct    240
ttgtggtatt ctgtttctgt tgtatgataa ttcttatgga actcctatgc tctctctcat    300
tgccttcttt ttcggctgtt acttaattac tttcttcact tgaaatttat agcttctctc    360
acaaatttga gctcattcaa gtatcaaaat tacacccatc tcataccata tttctatctc    420
tgaaggagga tttttcccct tttaaggagg gtagattgac aaagctgata gggtgagaca    480
atttaataac tcaggtcaga tgaattatac attgaagaac tctcatccag ggccagtgct    540
ttgtttataa caagatgatt aatgtgttgc tatcaaaact ttgctggttc actaaaaaaa    600
actcttggtc cttgaaagta ggcttttact agttttagct ttaatgcaca tctgtatgtc    660
aaccacgaac tccatttttc ttacttgatg catgtgcaac tttagcagct ttctaagttc    720
```

```
atatcaaagc aaatgtacct ttattcctat tgtaattcct tttctgcttt cctcttttat    780
gaattgtcaa aaatatggac aggaaagtaa gctgagcacc aacaggttgt acccctttt     840
catgtcttga aaatgaacta ccaggacaca aatcagatga tgattgttgg gagaaggaat    900
gtaagattat tcgttctgtt tgatataaga gatgtaagtt cacatgtctt acaacttttt    960
gaaatttgtg tgtcgcttat gtgcagattc ctgtatgtca ttagtggcat ttgtaagcta   1020
caattgttga atttttgtat tattatctta aaaggaaatg acaaaaggta taatcaaatc   1080
aagctgaacc taaaagaagg tacaggtttt tagtattatg catgaagaag gtttttcatg   1140
tctcttctgc catttggatt ttgtctgtga caagggacta agacactaca catgatgctg   1200
gaaactgcaa gagtgttttt accctaataa gattaaaacg tgaaaagcaa ttagattttc   1260
gtgcatatct atctttttgt gcattccacc aaactgttcg atcataactt gtcaagatct   1320
tgctttttcc ttttttttat aaatatttta atatccttct aatgtgaatg gtgaaaagag   1380
atgcacaaag ataagtgata ctatagatgt atctaagtat taccottata cctttgccac   1440
gtaagattag atacgagaag agaaaaaaat ctatgagtta gtaatagggc aacaataaac   1500
cacagaaaaa ccaattaata cctttcctca ttgtctaata atatctaaaa gaaacttctt   1560
ttcatgttaa tgaaccaaac tatgttgtgc tatagcatga gcacattatt tctacccttt   1620
agacaagtga tgagaatgga caatatttcg actgagttca ccagaatgta accaacggtt   1680
ttgcatttgt aatatgaatt tgaaagtttg agattcctta tacgaggacc ttttttcatg   1740
tatctaacaa cacgagaacc accaaaatga gaagggagtt ggtccaagcc aaaagaattt   1800
tgacctccat gaaaatccag atagtggggc atccttatct aaacaatcag aacctgaagt   1860
ccgacgtagc cttatccaca tttcaacttc aaaaacactc cctctaagat cctttcgaac   1920
caccaaaatc taagaaaatt tctcttcctc atcctcctcc gacacaaaat ctagcttcaa   1980
tttcattcct ctgtaaaaac                                               2000
```

<210> SEQ ID NO 89
<211> LENGTH: 2000
<212> TYPE: DNA
<213> ORGANISM: Cucumis melo

<400> SEQUENCE: 89

```
attcgtcttc gcattatcag taaatttatc attttaagag tttgttcttt tttaaaaaaa     60
attaatcatt tcgataaagt tggagaattc aaaaatttct ccaaataatt tataaaaact    120
ttcggttata tatcgaaaaa attaacatgg tattaaaacg atcataactc aattaacata    180
aacactccct ctcaacttta ataccaaatt tctttattaa cgcaaaattt aaaatttgtt    240
tttaaaattt tcacataaca taatagaaat acttttcttt atggcaaaaa tacaataatc    300
aaaattgatt gatggtgaca ggacaccaca caatattttt aaattttgaa tatacgaact    360
atataataag atatttatga gattcccatc ctaaagattc ctagagattt ccttgtgtac    420
aatattacac aagtatcttg gaagtccaaa gtcctgagaa aaaagctatg tataaagtaa    480
tgtgtttgtc gtaggaaatt tacttcattc gtgtcattag ctttttattg aaaaaaaaaa    540
ttaggtatat cttagtgaat ctcacttaat cgttgtcgat agttattctt ttaatatcat    600
tatatactaa aatataacaa tattgaaaag ctaaaactgt atataaaaaa aatgttacct    660
ctaaactttt atcgtttatt taaaagataa atatattctt tcaaaactta caatcaacat    720
cctacgacta tcattatagg tacaaatctt ttcatgttta cacaaaaatt agatttttaa    780
atggtgtaat gatgatatat aacgaaattt tgaatgatta ctatttgagg ttaccattgt    840
```

```
aattggtcgt gttgtttgaa atttaatttt attagaaaat ttgtcaaaag tagcaaaaat    900
gaataaacta tttaaacttt aggataaaat caagtgttat gagtttttgt ctagtttata    960
tatttttatt tttattgaaa acccttttcc tatcttttca ttacttcaaa atagttttaa   1020
aatgtctatt aaggctaaag ttagtataaa taaaatttcg gaaatttttt ttcgaaaaaa   1080
attgataaat tatttatatt ttatattaaa gtcaaaattt attacgcgta gatgtttatc   1140
aaattttctt tctttttgtt gataattttc caaaatttgg ataatttttt aaaatagtaa   1200
aattattaaa aaatgaaaac aaactattta taccttaagc aagaaatact aaaaaggcaa   1260
aaattcattt acttcatgaa gcgtaaaaat taaatatttt accacttttt gttatttttt   1320
accatctcta tcaattattt gtaaaaagaa aactacaaaa ttagatgttt tttctttttt   1380
aaggtttaat caatattaaa atttcttaaa ttggcagaca agttggtgtt ggtaattacg   1440
aataaatccc gaattgacta aaaataaatt cttctccaag taaaatagac acgtggatga   1500
agaaataagt gaatcaaagg catccacagt tcaataaatg gaaaaaaacta ctttctgctg  1560
actcattcat aagttttcat aaaatttcat aagaaaggcc aaagggctta tgaaagtgaa   1620
tgtcatagca gtaaatgaag cacagcgcca ttgaaagaca actcaaattg catgcaaacc   1680
cacataatta ttcaacaaac ccacatcaaa tttcccataa agatcaattc tttagggggt   1740
tcaattaccc aaaagtgagg tagttgaaaa ccattaaaca acaagaaatc aacaattttg   1800
taatttgttt gtacagaagt aagagataaa atcatcgtta accattcctt tatttcgtaa   1860
tacaacccat caaccatctc tctctctctc tctctctctc tctcggcctt tatctttctc   1920
ttcctcaatt aatttaagta ctacccaagt gagctaaaag caagttcagt ggacagtgtt   1980
gtaagaacca ctacagaaaa                                               2000
```

<210> SEQ ID NO 90
<211> LENGTH: 2000
<212> TYPE: DNA
<213> ORGANISM: Cucumis melo

<400> SEQUENCE: 90

```
aatcatcagg tctccttcca atgaaaccga cgacaacgac agtgtcggaa aagcgaggaa     60
gggatggcga aggcgaggaa ggagaaaacg aagtagaggg ttccggtaaa gcagaatgag    120
gagggagagg agttggggaa ggtgaagagg aagaggaagt gggagttgat aatggtggcg    180
gccggataag tactcggaca gaggaggaat tgggtacgtc catggatgag agaaaatttt    240
gagctttcag atgcaactga aaactgcttc actgctttca cttccgatga ccgccgaggg    300
gaaacttatt ttttccttgc cctttttgcc tcctcaatat tttcctttta ccatttcctt    360
tccaaattta tttttctatg ttttgatttt atgttttgtt atatttttga tttactttta    420
cgttattttt aaatattttt gatttaattt tgttatattt gaaaacaaga tattcattat    480
atactgtaaa tcttacttta ttattgttta aatgtcgttt tggtaattca aaattaagtt    540
gaataaacac aatattttaa atattatttt agtaaaataa tttttaggtt ggagaatggc    600
aaaagaaaca aaggattgaa agactgaacc catatttgag gatagaagtc aaagccaatg    660
tcaataagtg aaactcactt ggaccaaaat accaatttta gttttatatt tttaattgtt    720
caatcttagt ttccatactt tcaatgcata ttaaacttat agttcattat tctttttcaa    780
taaatcttaa cattttacta caaattttta aaatgtttca catactttat ttttttacat    840
gaaaatgatt gttattgttt aatccatttc aataaaatta aaatttgaaa agctaaaaat    900
```

```
tcaagaatta tcgatagaca attacaattt tgtcccatta aaattatcaa attgaagtgg    960
ctacacaatg gaatggtaaa tcctttattc ttgtattggt gtgatttgga ttgagatatg   1020
aaacattata atctaaagga acatgtttaa accgaacatc acgtattttg tctttcaaaa   1080
tttcgtaagt ttgtaggttg ttttttttt gtcattttat atagttacaa ttatttaagt   1140
cagatcggat aaattttgtt atacaccaat aggaaactaa aaattccaca aggagtatga   1200
atgacctcct acgggagcat taatgaaaat gaccaagggt taaaaaatgg taagaaaaat   1260
gttcttcact aatgacaatt cctcgtgaaa gtactaacat gttcttaaaa tgcttgcaag   1320
catatatgtc accaagaatt ctcattcatt cctctggctt ctttctctca tttctcatca   1380
acattaatat gacacacttt ttccttcttc tttttgtatg tgtttataat cttactcatt   1440
ccttattctc attgtcactc aacgattcca acaagcaata tgggaacaaa cgaaggaaga   1500
agagaaaaat acactaagaa gaagagatga acaaagttgc attagaacaa ggcgtagaat   1560
atcaaagaat tcaaaataaa aaggaaaaaa agattactag acgagagaga acgagacttg   1620
aaaagaatta gaataatttc ggtaatttta cattggacga cgaaagcaaa tgacaaaaac   1680
aatttttttt tcaaaaacat agctcaaatt tcatttagat ctttcatccc aaatggcata   1740
atttctctaa tttcacatac accacaaata taatgatgac tgattaaacg aagtaaatta   1800
caataggact aaatatataa ttaaacttct taaattgagt ttgagataaa acctttgaag   1860
ccacgagggg tcgggtcggg ggcgaaagag acatgccata taagcagttg gttgctgtaa   1920
agtggcacac gcatatctac tggaagcctc catttccaat ctcccattat cccattatca   1980
tcggcagttc cccatagcta                                                2000
```

```
<210> SEQ ID NO 91
<211> LENGTH: 2000
<212> TYPE: DNA
<213> ORGANISM: Cucumis melo

<400> SEQUENCE: 91
```

```
ctttcctgac ccaataagag atcaaatcac tgtctcctgt agcctttccc ttgccgctct     60
attattgaca tttgggccta ccttcccccc cccccccttct cccgattcat cacccttggg   120
ccttggccca ttaaaacatt acccagctcc ttactacttt ttaataacta tcacgtctat    180
tccttcgcaa gtgggtggaa gcgaatattt ataccaatta tcttttggtt gatcatgtag    240
ccaaaatttg gctcaccaaa ctcgtacaaa gacatttact tgttttccac tgtagatttt    300
aattttggaa gaagagatca gttgccaata gattgaatta atgcatttat gtacactttc    360
atacttaact tttggcaaag agttgaaagc aaggttttaa agaataaaat gaacttactt    420
tttttacaaa tctcatgatt tacgctagct caaacttagg atttctttcg tttgaaaaat    480
tggaccaaat atatatacaa tagattgaat aggagtcttt taaaatactg gcctcaaaga    540
aatagacaag ttagctaggt cgggataatt gcctcactca ttcttcacct cagagatgcc    600
tctcctccta ggcatgtttt ctaccctcat aatttaattc actcattttt gcttccttat    660
tgattagtaa aagtaccgat ttgccttctt ttctatgttg acaagttccc actagaaaac    720
aaattagatt atgagtttat aggaaagaat taaacacaaa tacataagtc aaattgtgaa    780
gtatcaagat aggctgttag gacagaaagt tcaaatttgg aaaacaaata tatatgttat    840
tgagttgtca tcttcttaga taatgataaa atgtgaactt ttgacacata taataaatag    900
catgttcttg ataaatagtt ttccattaaa acaataagct attattggat gatagaaact    960
cccctgggac tacaagaaaa agctaaaata gaatcagcat taaaacttcc tttaatagga   1020
```

```
tcgttatccc aaataacaac tccatctcaa aacacttcta aagaagtagt taaagaataa   1080
caatgtatat tagttatgga tgttgatgat agagaacttg gattttagct aaatttagaa   1140
tcttaaaaag ggaaggaaga aaaaaggaac aaaataaaaa gataacagta tgattactcc   1200
aacttgtgat gaacagtacc actcatggta tgtcaaacat atacatagaa tgagaacaat   1260
ttagatcaat taatttactc atttatcctt cttgctacag attgttgaga aaatagaaaa   1320
acaaattaaa gtaggaaaaa aaagaataaa tggggaatta tggaaccaaa atatcaagaa   1380
aaaggagggg caataaatta aagaggaata gtgtaggcct tctcacagtg gaagtattag   1440
cgtttaagtc agtaccttac ctttatttgt tttcatacta agttctttct ctttcatgtt   1500
aataaatttt caatcgatcc atctattcaa aatggtgtgt tttattagga agaaaggtaa   1560
tttcatacaa gaaggctaaa aaatagttga cagctgtggg atttgaaccc acgccctttc   1620
ggaccagagc ctaaatctgg cgccttagac cactcggcca aactgtcgga attgtgagtt   1680
gaataactaa gatgatcgga aatgtgacga aataaattgg gctaaagaaa agaaaagccc   1740
aaacaatgaa gaacaattcg gcccacttaa tttcacgcgc atggcacgtg taaagaaatc   1800
ccaatctgtt ctactaggtg gtggtggtgg cgaggcgaag caaagcaaag caagatcagc   1860
cttatcaaat tgtgtggtga agaatgaaga ttgtataatg tagatagaaa aagatccccc   1920
cattcccatt cccattccct tttctgaatc cgccattgtt atctctctca gacctccata   1980
acctccattt ctacccagcc                                                2000
```

<210> SEQ ID NO 92
<211> LENGTH: 2000
<212> TYPE: DNA
<213> ORGANISM: Cucumis melo

<400> SEQUENCE: 92

```
cttctaaaca tcctcaatgt tcgattttga tcaaggtcgt ttgcttctaa acatcctcaa     60
tgttcgattt tgatcaagag gtcgtttctc tatagtaaac atctgttaca ccttccattt    120
ctgttattca atttttccaa ttttattgag cagtttattt atttccgtaa ctactttgca    180
tcggaggcga tcatcagttt ttaaggtaca aaactagatt atatataatt atgaagcaca    240
gcaaagtata aaattttgaa gatgaaattg attggacctt gtgaacagaa ctctaaagag    300
aaaatgcatc agatagtctg gatcgttaga atttgaaatt taaatttcta tcttccacta    360
aagatatctc tgttttgcaa actaatgttc ctcattctaa acagagaatg ccagtggtat    420
tttgttcgtt ttttgcgaat atgattaaat tacccatttt atttgcatat tttatttatt    480
ctcatatcag ctccaaaaga atatgatccc tttttcctcg ataagaaaaa atatttaata    540
ctttcaactt catgcattgt gagactgccc atttgttttg tttaaagtag caccaacttc    600
tcaattgtat aagtttgtga tttttttttct atctaaattg acttgaatta tttttagata    660
taattaaatt aattgctttt aagagcaagt taaattaagg tttcgtaagg atatggatta    720
aatttaatta agaattggct tcttgctcta aatacaaatt agagtgagat ttgaaatagg    780
aggaaaaaga gagtatggtt acaaaggata tgaaagatca aatttcaaac ctttgccaac    840
tgaggctttt cagaactctt aaaccatcac agttttttct ttgcccaaat gaaatcaaac    900
attaagaaac agtgataacg aaaacgaatt atccctatgc caaccgtgac agatgatagg    960
caagaaaccc acgattagtc tctcatccgg attgttccaa caaatgaaaa agcgttttct   1020
gagactacac aaacaacaaa cacagagtta gatagttcaa gcaaatgatt ctagcagatt   1080
```

```
agaggataag gtttcttatt aaatgtttga atacattcta accaaaaacc aaaaaaccta   1140
tttgcaaatc agcttatgta aaccaaaaac atatttacta agaattcaga atttcgctgc   1200
ttgaaatttg aaggatacca tataaaacaa taatagattc ccccaatcgt gttcagtagc   1260
tcaatatagg caccgtgcaa aaggttgttt gttgtaagat taatgaacaa acacccgtgt   1320
ctgattttaa tgccaattca aactctaatt caaaaaccct acaaagacct aattgcagat   1380
aatgggatta gaaattttaa aaaatgtcga ccgggcattg tatcttaaaa ctattaagtt   1440
tcaaggatct tcctccggta acaaaatatc ggctccatgc ggcagacgga tcgccattaa   1500
aacggcgcct gctgctgact cgatgataga gccaattcag aataaccaac ccatttcatc   1560
gaaattttta aagagagaga aaataaacga ttcaagatat caaacgcatt tcgcttctat   1620
tgaaggagaa gacaatgaaa atcaaaacaa atcggaaatt aaagttaaag aagaaggaga   1680
taatctcagg acggacggaa gataattcta aaggtgcgat tcggttgaaa tttatagagg   1740
atttgtgaag gaaccctaaa ttctgattgt gaattttatc ggaaagaccg gagaggaagc   1800
ccattgtgtg aggcccaaag taactgatct gggccttttt tagtttcagc ccaaacggaa   1860
gcgacacgtc gtttctatgt agagccaaga gcgtgccacg tcaacagacg acgtcggtta   1920
gtaggaataa taccgatttg tggatttaag aattgttcat ttcggtttgt atcggaagtt   1980
ctgaatcttg atccgtggca                                                2000
```

<210> SEQ ID NO 93
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 93

```
aagtagaaat tcagcgaaaa atgcagatgg tttcatagac aataaaaagc aggaacaagc     60
gcagagaatg gttaatcctc cagaaaatgt gataaaaggc gccaccaaga ccagtaatcc    120
ctttaccaat cacagaatac tcaacaagaa aagcgattcc agcaaaaacg aagatgaaac    180
tctcacttac aagaagaggg tcgacatttt cccgcaaaac gatgagaatg gcgagtgccc    240
agaagaagaa aatggccagt gattgctggg agaatgcgaa tctgtaagtg gggtttccgg    300
aaaaagcgag aaaaaggaaa atttcagaga aggcgacgat ggggaggagg aggatgaggg    360
aatataaatc gaaatttttc catttcggtt ctgataaata ccaggttttt gatcggtaaa    420
gagatgggtt gttgaggtaa atggaggaag aacagaggag gcgacgaagg ccaatgggga    480
tgaggaaaag ggaggcggag agatgcgttg ctagtgatgc cattgaaagg gcttttgaat    540
ttgttgaagc attcagattc ttctctgtct atggttccgt agattgttct ccaattcttc    600
cattgggaag acggagttcg gtggctgaac gttgacccta acaagtttga tcacgttgat    660
ccgttcaatg ttaaacagct cgatgatttt cgtctaaaaa agaagtgatt tttttttaa     720
ccttttttatt attgaacaaa aaaaagatct gtttatacca tagtttacgt tcttccacat    780
gagaagtttt ataatagttt atagaatcta tccaaattgt gttttattgg gtttcgattt    840
tatagaaatg tcatatcaaa aaaaaattta aaaatgataa aaatcattat aattatttta    900
tgaaattttt actgtgactt aattagatta taaaccgacc attctttaat cattattttg    960
```

```
gatgtctatc gtatgtgtat ttatagatgt caaacatgag agcatagatt taaaaaacaa   1020

atagcttaaa caaacaacaa taacttttta tctttcagaa aagnnnnnnn nnnnnnnnnn   1080

nnnnnnnnnn nnnnaagaaa agaaaagaaa agaagtcttg aaaaaagtat taaatttcac   1140

aataaatttt ttaaaataaa atacattaaa tggggatgag gaagaaacaa ctaagagtcc   1200

aagaagagaa ataaaaaatg agaggtggtg tttttttgg tatgttaatc aaattatggt   1260

ctccacatac aagaaatgaa gccacgttaa tgacccaaca acactaacac atcaattctt   1320

aaaattcaat tccttctttt cttcccttcc aaaattatgg gtcctccaac ttacaaatta   1380

acaattgact ttagctaact atgtttttta aatataaaaa acgaatacaa gtcagtttaa   1440

taggacttga agattgtata aaccaatatt agacaatcaa aacaatcaat tttaggttca   1500

ttcccaacga tacatcaatt tggattagat taatttttca ttatggtttg atagagtgga   1560

tttagtttta gtggaatgca gggagggaaa agtaatttga aagaaaagga atgaggttgg   1620

tcaattccga agcctaggta tccaaataca agaatccata tcaaatttat gaacacctag   1680

aaaataatag taattttaat aataaaatgg agaaatgggg tccggtcgtc ctcttcctcg   1740

cggcggagat gaagccaccg cgataagaga aagagaccct tttcaataca attcaacaat   1800

cacatgaatt attccaattc acatctctgc ttttgaaact aaactaaacg ccaaaaaccc   1860

ttctgtggct cataagtttc ctctctcaaa tctccgattt ccctcaccca catcccacat   1920

ttcgcatcca aataaaaaag ggacacggac aacaagaagg agtttttaat tcagtagtgc   1980

ctctggaaga agctgtttca                                                2000
```

<210> SEQ ID NO 94
<211> LENGTH: 2000
<212> TYPE: DNA
<213> ORGANISM: Cucumis melo

<400> SEQUENCE: 94

```
ttagtgaaag ttcaagatgt aattcactct ctttaacaag gttgtttctt tgcttcacta     60

cgcatcaatt caaatattta gatattgatg tttaagctta atctcctatc ttagctcaga    120

acaaaattgt caaaatctca ttcttatttg tctacctggt aactttgctg ctatagttat    180

ttgtgggaga ttgtagcaaa tgactgtaga tcgaaaccat ttcagcatca atttcgaccc    240

actcttctcg tcaacaactt gatcggcagc ttcgacattc ttcaagcgcc agcttctatt    300

ggatctttag ctcaaccaca tcttcgtctt tgaattgcat gtgagctgtt gggctccttt    360

cttttgtgct tatcagttgg gagattatta ctataaatac aaagcctcac gggtatttta    420

agacacaaca aaaaattaaa agtctctcct ctgaatcacc acttccattt tctataaatt    480

ttgttctgag caacttttgt ttgtttctat ttcttattct gaagagtgca tgtttgagta    540

tggggagtaa tgttaacctt gaggaacaat tggcaacacg attggcacct cggtcaatca    600

tagttgcttt taggacagtg gttcgtcaca acacaacaat ttattttaag ttcaacattc    660

tcattctttt cttctacagt attcaaagtt atagtgttta tttctcttat tgttccttta    720

gttaacaatc taccctttaa ctaaagtaac aacttaaaag taaaatggat tattctactt    780

tttcttaatt gttactttta aaggtttaag aactgaattg ttactccgat gaaagtctaa    840

agaccaatag tggtttctat ccttaaaaaa ctattcaatg aaatttatgc taaaaaaata    900

atcactaatt catcgtgagc ttccaaacca cttgaaatta gctcaatgag attgtaactt    960

ggtcgggatc tcatcaaagg gatggtcttg gctagattct taaagatcat tttagaaagt   1020
```

agatcatgaa aggttgcaaa gatgctagaa acaactgggt tgtcgacgtt ttggaagcta 1080
aagcggtgat gattgacgta atagatatca ctaaacattg gcacaatcat acttggaaat 1140
agcttctata gatatattcc attttgtaag gtcttaaaga caagaacaaa gctacctata 1200
agcttgtatc ttagtttcct cttgcgatct tcttgtcgag agatgacttt ccggttttgg 1260
gttgtgtctt tgtttgtttt tctttataaa aaagtcaaaa caaaataaat ttggattaat 1320
tatcctcgta ctgaaatcaa ttggtttgga actaagtaac aataggatac atgcggcgca 1380
ccggatcatg ccattctccc tctttaaata tcaaagcaga tccctaaacc ctaacaaaga 1440
tccaaatatc aaacctcccc tcttactaca cgctccggca cctccaaaac tccatctcga 1500
ggtttgtcac ttttatgttc ttgtttttct ttatttagaa tatgatgatg attagaccga 1560
tggctatttt ctttaaatgc ctttactcct ctgactagag tggtctgtac tctgaatcag 1620
agggttcatt tcgaatcttc gaacgttgta tttcgcttca aaagctagac ttttcccaat 1680
ttacttgaac ttattgtaat tttagtgcta gcccattgat cttggtctcc aatgccactc 1740
tctgttccga ataactgccg attattgagg ggtttttttt ggacttcatg atttcgagtt 1800
gttgtaaaat gattggggat tcatttaaat atgaaatata tccatcgttt atctcaaaag 1860
tatatatctt aagataaacc atgaacaaga agtttccgat ctaattccca tgggttgtct 1920
aacgagttat tctcaacaga ttacgaactg ataactagac gtttgaattt tggcacagag 1980
agaaatcgca tcactttgaa 2000

<210> SEQ ID NO 95
<211> LENGTH: 2000
<212> TYPE: DNA
<213> ORGANISM: Cucumis melo

<400> SEQUENCE: 95
taaatgggaa attggaaact aacttgaaac gaccacaaac catggggact taaaaaagtg 60
ataatctaac aaaggcttta cactcctttt tcataataaa gaacaaaaag aaagctcaag 120
agcaatcaag tttatcataa ctaattaaag tcaaacacta catttctcaa aagaatgata 180
taaaatgacc aaacatctag ctgctttaca gtgtaatgaa cacccaccat taaaggaacc 240
aaggcaactg aataaattgg taacttaatt gccctccaaa tcagagtccc cataccaaca 300
tcctcttccc cattctcttg gggcatcgaa tcaacctcca tcgctttaca ttccgataac 360
aaacctctaa aacggacatt tctgcacaac cccaattgcg ttctacgact cccgcaggca 420
aatttatgag catcagtcga caaactcgat gaatttaaac gacccagatg aaagctgtga 480
tagtagaaga gtcaagaaga taaatggggc taaacgataa ggttttgaaa gaagatgtag 540
ttgccattgt gaagtggtac ttgccttgga gtaatggtgg tgaaggagag gtggtcgttg 600
agtttgttct ttagggcgcc gagttgggtg ggtatgcaga ctatggaggc cattggcatc 660
acatagctga agatgaaact gcagagtgaa gctgcttgtt gaagcagagg atggattaat 720
taaagtggga cgattttagt tgtgtcttat cttcttcaac tttatgtttc ctcttggttt 780
gacacggttt taccattatc gctaccattt taagtaacaa tagtagtgat gaatgggtaa 840
aatataaatc ttattccatt gttagaacct tcgacaagtt ttccattatg tgtggctgtg 900
tttgacccac caactcgagt agagttgaat ttgtttggtc tactatattt acaaactaat 960
attaaataac aaaactctat taatttcatc ggtgttcact gttgaaatat atacatttag 1020
tatgaatctt tatctatttc tctcttaccc ttcctctaac atttctagtg cctccatcat 1080
caattgtcat caacgacgaa atgtgacgat aactatagtc aacgagtatt tccaccttac 1140

```
tttgacaata ttcattgcca caatatgctc ttgacgacct ctagcactcc acgtatgata   1200

aagactacat ttgatgacca attaaggaaa tcgtatttga caccacattc caatggctat   1260

ctctagtgat caatttcgac tatcacttgt ggttatcgac tttcaaccat ttctaacgac   1320

taacttgacg accatcttaa tcaatcatat actagaaaaa caaaaaaaaa aataactcat   1380

caaatggaaa catttttaaa tgcaattttg aaactaccac ttctctgtat ttaatagtaa   1440

tttgacatta acaaaaacac ttttaagtac ataaaaaacc aaacaaactt gtatataaaa   1500

cacttttgaa aaaaacggat gtaaccaaac acacaagtat ttttctttta gattatgttt   1560

taaaagatag aaataaaaat attaaaagaa aagcaccttt ttacaaacat gtaaatccaa   1620

atcaaacatg ctatttttta atactaaaag aaatagaaaa aacatgttaa acatatccat   1680

tagcaaaata aagtgaaatt ccaagaatta gaaagatggt ttgaaaattg attttataaa   1740

gcgaagaaaa accttttttcc ccaaaagaat aatattctta ttttggaaaa aacagaaaac   1800

aaaaaatgtg acaaaaagtt acattcctgc ggatttgacc ctctggtggc tgcattcgaa   1860

tctttgattt cgaataactg aagtaaacat taaccaaagt ccgtcgaaat cttccttttt   1920

ttcatttggg attccctcaa tcttcatcac caccatcacc atcctccact ttcactctgt   1980

ttccctccaa acatcaaaaa                                               2000
```

<210> SEQ ID NO 96
<211> LENGTH: 1373
<212> TYPE: DNA
<213> ORGANISM: Cucumis melo

<400> SEQUENCE: 96

```
tttaaatgtt actttgatat gatctatgtt tagatttgaa gtatttttct catcattaaa     60

aagaactaca cgatcgtatt catttagaag aagaattgta cgtacgcgtg tagccgatta    120

atcacgtgtt gagtgaaaca ttttttatat ttttgctaat agacctatat attgttttca    180

tttttaaaat tgatatgtaa atattttggt ttgttatata tatatatttt ttttggaaaa    240

aaaactcctt tatttatttg tcgttaagta ttaatttctt tttttagtac ttttattacc    300

attgtggcct tgttttgctc ctcaatttag atatttatta tttgtggttt atttatttct    360

tttgttttcg ggacaagtga tgtttgggat attaaagtaa aggaaaaaaa agagagatat    420

tttgattgtc aaaatgtcag aaatatctaa acccggagct tctgccacgt aggcatcact    480

ttcattacct tttataaaaa gtacgaattg aaccttcatg acactgctcc cctgctccct    540

tatataaaac ccaatcctct tccatgctca gtattatctt cactctttgc tcgaaccgcg    600

tgtttaacag ataagattca actcacaagc attcatcgct aggttcttcc aaacaaaaac    660

cctacatctt ttccatttcg cctccttaat tctctcatat ttctgtatct taatccattc    720

taaaactaca ttttaatgca ctgccttgtg ttctgtattc cactatctgt tatcgtttta    780

ttgcgttttc tttgatcaga tcgctttgtt gttgcatgaa ctgctgagtt cgtttgatga    840

ttttgtttgc gcttcagttt tcatcgtttg ccgtccagat tgtttgattg gcgagagtga    900

agtgaaaatt ctgtatgata ttggagcgtt tcgtgtaaaa tctgtcttgt ttttctatta    960

tctgtatttt agtgatttgt ttttcgttga cgattttgta tgacgtaaag atattgtcca   1020

ttttaaagga ttttcttcca ctggttacta gagatcttag attgagcttt cattcggctg   1080

tattttgatg atgctttttg tgtttttttt tcctttcttt ctttagcttt tgcggactca   1140

tggagtcttt ttctgaacga catcttaaga tgtttaagat gcttatttgc tttttttctat   1200
```

ttttggtatg acggggtcga gtctgatttt gaacgacatg ttaatattta tgatattttt 1260
gaagctagtt gtgcttgatt ctgaaaattg cttttgatac acgagaaact tttttgtttt 1320
cttcaatggt aggattttga ccattattat tattattttt taaaagatca aat 1373

<210> SEQ ID NO 97
<211> LENGTH: 2000
<212> TYPE: DNA
<213> ORGANISM: Cucumis melo

<400> SEQUENCE: 97
ccgaattcgc tattgggctg cataacttta tcacttgctg ggagactgca atttgtttgt 60
ttagtgctat gtagttttca agtttactag gctagtatgt ttgtattgcc tgagagtgtg 120
catcatgagg tggataaaat tcttaggtct tatttttgga ggggtaagga ggatggtaga 180
gggggtgtta aggtggcatg agcggaggtg tgtcttcctt ttgaggaggg caggcttgcc 240
atccatgatg ggccttcttg gaaatattgc tatgtctatg aagattcttt ggtcgctatt 300
ggcgaattct ggttctcttt ggtggcttag gtggaggctt acattcttaa ggggaggtcg 360
ttatggacga ttgatagtga ggttggttga tattgtgtct tcgggctatc ttgtgtaagt 420
gggatagttt gaaagcactt gttcctatgg aggtggggga tgggagaagg tgtagagttt 480
ggcttgatac gtagttgcat ggcggtccta tccttgatta ggttggggag agggtgcttt 540
atgacgcgac gagtcggagt gaggcttgac tttctaattt tcttggtcat gatgaggagt 600
ggaggtggcc acgagtttct ttggagttgg ttaacttatg ggatacggtt cagactgttt 660
gttcgtgtct tagtgttagt gataggtgag tatgaattcc tgacagtcat ggtggttttt 720
cgaccgcgaa tgtgtgggat actctctgtc ctcgaagtag tcaggttcct tggactggtt 780
tattgtgggg tagggggaa ttgttttcca aaacatttct ttttgagttt gacttgccat 840
caaagatagg ttgttctttt tgtagttctt tcttttggtg ctttttgttt ctatggatcc 900
tgtgagggtt ttctgctctc gtgccttaaa ctcaggctgt gaggtcctcc ttgttatggt 960
ataataatat taccttttca aacaaaaaaa aaacaaattg attcagaatg attttttttt 1020
ctttcttttg tatttattct atgtttcctt attcaggcta ctagatttga atatgttatt 1080
tgttacttcc ttttctaaca aaattagtta taattaattt tatttggttt ctttaaaaag 1140
tgtggggttg aagcttcttg cagaatatag gatcacaaat gcctaataca cttctttcta 1200
cttctttgtt ttgcagcagg gtatgaaaaa acaaattaat atgtattttt tatacttctt 1260
tctcgtatgc attattcttc ttttgtttct gttggctttg cattgtagcc gttttcttgt 1320
tcttgtctca ttttttctct accttttgtt tcttctctaa attcctttta tgttcatttt 1380
tcataatgcg gattttttca aaaaagaaaa ttatagttgt tagttgtgtt tgatgagaaa 1440
caagaaaaga gagtgaaaag agaaaagagg tagaagagaa aagaaaagaa gaatctgagt 1500
agaggaaaaa aattgaacaa aaaagttgga attgtgttgg atgaagtgag agcaagaact 1560
aaattttgtt tgagcgtcaa gcccccaccc cacacgtttc taagaacaag atggtaattt 1620
taaatacaac taatataagc aaaatacaat ttctcgagga aataggaaac ttcattccag 1680
gcttcaaagg aaaaaagaaa aaaaaagaaa aagaaagtaa aacgattaga acgtgaattg 1740
cacgtcacta gacaaaacca tcttttggta gagaaaaaca cgtgattaca aaaaacaaac 1800
gaaacccaaa taaatatata tagaaaaaaa ataaataaaa gaaatagaaa aatctaaaaa 1860
aattgggtta gcgggcaaac aagaaaccct tgtttcgatc ccccaaaacc cccccaccct 1920
ttctcccatc ttctttcttc ttcttccctt ccccattttt gaagaaccaa ccagcacctc 1980
tgaccaacat ttgcttaccc 2000

<210> SEQ ID NO 98
<211> LENGTH: 2000
<212> TYPE: DNA
<213> ORGANISM: Cucumis melo

<400> SEQUENCE: 98
tagtttggtt cataggttat agtttccaaa tttgttaggc tatcattaat caaacacaat 60
acttctcttg taggatggct gccccctata gtactttttt aacttaggag aaggatataa 120
taattatatt ccttttagaa aatataataa taattgtgta gtgctttgat ataccttaaa 180
ttagctactc acgtttttag gaggaagctt ccgttgcttt tcatggtgtt atgatctttt 240
ttattttata aaggactgaa ctttaaaatt tctctttcat ctattttgga ttggattcca 300
tctattttat acgggaagtg aactctaaga tttctcttca cctattgtga atcggactcc 360
gtcatgtagg tcaagactac gacagataag aatagacttc cacgaaagaa agtggtcaat 420
cgagatggct atatttggct ctttcagctc aatttcttct tttttccttg catgttcttc 480
cgttggtaca tttcttgcac ttttttttgtt ctcacatgac taatgtattc caagtttatc 540
attggcattg tgcctctttt aggcttgtaa actctcgatc caaaattatc taggacatat 600
gtttcctagt gaagaaatac tagtatattc cttatgtcaa tatgtcaaaa ttttcaattt 660
cttaaccttt gagtaaatca atattatatt tttatggagg ttatttataa ttggaaaaaa 720
gttacaccca tctcaaccct aattaacacc aaatgaaatt gtaccatgcg gcacaatatt 780
tttttgtgag ttttttgcaa agagaaacaa agtagcagac aaagaacaaa cattccccca 840
aaaacagcag agaataccta agagagaatg ctctctcgta aaaaataata cccaagaatc 900
ttcccaaaaa gagggagtaa aagagtccaa aacaaacgaa ccgaagattg acaagaaggg 960
cactctcgcc ctccactgcg ccgctaaatt gtaagaagca tattttcttg agttaacata 1020
ggaataggtg taactcaaga gaaatgtaat tcgtagaatt gaactttgta tattaattta 1080
tatggtgttg tagatacaat ctttagtatt tactcatttg gtgctttctc tcaaatacaa 1140
tttaaactta gaactttttg atcttcgatt ttcaggaagt tggagttgca aatcaattcg 1200
agtttcaatc tctggaattt aataaaagtt tgatcttcca agttttcaat ctttcagaag 1260
acgatgatct tgatatggat aaaaaattgc acatcatgag agctttttga agtttaaatc 1320
ttcaattctc tagagcttaa attcttcctt aaaccaaaga tcaccaaatg aatgacaaat 1380
gtctctattt atcgaaaaat ttcatagact tttagatggg cttaggcaca ttacttgttg 1440
ggcttggact tgggcttatt tgcttggcgg gctcatgctc gagcccatta tttctttggc 1500
ctatttttca tgaggggctt gaacttggtt gtatacgaaa aaacttgact acctaaatct 1560
aatcaaatta taatcatcac aattttgacg tgttacgatt taattggcca aaaattcttg 1620
ttcaacactt gtctctaatc attttcctat ataatttaac taaaatattt aactttaagt 1680
aacttaaaag atatagttta attcgaatca aaatacaaat acaatttcgt ctatctattc 1740
ccatcataaa tgttgattga gattcatatt ataaacttct ttcaggaaaa gaaagaggaa 1800
aattcaccta aaccacgttt tcctattttg gtaagaatcc ccaaaccata aatcattcca 1860
aaattatttt ttttagaaaa aagaaattca catggcgtaa aatttcagcc ccgtgagata 1920
ttttcgaacc cccagataca atctacaccg tgaaaacaaa atcggacggt ggagattgct 1980
ataatgtccg tttagaggca 2000

<210> SEQ ID NO 99
<211> LENGTH: 2000
<212> TYPE: DNA
<213> ORGANISM: Cucumis melo

<400> SEQUENCE: 99
acactttgaa agtccatttg agagattagg gtaaatttga gtgaggatgg cgtgatgaca 60
acgataaaag tgaaaaatgt cagatccaag agagactcaa aagtgaatga cgtgaagaca 120
atcggaatcg aaattgaaaa atcagatttt aaattatctt aaaccacata ttaattaaat 180
ttcgattcca gtttcaattt ggtttgctgt gataaaacta aattcttaat tgtacctaat 240
tttctattaa ataaataggt aaaaaaagta tagtaaaaat attggcgtcg cccggactcg 300
aaccggagac cttcagtgtg ttagactgac gtgataacca actacaccac gacaccgttt 360
tgttacatga gtaaaatgtt tcctatttgt ctaatattat tattactact actacttctt 420
cttcttcttc gagaaaaacc aatttctatg ggtttaaatt tccaaattga tgttgagtgt 480
atcaataata tagcactcac atgctactta acaaaaatca attctttctt tttagttaaa 540
accttttctt ttatatttag tgaaaggatt aagctatgtt ctacgttaaa ttgttataaa 600
caaaatttga ttgttactta tcgagattaa tttatttaag tggatatgtt ggaatatgtt 660
actaaaatga taattgatag tgatacgtcg agtttatgct aaacacattt tgatatggtt 720
ttctttttca atataataat ttgacattaa ttacattttt ttttcatata ctctcaagaa 780
tgtttatttt tattatgtac ttttaaaaat taagattttt tatggtttta tccataaatt 840
tgtttcattt tttaatcgaa attttagtat tagactttag ttgttaaaga tcctaaaata 900
tagtcattat attttattaa agagtctccg tcacgtgtat aaattaaaat agtcttaacc 960
gttaaaagta tagtgaacaa aatttctaac aagaattgga tcggagtaga agggtgattg 1020
attcaacatg atccttgtgc cattattgtt gttactcaag ggacgttcat caatagataa 1080
cttgaaatca aaatggcata aactattgct cagttgaaag gttgtttgtt gattgaagag 1140
ttaggtttgg atatttgggt ggaagccaat ggccttgtcg tggttaataa ggtgctttca 1200
tttaattttg cactctctcc tcatggggtt tattacacta aagtggttca tttaattgag 1260
agcatattgg acgaaaataa acaattaaga ctaaggacga aagtaatatt taaacattat 1320
tttaagaaaa agtcatttta attcctaagt tctttttttag tataattttc atttgtttgc 1380
tatattttaa aaggttacgc ttttatcaat aattctttag tttagttttc atttgaccta 1440
taaattttaa aatatcacct ttttcctttt atattttggg tttaattttc cttccttgca 1500
ttttcatatt ttacactaat acctttaaac aactaaggct tactcctagt ctttgaaggt 1560
taaacgttga gtttcaacta attgatttaa tcatctaaaa ttttgagatt tttttaaaag 1620
caatgattag gtgcagtctt ctgcttccca tttatttatc acgtaaaaaa attataaaaa 1680
aatcattttt taaaattgtt acctgacaat tttttgagtg caactcgaac tgcctatcgt 1740
tgtaacccga ctgtacctaa atattttcaa tattttaaaa cctttgatta aatgataaac 1800
aaattaaaac taagggggaa attacatttt ccttaattta aaaacaattt tgttgataag 1860
atggggcctg gcccatgagg ttttgggctg ggccttttcg aatcgtctat ttataatgag 1920
caaacgagtc tgagcttcga agaaatcccc tttttttcac ttgcgaaaga gacgaacaaa 1980
cgcaaaacag tcgaaggaag 2000

<210> SEQ ID NO 100
<211> LENGTH: 2000

<212> TYPE: DNA
<213> ORGANISM: Cucumis melo

<400> SEQUENCE: 100

```
tgttggcaat gatttctttc agaaactttt gccaccttaa tgcttgcgta gtttcaaact     60
aaatgctgat tgctgtcagt aactgattaa attttgattt aagtatagta gctgccttat    120
tgtgttaaca agtttctcca tcattttttg cattgacttg atgatttgac ttcttttggg    180
tcatatcttt gattctttcc atgtttgaaa gttctaattt agatgttggt ttgtatagcc    240
attgagaagt ttaattggca aaacatttta tagcgacctt gacatagaag aagatgatat    300
cttcgtttct gatggtgcaa aatgtgacat aacacgactt caggtatgat ttgttttagt    360
ttggaacatc tttcatccat gtaatatttt tattttcctc atttttttg aactttaatg     420
ttggttacta accttagtta aatatgtaag atagcctggt aatcgtatct ttcatcttgt    480
tactatttaa cttctcttcc caattttggc agcttgtttt tggatccaac gtgtcgatgg    540
cagtgcagga cccatcatac ccggtgattt tctcttctca ttaatgaaaa ctttcgatga    600
ttaattggta cactaataat attttgcctg tccacctata tatcagacat ttacttaaat    660
gatcatttga aaaatatcaa gctcttgggc aatcattttg tgtgtctcat ctttactgtt    720
gtgcttgaat gagtgaccac gatggataga ctttttgaga aagatccctt tgttaatggg    780
tctttttgt tgtattcttt gtcggaaagc ggaggaaacc cagatcatct tatttaggag     840
tcttagtttg tgaggtctat gtggaatttt ctttcaaaag ttttgatgtt gtacttgctt    900
gctagaggga tgttcatttg atgattagag agtttctcct ctagttgcct ttcaaagaga    960
aatgacaact attgtgggtt ggcctagtac taaaatagga gacatagtct caataactaa   1020
ctaagaagtc atgggttcta tccatggtgg ccacctacct aggaattaat tttctatgag   1080
tttctttgac atccaaatgt agtagggtta gacgggttgt cccgtgagat tagtttaggt   1140
gagtgtaagt tggtttggac actcatggat ataataaaag agaaatgttg ttttctattt   1200
tgtggtttgt gggtgtgtca tgtgtgcttt gttgtggaat ctttaaggaa agaggaacca   1260
caaaccctat tgaggtttgg ttcttggtga agagtgtgag gtttcatgtt ctgggcttcg   1320
gtttcaaaga ctatttgtaa ttattcactc tcacttagtt gcaaacactt tcttttgagg   1380
gtttccgtgg gcttggtttt ctgtatgctg ttgtgttttt ttcacttttt ccctcaatgg   1440
atgcaattct ttattcaaaa gaaaatcttt actcttgaat ttgcatatgc accctttgat   1500
aacttttggt aggttagtca cttcagatca aaccacaaat aataatatat tttgttttcg   1560
caaaacttag aaaatatatt tttgatatca gtctgttggt ccattctccc acttattggt   1620
ttatgttttt ttggtagtta tgaagtaaca tccaaaggcc tgtattgttt aggctgtaga   1680
actttataca aacctctgct aagtcaattc ctaatcaaga atttgtggaa ctgtaggctt   1740
atgtggactc gagtgtcatc ttggggcaga ctggacagta ccagaaggat gttgagaaat   1800
atggcaatat tgaatacatg aggtgtacac cagaaaatgg attttttccc gatctatcta   1860
aggttcctcg aacagatatc atatttttct gttcaccaaa caatcctact ggctcatctg   1920
caactaggga acagttgacc caacttgtgc agtttgacta aaagaatgga tcaattatag   1980
tctatgattc agcatatgca                                               2000
```

<210> SEQ ID NO 101
<211> LENGTH: 1078
<212> TYPE: DNA
<213> ORGANISM: Cucumis melo
<220> FEATURE:

<221> NAME/KEY: unsure
<222> LOCATION: (1)..(1078)
<223> OTHER INFORMATION: unsure at all n locations

<400> SEQUENCE: 101

```
ataatattaa tttcatttaa aaataacttg aattttttcc tcctatattt atcatgcatt     60
tttacaaatc cacgttcgaa aatcccatta atcataggag ttaaattgtc atcacttgat    120
ttgaatattt attttttttt aaaattaata aataaataat gtcacgaaaa tgataaaaat    180
gcaaagtatc gaatttaaaa attaaacaga acaaaattta aaaattaaat gataaaaata    240
aatataaaat ataggtggat gttaaagata ataatttaaa tctttatcta tcatcaaatg    300
acgatcctcc aatggaaaaa gaaaaaaaaa actttattct ttacctcaaa ctcctcgcta    360
aaaagtaaca atggtaagat aaaactttat tttaaattat tcttccactt gcaagcaaag    420
taaatagtta tttgattctt acacaaaaga gaatttttac tttttacttt tcattagtta    480
tatataactt tataatacat ttccctctca tggaatttaa aactaccatt tgagcaaaat    540
attttaaact aaagaaaaat atgaaactta aaactatgtg acagggatga taatgacgtt    600
tactccaaat tttcatttta aattaacgta cgttatttta taagtatatg tcaaaatttt    660
aaggatctat tttattagac aattcaaatt atatgttgtg ctttcatatt ttgttaaatt    720
caataaatat gcctttggtt gattatacta tttttctaat taactctgga gacatttcaa    780
aagatttttt atttatttat ttaagaaaat atattaatat ggtcaataga tatgtattat    840
gcacatgata taaaaannnn nnnnnnngta ataatattat tacataatta aattctttca    900
tcttcctaac agagagagag gatcgtcctc tcagcgacgc tgatcccaac tgttccagta    960
ccaaatctct gtgtcccaat ccaacagatc cttcttttaa gctaaaccca ccattttttt   1020
tttttctga aacccatttc ttatctctcg ccggaccttc agattttacc tcaaaacc     1078
```

<210> SEQ ID NO 102
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 102

```
cactatctat catagataaa taagtgatag atctaaacga tcatttacca aagtctcaaa     60
gatcatgtac caatatctaa acgagtttgg tacaagattg tataccaaaa tcatttgatt    120
tgatacaaga tcgtgtacca aaattgttta gatttgatac aatatcatgt acaagatagt    180
gtatcaatat ttaaacaatt aatcgtctat cctagataaa caaagataaa ccactaggaa    240
atcgcacgaa gagaaataga ggaagtgaag aaaaaaatta ctcatataaa ttgatgaaaa    300
atgttatcct tctctaatat ggttttaatt tttgcactag gaaatcacac attaatgatt    360
ataatacaaa gtcctacaaa gagatctgaa ttgattcatt tgtgaaactt tacaatttta    420
atcgatacaa ttattaactt aagagtgtaa ttgatttaag ctacaaggtt taagcaaaaa    480
actaaaacat aaacagaagt caaacttttc ttaatttttg agtttagtga gctacttatt    540
tattgggtag ctttagaaaa gtcaaacttg aattgtcatt tttaagtatg atcaaactta    600
atttaaccca aacttctgtt gtaggtgaat tagcagctag tttgtatata ttgactgatt    660
```

```
tacaaattct tattttaatt aattttaacc atccattaaa atggagagtt atagttattc    720
aaggatttta actactctca aaatcatcaa gatcacttgc atatttagta taagttcaag    780
gacttaagtc cttattgata ttttcatcat catctggaaa actaatcaaa taatcatgtt    840
gatgcaactt agatgattaa gattaaagct aagacttttg aaatgataaa gaatataaat    900
aaaaaaggaa gtttttttaaa aatataacaa ataggtaaaa tatttacatt atataaaaca    960
attctagaaa cgaaaaaaac ccacggtctc acaatgaaaa atacaaaaaa taccctagtc   1020
aatagcaatt aatcagccag cttgcgcgaa gaatattctt ttaaacgact gtgtactaca   1080
atttcaacga ataatccagt attgtttagg tcatgacacg atcatgtagt tctattttaa   1140
cgatgggaaa aaaggttttg aatttaaatg atcgtattga tcatgaaaaa caactatgtt   1200
gattacgata agcgatcatg tagtccaatg taaatgaatt tcaagtctaa cgatcatgtt   1260
gaccatgcta aacgattgtg ttagctatgg taagcaattg tgtagatcat gtcaacacga   1320
tcgtttagat cattttaaac gatgtgaaaa agactnnnnn nnnnnnnnnn nnnnnnnnnn   1380
nnnnnccatg ataaacgatt gtgttgacaa tggtaaaaga ttgtgttgac gatgataaac   1440
gattgtgttg ataatggtaa agatcgtgtt gacgatggta aacgatcggc taaatcatgt   1500
caaaatgata tttagacgat gtagatattt ttgaatatga gaaagatgaa gtgactttaa   1560
agatgaagta gcttttaggt caaaagcaaa taaaaacata taaaaacata cgaggaaaag   1620
ttaacatatt tttagtctat tcagactcat ccaaatttta attgtgtcat caaatctcaa   1680
tccacagctc tcaccttgat taaatacata acatatctaa gatcttataa ttaagttcat   1740
gaacgtatct aactttttaa ttcattgatc tgccttgctt agttcaagtt acataccctc   1800
ttgcttaaaa aaaaaagtta catacccctct tgcttaaaaa aaaaaagtta tatacccctct   1860
ttgacaaata tcaaaggaga aaaagacaaa aactgacatt ggcttcccat catccagaga   1920
aaagaaagaa aagccgcgcg ggttgtttat ccacttgttt cccttattat cctcatcgat   1980
tccaagtttt gaactcaaca                                               2000
```

```
<210> SEQ ID NO 103
<211> LENGTH: 2000
<212> TYPE: DNA
<213> ORGANISM: Cucumis melo

<400> SEQUENCE: 103
```

```
ttcctattta aattaactgg ttttcttaga aaataacaga attcctgtgt ggaatcccgg     60
ctctaatcca aatttcatag ggatgaaaaa tgaaatgggg agtagacatg gagatgggga    120
gtggcattcc tgacctcacc ccgtccccgt ggacatcttt ggtgacagaa tcatcccatc    180
caaatcaatc tgtgggcaaa tttcaacact cacaacaagt tgaaagactt tgttttgtaa    240
tgtatttcga gttcaactca catgtggttg tatagtctac catttcaaac ccactccaaa    300
taagaaaaaa atataaaaaa acatatttta gaaccccaca acattttttt tatttgaaac    360
aaacaaatat ctccacgtgt ttctgtttga tctcaaattg tacaaaaggg agacaaacaa    420
gagcaactta atcgtgtggt cgaaagttca taaaaaacgt tgtttttcat tactattatt    480
acatcaacca atgcgatctc aatcttgtga agatttttct tccatgtgtg agtcatttct    540
tctcgatctt aattatcttc tcacaatcca tttattatag cataatctaa gttaatttag    600
attcaaaact atacaataat aataattaag aaaattacaa atttaaatag caaaagaacc    660
atttgttctt tatagtttct acactaactt ttgaaaaggt taaggttatt ggaaatcttt    720
```

```
ttctggggca tttttctcca attctacaat agacaatttt ttttaattaa ttaattaatt    780
aaatttaaag tttaccttgg agtagtcaat aattaatttt tatgcacatt tgtcttttat    840
atgattgaat gtaacaaaca ataacttatt cttcttcttt tattctattg ttttgatgca    900
aacccacaat atttaatgag ctcatagtta tgtgtttgct ttactaatta attattttct    960
tttcataaaa taaaaaaact tgtacaatat aaactctatt atcattgaat ttttagtact   1020
taatttaaac gtactaaaat aaaatacatc attctgactg acgatccatg taaataaaat   1080
ctaaaaataa aagaaaaatg tcagaaatag caaattgaca aaatatttac aagccatagc   1140
aaaatttcat attctaccga taacaaacat ttgatagaca ttgatattct tctgtcagtg   1200
gtattggtag acagtgatag aagtctatca atttctatca tcgatagaat tcaaaatttt   1260
gttatagatc gtaaatattt taatttattt gttactttta aaaatgtctc aatataaaaa   1320
ttattaaata aacattaatt ttttattttt caattttaat atctaagctc ataaatatta   1380
actttaccca ttatttattt ggtttcttac cgcttaaatg ttgcaaaaat attttaaatt   1440
ttatttttga aatttggtta aattcgtttt tacttaaaaa tttccgtgat aaaaatattc   1500
gaatttttta ggtttttata agatttaaaa gtaaactaca taaatgaaat cgttattttc   1560
taattctcaa tttaactttt ttatactttt taattaccaa atggaaacat gaaattttaa   1620
atatatttat tttaaatctt actcgttaca aacaaaacaa taaatttaaa attatttttc   1680
cgagttttaa attacaagat ttaaaattaa tttttcaaca agaccaaaag aattgtaagt   1740
ttcgaataaa aaggtttctt tttgggctat aaagtccaat ttcctataaa agaatttgat   1800
caattggagc ccaaagtcag atccattaac ttttgggccc aaatagaaca atgaaaagaa   1860
agcccaaaag ctgacccacc aattaacctt attattaggg ttttgctctc tcttttaaca   1920
tccgaaaatc aggactctct tgccgctttt ctcttcgccg tcgccttctt cgagcttcaa   1980
gtctcccatc ctcttcagcc                                               2000
```

```
<210> SEQ ID NO 104
<211> LENGTH: 1974
<212> TYPE: DNA
<213> ORGANISM: Cucumis melo

<400> SEQUENCE: 104
```

```
tttgctattt tcgtttcatg tgggaaaaat agtatagtat gtttacgtct taaattattt     60
caaattccta gctaggaatt aaaactttaa tatatccaaa acgtttctta tttattataa    120
agatctgcaa tagcacaatg ccaatttctc ttctttgaaa tccaggttca aatcccggtt    180
gcggaataat gttttgctat tttcgtttca tgtggaaaaa atagtatagt atgtttacgt    240
cttaaattat tacaaattcc tagctaggaa ttaaaacttt aatatatcca aaacgttcct    300
tgtttattac aaagatctac actagcacaa cggtaggtag tttctcttct ttgaaatcca    360
aaatctttgc tattttcatt tcattttcaa attgaatgca tagctttaga ttgtagtaaa    420
cattgtatat atatgtttag gttgtgctaa ctttaaatgt acaaaattca aaatgtaata    480
gaattagatg tacatgataa agagttgcaa tatttagatt aaaatataag aatttaaatg    540
taagacttgc atatatcaaa aaaagatttc tttataaaca atattttttt atacaatttg    600
aaggcaactt attgttactc atgggcttga tccaaacttt tgttgtcttc actaaaattc    660
ctctaaatag ttcaacataa agttgttcat gagaaaactc attaagatat attccaacat    720
tatgaattgt ttgtccttgt attttgttaa ttgtcattgc aaagtataaa tgaatggaga    780
tttgttttct tttgaacttg aatagatatc cattatcatt tggtgggttt aatggtattc    840
```

```
atggaagaaa aatttatttt tctgcataat cacccattat tatttcagca tgtataatat     900
ttttgctaaa taattgacat actaatcttg tctcgttaca caatccatta gatgaatcca     960
aatttttcaa taacaacgtt ggtaaaaaaa atcaagacag ccttttatat agtaaaaaaa    1020
atgttacaac aacttttcaa cgttcaagtc tttaaatttg tattgttgat tagaattaat    1080
aagatatttg atttgcaaca aatttctaaa atgtaaataa aaaaccattt gcattcaaac    1140
tctttacatc caatacttta attccttcgc atcctatact ttaattccac tcacttaaat    1200
ataattaatt aaaaatatag tggataaatg aaaaccaatt tgcatttaat ttttatatat    1260
gcatacttta attccactaa acttcgttag aattaattca aaaagttgtg ggagagaatg    1320
tgcattttat catattacaa gaaaaataaa attaaaaaag aatttaccat aaagtcatta    1380
aacaaaattc aaaggttgaa tggagagaat aaaatttctg cacgctttga tatatacaag    1440
atatttaaaa ttaaaaaaat agttttaaag agaatgtttc taaattatta ttctaacttt    1500
aaatataatt actcataatt atacttattt ttttttaaat ttagaaacta aaatgataca    1560
ttctcgaaaa ctataatcaa acgagttaat gttataaact ttgaaaacta tttttttgttt   1620
ttaaactctg catagcaaat agcatataga ggttttttaa aaaataataa taattaaaaa    1680
aacattaaag gcaaaatcta ttattccttg atttgtgtat agggtgtaaa tattttgtta    1740
ctgtgttatt tttaaccatt tgcgcactga tacggactaa aaggtaaaaa cataattttc    1800
tcgaattgtt attagaaaac tggggaagaa aaaggaaatc aaatcgcgcg aggtgggatt    1860
tgacccggga acctaagact agctcggtgt ggtgttgaaa tccacgcgtt gttcaccgat    1920
tttcttcata acaaacgcac ccaggctacg gcagtcttcg aagctctctc aatc          1974
```

```
<210> SEQ ID NO 105
<211> LENGTH: 2000
<212> TYPE: DNA
<213> ORGANISM: Cucumis melo

<400> SEQUENCE: 105

gtcgtcgagc agagctctgg cagttaccct acaacccgga gcacgataac tgcagtgatc      60
cctatcctca gcatcagtta aatgggccga ttcaaaactt ttatgggcct cagcccactt     120
ccacttacaa ctattacaaa catggatacg atagtcacga tcaggcccat catcttaatt     180
actccacaca ttccaatatc ttcggccgcc aaactgcctc cgtttttagc gacgaaaatg     240
tccataattg ctctattatg taataaggct aaacactaat catctatccc tttaaatctt     300
gaatttttgt aataaaacca atctatactt tttgccatag tttatttcta gaaaagttta     360
gaatacattg aagatttgag aaacttgtct acaaggcatc aacaaaacta cgtgaaaatg     420
acaaattgga aacaaataaa aatatcttat gtttgagtat atggaatgaa gggattgatg     480
taataaaact taacgtcaag tgttaatatt acgctatagt tattttcttg ttgtagtaat     540
tttctcttag ttaatttttt tattattgaa ataagtgata aattttctaa taagaacgta     600
aagatttaaa cctctaatta agttaaaaaa aaaaacttga attattgttt gagttatgag     660
gtaacgtaaa agacaactta aattttaaag tcaaaccgaa aggaaaagag ttaaataccc     720
acaaatggat caaagaagtt aataacacac acgcacgttg ggaagcttaa aaattagcaa     780
caaacaagca atcattggtg tgggacagta ttgaaattcc acaaaactac aagggtatat     840
tggaaaatcc aatttattta tttatttttt aataggaatt aaatttactg taaaaaaatg     900
taagaccgtc gattgacaat tggtggactg tgaaacgtgg caaaagttaa ttggcgaaaa     960
```

ggagaggaaa gattttctct tttcattata atgaaaaaaa ttaatgatag tacacgtggc 1020
aaaaaagtat tggagagaaa tttccgggaa ttatctctaa tacgcggcta atttggatgt 1080
caattttgca aagaccagaa tctttttgaa cagcgaagaa gaacaaatat atagacatac 1140
aataataaat aaaaataaaa atatattaag cataagagaa aaagaagatt tgaaggttat 1200
attgaagtga tattgttggt ttctccattt ctgtgggtct gactctgcct ctctcttttc 1260
gagccagaac caccaaaacg aaaaaaccca cacactgtat agcaaaccct aattctttgg 1320
tctcagatcg cccatggctt ccactaaaga acgcgacaac ttcgtttaca tcgctaagct 1380
cgccgagcag gccgagcggt ttattgtatt ggtttcccta ccttcctttc cacttttttt 1440
ttttgggttt gcttctcatt tctattttat gcttttctta atttgtgttt tacttttcac 1500
tctctctttg ctcagatcgt atttcttctg gttgtttaat tttgtgttta tgttttttga 1560
cttcggattt aagccacgat cgcttgcctt tttgtgtact attttcagaa gtgttgttat 1620
gtttatccgt ttacacgatc tgtttgaaat ttatggaaat ttagtttgct tataattttg 1680
ctacatttct attgtttagc ttctcgagca gttttttttt tttttggccg atccattgat 1740
ttatactgtt tttctgtctg atctgtttta tttaatggag aatactcttt ttttgcgaag 1800
cttggtagct catttttcac tcatacttac acagactact tggtcattgt ttttatctgt 1860
aagcacaaag caaattcaag tttctgcctg ttctttcttt gcttgtcaaa cgacaaaact 1920
atgtttgtag ttgcttttgg atgatagatg gtgattctga ttttaattta cgttttcctg 1980
ctgttttttt tttaaaagaa 2000

<210> SEQ ID NO 106
<211> LENGTH: 1643
<212> TYPE: DNA
<213> ORGANISM: Cucumis melo

<400> SEQUENCE: 106
tccattggcc ctctcaaacc tttatgtgca tatcactaat atggttgaat atgtatatct 60
tctttctcga atagatgatt cttggtggtt tcaataatca tttagcaaat ccagaaattg 120
ggacctcaag ttcggttgcc gtggaaatag ctaaattaac tctgaaatcc tcaaactgaa 180
atgtgagaat aatcacgatg aatctgaacc gtcaacggcg gaacatagca acagtaatca 240
gaattaccaa atttcaattg gggggaattcc tttgtatgat ccttccttgg gcctaacagg 300
gattcttgat ttgaacctct cttcttcgta aaaattacac aaaatattta gctgctagag 360
ctagacaaaa caagatttag attggaaaaa caacaatgca gctcccaaat tgcaatccta 420
attccactat ttcttttttc tttttctttt ttttaatctt aggattcaat tcatcattca 480
tcaattttat tgttactgct cattgatgac caatgttttg gattttgtgt gtcaaatatt 540
ttagtttata tatggtgaaa agataaaatg aatagtttca aattttgtgt tttatgaatt 600
cctcactacc tctttctttc actaatacgt atgaaatgtg tatggttgtt tataaataag 660
atggatggat gttttgattt tgatttgaat gttaatgtta cttaaattat agattttaac 720
catttgaatg aaatatggag agaacagttt ttatatgtaa aaacaaatta atgtgagaaa 780
gaaataaata gcaatgcctt tcttcactaa taaatgtatt tatatttttt attaacaaaa 840
taaaatttat attaattatt agtgtatgag gtgtgttctt gtacaaagga aagtattgca 900
aaattacaaa aatggaaagt tgaaattact gcactcattt gctaaaatca aattagttaa 960
ttatagaacg aaaaataaat aaataagttg tatttgatga tcctagataa ataacttttg 1020
aagaataaag atcaactatt taaaaaaaat atgtgtatca caaaaaagaa tagagaaaaa 1080

```
aatcacaaaa atcacatccc aaattataat aattcatatt ataataattt atataccaaa   1140

cataaactat aataatcacg tattattata actcatagac tataataact cactccacgt   1200

cccgtagtta ttaaataaaa gaaagtaacg gtaacattaa cattataact tcgccctcat   1260

ttatggcaag gaaaaattgg ggggattggc aagtattata tttgtttatg gaaaactttt   1320

gtgaaggtgg aaaatagaga gagccaaatt aacaaaaata ataacaaaat caaagggtgt   1380

agaattcatc cagtttgaga gcggaagatt agatgggtga agaaaggatt attctagaac   1440

cctagcccac gtgtcataat ccaaccctca ccttttcttc aaaaaccctt tctttcttct   1500

ccctccccta tatctccttc ttcgaccacc aaactctttt ctctcaattt cccagcatct   1560

tcttcatttt tcattcttaa ttcaacccat ttcttctctc ttttcgtttc tattttcatc   1620

gtttctctat aatttctccc tta                                           1643
```

<210> SEQ ID NO 107
<211> LENGTH: 2000
<212> TYPE: DNA
<213> ORGANISM: Cucumis melo

<400> SEQUENCE: 107

```
ggatgggcaa tcgtgcgaca cttgttctac tcgattaaca aattagccgt gtaaaatcca     60

aaaattgtgg acaatttacg gtatgatgta gcccctcttc acgttcttaa gaaatttttt    120

ataaaatgag aaagggaaag gaaatcattg aaaagatcat aaaagaaagc attgaagact    180

gttaattgca aagaaagctt agcttaaaaa gagtgcaaca aggcttagtt ggggatttaa    240

ctactatgtc tcccttattg tacattttga atatttttat ccttggcaga cttgcatatg    300

aaaatgtcga aacgtcacac actaggtcga caacataaaa atgaaagcaa tagagcaata    360

gattaaacta agtagaaaac ataaagacaa ggtgatttga aggtatttgg atatgtggcc    420

ataggcaaat aacgcgctgg acaagcatgt tcatgacata tgacactttg cacgcatgct    480

caatgtggat atatcagcat ggcgcacgtg cctcactcgg acacataaac atggtatgcg    540

cggcatcatg tgcgcacgcc ttacacgacc aacgagctag gtgtagtcca agcacacacg    600

cgatgggcaa acgtgcctat ggctgcccct ggcgcagaca gtctcgaaag atgcatgtcc    660

atcctaggcc catctagaca cgtccaaaag ttccaatgac ggtccaaaag gatacaatac    720

ctttagaagt gtcatggtag gtctagaatg ttctagagtc atttgtaaat tgttaaactg    780

ccttatatct tctagatata caggtcctcg gccgaccttc aaagcaccta ggtcggttag    840

gaaagctata aatagatgta aggtggctta tttgtaatca ccctaaaatc ttggcataac    900

ctagccaagt aagacaacct tgcctcatca tttgtacaca aggtaccttt acaaatggta    960

ataccctggc aaaggactac actcatttgt atacaacttg tacacaagca atcttggaac   1020

gcaaagtact cttccaagaa gtgtcaagct aagctccatc attctcacaa aatgatctct   1080

cttgcctttc aactatctta aatcttctac tgccatattc tttctcatag tgcttagtgc   1140

actaacctct caaaggctta cttggctacg tgggcgttaa tattagtcaa gtgttgtacg   1200

tttggttagt tgaaaaatct aaccacgtga caatagacaa acatcaattt tattttattt   1260

tagagtctca ccaagttctt aaataaaatg tttattgtaa gacaaacaaa aatgaaaata   1320

tgttattata gtgatataga attttcacta ttagtacaag atataaaagc gaaaggaaga   1380

atgaatgaac actcaacatt tagaaagtgt tttgagtaaa gaagtaaata gtgagaaata   1440

acgagtacaa atgtgtggaa agttataaac ttctaagatc tacagaacaa aagattgata   1500
```

```
agatataaaa ttgatgttag gataggagct acaaactcct ttgaccaaat atcgagcagg   1560

attcacaagt catactctct tactctacca aattcattag aagtacataa tgggcatgca   1620

tgtgaacgaa ttaaaaaatt ggtattttta tttttatatt ttaaaaaaat tggatgaatt   1680

ggcaatggcc atgaatgaac cagttgttaa agtttagagg acaaaaccca aaagagagaa   1740

gtgtacctca taaaaaacaa atccaccaat tgagaatcac ataaattata ggaagacgtg   1800

tcactctatc ggccgatcct caaactcttc caccaaatcc acatgcacaa tctccttctc   1860

ttcccttcca ccatacactc aaaatcccac tgatcttctt cttcataaaa acccatataa   1920

tcataaatta atttcctcaa gtttttcttt tccaattaaa caaacaactc tgcaaaagag   1980

gcctttcttc caccatttcc                                               2000
```

<210> SEQ ID NO 108
<211> LENGTH: 2000
<212> TYPE: DNA
<213> ORGANISM: Cucumis melo

<400> SEQUENCE: 108

```
agacgaagaa gaagacaggg tgtgatcatt taagaatatg cgttttaact ctgccctttt     60

tagggctttt ttcttttatt tatttgcctt ttttctcgct cctagggttt ttccctccat    120

tgaattagaa ggatgactgg gccacagact tatgatgggc ttcacggtca ttatttgaaa    180

gtgtgatatt ctaaaaaaaa taaaaactca tttgaattaa aatagggttt ccctccatgg    240

gagtatgaaa gacttttaat tgaattgggg tttttaaacc ctaaattgaa ctaaatatat    300

ttttatgatt tttacaaaaa ttaatactac aaaacaaatt atgattaata aaatttgttg    360

atatttttca aaaaacaatt atataataaa acaaactaaa tattcaattt ggtattttta    420

accatgctat aggaaaagat tcatatgggc atcaaaatga agcaagaaca tggcaaagca    480

agttgggtga agataagtat tgtcctaaat cgaaggacga ggcaataaac tcgatatctc    540

gaagagtctc caggtcaaca tcacaacgcc tgcacaaacc aaatattatt atatatatag    600

ccatcgttta ctataagact atgtatttac gaaaaattct atattgtttt cgacgattac    660

atttatatta tataggaata aaatacaaac ttttcgaaaa gtcatatatc ccaccatata    720

aagatcaaac gtggtagatt gaaaacatta tacagtatat tctctatttt tttctcataa    780

aacttattac gctttgtcaa gttataaaga ttaatggttt tggtatattg tgctaacttc    840

gtccatttgt tgtgaaatta cattttcact actttttttcc acattgcacc atttttcata    900

tgttttattt ccattatctc gtagaatatg agcaaagaaa aagattaaag atgaaatttt    960

tcaacgtgtg agagaaacat cattaaaggt tacttaataa ggaattagaa aaaagagcat   1020

gaacctagaa caacaagata caaaatatca aagacaaaag agttcgatgg agagctagaa   1080

agataaatca agattttgta aaagaaaagt gctcggtggg gaactagaaa aatgttatag   1140

aagctagaaa gataagccga taatttgtaa actataagag gccgtttaga ggaagagttg   1200

ggttgtgaaa tgttagtgtt atgataaaac tattgttatg tttggggaaa gagtttaaaa   1260

aggtactttt atgataaaat atgtctggga taagagttga aaaacgtagt tttatgggag   1320

agttgaagat atagggttat gaagagttaa aaaaggtata agaaaaggag agagagagag   1380

ggaatagggg ttatgatcat agtcttaaaa cagaattatc ataacccaat ccaagtgata   1440

acccttggac caaacgacct aaaatatcaa agagaaaact gtttggtgag gaactataaa   1500

aatgttatag aagctaaaaa tacgaactag aaagataagc ggagccaatt ataagggttg   1560

gttaagtgta gggtttattt atttgagggg aatgataatt taagatataa attaatagaa   1620
```

```
tggcaagttt tgtaagaaaa attaataaca actcgataaa cttttgtttg tgttggtaga   1680
gaaaacatgg gccacaaaca tgagcccaaa tgtggagaag cccagctgat aatttaattt   1740
taaaaataat aaagattaga ttatttttgt tcgcccaaaa ttcggcgcgg ctaggaggtt   1800
gcttataaat ggaaataaat ggaaagggtg ttaggtctcg aacaagtgtg cgacggtatt   1860
ttaaaggtcg gccacgttga ggcggccctt ttcactcctt tttcctcgct cgtattcaat   1920
ctagggtttt aggtttccaa cttctcttcc tccccttccc cttccccttc cccttccttc   1980
tctactcatc actattctca                                                2000
```

<210> SEQ ID NO 109
<211> LENGTH: 2000
<212> TYPE: DNA
<213> ORGANISM: Cucumis melo

<400> SEQUENCE: 109

```
atgggtagtt ttcaaattaa tccgaccttt gaagtacttt ggtttttaaa ataatttttt     60
atcatctgaa atcactccat agacttatgt taccgtaaat cattattctt tacaaatgat    120
ttgattttac ttaaaagtat attatttcaa acacgttata ggtattatga agttttaccg    180
tcaacaatta tagttagtaa gccaactatt tataaaaatt taaaaaggaa tatttgaagc    240
atggtgcatg atgtatgttc ttctctctct taagttgact atcaaaactt aatcatgctc    300
agaataacat acctcacata gcatgtgcaa tttaatctaa gcaattcaaa attcattaac    360
aataattcat acacactaca aagtcatacc acctatgtca cccaagaact actattattg    420
taacaagtca aataagaagt ccctatccta tccatcctaa gatggagtaa tttttctttt    480
ccttaaattt ttggaaagaa gaatattgaa attcaggaca ttaaatcaaa gctgttcgga    540
gataaatgaa ccattcttca agtaaaattc atatttgtca tcatgcaaac aaatattgaa    600
aacatgatat caagaaaaag aacaaattat ttaaaaacat cataccgcac atcaaactta    660
aaataacctt ttgtgcatat caaacttaaa ataacttttc tcaacaaatt aaagcgacat    720
aaaattgata atttttgttt ttttttaaa tatatattca agaaaatcga caaatccaaa     780
tgacaagttg ttcacctgta tattaaaaaa aacaataatg aaaatttgaa aggagagatg    840
agaaaaaaaa aatcaatcca tcaatccaac ttgaattttt gggtcgacag catatcccta    900
attataatag gaagcaccct actttttta caaaagtatc gaaattatta gtcgaaaatc     960
ttaattagag tccaaattgg atgcagcaag gatagtttta aatccaatta atagcatgcc   1020
taatgctatt acaaatatat tttggattat acataaatag aaaaaaaaaa gtgaacttcc   1080
agactcaaat agattttact ctattgttat aaaaactata cattaaaatt agatgtagag   1140
aatgagagct caaaaccaag aaaagtaaat gataaaaggg aaacaggagg tgaaaagaaa   1200
aggtgatacc gcggatttga tgtggctctc ggtttttgcc tcccaagcaa tccccattgc   1260
ccatctcctc tacaccaacc cacttttctc cctttctttc tttctttctt tctaaaactt   1320
ttgttttcca attttgacct ctcttcttgg gcccacttac taacaaatca aaaccaattt   1380
tcattttttt ttcttttctc tattcccttc cacaaataag aaaaaacttt atataaatca   1440
atacaagaat gacatttatt ataatagtat atactataag gtgggaggga tggcaattgc   1500
caattgtata agtaactatt aatagacagt aaaactttga aatagaaggt atttagatgt   1560
ctgagggtaa acttataaca ttttatgaaa tctaaaaact aaaattaaaa ttattgggac   1620
aatataaact ttagacataa gaagaaaaca tatttttgtt aataatttaa caaagaacac   1680
```

```
aacaagaatg gtagagtgtt gattaagagt gagcataata gacaaaaaaa aatatagtca   1740

atcagccaaa atagacggtg gttggtcgga gatgaagaga gtttcaatct aatcagttgg   1800

taaaaaattc aaacatcgtc acattcttta aaacttttaa aggtttaaat ctgctaagat   1860

ttatcgaaca atgacctatt tgtactactt tatgattgac atcaatttaa atatttaccg   1920

gtgaatttag taacgattag ggcgagagcg gttttaaaaa caggagtgga gtagtggaca   1980

aggagggggc ggaccaaccg                                               2000
```

<210> SEQ ID NO 110
<211> LENGTH: 2000
<212> TYPE: DNA
<213> ORGANISM: Cucumis melo

<400> SEQUENCE: 110

```
ataatactat aaaacaaata aattttaatt aagttgtttt tactttcata ttatactaac     60

aagaacagtt tgttaagttt tatatgtatt tataaaagat atatgagtta ttggttaatc    120

tataatatca atgtcgaatc tctaacaaat attttagtgt ctagacctta tgtaaaaatc    180

agaagtgacg ctcaatattt ggaaacagga atcattggga tacgtggaaa tcaatctttc    240

tgacattgtt acaaacaaaa gaataaacga aaagtatcac cttatagact caaagaatgg    300

aaggattcag attgagttgc aatggaggac ttcatcctga agtacctata tatttttctt    360

cttggttagt ttttcagtct tctcttctat ggatcaagtg gggaatacag caagagacaa    420

gaaagacatt ttcctataca aattcatttt attattcttt cattgtctct ataaataaag    480

aggcatttaa atccttttcc taatttaggt ttggtatcaa tattttgttt gtaacagagt    540

aatagaacca aaatatttca ttatgttact tgaaatgttg attttttttgt gcccattctc   600

ttctgagtcg acaagtgaga gtagatatga aagtagctta catttatatt ttaagagttt    660

ggaatctctt accttaaata ttttctaaaa gaatatcgtt gtgggaatat gatttttcta    720

ttttataaat ttgacactat cgatcaattt aaacacgacg tataatttta gttttatttt    780

tagaaaaata agctttttag tttaagtttt tttttacgta attactattg aatccctaaa    840

gttttaaaat gctatagctt tactcttata ctttgagttt agtttgtata tatggtcgat    900

aaattttaag attatgtacc gtaattctaa gttaaaacat tgctcacctc ttgtcctcaa    960

agttaatgta aatgaaatta taatactcat acataataga acttttttttt attcttaatt  1020

atgcaaaaag aatagtgaag gttaatttag ttataatcag ttctagaaaa ttaacacaaa   1080

cattctaaaa gtagtttgaa attgagataa aatgaaagtc aaattcaaaa caacgaaata   1140

aagttataaa tatgaaactt tgaaaaatat agataaaatt agaactacgc atgaaaactc   1200

taagacaaat agacaattct cgagatagaa gtttgaaatc gaaatctggg gaaggaaaaa   1260

tctttacatt tccattttat tcctatatct actaataagt tttgtattaa aaaagaacat   1320

caaatagagt aaataactgc acactaaaca acactcaccc aaccacccca tatctcaatg   1380

agaaatctta atgtgaacta caaagctagg gacagaaaaa tgattcatta gattccagaa   1440

caataataat tatgattaca ttttggattc attagattcc aaaataataa taattatgat   1500

tacatttggt gtttgaccta tttatttatt tattttatat aaatattttg tcgaagagat   1560

agaaaaaagg atgcatttaa attaaaaaag aaaaattata ttgataaaga agaagatggc   1620

gggctgacaa gagaagaccg ggaggctgat gtggcaatgg gaattccaat tttccaatca   1680

aaaactaaaa acaaaaaaga aaaaaaaaaa gcaaaataat tttggttcac tgaaaatttt   1740

catataaata catgtggcgg ttgatggccc aaaggatgag ctttgaaggt cgcattatca   1800
```

```
aaagtttggg gaagcagatt tttgctaact tcgaggtact ctcctctcct ctcctctcct   1860

cactttcctt tctctctata ctaactataa tttccattcc tcctccatca ataatttctt   1920

catcctcttc cttagctaat ctctctcttc tctaccagtc aaacgccctc ccttttggtg   1980

ctctctagcc tcctcctccc                                               2000
```

<210> SEQ ID NO 111
<211> LENGTH: 2000
<212> TYPE: DNA
<213> ORGANISM: Cucumis melo

<400> SEQUENCE: 111

```
ttctctctct cttttaatct acaacgtatc caattatatg gagaaagttg aggttgttgg     60

atttaattca ttttttcaca ttttttaggg ttaaaatcta aaaacacatt tcgattttgc    120

gactgttcaa ggcgtatatg tttctttaaa tattatagtt gaaattacga tcaaattctt    180

acgctggtta agaaagagaa aatcgtagga gagaaattgt gagcatataa gtgaaaataa    240

cctcctagag tttttttggat ttttgagcga aacaaaagta aggttgtaac gatttatgtc    300

taaaatgaac aatgtcatat cattgtggga atatgtgtga atgataaatt atcacaactt    360

ccaacaatga gtatcacaat acatatcatt gatgggtttt gagaaaatga gggttgactt    420

ggacatgaca acttgataga cttataactg tgtggtgtac ttataagaaa tcggaagttg    480

gtttaaaagg agaatcattt gcgtcgacaa gatgattatt attgcaaaag atgcaaccaa    540

ggtatgtcga tacataggct agataaaaag aagatcaagt aatgatataa ctatgtctct    600

gttgatatgt ttttaagtga aataaaaaac aaaactatta atcctatacc taaaatgaac    660

catatcgtac tatattagaa aagaataatg tacctcttga tagaaactta tagtaaaagt    720

gattaataaa atatcactag agagatacgt aaatacttcg ttatcataat ttattttact    780

tataaatgaa ctataacaaa aagtatttat atccacaaaa tcaacgttaa gaatattagg    840

gcgtcgaaga agacgccaaa ctattttaat ataggttacg tttggtatct catctacata    900

acaatctttt gctttcaaat acactcaata aagtaaatgg aatgattttt tgtttttctaa    960

ttttgtcatt aaaaacagtg ttttacattg tacttgaatt tgtgacatat aatgatatat   1020

ttctttttac aatacccaaa atcaacagta aaaaaacaaa tacttacttc ttttcattca   1080

aatttttcat atgcttttga ccgttattag cctttagtag tttatcgtaa atagattgtg   1140

atatttttat caagaagttt tattttttaa aataaatttc ctttttcata accacaaaaa   1200

gcacccttgc aaaatcaata tttcattttg gaccgggttg acattaggtg ctttaaggat   1260

cggcccaatc tagattcaat aatctcagta aggcccactt gtaaaccaca aaaaggcatg   1320

gcccaccgag cccactatgc caatagttgg gcctttcttt cgcaaatgca cgcagctaat   1380

taaggcttca ttacttaata atcagtaatt aattttgctc caaaacgggt caaagagcga   1440

cccgacccgc gaatatgtat ctgggccgtt gattatttta gtagtaatct caaccgttca   1500

gtcggtcctt ttatatgtct gtcctccctc gtaatcaatt cttagggttt tctagggttt   1560

ttagttcttc tctacgcttg gttggaagtg ccccttcctct cattcttcct gctttactac   1620

aggttttcaa tcttcaacaa tttaaatctc aacatttaat ttgttttgca cattgattca   1680

agtgtgtttt ttttctttcg tttgggcttt tgttgattga aattactcaa gaaattgcag   1740

ccacaaggat agtctaaaaa tgcatttgat ttagtgtagg tgctgctctc tttttttgtga   1800

ttgttcttag cttacttgga gctgtatgtt aatgctagag ttcattgagt atcaatgctc   1860
```

```
aattacagat agttttgttt tgtaatttcc acatatattt tcgtatttgt gaaattaagc   1920

tcgtttgttt tcattgtttg ttggcaattt atgttttatg ttatgccaac gattcatgat   1980

ttgtagcttg actcgaaagg                                               2000


<210> SEQ ID NO 112
<211> LENGTH: 1027
<212> TYPE: DNA
<213> ORGANISM: Cucumis melo

<400> SEQUENCE: 112

ggggggggtt gtcttcctca aactctgtta tcgaaattag gtttacattt agtatctggt     60

tgacgttttg attgtattcc tgggcctgaa atatgataaa taaatatgac cattgaagtt    120

ggtgtttatt ctgggtttct atcattaaga gggtgtgaac ttacgaggga accaagaaag    180

ggatggaaat aggaatattt agaatagtag gaagctcaaa tgaattattt cgttcgataa    240

ggcggagtga atataaataa tatgcaagga gatgcggaga atattaccca ccttatgaga    300

gagagccaca aatcagaaaa cagtaacaaa tataacaaat caaacaacac catttgcaag    360

cgaattcaaa cgtttttcgg gtatgttgtt ccattaccac attcaaacat gaattgaaac    420

ctgagctctt gggcacttta attttatttt caacacatta cgtttaaatt gccgagtggt    480

caatatcatg tattgcttag tactaggtgg atacaaacct tacatataag gtcaaagtat    540

tgtgggcatg atataaatgc tctagcatat tggtctcata gagtttttta tacttttaca    600

tatccattaa tgagataagt taatgtttca acattaaatt tttagttaat atgaattcta    660

gatgcatttg ttatacaaat ggtctgatgt atttgaggtt ctgaatgtca aataggattg    720

tagtttattc acgttgaata ttgtaaagag ttaggacgtt tttttaagat tagatgatgg    780

gtgccatatg ctaccccata cgccaacaat tataatgaaa attatatttt gtcatttggt    840

atttaacaat ttttttaaa aaataagcta ataacgcata gaattcctga gatttaaaca    900

actttctgta atttcttttc tatgtactaa ttgttataga acctgtgatg tgcttgtcca    960

tcatgcagat tacaacgact ttgaacataa cttcaaaatt gttgataatg gtagccgagt   1020

ttttgcc                                                             1027


<210> SEQ ID NO 113
<211> LENGTH: 2000
<212> TYPE: DNA
<213> ORGANISM: Cucumis melo

<400> SEQUENCE: 113

agccaaagtt taatatgatt caatcttgca caaatgcagg ttacccaaat ggttaaggtt     60

aagacaggca acaccactct agcagttggt gatggtgcaa acgatgttgg aatgatccaa    120

gaagcggata tcgggatcgg tattagtggt gtagaaggga tgcaggtaaa tttaaaacag    180

atcccagctg gagtgataaa atatagcttt cattcatctc aattttgttt tatacttctt    240

atctttctga atttcaggcg gtcatgtcaa gtgatattgc aatcgcacag ttccgatact    300

tggagcggct gctccttgtg catggacatt ggtgttacag aaggatctct tccatggtac    360

attatgatct ataaatatta ctttatatta gcttcttagt gagaatcatc cagattaatg    420

tgcaactata cagtctcaac atcattttca gcttgaaaat ctttgaaata tgtcgaactc    480

atcgcatttt atatatggca gatatgctat ttcttctaca agaacattgt ttttgggttc    540

actctattct tctttgagat gtatgcatca ttctccggcc aaactgtata caacgactgg    600

ttcctttctt tgtataacgt ctttttttact tctctccctg tgattgcttt gggagtgttt    660
```

```
gaccaagacg tctcatcccg gtactgtctt aaggtaagtt caactttcct ttatttcatt    720

ggtgcaatct tttgccttcc ttaagtacaa tatcaaatgg ctcattgccc tcaacatttt    780

tggattttca gttctcactt ttataccaag aaggtgtcca aaatgtgtta tttagttggg    840

ttcgaatttt cggatgggtg ttcaatgggc tactcagttc tgtcatcata ttcttctttt    900

gtgttggggc aatggaccat caagctttcc gcaacagcgg agaggtcgtc gggctggaaa    960

ttcttggtgc caccatgtac acttgtgttg tttgggttgt aaactgccaa atggcattgt   1020

ccatcagtta cttcacctat attcaacatc tcttcatctg ggcagcatc attctttggt   1080

atttattcct catggcatat ggagctataa acccagccat atccaccaca gcatttcagg   1140

tattcattga ggcctgcgcc ccggcaccat cattttggat cctcacacta ttggctcttg   1200

gagcttccct tcttccatac ttcgtctttt catcgatcca aatgcgattc ttcccaatgt   1260

atcatcaaat gattcaatgg ataaaagctg acggacaatc gaacgatcca gaatactgtc   1320

aggtagtgag acagaggtca ttacgtcaca caaccgtcgg ttacacagct cggttcgaag   1380

catcaaagca ttttgaagaa ttctcagaaa tcaagagtca ctaggtttga tgattagatc   1440

gtagaaagat tcaaaacatt ttttctacgt aaagtttctt ctcagtgtat atatatatat   1500

acatttatat atttatacaa catgtgtaca taagattctt gtgtagtttt gatctccttg   1560

tagcttaagt gaccattccc aattcaaatg gtcaaaaatt ttcttccttt catgaaattt   1620

ttaggaaata agccaattgt agtattcaat cgtatatttc aaatagtcat tgagaagttc   1680

taactctact atagttctca attataagta tgatggtttt gtcttattca tcttgtagta   1740

gaaacaaaag aataaattta cgaaggatga agcattgtta ttttaattat aatttgggaa   1800

atttggagcc acgaaatgaa atccaatttt gtgccaagta gatgtgcaac aatgggcaaa   1860

gaatcacttt ttctttttca taattttccc ttccaacact caccactaat tcatcacctc   1920

aatcctcttc ttcttcttct tcttcttctt cttcttcttc actcgccttt gggttgaggt   1980

tggctctgtt acagtcatcc                                                2000


<210> SEQ ID NO 114
<211> LENGTH: 2000
<212> TYPE: DNA
<213> ORGANISM: Cucumis melo

<400> SEQUENCE: 114

aaaagagtca tagtgaaaaa agctgagatc ataatagttt caccctaaac acaacttata     60

ataacacata ctatcataat atacacacca aacacagact ctatagtctt cactctaaac    120

gcagattaca atagtctgca ccccaaacgt agactattat aatcttctga ctattataat    180

actcttttca cttatcgccc caaacgtccc ctaagagaac aaagataggt tataaaagag    240

agatgagggt ttatattatg caacaagtat aaggttctag aacgatgtag tcttcaaagt    300

aacgaaagca ataggctaca cgagaaaaat atttttaaaa tatagtgctt tccctaaact    360

agatttcaat gacaaattat tataaaaaat agaatcatta atccaacatg gcttgcatgt    420

cacaccttgg ccaaaactga agacggatgt catactcgac ttcaatatat ttttttaatt    480

aattttcatg tgacaacaca taaatattta aaatttagat tgggttggat ttttttttcaa   540

gtgggtccca aaatactctt caaacccaaa ccaacccaac ttgtttaccc atctaataat    600

aacccaccag gttcaagaag acgaaccgaa ccgaaccgat ccggtctaac tttgtttcat    660

acttaagtcg aacttagcgg tacttttggt tcggttctcg gtttccccaa acagagccac    720
```

```
tcaaaattag atttagggtt ccgttcgcaa ttttcagcgc atttttattt gaatcggtcg    780
tttgttgaac acgttctctc tcagctggtt tagggttcat cgttctctct tctcgcgcta    840
tatctttctc tctctcaggt tcgtttcttt ctcttaggcc attttatcag aaagatcctc    900
ttcgtttctc cgattttctt tccgtgttcg ccctcggttt ctcagcagac gtaggaagtt    960
tggtttccgt ttagtgaatc tgtttggggt attacgaatg atattttgta ctgggctttc   1020
cgcatagtct ttttctttct aggaatatat gcatctgaga atttatttgt ttggcttttc   1080
tttataaagt atgaggacat atacatctcg attgctaatc cttgattata atcttttttt   1140
ttctatgttg tttgaatctg tttttttttt tttaatttct aggttttttg aatctaaaaa   1200
tgtatttctt ggatgaattg catactgttg aattagaagt ttattgatta gattgttgat   1260
atttgcccta agttccatgg ataggtttgc gtctttcacc ttttcgtttg ctttttcttt   1320
tggctgacga catcttacat agcctctgct ctaaaaggtg ccatgatttt ttttcctggc   1380
tttatctgag tttgcgcaat ttagatttga agtgatgatt tgtctaaata taaatatcta   1440
tcggccatac tattttttgt tattttgagt ttttcaagga tgactgctag agaatgaaaa   1500
atcttgaaaa cattgtgttt tgaagttcaa ggatcttgta gttttgttct tttctagact   1560
atctcatttg atatagccct ttaaatttaa tcaaaatttg ttaatattca aatcctcgga   1620
cattttaatt atttatctaa atagttgttt aggcattact caggttgccc actattttaa   1680
gcttagaagc ctactctggt tgacctaaag tttgcatgct atttgcctta tttcgcacga   1740
ctctaaactg ttatagacat ctttttttcag ccttcaggta aatgaacaca aaaaggagtg   1800
aaagtctgac ttctgtgtga tggtctttta atcaattata gggattaaga tggttttttt   1860
attcattgta taaatattaa attagaatga tgacaaccaa taatattaaa actgacaatg   1920
gaaggttcct tatattattt ggagtgtaca ttacaacagc ctgattcttg gcttggcagg   1980
ttcctgatca ccttgtaaac                                                2000
```

<210> SEQ ID NO 115
<211> LENGTH: 2000
<212> TYPE: DNA
<213> ORGANISM: Cucumis melo

<400> SEQUENCE: 115

```
aatgtaaata gtttataaac ttaagataaa attggtaatt gtttaataca aatacaaatt     60
gttaaatgaa atgacacacc ttgagcaatt ttcttttcta atcttctctt atagattaat    120
tttatttaat catgaaggtt agaatttctt tagcattatt tatttattta tttattagaa    180
aaagatagtt tgtgtatatt ttatatcata aagtttcaga agaaaccata aaattaatgg    240
agaataataa aaggtgggga tctctaacat ttttgccata aacaaatcac taagttaaga    300
atatgacact aaacttcttc taatttaata ttatatacaa agattttaaa attataaagt    360
aagagccttg aattgtagct aatttaagaa tatgctctaa gttttttaaa atcacttttg    420
ccctacggtt attatttatt tttttgttga aatatgttta atccaaatca atttcaatcg    480
aacatagtca aggatatgac tgcggattcg tatattagtt gattttgaaa cgattaaatg    540
tttgaaatat tgtagtttag gaacaattac aattataaca atcagattca aaattttagt    600
atatacagta acatttaaaa gaataataaa tatatcaaaa tctatcgaca atagacttct    660
cttcatagat aaattatcag ggtctgactt ctctcataga taaattatca gggtctatta    720
gcaatagact aaatccttga tggtttatca ttggtagacc aaaagagttt attagtgtga    780
tagactttac tacataattt gcaatttgtt taaaatgttg ttatacattt ggttgctatc    840
```

```
cttaacatta caatccataa catttgtcgt gtctttaact tgaattgatt gttatctgtg    900

ataaaaagag atgatcactt tttgtcatga gatttgaaca attgatgtta aaagtggtaa    960

ttaatgtacc attcactaac caatgtcaat atttattttg tttaataaaa agaaaaagga   1020

gattgtgaca ttagttttat actcttttct aaacataggt ttggtttgtg ttagatttgg   1080

cctacactta gctcaaatcc actctttata aaattccctt acttattaca agttatattt   1140

tcactccaat cataatcttt taaaggataa tatttgtatt agaagatacg acacatgtag   1200

aagataattc ttttttaacc aaaacaacat acaatttcga ggatatgaca aattaccttt   1260

tctattttta actatttgat cttcaagtcc catctaaaca tcaaatgaaa gttgattagg   1320

ttaaagaatt ggacaattag agaaggaatg gagaatcaaa cctctaactt ttaaggaatt   1380

aggtcattca cattttcatt gagctaagct cacattaaca agatcaatat tacttgtatg   1440

tagttaattc agatgtgaat ccttgaggtt tcaaaagtga cactttagtt cgaggtttaa   1500

aaaatattta tatatataca catgttacaa cccaaattta aggtatatat ataaatatat   1560

ataatttaat tatcttgaat tataattacc ttaaattact taaagtaaag attggtttat   1620

ttatgattaa gttatgatga atgttaagta atttgaaaat ttgaagttta gaggattgtt   1680

aattcacttc attgtgggcc tcattaattg gcccattaaa tctccatatg ggcctgtcta   1740

gggcttcatt tccccaagct tccaactgta atggcggcca cagttctctc ctccatctcc   1800

tctcttctta cctacttatt atgttaatat ctacgttttc cagattcatt ttctttttat   1860

ttgtattatt ctaaatctcc agaactgctt agctgctctg gtttttgggg attttagggg   1920

gctcgatctg gtgggtttac ggttaaattt tgcagctttt cgaggtcctt ttcggcttcc   1980

attttgtcgg aagttacaaa                                               2000
```

<210> SEQ ID NO 116
<211> LENGTH: 2000
<212> TYPE: DNA
<213> ORGANISM: Cucumis melo

<400> SEQUENCE: 116

```
acacttgtaa tgttgagcag ggtaacttat ggtaaatttg acatgagctg gcgcacaaag     60

gcctagcatg ctcggagctg tttttccatg gagtcaatgc ttgatcgcat tattggctat    120

attctaaatg aaactaaaat tattgatggg ttccatctgt ttggatacca actttataca    180

caggtgtttt tctatttatg agtgtaaagt ttgatttgct tcatcatcgt atattcaacg    240

tagagtttct tagttaatcc aatccatatg cctcaactat catgctcttt tccctgtaat    300

tgaatgtttt ttttggtgtc cacatggtca tggaggtttt gttctgcact agcttcacga    360

tgctactaaa catgatgatg aagcttgagt ttatttattt cttagtactt tgtgatgaaa    420

aaaaagtaga agaaaacggt agaaaattgg aatggatacg gtacaatgga tgggttgtgc    480

taagtcacgt ctcgtggata caactacaat tagttatttt gttttgtaga tttcatatta    540

gcatttcctt ctgaatagtt gaaatcacca tagaatgtgt actgatgttt tgtgatttta    600

gtgcttcggt ataatttgaa cgctttacaa gtaaaaattt cctcaggtaa acgagtcttc    660

cgaagtactt gttcataaaa tgttcttgtg tgggagagtt gattggagag gatcatggtc    720

aaattcttct tggtgtgttt tatataaggt tttaatgatt ctttgaaatt gtaatgtttc    780

cttagttttt ttaagtgata ctggtgggtt ttccttggaa taaatattaa gggctgaaac    840

ttaggaatta tatggatttg agggaggttt gtggattctc aaatcaaatc aaaccaaaac    900
```

```
cagataattt taaattctag aattttgaag ttactatttg tgtttagaaa taaaaagaaa    960

gaatatcgct tctttgtcct tccaatattc tttagaacca aaagagaacc aaaattatat   1020

ataaaagagt cgataaaatc aaatatatat ctataatata gtttattatt atttttcatt   1080

tgctatcaat aagaatttg aaatgtaata tttgctccaa attatattaa aaacagctgt   1140

tgaaatttca acaaaatgag aatttgtact ctggattttg ttattagttt ttttttcaat   1200

atcttaaact atttcttaaa tattctcatt gcgagtcctt ccatttacat agaactaaaa   1260

atggattgag tttggttaga gaataatccc aatcttactc atatttttag gttgattaga   1320

ttggtaattt gattagcggt taagttattg ggttgtattg tttcataaat tcgatagatt   1380

acatcgatgg caatgtagtg tggaacataa aaaataatga aataccagcg gaacacaatg   1440

gagactgaaa aggatagacg atcgaagatg atgaaatgag aagctgacaa caatgagggg   1500

cgtgagttga gaagccgaga caagagggag agagtgagtc ggaaagagat gtggggcgtt   1560

acaagttgtg ttgaacaaag tgaggtcaaa tttaaattta ctatttgcta aattaataat   1620

aaaataaaat ataaatataa acatataaat atatatatga ttgggttggg ttgatacaaa   1680

atttctaacc ctaactcgat aaagcaaaat gcaacccaaa ttttaaatta accagatcgg   1740

gttattctta tcctaacctt aggacagtga ttacttaatc tgtacgcagg ggcaattttg   1800

acctttgata aactctccca ttttgttttc ttttttcggc aattttccct ccctctctag   1860

tctcttctgt tctcagttca gctctctagg gttttgtcga acagccattt ctaagtgtac   1920

atctcctctc aatttccctc gctttattcc attttttcac gtactatcgg cggatccttt   1980

gagctccaac tctctcatcc                                               2000


<210> SEQ ID NO 117
<211> LENGTH: 1025
<212> TYPE: DNA
<213> ORGANISM: Cucumis melo

<400> SEQUENCE: 117

tttttcttac ttcattatcg aacaataatt tgatttccaa gcgacccttt caaattcaaa     60

caaacccatt tctcctctca gccagagcaa gtgattgaac tgctgcgctg cgcgtgacct    120

gttatcttct ccgtttttct taccgccgcc cgcccctcac ggcggagtag tttcaccgcc    180

gacccatttc gccggccgcc ggcggtgttt cgattcctct tgttttgtcc cttttcgtct    240

taccagtttt ctctctgtct acattgtgtg ctcgttaaca gccagctgta tagccactgc    300

tttttttatt gactcttgaa acagagagat aggggagatt ctgtatagtc ccactgtttc    360

tgctcaactt tttcggttta atgtctgttt ctatattcga ttcttcgttt tatgttcgtg    420

attcgatatt gcttttgctt ggaatcgttt agaggcaagt gattgtctct gcttttgcta    480

tgtagttact ctgttttttt tccctttctc tctctctctc tctccccccc tctttctcaa    540

aagggggttg gttttttat cgtcggagga tgttgggttg atcttttgat agggtctgtt     600

gactaattta gctggtgttc ttggtctgct gaatccgaac ttctcttagt tttagagttt    660

tcgatgttgt tggtttacac tgattcttct tcgtttgttt gggattattt ttgacaggac    720

tatagtgttt aactgctagc tgccatggaa catgcagaat ctgcggtgag tttttagaat    780

aaacttgttc ggttggtgag aaaagcatgg gaaagaggag ggggaggttt ttctttatgt    840

caaatatttt ctcaaactca ggttttagaa taaaaaagcc tttgtttctt aaccaaatag    900

tttatttgat aatcagctgt tttgttttag ctccctcatc tcattttcgg aaatcttagt    960

tatcagttta atcaactctg tgttctatga tgctcatttg tacttaggca aaggttataa   1020
```

```
agaac                                                               1025

<210> SEQ ID NO 118
<211> LENGTH: 2000
<212> TYPE: DNA
<213> ORGANISM: Cucumis melo

<400> SEQUENCE: 118

tgcattttat cagagatgaa attgaaaaag gaagaataaa cacgtactgt aaaatcaaaa      60

cataagaaac ccagctgact tagcttgtta attaaccaaa caaagtttga gcattgtcta     120

aattaaagtt gttcaacttg actgttgtag ggttattaat ttttcttgaa aagaaaacgc     180

agcatataat attaaaggag tattttgtct cgagggggaa gattattggt taaaagtata     240

tatggtgtga cataattaaa tactttgtaa ctaaaaaata aaacataatg ggaagttatc     300

tctaccaatt tttttgttaa agggctgaat atataacctc caacattact tagttactga     360

tatatcagtt tctctagccg tcaacagtac tacatagttg ctgatcataa atagaagaaa     420

caagttagaa attttgtgaa gagaaaggcg agattatgtg atttttgctt tgtataattt     480

tgaaaaccct tgatataagg aagttccttg ttgctgcatg ccttcttaga gatcagcagt     540

tactgtatgt ctatatataa ttctctctct caatattttt ttctgttctt gagcttgatt     600

gtttactgct tcagaaatct tctttacaac tactactgta tttggaagtt ttagttccat     660

atatatttct atttttttaa tgatttcaaa tcttgttgtt tcaaacagta ctctcctaat     720

tacaaataca ataaaattat atctagcatt acaattttac aaagtccttt tcttgtgaaa     780

aataaattac gtgagacttt gtaaatggta ttttgaatgt attaaggtac tatatgacac     840

ttagaattgc tttgctttag ctctaaccat gggttcaaat gtaaagttaa aaataaaaca     900

atcaactatt taaggtttta cttaaaaatg taattatttg tcaaaataag cataataatt     960

gagtagtaat ttacatatat tgcctccaca tttgagatca aaactagaga tgttcatttt    1020

cttagatata ttattaagct aagaatgaga gaatgggtga ggggaaaagt gaacggaggc    1080

aggaagacca aatcacccat tcctgaaaat ggaaggatta aaattgcaat tttccttgca    1140

atttaatacc aacatgattt tgtatatata tatttgaaga ggggttttaa aaaaatataa    1200

caaactgtta aaatatttac actatataca acaatcgtta agataaaaaa actcataggt    1260

ccacaatgaa aaatataaca aatgtcatag tcaacacgcg attaatcagc cacactcacg    1320

ttcgagtaat cttcttctga atgattgtgt attacagtca aaatacacaa tcgtagagtt    1380

cttttctaat gatgttgaaa aatacttcaa atttagggtt tagggtttag ggtttaatga    1440

tcgtgttaac cgtgaaaaat aatcgtgtta atcaatggaa aacgatcgtg ttgattatga    1500

taagtgatcg tgtagtccaa tgtaaacgat cgtgtttgac tatgttaaat gatcactatg    1560

gtaagtgatc gtttaaatca tataaacacg acgatcatgt agttcttttt aaaagatgga    1620

aaaagaattc aaatgcaaac gttcgtgtta acaatgacaa atcattgttt agatcatgtc    1680

aaaattaata tttaaacgat ctattgatat tcttaaatag gaggaagatg aagtagttct    1740

aaagaatact gtcgaaaaca ataaagatag aatatgatat ttaaattaaa aaataaatga    1800

tatcggaaga gaagatgaat aaatcagaga aacagatata aaaggggaag tgactgatcc    1860

tccaaatcta aaagataaaa atattttaca tgactctgta aactttggtt tcttttgcta    1920

ggcagtaaat atttgagggt tttggtattg tatttgtggc ggaatggagt aagtgggcct    1980

ggcattgggc cgtatacgta                                               2000
```

<210> SEQ ID NO 119
<211> LENGTH: 2000
<212> TYPE: DNA
<213> ORGANISM: Cucumis melo

<400> SEQUENCE: 119
tcattccaga aaaggtaatc tttgattttg agaagttaat ttgaatttta ttttaaggga 60
attcaggcag caagattaat catctggctt cctggaaaaa ggtcaagttt tctcaatcag 120
aaggggggct aggtttgggc agtttaaaaa ataaaaaaaa taaggccctc tttctttact 180
aaataaatgg tgttggaggt ttttgaaaga agactccaca ttgtggggta agttatcaaa 240
agtatccatg gcttcaaaaa aatttaattg gcagactcta aacaaactag aaaatagcct 300
tagaagttcg tggatcatgg gaaagttgag ttggcaactt tcaaaacaga gaacgaaagg 360
agagtaactt tctggacaga ttcgtggatt agtgatctcc ctcttaaata tccatttcca 420
aatatattca gattagctca acaacccaat gattcaatta ctgcgcactg ggattatgtc 480
actaattctt ggtcattagt attttgaaga ttgctaaaag atgaagaaat tcaagatttc 540
caaaggcttt taacactcaa atcctagaaa gtaatagact tggatgatag aagagtttgg 600
tcattaaaaa cctcaggcca tttttcagtt aagtcccttt cgaagcacct ctctccttct 660
tcacctttgg aaaaagatta ctttaaagca ccttggaaaa ccaggagtcc aagaagaata 720
aatgttctgg tttggattat agcagtgggt tctctaaact gttatgagac tatataaagg 780
aagcttccta atatgtgttt actaccttta gtgtgctcca tttgcttgaa aaacagtgag 840
ctcctaatac acttattcat tttttgtccc ttctcatcta cttgttggtt tagcatattt 900
tctatgctca aacaacttgg gtctttgatg gttcattaaa caccaacgtt gttcctaatt 960
ttttaggggg tccttattta tatatatata tataaaaaaa acttttctaa tttgggttaa 1020
tttgataaaa gcactcctag ctgagatttg gtttgaatgt aaccaatgca tcttccatga 1080
taaaagagag agagagagat tgggttgaca ttgtagacaa ttctaaaaga aacgtggtag 1140
cttggtgttc ttcaaatgca gaattcaaat gcaggatatc tacttattgg actaccttca 1200
tatgaagaga ttcaatgcag tttcccccga ctactagttt agaatttgtg tttttgtagt 1260
tttaatgggc tgtaatatgt atttctacct ttaagttttt acttttcagt cttgcttctg 1320
tctaccatag gtagtattgt tattttgggt atttactttt gtcttttcat gaccttagtc 1380
ttgttcttgt attttggata taatgagggt gctatcgggg tatcaaccta gttgagatgt 1440
tcgagtgcac ctactgatcc ccttatttgt aggcttctct attattctca atgtataact 1500
ctcttgtact ttgagtttat caataataaa gaagcttgtc tcattctaaa aaaacaaaaa 1560
ggaaaaggaa gataattgct cctaatcgtt gaaattacta ctaattactc ttaattactc 1620
caaatgatcg tataacatac atttataatt tttaactttc ttttcctttt taaataccaa 1680
cattaaattt taaatacatc cattaatttg aaattagttt tcaaattcca aatcgaaaga 1740
tttaaagtcc tttgaatcca aagggagaat gagcccatcc aagcaagttt ttgtgtcgta 1800
gttgcatatt ttaagtcgtt tcatattagc ctcgagtttg gcttaatgac ttggtggtgt 1860
ctagtgcagg cttgtggcga ctggcgagcg tggttctaaa gataaggttt gcattcgctc 1920
cttctccctc cctttcacta cttcatatcc atttcctttc tcgatttctc gtcttccctt 1980
ctgaattccc cattccagcc 2000

<210> SEQ ID NO 120
<211> LENGTH: 2000

<212> TYPE: DNA
<213> ORGANISM: Cucumis melo

<400> SEQUENCE: 120

```
atttatttgt ttagagataa gacgcacatg agaatatgag atggattcca ctccactcac     60
actccaattt ctacctatcc tattactgtt tactattatc attccacccc tcgacccctc    120
attcttcttc tcaccttact tttttatgat ttactactac ttcattttgg atcacaatct    180
gatcaatgct gggtgggctg ccctcggcct gtcaccaggc ccagcccact tccaaattaa    240
acctcttggc ccaccgccca ttgtccccat cccattccat ttaatattcc caaccttccc    300
tttttctttc ccaatgcgat gcttctccaa tataccttc ctgccctcca tgtttccttt     360
ttactgcttt cttatattta taacacacct tctacagtct tttggctggg aatgctgcgt    420
atgtgaatga gattcaagat ttcgttgatg ttatttgagt ctctatattc ataagttttg    480
ttcttagttt tctctagacc aactgcaaga gttagcgttc catatgctca taagtttcag    540
atttctgctg tgtggtttga agacagtcat cgatccatgg gtgaattcgg ctttttatta    600
ttattattat tattatttat tgttgtctta cttttctatt tgaatcttcc tatcttttta    660
ctcattgttg gactctaata attcttgcta aacacaatct ccatttttat tggacatttt    720
aaatcccatc tcaactcata attttagtta ccttccacca tcaccatatc caaatccgaa    780
ataaactcaa ataaaatcct tcacgtgcat gtgctctcca tatatttttt ctacatggta    840
aaaataaaat gaaaacaatc taaatttaat aaaataacat atatggcaga cttttattga    900
tgtagagact gggtgttgta caagaacagt gcagccaaga aaaaaaaaat acttccaatg    960
aatcgtacat tttaaggatt atgaaactaa ctagttccaa ccattttttc acgaccacgt   1020
gcttgttaaa cacgcaagta gaatcaaaat gtgggcttct tcgctttata taactgtgaa   1080
tcattctcca aaaagggaag gggatctcat tccctaattc aataaagaaa aagaaaaatg   1140
ctagcgaact tcatccatct cattcctttt acctatttca tgagatgccc attgtatata   1200
agtatttttt tttttttat ttcattttac ttagtttact cctcacctct aaaaaaaatt   1260
aggagagttt gctaaatcca ttctcaaact tagctttatt tttttaattt tatttaacct   1320
cgtcgtggat gttaacctca aatgtcagtt ctttttattc tatttattga tgttataatt   1380
tactttagga ttccaatttt ataaaaataa gaatacaaat aaagataaag agtgtgaaag   1440
ccagaaagaa aaaaaggaaa tcgtaatatg ggtaaaattg gtacaaattg ggtcccgtta   1500
aatattaact caaaaaatgc gagaaaatgg tagaaaagga aatagggggt aagagcaaag   1560
tagtggaagg agagcattga acatattctc tagtttttgc acttggatct aaacacgagg   1620
aattataggt ttattcattt actaattaca taaataggat tggattttaa aatttgaccg   1680
agtgattatg catatttgat agagttagaa aatagtggtg gggcaggtac aagttacaag   1740
taatgtataa gagatatgat gagcatatta ggaaactata gatttaaatt cgtccgtaaa   1800
taaataatta gaaatataat attcgagtgg aagggtatta gggttaggcg aaaccaattg   1860
cagttgcacc tataaaaccc cttttacgcc tccacccgct tcaacagcgg tctcggcgtc   1920
tacaactaca cactacacac tacacactac acactacaca gttgcagacc agaagcataa   1980
cgtaacgccg gtccacaaaa                                               2000
```

<210> SEQ ID NO 121
<211> LENGTH: 2000
<212> TYPE: DNA
<213> ORGANISM: Cucumis melo

<400> SEQUENCE: 121

```
tgaagagccg gaaaagcatg gcaaggtcaa ggcatttcag caagaatacg aggatgaatt     60
ctgggtttgt aagtccggtt cttcttcgga gttgtggttc gaatttcaaa cggccatgag    120
gagccctaca gcttaggaag cttcaggtct gagactctga ctccgacaga aattgctgat    180
ttttgtgtgt gttttgaata accattgtat gagtatgatt ggttgtatag gtttgaaatg    240
agggaaagtg atccatctcc ttgttgtctt tgcaggaaag gctcatattc gaccaagaac    300
gctttgtcat tgctttcgat aatcatagaa tccacaatgg tttggcatat tagcaaacaa    360
atcttcttta ggcattgcag acagaaaatt ggagagtaag ttattataat taaggattct    420
aaatgagtaa gaataataag atcaggcaaa gattggaaga actaaagcgt ttagtatttt    480
gtgtggtaca gaagaattgt aattagatac gtagtctaga gaagcagatg gtgagatttg    540
tgaaagacaa atgttagtgg agagtgaaga gtgtttctca acaaccgaca tagaaggatt    600
ctcagaaaat gagaaagatt tttattgcgc aaaatagctc ccatatcatc atatgccgtt    660
gccattccct ctggggttgc atgtaatgag taatggaaag ctgtagacag gctaacttca    720
ccctttgtct tgggtatagg gtgcattttt ggtcactcca ttttaagttt tctaataata    780
aaaggatgaa gaaaagatat tgaaaaacag ctcaggtttt aaagttgtca cacttgagaa    840
taatgcattt aacagttaga attttgcatc aacgtctttc aaatagaaaa gtaaaggaga    900
gtctagtttg agctggatag ctaaactggt ttaatcatat cttctatcaa gtggttagag    960
ttttagacct cccaacttta tatgtcgttg ccctaacaat gttgatggat gtttagtcct   1020
aagctctaac attgtccccg tatcatattt cataatagaa tgtactgagt aatggaaaac   1080
tagagaggta ggaagttgga cgaactttga atctatattg attttactat agtctttctt   1140
ccaagtctta atgagagctt tagctaaagt ttttcaaaaa ctcaaaagaa gtttttgttt   1200
tccaattctt cgatccatag attgtcaaga tggctataat atccttgaag ttaatagcct   1260
tcaaagtttc atagctttta tcctatgatc tttagaaatt caagagttat attctttaga   1320
actacagaac tttgatcttc gattcttcac ctcttccaga acctttatag tagagtttct   1380
tgaccttaca tgggcttggg attgggcctg gctacttatg ggcttagaga ttgaccttgg   1440
gtttaagcac attcgtttta cttggcccaa ttttcttaaa cttctgcaaa atcctaatta   1500
actaacacct caacaaaagt ccagtattaa atggggcata taaacaaaag ttaaacaaaa   1560
ttgtcgtaca gaatcctaat ttgctaacct cagcaaattt tatgccattc gtccttgtgt   1620
atctaattag tgttaatttg aggaaatata ataatataga cgtaggacgg atattggtat   1680
ttggtgcaac atcctccgaa ccaattcctg gaaagtaatt ggggcaacaa gataatgtta   1740
tcgtcagttt caagtgcaaa acttgccacg tggaacagcg gcaacatgat atctcaaata   1800
tggacctctc acccggtcaa gcttccacca ccaccaccac ctccgtattc taaaataaag   1860
tcaggaacaa gaacagacac accttaacaa aaccaatatt cttcatctct atctctctct   1920
catttcagca tagaagagag ctgagtaaaa ggaaaaaact tcaatcaaat ttgacagaga   1980
agagcccaag agaaaaccaa                                                2000
```

<210> SEQ ID NO 122
<211> LENGTH: 2000
<212> TYPE: DNA
<213> ORGANISM: Cucumis melo

<400> SEQUENCE: 122

```
agatgaacca gaaagatgga aaatctactt ggggttcagc agtgagtttg gaaaagagag     60
```

```
aactatttga agaaagagca gaaaccatct tgctaatact taaacaccgc ttccctggaa    120
ttccacaatc ttcactagac atcagcaaaa ttcagttcaa ccgggtaaaa gaacgctcct    180
tccttgtcta taatctcatc taaaattatc aacaatccaa acacaattta tacaaactaa    240
aatgaaagct tctcaacttt aggctacaaa aacagatgct tattataatt ctgcccaaca    300
atatcttctc ctaaataaga tgatatatgt tttttgccca tataatcaaa taggaaataa    360
caatcctgtg cccatttctt tggagtgtga gatcataaaa cactgtctaa aacaacatgt    420
ccaaacatat cgtaaatacc tagtttcata gtgtgatgaa ccaccacaaa caaacttact    480
ctttggtgaa ctgcaggacg tggggcacgc cgttttagag agctactcca gaatactgga    540
aagcttagcc ttcacagtga tgtcacgaat tgaagacgta ctccacgccg ataggttaac    600
tcagaaccca tcacaaatag caacaaggag gaaaccgacg agcgaacccc caatggagaa    660
atcagaagag ttgaacaaca acggcccaga aacgccagct tcaatgacgc tgttggattt    720
catggggtgg ggacaggatc aaaacgagtt ggagatgaag aaggaatggt ttgggaattc    780
agatgattta aacgcggatt cagatctgaa acaagggaat aagccaggga atatagtgac    840
gaacaagagg gtttcatacc tggagaattt gagcgctgtg agaagtccaa cggcgcgcca    900
ttgaagaaga agaatagata gagagatgat ttggaggcaa aattccatga tttcagttat    960
atacattcct tttgtgtaaa taggaagaag aagaaggaga atgagatcaa ccccattttt   1020
ttctctcttc tttttttaat ttggattttg gaatcacaac tctttgtgtt tgtgtaaaac   1080
caaaattgtt ctatgtatca tttgtatcaa ttaatgtagt cattttagat tcatacattc   1140
aaaaatatca actccatttt ccaactacta tcttcctcca tctcacctct aatcataatt   1200
caaagcggat acaaattcat gttagaatga aagattcgag tatagcctat tccattgatc   1260
aaatgcatgt atctatacta ttgacacttt tcaactcaag tcatgcttga acaattgttt   1320
tttataaatg ttaattacaa gagtgtacac aaatcgagtt gggaaaaaat atgaaccaac   1380
ccaaaccaaa aactttgagt tggaccgaat ttgaataaat aattcaattt tcattatttt   1440
tatatagttt ttcaaccaaa ttttttatct ttttttttctc aaatttcaag tttacaataa   1500
tgtccattca aaagtttaaa ttttcatatt tcgaacattg aagttggaag gtccaaacga   1560
aagaactaaa tgattatgac acatgtctag ggtttatata tattgttgag ttgagtaatc   1620
caagtttttg aaacaccact agttatttat gttaaataat taactgagta ctcgactttc   1680
ttagttcgag aatatttttt agaaaaaaga agagaggatg tgtttagaaa taatagcaag   1740
ttagggtgtt ggtgagtgag aaatattttg ggatcttctt gtaatagtta ttaagaagat   1800
ttttcaaaga atttgagagt taaagaaata ataataataa ataagtaaac atttaatagt   1860
aaacgacatg tcgttttata cagcatcgta tttacttacc atgtgctcat tcacacacga   1920
ttcctcctcc tcctcctccc gttcatctct tcttatcttc gtcttcttca tttcggataa   1980
cacaaaaatc cctaaaaaaa                                               2000
```

<210> SEQ ID NO 123
<211> LENGTH: 2000
<212> TYPE: DNA
<213> ORGANISM: Cucumis melo

<400> SEQUENCE: 123

```
tcattttcgt ttggttaaag aatatatcat cgtttctttt ataaaatgtt tttgtagaat     60
taatcttcga gtacttctca taaaaacatt ttttttaatt acatagagtc agtaataatt    120
```

```
agaactatct caaaccaaag tactataaca tttcaaacca taacactgta tttttttagaa    180

aagttattgt aaaggataga attacaaaaa tattatagca tatgaaacat tattgttata    240

ttttataaat attccatata caatataatt gattctagat gtctctaaaa atagggaagc    300

atatgtgtta ataactaaat ttaaaaatta aaaaattact cgattactgt ttatttattt    360

atgtgttgag gctatacata ctatatttta gtaattattt taaaattaaa aacaaaatca    420

catggctaat agaaacgata gatatctagt agtaaaattt tgttatattt ataataagtt    480

gtcttatttt acttaatgta actacaaata tctcactgtt attttccttt tttttcagc    540

ttattggttt atatgtttag aaaatttggt aaaatatttg tgtagctgcg gttatcatgt    600

atcaacttaa ctatgtaatc tatgaaaaaa tagtcattct ttaaaaaaaa aatgaaaagt    660

taaaaaagaa aaaaaggata aatttataac aatattcttt aattgaattt tatcatttga    720

ttcaaagata ttcttatact tttaaaagct gcaatgttat ttatgaaatt gttttaaaat    780

tacatttata atgaaaaaat ctttaaaaat gtagaaaaat caaggcttag aattgtattg    840

tcatttccat caaggagagg atgtaatttt ttctttatca ctttatttga atcctcaaat    900

tttcgataag tatatatttt gacatttgag aatatttttg tttactttaa atttaaagtt    960

atttttaaaa caaatgaaac aaaatattca taacgtggat caaatcacca taatttagaa   1020

agcgttcttt tgaaacatga ccccaaaact ttagaagata aattacaatt tgaactattt   1080

tgaaaatggt agcaaggaga caggtaaaaa aagaccacat aaatcacttt aggctttaaa   1140

gaaacaatgt taattggaga aagattcatt ggcatataat tttgaaatat gattgtattt   1200

tatatttcaa atcatattcc atgaatttat ctatctttgc ttgtagtcta aatcatgcaa   1260

actttgaaaa taacaatgtt attgtatcaa aatttaaaag tttaaaacat ataattgatt   1320

aaataaagaa aaatatttag aaatgttgta tgccaatagg tattatgtaa taaattataa   1380

atgatataat attaaaaaca ataattcata ccattttttta aacataaaaa catgcttagt   1440

agattagtta taaacagttt caagtaatat ttaaaagaga gtcataagta gttttataat   1500

ttataaaata caatatcaaa cgtacttaaa actaattgct tttaacttca aatctaaatt   1560

aagaataaga aaagggagag tgggaaagag caaaatgaga gaaaatgtcg aaaatacgcc   1620

caacggttcg gaccggtcca tttttgtccc gcgcaatggt aaaaatagat taggttacga   1680

caatcaccat gatgatgagg atgatgatga tcatagcaat tcaagaagca tagggcccca   1740

cttttggccc tcttattttc tcttctctta cttactttaa agaatctaac tgtcctccat   1800

taccccgccg atcaatgctc tatttttctc tctctttttt cttttcttta ttaaacaata   1860

ataacaaaaa ccatcaaatt ttcaaaattt tgaattatat tcccttaaca caaaacactc   1920

tcctcttttc ctttctctta taaatacaag tggagctcca cacacttgtc attttgtacc   1980

cttcttcccc aacctcccaa                                               2000
```

<210> SEQ ID NO 124
<211> LENGTH: 2000
<212> TYPE: DNA
<213> ORGANISM: Cucumis melo

<400> SEQUENCE: 124

```
gggcttccat tggcctcctt cccgtcgccg tagtgagaga aaaaagaaag aaaggggaga     60

ggcagaagaa tttgagagat ggatcgagga gaggttttgg aatgaatggg aaatttgaag    120

gaagaggttt aaacataaaa gtgaggcacg tgcgagaatg caaatattta cggggctaaa    180

aatgggagag ccaacggatt caccccagta aaaaggtaaa ttcaaacacg tttatgcctt    240
```

```
tttacctttt tctttctttt tttaacacct atagatgtaa gatatttcat attcttaact    300
ttctctttct cttttctttt ttgttttact atttcccttt cgttggctaa taataaaaat    360
tgatggatac agtatatttg gtatgtcatc ataaatttag agaaggtatt aagattttgt    420
gacataaaaa cccaatttct tttaatgaga ttcttagaaa ttttattgaa gagaattata    480
aactttacgt aaattaggta aagtctttcc ctccttctcg atagaagttg ataataaaca    540
tagcatacct agataaaagt ttgggaacat ttttgttgtt tggagggttg aaaaaaatta    600
agaaatttca atttggttag gatttgatgt cttgattttt tgaaatataa actttcaatt    660
ccaaatggtc ggacttggaa cctaacaaat cgtgttttca attttacctt gatattttag    720
atgtgtgaga ctccattaag tattctcttc gctctcttct tactatttct ctgttttgct    780
atcgaacgat attttttta aaagatttat tttttaattg gtggaatgtt tgtatgagag    840
tatataagtt aaggtaaaca aataataatt ggttatttag caatcttcct agtcaataag    900
caaaacagac ctaacatgca tcaaagaaac aaaatcaaaa ccttaaaata tcatggttgg    960
gcgttgattt ttttttcttt ttaatgtttg aaaatgtggg ctttgggtgc cgcagtcgta   1020
tggttgtagg gatttctttt aagaaaatta ttttatattg tattcgtttt gatctgaaga   1080
tatcaattat acaataattg gaatataagg agtaatttaa ctttgttcgt gattgttttc   1140
tactttattc gatgtgtatt ttggaattaa atatgatttc aaatgatttt gtttatttct   1200
ttttattgat tttgttttga ttttactttg tatcaatttt gaatatcaat gtagtgatgt   1260
gcttgtatta aatgtattgg ttgataaatt tactatgcaa atttttttc aaaatttatg   1320
caattcattg tagtattatt aactatatca acacatcagt aaagtgaatc attatcaagt   1380
atatcaatta agttacaaag tgtatatatc aataatgtat caagtttatc agtagcactt   1440
taagcatata aagtgtattt aatcaattaa ctgtaccagt gaatcttact agatgtattt   1500
gcagtacatc cgacgtatca aacatatcat gtgtatcata tgtttaaatt tgttgagtat   1560
attagtgaaa cataacaagt ttattagtag tgcatcaagt atatcaaatt tatcagttaa   1620
acatttaagt ctactaagaa aaaatgagtg caataaaaat tatttttcgg atatataaaa   1680
aaatattgag tgtatcgaag agttccatgg tgcatcaaat atataaagat aaaaaaatat   1740
caagaaatat taaatgtata tccatatatc aagaaacaaa cctaacatgt atttcgtgat   1800
ccaacaaccg gactggaaga caaatttcgg cccgggactt tcatagtcca aataaaggcc   1860
cattaaactt aacctgggcc caaattaatt tgtaaatttt aagtataaaa agaagagaaa   1920
ccctagggtt tccttcattc accaggcctt cctatcccct tcccttcccc ccctccccat   1980
tcccattttt gccggccgcc                                                2000
```

<210> SEQ ID NO 125
<211> LENGTH: 2000
<212> TYPE: DNA
<213> ORGANISM: Cucumis melo

<400> SEQUENCE: 125

```
ggacttatgg ggaatgggtt caagtgatgg taactagcta cttcagattt aatatcctaa     60
attgccttgg caacccaatt caaatgtatt aggattagat aggtgttttg tgaggatagt    120
taataaggtg cttgcaagtt ggtgtcgaca ttcccaaatg tgaagggaaa aaaaccccaa    180
tctttggtct caactggact ttggttcatt gcagttgaaa ataaattatt ttagttcaaa    240
ccaataaaac acatttttta aaatctttgg atatttgttt cttaaagttc ctgaaacagc    300
```

```
ccaccaagtc catagcaatt aggaaggcat aagttagagc tagtatgctt ggcatggttg    360
ggggtgggtt accttgttat gtaaattcat agaaatattc atatcttgtg ctaaaagtca    420
aatggaaaga gggtgattgc tgtgatgctg tctaatacaa agtgctagaa gccatatgga    480
gaaagggtat ttctacagtg tctaataagt taattacata ataaatttct aggttatgag    540
aatccaatcc gcatgaattt aaggactgca cacttgctcc atttgcaaca tgtgtaccac    600
tttagaatca tatttcacct gagttcatta ttcaactaga ttaatgtatc tcttttggtg    660
ttacatgttt ttaagaacat aattatttta gtttactgtc ggagagaagc aagtactggt    720
tatgcatggt tctagtgagc ctaatagagt aaggctatgg tttgggcatt tggaagtttt    780
agtggattag aattttgaag gcaaagctaa ggatcataca cgcccttctt cccttttgac    840
cagttggaga tctatcatgt aactctattg tcttgggctt cggccttatt ttataaattt    900
catatatcaa tgaaatttat ttcctataaa aaaaagaaaa aagaaaaaaa gctaaggatt    960
ttaatatcat tgttagtttc tttaattttt ttctttggga agtgtgcatg tagagctcct   1020
ttgaaagaga aaaagcaaag aactcttgaa tgtaaaatct ctatgtttga gttttatagt   1080
agcgtaccac attcacttca tggtgatgta gttatagttt tcctatggaa tatggctatt   1140
aatttttgcg aggctcttat tttatagttc ttttggggtg ttctttcctg taccccctcc   1200
cctttttgtg agaaggggag gtttctgtgg ctagctgggt tggtttagat ttgtggacct   1260
tttttgtgag aggaaccata gaaccttttg atgaggacct cgagcactat ttgatcattt   1320
ataagtttcc ataggctttt gtaattacct ttttggtctt attttaattg gagtcccctt   1380
cctccccttt tgttggcttt tttgttgtat ggttgggcat tctttcgtta gggaagtttg   1440
ataattcaca taataaacat acaataaaca accatcaata caatcaacaa gcaggattag   1500
tgtaatactg taaatgtctt ttattttctt tactcctttt ttcttttgag gtctatgata   1560
attgatatcc aacagtgtat tggccaaaat gatttatcat ggtcagtacc ttaggggttt   1620
gacttccaat ccaggattta aggtttgaga ccagatattc tgtgcctcaa ggccctcaac   1680
aaccttctca tggctttttc ctgtatacat attattatat aaagttataa ccaataaaag   1740
ggacaggtca aatcctctta atatatgcga aaatcaacct aatgtctact gtataccttc   1800
tcaatcgcca ccttcctcct gctgtcatcc aaggtagggc cttattgtat cagctagctc   1860
cctttactta tttatttatt ttttgaagtg cgcagtttgt ttgtttacct tgttatagga   1920
aattcaatct attctcattt tattggtgca ttcgtctcag aaattcttgt acggtttcag   1980
gttatcatct acccttgtag                                               2000
```

<210> SEQ ID NO 126
<211> LENGTH: 1397
<212> TYPE: DNA
<213> ORGANISM: Cucumis melo

<400> SEQUENCE: 126

```
tatatatatt aacttttaaa attttgaaaa cgtcatagat aaattatata caaaataaaa     60
agtttgatta tttacgaaag ttaaaaagtt tatccgaaag ttgactcaac gataaaaaca    120
ctaaatatca cttttagaga tgatgatatt atacataaac atacgaactt acgcgtcaaa    180
cttttatact aacacaagat caaaacaact ttgttgagta gtgagaattt tatctgctga    240
tatggttgaa acttgggaag caagcagagg aagttccatt cattaccaaa atccattttg    300
tattcatcaa aatatgaagt ttagcgactt gataaagtca agtcaagtgg tcctatcgat    360
ttgttaatgt caatgtttgg ttttgaattt gatacctatt agacaatgat atataatttt    420
```

aagtatggtt tacactgtga tgctttatat atttttaaat gtaaaatatt agaacttgta 480
atttcaataa attttaaaaa tgattttgtg ttatttcctt ttttaaattg aaatatcaat 540
gtatcaatat tgcgtcatag agtattgcaa cacaacctta tgttaaattg tttattgctt 600
attgctctaa ttcaactcct tcatcaaatg tgcacagaat ttaaacaaga aaaagagtag 660
gtgctttttt actaaaatat actaaaagct ttttatacca aatcttatga caaaatcatt 720
ccaacaaaat gactatttaa atataagatc gaatccctaa tttaaaaaaa aaaaatcaaa 780
gatgttaatt tctattatta aactcacttt agcgtagcta acaaaaaaag gaaaaatgag 840
aggctacaaa gcttgagccc tctgcctccc tttattgcat tgtttgaaat tagatcaata 900
ctttgtattt ttttcaaaat gaaaaatcgt acatagaatt aattctatgg acaaaaaatc 960
agagaaggaa ataatctaga ataaaattcg atttttaacc caaaaaaaaa aaaaaaactc 1020
gattctgatt tttgtaagca atcacccaaa ttaccataaa taaatggtat tcaattactc 1080
aattatggat attttagaaa tgataaattt ttattcataa actcttttct ttctctttca 1140
aaaagaaaaa aattagcata aacttcaatg acatttattt attcttcttc gtttggagtc 1200
aaaagtttaa attgagcatc agtccagccc aaaagcccac gaagaagccc aagaatcttc 1260
agctttttcg ttcaaacgtc cctttttggt ttataaaatt aaagaaaata aaaactaaat 1320
ttatttgtta tttaacaaaa catttttggt taagacattc tctttgatta tttttcttcc 1380
attcttcgtc gtcaatc 1397

<210> SEQ ID NO 127
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, c or t.
<220> FEATURE:
<221> NAME/KEY: unsure
<222> LOCATION: (1)..(2000)
<223> OTHER INFORMATION: unsure at all n locations

<400> SEQUENCE: 127
tttatattta tgaaaatgaa gtctctaaac aatttttcta ctcccaaatt tgttgatttt 60
tctgcctatt ctttatcggt gctttaaaaa atgaaaccaa atttcaaaac taaaaaaacc 120
aagcttttaa aaaaatgtta ggttattttt gaaattcaac taaatgttga actcttttac 180
ttattaaata ggcaaattat tgaaataaat ttagagcaag taagcttaat ttttaaaact 240
aatatactta ccaaatcgag gactaaaata ttcaaatact ctttaaaatt aagattaaca 300
ttaatcactt tgttatgttt aaaaagttgc agtgtcactt gaaccttttt aaattaatat 360
aatgaaaatg aatccaactc aatatatata atatctatat tattaatctc gatgtcagat 420
gtttgatacg cacatatctc aaaaattata cctcaactaa catcggtgca cgatgtatta 480
tttcgtgagg ataaaaatcg tttttagtat aaattgatgg aaagattatt tgaattactg 540
aaaaatgcac cggtacatta tttgaaactt ccccttcatt taaagaggct aatattagaa 600
aaagacacgc tgaggctatt tttacaatta atgtgggctg ttgacttggc ccagcccaaa 660
acataaaccc taaagtagca caaacaaacg cctctttctt cttgaaaccg catattaagc 720
gttttatcac ttctcaccac ctctcattcc tcctcttccg cacgttgttt cgctcctcaa 780
cgggagtgcc ttccctttgc tctccctcca ggttcttctt ccttctcatc tcatttccaa 840

```
gtaatttcat tccgtttctt ttctcttaat cgtatcttgt tcagactctt tcgcgttttt    900
ttttagttgc gccttaccag atctgtgttt tcactcgttt ctattcgata catgcttcca    960
agatccattt cttaatcgca tgtattcggt tgattggatg attgtctttt tgtaagtttt   1020
gattactttt ttggaatgga tcggttgaac caacggggtt taagtcgatg gaagtaggtt   1080
atgttaaaga tttgcttctt ttttttatg aagatgtgtg tgttcttttt ctttgctaga   1140
tgatgttatt atttgattgt tttaacagtc gtgttttgtt tttctgcagt ttatagtcct   1200
cggtcttttg aagacttgtc aagatggtta gtacacctct tgtcatcgtg attttgattg   1260
agtgatgtgt taagtgcttc tttaggttac agctaacgcg attttttata ttcaattgtg   1320
cctgtgcagg tgaagtttac agcagaagag ctccgtcgga ttatggacta taagcataac   1380
attcgtaata tgtctgttat tgctcacgtc gatcatggta agctacttag tttaagttta   1440
tttatgccga gcgtctattt aagaagatta acatcttagc tttcatttat tgtttatttg   1500
gtaagcatcg tttctttttc tccgaggaac tgtacatgtc agttcacatg acaataaaac   1560
gatcttcctt ggacattagt ttttgaagtt caattagacg ccaaattttg ttggttaaaa   1620
gatgcttgtg gagcatatgg acctaatgga atcagtactt tttgatggat ggacttgtct   1680
tttgttcttt tattttcaaa agaaattgca tgtgcaatta catcatcttt gatcgaaaga   1740
ttgggtaatt gggtaattgg ggtaaagaca tgttgtaaaa actaatgtta attatcaatt   1800
accattatat accttattta gtgcttattt atatcctttt tccccatttc agggaagtcc   1860
actctcacag attctcttgt ggctgctgcc ggtatcattg cacaagaagt tgcnnngatg   1920
tacgaatgac agatactcgt caagatgagg cagagcgtgg tatcaccatt aaatctactg   1980
gaatctccct ctactatgag                                               2000
```

<210> SEQ ID NO 128
<211> LENGTH: 1657
<212> TYPE: DNA
<213> ORGANISM: Cucumis melo

<400> SEQUENCE: 128

```
ggcaaaatgg agagaaaaaa gtttctccct attgccacat ttatatatag tatatagata     60
tatactatag acatgatgga gaatcataag ataaggtaag gctgaggaag attttgacga    120
tatagaatgg aaaattttga agatataaaa tggaagattt tgaaaatata gaataagatc    180
atcaaatgat agcaaaaaaa tccaaatgag tcagatgaaa cactacgcca aattttcatc    240
actccaaaat tgttgcaaag gagattgatt aatagggtat tatacacaat catatttttc    300
gtagcatgat aattggttaa taattagaca taatggcaat caattagtta actaatacaa    360
cattttaggt agcaatatta aaattggaga tccggaaaaa aactaaaaac tcagaaaaat    420
cttgggcaaa atgagcacgg tttatcaaat ttttaggctt ttttggtaca attttgtcta    480
ggatgaaacg agatccataa ttttctttga gaagataaaa aaaattaaga tttggtgtaa    540
gatttgggaa gatttgaata attttttttaa aagaaaaaat aagatttgga aaatggtaga    600
ataacggtct aatgtctccc aagatgcacc gggaaagcaa aaaacaacca aaacaataaa    660
taaattggaa aattttaata ttttaggaaa atctcgatgt caatttcgtc taagattgga    720
tcgagaaaaa cagttttacg agtttttaaa aaatgtgtta tatttaaaaa taaaatcaaa    780
attgtgctac ttttgtcaat ttcccaagat aaaaatgtat gcttccacgt aaaaagtaac    840
attactaccc ttctttcatt taatctctat atttggaaat gtcgcactag ttcttggtag    900
ctaatatttg gatactaatt atcttatatg acaaaatatt taatgtactt ttttttaca    960
```

```
acaaatattg aatgaactta aataatcttt tcactgcaat gaaaaaagat aaattagagc   1020

atcccaaaaa gatgaaaagt tcgaaagtct gctaactaca ttgaaaaaca aagcatttaa   1080

ttcttcaaac ttgatagttc aattaaattt ctaccaacta actcaagtaa atctattatt   1140

agtgtttgag tgaggctatg aactctaaga ctaagcctat aagtttggtt aaatttaatt   1200

ataccagccc ttttgtaagt aatttgattt gaaaggtaag acgtaatacc gattacccaa   1260

cccaaaatta ctgtgaatga gttaaaaaat aaaattagtt gaattttaaa taaaaagcat   1320

accaataaga cgatgacaca tgtacaaaat cttagaagga gaagcttcat ttgaggacaa   1380

aaaagagtgt gtggagtgag aagaaagaat agtcacgaat attgctgact gtgcaacaaa   1440

tgtacatttg gcaccaatca aaacctataa aaccttatcc aaaaatcaat aatctcatcc   1500

cttcttcgct gttcttcccc aatccaaacc ccaaccattc tcctccacac acacacacac   1560

tcacatacac aaatccttcc aacattattc tatacccact tcccaattct cattgcattt   1620

cacaatcatt gttctaactc acttacaacc tccatca                            1657
```

<210> SEQ ID NO 129
<211> LENGTH: 2000
<212> TYPE: DNA
<213> ORGANISM: Cucumis melo

<400> SEQUENCE: 129

```
atgaacgaag gagaatatcg gataatgaag aggagatcca tgaatcacag agaatgaatg     60

aaggagaccc acgtgaatta aatagaacga aggagaatga agagaaagga tgaatacttc    120

ttttctttaa ttttaaccta atcgggtgaa tcaaactcaa atcgaaactg gtttagttcg    180

attatgtttg gtaccattgt cttttaaacc gatcaaacct gaaccaaacg aatcggtacg    240

gttttttgca cccctaattt atatcatgtg aaaggtttta agttaagggt cagctagtgt    300

cgtttagagg gaatgatatt ggttgacttc atgtcgtctc ttggatcaag agtaggagat    360

tcgggagggg tgtgacgaaa tcaaccccga gattgtccta cagatggcat gtaaaatgca    420

tcatatctcg ggactccttc tacaaactcg agaaaaatgt ctcttgagat tcttcttcta    480

cacagcccca aattgatgaa atgactgaga ttctttgaaa gacaccacat gcattaactg    540

aaactaatgt tgtacatcta aaaaactaca tcacgccacc aactaaaaag ttttccattt    600

gcctgatttc aaactaaaaa caaaagactt aaacgataaa ctaaaaacta aaccacaaac    660

aatgaaatcg ttaaaagtgc accttgagag atttaagaga gtaaatgagt tcacatagtt    720

ttttgaagga aaaatcacta aaacaagttg gattgtagga gcgaaattgt tcactcctta    780

accgaaatta gcaaaatgtt tggagtttag cgtttttaga gaatatgtaa cgttatgaat    840

aataagggta ttttggtaat ttgatatatc cctttatttt caaattttta ataaaaaaca    900

cacatcttgg tgacacactc gactgaaaag gaccaagata tttccttgaa agattttttt    960

ttttaaattg ggaaagaatc ttggggtcga tctcgatcga gattgatcga gaaaaataga   1020

attacgagtt ttctaaaact gtgcttttga aatatcacac caaaaaagcg ttatttctca   1080

aaatttccca agtttatatg tgggggttat tgcgagttag cttttgatgg gtttgctttt   1140

gggtgtttgt atataggttt gaaatgtacc tttaatgtcg atttttgaag aaaggtacct   1200

ttattgttta aaattgacat tgtaccttca tatttgattt cagtttaaaa ttgatattaa   1260

ttatccgcat tttaaaaacc aacatcaaac atccatgttc atttcttttc aaatttaagc   1320

ttgaggatga cttcgtgaaa ctttttgagc aaacacgttt atcggttgtt caaagtaaat   1380
```

caccttcaca aatttaagct tgaggacgac tttgtgaaat ttcggcaagc aaaaatcaga 1440
caaatctctt caatcttttt tgagcaaaca cactttatct ctgctgaaat gagcacaagg 1500
tttagggttt tgagaatatc tagcatttag gctttcaatg gtattttggt catttgagaa 1560
taccatttat tttgaaattt taaaacaaaa acctaccatc ttggtgacga tcatttaggc 1620
cgagatgtat tgaaaaatta tgttaaaatg agtttttcaa atttgattag aacctcgtgt 1680
tgaggtcgac cgaaattgac cgagaaaaat aaatttacga atttttttc aaaatgtgct 1740 acttttaaaa tataaaacta aatgggttac ttctcaaaag ctaaccgaaa ctattagtta 1800
tattgcggaa atatcaattt cgcccaattt tagtcatcca gagcctgact catcgaattt 1860
aggagattct agacgttgca ttcaggagat ttttatccgt tgtcgccgac tctctttact 1920
gatctacatt gtacttcatt gctgaactca acgagtcaac tcaatcgttt ctagatttgg 1980
aagaatctgc ttcagcgacg 2000

<210> SEQ ID NO 130
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 130
aaaaggcgaa aaaaaagtta gcttcccgag aaggagaaga cgaggaagag tttgacttcc 60
cggggagata aagtttgtgt ctcgagggaa tctctaatct ggagttgacc gtcgacttat 120
gtgtcgagcc tggatttagt tgcatggtgc gacaaagcga taaggcggca tatgtaaagt 180
agtaattcaa aactagcggt taaagaaata atcagccaaa aaatttagta caaatacggg 240
tggaggccct aagtgaagtg ctgctattca gaggttttgg caaaagagtg caaagagttg 300
agttgtgcag agaaagtact aggtgaggag aggcgtttgg aaaagaaaag gatcaaacat 360
ttgcatgagt gatattctta aactaaacac tcttgtgtga gtgacttgcc taagctaaac 420
actcttgcat gagtaacttt cttaaactaa acgttttgta atgttttctt aatggattct 480
tttcgagtct gagttatgct taacacgttt tgtttctctc gtgttattgt tgttgttgtt 540
tgaaaagaga aaactattgt tttctatgtg ctgattgtga tgaatgtgtg cgaaccatta 600
gccttaatcc tatcaagtga atagtgatta tgtggtgtgt gcacataatg taaatgacat 660
tgtgtggatg gccagtgcaa caagaaatga atcagaaagc ttcccaaata ctgtgaatgg 720
agtgaacatc acactagctc aatggcaaga tattggcgat agtgaatcac aataggcttg 780
acaaggggaa ggattcatgt tcttggttga aaggaataag agaggctaat gtgagatttc 840
tgtgatttgc aaaatgaggc gttggaagac acgtttgaga aatgaaaacg aattagtgct 900
tgacttgtat tcctaaaaaa gttgtccaat atcttcaatc actaaatatt tgatgtgcct 960
aagttttcct tccttagttg ttgaggcgtt gaggccgagt aaggaaagat aagataatta 1020
tgacgttgaa aagctggtca agttatccat ctttggatgg tttaaagtta ttacatgtag 1080
ggagggttgc attccaattt tgtgtgtgag atgagtctta ttttcgagat gggttgctag 1140
gcgatcaagg agaagtataa gaaatgagtt cttatactct tgaacaactt gacacgaaga 1200
ataacatcct agtggatgaa ggaaggtgat ggaacttaaa gtttaggttt tattttnnnn 1260

```
nnnnnnnnnn nnnnnaaatg taattgtaaa gtattagatc aagtaataaa acagagttgt   1320
gttttctatt tttgctgtgt tgggttgtgt atctttattg tgcttatggc ctagttgcta   1380
aagagttaag gttattacct aaatgtttta cggtgtgttg agttgtaaag atctcctgag   1440
ttaaagttgg aattttgtat tggagattgt tttgagaagt ttagcttact aattgtttaa   1500
ctcattaggt gtctaagcga cacgcctcct tttggtcgca tgaagtggct agcagggtgg   1560
ggcggaccgg ggtggggtgt gataataaac ctaaaaaatc acccagataa gcctaaatta   1620
tacgttgaag ttaaacttac aatttgatta gaagaagaag gaatatctga tttggacatg   1680
aattaattac aaatacggcg ccaatcatac aaagcacatg taagatcaac gcattctaca   1740
ctcaatctca gccgttgatt gctttcaatc cttcaaaaag aaaaaaagaa gggcagttcg   1800
ggcagagtca tacctacccg ttgactataa aagcaactac aaatcgaaaa cctccatttc   1860
tccgttacca ttacagagaa aatcaaagaa atttggcgtt gagagattgg gagagaggtt   1920
tctctttcta gggttgcttc ttcttcttca tcctccattg ttgcaaattt cacttccttc   1980
tcctcttgtt ctcatctccc                                                2000
```

<210> SEQ ID NO 131
<211> LENGTH: 2000
<212> TYPE: DNA
<213> ORGANISM: Cucumis melo

<400> SEQUENCE: 131

```
atagagtaac caatatgccc ttttcagcag ccaaagtttt ctatgggcag acttaatcaa     60
ttaaggttcc tattgaggcc ccactcttag tgaaaagcct agacccttct ttccaacatg    120
tctcaattgg tcacctccat caaaagcttc tatcatttaa tctaaaagca tactcttttt    180
tcctttttaa atttcatttt gatggtctat atttgaaaat aataatcact acaacgacga    240
cacgttgttt tcaaactatt attttgtatg aattaataat ttttttaata gtatagttgt    300
tttacttatg gaatctatac gtttaatcga ttcggtcaca tctatttact ttgatgtttt    360
tgttatttta tttagacgtg gttgtaaaga gtttaaagca atggagaaga aattgatgct    420
ttccaaagca atacaaattt atatatacct tcaaatgaga ctaacattag acaatacata    480
aactataata aacattttga aagtacatag atcaaaatga accaaagtcg aaaaagtaca    540
attatcaaat tagtttttaa accttggata aacttcagca ttcaaacttt gtatttcttt    600
tttttttcga tcgatatata tagtgataga agattttttt tttctgttta ttatttttga    660
cgatacgttg agtagaagaa tcgaacatca aacctttaaa tcaataatat atattttacg    720
actcaatatc tagccatcaa tattttaaaa tagcaattat tattcactaa attatgttag    780
agattggatg tcatacaaca attgttaaag attatttgtc tagtttgttc aattaatcaa    840
gagagcatta agcattaaag tcaattattg tgataagatg cttttgcact atgtaactaa    900
aaatagttgg atacaccatt taaggcccta catgcaaacc atgataggcc cacaaaaaaa    960
aatctctttt tggaaacaat ggtcaaataa tttctttcaa ataataataa taattacaac   1020
aaataaatac ataaaccaaa ttactaaact aatgtatcaa gttctagaga aaacaaaatt   1080
atgccctttc aagttgcaac atcccctact ataatttttc ttcaaatttt ccatttaata   1140
taatccaatt ctaaacatgg aaaagaaatg taacaatatt tacattattt caatctttcc   1200
tatattcatc gactaatttt aataagacgt gaaatcaaca tttttctaaa ctcgttgatg   1260
tcataaaaaa taaacttaaa ttatgtacaa gatcgtctat taaattatgt ataacacgtg   1320
```

```
tggtgtatga gtaatagaaa ctttaaactc ttgatcaagg acatgtacct ataaataaat   1380

agatttcttt aagtcttgac tattaaccaa cttgtattca gtaaggttaa agtgatctat   1440

tatcatacta aatacacaag tttatttcga gtatgaatgc aaagaatcaa agatatatgg   1500

tttaaacaaa atctattata ccaataaaaa aggttaacca tatgcaataa aaactaaaaa   1560

gtctattgct caaatctctt tcgagaccat attaaaaatg ttagtttaat tgacgtatgt   1620

atttattgga tttatctaat aacattttaa gagattgttg caaatatagc tattagattc   1680

aaaataatta agtatatagc aaagtctgtc aaattctatc gatgatagga ctatgttaaa   1740

attgttgttc gatcgttggt aaactataaa aatctacgac aataaactac tattcaaaaa   1800

tttttacta cccaaatttt aaatccatct catggatcga gtcaagccca cttctaaatt   1860

gggccacgaa tattgattgt gaagctcaat aatcccatac gtatggctga aaacgcatta   1920

cgaacgaacg cccttcaact atccaaatcc gaacccaccc aaattccggt taggcttctt   1980

ctccgagatc gacgaccgcg                                                2000
```

<210> SEQ ID NO 132
<211> LENGTH: 2000
<212> TYPE: DNA
<213> ORGANISM: Cucumis melo

<400> SEQUENCE: 132

```
tgcagctgca caaaagattc caaatgatat aacataatag tttatgaaaa tttaatgcat     60

ttaatttccc cttccacaga agacactata tttttcaact acccaacaat accaataatt    120

atcattatta ttatacctct aattagtaat tagtcacaac ataaacagct attctcatta    180

atacatataa tcaacaactt cataaattct taaatttgta tgtgtacttg atgggtgtag    240

atttaagaag tccaagagtt tgacaccctt tgttaaaatg atatacaaat tcctgcaaat    300

taaatttacc attggtatga ttgttgttgg agtggtcaca acactaattt actaattagc    360

ttcgtattta acatagttgg ccatgcgagg aggtagcttt tgaacttcca ataacctggc    420

ttggaaggac gtcgataaac agaataacaa ctatgctaaa ttttgaataa tatactttat    480

atatattata taaagacgac aaagttgagg agcatccgtc ccctacattt gttggtgctc    540

atatcatcct attgcatatg ccttttacca atgaaaccct atctccttaa ttatttctac    600

tccacactca taattatcat tcatttattt tcatgcatga ctttctttta ccaaatttag    660

tttccaatta aactccatta actaccaaca atcaactcca ataacgtaac tcacattcat    720

tctaaccaat tgtttggatt gactcgagaa aaaaaaatgt tttttctaac tcatttttac    780

ttatacattt aaaaattctt ttggaagtga tcgtcaaaca ttttgatatt tttttccttt    840

taaaatgact tattttttaa aaaacttaaa tattcaaaaa ggttttccaa atgaatgtaa    900

ttaattactc aacatagatc tccattaatc attattatat gtaacaatag taattcaaag    960

taaaaaaaaa attatgtgga gtgcaaagat gaaaattttg acctatttta catgatttga   1020

actatatgtt tatgcgtacc tatgatttaa ctcttatata cacatatttt tgtctcaatt   1080

taatttaatt ttacgatttt cttgaataat tttattctct aaccactttt gaaaaacatt   1140

ttttaaactt tagaaaagaa tatctttacc aaacttaatt caatatatga aaatagctaa   1200

ataaaattta aaaaacagat aaccaccctt tgataactgt agctgatatt attaattaat   1260

tgtcatattt atatttgcaa tatgaaaaag gagatgtcat gagttttttt ttttttaatc   1320

aatctaatgc aattttctta aatttaatta atgtgaaggt gagagagaga ggcaatttca   1380

aattttaggt aagtattatg aataaggtta cttaacatta ttttaattta attttacatt   1440
```

```
atgttttatt tgaatttttt taaagactct catttttcca ttttggaact tttggaaaag   1500

aaaattttac ttcaatctct tatgcaagca agttaaaact acatttgtct tttcatggga   1560

tttttaagga gatgtgtggg gaaatacaat aagccttttt ttatttgcaa tttgctaaat   1620

gtgtattctt ccaattggct aattattaaa gtgaaattta gattgaaaaa agagataaaa   1680

ttgaattgaa gttgtataga tgggttagga atatgaaaat tgtttgagat atagtgagta   1740

ttggttttat ccaatgccat gtcatagggg tggaatccaa atgaaccaat gagaatcact   1800

caaaagaaaa cagatataat gcactatcca aacctaaaac taaaagccac acattgctca   1860

tccattcact cccattctca aaaccacaca aaaataaata tcaaatcaat ctctttccct   1920

tttccatata taccactttc ccctctcttc gcctctttga ttattaccca ccaaatattc   1980

ccatatatct tacaacaacc                                                2000


<210> SEQ ID NO 133
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 133

aagcttgttt gaccctattt ttaatgtctt aacacaggat tatgaacaaa agaagaaact     60

agtgaatcac agaggaactc acgcaaagac taggtgagaa gatcatatca aaatgagaga    120

ataagttcgc tagaagataa aagtggtagt tgaagttgat gtgacttgac caagaggcag    180

cttctggtgt tgatatattc agaagactag atttcctgcc taaatctacc tatataaaga    240

actccatctc cattaagaaa atgaggcctg aatggaccac ccaagtggtc gactgtgtga    300

agagccaaat gtttgtgaac tgcccatgag tgcctgaaag gcccgatcct agagagtggt    360

gggaaggagc agcctttcca ccatctgtaa agtctttctt catcttctcc agttagttta    420

agagtgaaag tttgaggttg agtgaagaag attccattcc tatctttttc taactggtaa    480

tgtcatttct attctttcca tttttgtata tttctttgta atgtatttnn ncatattgta    540

cagtggccta agacctatat tctttaatac atttcatgtt tatatctttt caatctatca    600

cgtttgttat tattcatctg tccttgtgct attggtagct taagatttat gataagttct    660

tgataagaag gttagcttat atttcttatg tgtgttagtt gtgagctatt ttcatcacct    720

ggctagtgta tattgcaaac tacctgagag ggtaagtagc aaagatatgg cttaggcgca    780

caaggaggag tttggagaca aaatccacat tggcaagata acttccatca tttgtgtctc    840

aaaaggagaa caagtgtggg tattaagcat tgagatgttg tgacccttaa acgagaagct    900

atataagtct tagtgaaggt cgtttggatc tcgagaggtg agcaagtgtg gtgtttaaag    960

acaccgagag gtgctcgtct taatcataag ctcgttaact aagttatatt gcattaggga   1020

tattttattg cttaatttct tggtaatgca cgaacttttt ttcacccatt cttttatgcc   1080

agctagttca caattccatc tcgcatccat tttaatcccc ctttacagat tctccggtgt   1140

agataagtag atatagttta aacttacatg ctttcacact atatatttta ttcttttata   1200

ctacctaaat gcctagtgaa gcctagaact aagctttgat atcgattccc tgcattcgac   1260
```

```
tctaaatcgc ccatataaac ctattgtttc gcttacactt gggcaagcaa taggaaaact   1320

tgtactcaac gaggacttat gagttacatg atgacgagat acatagagag catctaatat   1380

gcattgacca tgatcattga ctcttcatgt agatttaaat acctttcagc ttaattagat   1440

agaagatata taataaagcc attccattag tttaaaagaa ttaagttaga ggtagttgaa   1500

atgctttata agtgggggtt aattctattt tagctgtaat gctgagctga tctcaagcca   1560

aggttgcctt gagatatccc cgagtttaaa aacagaagct aaaatggaaa ctaaaaacta   1620

agacatataa actttttagt tacttttagg gaaatatctt agctataaat taaagaatat   1680

gaccaacatg gaagttcctc catcactttt ccaccaactc attttattgg gggttagtca   1740

ttttaaggcc aattagttta aattaaagtt caatctcagt gatgcactag gccgagagag   1800

accgagataa atcattcaaa tattttttta aatttgggaa gaatcttgag gtcgagattg   1860

atcctgagaa aaacaaaatt acgagttttt taaaactgtg aaatataaaa caaaaaagtg   1920

ctagttttgt caattcccat ttatcttgct cattgttgat acaagatcat taaaagttta   1980

tggataaatg ttggttgaga                                               2000
```

<210> SEQ ID NO 134
<211> LENGTH: 1696
<212> TYPE: DNA
<213> ORGANISM: Cucumis melo

<400> SEQUENCE: 134

```
tatatatata tataaaaaga ggaatacaat taagacatcc cattgttaat aaggggtgga     60

ataaattggg aaattaccat tcgagaaatc attgacgaga gcaaatatgt caaagtagaa    120

aattagtcat ctcaaaagaa tgtaatcgtt acaaaaatta aaagtacgta aatttaatca    180

tcgttacaaa aattaaaaga atataaatta caccgttaca caataatacc aacaatccat    240

ttataatatg ttgtttttat ttcaactttg aataaaattt gaactctttg ataaaatttg    300

tttaaaataa atttaaaacc atttcaaaag ctatttttat attatccaaa tacatatatt    360

cttttctttt tccaaaatga cttgtttcta aattcgaaca tccaaaaatt aaaacataac    420

atttttagta tattaagaat tataaattaa gagataaaat attcaatact attataataa    480

aatcggtgtt ttcagtaatt gtatttgtac aagtaaataa aattaatagt aaaattttta    540

atatataaac aagttttaaa agaaacttaa agatataaaa aataaattga aataaaattc    600

aaacccatca acaaataaag aaaataaaga tggttttatt gaaatgaatg aactaaaatt    660

tgaaggaggc aaaagtaagt acaccaaaaa tagaatacta aaatggtaga ggacaataat    720

tgcatatgtt tggtagattt ttcattaact atcataccaa ttaacaataa tgaaataaac    780

tttctcgttg atattgatta caatcgtaat agggcaaccc actgtttaac ttgtcaaagt    840

tttcttaact ttattatttt tgactttatt tgtttgtttt attgattaga ttgatagatt    900

atatatttta atcatattat ttatagtaca acaactacga ggtaagtgat tgaagcttta    960

gtctctaaga acaaaggttc gacctaattt tttagtctgt ttttatttga catattttgt   1020

ccattgatag aattactatc acttaagtta aatgtattat tattgcaaac cactaattct   1080

acgtaaaatc tctaagtagc aagtgttatg tcaataaaat agcaattttt tttttaccaa   1140

ttacacacat catggtgata attattatca tgcacgggta aatttttaat tataaaattt   1200

caactttcaa aattatacca atactaaatt tattacaaaa gttattttag gtaaattata   1260

aaaacttgat aacaattaca agtacattct aaaactttca ataataaaga ttgaatcatc   1320

caattcatcc aaatgttaaa tttataatcc gatttcaaga agaaaattaa aaactcaatt   1380
```

```
tttatgaaaa tgtaactaca accacaacca tattaaacaa aaactcacaa tttgtccata   1440

tttttaagt taaaaatata ggtttaggat tcaaatattt ataaaataaa ataaaatgaa   1500

actatttgaa aacatagttt aaaaaagaag aagaagaagt gttaaataaa gtcccatttt   1560

ttaaaaaaat atcaagaccg atattaatat tatatatata tagaaatgta cacaaagtta   1620

aaaaaaagta tcctataaat atctaagttt ctccccgtct agccttcgcc aaccttatct   1680

caaaaactcg gaagcc                                                   1696
```

<210> SEQ ID NO 135
<211> LENGTH: 2000
<212> TYPE: DNA
<213> ORGANISM: Cucumis melo

<400> SEQUENCE: 135

```
tttacatatt tatgaacatt ttcctatttt tgtaaatatc ttgattcaag atttttgttc     60

gatatattta aaaataaact tattttaaat tcatacttct ttctccttct atatgattat    120

ataagtattg tagttactat agattaaact cataacctcc tagttagata ttgagattat    180

tactttcttt tattatcggg ccagtacaga aacgctttta tgacgattac attcgtcatt    240

cgtcacttat ttgtgcatta aagttggcat tgtaatgttt gtttttacat gattctctat    300

tccatagatt tcctttatcc ttttccttgc atttgagtgg ccctttccta agatgtattc    360

ttcggacttt caaataaata aagattagaa gcattttttct cttcaatatt gacttcatcc    420

ttaatcctta agccttaagc ggaggctaaa aaggctttat ttgcctcgaa tcccaactaa    480

ttctccctct catgcccatt tcaatctctt gcctaattgt taattaatgg gtcaaatttc    540

gtattgaatt tcaattttgg atcaatccta cgattatctc aattaggggt caaaattaat    600

ggttgatgta ggagcaagtg gaagacacaa ttttggtgta gcaattggag cttcatcatc    660

aacaacatga gatttaatcc cgtggttgca gttaaatggt gtagaagaag tagtcaacac    720

aacccaaggt gaagaagagg gagacaagag aagtggttga ggttgtggct ctatttgcct    780

atggcagcct tcacctcttc tctctcgctc cctctccgtt tcaatccctt atccccttcc    840

tctccccgcc atttcttct tctcttcttc ttccctccac caatttcacc tcccgattct    900

ctgccctaac catctcttcc tcctccttgc actccgcctc cgacaatttc gatcatgcca    960

aaagctcccc tttttcatct aaggtctgat tcatttctgt tgtttgttta actcaatttg   1020

tcttagttat attcaatcgg gattttgctt gcttgtggaa ttaattttcg tttattaagt   1080

ggaagatatg ggtatgcttg gtgacactgt atttactgtt aaatttcaaa caatcctacc   1140

aaattttggt ttaaattgag tatttttagt tccttcttgg taaattggat ttgcgaatga   1200

ttaacttaac tatgttggca cttcgttgta agaccgttaa ctatttagct tccttacggg   1260

taatgatgtt tagaaggggg gtgcttggtc cactaagtgg agttaagtct atggtaaaca   1320

tgttggcatt agtaagtttt tggtaaacat gttggcatta gtaagttttt ggtaaacacg   1380

ttggcattag taagtttttg gtaaacatgt tggcattagt aagtttttgt ttgtgatgta   1440

gagttgtaag attgagttct ttaataattt gagttgtaag attgaattct tcgataactg   1500

tgaaaagtat attaagaaag taagatagag ttacttgata aatttgaata gtggagatag   1560

gggcaagatt gagttccttg ataaaagtat aataaagtaa atgtgcaact cttgcctata   1620

tacagcttag caggaactct tacttttgtg tgtcatgtat tcttattggt tcgttcttat   1680

tgcatttagt agatagtgga tcccagtgaa cttttttaat cgctagaatg gcgccttaaa   1740
```

```
aagttagttg gagcttctac ttgttggttg gtatggtgcg gttgcaagta tttttccttt   1800
ctatgattat gtttttagat ctaaatttta aagcactcga tgaatgctga tgcttgatat   1860
gttttctgtg ttaaattctt ttgttgatga atattatttc catttttcag aaatcagttc   1920
tttcatcttt gatacaagag atagagccgt tagatgtaag cttaattcaa aaagatgttc   1980
cacctactac tgtggatgct                                               2000
```

<210> SEQ ID NO 136
<211> LENGTH: 2000
<212> TYPE: DNA
<213> ORGANISM: Cucumis melo

<400> SEQUENCE: 136

```
ttcttgatta gcttggtgtg ctgttgtata tcatatttgg tgcgagcata acttaccctt     60
ggctaccttg catctaccct aagtggttta gtcagattgt atgatttgag gtatttcgtt    120
tctttgttgc tctaagtggc tttgagcttc tactgaggga acctaggacg tctcttcttt    180
ttgggatctt ttttctcgag tagttggatg cctagttggt ttttttgttc ctttactcaa    240
gtcctttgtt tgtcatttga tcgtgtcaaa gtccaaatgc tttctattgc aattcagtat    300
cttaaaaaac tgttctttgt tgatttatgt aaatgacata ctgtatgtat aaaaggacag    360
aatgctacca tttcttgaag tttctggcac ttaccctgat aatcgttacg gtaattatta    420
tgtgcagatt gacggcaata acgcagctag cacatcatgg tatgatattt gtacctcttg    480
ggtacacatt tgggagtaag atgatggaaa tgaatgaggt gaaaggtggc tctccttatg    540
gtgctggaac ctttgcagcc gatggaactc gacacccgac tgagttggag cttgaacagg    600
ctttttacca aggtaagtat gttgctgagt taaccaagaa actcaaaaac taatgccatg    660
tttgaaatgt tgttgggtat ttgaaaacgt gttattacac tagcacactt ttactgtact    720
tccttccaac atctattatt cagcttctca catcatggct atataaataa aggttaatgg    780
aagttactaa aaatgatgta aatctatcac attgttaata ctcctgtaat tatattgatt    840
gatgaacaat tcgatcacca tcttttgtta tttaaaatta aacttgtaat atgtattcga    900
acgtttttag ctttattgca tgcttattat ttcactgttt taaaactatc tttagacttc    960
aaatcaaatt ctgaaaaaca aaattaagtt ttcacataca ttatgtcatg aatataaaat   1020
tttagatatt ttagttcatt ttactatatt taaaaatgtt ttattattat taattttgta   1080
aaacaaccat gatcgtttat taattgaatt gtcacaatta agccattatt ttttttttta   1140
ctttcctttt tcccatcaat ttctttattt tctaaaaatt attggcctcc cagactcttt   1200
gttatttgca aataatgagt ctaatcataa tagaatttca ttgataaaac caatcatagc   1260
gagtcttaaa accaatcata gcgagtcgta attataaata ttattgaatt gctcttggtc   1320
cagtttagct agaattatga atttgatcaa attttctgtt atcattaccg tataacaata   1380
aatgataaaa ttcaaaaaaa aaaaagaaag aaaattgata tgttaacgac aatggtaatg   1440
ataaccataa ttgtaatggt aaccgtaact acaatacata atttttgaat ccaatgagat   1500
gaatcactta cttagttgat ttgcgtacca aattatagaa caccaatcat ttttgtaatt   1560
aggattgatt tactagcgtt agattagaga aaagcttggc ttatttctaa ttcctcctcc   1620
ctcttccact cattttgtcc ttaactaaaa catagtgata gttccctttt tcttttagag   1680
aaaagaaaag aaaagaaaag aaaaagagtg ttaattggta atacataata acatatcaca   1740
tacataaata aatcatgccg agttcgcctt agaaacgacg ccgtttaaag taagtcaaca   1800
agtcaacact gacagctaat ttccgcaata aatacgtaaa aatgaaaaga aaattaaaaa   1860
```

```
acgatataat ataaatagaa gcaagaggct cccatcacaa gatcccattc gcaaccacat   1920
tccggccttg aggcttcaaa aaatcgaagg aaaacactct ctgtatctct cccctctacc   1980
caccgattcc gtcgcggccg                                               2000
```

<210> SEQ ID NO 137
<211> LENGTH: 1575
<212> TYPE: DNA
<213> ORGANISM: Cucumis melo

<400> SEQUENCE: 137

```
atatatatat atataattta actaaataaa caaatgaaag aaaaaagtga gttcccattc     60
ggaaaatgca gatggatcca tttcttcaaa tattaaaaaa taaaaaataa aataaaataa    120
cttaaatatg caaatagaaa gaattttaat ttctggatta tccatatggg acaattttta    180
aaactcattt attttatttt ttttatttat ttgattttga tatatctatg gggaaatttt    240
tcgtaataat tttcgaaaaa atattgcaat atatcatttg atcagatcgg tattattaaa    300
tctctatcac atttggtctt aaattatcca aagattcctt taagataatt tagataacca    360
tctacagatc actactataa tcaacaaaag gaacaactta aattatttaa acaaattcat    420
taatattaga ctttgtgctt cattagaaaa tgatcttatc acaaccacaa ccatagtggt    480
ggtttaaaat tttattttaa actcttatta gtattatttt aattcatact taatcaaact    540
aattacttta aaaaacatat atatataaat aagttaaatc attccccctt atctaaataa    600
cataaaaaaa aattgtttac tctacaagaa gtttgtatat atatatgctc ggtactattt    660
agcatcttta taataaaatt tctaaatcaa ttttttatat ctctttatta aatgtatagt    720
catcaaaaaa tttaacgaga taatgtgtca aagatttatt ttattaacgt tcataaatat    780
caaattatac ttagcttata attgaaaaca tgttcgataa atataagtaa ataaaatttt    840
atttttttta aatattacaa aataaactaa ataagttata aatatgacaa taaacattat    900
atattttatt atatttataa atacttaata atttagtcgt ttaaaataat tttcttaatt    960
ttcaaaacat gtttcatatg ttaataataa ataaatggaa aaccttccaa aagaagaaaa   1020
aaagatatct taaaatttaa aaattgagat tttgaggatc aataattaat aaaagaagga   1080
ttaataaggg tgaaattaaa tcccaaaaag aaaattgaaa atgaagaaaa gaaaagtgaa   1140
gaaataattg aacgtgggaa gtggattcga tgtctccaga gaacaagcga aaggagacga   1200
aatccacata atttgcacgt tacgtgtccc tatcaaccgt agacacgtgt caacatctca   1260
acaccctacg ccgaattgct tcgctggatc tggacggtca tcggataaca gcggcaacca   1320
attaatattt ccccttatat ttcacagcct ggccatgtcc accaatcacg ttcaactatt   1380
aattcatttt tcatttcctt tttctttttt tttttaattc ccctcaatta ttaccgacaa   1440
cctgttgtag ccggttaacc ctaccctcca acgttccatt ataaggccta gaaaatggac   1500
gtgaaaatgg agtactacaa actacaatta attttaaaga attttaattt taaagttctc   1560
taattactat tagcc                                                    1575
```

<210> SEQ ID NO 138
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:

<221> NAME/KEY: unsure
<222> LOCATION: (1)..(2000)
<223> OTHER INFORMATION: unsure at all n locations

<400> SEQUENCE: 138

```
ccgtcgggaa cctctgctct gacataatta atattcatgt atttcctgat acccatgcaa     60

gtcgtcggga aatatgttac caattttcga cgccagacga gaatcgttag gaacaagtgt    120

caccatgccc aacttcttgt atggggcatc aggataagtt aaatttcttt tttagttgtg    180

aactattccc gacgccataa acctagatgt cggaaatgtc ttcttgtttt tcgacggctt    240

cgtgaatctt cgaaaaaacg taagattaaa ataatgtttt cgacgagttc cgacctgtgc    300

aaaacgacat cgggaatagg tatttattcc aacgttctag cttctgacat ctagaaccct    360

tcaatttctt gtagtgccag tgcaaagatt gacactctta aacgatggga cttgtcaaat    420

agatgttgcg cagatatcca taggttatct aaggttttgt tttgttacct aagttatcat    480

caaacttctt catgaattct cttagctatt tctaagtacc taagttctcc tctatccact    540

aggattgtct ctcttaaagt caagggtggc tgttggtagg atgtagactt tgtcggcatt    600

ggtctaccaa tttaatctct tatatcccta aagacctaga ctccatggtc tccacctatt    660

tccataaatg tacccataac atcattaaat gaaattatta ctcaagtaca aaaaaattgt    720

ttaattttat tgataaaaac catatgtgaa aaaatagatg acatttttaa aagcttgtaa    780

acagtgtgtg aaataagtat cctaagtgaa ggctattaat ttaacttaaa cacaataatt    840

attattgttt taatgatgaa aataattaac ttatataacc aattttcatc aacacataca    900

tacctttgt ataaacattt atttgaacac aaatgagaga caaatagaca tttttatttg    960

gtaattttct cagcattatt aattatcatt ttcagatatc ttaattgaaa tttctgaata   1020

attttttatt tttcggattt tcacattata atattttgaa ttagttagtt gaaaaccaaa   1080

gccagcatca gtgaaaactc attaatacat gtaaaatact aaaattgttt ttttaaactt   1140

ctcaaagaaa aaaagtctta atttttattt tcttaacttg acataaaaat cattggtgtt   1200

gtttttaata aagtaaatgt taaagtagac tcagttaaaa acgaaaaaaa aagttaaagt   1260

ggactcaaca cttggagtaa acattttttt taaaaaaaat taatcctaaa attatgatta   1320

taatttttat ttggcttaaa tatttcaaaa tgtgttacac atggtttagt ttcaatttag   1380

ttgttacaaa atttattatt gtatttgaat ttttgataga ctaattaaaa tttgaaaatc   1440

aatttattta tacagttgtt tttcttttaa tgatgtaaat agaggtctaa tgattttaac   1500

ttgtaagggt taatttttct tatgatctaa tgtaattcaa tgagcattaa ttttagaaga   1560

aaatgtgtac ttattttgtg taaaaataaa ttataataac aattttttca ttttggtata   1620

acgtatgatt aagttccatg aaaaaacaaa ataaaaaaga ataaaatatt tttccattta   1680

aagaaaaaca ataataaaaa tggagggatt caataggaat ttcggagggc ccacttccca   1740

attccaactc cccactcact cactcactca cnnnnnnnnn nnnnnnnnnn nnnnnnnnnn   1800

nnnnnnnnnn nntttttttt attattatat tagaaattaa taattattgt ttatttcgct   1860

gtcaaataaa aataaaattg tggggcaggt gcagctcacg tgcctcctca cattgacacc   1920

acatttaaac actttcattt tcaaaggctg ctgctttata ttcttcacaa aaacttcctc   1980

ttccctttct cacactacta                                                2000
```

<210> SEQ ID NO 139
<211> LENGTH: 1006
<212> TYPE: DNA
<213> ORGANISM: Cucumis melo

<400> SEQUENCE: 139

```
ataataataa taaatacata aaataaaaaa ataataatag taatgaaaat caatagaata     60
attttaaaat cgggaaggaa gtcgtgtaca atccttgcac gttggagagt caaatggcct    120
aagtggtgat gtggaagtcg tgtaccgggt acacgatttt cctacaagtc aataataata    180
atatggttat ttttttcta gtttagggtt catgacaaaa gattgttcag tcgactggat    240
gtagacaaat ctaaaaaata aattaaaatc taatatgaaa actagtttta atttccaaat    300
tattaagggt tgaattcgac caataaataa taataatacg gttattttga aatttaggaa    360
attgaataaa gttgttaaaa tcttcaagca aattgttaag ccccgagata ttaagaagag    420
gtaataatag aggattctat atttataaca tgttaaaatt aattgcaaac tcataaatgc    480
atcacacaga ttaacaacat aggagggact tccgataaaa gtgcaaatat tgaaataatt    540
acagttcgcg aacatgagta ttttaatatt ttataaaata gtatgcacgt gtatttttgc    600
caaaagaaaa aaagaataga ttttgccatt tttcaaagtg actctcggtt atatctttta    660
tggcgattgt attttatagc gtatgttgtt tgtagttaac ccatttctca ttggcaaatt    720
caatcgtggg ccacaacgtt tggcatagc ttcaatttgg attaactcaa ttatgtctga    780
atgggttgga ctagttcgga ctcttcggct gggccagaat cagattcggg ccgcaatctg    840
ttcatttcac acctatatcc aaacaccccc aaaatcgata cccatcaaac cctaactctc    900
aataaccccc atatataaat tccttcttta gggtttttca tcctcataca ctctcaaacc    960
tccggtcatt ctcattttcc ctgccgcttc ttcaataacc ctaatc                  1006
```

<210> SEQ ID NO 140
<211> LENGTH: 2000
<212> TYPE: DNA
<213> ORGANISM: Cucumis melo

<400> SEQUENCE: 140

```
aaggagtaga ctctcaagtc cactattcta acttcttacc cgaaagagcc aaaacttttc     60
attcaaattc aactagaaag ttattattga tctatcaatt tgattttaat ctacaggcgt    120
gcgttgcaat ttgggaaggg attgagtttg taactggagt acgggcaacc tcattgaatt    180
ctcttcgatc aacgtgggga tgaagttctt tcaccagttg gagtctggaa aaacttttgc    240
tagactaacc tattgctact gccttttggt gaaatctttg tgctctaata ttaaaaagac    300
tccaactttg aatcgttaat tataaactag tgttatttgc ttgtaaatct tacttatagt    360
ttgaaatgag tgcttggcga aagtgttgtt caaatcggta cgtgtaagtt taaagattct    420
tatttcagct ttgaatcaga tcagagtctt ttaaacttaa tcaaccgaca ccaccacacc    480
ccactcttgt tcttctccac gtgggagttc ccaaattggt tgatttgtta tctctttgaa    540
tcatctcaaa tcaagaaatt tcagaacagg tttggggaaa tttgataaac tacactctct    600
tgctcgaact ttgcaaggtt tttactgttt gttatatgat tcaatattcc catttcttct    660
aattggatga actgttgaaa attggaaatg ctcagctgcc aagttttttt ccgaaatagg    720
tataaattca aagattcaat cagtgtgggt ttacccaaaa aaccaatggg gtaagtccat    780
tttggactca tgtggagggc acatgtttag gcaaagcctt atctctttgc cagtgggctc    840
acaatcaata cggacaagac aagaaatgct tcctaacacc gtcattgtca gcgaccatgt    900
gagctttcag caaattggat ccttcaagta actcacgtga aagatattta gtgattgact    960
taattactct ccccttcctg tttatctaaa ttaggcgaat agatccaaag tgggtatttt   1020
```

```
tggagatcat ttatctgttt cctgttcttg tttatcgttt ataattattg attgtttttc   1080

tggctcaagt aaaacgagga ctttgacatt tcaataccc ctttttgtt ttctggtagg     1140

tagcgctaag tgggtttctg atatcgtact gaaaaagtta tagttttgct agaacactcg   1200

atagatttta gcttttgtat tgattttttt gttgatattt cctggtttca gtgaatgaat   1260

gatattcttt tatgacggtt gttgtgaaga ctcataagtt tgtctcagat cttcagttat   1320

actcttgaag cttcttcgtt catacttcaa cagttcttgt acattttacc ccctctgttc   1380

ctctttccat cggcttgtga atctgtgatt gtaaattgtg ctgatgattg tttttaagct   1440

gttgagatgg cgttggggtt gtgtcctaat ttgagactgg tcaacttgat catttggggt   1500

agtgatggcc ttcttttcta tatcattctg tgaagagtac tttctaaccg attttgttaa   1560

aaacacatgt cggattgctt gcttgttttg tggtgtttct gatttgtgat atgatttgat   1620

taatctctga tcgagttgtt atgaatttga ttgacagcaa ttgggggacc atggaatcat   1680

tgtggttcct ctcatagatt ttgatttctg aggtgttgag aaggctttaa ccttttttgtc  1740

actgaaatgg atggtggaag ctctgaatcc ccagatatgg gttgtaacaa gaccatagta   1800

tggtttcgta ggacctcagg attgaggaca accctgcttt agctgctgct gctaggaatg   1860

gttttgtata tcctgtgtac atatggtgtc ctaaagaaga gggacaattc tatcctggtc   1920

gggtatcgag gtggtggttg aagcaatccc ttgcccattt gaaacagtct cttaaatcac   1980

ttggtgctga cctagtgctg                                               2000
```

<210> SEQ ID NO 141
<211> LENGTH: 1556
<212> TYPE: DNA
<213> ORGANISM: Cucumis melo

<400> SEQUENCE: 141

```
ttttagtcat tatacttcaa catctcgttg gttttaggtt tttggaaagc aaacctacaa     60

aacacactct ttcattcatt ggttttaagt tttgttgaca actttttagg agtgctttga    120

ctaagatttc aaagtcttgt acttaaaatg atgcatacta tcgtaaaatt agtataagag    180

actagatttt taaaaaagaa gaagatcggt ggaagtatgt tctaatttct aagtttttca    240

acacttacaa atttattgaa aaacagctgt cggtacatgc acacatacta tttatggatc    300

tacaattcca agcatagaag agtttagtat atatccaaat tcttattttt aaggggaaaa    360

aatgaacgaa agaatgcatt gtattctcgc ttttgtcgtg ataacgtatg attttcaagc    420

tctttcgtcg aaaaacatca acaaacaaac aagctaagtg taatctaaat aatcttcaac    480

atccttggaa atttattgaa aaataaagat ggctagcaat gcatactttt tatggatcta    540

tatcccattt caaccgtaga agattcaaag tattcgaatt cttaaaaaaa caaaacaaac    600

tgccttgtta agataaaatg gaattagaat gaaattttca aaattgaagt ggggccttgt    660

aaaagaataa actttgtttg aaaattaatt tccatcgttg gttggtagat gtgtccttaa    720

ttgaaaaagt ggaagaaatg aaggatgaat atgaaagttc tgaaaagaat atggacggaa    780

ttggaaaaaa caaaaaacct aatttcataa attaaccaga atctaaacat tgggggatga    840

agggagcgga ggccattcat gtaattggcc gtacagattc atggtttaac aaaagccaca    900

acgactccca ttcttccacc acagaaattt cctctcctcc taaattcact tatctctttc    960

tatataattg cttcgttccc caactttcta tcttcgtgca gccccattca atccccccatt  1020

ttacccactt cgtcttctcc tttctccttc gtcttccagt tccgttttcc ccatctgggt   1080

tctcctgatt tctctttaaa atcaactacc catgttcgac tttgaggaac tggtgcgttg   1140
```

```
gaattgagct ttcgaaggag atttattgtt tttatcacaa cccatctgct cgaggtaagg   1200

ggtaaaaccc gggttcgtca ggctgtagac atcacggcta tacacgtagt ttcccggtcg   1260

ttctttcatg tccgggctgt acgacggaag ggttgtataa ctccgacaaa cccttcgccg   1320

cacggcggac gtggtgcttt gccttccgaa ggtggtagtc cttctgatct tctttttctc   1380

gccggcggtg gattctcttg cttcttctct tcttcgtatt agctttgcaa cgagtccgtt   1440

tgtgttttag ctctaccggt ttaggatttg acatcagcaa gtttctgttt tgcgtttctt   1500

tgttttgggt ggggagattt tggtgttggg tttggtttga attagaagca gacgat       1556
```

<210> SEQ ID NO 142
<211> LENGTH: 2000
<212> TYPE: DNA
<213> ORGANISM: Cucumis melo

<400> SEQUENCE: 142

```
gagtacctaa tctaaactaa ttaactcgct caccctctta tttactgccc catactaatg     60

atcctaatag attgtttggt tgggttgata aattctcttt aaaattatca agttttccaa    120

tttttgccac ctaagttgtt ttcttacaaa aaataaaaaa taaaaaaagg caatgttatt    180

tctcgtatgc attaattgat tgattttctc aactaaccct tcaatttgac tttatatgta    240

ataatagtgt aaaatatata cgcacatacc tacatatgac caacaataaa aacgataaca    300

ttaaattcag acagaaataa aaattacgat tatgatttta ataaatataa atgcacataa    360

ataaaattta cagttcatag aaaaatccga tgtaatgaag tttaaatcgt tagttatttt    420

atttcgtaaa ataccaattt atgatttgca tgacaaattt ttaaaatata acttatgaaa    480

ttaaaagttg gttttgagaa aacattcaag actttattac aaccaaacaa aaattttatt    540

gagttttgtt tcattaaaaa aattattaaa ttacaaatat ttggacttac gtaatttgtt    600

ttctttcttt ttagggtaga aaaatatgat agattaaaag gattcgaaat caaactttat    660

atcaatttcc ttttaaataa ttatttcttt ccaaatttag tttttatatg atagcctaag    720

tctccatcat aagaaacaac gttaattata ataaaaaatg gatgtagatt caccaatatt    780

ttccaactat attattactt tcacgtttac attaaaatta aatccacaca ataatataat    840

agttttcttt gtttgattca aagtttctct tggttaaaat taaatttcga aatgataata    900

aataaactcg tgattaataa actttaattt aaatttcaaa cttaggtgtc taataaattc    960

ctatattttg tatcacaact tttcaattat gtgcaataaa ttttctaatg atttattatt   1020

ttttttaaga atgtaaagtt gattatattc atattaaaca taagattgaa aagagagagt   1080

tgattatata ccgagtagcc gacagtcatt ggaagcatta acccattatc atctccggcg   1140

agcaaaagca aggatctaca aacaaacatg acaattaata tgaaactcat caatccacgt   1200

atccaaacat tccatatgtt agacatggaa gagcaataat tacaaagctc tctcatcgtc   1260

tccgatcact ccatttatcg tacaaatccg tctttcttca ccttaatcat tttccccgaa   1320

attcatccca ctgtttcgca acaaaatcca agtttggaaa gatgagtttg tttttagtga   1380

tcaaggaaag gacaaagaat gtagcattgg caatgacggg caaacaagag aggtgtggct   1440

aaacttatac atgcttttgt ttggtgaaag gttaaagcga agaacgccaa agacagagga   1500

aaccgtataa aatatgagta aatgtcaatg ctaatgaatg ggcagaggtg aagcggtcgt   1560

ctatggctgg agaagggcag atgtgaaaca atatgaggta gacgaaggtg gagacaaaac   1620

aatttagtaa agtcaaaaca attcatccat atcctaatcc aattatattt ctttaaaaag   1680
```

tttaagtatc aaaattggac tgcttgatca tctatcaagt tatttttgaa ctttatttta 1740
aaaagtttaa gattattaat aaaaatgtaa tgtttaaagt ggttagtgct ttggaagcca 1800
ttacgtccta tggattatgt ggtgtgttgg gctactctct atttggacat gttttgacgt 1860
accgtgcgaa gtcctgactc tatttgtaaa acgtcacccg gcaaaaaccc aacttaaaaa 1920
acagaacttt atttcattta atttgcgggg tttatccgga aagaattgtg agagctctct 1980
tgtgtttggt ttgcttatct 2000

<210> SEQ ID NO 143
<211> LENGTH: 2000
<212> TYPE: DNA
<213> ORGANISM: Cucumis melo

<400> SEQUENCE: 143
gtaatgcaat attagcaatt attttggagc aatacaaaca actaggtttg gatcaaatat 60
cacgaaatac aggagcaata acattaacaa caaataaatg cacgaagttt ttttttttga 120
acaaacactt aactctctcc aaaccaaaac gagctaagtt agacctaaaa aaacaaagta 180
tcggaataca atatagctta aacaaaaatc atgtttagat tattggttag gttcatctaa 240
actagtggtt agccattttt caaaagaaaa atatgatttg tccttgctaa ttttccaaat 300
ctatatttta aaagtatcac tctcgtcata attttccata gctcaattaa tactaatctc 360
acggtagctt ttaattgttc ttgacaagta atggattaac ttaaaacatt tatataactt 420
tgtaggtatt attttataga aaaattagtt tatacgtgaa aacttcttaa atatctaact 480
acaatcaaat acctagatta cataatgtat ttttcataat atttatacat tatatttgaa 540
aaaggactct catttctttt attggtatct acgcagaaat taagattttc gagttgcgac 600
atctcaatca acgaaccagc taagaagacc ggcaaattcc aaacgtatcc ttcgggaagc 660
actgagtgtt tccacgtcaa taacaaaata ttgacccaat aaatttcagc cacgtagaaa 720
caaagcaatg aaagccgtcg gattctccac atcggctacc gtatgccgtt aagatcatca 780
agtagacttc taattcccat gtcttccgtg ggggccagaa atggaaaatt gaaatcgctt 840
tatccacgtc aagctaacaa aaaacaacca ataataattc gccacgtttt ctcattagaa 900
aagtgcaccg ttggatcatc cacgttggca acatagatcg atccgatgga cttatataaa 960
tttgggtagc tcgtcgagaa atcagatcag tgatcgaagc tactggaagt ttttgctaag 1020
aaccatgagg aagtggacga tcgcttctgc tcttctcctt ctttgcattc tctctctcgt 1080
tcccgatgaa ggtgtgattt cgtttcttcc ttcagcagtt tgatttattt gttggaatgt 1140
aaactgaatg cattgcatta tcttaatcac gagggctgat gctttaattt ttgggggttc 1200
gaggagaaat ttggatgaga ttcgagcttc gtttgaactg cgaaggtttg atggtgatat 1260
ttctattgtg tttgaatttt caggtcctag atttcatgcc aaggccgacg gtgatgccga 1320
cgaggttgta gatccaccaa aggttgagga aaaaatcggc gccgttccac atggtctttc 1380
cactgattct gatgttgtta agaggttcgt gaatgtctaa tctcgttgat acacgcttca 1440
agtatagatt tgtccacttc gggaaaaaaa attatcgaac cttcttttga atgttgattc 1500
agagagtcgg agtcaatctc gaagagatct cttcgcagta gcggggagaa atttgagttc 1560
caagctgagg tgtctcggct catggatatt atcatcaatt ccttatatag taacaaagac 1620
attttcctaa gagaattgat ctccaacgct tctgatgtaa gttcactctg cctcttctca 1680
cttcattaga tctagtaatc tcattgttag atttgtgtta gttaataatg gcgtctctgc 1740
atttcaggcg ttggataaga ttaggttcct ttccctaacc gacaaagaga tattgggtga 1800
gggagacaac tcgaagctgg agattcaagt gagttcgacc ttcatactga catattgttt 1860
tcttattacc tcgctgaaaa aagctgctcg ttctggttga tgaaccttgc atacttttat 1920
tgttgtccat aaatcaaata tcgcagatta agttggacaa agcaaacaaa atcctttcaa 1980
ttcgcgacag aggtattggt 2000

<210> SEQ ID NO 144
<211> LENGTH: 1337
<212> TYPE: DNA
<213> ORGANISM: Cucumis melo

<400> SEQUENCE: 144 tttttttaa ttttctttt gcagattgtg gggctgatcg tccacgatat gattccactt 60
tggctacgag gggtgtcggg caccttgtcc gtaagggcac tggtgggaga tcgtctgtta 120
ggtaacctag ccctagcttt ttcgtgtttg gattcttcta tttaattgtt ggcttgatgt 180
tgtagatgta atgctgggtt tgagtgcttt gaaatgttga gggaaattta agaaatttaa 240
tgggatgaag atgaacagtg gtacttcaag cctcaaattg aattaaaatt attttaaaca 300
tcctaaattg gtatgactaa gtattgctaa acatgatagt catataaaag cgcaaaagaa 360
aagaaaaatc acccctctac taggattggt ttattctatg gatttttgcc ttcagtgttc 420
ttgaagtcac aataataaaa gtagtaatag ttgcagtcac aactcaaacc tttatatgtt 480
ttttaagatt gtggtaaata ttgttttgat cattagacaa gacatagaga ttttaagtct 540
ctgggccttt tcacgaagcc ataagcctct tatggttcag caaaggcata ctcaaggcta 600
gaagttaaaa aagccttgcc ttgagatgta attctgaata cctttttaaa acatttggta 660
cttcaaattt ataagtttat tagtggaaaa tataatcttt cagtctcttt tttagctgaa 720
atacttatac ctttttttccc cattgtcatt gatttcttaa ttcatatgca gaggaaagga 780
ctaattagat atactttgtt ttattgagta atctaaaaga tgtggcacta cccactatga 840
acattttgac gtcattccag cttttatggg atattgaagc aggcaatttt aatctgagct 900
ggtttctctg tcgctgtcag ataatccttg tttgtgctta tgtgttctct ttcaagcatg 960
cacattagga ttctcaggca gatcagatca ttgatattta attcaatttg tggatttagt 1020
ttgtagtgaa tacactaaat tctgtctctg gtttctctga tcttactgtt ttattacaaa 1080
attgttttgc agtgggattg ttgctactgt cttcggagct actggattcc ttggccgata 1140
tgttgtacag caactaggta ataggtgaac ataaatggta ctagcattcg actttctttt 1200
tgcttagata tgtaatttat tacgtttctc tataccttct actactagtg ggttttggca 1260
gctttggctc tattcttgat ttttatatca attttatgct aagcatgatt ttggaaatga 1320
attgtgtttc agctaaa 1337

<210> SEQ ID NO 145
<211> LENGTH: 2000
<212> TYPE: DNA
<213> ORGANISM: Cucumis melo

<400> SEQUENCE: 145
atatgtgacg attaattacc taaaaattaa ttatttacat agggttagtc aagttgtccc 60
gtgagactag ttgaggtgag cataagttga tccgaaagct cacaaaaata taaaatacgt 120
caatctccat gctttcataa aaataacaat ttgattctca tgactactca ttcacttatc 180
gtaaactctt ttaaagaata ttaagagcgt attagtgtag tgggctagtt tgttacaaaa 240

```
gttggcgaca aatagatgaa attagagtta tctcgagatt cgacgagggt taaaaagagc    300
atttgcttta ccctgtattt tcatcgtagt tcatatttat ttatattcaa attctatcaa    360
gttaaggcca cgtatattcc aagaaaacat aatccattaa tggtaatatg aaaaatgagt    420
tttaatttga tcatgttgtc ggcattatgt aatcacaaag atatctaaag ctcaatgtta    480
aatctaatta atggaggccg ataatccaat tatatttgaa aattaagtgg aacctacggt    540
gagatatttg tactatcaca attacaatta ctcttacttg ttcggaaaag aaattttgta    600
aacatgtcaa aattatcgtt actattccaa atattgtcac tgacctgaac attgtcaaaa    660
agaaataaat aaataaaata atattagata atgtaaaata aaccacctaa actttaatct    720
attatggtcg caaatgcttt gataacacat aaaccgattg atccgtcaat gaaattttac    780
cataatcttt attatggatc gataaatatg acttaatttt cttttaaaaa agtgtttttt    840
aatttaaaaa aaaaaaagga aaggaaaggg ggaggggcaa aggttctaga gtgttccaaa    900
taggacaatg gaggagggtc tccaatggag ggaggagcca aatccaacgg ccaacaattg    960
ctggaagctt caggagccta catgattctt gggttcgttt ttctctcctc ttcctatcca   1020
tccttttgaa atttgctata aagaaaccta cttctcttct ccttacaaaa aatccatttt   1080
acactctctg taataccccc agttttgcct cactcgcagc gctcatttct caccctctta   1140
tccaaatcaa tccttctccc tctaaaccct aaaacccctt tgcacctccg ccgttttctt   1200
gtaagattcc ccctctcttt tcattctgtt ggactttctt atccttttac tttactgggt   1260
catgcttaca tttctatttg ggttttgttt ttgcttgccg attcagtctt ctgtattgtg   1320
ttttgagctt tctgactgtt ttggctttct gggtttcaat tgttggtgta gacttatcga   1380
ttgattcgtt tgttttgtgt cctttcattt ctgggttttg atttctttaa cattttcttc   1440
atgggttttg gattttgggt cttcttcttg tgtgcatctc tgtagcttgc tgattcattt   1500
gtatctcgtg tttatctatt tgtttgagtt cctgacatgt gggtttttgt tgttgtctga   1560
gaattatgtg tcaaatgtca attgtcaatt cctatgttct tgaatttgtt tatgtcattt   1620
cctttctggg ttttctctgt tcaatcttgc tacatgggtt ttgggttttc ttacccttgt   1680
tgtgtgtagt tttagctgat ttttgtttat gcttactgat tcggttctgt attctcgatg   1740
atttgcttac ctggtttttt atgtcgtttg agaattgtgt gtcaattcct ttgttgttga   1800
ttttgtttgt catttctggt ttgacattcc atccaatcct ctctgctcta agtctacttg   1860
gttttcaatt catgaatttc catcagacgc attgtcggcc ccctgctcta tttgtttaca   1920
attctggttg tgaagttgtt tcagtttgaa ctaattgatg gtctggtgat tacgttctgt   1980
atcagtttgg aagagggtaa                                                2000
```

<210> SEQ ID NO 146
<211> LENGTH: 1212
<212> TYPE: DNA
<213> ORGANISM: Cucumis melo

<400> SEQUENCE: 146

```
atatatatat atataatgga ataggctatt tgatttagat gaaagctatt acgtcctggg     60
gtttacatca taatctctat tataatgtta atcgagaaac tttataaagg ttaactcatt    120
atctctcttg tcttcagttt attattgttg tttttatatc ggtggaattc cacctttcac    180
caactctcaa gctgtggtgt gaatctatgg gattaatcta gggcgaataa gggagctgag    240
tattttctat ttgtggaatt aaatctatag tacacaaaac atttgctcaa ctactaagga    300
tatgaaaacc cttggctctg ccaacatggc ttatagaaag tatctgaaaa cgttcaccac    360
```

```
tttgcaattt caacaataag tgtaaattct tttcctattg ttgttattta gtcgatttga    420
tcgttgtaca atatttgctg taacatgttt gatttttggc cattttagtg ttcacaagaa    480
gatattgttt gttataagaa tctacctgat ccttttcaat tgttattcaa tatattgcct    540
actccgttga cagcaggtcc atgcagagga acaagttcta aagttcaaac tcgatgctga    600
tattcttcag gtactacttt tctgttttca caagtttgtt gtttcaatag ttctaagaca    660
gtgacactca tccctttatc tccgtaaccc aattcattaa cgatgacttt tgatcggttt    720
gaagaaaaaa tttataacac tttctcatct cgttcccttt ggattttcag tttttaaaat    780
tgcatctata tgtattcttt tgttatcaaa ttttacttga taatgacttt taaattgtac    840
taactcattt agatgtgaat attaataatt ttaaacttca tttctgacgt ctaatactaa    900
taaaataata ataacaatta tccttcttaa ttaaatatgg tttacctacc ggtctattgt    960
tctgaactgg atatattcaa tttgttttat ctgaataatc ttttgaggtt gagttatcaa   1020
gagcctgttt aacttaccta aagcatttct aacctgaact atgccccata tgaatacttc   1080
attttcttta ttctattgta aaacattgtt gttattataa tttgaaacgc ctgtaatagt   1140
ttttacgatg tcttgcagga gtctatcgtt cggcatgtaa acgaacaccc acaggctggc   1200
tggaaagcta cc                                                       1212
```

```
<210> SEQ ID NO 147
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 147
```

```
acatagtatt aataaattag ggaatgactt agttatttaa tttaagcggt agtaaatatt     60
attaactttt gttcgttgtg ttattttact ttcaaaacgt tcatcttgat ctttatcctt    120
tctaatattt atttatttta gttaatatca aaaaactaaa tttaatttat acgttaagtt    180
acaacttcat ttatttcaat ctaaaacttt tagaattaca ctttattcac taaaaaatta    240
ctcgtaaatg caaccattcc aaaaaggttt caatattata taaaatatca taatttttcg    300
aacattctta aaataaatta aacaaaatag tagttttcat atacataaaa ttcgaataaa    360
tcctcataca aaaattttaa atttgaatca tcacattgtt ttattttaga taatcaatca    420
aataatttag gaaaagagaa gaaagaaaag taaaaggaag ttgaaggtat tttatttagt    480
gatagaatta taaaataggg tattttagaa ataaaaacac aaatatataa aaatacagaa    540
attgatgcat ttaatggaac actatttgac aatcaataag aaagaaaaaa aagaannnnn    600
nnnaaaaaaa gaaaaaagag aaaaggtttg gtattgggtt tgtgggattt tattaataaa    660
tgaaataaaa aaaaaagaaa gaaaaattta attgattaat ttggtgggag aatattacaa    720
tgaaacccca ctttgtgaac aaatacattg catttgggtt gtaatcaagt gtacatgcat    780
ctacccaaac ctttcttgaa ctcaccataa atccttcttt tagaccgctt cgacttccca    840
atttttcttc actttttttc cccttctct ctcttcctcc gtttcccccc cccttttttt    900
tccctatctc atagggtttc catccacctt cttcttcttc cgttctctca tgcattgtca    960
```

```
ttcacaatct cattctgaat tcctcttgat cttcttcatc ttcatttcct ccttattttt   1020

tgctctcttt cgagggtttt tcggttcatt tccgtccaga ttccaccacc tcccgtggtt   1080

ttttcaccca tactcatgtc gaagctcttc gccttttccg gtaagtttat ggatttttac   1140

tgattttttt tttttgtttg ttttgccttt ctttggattt gacttagatt gggtagctgg   1200

tagggttaag cgtcgtgttt tgtatgggtg tttggattgt tatttggatc gtagggaaag   1260

atttggaatt attggtttta gtttttgggg gtttcttgat tcgccaggtg gcggatcatg   1320

gcttggtatg aattgtgagg gaatatggat ttgggtttct ttctattagg attgttttat   1380

tgtgttgatt gattggctat tttattgtct tgaacagtcc atgccagatg taagtttctt   1440

gaaaagagat atcgtagttt gaagatgggt ttacctttta agtgatgtgt atgtgttgtt   1500

gatctgtcgt tcccgtacag atttagattt gaggtttaga ataagagagc acatcaatag   1560

taaatattaa agggtcaaat atagttttgc agagattgct tcttgttttt ctctgttgat   1620

aaattttcga tcttttgatc tagaagttga ggggtatttt ggtctgagga tttatttgtg   1680

atgttggatg atgtatctaa cttgtagttc ttgttgttga aatttcaggt agtgaagatt   1740

tttgcactgg agggtcaata tacccaaatc ccaaggactc cagtttattc ttgtcccttc   1800

ctcaccacgt tgatgtctat tttcctcctc gaaagaggtc tcgcatcact gctccatttg   1860

tgtttggtgg agaagaagtt gaatcaaaag caaatgtttc tatcgagatt cttccggatg   1920

agtgcctgtt tgagattttc agacggttgt ctggtggcaa agaaaggagt gcctgcgcaa   1980

ccgtttctaa acgatggcta                                               2000
```

<210> SEQ ID NO 148
<211> LENGTH: 1254
<212> TYPE: DNA
<213> ORGANISM: Cucumis melo
<220> FEATURE:
<221> NAME/KEY: misc_feature
<222> LOCATION: (1)..(1254)
<223> OTHER INFORMATION: n=g, a, t or c.
<220> FEATURE:
<221> NAME/KEY: unsure
<222> LOCATION: (1)..(1254)
<223> OTHER INFORMATION: unsure at all n locations

<400> SEQUENCE: 148

```
tcataaatat atatataaaa aaacaaatat tataacctac cttttgcaaa tgataaaatt     60

gtaaagtctc gtgccgataa tgtgttataa aataaaagaa caaagaaact aaataagaac    120

aatgcaacaa nnnnnnnnnn nnnaatagag aagagaggaa gaaggggaaa caattaaaaa    180

ctcaattgta gtgtgactta cacaaatgca acacatatat ctatttatag gacatatcat    240

ggtatatgtt atattatgaa attcaatgaa atgaatgtta caataaagaa ttgaatgaga    300

gttgtatgaa aattgtaacc ttcataaatt atggatatct actcttataa tatatcatta    360

tatttataat gtatactata tgtttgtatt ttaataagaa aattatccca ttggatttgc    420

gatcttagat ctaacctact aaacaaatat tccaacgaag aggaacgaga tgagaacgcc    480

gttctaacct acgcaatatc aatcgtttct tcgctgctac tttacgcctc aagttcctac    540

ccttcaagtt tcatcttcaa cgatcaaccc aacgattaac ccactgcacc accttatctc    600

ttgttggtgt catctaatcc atcttcttcc tgcatcttct gcaaatgctc tcaggttctt    660

tcctctctct tgtgcacaaa ctgatcaccc atgttgttcg ccggaaaatg attcagattc    720

ttcgtatctt gcctgcattg tctttgacta taatatgatt gaaattcact tgttgattgg    780

ttttcaattg ttaattaccg ttggttttgc tgtttagtga tagtatatta tgaggttttt    840
```

gttcgttttc gggtttttgg atgtgatttc atcctataga atgaagagta tgcaacgtat 900
gctgtcacct tgcgggggaa atggtacacg tggacccgaa atggagctag gttttgatac 960
gtgcagtttg agttttggtt ttgggaggat ttggcattcg ttatatgaat tttgtaatta 1020
actatgccgt ttgattgtta tttataacgg tgcattgctt tttgaggttt agaatttgga 1080
cttaacgcct ctttctattc atggttattg gttttatttc ttccttttttg ttgactgaga 1140 ttggtcgtag aactcgttgc ctgtctatgt tttaatgttg gcctgatttt gaatttctaa 1200
tccatgacta agtatttctt tattgtcttg atatagttga ttgaatcatc aatc 1254

<210> SEQ ID NO 149
<211> LENGTH: 2000
<212> TYPE: DNA
<213> ORGANISM: Cucumis melo

<400> SEQUENCE: 149
cattttaaat tgacctttca tgaaaaatcg tatgtttttg gtgtgatttt gagtataata 60
aaaatgattt taaccatttg aaaatcactt taaattacac ctaatgggtg actgaggttt 120
tagctttcgt ctttgtttag ctctaaattt gcatggcaag ttttccattc caatgattga 180
tgtggcttgt aatagttgaa atatatatat atatatatga ggtatcaaaa tccccagcct 240
tgtgttaggt tgaatatgga gggagtgggg agttattttt cctgctctta ccccgttcct 300
aattcccacc ttgtttacta tgtgttattg ttattgccat atttactatg tacataaatat 360 ttcgattaga aattttattg tttaaccatt agacaatttt atatgtctaa accataggtt 420
tgaacaaacc atttagatta tatatatgtt gacaattaga ttgatagggc aattattttg 480
tttatcctaa aaatggtaaa taatgttctt aaacttggtt ctttgtgaaa taccttcaac 540
tttcaaagtt tttaataata ttcttacgct tataaaaaga aaaaaaggat aagttgaaaa 600
aagaatactt ctatgataag ttttagatgg aaactattta ctttttcatt taaaaaatac 660
ttttcaaatt tatgaagttc caaaagtatg acttaaagaa atagttatac ccttattgat 720
aatatacgac aaaaacaacg caatatttcg ttacaaaaat aaatctagct gcattactat 780
cttactttaa agatactctt atcgtctatc taaactacct tactctagaa ttaataatta 840
agttcctttt actttataaa tataacttat tcctactatt agtatatatt tatattggta 900
tctaatagct aattttgaat tttgttccaa aaaaaaaata tcgctgagtt ttgttttgaa 960
gtcttttttt ttttttaaat atatattttc gattaaagct agatgttgca gttgatatgt 1020
agatttaaaa gaaatgtgtg agatcgttta taactatata gaagattaag catttattac 1080
ttcaaaatat atcgttaaaa ttattcacat aaccaatttt tactcatcaa atattatgtc 1140
agagaaaaga aaaacgaaaa agaaaaccta cttcaacgga caaagaagtc cttagttcaa 1200
atcttcaaac ctttatttgt attaaaaaat ggcatataaa tttttttcaat ttttacgcat 1260 tacctgttgc gtgaaaaaca ttgatttaat agaaaagaac tgtcctttca gttttgtttt 1320
tttaaaacca atttcgaaat tcaagaatag aaacaaaact ttaagtctag aggatcacta 1380
aaatctatca taaggctaga aatacatctt gtaatctgca gtaggcattt gccgggatga 1440
caattttctg gtgcttggat taagaaaaaa gaaaaaaaga aaaaagaaaa aaaaatggtg 1500
aggacttaga ggccataatg agtttggcat tgggcccaca gtaggatgag taaattataa 1560
ttgggagaaa atgagcatag ggtgtggagg ggaaaaggag aaggctaaaa cactatcaca 1620
aatcacacag tagaagatac acagaagaag taaccacagc cattcattga gtgagaggct 1680

-continued

```
atccataatc tcatcctctt acccttctca tcattcattc aaagccattc aactcaacat   1740
cccactctta gttaaccaac aaaatatata tacatccttc tcaatttccc ttctctctac   1800
tgctttaatc ttttgcttct tcttcttctt cttcttcttc ttctgctttc tcaataccct   1860
caaccatggc tacggctact ctatcagtag ccaaaccatc tattcaggtt cctccattac   1920
taaacaccat cctctttccc ttccactctt ctttaatttt ttgtatctga taaacattac   1980
tgcattttct tgcatagcag                                                2000
```

<210> SEQ ID NO 150
<211> LENGTH: 1680
<212> TYPE: DNA
<213> ORGANISM: Cucumis melo

<400> SEQUENCE: 150

```
tttttatgaa gggagttgtt attttccttt gggatttgga gggatatgat atatatcctt     60
tttttgcaat ttgatgacag aattctgctt ttagagactt ttcaaactgt ttcgtaatga    120
atttgatggg ttgggggtgg cttagttcaa tactttgtgg gttgaaaatt ttgatttgca    180
ataaatgaaa gccaaaaatg tggggaagct ttcagttcaa gtaagttaag ggaaaactgc    240
agaatatctg gcttgaaata agagatgtct tcgaaggtta atagttttac attgactttt    300
ttaaaaaaaa gattatatta taagtacaaa tatgggtgga tgtgaactta tattattcaa    360
agagactaat ataagttttg ggcgcttaat attttatatt ttcatttagc agtcaaagat    420
gtataagaaa actttggtaa tgcattttat actagtttat ttatgtagga tgtaggatct    480
atcgaataat acaacatatt tttaaatgat gtgtacaatt gtgaaaaaaa aaggaacata    540
cagtattgta gaaactaaaa tattttctaa gatatatcga gatgtaaaaa aaatgaatgg    600
atgtcaattc cagcataact taattgttga actaaaaaca aaaagaagaa ataaaggggg    660
caatggtttg atcctcatgc cccacatgaa agtcaaagtt atgtaaaggt tccgtgtagg    720
atatccttcc tcctaataag gggagatagg attttatgag ggtgccaaca gctcagaatt    780
ccaaattccc aaaataccct cttgcttgaa aatttcaaac tcttctgttt ttgccttgtg    840
taccattcac tattccgatg cgtacagttc attaaccaca caagttctcc ttttgcaggc    900
aggtttagct aaacttattg gacttgctgg agagaccaat gttcaggtaa gatcttattt    960
gttataatga actcacaaac taatttagat tagccaaaga attctgtttc tgaagaaaga   1020
gaggatgaaa atcatctcat accaaatttc tttctttttt tggaattatg tcttcacatt   1080
tattcatttt ccttgtcaac agggtgaaga gcaaaagaaa ctggatgtgc tctcaaatga   1140
agtctttatc aaagctttgg tcagcagtgg cagaactgta agctgctatc taatcataca   1200
aatgacacga caaaaatatc tggtgactta ctctaatagt tgacaaattg gtggcagtgt   1260
attcttgttt ctgaagaaga tgaagagcca acatatgtcg agccatctcg gcgtggaagg   1320
tttgttttcc attcttgatg atttttgtct aatgcttaca attatcatca gtatcaactc   1380
ctcttacttt gttttaattt taatgttatt tcttcttatt ttccaatgac aaaggtattc   1440
tgtggtgttc gatccactgg atggttcctc caacattgat tgtggtgttt ccattggaac   1500
ggtaacatcc ctatgctacc ttctgaatga gatttcaaat atttttggta taatttcttt   1560
ccaataagct gagtgtatga ttgtttgaat atctactttt tcatgtagat ttttggaatt   1620
tatcacttga acgacagcca cgaacctaac ctagaagacg tcttgcaacc tggaaagaat   1680
```

<210> SEQ ID NO 151
<211> LENGTH: 1524

<212> TYPE: DNA
<213> ORGANISM: Cucumis melo

<400> SEQUENCE: 151

```
tatatatata tatataggta atgagtaaag aaatgaaaaa gaatgagttg aagaatcaca     60

cccttaccat tctatttgaa actcgtgagt cttgtagact tttacatgtc ttctccttca    120

cttaatatca ttctggattt tgattatatg tatctttatt tctaaacagc ttggacagat    180

ttattattgt tagaatacct tgaatatgtt ttctggtgct tagaacgatc atacatgggt    240

ttttctaggg ttagaggagt gcgctataca taaactttct agttctagag gcattgctgt    300

aatcttaagt ttaacagttt ctctttaata acaaaaactg ctcttcccct acggtttaag    360

ttttctcctt atcttaacag ttataattat gaaaaatgat ggaaccaaaa caaagttctg    420

ttaaaatttg actaattgat tgaatgaact tttgtttcca agattcttaa tttgtaaagt    480

aataatgttc ttacaaatca ttattttgat gtctgagtta taacccttaa gcttggtggt    540

tcatattcca ttcaggtgaa gaagattgtg agtgaaagct gttcccaaga ggttttagaa    600

gtggcgttaa actccatctc atccctaatt accatcctct cctccatgtc atcgtctacc    660

aaactccatt cttcactttg atggtataag aaagtgaatt agatttggga ttgagcttca    720

aaacatgtat gatgatgtga atatttactc gtgtaaataa tataacatgt tgtattcttg    780

cttgtttctc tttgctcatc ttcgttttgt taagagcaaa gaaaagctta cgagcatgaa    840

catgtgcaaa tttatgaagg tcaatgggct tcgtaatttt ttttccccat tgatttaacg    900

atttatggaa gatggatata gtaaatttag gttaagctgt acaaaaccag agaattttca    960

ttatagtaaa tactttacaa ttttcaatta gctacaataa acaccgtttc aaaatctccc   1020

tcatttgcta ccatatttac tattcgatat ttatcatttt ttttattcct gttgtaatgt   1080

ctactatttt tcttttaaac tattacacca caaacacata ctattataat tcaaattaaa   1140

ataatcacta gtataactca actataataa ctcagatgat ttcattccat gaaagtggta   1200

attataaata tttaatatct tatatgataa ggataactat ctatttggtg aaaccaaatc   1260

acaatgatgc agtggtaagt gctttggact ttgaatctct tttttatagt atttcattct   1320

tttttcaacg aagcagcatc atgggccttg aatggaggcc agctagaacg agcccattac   1380

atttgacaga gcatctcttc ggcccatgag cccaaacact attcatcttg ttaaaccacg   1440

aacaaatcga gactgccgag agtgtaagag aattgagtaa tttttttcga gacacaggga   1500

gtttagagag taagtcggag aaca                                          1524
```

<210> SEQ ID NO 152
<211> LENGTH: 1851
<212> TYPE: DNA
<213> ORGANISM: Cucumis melo

<400> SEQUENCE: 152

```
ttgggtcgtt acaatatcac tgtttaaact taagtttatt tttatttatt tttttatttt     60

ttaatctttt tcccttcttc ctttcatctt ccattcattt atacaaaaat aaataatgag    120

aaaattactt ttcacttttg agtttaatta tttttaagtt ctaaaatcta cattttaatc    180

tttaaattta aaaaaaaaag gatttacaag attcttgagt aatttattat tattattatt    240

ttgaacgtaa atataacctt ttacaaaatc taaatgagtg tttgggacaa tgagttgatt    300

attataagta ttgaattata ataatttttt gtggggtata gactatttta atttgaagaa    360

taataggtac gtgtttgaaa tataaattat gttagttggg aaagaaaata gtaaatatcg    420
```

```
tagaaaaaaa taaaataaat gaacaataag aatataaaat atggtaataa attgggactt    480

tgaaataatg gtaataatta attaattaat tgaaagctac aaaacaatgt tcacttcatt    540

gctatagttc taaacagact aacaatctca atcaatgacc taatgggtca ggccattata    600

ttgggctcaa atagattttg gcaaaacgaa tcgaaagccc aatggggcct atattatgta    660

gggccgaaat gaatttcaac gaaaggaacc caaagcccaa taggcccaaa ttgagactta    720

caaaggcgca tgttagcatg aagagagaat tgaaagctta aacagcgcca tcacaaaaca    780

tttgcatttt cgtgttgaaa tcgcatttgg gccgtaaacc aatgaaacac aaaacaaaca    840

aatcctggaa tagcctcaac ggttctggaa gaagaagaat cttctggaac ctccaatccc    900

acaataaaaa tcaaacccta aactcttaca ttcagctctt tgcttacctt atcccaacaa    960

accttcacca acgctctacc ggaactaaaa cccctccgac ctcccacttc cgacttacga   1020

cctctgttgc ctgaacatgg cgtctgccaa tgctctttct tccgcttcta ttctatgttc   1080

ttctcacaag gtacttcact tataaccccc tcatttcttc cttgtatttt tcacaattcc   1140

tctttggaaa tgatgatatc tagattgtag tagttgggat tgtatgttag gtagagattt   1200

tgtggagtta gctgagagcg gctgagaata ctaatatatc gtttccagta gcttacgttg   1260

cgtttttcta atgttgcaga gcttgagaaa ggtgaatcaa acgcagaaca acagagtaaa   1320

ttacagacag gctggtagta gatttgttgt gagagccact gcaaaggaga tagcattcga   1380

ccagagttct agaactgcac ttcagtctgg gattgataag cttgctaatg cagttggttt   1440

gactcttgga cctaggggta actttctgtt tatatttatt tatgaattgg ttagtattgg   1500

atgttgttct aatattgaaa tccctacagg atatattcat cacatttata gattcgtgtt   1560

atggttatgt tgagaaattt gggttcttca cataattctc aatcttgttg tgatattttg   1620

tatttgaagg gaggaatgtg gtgttggatg agtttggtag tcccaaagtg gttaatgatg   1680

gtgtgacaat tgctcgggca attgagttac ctgatcccat ggaaaatgct ggtgcagctt   1740

taattagaga ggttggtttt ttatactttg ttatgaagca aaattttctc atctatcgat   1800

tattgaagtc ttattagttc ttacattgcg ttgacaagta ttctatatgt c            1851
```

<210> SEQ ID NO 153
<211> LENGTH: 2000
<212> TYPE: DNA
<213> ORGANISM: Cucumis melo

<400> SEQUENCE: 153

```
actaattaat agtaatttgt atgggatata tgtatatgtg tgtataacag gaactacaga     60

gatagagatt cactttctag aaataaagtt gactgccatt ggagtttatt tggagccttc    120

agttgtggag catttgcaac aatggaaggg aaaagctgct aaggacttag tggaagatga    180

tgacttcttt caggctattg tttctggtat ctccctagtt atcctatttt taactatact    240

atctcatcac attcctaaat gtgaattact tgacgatctg ttcaaacata tatatttcat    300

tgtttgatcg taatgtttca tatttatgat gtttcatata ctacctcgtc acacgtgcaa    360

aggatttaga tccgttcaaa catatttcat tattggatcg taatgtttca tatctatgat    420

gtttcttata ctatcgcatc acacatgaga tccattcaaa catatctcat tgttagaaag    480

attatacatt atttcaattc aaatagctct aaccaatgac aaaattagat tcgtcccgtt    540

tagcttattc tatatatata gatagataga tagatagata gtatggatat gcttgtgata    600

agtgtttttt tcttcttttt tttttctttt tttgtttttt ttcttttttt gtcactttct    660

aaattatcta tctcacagtt agctagttgg cggggtgatg acttttggtg tgtcagtcta    720
```

gtgagaagtt tgggggttat ttttattttc gaaagcttcc taattgaatg acttgtaaag 780
gttaatgttt atgtttttgt acatgttttt catgaactat tggttttaca agagttacaa 840
ttctatttat ttgtgtaaga aagatcatat cacattttta cccctggtgt gttcgtttta 900
tgttcttgat ttgctttttg tttttcaata atttacgggg aaagagagaa taaaattttc 960
tttctccgat ctccgcattc aatttttttt tttttgaaag gtgcattcaa ttttttttgtg 1020 cttattaaat attcacttac atcttttgtt ttgtttattt ttttattttc atctttctta 1080
tatgaaaata aaatattttt tagtacaaca atagaacctc ttgttaccat tgaaatgaat 1140
tacaggaaat taaaactttt actttttatt tgagagaatt aaaagagtag tttttaaata 1200
taacaaaacg actttcgcaa tagatccaga tgatcattta ttaacaattt tctaattaaa 1260
attgttacta aattttaaca attattaaaa aatattaatt gaaaaacacg tgtatatata 1320
taggaacatt ttcaattata gccaaaagtt ataattattt actctataaa attctttaga 1380
gtctatttaa cctttttgtt aaattttgtt aatagtttta ctttgccatt cataaaaatt 1440
tctcatatta tatacagtga gaattttata agtctcaaaa gtcaaagatt tgattaaaaa 1500
aaaaagaaat gaaagcatat ctaaatatat tatttatact ttgaaaatta cttccgaagc 1560
aaaatgtaaa accgttataa gtgaacttag aatccaaaaa catatattaa attaagttta 1620
aattatataa caacaccttt ggattttgtc attttctaaa ataccttttta tcatttcaat 1680 aattgtaaaa tgagtcctaa attttcacaa atgtttcaaa aatatttgga ggagacaatt 1740
ccttgagaat ttcaaagata tattaaagag gacgtattga cccaaatctt ttgttctatg 1800
tcactatgat caccctttta tatcacaatt tatttccatc tacaattcta aagaatttat 1860
aatttaaaag tagtttcaaa atgtttctaa attttcgagg gtaatatttt aacttttgga 1920
agtacggaaa gttaatcaaa tctttgtctc aaaatctcaa ctaataactg gaattgggaa 1980
agctaaagtc tagaccttaa 2000

<210> SEQ ID NO 154
<211> LENGTH: 1288
<212> TYPE: DNA
<213> ORGANISM: Cucumis melo
<220> FEATURE:
<221> NAME/KEY: misc_feature
<222> LOCATION: (1)..(1288)
<223> OTHER INFORMATION: n=g, a, t or c.
<220> FEATURE:
<221> NAME/KEY: unsure
<222> LOCATION: (1)..(1288)
<223> OTHER INFORMATION: unsure at all n locations

<400> SEQUENCE: 154
cgagaagtac ccggcgttgg tcaccggatt tttcttcttc atgtggtggg tttaattgtt 60
ggtcacgtgt tttgcacggc gaaggccggg tggtaattat tacgttgcgg caagtttgag 120
cttggttgtg tgaaattacc gtgttgtcct ttctgttttg taggtacttt ttgaacgtga 180
ttttcaatat cctcaataag aagatatata attacttccc ctatccatag tatgtatttc 240
caatttacat tttcatccct gtatttttct tcttcttctt cttnnnnttt tttttttaat 300
attgttatta atatttgttt acgttccagt tttgtgtcgg tgatccattt agttgttggg 360
gttgtgtact gtttgataag ctgggcagtg ggtcttccta agcgagcagt aagtcaactc 420
tttctatagc ccaatatgcc aattttgtct ttttctttca ttaaaattgt tatttttaac 480
tttttcatac ccaatttagt ttttttagtc tgtttattag tcttgttttc ttcaaattta 540

```
gtagtattgg tagtctaatt ggtagggctg ttttgaaagt aattacctaa tataatgagt    600

atttagattg agacagtact atagtctaaa cgatgtcatt gcagttttga ttgaaatttt    660

ttctccttta tttatttcga aaatgacaat ataacttctg taatctttgt aaccatgttt    720

atttgaagct acgttgtaaa ggggaaaaag aaaaggaaag tgtaaaatgg tcaaataaat    780

tatattttta agtgaataga ttatataatg tgcggtaaaa tatagcactc acaagtaaat    840

gcaacttagt aatctaaaga ttgaactatc aattcatgaa tttttttata attagcatgg    900

ttttctatag tttttgggag tctgtttttc aatgaaaata ttgccagtat ggtaatcttg    960

tatgacaatg tattttctaa agtatggata taattaaatt ttctttaatt tatcggctta   1020

aacttttcgt tgtactaaaa atctaggata ggacgtttaa tatttgaacc tttgtaatgc   1080

catttaatca ccgattaata tagatctaac tattgaaact tcttcaaaag ttttaatcca   1140

acggatggct aagagtgtta aaatattgat acaattaaat ttatcgtagc ttaagctttg   1200

acagtgtcaa aagctaattc agttattttc tctgcccttg gtataagggt aactctgttc   1260

tctctatttc acacaagtga ttgctaac                                      1288
```

```
<210> SEQ ID NO 155
<211> LENGTH: 2000
<212> TYPE: DNA
<213> ORGANISM: Cucumis melo

<400> SEQUENCE: 155

ttatgtttta ttaactccat agttttacta accccatttc acgggaaagt acaataaaac     60

atttgtgtta aaaaggagtt gtttgtatag atcgaataaa cattttgtac taattccaat    120

catattacca aatgttttaa gagcatgcgt tcttgtgtgc ttgaataggg gtgatcatca    180

attgagtggc gtcagattta aatttaaagt ggcaccaatc atcgacttgt tggtttagat    240

cgatcggtag ttgttgtttg tgggacaatc atagttatca tttttctcct tctatatgaa    300

taatagtcaa ctagatagaa ttgacatttc ttagtattaa aaaaacgacc actgacctgt    360

ctatatcact aaactgcttg acctaagtga gtttggttgg acttgattgc ttcgttgtgg    420

tctaattcac ttaaccctac ttgaaagtaa aggtagaata taacatgatt ctttccaaat    480

tggcaagttg tgacttgatt tatgcatgca cgaagattct tccactctcc acctaactag    540

tactcgatca cattggaaaa tggatctgtc ccgtgaagga tcgcaatatt acatgccttc    600

ctactttttt cttttcttcc accaaagaaa aagaaaacgg gacacacaat aactatacat    660

tatcaataat aattaaacga atcatcccac caaatgtaaa ccatgaatat tgaaatcatc    720

atgttttaag aatcatttta ataattatgt tatttcattg ttttatatag aacacaccgt    780

tcatgaaatc aaacaaagag agagaaatta taattttgta acaaattacc aacattcttt    840

ttctttctat ttttcataaa tgagcatatg tttgtgtata tatacatact gttatttgat    900

ctccacattg ttgaacaaaa aagttggtgt tcttgaaaat agctatcacc gaaaatacgt    960

catatactgg gttgttatgt accaaggccc agaagaaagc ccaaaatcac cggcccatga   1020

gcagtgaaca aataattggg ctaaaagccc aatatacgtg atgatgggcc aacccagaga   1080

agtttatagt tatgttatta tagaattcca gatcagggag tatcgaaaca aaagcctcca   1140

ttgtcctcgt tctcttctcc ttgtgctctc tctctctctc tcttgctctt ttctctttct   1200

ctttctctcc gacgacaggt tcctgaagct cgaccagcca agggcattga tctaggtgag   1260

tccgctttca cttttccact ttcctctgcc gtttttcttg tcatttccaa ttctccattc   1320

tttgttctgg atttcacttc tttacttcgt cgttgattag aagataatag tgagatcgaa   1380
```

```
ttctatgtct cgcatacctt cagtttcaag gaacaagaca atgattcaac cgcgccgtcc   1440
acgttatgga tagagggttt tgattctcac ctttatagct gcataacacc gttcttaggg   1500
ttcggacctt tgaatctgcg atatttctca cactgttttg gacgttttta ccgttttcct   1560
atggttcttt agccttacct tatcttgcct tcagatcttc gattgcggat ctgattcgtt   1620
catttctact tgttactttt tcttggaagt cgaggattat aaatcaacaa caaagcattc   1680
aaaatctcta gtgcaattag tgttttccat ctagttattg gagatcgttt gtagctttga   1740
ttttgtccac tttcttattt tgaacgtctg gaagacgttt tatacatgtt ctttgggtaa   1800
agttgcgttt gggcactgtt cttcacctct gggttttcgt tcttatgcta tgtttcatga   1860
tttcttttga tatctttgtt attgtttccc catcatcgag tatctgattc ttattcggaa   1920
gccgtcttct tgaagctgcg aaccggtttt ctttttctcc ctcatcaagt ctttaatttt   1980
acaggaaagc gctgaataag                                               2000
```

<210> SEQ ID NO 156
<211> LENGTH: 2011
<212> TYPE: DNA
<213> ORGANISM: Cucumis melo

<400> SEQUENCE: 156

```
ttgttagagg agttagcttt tcagggagtc ggttacaact tacaagacag acaaccatac     60
tgtacaatca atcactactg cctcaaagtc gaaaccattt aataccagtt gagcctcatt    120
gtgactgcat aattttgacc cctaccacga ggtaatttca gttcaaatca attgtatctc    180
tcttctggat atcagtcaag aatctcatgt tctcaagtta tagtacattg ataattactg    240
tgcattttta ttaatttatg agttaaaatc ctgctgatta attcaactaa aggaataaaa    300
tagttattgg catttggatg agaatagaat gtgaatccca tcattcatcg ctagattgga    360
ccgtaattat aagtgagagg gagaaacttc tgttgctatt ccctttttat ttcttaattc    420
atttataaat tgtttttagg ccttttatat atatatattt ctaccatttt tacatttaaa    480
attcttttaa ctttattatg tatggactca aactaacaag ctttatttga taaaattgtt    540
caaactatta tattagtttt atatttgtaa accataaaac aaatccataa aattccacct    600
gcatcactca ctcatgttgt tgaatggtac gaaataaaca atacatgtga aagatgaaaa    660
taagaattgt tctcttatta aatctaaaat ctagattttc tttttagtac atttaacact    720
tcaatgaaag gtctaaaaca ttattgaatg acgtcacgaa ctattacaaa agattattcc    780
gatttatctc aaaaggggtc tatttcacta attttggtgt cccacatctg taaagagaat    840
tttcgtgata tgtgtagata tttaaatata attgaattcg atgaaagcaa agcaagaatc    900
gatatccgta gttattttga tatagatcgg tgataaataa aagacaatat gcataaagtt    960
tgtgggtaca gagtcggcta gttgcaatga ggggtatggc cccaagactt ttccccaacc   1020
ccaacggtca attaatcacc ccaatggggc atcgaatctt ccccaccatt ttcctttttct  1080
tcgccgactc ttctacccat ctcttttgcc gactctttct cacaggtttg attaaatccc   1140
attcatattc agatacacta tttcaaaata ctcgcaaatt aatttgtttt tttaaatatt   1200
ggtataataa taaaattaat tataaattgt gacctaaaaa gtactttgtg gaagagggga   1260
tatagtctgt ctaatatatt attgattaaa tatataatag aaccataaat gcaaaccact   1320
agaattgtta ataaaaatca acgctctttt aagtctttcc atagaaagaa aggcaaagac   1380
gcgcaacgtc tagaattttc tttataacgg aagctaactc tgttataacg gccgtccaca   1440
```

```
taatatggta gatttaaaat gacgtcagca tgtcgcttct aaatttgggt ccaaaggggg   1500

gattcattta tagggaaggg aaacggcaaa tgcaagcata gtgagtaaat acgtggcggc   1560

aaagtaatgg ataattctgc ctctgccgtg acgacattgc ccttccattt cactataaat   1620

acacctcctc tatccctcga tttcttcgca attgaatttc tcttctcatc tctgtcgtag   1680

caaaccaaat cgatttcttc aaaggtattt cttcctttcc tttttttttt tttttttttt   1740

tttttaaatc atgttgttca aactttgaga gatgaaatga ttaggggctt tcaaagtggt   1800

tttcgtttga tatgtttctt agatcgatag ggtttagaat cgagcatcct tgtaggtatc   1860

ctgaggtttg gtggttggat ctgcttaatt tttatgtggt tgcatggaaa attgggattt   1920

tttttttcta attacgtgat tctggaaata ttgatctgtg gttcagatgg aattgaatct   1980

gatctttctg ttttgttctg tataggtggg c                                  2011
```

```
<210> SEQ ID NO 157
<211> LENGTH: 1698
<212> TYPE: DNA
<213> ORGANISM: Cucumis melo

<400> SEQUENCE: 157

ttgttagagg agttagcttt tcagggagtc ggttacaact tacaagacag acaaccatac     60

tgtacaatca atcactactg cctcaaagtc gaaaccattt aataccagtt gagcctcatt    120

gtgactgcat aattttgacc cctaccacga ggtaatttca gttcaaatca attgtatctc    180

tcttctggat atcagtcaag aatctcatgt tctcaagtta tagtacattg ataattactg    240

tgcattttta ttaatttatg agttaaaatc ctgctgatta attcaactaa aggaataaaa    300

tagttattgg catttggatg agaatagaat gtgaatccca tcattcatcg ctagattgga    360

ccgtaattat aagtgagagg gagaaacttc tgttgctatt cccttttttat ttcttaattc   420

atttataaat tgtttttagg ccttttatat atatatattt ctaccatttt tacatttaaa    480

attcttttaa ctttattatg tatggactca aactaacaag ctttatttga taaaattgtt    540

caaactatta tattagtttt atatttgtaa accataaaac aaatccataa aattccacct    600

gcatcactca ctcatgttgt tgaatggtac gaaataaaca atacatgtga aagatgaaaa    660

taagaattgt tctcttatta aatctaaaat ctagattttc tttttagtac atttaacact    720

tcaatgaaag gtctaaaaca ttattgaatg acgtcacgaa ctattacaaa agattattcc    780

gatttatctc aaaaggggtc tatttcacta attttggtgt cccacatctg taaagagaat    840

tttcgtgata tgtgtagata tttaaatata attgaattcg atgaaagcaa agcaagaatc    900

gatatccgta gttattttga tatagatcgg tgataaataa aagacaatat gcataaagtt    960

tgtgggtaca gagtcggcta gttgcaatga ggggtatggc cccaagactt ttccccaacc   1020

ccaacggtca attaatcacc ccaatggggc atcgaatctt ccccaccatt ttcctttttct  1080

tcgccgactc ttctacccat ctcttttgcc gactctttct cacaggtttg attaaatccc   1140

attcatattc agatacacta tttcaaaata ctcgcaaatt aatttgtttt tttaaatatt   1200

ggtataataa taaaattaat tataaattgt gacctaaaaa gtactttgtg gaagaggggga  1260

tatagtctgt ctaatatatt attgattaaa tatataatag aaccataaat gcaaaccact   1320

agaattgtta ataaaaatca acgctctttt aagtctttcc atagaaagaa aggcaaagac   1380

gcgcaacgtc tagaattttc tttataacgg aagctaactc tgttataacg gccgtccaca   1440

taatatggta gatttaaaat gacgtcagca tgtcgcttct aaatttgggt ccaaaggggg   1500

gattcattta tagggaaggg aaacggcaaa tgcaagcata gtgagtaaat acgtggcggc   1560
```

```
aaagtaatgg ataattctgc ctctgccgtg acgacattgc ccttccattt cactataaat   1620

acacctcctc tatccctcga tttcttcgca attgaatttc tcttctcatc tctgtcgtag   1680

caaaccaaat cgatttct                                                 1698
```

<210> SEQ ID NO 158
<211> LENGTH: 313
<212> TYPE: DNA
<213> ORGANISM: Cucumis melo

<400> SEQUENCE: 158

```
tcaaaggtat ttcttccttt cctttttttt tttttttttt tttttttaaa tcatgttgtt     60

caaactttga gagatgaaat gattaggggc tttcaaagtg gttttcgttt gatatgtttc    120

ttagatcgat agggtttaga atcgagcatc cttgtaggta tcctgaggtt tggtggttgg    180

atctgcttaa tttttatgtg gttgcatgga aaattgggat tttttttttc taattacgtg    240

attctggaaa tattgatctg tggttcagat ggaattgaat ctgatctttc tgttttgttc    300

tgtataggtg ggc                                                       313
```

<210> SEQ ID NO 159
<211> LENGTH: 2010
<212> TYPE: DNA
<213> ORGANISM: Cucumis melo

<400> SEQUENCE: 159

```
tagaaaaaaa ttgaagatct tcttaatgct aataataaaa gcatatataa aaaggcttca     60

tattacacaa gcatcttaaa accaaaccga acttgatttg aaattatccc actaattctg    120

tagatttcac caaagtcctt aacctttata ctaacatctg catttgactc tttcatttga    180

cctccaacat attctttctc attttccttc cattcaccac aaaaaccaac aaatacaaaa    240

aaccacaaat acatagaaaa ttaataaaaa aatcaaaatt tcgagatgaa atcattataa    300

actcatccga taactttgag atttgaaacc ttacactata taaagaaact catccgataa    360

ctttgaattc gcatcgaaat tacgtaagtg aagacgaaaa tgtaaatgat tagatgcgaa    420

taacaaaaaa aacataattt ctaaacgtaa aacactatat tcaccttatt atacttgatt    480

attttggaaa agtatgaaat ttgagtgtgg gagaggagcc aaagaattgg aaacttgtta    540

ttaggagtcg ttatgaaaca ttttcaacaa gccaatattc tttcacatac tataatgata    600

tacatagaaa taatacaata atatttttga aattgaggca tttttgtcgt aatttatcta    660

aaaatgtcag ggtagattca tcatgtatac aaatctctcg ctatcaaaac tatataaaaa    720

tcttgtgaat gatttcaatc gaaatggacc gagaaaaaac atcgtaacca cctctaaaat    780

cgataaattt gtttcaattt caaatcccta aaactaaagg tgctactttg tacaatttcc    840

cctgattagg gtgctaaagt taaaccctaa ataaaggtgt gtacgtttcc ggaagtttct    900

agaatcccca gcgaagttct ccaaatcgtg gcttgcagac caaggacccc cattaaaatt    960

cgtttcttcc tctaaacctc ctcccttaat tttggcattt tggtattttg gctcctataa   1020

attcaccccc tccttatccc taatcctttg tcttccaaat tttccttcaa agcctgcttt   1080

tcccatttcg tcgtgctttt tcttcatcta aaggtatatt tcagttctag ttttctttct   1140

ctgttgatct cttggatttg agggacgttt gaagttggct ttgtttaatt ctttgttatt   1200

caatctcttt ttttgttaga gttgttgttt aatcgtttcc cttgttgttt ttctcccttc   1260

tagttcgatt ttagaacgct ttttgtgggt tgattttaat ttctccgttt tcttacatct   1320
```

```
ttcacaaaga aacgattgaa atcgtgtttg tttttttcc cacggcatac gttattagat   1380

cttgtagata atgatctcaa tctattgttt agtttttgca aataagaagt tggtttttta   1440

tctccaactt ttatatattc gattcgatga gatgttctac accgttagga tggaaccaag   1500

aagtgaggta agggtgtttg attgaaaaat tgaactgaga agttaaagtt ccttcctaac   1560

tttttaatgg attgtataat tcgttcaatt ccttgtcgtt ccatttttat ttctgtttcg   1620

tttttcgtgt tgctgcgtat cgcttccctt gttgttttcc tcccctattg attttgcgtt   1680

tcttggagtt tctctgtttt ctctcttcat ttttctacaa aaatcaattc tatttttatt   1740

cgttttcaat tcccgagctc cttggaatgt tatccttttc tcctgtgtaa ataagaaccc   1800

gtattcaatc ccagttcata gtttggcttt cccaaataag agcaaaaaga ttgtactgag   1860

aagttgaaga tttcaaaatt ttgtacatga tttcttctaa tttatcaatt tgattggact   1920

ttttgtatat agatttggtt cttgagctat ttatgttatg acgttttcat attgaggcca   1980

tgcgttgaat tggtttctta acaggtgggc                                    2010
```

<210> SEQ ID NO 160
<211> LENGTH: 1107
<212> TYPE: DNA
<213> ORGANISM: Cucumis melo

<400> SEQUENCE: 160

```
tagaaaaaaa ttgaagatct tcttaatgct aataataaaa gcatatataa aaaggcttca     60

tattacacaa gcatcttaaa accaaaccga acttgatttg aaattatccc actaattctg    120

tagatttcac caaagtcctt aacctttata ctaacatctg catttgactc tttcatttga    180

cctccaacat attctttctc attttccttc cattcaccac aaaaaccaac aaatacaaaa    240

aaccacaaat acatagaaaa ttaataaaaa aatcaaaatt tcgagatgaa atcattataa    300

actcatccga taactttgag atttgaaacc ttacactata taaagaaact catccgataa    360

ctttgaattc gcatcgaaat tacgtaagtg aagacgaaaa tgtaaatgat tagatgcgaa    420

taacaaaaaa aacataattt ctaaacgtaa aacactatat tcaccttatt atacttgatt    480

attttggaaa agtatgaaat ttgagtgtgg gagaggagcc aaagaattgg aaacttgtta    540

ttaggagtcg ttatgaaaca ttttcaacaa gccaatattc tttcacatac tataatgata    600

tacatagaaa taatacaata atatttttga aattgaggca tttttgtcgt aatttatcta    660

aaaatgtcag ggtagattca tcatgtatac aaatctctcg ctatcaaaac tatataaaaa    720

tcttgtgaat gatttcaatc gaaatggacc gagaaaaaac atcgtaacca cctctaaaat    780

cgataaattt gtttcaattt caaatcccta aaactaaagg tgctactttg tacaatttcc    840

cctgattagg gtgctaaagt taaaccctaa ataaaggtgt gtacgtttcc ggaagtttct    900

agaatcccca gcgaagttct ccaaatcgtg gcttgcagac caaggacccc cattaaaatt    960

cgtttcttcc tctaaacctc ctcccttaat tttggcattt tggtattttg gctcctataa   1020

attcaccccc tccttatccc taatcctttg tcttccaaat tttccttcaa agcctgcttt   1080

tcccatttcg tcgtgctttt tcttcat                                       1107
```

<210> SEQ ID NO 161
<211> LENGTH: 903
<212> TYPE: DNA
<213> ORGANISM: Cucumis melo

<400> SEQUENCE: 161

```
ctaaaggtat atttcagttc tagttttctt tctctgttga tctcttggat ttgagggacg     60
```

tttgaagttg gctttgttta attctttgtt attcaatctc tttttttgtt agagttgttg 120
tttaatcgtt tcccttgttg tttttctccc ttctagttcg attttagaac gctttttgtg 180
ggttgatttt aatttctccg ttttcttaca tctttcacaa agaaacgatt gaaatcgtgt 240
ttgttttttt tcccacggca tacgttatta gatcttgtag ataatgatct caatctattg 300
tttagttttt gcaaataaga agttggtttt ttatctccaa cttttatata ttcgattcga 360
tgagatgttc tacaccgtta ggatggaacc aagaagtgag gtaagggtgt ttgattgaaa 420
aattgaactg agaagttaaa gttccttcct aactttttaa tggattgtat aattcgttca 480
attccttgtc gttccatttt tatttctgtt tcgtttttcg tgttgctgcg tatcgcttcc 540
cttgttgttt tcctccccta ttgattttgc gtttcttgga gtttctctgt tttctctctt 600
catttttcta caaaaatcaa ttctattttt attcgttttc aattcccgag ctccttggaa 660
tgttatcctt ttctcctgtg taaataagaa cccgtattca atcccagttc atagtttggc 720
tttcccaaat aagagcaaaa agattgtact gagaagttga agatttcaaa attttgtaca 780
tgatttcttc taatttatca atttgattgg actttttgta tatagatttg gttcttgagc 840
tatttatgtt atgacgtttt catattgagg ccatgcgttg aattggtttc ttaacaggtg 900
ggc 903

<210> SEQ ID NO 162
<211> LENGTH: 1235
<212> TYPE: DNA
<213> ORGANISM: Cucumis melo

<400> SEQUENCE: 162
aaattttaat aattaaaatg aacaattttt caagagtaat agagtttgag agatgtcaga 60
gaagtttgag gaagaagata acaagtggga gaagagaata agtttgttgt gtgaaagaga 120
aggggaaatt tcattcaagg gtatattgaa ctttttactc aaattttgta agtctatttt 180
ttccgatcaa tcctaaaatc acacacaccc ttaaaaaatg gattatattt ggcaattttc 240
catgataaac tcatttttaa tttagagtta ttttttcaac gagatattaa cagttttagt 300
tcatatacta attgtaagaa tagtttcttt taagttgaat agaatttttg aaacttttaa 360
tagttcaaaa ggtatttttg aaacaaaata agaatgtttt tgaacttttt ataaaaagaa 420
ttgagatttt tttgaaattt ttgataaaga gaaaagaaaa gaagaaagaa aaaagaaaaa 480
caagtttgta gaactccgtg ggaaaatcgt cgagggccct gtgaaggaat tttgaaatta 540
taatgagggt attttcgtca acaagggaat ttagacatcg tatataagca tcctcaaacc 600
ctataattaa gcccttcaat ccaattgcca ttctccatct ctcgccgcaa gggtttaaga 660
gcagcttctc tcctcaggtt ggggtttccc cctatcttct tcattcttcc tcttctcgat 720
ttctttcttc tatttgctcg atagtctctt atttcttgag cttttgctgt ttttctcctg 780
tacatcctaa catgaattat aacttggttt tgattttgtc ttttacttct gtattaaaca 840
acttttctta cccttttatt cttctcttct tcttcgtgtc cctgcccttt tgtttttatg 900
ctaattttat gtttctgttt atcaatctat cgaggcgtga cctgtcgttc ttccaatagc 960
gtagatctgc acttaatcta ttctagctga ttggattggt cgtttttcgt ttttttaatt 1020
tattttctct gttctagttc cgataaattt ttttatatat aattaacaag ttctccagcc 1080
aaaagggtta atattgcgtt ggatatttta atttttacgt tatttagatg tgtgaatcta 1140
ataaaattag ggttattcat aaatttcagt aatgatattt tggttatctg ttcttgctgt 1200
tcctgtttcg cagttctttt acctaatatt caagc 1235

<210> SEQ ID NO 163
<211> LENGTH: 617
<212> TYPE: DNA
<213> ORGANISM: Cucumis melo

<400> SEQUENCE: 163
aaattttaat aattaaaatg aacaattttt caagagtaat agagtttgag agatgtcaga 60
gaagtttgag gaagaagata acaagtggga gaagagaata agtttgttgt gtgaaagaga 120
aggggaaatt tcattcaagg gtatattgaa ctttttactc aaattttgta agtctatttt 180
ttccgatcaa tcctaaaatc acacacaccc ttaaaaaatg gattatattt ggcaattttc 240
catgataaac tcatttttaa tttagagtta ttttttcaac gagatattaa cagttttagt 300
tcatatacta attgtaagaa tagtttcttt taagttgaat agaatttttg aaacttttaa 360
tagttcaaaa ggtatttttg aaacaaaata agaatgtttt tgaacttttt ataaaaagaa 420
ttgagatttt tttgaaattt ttgataaaga gaaaagaaaa gaagaaagaa aaaagaaaaa 480
caagtttgta gaactccgtg ggaaaatcgt cgagggccct gtgaaggaat tttgaaatta 540
taatgagggt attttcgtca acaagggaat ttagacatcg tatataagca tcctcaaacc 600
ctataattaa gcccttc 617

<210> SEQ ID NO 164
<211> LENGTH: 54
<212> TYPE: DNA
<213> ORGANISM: Cucumis melo

<400> SEQUENCE: 164
aatccaattg ccattctcca tctctcgccg caagggttta agagcagctt ctct 54

<210> SEQ ID NO 165
<211> LENGTH: 545
<212> TYPE: DNA
<213> ORGANISM: Cucumis melo

<400> SEQUENCE: 165
cctcaggttg gggtttcccc ctatcttctt cattcttcct cttctcgatt tctttcttct 60
atttgctcga tagtctctta tttcttgagc ttttgctgtt tttctcctgt acatcctaac 120
atgaattata acttggtttt gattttgtct tttacttctg tattaaacaa cttttcttac 180
ccttttattc ttctcttctt cttcgtgtcc ctgccctttt gtttttatgc taattttatg 240
tttctgttta tcaatctatc gaggcgtgac ctgtcgttct tccaatagcg tagatctgca 300
cttaatctat tctagctgat tggattggtc gtttttcgtt tttttaattt attttctctg 360
ttctagttcc gataaatttt tttatatata attaacaagt tctccagcca aaagggttaa 420
tattgcgttg gatattttaa tttttacgtt atttagatgt gtgaatctaa taaaattagg 480
gttattcata aatttcagta atgatatttt ggttatctgt tcttgctgtt cctgtttcgc 540
agttc 545

<210> SEQ ID NO 166
<211> LENGTH: 19
<212> TYPE: DNA
<213> ORGANISM: Cucumis melo

<400> SEQUENCE: 166
ttttacctaa tattcaagc 19

<210> SEQ ID NO 167
<211> LENGTH: 2003
<212> TYPE: DNA
<213> ORGANISM: Cucumis melo

<400> SEQUENCE: 167

```
cagtgtgctg gaattcgccc ttatccaagg agattaatgt cgagagatta ttatcgaggt     60
ttgaatttat tttgtccaat catatgattc caagagctga ccatcaattc aacagaacat    120
gaaccggaac ctcataccta ttgtaatggt tcacagcatc ctaatacaga acatgaaccg    180
aaacctctta cccattgtaa tggttcacag catctttata cgtattatag gtagtaccat    240
tgaagatgca tttaaatgct gtccatgctc tgttctctaa aaagttggac ttggacttgg    300
acgtcagctg aaagtatgaa atgcactgta gccaacgaag ctatgttttc aggcttcaac    360
atggttttag gaaagtggag gctctttggt tgaagggttg aatgaatgct tttctaattc    420
cagcatgatc ttcaaatttc gacacaaaaa gcttaagtat tttgttccgt tattctttta    480
atccttgtat tgttatatat tcttttctct gaactgaatg tacgatgatt gcaggggtcg    540
agagcaagtc cgatataatg aaacacgtaa ggacgtgatt gaatgaaaaa ctatgagcag    600
agatacaaag tctaacttac gggatgaacg atgagaggtt tgaccaagag ctgtgacgcc    660
tgtatatttc aacaaaagtt gatgactaac atcacatgtc agagtaatca aagaaatgca    720
gccgcacata tatatatcta tatatatatc gagttttttt tttttttttt tttttttttt    780
tttttttatc taatatattt taatctattt tcctctgccc tcctccccct cctcttcccc    840
caccccttctt ctgcacatag tagccaagga ttgatcggtt tcttttgatt cggggggaaa   900
atgttgtaca atttttgctt ccatagaagc ttgaaagttt tgcagattat gttgtaaaat    960
taccccttgtg tactcacact agttcttctc gtggaaactt atattacaat ggttgagttt  1020
taaggggcat attcacactg gtaactacca ttttctaatt tatgaatgcc gagtttctct   1080
ccatgaaaga cctttcaaat gccctttcct ccgcggtgcg tttgttgttg taaatgtgca   1140
gtgtcgttgg atacacgatt gtgtgaaagg gaaaagggaa tacgattaac tcttaaattc   1200
aacccctatc tccatcagta tcaatcacat ttcagcaact agctcttgaa taacattgag   1260
attcttgttt aatccacgta ctactactac tattactact atttgacagt tgatatctca   1320
aataacatcc atatttatca aattggtatt ttaaggactt ttaatttctt cgtacatatt   1380
tcattataat ttaactactc tgaccatcat tgaaaatttc acaaagaaga cattttaaat   1440
tgaattgagt tgaattaagt tgatataatg gttgaacgtt ggatttaatt tataatttag   1500
tggtgtatgg gtccattgta ataattctta aaaaaaatat catattctga attctaaaga   1560
accatctaag accaaaacta aggggtcacc aatgagtatg gtaaagtcaa caaagtttgt   1620
ctacttttct tatccttatc atcaagagtg caatatgata tcaaagataa attgtacgtg   1680
ggcgtcatcc attgggtaag accaagaagc aaaatatcat agagaagttg ttttagtagc   1740
cataggaagg aaggaagcaa aataataata tagatttgaa attgtggatg ataaactgcc   1800
aaatgggaat tcaaaataaa ctaaataaat aaaataaaaa gagaaatctt gggagtttcc   1860
attttagcca atgaggaaac agatagagat ctcatcaaga taaggaccct attctcttct   1920
tcatctataa aacaaaaaca aatcaaaccc tcatttcact cattcaaaac aaaaagtact   1980
ccaaagtcaa actaacaaat acg                                           2003
```

<210> SEQ ID NO 168

<211> LENGTH: 2004
<212> TYPE: DNA
<213> ORGANISM: Cucumis melo

<400> SEQUENCE: 168

```
tggatcgacc atgacattca aaaaccttta agatatggat cttataaaat aaatgtaaag     60
ggtaaacaat tcttccttgc ttaacccaag ctatatattt tatgcactaa tttaggtatt    120
agagtatatt cagctgaaca ccacctacca atgctagtac tttaatcagt caattctaac    180
ttcgataata tatctcaacc aaattagtga aaaagagtcg taaatgaaaa actatgtacc    240
aagatattct atttgttttt tttatgttta aatatctcaa agataatacc taaaacgttt    300
tctcctcgta caaagattcc tcatttactt tttattgtcg taaactctaa tacaataaac    360
taaaacaagt acaaatacac tagctttaga aatctacttt ttattgaaac caaaaccaat    420
aattcaacat ttcattttca ccgacaaacc tttgtaaaca attgaagtaa tttttgttgg    480
tactatgaat agtaacatca agtcttcaag tgcatcatat caaccaagac atgttcttaa    540
aagcgacact aaaagattta aaaccaaaag catttatgaa atccgaactt aatcaaatcc    600
taaatatttt tcacttaaaa aaaaaaaaat aggaagaaaa attgacataa atgggatatt    660
ttcgttttca aactggcaag ccagcatgca ccacgttgtt gacgtgtcct tccacgtcgg    720
aaaaaaaaat attaccacag taaaaagaga ataaaatgaa agtcgttgac tctcccttag    780
tcggaggaag cgcgtgaagc tgaagccgga ttagaaatcg gcaataaccc cgacacgtca    840
tcgaaatgct agtatcaaat attgtccgtt ggatcttcct tcaccaactc tatttgaacg    900
gccacgatct tccaggtcca acggttcgga agaatctttt cgaaattcca tggctagtcc    960
ctacactcct ccctattggc tccctagggc atcccgaccg gttattccgg ttgccgggaa   1020
ggtggctgga cgctataaat acccgctttg ttcatctcgt agtccttgta ccgttgagct   1080
tcgccttcta atagagctct ggttcggttg gcgtattagc tcgaattctt tctctcttcc   1140
agatctacgc tgccgatttc atcaggtttg cgagctctgt tccaccattt ttcttttcct   1200
gaagctttga gcatgcttgt gattcttcat ttcctcattt ctttgatggt ttatgaaaga   1260
atttagggga attttctctt tttgtattct agtggtactg gtagatttgt ttgaagtttg   1320
tttctcttct tctgagaagt gaattcttcc agatctgaca gttgcttttg atttttttctt   1380
tgggaattag tgaatgatac ttcgatactg tttttttgctc tctgagattc tggatctcgg   1440
gccttggggt tttctattgt cttttggtag ctatgtttcg tttgtcagct tgtatttgtc   1500
attgttgaat ggttcgatcc ggtttgtaaa taaaataaat tttgtaggcg cacttgtttt   1560
ccacggtttt cgtgttacgg tttcatgatt ccctagatct ctggttagaa ctaagttttt   1620
tgtcggtaat tggatttggt aagggactgt tactgtggtt gaattgtaga tccagtcatc   1680
ttctacatga gtgtagggtt ccttagggca gatcttgtgt tttataattt taattttgtt   1740
gtttccctga ttttgaacct gtttggttgt tcagattcgt cgagtcattt ccattcatta   1800
aaagtttcta taattttatt tgaatcttct gaatctgtgc ttgtattacc cagatttcta   1860
taaacctatc ttgatttcaa gtgtgctatg tggtaactgt tgatattttc aagcttaagc   1920
aatactgatg tgactaaaac ttaactaatg aactgaatgt tttttgtaca cgaactaata   1980
tggtgttttg ttatgtttca gagg                                          2004
```

<210> SEQ ID NO 169
<211> LENGTH: 1067
<212> TYPE: DNA
<213> ORGANISM: Cucumis melo

<400> SEQUENCE: 169

```
tggatcgacc atgacattca aaaaccttta agatatggat cttataaaat aaatgtaaag     60
ggtaaacaat tcttccttgc ttaacccaag ctatatattt tatgcactaa tttaggtatt    120
agagtatatt cagctgaaca ccacctacca atgctagtac tttaatcagt caattctaac    180
ttcgataata tatctcaacc aaattagtga aaaagagtcg taaatgaaaa actatgtacc    240
aagatattct atttgttttt tttatgttta aatatctcaa agataatacc taaaacgttt    300
tctcctcgta caaagattcc tcatttactt tttattgtcg taaactctaa tacaataaac    360
taaaacaagt acaaatacac tagctttaga aatctacttt ttattgaaac caaaaccaat    420
aattcaacat ttcattttca ccgacaaacc tttgtaaaca attgaagtaa tttttgttgg    480
tactatgaat agtaacatca agtcttcaag tgcatcatat caaccaagac atgttcttaa    540
aagcgacact aaaagattta aaaccaaaag catttatgaa atccgaactt aatcaaatcc    600
taaatatttt tcacttaaaa aaaaaaaaat aggaagaaaa attgacataa atgggatatt    660
ttcgttttca aactggcaag ccagcatgca ccacgttgtt gacgtgtcct tccacgtcgg    720
aaaaaaaaat attaccacag taaaaagaga ataaaatgaa agtcgttgac tctcccttag    780
tcggaggaag cgcgtgaagc tgaagccgga ttagaaatcg gcaataaccc cgacacgtca    840
tcgaaatgct agtatcaaat attgtccgtt ggatcttcct tcaccaactc tatttgaacg    900
gccacgatct tccaggtcca acggttcgga agaatctttt cgaaattcca tggctagtcc    960
ctacactcct ccctattggc tccctagggc atcccgaccg gttattccgg ttgccgggaa   1020
ggtggctgga cgctataaat acccgctttg ttcatctcgt agtcctt                 1067
```

<210> SEQ ID NO 170
<211> LENGTH: 92
<212> TYPE: DNA
<213> ORGANISM: Cucumis melo

<400> SEQUENCE: 170

```
gtaccgttga gcttcgcctt ctaatagagc tctggttcgg ttggcgtatt agctcgaatt     60
ctttctctct tccagatcta cgctgccgat tt                                   92
```

<210> SEQ ID NO 171
<211> LENGTH: 845
<212> TYPE: DNA
<213> ORGANISM: Cucumis melo

<400> SEQUENCE: 171

```
catcaggttt gcgagctctg ttccaccatt tttcttttcc tgaagctttg agcatgcttg     60
tgattcttca tttcctcatt tctttgatgg tttatgaaag aatttagggg aattttctct    120
ttttgtattc tagtggtact ggtagatttg tttgaagttt gtttctcttc ttctgagaag    180
tgaattcttc cagatctgac agttgctttt gatttttttct ttgggaatta gtgaatgata   240
cttcgatact gttttttgct ctctgagatt ctggatctcg ggccttgggg ttttctattg    300
tcttttggta gctatgtttc gtttgtcagc ttgtatttgt cattgttgaa tggttcgatc    360
cggtttgtaa ataaaataaa ttttgtaggc gcacttgttt tccacggttt tcgtgttacg    420
gtttcatgat tccctagatc tctggttaga actaagtttt ttgtcggtaa ttggatttgg    480
taagggactg ttactgtggt tgaattgtag atccagtcat cttctacatg agtgtagggt    540
tccttagggc agatcttgtg ttttataatt ttaattttgt tgtttccctg attttgaacc    600
```

```
tgtttggttg ttcagattcg tcgagtcatt tccattcatt aaaagtttct ataattttat    660

ttgaatcttc tgaatctgtg cttgtattac ccagatttct ataaacctat cttgatttca    720

agtgtgctat gtggtaactg ttgatatttt caagcttaag caatactgat gtgactaaaa    780

cttaactaat gaactgaatg ttttttgtac acgaactaat atggtgtttt gttatgtttc    840

agagg                                                                845
```

<210> SEQ ID NO 172
<211> LENGTH: 2018
<212> TYPE: DNA
<213> ORGANISM: Cucumis melo

<400> SEQUENCE: 172

```
actattggag acgacgaagg aaaactctaa tgtgagctta gaattgaaga tggtgaacaa     60

ttgggagtct tttttaaaaa tctttcgtcg gtatattgaa atttcctttt acactcaaat    120

aacccccctt ttcacgcgtt caacgtcttc aaaccttcct ttttcaatta ttttttcgtt    180

tacattaatg acatttaggt aataagataa attagtggat tcttttgtga aaaatgttag    240

cccatttaag acttttatga aatatattag aaaaaaatca tatagcaatt tatattattc    300

tagttaaaag cccataatag aaactaaccc aacctaaagt aacgtaaaca ttcaataaga    360

gagacaaatt ttaaaataat ttctaattaa aaaaaaaatt gtcaagaccg tccgggtcgg    420

atccaaaata taacccgaac cggccggttt agcatctata taaatacacc tttagggttt    480

ttattctctc aagacttcac cgcatttcca cttctctgag gccacggtca gccattggag    540

cagctcaata atcctttgac tccctactac ggtaagtcga ccttactgct ttcggcttct    600

agtttttca atcctgtcat tagtcctttg gagttcttct gtacatttat gacgttttcg     660

gctcgtgttt tgtttcgcct gtatgtagtg ggtttttcga gttttgtttt tacttttttt    720

tatacttgca ggaattagtt gaaatctatg tacttcatgc cttggataat actcttgatc    780

tgttgtgtta ttcaaaaatg aattgtttta agatggtatt tgagaatggt catgtgagtt    840

ttgcctactt ggttattaaa atgaattgtt ttaggatggt atttgagaat ggtcttctgg    900

gtatttggtt ggaacctttg tgctctgcta tgaattaggg tgttctcccc gttttttttt    960

ttttttttct tttggttatt aatatatctt ttatgactac ttattcatat atgatatctt   1020

ttactcgtaa attttgactc atttgaaagt tttatcctta gtcctttctc attcagggtg   1080

taaaggtatg ttgttagggt taaaatagcc tatgcaggaa agttctgtat ttgttctaat   1140

tattgcattt gtgtgcattt gtatctagtt tatttcttgc tgagagtatg cttcattttt   1200

tagtacacat cacttgtgcc actttattat agttgcacat ttttgtttat ggagaggatg   1260

aatagcattt agggatgtca atttttttatt gagaaaaccc tctctcctac ttaagcttgg   1320

ggaatttttg ttctaaatgt ggtaaacata atacttcttc ttattttaat ttgaatggaa   1380

ggggaagacg aatactaata ttttcaacga accttcacaa cttttttttc ttatttagga   1440

agccatgttt ttcaaaattg tactgtgtga tccacatatt tatcgattat tagtgaatcg   1500

aataataatt agagttttat tggtataatt ttgaagttca gacttattac atttgtggaa   1560

agtttggtta caattttcaa ttttattgga atcctaagaa ctttgtgtta acatatattg   1620

agttttcttc tcttttttttt tactcattaa gttctctatt aggaatgttt ggttcaatgt   1680

cacatagtcg atagctaaga ccagtgaccc acaaagctat gattgaacga aaaacaagcc   1740

tttcacatct tggtaggaat ttgttatttc tcaatagatt tacagagctg tttcatgtga   1800

tcacaatttt tttctatttt tctgaagttc tctattagga atgggctatc tggttagttg   1860
```

```
cttttgagag aacatgtgga ttggtgttgc tcggtttcct tgcctttgta attttgtcct   1920

tggaaaaagc aaaatgatta ggtatcctga tatgcataac atgtttaagc caactagttc   1980

tcactttttt agtgcaaata attgatcttc aggaatcg                           2018
```

<210> SEQ ID NO 173
<211> LENGTH: 565
<212> TYPE: DNA
<213> ORGANISM: Cucumis melo

<400> SEQUENCE: 173

```
actattggag acgacgaagg aaaactctaa tgtgagctta gaattgaaga tggtgaacaa     60

ttgggagtct tttttaaaaa tctttcgtcg gtatattgaa atttcctttt acactcaaat    120

aacccccctt ttcacgcgtt caacgtcttc aaaccttcct ttttcaatta ttttttcgtt    180

tacattaatg acatttaggt aataagataa attagtggat tcttttgtga aaaatgttag    240

cccatttaag acttttatga aatatattag aaaaaaatca tatagcaatt tatattattc    300

tagttaaaag cccataatag aaactaaccc aacctaaagt aacgtaaaca ttcaataaga    360

gagacaaatt ttaaaataat ttctaattaa aaaaaaaatt gtcaagaccg tccgggtcgg    420

atccaaaata taacccgaac cggccggttt agcatctata taaatacacc tttagggttt    480

ttattctctc aagacttcac cgcatttcca cttctctgag gccacggtca gccattggag    540

cagctcaata atcctttgac tccct                                          565
```

<210> SEQ ID NO 174
<211> LENGTH: 1453
<212> TYPE: DNA
<213> ORGANISM: Cucumis melo

<400> SEQUENCE: 174

```
actacggtaa gtcgacctta ctgctttcgg cttctagttt tttcaatcct gtcattagtc     60

ctttggagtt cttctgtaca tttatgacgt tttcggctcg tgttttgttt cgcctgtatg    120

tagtgggttt ttcgagtttt gtttttactt ttttttatac ttgcaggaat tagttgaaat    180

ctatgtactt catgccttgg ataatactct tgatctgttg tgttattcaa aaatgaattg    240

ttttaagatg gtatttgaga atggtcatgt gagttttgcc tacttggtta ttaaaatgaa    300

ttgttttagg atggtatttg agaatggtct tctgggtatt tggttggaac ctttgtgctc    360

tgctatgaat tagggtgttc tccccgtttt tttttttttt tttcttttgg ttattaatat    420

atcttttatg actacttatt catatatgat atcttttact cgtaaatttt gactcatttg    480

aaagttttat ccttagtcct ttctcattca gggtgtaaag gtatgttgtt agggttaaaa    540

tagcctatgc aggaaagttc tgtatttgtt ctaattattg catttgtgtg catttgtatc    600

tagtttattt cttgctgaga gtatgcttca ttttttagta cacatcactt gtgccacttt    660

attatagttg cacatttttg tttatggaga ggatgaatag catttaggga tgtcaatttt    720

ttattgagaa aaccctctct cctacttaag cttggggaat ttttgttcta aatgtggtaa    780

acataatact tcttcttatt ttaatttgaa tggaagggga agacgaatac taatattttc    840

aacgaacctt cacaactttt ttttcttatt taggaagcca tgtttttcaa aattgtactg    900

tgtgatccac atatttatcg attattagtg aatcgaataa taattagagt tttattggta    960

taattttgaa gttcagactt attacatttg tggaaagttt ggttacaatt ttcaatttta   1020

ttggaatcct aagaactttg tgttaacata tattgagttt tcttctcttt ttttttactc   1080
```

```
attaagttct ctattaggaa tgtttggttc aatgtcacat agtcgatagc taagaccagt   1140

gacccacaaa gctatgattg aacgaaaaac aagcctttca catcttggta ggaatttgtt   1200

atttctcaat agatttacag agctgtttca tgtgatcaca atttttttct atttttctga   1260

agttctctat taggaatggg ctatctggtt agttgctttt gagagaacat gtggattggt   1320

gttgctcggt ttccttgcct ttgtaatttt gtccttggaa aaagcaaaat gattaggtat   1380

cctgatatgc ataacatgtt taagccaact agttctcact tttttagtgc aaataattga   1440

tcttcaggaa tcg                                                      1453
```

```
<210> SEQ ID NO 175
<211> LENGTH: 1999
<212> TYPE: DNA
<213> ORGANISM: Cucumis melo

<400> SEQUENCE: 175

ggtctcagac ccataggaat agatcattta ttgccttatg aattagttta tgagtacata     60

ataattgtca accgtataca aatcaacatg aaagaatata atgttgtaca tagtcattcc    120

aagtttacta atattatatt ttaggagtgt tctacaccga acctgtcaca tgtacactgg    180

gtatgctacc cctgaattca atatcataaa gcaactttaa ttgtcaagca ttctcttgac    240

catttgtgac ccatttgctc ctactttttc aatcaataac tatcacaaaa agctagatac    300

cacatgtgat aaactcactg aaatcaggta tatggttacc tgtgcttggt cagcactcaa    360

tcagattcga aggcctagtc tttgtatttc ccccctctg cacactacaa atagtcctcc    420

acgtaaagac ccataacaaa acgcaaacca agtacagaaa atctagccga aatccagacc    480

actcaaacat aacaaatctt ctggtaagtt tgaataaaat ataaaactaa cctatttaat    540

caaataatac aataaaatgg aagcaactaa cataacatat ctaaatatga tcacgtagta    600

ggaaaaaaaa aaacattcca aaactattaa caatcattct taatggtatg ggtcaatccc    660

cattatttag gactataaca agaattcctc atacctaatg ccacatccta tgtccaaccc    720

tcgagattac ctcgtgagta atcaatctta ttcatcctta tttcaaatta tgtgaaattt    780

ctcatcaggt tgatcatatt gactttcaat acaacttatg attaatcttt cccttgatat    840

aatttcgtat gaaaaggaag ttgacattat gtgattttct cataaggtaa accaagtaaa    900

cttgacatga cgtcttaaca agtcttggtt tctaagtgta atttactgca gaaaaaatcc    960

taaattctat gacttttcct atgagattga ccaaatcaac tttacgagaa atcttgggaa   1020

gccataccta caaagtcttc cccaagaaa ttacaatttc tagtaaagat tgttgaaatt   1080

taccctccaa tttttccgtg aaaatttgac aaacttgtaa gaatatcaaa tttgggttgg   1140

atattgacat tccaaaataa gtagttttaa aaaggattta tccaacaata atagaagaaa   1200

aaagatagga aataacatac ccacgtaaat ggaatgtaaa tatttatata ttaggtgtct   1260

tgaacgaccg tcaaacgaaa ataaattgtt catccgaagt tgaaactctt taagtgtaca   1320

tttatctttt cgtaagaata aaatgtaaaa ttaacgtgtg aaaggttggg ttaaataagt   1380

tatgtagaga taatattgaa gatgatagaa taatcacgat cgatgaatta gtatagtccc   1440

agagcggatt taaacctctc tcactttcat gctttctata tatatcaaaa taatttcaag   1500

tagttggttt agtcgtaaaa aagtcaacca atctctttta gataaacctt gagttattaa   1560

aaaattagat caaagataat cgttgaaatt gaaattttaa gagtataatt ataacaaatt   1620

ggaaagttct aaagtagttt ttgcaatatt ctccatcaaa atagagtaga aaaatatttt   1680

agtaattttc ttatcttaat tttagttttg taatagttat taggatggtc ctaagttctc   1740
```

```
aatccgcttt tagtccataa aaagaaagaa gagagagaaa aaaagtcccc gatccgcgac   1800
acataccaat ccaaccaatt atgcacaatc catgtgatat cgaacggtca caagaataaa   1860
tgctttctac acacggatca ccatccaacg gctttccttc catctcatcc tctatataat   1920
ctaccaactc tgtcatcttc gacacacttc aattatctca gcttttattt catcggattt   1980
tccatcaaac aaggcaaca                                                  1999
```

<210> SEQ ID NO 176
<211> LENGTH: 2004
<212> TYPE: DNA
<213> ORGANISM: Cucumis melo

<400> SEQUENCE: 176

```
tatagtttgt aacaatctac tctatgttct ttcaattttg atacatttga atcttaaact     60
ttattgagtt acacaatata gtccttgtat ttttaaaatt tataatgact ctatttatat    120
taatattata gaaatttttg ttaaggttta ataaaaattt ttctgtataa ataaatcgaa    180
cacgaagtct atatttagac tgcaatatag taaaacctga catctaagtt tggtgaattt    240
tgttttgctt taaaaactaa actattacaa ttttaaaaat attttaattt agttaatgca    300
cattaacttt acggagtaaa tttttacaag attgaatata catagattaa atagttataa    360
aaccaaagat tagagtaaaa aacatttaaa tagaaagaac taagattttt ttaaaacgaa    420
aatgatacta gatacatata tatgtatcta tattataatt actcatttta acatatagtt    480
ttgaaagaac aaagattagt tgcatgtgtt gattgttttt aagaaggaaa taatttttga    540
atggaaaatt ttcaaaagtt ttaaatttga caataaactc atatttaaag tgtactacaa    600
attttaactt ttggttaaac tccttgttta gttcaatcat gtaataaatt ctcattccaa    660
gaatcgtttt agaaaatttt attgtgcatt taataaaata tagaacatat atggcatata    720
aaaattgatt actttttttct ttttttggga cgaaaaacac attagatata atcttttttg    780
aaagtttatg aactttaaaa atgggttatt ttatacggtg gtcaacttta ttttattgaa    840
attattgagt ttataaagat tgttatatca ttttcttctt ctctttcact agaatacaat    900
caaacctatc aaactctcta tgacttattt agaattcttt ttgttatatt tttgaaatta    960
ataaatgaaa agcttagagt ctaaattata acaattaaaa ttgaaaattt tgcaataatt   1020
ttatttttag caaaatgacg tttggttttt ggggattggg aatggatcga tactatcccg   1080
attccggaca aagaaaccga cccgagattc gaatttttttc cattcccaaa cagagcactt   1140
aaaatttaag caacgttata acggcgtcac cgaactaaac ggaaaaatat gaagaaaatt   1200
agaaaaagaa aaacggaaca gtcaaacgtt acttcacgtc aatggcaata ttcatttttt   1260
tttttgttta aataattgaa tttaattaat ttggtttata aaaatagagt cctcatatat   1320
cgcgaatgcg catttgatcg tgaaggacag cttctccctt gtgttcaaga gagagagatc   1380
tatcattctt atttggggcc gatctctcta ttctcctctc ttctattccg taagtttttc   1440
tcattcattc tcctctctca tttctctccg agatctgttt acaatccttt tgattttcat   1500
ttttcctgct tcgatctgtg ctcctggtga ttccctttc ctgttttatc ttttgttgat    1560
cttggaattg attgttcttt tgtgggtttt cattgatttg tattttctga tctgggtttc   1620
tgttttctcg ccttgatgtt ttgtatttgg atctgatctg acgacccttt tttttttttt   1680
tttttatttg aattgctttt ccaatgttta tacctggatt tttattgatg catgggttta   1740
accgattggt tggatgcgtt ttctttgtgc tggatctagg tgtccttgtt tttaatttga   1800
```

```
attgtgggta aaaatggcat tattgtaatg tgtttggagt ttgattttga atcttggcta   1860
gttgattttt gaattacaaa gatcggatcc tcttcttttt tgggttgtct taagattttt   1920
ggctggttta agtatttgat gtcgttgtat tttaaggggt aactgatgcc ggcttgttgt   1980
gtttgtattc agtttacttg aaaa                                          2004
```

<210> SEQ ID NO 177
<211> LENGTH: 2005
<212> TYPE: DNA
<213> ORGANISM: Cucumis melo

<400> SEQUENCE: 177

```
aattagcaaa ttgtatgtaa caacgtcatg aagaggcatt tcatcgaaca atttaatagc     60
agagtcaaga tggcccagtt ttataagttt attgatttct cgattcttaa ggtaaatgag    120
atcgcgagca tggaaatgca gacccaaacg agaatatggg tgtggtaaat ggaccggtga    180
tgttgtggct acaaattcgg attttacagc agtaatagtt ctgacgaagg aagcgaattt    240
agtgaccttt cgcatcacag tttaagctta tcagagacct gaacaagggc tctagctcta    300
caacttagaa aggtttgata tggtccgtga tcgggaggga ccgaataaca ggcgcttaaa    360
ttgttgttca taaagaagag gattgtcgtt gatgtatttt aaccaagaga tgattagtta    420
tccacatcca cagagagaac agaagacggc tttctaaatc tacaccgata aaaataaccc    480
taccactttg tttctttaga aaagggtcac attctttaaa aacattagcg tcgaggatta    540
atagggtata ttgactaatg ctctgtttgg atttcgagaa ataccaattt acaattgatt    600
tcaaattaat tatgttttgt tgttgcacga aagataaaaa gaatttaaaa ttcaaaagga    660
tctcaaatct tatttttaac ttaaaaactt ttatgaccca aacggtttat gtatgattta    720
aaagtagaat acctctgtga attcttaatt tttttttctt tccaattacc acataaatat    780
gaaattttaa atacatttat tttaaatttt atatccgaaa caaaataata atttaaaact    840
atttctcata tatgaagtgt gattcgatct aaattataaa ataataaaaa tttacatcta    900
gttttgatta tttttttttc gttagatact aaattgttaa gaaaataaca tttttaatcc    960
aaagttttga agaatatatg acttttaaaa tggtatttat ctttttagtg tctgattttt   1020
aaaaaatgga tttcaaaagt tcatcaaata gcattgtatt tttattttaa ataattttga   1080
catttaaaat tagagtaatg gtttataaaa gacacttgat ctctaaaact attttcttag   1140
atataaatac gtatgattat ttttaaaaat caatcaaaat aggtaaattg taaaaaaaaa   1200
aaaaaaatca taaaacatga tagtagttgt aattatgctc tcaaactttc ggttatgaaa   1260
aataaacatt ttaactttta gacgtgtcaa agttgagtca agttggacct tcaaagttat   1320
gtagttatat aaattgtaat atatgtataa gcttgtggat tcaattttat catttatggg   1380
tccaatctct acaattatcg taagtctatg ggtcaattgt aacacatgtg gagtttaaga   1440
gctcaatttt ggacgtggat gtgttttgca accaactcca caccttaaaa aggtgttttt   1500
ttttaattta tcaaaaaaca agaatttaga atctttaagt ttatctttaa aaatcaacgg   1560
acattttgaa aaccaattga aactactgtt ataaacctaa caactaaaag tatatttttt   1620
aagaccgaaa gcataaatcc ataaaaaaaa aatccagaac tgaaaatgta acttttatag   1680
ttgaaaattt agctaaatta tacatattaa aattcaagga ccatataaaa ttaaagtacc   1740
tgattaaata ataacgaatt aatgtttggt atttttaacc tacattagaa aaaaaaaaca   1800
aaagaaaaac ggcatactat ttgtcaagcg tccgatggga agaaaatcca acggtgagtg   1860
ttagtattga aatacgcagt tctcgtgaat gagcctggct tagatttggg aacaagagcc   1920
```

```
aacccctttc gaccgagaag ccgtcgtctt caccatattc gcctcaacca ttcgatagcc   1980

acgtttgaag aagaatagga ttgcc                                         2005


<210> SEQ ID NO 178
<211> LENGTH: 1978
<212> TYPE: DNA
<213> ORGANISM: Cucumis melo

<400> SEQUENCE: 178

aattctaaca actccggaac aaataattta gcatggattg aaatataaat cttcttgact     60

tgcaaaaaaa tcattgtaat ggtcttatgt tggttatagt tagggtatcg aaacgccata    120

caggaatatg ggattaaagt taacttttgt tcatcaattt cagcttatga acttctaaaa    180

tatcaatttt acctttgaac ttatatgtta ttaccccttt cgattgtggt atgttaatta    240

atatctgaat ctcagtcctt atgaaacttt tttatactgt cacaaacata tgaagtttta    300

ttgtaagttc ttagaaatca tctaaaaaga gtagtttgtt ggactattta ttttattttt    360

tcttattaag ttgttttcac gccatttcag taaaataact atagtgaata gagaatcaaa    420

cttctaatct taagttaagg tagtagggta tatgctaatt caataagata atccgtgatg    480

cttgacatct gacttaattg ttataagttt taaatttttt attgtaatat ttaaaatact    540

agtttttggt ttctaataaa gaaataattg aacaattaca aatatttata caaaattaaa    600

ctagaatata tgatcatttt ccttcgtgtt agaaaaaggg aaatatatgt gtgtatttat    660

acatattaga tattgtttta ctatattcca ttttcctcac gggaaatgga ggattgagtg    720

ggagataaac attgtcccca agagaattgg gaatggaaat gcaaatgaca tggccctcca    780

caaaattgtt cgcctaaaaa tgggctttct cacttctcac tccgcaagaa aaatatcgtt    840

tcccttcgaa ttcgggcaag atctcaaaac cacatgtttt tctttcttta tttttcaagc    900

ctacattatt tataaaaata taacttaagc agagaattat gtaaattcaa gtccattttt    960

cgcttcactt agctaaatca ttaacaaatc tgtaattttg ttcataaatt agctcaccaa   1020

ttatgtttta gcccactaag gcccattaga catttttatt agaaaaacat gaaccgttgg   1080

atcaagatgt gtgttttctt ttctttttct ttttattttt tttgggtttt ggtggatcaa   1140

ttcgtagctt tagcaaccta ttattatatg gagggaaagg gcgtattaat ctgttagcgc   1200

cgtccgggag tttagctttc ttccccgagc ctcggtctta tcccctaact ccaaaaccct   1260

agcccaaagg taatccactc cttccccctc cgctcttcat ctttttctat tcatcatctt   1320

taatctgttc tccctttttgg ttcttagatt cttcttttgt tggattcttt taatctttac   1380

tcatggttgg ccttgtaagt ttagacgacg tttttataca ttggttaatc ctgcttctct   1440

atctattcgc acgctagggt tttcctattg ttttctattc tgctctactt ctgcaaggtt   1500

gtgttcttct tcgttcaggt ccctttttttt aaccgaaatt aaattaatgc aaattcgttt   1560

gtgcttctaa ttaggaagcc ttttggaaca tctcgacatt ttgattgctg catttcattt   1620

cgggtatatt tctatgattg aaggatgtgg gtctgttcac tgcatggtca ttacttatgc   1680

agctatgctt atcgagtcca ttatgtttgt gcaatctgtt tccggattca taattttttta   1740

gtaattgatc agtagatgaa aaaagatatt gtaatattcc ttgagtgttg caccagtctt   1800

ggtgggtatc tgctcctgct ctttgcttgt ggattttact tttattatat ctgtattatt   1860

cgaaatgttc tgttcttgtt ataacttata cccgaagatg tgttcctccc cgcgtctagc   1920

gttgtgggtt acttatgatg gacatggttt tgattctgtt tggtttgtgc agggtacc     1978
```

<210> SEQ ID NO 179
<211> LENGTH: 1263
<212> TYPE: DNA
<213> ORGANISM: Cucumis melo

<400> SEQUENCE: 179
aattctaaca actccggaac aaataattta gcatggattg aaatataaat cttcttgact 60
tgcaaaaaaa tcattgtaat ggtcttatgt tggttatagt tagggtatcg aaacgccata 120
caggaatatg ggattaaagt taacttttgt tcatcaattt cagcttatga acttctaaaa 180
tatcaatttt acctttgaac ttatatgtta ttaccccttt cgattgtggt atgttaatta 240
atatctgaat ctcagtcctt atgaaacttt tttatactgt cacaaacata tgaagtttta 300
ttgtaagttc ttagaaatca tctaaaaaga gtagtttgtt ggactattta ttttattttt 360
tcttattaag ttgttttcac gccatttcag taaaataact atagtgaata gagaatcaaa 420
cttctaatct taagttaagg tagtagggta tatgctaatt caataagata atccgtgatg 480
cttgacatct gacttaattg ttataagttt taaatttttt attgtaatat ttaaaatact 540
agtttttggt ttctaataaa gaaataattg aacaattaca aatatttata caaaattaaa 600
ctagaatata tgatcatttt ccttcgtgtt agaaaaaggg aaatatatgt gtgtatttat 660
acatattaga tattgtttta ctatattcca ttttcctcac gggaaatgga ggattgagtg 720
ggagataaac attgtcccca agagaattgg gaatggaaat gcaaatgaca tggccctcca 780
caaaattgtt cgcctaaaaa tgggctttct cacttctcac tccgcaagaa aaatatcgtt 840
tcccttcgaa ttcgggcaag atctcaaaac cacatgtttt tctttcttta tttttcaagc 900
ctacattatt tataaaaata taacttaagc agagaattat gtaaattcaa gtccattttt 960
cgcttcactt agctaaatca ttaacaaatc tgtaattttg ttcataaatt agctcaccaa 1020
ttatgtttta gcccactaag gcccattaga catttttatt agaaaaacat gaaccgttgg 1080
atcaagatgt gtgttttctt ttctttttct ttttattttt tttgggtttt ggtggatcaa 1140
ttcgtagctt tagcaaccta ttattatatg gagggaaagg gcgtattaat ctgttagcgc 1200
cgtccgggag tttagctttc ttccccgagc ctcggtctta tcccctaact ccaaaaccct 1260
agc 1263

<210> SEQ ID NO 180
<211> LENGTH: 715
<212> TYPE: DNA
<213> ORGANISM: Cucumis melo

<400> SEQUENCE: 180
ccaaaggtaa tccactcctt ccccctccgc tcttcatctt tttctattca tcatctttaa 60
tctgttctcc cttttggttc ttagattctt cttttgttgg attcttttaa tctttactca 120
tggttggcct tgtaagttta gacgacgttt ttatacattg gttaatcctg cttctctatc 180
tattcgcacg ctagggtttt cctattgttt tctattctgc tctacttctg caaggttgtg 240
ttcttcttcg ttcaggtccc tttttttaac cgaaattaaa ttaatgcaaa ttcgtttgtg 300
cttctaatta ggaagccttt tggaacatct cgacattttg attgctgcat ttcatttcgg 360
gtatatttct atgattgaag gatgtgggtc tgttcactgc atggtcatta cttatgcagc 420
tatgcttatc gagtccatta tgtttgtgca atctgtttcc ggattcataa ttttttagta 480
attgatcagt agatgaaaaa agatattgta atattccttg agtgttgcac cagtcttggt 540
gggtatctgc tcctgctctt tgcttgtgga ttttactttt attatatctg tattattcga 600

```
aatgttctgt tcttgttata acttataccc gaagatgtgt tcctccccgc gtctagcgtt    660

gtgggttact tatgatggac atggttttga ttctgtttgg tttgtgcagg gtacc         715


<210> SEQ ID NO 181
<211> LENGTH: 2000
<212> TYPE: DNA
<213> ORGANISM: Cucumis melo

<400> SEQUENCE: 181

aaataatttg tggattttat catattatgt accttagact ttgtaaggtt tataacacaa     60

gatgtggaga aatcccatga tgaacattgg acgttattat atcctttgaa actaaaaaca    120

aaggaaaaaa gacaaatggc tgagtataag aaaaagagaa gaaacaacca aaaagctaaa    180

atgtcatgct ctcatatgta acatatttga attgggattg atttcaagat gtattttaaa    240

ataatttaac acacgataaa ataattctaa caaactcaaa attactctta aacatttact    300

tgatatcttc gacataatga cttttgtttt aatacaactc aaaacataat taaggttggt    360

tttaaatgac aacaaacgaa aaactcgatt ctaatttcaa tactagtctt tgaaagccct    420

aaggagcgtg gttttgaatt gtatagcaag gtttcgaaaa ttttaatcat caaacaatag    480

gtatatttac ctgttcctca agtacagtta attcatagct acttgtcgtg cttcctacga    540

caacattgta agacttgcca cacactaatt gaagccgttg ttgaaggtag ttttccatgt    600

atagcttgaa tcgacggatg accaaagagg ttgaagaagg tttgaaaaat aggggaaggg    660

atatacaaag tttgagagtg agagagggag agaaatagaa atagaagaga ctgaaaaatg    720

taaaagaaag gatgaaaaaa tgtggggtaa acgcaaattg gatttttata gtagtatttt    780

gaaaatgcta tagaaaggct atgtatagta gtgcttccaa agttctatat gaatgagaca    840

aatcaaaata tatttttttt gattaattaa ccccaaaaag actcataaaa aaatcttata    900

aatcccacta agatattgca tgttatatgt agtaaaattt atcgttcaaa taaaccttaa    960

acataattca aacgaagaaa gtaaaaattt gaatttctta tcttacatca ttcaaccaaa   1020

caatttccat ataagagatt aaacttctaa ctttaagaga gagatatcca gcatatgcaa   1080

cctaaaccaa cagtgacttt gctatatatt tgcacaaaat gtgggggaca aagttgtaat   1140

ttcggaatat caatgattaa agaaaaggta aaatttaaaa ttcggaagct tgacgtggca   1200

acacggaatg gtgatgatat ttccaactcc tcgcgacttt tagaagttgg cctcaccaac   1260

cgcatatccg cccctttgcc acgtgtcaga ctacaacaac ttccaacaat ttcctttaag   1320

aacaccaaat tatatcaata aatatttaac ttaaattaag aatatatttg ttacaatttt   1380

cctactgagt tagatagata gacagacttg tcaattaact aataagtcca aagtcaattt   1440

actcaacata gatacaattc taatttgagt gtgaaataca tattcaaatc aaaattatta   1500

ttaagaggaa aaactgattt gctttctcaa tttaaaatat aatattttga aaaagaaaca   1560

cacatgtatt atggttttca atatatttac tttcttagtc acctaatctc aaactaattt   1620

ttgaagaaat taaatatata tattatcatt tttattttct tggttatgat attggtatag   1680

aatcaacaaa actacaagtg tcctctcctc tgctatcgat ggggattaga ctctaaactt   1740

gtttagcgat tagtaattat atattagaaa aagtttatgt taatgtggac ccgacaatct   1800

caccaatagg ctcttcactt caccaacccc cgacccattc cctctaataa ttcgacacgg   1860

ctcatccccg gttcgaaccg ggccgacgtc ttcctattta acacacctcc atttcctctt   1920

ccctccgcaa cacaaacaga gacctcaccg gaaaatcaag ttaaagcaaa accaaagaga   1980
```

agcttcatca ctctccggaa 2000

<210> SEQ ID NO 182
<211> LENGTH: 2000
<212> TYPE: DNA
<213> ORGANISM: Cucumis melo

<400> SEQUENCE: 182
gcatcttatg gatgtagtca caacatattt atatggattt tctgataatg atatttatat 60
gaaagtccca aaaggattta agatacctaa aacatataaa tcaaattccc ataaactatg 120
ttcaataaag ttacagagat cattgtatgg attgaaaaaa tcatgacgaa tgtgatacaa 180
tcgcctgagt gaatatttgt taaaaaaata atatcaatat aattcaatat gtccatgcgt 240
ttttataaag aaatcaccgt caggatttgc tattataact gtatatgttg atgatttaaa 300
tataattgaa attttgaaga gttttcaaag gcaatagaat attaagaaag aatttgagat 360
gaaagatctc agaaaaataa aattttgtct tgattttcaa atcgagcatc tagtaaaagg 420
gatatttgtt catcaattaa cttatacaga gaaaatttta aaaagatttt atatagataa 480
aacacattca ttgaacattc taatgcaagt tcattcatta aatgtgaaga aagatatttt 540
tcgacgtcga gatgataatg aagaactcct tagtccagaa gtaccatacc ttaatacaat 600
tggtgcactt attttgtcaa taatcaagac cagatattgc attttctata aatttattag 660
ctagattcag ttctccaaca aaacaacatt ggaatgaagt taaacatata cttcgttatt 720
ttcgaggaac aattaatata agattatttt attcaaataa atcaaatttt aacctagtta 780
gttttgcata ttcttgattt ttatctgatc cacataaatc tagatctcaa acaggttatc 840
tattcacatg tggaggaact gctatatctt aacgatcagt gaaacaaatt accataacag 900
tcaactcttc aaaccgtgct gaaattctta caattcttga ggcattcatg aggctagcgg 960
agaatgaata tggttaaggt cgatgactca acacattcga aaattatgtg gtttgtcttc 1020
tagtaaactc cttccaacaa cattatacga agacaacaca acttgtatag ctcaaataaa 1080
atgaggttat attaaaagtg atagaacaaa acacatctca ccgaagtttt tctatactca 1140
tgatcttgaa gaaaatggtg acatcacagt acaaaaaatt tgttcaaaag ataatttggt 1200
agatttattt acaaaattat tacctactgc aacctttgaa aaattggtgc acaacattgg 1260
aacgcgacga cttagatatc tcaagtaatg ttacatctta cttgccaagt taactataca 1320
tagtgacatt tggtggagtt gtaagaaaca ctaatattgg agaaaaatcg aaagaaattg 1380
gaaaatatgg agaattgaat ttttttaga tttttcttat tttctaattt taggtttccg 1440
tattctgatt atgcctcatt ttcacaacat taataacttt aataagatga tttcttgggt 1500
taagggaaaa aaatcatttt tttagagttg cacgtacaaa aatattatca taacatatcg 1560
attataataa accaattcac cgtcaaccta acctaggtag agtttgagtt aaatgttaaa 1620
agaatatcca cccctcaaca ttgtaatccc aactaataaa tcagcaacct aaagtttttt 1680
ttaaaaaact aaaaagaaga gcaatatatt ttttttacta ttattttttt aaagagtgga 1740
tttatttatt aaattaaaaa atgaaaagaa gaaaatttgt tagtttgggt aatccgaaaa 1800
cccgattatt tgggcccgag aaaccgacgt tttgtttatt gttcctcacg gcaataagta 1860
atggcgtgaa tcgaccgcgt gcgcttcaag ctatctagac atttttatat cctccgatta 1920
gaaaccctaa ttcagattct ccgtattacc caccctggaa catctttgaa acgcgaaaag 1980
gtgacccgaa gaaacttgaa 2000

<210> SEQ ID NO 183
<211> LENGTH: 1989
<212> TYPE: DNA
<213> ORGANISM: Cucumis melo

<400> SEQUENCE: 183
attacttgaa cttaatccac atttatgtct ttatataaag ttcgaatact cataatatag 60
ccaagaaacc ttgtttattg gattttgagt tttatcataa gcaaatctct tatccaataa 120
caaattatta aacaacactt caacaataac tttattcaac aatatattag tttaacattc 180
acaaatcacg agtattagaa cataaaacgc aacaaagaat ggactaaggt actatattct 240
aacttaggtt gtttaggatt tccatatgtc aatgcttttg tgatttttga actagatttt 300
cttgttagat taattcaatt ctatttttaa atggcttaat atcttatttt cggatgcttg 360
gggattgcta gactaccgct ttgttgaagc aataagttaa atttgtttgt tacaggtatt 420
gatcaatcta acatagaatt gaatttgtat gaatatttag ttagacgctt gaaaactaat 480
tattctacca atgagccgta gatcttaatg caattgttat taatttgaac tttgtatgct 540
tctcatcgat taaatttata tcaagtagtt aattaggaca aatctattgg ctttttcatt 600
taattttgtt aagtaaaagc aacttagaat tttgaaaatg atgaacccat gatccaatac 660
attgaaagag aattttgttt aactcaaact aggattcttc tcacattgat ttcgtataat 720
ttaacttttt caatttatat caatcccccc agggtgaaaa aaatttgttt gaagaattca 780
tgtgctttct aaatctgatc tagacttgcc actaaaatta acttttgata tgtaatttgg 840
ttaaatattt gattcggatt tcgacgacaa acaattgatc aatgtggtat taaattctga 900
tctccatgta agaaatttac acattttcat aagttcaatg ttgacacaaa gagagtaaga 960
gcattttaaa aaaaaagata cttttaatct tttctaaaaa aacaccaaaa tgccattatg 1020
taaatgtaac ctaaataata aacatttaaa cttagaattc atgcaattag gctttgtatg 1080
ggacattgaa ttgattatta aaatcagtag ttatagaccg tgagttataa tggtttgtat 1140
tagaagcata aattatttta attttgatcg taatagcatg tatttgagat ataaattaat 1200
ttagtttggg tggcaaatag taaacagtaa agcaaaatat aaaaaaatga atttaaaata 1260
gtaagatttg taacaaatga ttaatactat aacaaacgtg gttttaaaat aacgttgatc 1320
gtagctaatt gaacattatt tattgtaaaa ttgagtgttt ttaatatttg gagcctcaaa 1380
cttcgggtgg atcaccacaa tataatcata ttcaaattta aaattttatt tttattataa 1440
atattgttaa tagatgctca ttatgggcca tctgtcactc cctccgtgca tatcctacct 1500
gaaacatcat atatcttaaa caatgtccat tgccatgtgt cactattttt acatcccatc 1560
cacttgacaa atatgttgaa gatgcctact tttttaggga tcatgtaatc tatctcatgc 1620
ttgtcaaatt gttcgataat agtgttacaa aaaatttagt aattattatt attatatttc 1680
ttcgatattt atgcttcata tgccattgtg ctctccattt ttaccatact taaaaaaatt 1740
tcttattata aattttttca aaaaaaaatt tactatatag tcatcatctt tattaaaatt 1800
aaaattgaga acctgatatt tttgatatta ataatttaaa atttgaatta atccacttta 1860
aaattattaa taatttattc gaatttgggc cttaaggaag agatacggaa acaaacccta 1920
gatcccatct atatataaat cgccacaaaa ccctaccttt ctctcagttt ctcgttttag 1980
ccggcaaaa 1989

<210> SEQ ID NO 184
<211> LENGTH: 1463
<212> TYPE: DNA

<213> ORGANISM: Cucumis melo

<400> SEQUENCE: 184

```
ttttcttctt gatttgaaat tcttcctcct tcctgttgca aacaaaccca gatgaataat     60
cagacaaaaa aagcagcaaa tttgaagata tgcatatacg aagaagaaga agaaaaagag    120
agggaaggat aaggtaggag atagcttgag attacagcgt agaaaccgat cgaaccggag    180
atcaacggcg cgaattaggt caagaagaag tgagggtttt tatgaagaag aagtgagggt    240
ttttatgtgc cgatgaaaaa ccctacttct gtgttggtga tctaacgttg tttgatcggt    300
tcggtttttt tgagaatcga gtaccctcat tattattatt attattgtta ttattataag    360
tttgttgtaa gaattaataa attatttcaa aaattacaat ttttatttat atatagttta    420
aaaaatttta taattttttt aaataaattt cgaaatataa ggttggattt cttaaaaata    480
tatgaaaaaa gagatgaagt ttataaatta aaaatgaaat aaaaatagta agtttgtact    540
cttattctta tttacaattt aattttccat taaaatttta aattaaatag aaatataatt    600
aaaatcttaa attagataga aatataatta aaattttcag aatgtaaatt taaattagct    660
tagtgtatat ttaaaatata taagattgaa ataattgatt ttgtttatct aaatatttta    720
tattattatt tattgaataa atataattat atatggtaaa ttgttttgga taataagaaa    780
gtaaagatgg tatttatata tataattaac caaaatttaa gtttgttaaa aagaaaagtt    840
ttcaaaaata ttttttacg agtaattagg aaaaacccac attttacatc gaagtcatag    900
actgggtcta tgtcttcatt gccttgtcgt gtacccgatc cacgataacg cattatgaac    960
cgagtagatg acttaacttt ttgtaatagc ttttcttcta ccatattttt gacatttttt   1020
taaaagtaac attatttata aaaaaaaaat cgtagtttga tctcacatga aactattatt   1080
acatcattaa ctaatatatc tatatttaat gtagttttct tgacatgatt ttaatgctaa   1140
ttgaaatagt tacaattttt gtgtcccatt ttgtttagat caatatgact tcacgtatta   1200
tgacatatgg ggccatctta ccagaaattg gtgccaatga gaaaatgaat gtaccttaac   1260
caatggagca acccatgtga gccattgatg aacccaactt tcttggtttc ccatcttcta   1320
ttcatatgtc acaatacctt ctcttttctc attctatata tagactctaa acaaacaact   1380
aatctccaac ttcaaatctt tcacatattc tcattcaagc attgaagttt accacttcca   1440
aaaagattca atccaattta gcc                                           1463
```

<210> SEQ ID NO 185
<211> LENGTH: 2006
<212> TYPE: DNA
<213> ORGANISM: Cucumis melo

<400> SEQUENCE: 185

```
cagcgatctt cgtagaaact aattcaatgc tagctcatta tttgactttt ctcaggcaag     60
gctccgcgag gaagagaaaa ggtccaattt caggaaccaa gggcatggac aggttccggt    120
cagaagaagc tttttacgta aaccctttgc cagattgttt atgtcaagga gaattaccaa    180
atggaagtac gacttccatt ttcagatagt tcagtagaac atcaaagata aaatgctctt    240
agagagctca atgtatatgc aggcgaccac tcaacgtgtc accagctttg tacatccaat    300
aagccagcta cgatggaacg acggagtgtt tataacctga gttttggtag ttggcggagg    360
cggtgatggt ggtatagaag gaaggtcgag ggatggcaaa ccctttacgc caagtagtgg    420
aagggagtag ttggagatga acacattttg agaagtttcc aagatcactc catttggggg    480
agaggggatg ttggttattt agcacaattg ttttcatgtt ttagtaattt tatccaataa    540
```

```
tgagcgaggc attgaagcaa ttaaatttat ttttaatgat tttttcaccc ttccataggc    600
tttttctttt ttcttttcct tttagtttgc aaactttagc tccttttatc ggctgtcgaa    660
ctcatttttg aagttattga atgaaacaca gtttgggctg tgtcagatgg gtggtgaaat    720
tttatacatt ataattacta cataaaatga aatcatattg taattttcta tctatgccac    780
aatttttttt tattgcatca tgaggattaa attgtacgag tccaaatttg tacagtcatg    840
tttttaaagc tttcgagcat tgttactaat gcatggaaag gatcgattat caagtatcct    900
cccaacttca tgaaagttat tatttgtctt ctaaatttgt tttagaaaat gtttaattaa    960
ttatttgaga agaaagttta actaaatcct attggtttcc tctaaggttg tcatacttat   1020
ccaataacaa ttacgtttaa aatcaaaatt attctaatgg tataagacta atgttttaaa   1080
agcataaaat tgatgaggaa ggattggaag taatactatt tattttgaag gtaaacattc   1140
ttgaatgtct gtcctaaaat cactaatgtt ttcttagttt gagactttga gtcgttgaac   1200
ctctccatct ttataaaata taatacgagt ccttcacaat aacttaaaat atatactaaa   1260
tcctaattaa tgaaaaataa ataaataaaa ggtacaaaat cattaaagcc taaaaatcta   1320
ttactccttt aaaacttttc aagggtccct acaaccaatg agaaactacc acgtcatttt   1380
cacaatccgt tcagtgttta gaaaagtcaa atcgcaccgt ccatttatcc actcgtacca   1440
agtacggtag gaatctatct accgtccgat taagcacaaa gaagcacagt aaatgtcaat   1500
cgtgtccatc cgccgccata ccgcacatcc ttcgtccgac cggaaggccc tatataaagt   1560
cctttggttt tccgaatttc tacttcattc gcttttgaaa gatttcccaa tctcttcgtc   1620
ggccaaaatt ctctctcgct tctcaaccct tcttcggctt tttcatccag gtttgtttct   1680
cttctctttt ttcttccttt gttgttcttg gaatatgttt aatttcattt gtttttccat   1740
tcaatttcat gctagatttt acgattaggt tgattttctg ttcgtagatt gtaattgatg   1800
gttagggtta gctttttctc ccattccttc tggaatctgt ttcttgacct tcgaacttcg   1860
ttgataaatc tttagaaaca tttacataac caaacaataa ttgaacaact cgtgttgtta   1920
tgcctatata atagcggtta ggaaactgga aacgccctta taattgaaat cgccttagaa   1980
atttgttttg attcatacag ggtacc                                        2006
```

<210> SEQ ID NO 186
<211> LENGTH: 1664
<212> TYPE: DNA
<213> ORGANISM: Cucumis melo

<400> SEQUENCE: 186

```
cagcgatctt cgtagaaact aattcaatgc tagctcatta tttgactttt ctcaggcaag     60
gctccgcgag gaagagaaaa ggtccaattt caggaaccaa gggcatggac aggttccggt    120
cagaagaagc tttttacgta aaccctttgc cagattgttt atgtcaagga gaattaccaa    180
atggaagtac gacttccatt ttcagatagt tcagtagaac atcaaagata aaatgctctt    240
agagagctca atgtatatgc aggcgaccac tcaacgtgtc accagctttg tacatccaat    300
aagccagcta cgatggaacg acggagtgtt tataacctga gttttggtag ttggcggagg    360
cggtgatggt ggtatagaag gaaggtcgag ggatggcaaa ccctttacgc caagtagtgg    420
aagggagtag ttggagatga acacattttg agaagtttcc aagatcactc catttggggg    480
agaggggatg ttggttattt agcacaattg ttttcatgtt ttagtaattt tatccaataa    540
tgagcgaggc attgaagcaa ttaaatttat ttttaatgat tttttcaccc ttccataggc    600
```

```
tttttctttt ttcttttcct tttagtttgc aaactttagc tccttttatc ggctgtcgaa    660
ctcatttttg aagttattga atgaaacaca gtttgggctg tgtcagatgg gtggtgaaat    720
tttatacatt ataattacta cataaaatga aatcatattg taattttcta tctatgccac    780
aatttttttt tattgcatca tgaggattaa attgtacgag tccaaatttg tacagtcatg    840
tttttaaagc tttcgagcat tgttactaat gcatggaaag gatcgattat caagtatcct    900
cccaacttca tgaaagttat tatttgtctt ctaaatttgt tttagaaaat gtttaattaa    960
ttatttgaga agaaagttta actaaatcct attggtttcc tctaaggttg tcatacttat   1020
ccaataacaa ttacgtttaa aatcaaaatt attctaatgg tataagacta atgttttaaa   1080
agcataaaat tgatgaggaa ggattggaag taatactatt tattttgaag gtaaacattc   1140
ttgaatgtct gtcctaaaat cactaatgtt ttcttagttt gagactttga gtcgttgaac   1200
ctctccatct ttataaaata taatacgagt ccttcacaat aacttaaaat atatactaaa   1260
tcctaattaa tgaaaaataa ataaataaaa ggtacaaaat cattaaagcc taaaaatcta   1320
ttactccttt aaaacttttc aagggtccct acaaccaatg agaaactacc acgtcatttt   1380
cacaatccgt tcagtgttta gaaaagtcaa atcgcaccgt ccatttatcc actcgtacca   1440
agtacggtag gaatctatct accgtccgat taagcacaaa gaagcacagt aaatgtcaat   1500
cgtgtccatc cgccgccata ccgcacatcc ttcgtccgac cggaaggccc tatataaagt   1560
cctttggttt tccgaatttc tacttcattc gcttttgaaa gatttcccaa tctcttcgtc   1620
ggccaaaatt ctctctcgct tctcaaccct tcttcggctt tttc                    1664
```

```
<210> SEQ ID NO 187
<211> LENGTH: 342
<212> TYPE: DNA
<213> ORGANISM: Cucumis melo

<400> SEQUENCE: 187

atccaggttt gtttctcttc tctttttttct tcctttgttg ttcttggaat atgtttaatt     60
tcatttgttt ttccattcaa tttcatgcta gattttacga ttaggttgat tttctgttcg    120
tagattgtaa ttgatggtta gggttagctt tttctcccat tccttctgga atctgtttct    180
tgaccttcga acttcgttga taaatcttta gaaacattta cataaccaaa caataattga    240
acaactcgtg ttgttatgcc tatataatag cggttaggaa actggaaacg cccttataat    300
tgaaatcgcc ttagaaattt gttttgattc atacagggta cc                       342
```

```
<210> SEQ ID NO 188
<211> LENGTH: 2003
<212> TYPE: DNA
<213> ORGANISM: Cucumis melo

<400> SEQUENCE: 188

aactagacta gcgagtgcac aaccaaatta caaaatcctt aacagagaca accatctatc     60
tcctttaaag caacaataac atcaaccgaa ttagaatcca caatcagtaa agacgatgcc    120
gacaccaatg accaaaaccg atcaaatata gcttattacg gaccattact tcaacagtta    180
catcaacaaa aaaaaaaaaa ttaaacattg ctaataaaat ctgaaaatga ggaaaaagag    240
attaaaagtt ttgaagatag aaagaataaa tctgaaatgt tctaatttga tatataagaa    300
atatgaggta atatgacgaa agcattttga tagttttcac caactccctt tgtgaaagga    360
tacatccaac caattttaca atttctgttc aaattttgtc cacctaccct tctcttctgc    420
cccccaaggc tgctttcttt cttttattat ttgctaaatt accaaaaact attttcgaat    480
```

```
taaaccatct atttcaatta tatacgtcat tcgaatttta acttaattaa cattagtata    540

tgtttcggat caaggatagt ggtataaatc atcctaattt caatttgtat ttagaaaagt    600

tcaattatac ttaaaacttc taaaaatttt atattttaaa tttggatata aattaaattt    660

aagatttatg gaaggtaaat aattagagca aaacaaactt caaactatat ggaaaataga    720

aaaggaatat tttagccaaa caaaaacact tattatttta ttttgttttt ttgttttttt    780

tttaatttaa caattttttt ttttattggt tgaatgtgtt tctccactgg tgagtctcca    840

actttgacct gcaaagggtc tatatagcga gtttcacgag cacctaacca atatctgtgt    900

aataattccc atttttcttt catacccact tcatttgatc atctttttca caaccccgga    960

tctctaattc ttgggaattt gcctctttct cgatccattt ccaccgtaat tgaaaaatat   1020

tcaggtttga tttcttctgg gttttcattc aactgtctaa cttcattatg ccctttatgt   1080

gtttgttgaa agccccccac ccaccatcgt tcaatgcggt ttctttacct tttgttcggt   1140

ttcaacgatg atttagaagt tatagatgga tgctaattgt ttcgttgttg gtttgatcca   1200

ctgatctgcc tttgattggc ataaaaggag attctagatc ttgttttgat gttgtgattt   1260

atggatatta ttgttatagt cgtggaagtt tttcttgtcg ttctgcggta tatggttgtt   1320

ttattttttg agtggtaaat tgagcagatt gtgaactttt gggttttatg gtgaaagcat   1380

gaattagtaa atgtagagct gctgaaacaa aatggaggtt tgctagacct ctttgtgaat   1440

tcttaatggt cagcctccat cttaagaggc taagtccaaa aatttaaggc agtcttttgt   1500

tattgttaca aaggacaaga aataacagag gagttatttt aattgaatca agttggaaag   1560

aagtactact tcatgcttct ttcaaaagca ggtcaaagtg ctttaaagtc ttcttattta   1620

tttatttttt cctgaatcaa tttaaactaa tgatagaaag aagtgttttt taatgggtta   1680

ttataagtaa catcaatttt taaccattcc aaaagttaca tcaaattcat catagtgtga   1740

gtttacgaat tttggaagtt gtaattttaa gttaatactt cttttaagga aatgtacact   1800

ttgcatgttg tgttcataag ggtatttct ttgacaaacg cagcaaccac cccttaatga   1860

aaactacacc acggtggttg gttttttctt gttatttttt tacttggaat ttacaataag   1920

ttgttatatt cggatatatg gcaaagcaga tatctgtttt tatccgaaac ctcataaatc   1980

ttgaatgtgc agcaggtaaa aac                                           2003
```

<210> SEQ ID NO 189
<211> LENGTH: 1024
<212> TYPE: DNA
<213> ORGANISM: Cucumis melo

<400> SEQUENCE: 189

```
tcattgatga agaaggaaac tttaagccaa ttcgacaact tatccattca acaactttcc     60

accttcagac attcagattc aactataata taacataaat tgatagtcaa gtctttttttg   120

agacaaccat aaatcatctt agcttcgaga actgtcactt ccttaaattg gtgaatatat    180

cacattccat ccattcaaaa ctttgtttcg aactttactg tagttatgaa tcaataaatt    240

gggagagata ttgttaaaaa gagagagcat atttgtttct attatttact ctctcctaag    300

agagggttaa ttagtctata aatgatctat tcttctcgtc cattgaaatt ttgttatcct    360

aaatttatga atacttctac ccaaaataaa gacttttttt ttttttgaaa agtgtcaaaa    420

aaacataaag aaattgacaa aacattcatt tttagtggat tttttacgga cgtaaatagt    480

ttgtttttgt ttcttttaat aatacaattt ttttttactt taaaaaatat ttttgttata    540
```

```
aaaccaccgt atttttattc aattttaata aataaataaa tgaaagaata taaaaaagag    600

gaaggaaaaa gaagccaacg aaccaacggt tgccacgtat caaaggtcta aagtgcgcaa    660

aacgaggcct tcggaaacca aaatgcgtgg cttcaattgg agcaagtaaa catggaaacc    720

acgtccattg taacgcttcc tgatctcttc tttacaaccg ttggattcga gtacttttc     780

tcaacgatta acgactgagt ggacctccac ttgcttctgt tccacgcgcg tgggattgac    840

gtgtggtcca cgcaactctt ctcgatagga tcattcgaga acatccttta cttaaaccgc    900

ctctctctgc ctcaatttct cgtcacttcc ttctccttct ttaccctttc cactgcggct    960

gattcttctt cgccttttat tctctcgtac gccgccatat tcttcacttc tttttccggc   1020

gaca                                                                1024
```

<210> SEQ ID NO 190
<211> LENGTH: 2001
<212> TYPE: DNA
<213> ORGANISM: Cucumis melo

<400> SEQUENCE: 190

```
attcgtcttc gcattatcag taaatttatc attttaagag tttgttcttt tttaaaaaaa     60

attaatcatt tcgataaagt tggagaattc aaaaatttct ccaaataatt tataaaaact    120

ttcggttata tatcgaaaaa attaacatgg tattaaaacg atcataactc aattaacata    180

aacactccct ctcaacttta ataccaaatt tctttattaa cgcaaaattt aaaatttgtt    240

tttaaaattt tcacataaca taatagaaat acttttcttt atggcaaaaa tacaataatc    300

aaaattgatt gatggtgaca ggacaccaca caatattttt aaattttgaa tatacgaact    360

atataataag atatttatga gattcccatc ctaaagattc ctagagattt ccttgtgtac    420

aatattacac aagtatcttg gaagtccaaa gtcctgagaa aaaagctatg tataaagtaa    480

tagtgtttgt cgtaggaaat ttacttcatt cgtgtcatta gctttttatt gaaaaaaaaa    540

attaggtata tcttagtgaa tctcacttaa tcgttgtcga tagttattct tttaatatca    600

ttatatacta aaatataaca atattgaaaa gctaaaactg tatataaaaa aaatgttacc    660

tctaaacttt tatcgtttat ttaaaagata aatatattct ttcaaaactt acaatcaaca    720

tcctacgact atcattatag gtacaaatct tttcatgttt acacaaaaat tagattttta    780

aatggtgtaa tgatgatata taacgaaatt ttgaatgatt actatttgag gttaccattg    840

taattggtcg tgttgtttga aatttaattt tattagaaaa tttgtcaaaa gtagcaaaaa    900

tgaataaact atttaaactt taggataaaa tcaagtgtta tgagtttttg tctagtttat    960

atatttttat ttttattgaa aaccctttc ctatcttttc attacttcaa aatagtttta    1020

aaatgtctat taaggctaaa gttagtataa ataaaatttc ggaaattttt tttcgaaaaa   1080

aattgataaa ttatttatat tttatattaa agtcaaaatt tattacgcgt agatgtttat   1140

caaatttct ttctttttgt tgataatttt ccaaaatttg gataattttt taaaatagta    1200

aaattattat aaaaatgaaa acaaactatt tataccttaa gcaagaaata ctaaaaaggc   1260

aaaaattcat ttacttcatg aagcgtaaaa attaaatatt ttaccacttt ttgttatttt   1320

ttaccatctc tatcaattat ttgtaaaaag aaaactacaa aattagatgt tttttctttt   1380

ttaaggttta atcaatatta aaatttctta aattggcaga caagttggtg ttggtaatta   1440

cgaataaatc ccgaattgac taaaaataaa ttcttctcca agtaaaatag acacgtggat   1500

gaagaaataa gtgaatcaaa ggcatccaca gttcaataaa tggaaaaaac tactttctgc   1560

tgactcattc ataagttttc ataaaatttc ataagaaagg ccaaagggct tatgaaagtg   1620
```

```
aatgtcatag cagtaaatga agcacagcgc cattgaaaga caactcaaat tgcatgcaaa   1680
cccacataat tattcaacaa acccacatca aatttcccat aaagatcaat tctttagggg   1740
gttcaattac ccaaaagtga ggtagttgaa aaccattaaa caacaagaaa tcaacaattt   1800
tgtaatttgt ttgtacagaa gtaagagata aaatcatcgt taaccattcc tttatttcgt   1860
aatacaaccc atcaaccatc tctctctctc tctctctctc tctctcggcc tttatctttc   1920
tcttcctcaa ttatttaagt actacccaag tgagctaaaa gcaagttcag tggacagtgt   1980
tgtaagaacc actacagaaa a                                             2001

<210> SEQ ID NO 191
<211> LENGTH: 4175
<212> TYPE: DNA
<213> ORGANISM: Cucumis melo

<400> SEQUENCE: 191

tagtttggtt cataggttat agtttccaaa tttgttaggc tatcattaat caaacacaat     60
acttctcttg taggatggct gccccctata gtactttttt aacttaggag aaggatataa    120
taattatatt ccttttagaa aatataataa taattgtgta gtgctttgat ataccttaaa    180
ttagctactc acgtttttag gaggaagctt ccgttgcttt tcatggtgtt atgatctttt    240
ttattttata aaggactgaa ctttaaaatt tctctttcat ctattttgga ttggattcca    300
tctattttat acgggaagtg aactctaaga tttctcttca cctattgtga atcggactcc    360
gtcatgtagg tcaagactac gacagataag aatagacttc cacgaaagaa agtggtcaat    420
cgagatggct atatttggct ctttcagctc aatttcttct tttttccttg catgttcttc    480
cgttggtaca tttcttgcac ttttttttgtt ctcacatgac taatgtattc caagtttatc    540
attggcattg tgcctctttt aggcttgtaa actctcgatc caaaattatc taggacatat    600
gtttcctagt gaagaaatac tagtatattc cttatgtcaa tatgtcaaaa ttttcaattt    660
cttaaccttt gagtaaatca atattatatt tttatggagg ttatttataa ttggaaaaaa    720
gttacaccca tctcaaccct aattaacacc aaatgaaatt gtaccatgcg gcacaatatt    780
tttttgtgag ttttttgcaa agagaaacaa agtagcagac aaagaacaaa cattccccca    840
aaaacagcag agaataccta agagagaatg ctctctcgta aaaaataata cccaagaatc    900
ttcccaaaaa gagggagtaa aagagtccaa aacaaacgaa ccgaagattg acaagaaggg    960
cactctcgcc ctccactgcg ccgctaaatt gtaagaagca tattttcttg agttaacata   1020
ggaataggtg taactcaaga gaaatgtaat tcgtagaatt gaactttgta tattaattta   1080
tatggtgttg tagatacaat ctttagtatt tactcatttg gtgctttctc tcaaatacaa   1140
tttaaattta gaactttttg atcttcgatt ttcaggaagt tggagttgca aatcaattcg   1200
agtttcaatc tctggaattt aataaaagtt tgatcttcca agttttcaat ctttcagaag   1260
acgatgatct tgatatggat aaaaaattgc acatcatgag agctttttga agtttaaatc   1320
ttcaattctc tagagcttaa attcttcctt aaaccaaaga tcaccaaatg aatgacaaat   1380
gtctctattt atcgaaaaat ttcatagact tttagatggg cttaggcaca ttacttgttg   1440
ggcttggact tgggcttatt tgcttggcgg gctcatgctc gagcccatta tttctttggc   1500
ctatttttca tgaggggctt gaacttggtt gtatacgaaa aaacttgact acctaaatct   1560
aatcaaatta taatcatcac aattttgacg tgttacgatt taattggcca aaaattcttg   1620
ttcaacactt gtctctaatc attttcctat ataatttaac taaaatattt aactttaagt   1680
```

-continued

```
aacttaaaag atatagttta attcgaatca aaatacaaat acaatttcgt ctatctattc   1740
ccatcataaa tgttgattga gattcatatt ataaacttct ttcaggaaaa gaaagaggaa   1800
aattcaccta aaccacgttt tcctattttg gtaagaatcc ccaaaccata aatcattcca   1860
aaattatttt ttttagatta gaaaagaaaa aagaaaaaaa gaaattcaca tggcgtaaaa   1920
tttcagcccc gtgagatatt ttcgaacccc cagatacaat ctacaccgtg aaaacaaaat   1980
cggacggtgg ttgctataat gtccgtttag aggcaatggc agggatgaaa ttgccaacgc   2040
aagataagga acgaataaga gaaggacacg taagtacaag tttaggatgg gcgggcccac   2100
agccacaagt gccgttcgtg cttatataca agtcgctcat attcctagaa gtgtctccaa   2160
ataaaggaaa gaaaagttca ctcatagaga gaaagagaaa aataaagctt cgttgccggc   2220
gatctgaagg cggcggccat ttctctcggg agagagaaag agagagattg atagagcgga   2280
gagttcgagg ctctctcaaa cttcggtcct cttcttctct ttcaggtatc gttcttctct   2340
atcccttcgt attctgtttc ctcttttctc tttcttcgcc atcatgctct ttctcttgtt   2400
ttgtactcac tcaatgtgat tgactttatg ttgtttttct gttttatttt tccattaatg   2460
ctcgttgtaa tgtgtagatc tatgataaga tttgaattat tgctcattaa tgtgttgcat   2520
gcttttgatt tcattttaaa aacagagatt actttctcta tattgattaa atcgttggat   2580
tttaggttct tacagagttt gtaaacagtg atgttaagga ttgctgagat ttatgactga   2640
tgagagttag tgtttgtctt ttagcttgtc gttttcctct ttgaaatcac atggattcga   2700
tctggatatc tgggtttggc tcgtctgaaa tggctacact atagcatatt tgagtttgtg   2760
atgttgaaga tttgttaatt tcttggaaaa tcgggagttc gttttgtttt tcctcttttt   2820
acaggtttta ttgattggtt tattgatcgg cgatatctcg ttttcaactt ccgaaatgct   2880
atttttcata agaagaaatt gtggatgtct ttttctactc gattagagat ccttgaaact   2940
atgccaaaaa aaattggttc tttcaccaaa ttgtttttg tcgtttgtga tattaatgca   3000
ttttcttatt cttaattaag ttcaagtatt cttttattat tttttaatga tggttgttgt   3060
aatggttttt tccctttttac taaaagcttt ttccatgtga ttcaaaggtg tacttggggt   3120
ttcccggtct ttgttcccaa gtcaattagg atgggcgcca attcgatttt agcttctgta   3180
tcattggtgt atattctgtt ctggggagga aaaaaaaaaa gaaaaaaatc ttccgtccta   3240
cagtgtgctg agtaacaatt tgaccagcct tttctgccga aaactttttg aaattatttt   3300
ttaattgtga tttggtgaac ttaaattgtt ttaataaata aggtggattg aatcttaaca   3360
gaaacatcaa ataaaatcga gttttaaaaa aaaaacatat ttttagtgaa tgtttatttt   3420
atttaaaaga tctccatcag tcctgatgtt tcctagaaaa cttatacatc ataggtcttg   3480
attaacaaat ttggaggaag tcaataggtt attctttttt tctttttcca ttctagtttg   3540
aaacaatttt cttttctttt ttaacttaga aaataatggg tagctagaaa tatggaaatc   3600
aatgtatttt gggcttctcc ttgaaactgg agcagcggtc aatttctctt tcgtttgtat   3660
agatgtgata gaaatagaat gtttccttcg cttacggcat cagagagttg gaattggtct   3720
ttctcaacct caatatcaat taaatcaagt ttcgtcataa acaggttttt tttttcttcg   3780
tttcaaatgt ttggtagggt caaataattt gtaaaatacc tagccgtcca atatgataca   3840
aactggagga tttcacttgc tcttttaaat tacaaaaaat attttatcat tgatgttgcc   3900
tgtctgtgtt tatcttttct ctttccgcct caagtaggcg tctaattgtc ttggcaagtt   3960
ggttttttgt acttccgccc cttgtccttt ggccctttttg attaagtttt tcatttaatt   4020
ttctggtcgg cgtacgttga attattaggt ttgcatttaa tgtggtacct ggtgctttga   4080
```

ctcttatttg ataaggtatt ttgaagtcta aaacgttaaa ccctttgttt gatgtttatt 4140
tttttatcgt tccaggacaa tatcctttgg aaaaa 4175

<210> SEQ ID NO 192
<211> LENGTH: 1999
<212> TYPE: DNA
<213> ORGANISM: Cucumis melo

<400> SEQUENCE: 192
aaaagagtca tagtgaaaaa agctgagatc ataatagttt caccctaaac acaacttata 60
ataacacata ctatcataat atacacacca aacacagact ctatagtctt cactctaaac 120
gcagattaca atagtctgca ccccaaacgt agactattat aatcttctga ctattataat 180
actcttttca cttatcgccc caaacgtccc ctaagagaac aaagataggt tataaaagag 240
agatgagggt ttatattatg caacaagtat aaggttctag aacgatgtag tcttcaaagt 300
aacgaaagca ataggctaca cgagaaaaat atttttaaaa tatagtgctt tccctaaact 360
agatttcaat gacaaattat tataaaaaat agaatcatta atccaacatg gcttgcatgt 420
cacaccttgg ccaaaactga agacggatgt catactcgac ttcaatatat ttttttaatt 480
aattttcatg tgacaacaca taaatattta aaatttagat tgggttggat tttttttcaa 540
gtgggtccca aaatactctt caaacccaaa ccaacccaac ttgtttaccc atctaataat 600
aacccaccag gttcaagaag acgaaccgaa ccgaaccgat ccggtctaac tttgtttcat 660
acttaagtcg aacttagcgg tacttttggt tcggttctcg gtttccccaa acagagccac 720
tcaaaattag atttagggtt ccgttcgcaa ttttcagcgc atttttattt gaatcggtcg 780
tttgttgaac acgttctctc tcagctggtt tagggttcat cgttctctct tctcgcgcta 840
tatctttctc tctctcaggt tcgtttcttt ctcttaggcc attttatcag aagatcctct 900
tcgttctccg atttctttc cgtgttcgcc ctcggtttct cagcagacgt aggaagtttg 960
gtttccgttt agtgaatctg tttggggtat tacgaatgat attttgtact gggctttccg 1020
catagtcttt ttctttctag gaatatatgc atctgagaat ttatttgttt ggcttttctt 1080
tataaagtat gaggacatat acatctcgat tgctaatcct tgattataat cttttttttt 1140
tctatgttgt ttgaatctgt tttttttttt ttaatttcaa taggtttttt gaatctaaaa 1200
atgtatttct tggatgaatt gcatactgtt gaattagaag tttattgatt agattgttga 1260
tatttgccct aagttccatg gataggtttg cgtctttcac cttttcgttt gctttttctt 1320
ttggctgacg acatcttaca tagcctctgc tctaaaaggt gccatgattt tttttcctgg 1380
ctttatctga gtttgcgcaa tttagatttg aagtgatgat ttgtctaaat ataaatatct 1440
atcggccata ctatttttttg ttattttgag tttttcagga tgactgctag agaatgaaaa 1500
atcttgaaac attgtgtttt gaagttcaag gatcttgtag ttttgttctt ttctagacta 1560
tctcatttga tatagccctt taaatttaat caaaatttgt taatattcaa atcctcggac 1620
attttaatta tttatctaaa tagttgttta ggcattactc aggttgccca ctattttaag 1680
cttagaagcc tactctggtt gacctaaagt ttgcatgcta tttgccttat ttcgcacgac 1740
tctaaactgt tatagacatc ttttttcagc cttcaggtaa atgaacacaa aaaggagtga 1800
aagtctgact tctgtgtgat ggtcttttaa tcaattatag ggattaagat ggttttttta 1860
ttcattgtat aaatattaaa ttagaatgat gacaaccaat aatattaaaa ctgacaatgg 1920
aaggttcctt atattatttg gagtgtacat tacaacagcc tgattcttgg cttggcaggt 1980
tcctgatcac cttgtaaac 1999

<210> SEQ ID NO 193
<211> LENGTH: 2000
<212> TYPE: DNA
<213> ORGANISM: Cucumis melo

<400> SEQUENCE: 193
atttatttgt ttagagataa gacgcacatg agaatatgag atggattcca ctccactcac 60
actccaattt ctacctatcc tattactgtt tactattatc attccacccc tcgacccctc 120
attcttcttc tcaccttact tttttatgat ttactactac ttcattttgg atcacaatct 180
gatcaatgct gggtgggctg ccctcggcct gtcaccaggc ccagcccact tccaaattaa 240
acctcttggc ccaccgccca ttgtccccat cccattccat ttaatattcc caaccttccc 300
tttttctttc ccaatgcgat gcttctccaa tataccttc ctgccctcca tgtttccttt 360
ttactgcttt cttatattta taacacacct tctacagtct tttggctggg aatgctgcgt 420
atgtgaatga gattcaagat ttcgttgatg ttatttgagt ctctatattc ataagttttg 480
ttcttagttt tctctagacc aactgcaaga gttagcgttc catatgctca taagtttcag 540
atttctgctg tgtggtttga agacagtcat cgatccatgg gtgaattcgg ctttttatta 600
ttattattat tattatttat tgttgtctta cttttctatt tgaatcttcc tatctttttt 660
actcattgtt ggactctaat aattcttgct aaacacaatc tccattttta ttggacattt 720
taaatcccat ctcaactcat aattttagtt accttccacc atcaccatat ccaaatccga 780
aataaactca aataaaatcc ttcacgtgca tgtgctctcc atatattttt tctacatggt 840
aaaaataaaa tgaaaacaat ctaaatttaa taaaataaca tatatggcag acttttattg 900
atgtagagac tgggtgttgt acaagaacag tgcagccaag aaaaaaaaaa tacttccaat 960
gaatcgtaca ttttaaggat tatgaaacta actagttcca accatttttt cacgaccacg 1020
tgcttgttaa acacgcaagt agaatcaaaa tgtgggcttc ttcgctttat ataactgtga 1080
atcattctcc aaaaagggaa ggggatctca ttccctaatt caataaagaa aaagaaaaat 1140
gctagcgaac ttcatccatc tcattccttt tacctatttc atgagatgcc cattgtatat 1200
aagtattttt ttttttattt cattttactt agtttactcc tcacctctaa aaaaaattag 1260
gagagtttgc taaatccatt ctcaaactta gctttatttt ttttaatttt atttaacctc 1320
gtcgtggatg ttaacctcaa atgtcagttc tttttattct atttattgat gttataattt 1380
actttaggat tccaatttta taaaaataag aatacaaata aagataaaga gtgtgaaagc 1440
cagaaagaaa aaaaaggaaa tcgtaatatg ggtaaaattg gtacaaattg ggtcccgtta 1500
aatattaact caaaaaatgc gagaaaatgg tagaaaagga aatagggggt aagagcaaag 1560
tagtggaagg agagcattga acatattctc tagtttttgc acttggatct aaacacgagg 1620
aattataggt ttattcattt actaattaca taaataggat tggattttaa aatttgaccg 1680
agtgattatg catatttgat agagttagaa aatagtggtg gggcaggtac aagttacaag 1740
taatgtataa gagatatgat gagcatatta ggaaactata gatttaaatt cgtccgtaaa 1800
taaataatta gaaatataat attcgagtgg aagggtatta gggttaggcg aaaccaattg 1860
cagttgcacc tataaaaccc cttttacgcc tccacccgct tcaacagcgg tctcggcgtc 1920
tacaactaca cactacacac tacacactac acactacaca gttgcagacc agaagcataa 1980
cgtaacgccg gtccacaaaa 2000

<210> SEQ ID NO 194
<211> LENGTH: 2000
<212> TYPE: DNA
<213> ORGANISM: Cucumis melo

<400> SEQUENCE: 194

```
tgaagagccg gaaaagcatg gcaaggtcaa ggcatttcag caagaatacg aggatgaatt     60
ctgggtttgt aagtccggtt cttcttcgga gttgtggttc gaatttcaaa cggccatgag    120
gagccctaca gcttaggaag cttcaggtct gagactctga ctccgacaga aattgctgat    180
ttttgtgtgt gttttgaata accattgtat gagtatgatt ggttgtatag gtttgaaatg    240
agggaaagtg atccatctcc ttgttgtctt tgcaggaaag gctcatattc gaccaagaac    300
gctttgtcat tgctttcgat aatcatagaa tccacaatgg tttggcatat tagcaaacaa    360
atcttcttta ggcattgcag acagaaaatt ggagagtaag ttattataat taaggattct    420
aaatgagtaa gaataataag atcaggcaaa gattggaaga actaaagcgt ttagtatttt    480
gtgtggtaca gaagaattgt aattagatac gtagtctaga gaagcagatg gtgagatttg    540
tgaaagacaa atgttagtgg agagtgaaga gtgtttctca acaaccgaca tagaaggatt    600
ctcagaaaat gagaaagatt tttattgcgc aaaatagctc ccatatcatc atatgccgtt    660
gccattccct ctggggttgc atgtaatgag taatggaaag ctgtagacag gctaacttca    720
ccctttgtct tgggtatagg gtgcattttt ggtcactcca ttttaagttt tctaataata    780
aaaggatgaa gaaaagatat tgaaaaacag ctcaggtttt aaagttgtca cacttgagaa    840
taatgcattt aacagttaga attttgcatc aacgtctttc aaatagaaaa gtaaaggaga    900
gtctagtttg agctggatag ctaaactggt ttaatcatat cttctatcaa gtggttagag    960
ttttagacct cccaacttta tatgtcgttg ccctaacaat gttgatggat gtttagtcct   1020
aagctctaac attgtccccg tatcatattt cataatagaa tgtactgagt aatggaaaac   1080
tagagaggta ggaagttgga cgaactttga atctatattg attttactat agtctttctt   1140
ccaagtctta atgagagctt tagctaaagt ttttcaaaaa ctcaaaagaa gtttttgttt   1200
tccaattctt cgatccatag attgtcaaga tggctataat atccttgaag ttaatagcct   1260
tcaaagtttc atagctttta tcctatgatc tttagaaatt caagagttat attctttaga   1320
actacagaac tttgatcttc gattcttcac ctcttccaga acctttatag tagagtttct   1380
tgaccttaca tgggcttggg attgggcctg gctacttatg ggcttagaga ttgaccttgg   1440
gtttaagcac attcgtttta cttggcccaa ttttcttaaa cttctgcaaa atcctaatta   1500
actaacacct caacaaaagt ccagtattaa atggggcata taaacaaaag ttaaacaaaa   1560
ttgtcgtaca gaatcctaat ttgctaacct cagcaaattt tatgccattc gtccttgtgt   1620
atctaattag tgttaatttg aggaaatata ataatataga cgtaggacgg atattggtat   1680
ttggtgcaac atcctccgaa ccaattcctg gaaagtaatt ggggcaacaa gataatgtta   1740
tcgtcagttt caagtgcaaa acttgccacg tggaacagcg gcaacatgat atctcaaata   1800
tggacctctc acccggtcaa gcttccacca ccaccaccac ctccgtattc taaaataaag   1860
tcaggaacaa gaacagacac accttaacaa aaccaatatt cttcatctct atctctctct   1920
catttcagca tagaagagag ctgagtaaaa ggaaaaaact tcaatcaaat ttgacagaga   1980
agagcccaag agaaaaccaa                                                2000
```

<210> SEQ ID NO 195
<211> LENGTH: 1400
<212> TYPE: DNA

<213> ORGANISM: Cucumis melo

<400> SEQUENCE: 195

```
tatatatatt aacttttaaa attttgaaaa cgtcatagat aaattatata caaaataaaa      60
agtttgatta tttacgaaag ttaaaaagtt tatccgaaag ttgactcaac gataaaaaca     120
ctaaatatca cttttagaga tgatgatatt atacataaac atacgaactt acgcgtcaaa     180
cttttatact aacacaagat caaaacaact ttgttgagta gtgagaattt tatctgctga     240
tatggttgaa acttgggaag caagcagagg aagttccatt cattaccaaa atccattttg     300
tattcatcaa aatatgaagt ttagcgactt gataaagtca agtcaagtgg tcctatcgat     360
ttgttaatgt caatgtttgg ttttgaattt gatacctatt agacaatgat atataatttt     420
aagtatggtt tacactgtga tgctttatat atttttaaat gtaaaatatt agaacttgta     480
atttcaataa attttaaaaa tgattttgtg ttatttcctt ttttaaattg aaatatcaat     540
gtatcaatat tgcgtcatag agtattgcaa cacaacctta tgttaaattg tttattgctt     600
attgctctaa ttcaactcct tcatcaaatg tgcacagaat ttaaacaaga aaaagagtag     660
gtgctttttt actaaaatat actaaaagct ttttatacca aatcttatga caaaatcatt     720
ccaacaaaat gactatttaa atataagatc gaatccctaa tttaaaaaaa aaaaaaaatc     780
aaagatgtta atttctatta ttaaactcac tttagcgtag ctaacaaaaa aaggaaaatg     840
agaggctaca aagcttgagc cctctgcctc cctttattgc attgtttgaa attagatcaa     900
tactttgtat ttttttcaaa atgaaaaatc gtacatagaa ttaattctat ggacaaaaaa     960
tcagagaagg aaataatcta gaataaaatt cgatttttaa cccaaaaaaa aaaaaaaaaa    1020
ctcgattctg atttttgtaa gcaatcaccc aaattaccat aaataaatgg tattcaatta    1080
ctcaattatg gatattttag aaatgataaa tttttattca taaactcttt tctttctctt    1140
tcaaaaagaa aaaaattagc ataaacttca atgacattta tttattcttc ttcgtttgga    1200
gtcaaaagtt taaattgagc atcagtccag cccaaaagcc cacgaagaag cccaagaatc    1260
ttcagctttt tcgttcaaac gtcccttttt ggtttataaa attaaagaaa ataaaaacta    1320
aatttatttg ttatttaaca aaacattttt ggttaagaca ttctctttga ttatttttct    1380
tccattcttc gtcgtcaatc                                                1400
```

<210> SEQ ID NO 196
<211> LENGTH: 2019
<212> TYPE: DNA
<213> ORGANISM: Cucumis melo

<400> SEQUENCE: 196

```
tttatattta tgaaaatgaa gtctctaaac aatttttcta ctcccaaatt tgttgatttt      60
tctgcctatt ctttatcggt gctttaaaaa atgaaaccaa atttcaaaac taaaaaaacc     120
aagcttttaa aaaaatgtta ggttattttt gaaattcaac taaatgttga actcttttac     180
ttattaaata ggcaaattat tgaaataaat ttagagcaag taagcttaat ttttaaaact     240
aatatactta ccaaatcgag gactaaaata ttcaaatact ctttaaaatt aagattaaca     300
ttaatcactt tgttatgttt aaaaagttgc agtgtcactt gaaccttttt aaattaatat     360
aatgaaaatg aatccaactc aatatatata atatctatat tattaatctc gatgtcagat     420
gtttgatacg cacatatctc aaaaattata cctcaactaa catcggtgca cgatgtatta     480
tttcgtgagg ataaaaatcg tttttagtat aaattgatgg aaagattatt tgaattactg     540
aaaaatgcac cggtacatta tttgaaactt ccccttcatt taaagaggct aatattagaa     600
```

```
aaagacacgc tgaggctatt tttacaatta atgtgggctg ttgacttggc ccagcccaaa    660
acataaaccc taaagtagca caaacaaacg cctctttctt cttgaaaccg catattaagc    720
gttttatcac ttctcaccac ctctcattcc tcctcttccg cacgttgttt cgctcctcaa    780
cgggagtgcc ttccctttgc tctccctcca ggttcttctt ccttctcatc tcatttccaa    840
gtaatttcat tccgtttctt ttctcttaat cgtatcttgt tcagactctt tcgcgttttt    900
ttttagttgc gccttaccag atctgtgttt tcactcgttt ctattcgata catgcttcca    960
agatccattt cttaatcgca tgtattcggt tgattggatg attgtctttt tgtaagtttt   1020
gattactttt ttggaatgga tcggttgaac caacggggtt taagtcgatg gaagtaggtt   1080
atgttaaaga tttgcttctt ttttatgaag atgtgtgtgt tcttttttct ttgctagatg   1140
atgttattat ttgattgttt taacagtcgt gttttgtttt tctgcagttt atagtcctcg   1200
gtcttttgaa gacttgtcaa gatggttagt acacctcttg tcatcgtgat tttgattgag   1260
tgatgtgtta agtgcttctt taggttacag ctaacgcgat tttttatatt caattgtgcc   1320
tgtgcaggtg aagtttacag cagaagagct ccgtcggatt atggactata agcataacat   1380
tcgtaatatg tctgttattg ctcacgtcga tcatggtaag ctacttagtt taagtttatt   1440
tatgccgagc gtctatttaa gaagattaac atcttagctt tcatttattg tttatttggt   1500
aagcatcgtt tctttttctc cgaggaactg tacatgtcag ttcacatgac aataaaacga   1560
tcttccttgg acattagttt ttgaagttca attagacgcc aaatttttgtt ggttaaaaga   1620
tgcttgtgga gcatatggac ctaatggaat cagtactttt tgatggatgg acttgtcttt   1680
tgttctttta ttttcaaaag aaattgcatg tgcaattaca tcatctttga tcgaaagatt   1740
gggtaattgg gtaattgggg taaagacatg ttgtaaaaac taatgttaat tatcaattac   1800
cattatatac cttatttagt gcttatttat atccttttttc cccatttcag ggaagtccac   1860
tctcacagat tctcttgtgg ctgctgccgg tatcattgca caagaagttg ctggtgatgt   1920
acgaatgaca gatactcgtc aagatgaggc agagcgtggt atcaccatta aatctactgg   1980
aatctccctc tactatgagc agaagagctc cgtcggatt                          2019
```

```
<210> SEQ ID NO 197
<211> LENGTH: 1999
<212> TYPE: DNA
<213> ORGANISM: Cucumis melo

<400> SEQUENCE: 197
```

```
aaaaggcgaa aaaaaagtta gcttcccgag aaggagaaga cgaggaagag tttgacttcc     60
cggggagata aagtttgtgt ctcgagggaa tctctaatct ggagttgacc gtcgacttat    120
gtgtcgagcc tggatttagt tgcatggtgc gacaaagcga taaggcggca tatgtaaagt    180
agtaattcaa aactagcggt taaagaaata atcagccaaa aaatttagta caaatacggg    240
tggaggccct aagtgaagtg ctgctattca gaggttttgg caaaagagtg caaagagttg    300
agttgtgcag agaaagtact aggtgaggag aggcgtttgg aaaagaaaag gatcaaacat    360
ttgcatgagt gatattctta aactaaacac tcttgtgtga gtgacttgcc taagctaaac    420
actcttgcat gagtaacttt cttaaactaa acgttttgta atgttttctt aatggattct    480
tttcgagtct gagttatgct taacacgttt tgtttctctc gtgttattgt tgttgttgtt    540
tgaaaagaga aaactattgt tttctatgtg ctgattgtga tgaatgtgtg cgaaccatta    600
gccttaatcc tatcaagtga atagtgatta tgtggtgtgt gcacataatg taaatgacat    660
```

tgtgtggatg gccagtgcaa caagaaatga atcagaaagc ttcccaaata ctgtgaatgg 720
agtgaacatc acactagctc aatggcaaga tattggcgat agtgaatcac aataggcttg 780
acaaggggaa ggattcatgt tcttggttga aaggaataag agaggctaat gtgagatttc 840
tgtgatttgc aaaatgaggc gttggaagac acgtttgaga aatgaaaacg aattagtgct 900
tgacttgtat tcctaaaaaa gttgtccaat atcttcaatc actaaatatt tgatgtgcct 960
aagttttcct tccttagttg ttgaggcgtt gaggccgagt aaggaaagat aagataatta 1020
tgacgttgaa aagctggtca agttatccat ctttggatgg tttaaagtta ttacatgtag 1080
ggagggttgc attccaattt tgtgtgtgag atgagtctta ttttcgagat gggttgctag 1140
gcgatcaagg agaagtataa gaaatgagtt cttatactct tgaacaactt gacacgaaga 1200
ataacatcct agtggatgaa ggaaggtgat ggaacttaaa gtttaggttt tatttttggc 1260
cttgtgataa aaaaaatgta attgtaaagt attagatcaa gtaataaaaa cagagttgtg 1320
ttttctattt ttgctgtgtt gggttgtgta tctttattgt gcttatggcc tagttgctaa 1380
agagttaagg ttattaccta aatgttttac ggtgtgttga gttgtaaaga tctcctgagt 1440
taaagttgga attttgtatt ggagattgtt ttgagaagtt tagcttacta attgtttaac 1500
tcattaggtg tctaagcgac acgcctcctt ttggtcgcat gaagtggcta gcagggtggg 1560
gcggaccggg gtggggtgtg ataataaacc taaaaaatca cccagataag cctaaattat 1620
acgttgaagt taaacttaca atttgattag aagaagaagg aatatctgat ttggacatga 1680
attaattaca aatacggcgc caatcataca aagcacatgt aagatcaacg cattctacac 1740
tcaatctcag ccgttgattg ctttcaatcc ttcaaaaaga aaaaaagaag ggcagttcgg 1800
gcagagtcat acctacccgt tgactataaa agcaactaca aatcgaaaac ctccatttct 1860
ccgttaccat tacagagaaa atcaaagaaa tttggcgttg agagattggg agagaggttt 1920
ctctttctag ggttgcttct tcttcttcat cctccattgt tgcaaatttc acttccttct 1980
cctcttgttc tcatctccc 1999

<210> SEQ ID NO 198
<211> LENGTH: 1578
<212> TYPE: DNA
<213> ORGANISM: Cucumis melo

<400> SEQUENCE: 198
atatatatat atataattta actaaataaa caaatgaaag aaaaaagtga gttcccattc 60
ggaaaatgca gatggatcca tttcttcaaa tattaaaaaa taaaaaaata aaataaaata 120
acttaaatat gcaaatagaa agaattttaa tttctggatt atccatatgg gacaattttt 180
aaaactcatt tattttattt tttttattta tttgattttg atatatctat ggggaaattt 240
ttcgtaataa ttttcgaaaa aatattgcaa tatatcattt gatcagatcg gtattattaa 300
atctctatca catttggtct taaattatcc aaagattcct ttaagataat ttagataacc 360
atctacagat cactactata atcaacaaaa ggaacaactt aaattattta aacaaattca 420
ttaatattag actttgtgct tcattagaaa atgatcttat cacaaccaca accatagtgg 480
tggtttaaaa ttttatttta aactcttatt agtattattt taattcatac ttaatcaaac 540
taattacttt aaaaaacata tatatataaa taagttaaat cattccccct tatatctaaa 600
taacataaaa aaaaattgtt tactctacaa gaagtttgta tatatatatg ctcggtacta 660
tttagcatct ttataataaa atttctaaat caatttttta tatctcttta ttaaatgtat 720
agtcatcaaa aaatttaacg agataatgtg tcaaagattt attttattaa cgttcataaa 780
tatcaaatta tacttagctt ataattgaaa acatgttcga taaatataag taaataaaat 840
tttatttttt ttaaatatta caaaataaac taaataagtt ataaatatga caataaacat 900
tatatatttt attatattta taaatactta ataatttagt cgtttaaaat aattttctta 960
attttcaaaa catgtttcat atgttaataa taaataaatg gaaaaccttc caaaagaaga 1020
aaaaaagata tcttaaaatt taaaaattga gattttgagg atcaataatt aataaaagaa 1080
ggattaataa gggtgaaatt aaatcccaaa aagaaaattg aaaatgaaga aaagaaaagt 1140
gaagaaataa ttgaacgtgg gaagtggatt cgatgtctcc agagaacaag cgaaaggaga 1200
cgaaatccac ataatttgca cgttacgtgt ccctatcaac cgtagacacg tgtcaacatc 1260
tcaacaccct acgccgaatt gcttcgctgg atctggacgg tcatcggata acagcggcaa 1320
ccaattaata tttcccctta tatttcacag cctggccatg tccaccaatc acgttcaact 1380
attaattcat ttttcatttc ctttttcttt ttttttttaa ttcccctcaa ttattaccga 1440
caacctgttg tagccggtta accctaccct ccaacgttcc attataaggc ctagaaaatg 1500
gacgtgaaaa tggagtacta caaactacaa ttaattttaa agaattttaa ttttaaagtt 1560
ctctaattac tattagcc 1578

<210> SEQ ID NO 199
<211> LENGTH: 1023
<212> TYPE: DNA
<213> ORGANISM: Cucumis melo

<400> SEQUENCE: 199
ataataataa taaatacata atagtaataa taataaaaaa aataaaaaaa taataatagt 60
aatgaaaatc aatagaataa ttttaaaatc gggaaggaag tcgtgtacaa tccttgcacg 120
ttggagagtc aaatggccta agtggtgatg tggaagtcgt gtaccgggta cacgattttc 180
ctacaagtca ataataataa tatggttatt tttctagttt agggttcatg acaaaagatt 240
gttcagtcga ctggatgtag acaaatctaa aaaataaatt aaaatctaat atgaaaacta 300
gttttaattt ccaaattatt aagggttgaa ttcgaccaat aaataataat aatacggtta 360
ttttgaaatt taggaaattg aataaagttg ttaaaatctt caagcaaatt gttaagcccc 420
gagatattaa gaagaggtaa taatagagga ttctatattt ataacatgtt aaaattaatt 480
gcaaactcat aaatgcatca cacagattaa caacatagga gggacttccg ataaaagtgc 540
aaatattgaa ataattacag ttcgcgaaca tgagtatttt aatattttat aaaatagtat 600
gcacgtgtat ttttgccaaa agaaaaaaag aatagatttt gccatttttc aaagtgactc 660
tcggttatat cttttatggc gattgtattt tatagcgtat gttgtttgta gttaacccat 720
ttctcattgg caaattcaat cgtgggccac aacgtttggg catagcttca atttggatta 780
actcaattat gtctgaatgg gttggactag ttcggactct tcggctgggc cagaatcaga 840
ttcgggccgc aatctgttca tttcacacct atatccaaac acccccaaaa tcgataccca 900
tcaaacccta actctcaata acccccatat ataaattcct tctttagggt tttttcatcc 960
tcatacactc tcaaacctcc ggtcattctc attttccctg ccgcttcttc aataacccta 1020
atc 1023

<210> SEQ ID NO 200
<211> LENGTH: 1654
<212> TYPE: DNA
<213> ORGANISM: Arabidopsis thaliana

<400> SEQUENCE: 200

```
tgatgattct tgttgttgta gttcttttta aaagtcccac ctgagcctct atagactctg     60
attctctttt aagttactat tttcaccgct ctctaataag gctcgtgatt ttttgggagc    120
catactgtat actcgccggc cctctcacga tgttgttcaa ttcacagact aaatttgatt    180
tatctatttc gccaaaacat aacttcatta aaaaatgttc tccaaataac taaacgaatt    240
aaataaaaga aacctttcat gtaaagttaa aggtatgaga ctttaagggc agttgctgaa    300
cattcgtaac acatgggaga acaatagaga aagttgaaaa gaaacgtagc atatagaaaa    360
attatctttg taaccaagtt gatttagaaa aatatcacta tttgtgaaaa atactagatc    420
agtttattat tacttttttt tttttgtata ttcacaaata tcatattcat atagaagaaa    480
ataaacaaag ttgtaaaaat ctggcattta aaataaaatt gaacacttca atttatttcc    540
tttcataata ataattttgg cataagatat ttgcaaattg atctggttcg gtatggtcga    600
caaaataatt ttccacgcta cccttccagc cgtccattca ctatttgccc tcaacgttac    660
caaataacgg tccagattcc tagggcaaga tctaacggtt agcaagtaaa gtcgtaccat    720
cagaaagaat aacaattctt tcacaaagta aacataacca acggttaaca agttcttagg    780
gttaaatcag taagatccaa cggatattaa attgcaaggc ccaaatagtt tttttgcagc    840
agataataac tcgtccccac tggcgagtga cgaccgagac tctgtgaccc tatttttcga    900
gacgataaaa gggcaaacaa tcgctctttt caaagctcgc ctcttcacca cagagaaaac    960
ttcgtctctc ttctctgctt cgccctctca tttcctgtga gataaaggcg gagtctctct   1020
ccagttattt tgctcatcca tcgattctta ggtatgactc gtttctctca gatctgtgat   1080
tctttataat ctcgtcgttc ttcaaatcat tgttatattc gtttcttcga tctgtgtttt   1140
ttagatctgt aaggtaaatg agacgtttcg atctgtagat ctgattgtta tattgataga   1200
ttatgttatc tgctttgctt aaagtccgat cggaatgttt tgtgctcatt gtcgaatatc   1260
tgatgtatcg gtttcataga tctgcttctt tttgtgcgtt tcgttgatct gataatcttc   1320
tagtgatcaa aatcgtttgg atctgttgac tttagtttaa aatgtatccg atctgatgtc   1380
gaggcttcat tattggaagt tgttattgtt gtaatcctga tttaagttgc tgttcttaaa   1440
tttatatgat ctttgcgtta taatatgaca tggtagatct tggttcatgg ttcactgttt   1500
tccaataaac ttggtttgtt tggttggata gcgttctgtg atacgaccat gtcttgtgtt   1560
ggataagaat tctctgaatt tccttggctg gtttgtagta tgttattcac gtctggtttc   1620
tcatcaatga ttatgtgatt ttgcagagtt cacc                               1654
```

<210> SEQ ID NO 201
<211> LENGTH: 712
<212> TYPE: DNA
<213> ORGANISM: Artificial sequence
<220> FEATURE:
<221> NAME/KEY: misc_feature
<222> LOCATION: (1)..(712)
<223> OTHER INFORMATION: Chimeric transcriptional regulatory expression element.

<400> SEQUENCE: 201

```
ggtccgatgt gagacttttc aacaaagggt aatatccgga aacctcctcg gattccattg     60
cccagctatc tgtcacttta ttgtgaagat agtggaaaag gaaggtggct cctacaaatg    120
ccatcattgc gataaaggaa aggccatcgt tgaagatgcc tctgccgaca gtggtcccaa    180
agatggaccc ccacccacga ggagcatcgt ggaaaaagaa gacgttccaa ccacgtcttc    240
```

aaagcaagtg gattgatgtg atggtccgat tgagactttt caacaaaggg taatatccgg 300
aaacctcctc ggattccatt gcccagctat ctgtcacttt attgtgaaga tagtggaaaa 360
ggaaggtggc tcctacaaat gccatcattg cgataaagga aaggccatcg ttgaagatgc 420
ctctgccgac agtggtccca aagatggacc cccacccacg aggagcatcg tggaaaaaga 480
agacgttcca accacgtctt caaagcaagt ggattgatgt gatatctcca ctgacgtaag 540
ggatgacgca caatcccact atccttcgca agacccttcc tctatataag gaagttcatt 600
tcatttggag aggacactct agacagaaaa atttgctaca ttgtttcaca aacttcaaat 660
attattcatt tatttgtcag ctttcaaact ctttgtttct tgtttgttga tt 712

<210> SEQ ID NO 202
<211> LENGTH: 938
<212> TYPE: DNA
<213> ORGANISM: Arabidopsis thaliana

<400> SEQUENCE: 202
caaaagccga gccgataaat cctaagccga gcctaacttt agccgtaacc atcagtcacg 60
gctcccgggc taattcattt gaaccgaatc ataatcaacg gtttagatca aactcaaaac 120
aatctaacgg caacatagac gcgtcggtga gctaaaaaga gtgtgaaagc caggtcacca 180
tagcattgtc tctcccagat tttttatttg ggaaataata gaagaaatag aaaaaaataa 240
aagagtgaga aaaatcgtag agctatatat tcgcacatgt actcgtttcg ctttccttag 300
tgttagctgc tgccgctgtt gtttctcctc catttctcta tctttctctc tcgctgcttc 360
tcgaatcttc tgtatcatct tcttcttctt caaggtgagt ctctagatcc gttcgcttga 420
ttttgctgct cgttagtcgt tattgttgat tctctatgcc gatttcgcta gatctgttta 480
gcatgcgttg tggttttatg agaaaatctt tgttttgggg gttgcttgtt atgtgattcg 540
atccgtgctt gttggatcga tctgagctaa ttcttaaggt ttatgtgtta gatctatgga 600
gtttgaggat tcttctcgct tctgtcgatc tctcgctgtt atttttgttt ttttcagtga 660
agtgaagttg tttagttcga aatgacttcg tgtatgctcg attgatctgg ttttaatctt 720
cgatctgtta ggtgttgatg tttacaagtg aattctagtg ttttctcgtt gagatctgtg 780
aagtttgaac ctagttttct caataatcaa catatgaagc gatgtttgag tttcaataaa 840
cgctgctaat cttcgaaact aagttgtgat ctgattcatg tttacttcat gagcttatcc 900
aattcatttc ggtttcattt tacttttttt ttagtgaa 938

<210> SEQ ID NO 203
<211> LENGTH: 633
<212> TYPE: DNA
<213> ORGANISM: Pisum sativum

<400> SEQUENCE: 203
agctttcgtt cgtatcatcg gtttcgacaa cgttcgtcaa gttcaatgca tcagtttcat 60
tgcgcacaca ccagaatcct actgagtttg agtattatgg cattgggaaa actgtttttc 120
ttgtaccatt tgttgtgctt gtaatttact gtgtttttta ttcggttttc gctatcgaac 180
tgtgaaatgg aaatggatgg agaagagtta atgaatgata tggtcctttt gttcattctc 240
aaattaatat tatttgtttt ttctcttatt tgttgtgtgt tgaatttgaa attataagag 300
atatgcaaac attttgtttt gagtaaaaat gtgtcaaatc gtggcctcta atgaccgaag 360
ttaatatgag gagtaaaaca cttgtagttg taccattatg cttattcact aggcaacaaa 420
tatattttca gacctagaaa agctgcaaat gttactgaat acaagtatgt cctcttgtgt 480
tttagacatt tatgaacttt cctttatgta attttccaga atccttgtca gattctaatc 540
attgctttat aattatagtt atactcatgg atttgtagtt gagtatgaaa atattttta 600 atgcatttta tgacttgcca attgattgac aac 633

<210> SEQ ID NO 204
<211> LENGTH: 315
<212> TYPE: DNA
<213> ORGANISM: Gossypium barbadense

<400> SEQUENCE: 204
tgatcacctg tcgtacagta tttctacatt tgatgtgtga tttgtgaaga acatcaaaca 60
aaacaagcac tggctttaat atgatgataa gtattatggt aattaattaa ttggcaaaaa 120
caacaatgaa gctaaaattt tatttattga gccttgcggt taatttcttg tgatgatctt 180
tttttttatt ttctaattat atatagtttc ctttgctttg aaatgctaaa ggtttgagag 240
agttatgctc tttttttctt cctctttctt ttttaacttt atcatacaaa ttttgaataa 300
aaatgtgagt acatt 315

<210> SEQ ID NO 205
<211> LENGTH: 315
<212> TYPE: DNA
<213> ORGANISM: Gossypium barbadense

<400> SEQUENCE: 205
accatatgac actggtgcat gtgccatcat catgcagtaa tttcatggta tatcttaatt 60
atatggttaa taaaaaaaag atggtgagtg aataatgtgc gtgcattcct ccatgcacca 120
atggtgaatc tctttgcata catagagatt ctgaatgatt atagtttatg ttgtagtgaa 180
attaattttg aatgttgttt ttaaatttta atgtcacttg gcttgattta tgttttaacg 240
aagcttatgt tatgtatttt actttaatga tattgcatgt attgttaatt taacattgct 300
tgatcagtat actct 315

<210> SEQ ID NO 206
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Codon redesigned coding sequence.

<400> SEQUENCE: 206
atggtccgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240
ggccagcgta tcgtgctgcg tttcgatgcg gtcactcatt acggcaaagt gtgggtcaat 300
aatcaggaag tgatggagca tcagggcggc tatacgccat ttgaagccga tgtcacgccg 360
tatgttattg ccgggaaaag tgtacgtaag tttctgcttc tacctttgat atatatataa 420
taattatcat taattagtag taatataata tttcaaatat ttttttcaaa ataaaagaat 480
gtagtatata gcaattgctt ttctgtagtt tataagtgtg tatattttaa tttataactt 540
ttctaatata tgaccaaaat ttgttgatgt gcaggtatca ccgtttgtgt gaacaacgaa 600

```
ctgaactggc agactatccc gccgggaatg gtgattaccg acgaaaacgg caagaaaaag    660
cagtcttact tccatgattt ctttaactat gccggaatcc atcgcagcgt aatgctctac    720
accacgccga acacctgggt ggacgatatc accgtggtga cgcatgtcgc gcaagactgt    780
aaccacgcgt ctgttgactg gcaggtggtg gccaatggtg atgtcagcgt tgaactgcgt    840
gatgcggatc aacaggtggt tgcaactgga caaggcacta gcgggacttt gcaagtggtg    900
aatccgcacc tctggcaacc gggtgaaggt tatctctatg aactgtgcgt cacagccaaa    960
agccagacag agtgtgatat ctacccgctt cgcgtcggca tccggtcagt ggcagtgaag   1020
ggcgaacagt tcctgattaa ccacaaaccg ttctacttta ctggctttgg tcgtcatgaa   1080
gatgcggact tgcgtggcaa aggattcgat aacgtgctga tggtgcacga ccacgcatta   1140
atggactgga ttggggccaa ctcctaccgt acctcgcatt acccttacgc tgaagagatg   1200
ctcgactggg cagatgaaca tggcatcgtg gtgattgatg aaactgctgc tgtcggcttt   1260
aacctctctt taggcattgg tttcgaagcg ggcaacaagc cgaaagaact gtacagcgaa   1320
gaggcagtca acggggaaac tcagcaagcg cacttacagg cgattaaaga gctgatagcg   1380
cgtgacaaaa accacccaag cgtggtgatg tggagtattg ccaacgaacc ggatacccgt   1440
ccgcaaggtg cacgggaata tttcgcgcca ctggcggaag caacgcgtaa actcgacccg   1500
acgcgtccga tcacctgcgt caatgtaatg ttctgcgacg ctcacaccga taccatcagc   1560
gatctctttg atgtgctgtg cctgaaccgt tattacggat ggtatgtcca aagcggcgat   1620
ttggaaacgg cagagaaggt actggaaaaa gaacttctgg cctggcagga gaaactgcat   1680
cagccgatta tcatcaccga atacggcgtg gatacgttag ccgggctgca ctcaatgtac   1740
accgacatgt ggagtgaaga gtatcagtgt gcatggctgg atatgtatca ccgcgtcttt   1800
gatcgcgtca gcgccgtcgt cggtgaacag gtatggaatt tcgccgattt tgcgacctcg   1860
caaggcatat tgcgcgttgg cggtaacaag aaagggatct tcactcgcga ccgcaaaccg   1920
aagtcggcgg cttttctgct gcaaaaacgc tggactggca tgaacttcgg tgaaaaaccg   1980
cagcagggag gcaaacaatg a                                             2001
```

<210> SEQ ID NO 207
<211> LENGTH: 1653
<212> TYPE: DNA
<213> ORGANISM: Artificial sequence
<220> FEATURE:
<221> NAME/KEY: misc_feature
<222> LOCATION: (1)..(1653)
<223> OTHER INFORMATION: Codon redesinged coding sequence.

<400> SEQUENCE: 207

```
atggaagacg ccaaaaacat aaagaaaggc ccggcgccat tctatcctct agaggatgga     60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
```

```
tctactgggt tacctaaggg tgtggccctt ccgcatagaa ctgcctgcgt cagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttt tacgatccct tcaggattac    840

aaaattcaaa gtgcgttgct agtaccaacc ctattttcat tcttcgccaa aagcactctg    900

attgacaaat acgatttatc taatttacac gaaattgctt ctgggggcgc acctctttcg    960

aaagaagtcg gggaagcggt tgcaaaacgc ttccatcttc cagggatacg acaaggatat   1020

gggctcactg agactacatc agctattctg attacacccg agggggatga taaaccgggc   1080

gcggtcggta aagttgttcc attttttgaa gcgaaggttg tggatctgga taccgggaaa   1140

acgctgggcg ttaatcagag aggcgaatta tgtgtcagag gacctatgat tatgtccggt   1200

tatgtaaaca atccggaagc gaccaacgcc ttgattgaca aggatggatg gctacattct   1260

ggagacatag cttactggga cgaagacgaa cacttcttca tagttgaccg cttgaagtct   1320

ttaattaaat acaaaggata tcaggtggcc cccgctgaat tggaatcgat attgttacaa   1380

caccccaaca tcttcgacgc gggcgtggca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gtccaaattg taa                                1653
```

```
<210> SEQ ID NO 208
<211> LENGTH: 936
<212> TYPE: DNA
<213> ORGANISM: Artificial sequence
<220> FEATURE:
<221> NAME/KEY: misc_feature
<222> LOCATION: (1)..(936)
<223> OTHER INFORMATION: Codon redesigned coding sequence.

<400> SEQUENCE: 208
```

```
atggcttcca aggtgtacga ccccgagcaa cgcaaacgca tgatcactgg gcctcagtgg     60

tgggctcgct gcaagcaaat gaacgtgctg gactccttca tcaactacta tgattccgag    120

aagcacgccg agaacgccgt gatttttctg catggtaacg ctgcctccag ctacctgtgg    180

aggcacgtcg tgcctcacat cgagcccgtg gctagatgca tcatccctga tctgatcgga    240

atgggtaagt ccggcaagag cgggaatggc tcatatcgcc tcctggatca ctacaagtac    300

ctcaccgctt ggttcgagct gctgaacctt ccaaagaaaa tcatctttgt gggccacgac    360

tgggggggctt gtctggcctt tcactactcc tacgagcacc aagacaagat caaggccatc    420

gtccatgctg agagtgtcgt ggacgtgatc gagtcctggg acgagtggcc tgacatcgag    480

gaggatatcg ccctgatcaa gagcgaagag ggcgagaaaa tggtgcttga gaataacttc    540

ttcgtcgaga ccatgctccc aagcaagatc atgcggaaac tggagcctga ggagttcgct    600

gcctacctgg agccattcaa ggagaagggc gaggttagac ggcctaccct ctcctggcct    660

cgcgagatcc ctctcgttaa gggaggcaag cccgacgtcg tccagattgt ccgcaactac    720

aacgcctacc ttcgggccag cgacgatctg cctaagatgt tcatcgagtc cgaccctggg    780

ttcttttcca acgctattgt cgagggagct aagaagttcc ctaacaccga gttcgtgaag    840

gtgaagggcc tccacttcag ccaggaggac gctccagatg aaatgggtaa gtacatcaag    900
```

agcttcgtgg agcgcgtgct gaagaacgag cagtaa 936

<210> SEQ ID NO 209
<211> LENGTH: 253
<212> TYPE: DNA
<213> ORGANISM: Agrobacterium tumefaciens

<400> SEQUENCE: 209
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

<210> SEQ ID NO 210
<211> LENGTH: 622
<212> TYPE: DNA
<213> ORGANISM: Cauliflower mosaic virus

<400> SEQUENCE: 210
ggtccgattg agacttttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240
aagcaagtgg attgatgtga tggtccgatt gagacttttc aacaaagggt aatatccgga 300
aacctcctcg gattccattg cccagctatc tgtcacttta ttgtgaagat agtggaaaag 360
gaaggtggct cctacaaatg ccatcattgc gataaaggaa aggccatcgt tgaagatgcc 420
tctgccgaca gtggtcccaa agatggaccc ccacccacga ggagcatcgt ggaaaaagaa 480
gacgttccaa ccacgtcttc aaagcaagtg gattgatgtg atatctccac tgacgtaagg 540
gatgacgcac aatcccacta tctagacgca agacccttcc tctatataag gaagttcatt 600
tcatttggag aggacacgct ga 622

<210> SEQ ID NO 211
<211> LENGTH: 1446
<212> TYPE: DNA
<213> ORGANISM: Cucumis melo

<400> SEQUENCE: 211
tcccttcagc cacttaacac ttaaaaatct taggaaactc catgggctcc tctttctcca 60
atgaaatttt gacatctgtg ttgttgatag ctcctatatc ctttgagaat ttgatataca 120
cctgtcattt gctgatttgt ggataactgt tagccttttg atattgatac gttccttttt 180
ttatgaattt ttgtaaatcc attcaatttt aatgctgtcg taaatgaaaa gccctttcat 240
taatgttgtt tatatacata ttttaaaatt aattcaataa caagtttagt tctgttagct 300
tctaggtttg tatctatttt atctattaaa ggtatgtttg ggcttcaggt tggaatggag 360
tagaattgaa tgggttgggg agtaaatttt ccattcaaca agttcaattt caaaatggct 420
aataagtttt gaactcaatt ttattttcaa taaattcctt aattttttgt tccttgtttg 480
taaactattg acttattcga tatattttaa aattgaggta ttttaaaaaa ataatacaat 540
attaaaatta tttataaaat ataacaaaat ttatgtatag tttatttgaa aattttacta 600
tagtttcatt tttatattat tcctaaccat ttccatttaa aattatttca attatttctt 660

```
ttattaatat aattgaaatt tcatggattt attagacaca tgatttgaaa ttttatgggt    720
ttattaagta ttttctaaca caaaatcgct tccgcatcgt tttcaattca ttcagtaata    780
gaagtaattt tttaaaagaa ccaaatttgc caaattttga gttccataag gactctgaaa    840
actcattatg tctattactc ttcactaatt gtagagactt aaattcaaga taagagacac    900
taattgatga taattgccca aaaaataaaa ataaaaatgt ttcttcccca tcctcaacct    960
ccatgaattc acagagccca aagattaatt attgggcccc aattcctact catatatacc   1020
ttacagtccc tcaaagaaat cttaggaagt aatcaatttc tgtttattca agatgtagcc   1080
tcccaaaaga aaaatacatc acatcaaatt caaacaaaaa tatctacagc tagcaaaacc   1140
tcaaaccgtt aaaatttcaa gccacataaa tgaaattttc atctgaaaaa aggacaatct   1200
atctagacgt tagatttcag ccctaatatg aatctgaagc atttggtgga cgagaaagag   1260
ccatgtagga atgcatcaaa caaaggaaaa atctttgaac tccaatggga ttgaagatac   1320
agataccaat ggataagaat ctgttctctt tgcccactat ttaaactcac caaacccacc   1380
agtatcttcc tcaccacaaa atacattcca ccgttgatca caagccttat tccaccacct   1440
ccaaca                                                              1446
```

<210> SEQ ID NO 212
<211> LENGTH: 2018
<212> TYPE: DNA
<213> ORGANISM: Cucumis melo

<400> SEQUENCE: 212

```
actattggag acgacgaagg aaaactctaa tgtgagctta gaattgaaga tggtgaacaa     60
ttgggagtct tttttaaaaa tctttcgtcg gtatattgaa atttcctttt acactcaaat    120
aacccccctt ttcacgcgtt caacgtcttc aaaccttcct ttttcaatta ttttttcgtt    180
tacattaatg acatttaggt aataagataa attagtggat tcttttgtga aaaatgttag    240
cccatttaag acttttatga aatatattag aaaaaaatca tatagcaatt tatattattc    300
tagttaaaag cccataatag aaactaaccc aacctaaagt aacgtaaaca ttcaataaga    360
gagacaaatt ttaaaataat ttctaattaa aaaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccctactac ggtaagtcga ccttactgct ttcggcttct    600
agttttttca atcctgtcat tagtcctttg gagttcttct gtacatttat gacgttttcg    660
gctcgtgttt tgtttcgcct gtatgtagtg ggtttttcga gttttgtttt tacttttttt    720
tatacttgca ggaattagtt gaaatctatg tacttcatgc cttggataat actcttgatc    780
tgttgtgtta ttcaaaatga attgttttaa gatggtattt gagaatggtc atgtgagttt    840
tgcctacttg gttattaaaa tgaattgttt taggatggta tttgagaatg gtcttctggg    900
tatttggttg gaacctttgt gctctgctat gaattagggt gttctccccg ttttttttt    960
ttttttctt ttggttatta atatatcttt tatgactact tattcatata tgatatcttt    1020
tactcgtaaa ttttgactca tttgaaagtt ttatccttag tcctttctca ttcagggtgt   1080
aaaggtatgt tgttagggtt aaaatagcct atgcaggaaa gttctgtatt tgttctaatt   1140
attgcatttg tgtgcatttg tatctagttt atttcttgct gagagtatgc ttcatttttt   1200
agtacacatc acttgtgcca ctttattata gttgcacatt tttgtttatg gagaggatga   1260
```

-continued

```
atagcattta gggatgtcaa ttttttattg agaaaaccct ctctcctact taagcttggg   1320

gaatttttgt tctaaatgtg gtaaacataa tacttcttct tattttaatt tgaatggaag   1380

gggaagacga atactaatat tttcaacgaa ccttcacaac ttttttttc ttatttagga   1440

agccatgttt ttcaaaattg tactgtgtga tccacatatt tatcgattat tagtgaatcg   1500

aataataatt agagttttat tggtataatt ttgaagttca gacttattac atttgtggaa   1560

agtttggtta caattttcaa ttttattgga atcctaagaa ctttgtgtta acatatattg   1620

agtttcttc tcttttttt tactcattaa gttctctatt aggaatgttt ggttcaatgt   1680

cacatagtcg atagctaaga ccagtgaccc acaaagctat gattgaacga aaaacaagcc   1740

tttcacatct tggtaggaat ttgttatttc tcaatagatt tacagagctg tttcatgtga   1800

tcacaatttt tttctatttt tctgaagttc tctattagga atgggctatc tggttagttg   1860

cttttgagag aacatgtgga ttggtgttgc tcggtttcct tgcctttgta attttgtcct   1920

tggaaaaagc aaaatgatta ggtatcctga tatgcataac atgtttaagc caactagttc   1980

tcactttttt agtgcaaata attgatcttc aggaatcg                          2018
```

PLANT REGULATORY ELEMENTS AND USES THEREOF

REFERENCE TO RELATED APPLICATIONS

This application is a divisional of co-pending U.S. application Ser. No. 15/802,843, filed Nov. 3, 2017, which is a divisional of U.S. application Ser. No. 14/117,342, filed Oct. 23, 2014 (now issued U.S. Pat. No. 9,845,477) which is a 371 National Stage application of International Application No. PCT/US12/037561, filed May 11, 2012, which claims the benefit of U.S. Provisional Application No. 61/485,876, filed May 13, 2011, each of which is herein incorporated by reference in its entirety.

INCORPORATION OF SEQUENCE LISTING

The sequence listing that is contained in the file named "MONS304WO.txt", which is 463 kilobytes (as measured in Microsoft Windows®) and was created on May 9, 2012, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements such as promoters, leaders and introns derived from *Cucumis melo,* a plant species commonly referred to as muskmelon, for use in plants. The present invention also provides DNA constructs, transgenic plant cells, plants, and seeds comprising the regulatory elements. The sequences may be provided operably linked to a transcribable polynucleotide molecule which may be heterologous with respect to a regulatory sequence provided herein. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule, such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, a transcriptional regulatory expression element group, or promoter, or leader, or intron is at least 90 percent, at least 95 percent, at least 98 percent, or at least 99 percent identical to any of SEQ ID NOs: 1-199, 211 and 212. In particular embodiments, the heterologous transcribable polynucleotide molecule comprises a gene of agronomic interest, a gene capable of providing herbicide resistance in plants, or a gene capable of providing plant pest resistance in plants.

The invention also provides a transgenic plant cell containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. Further, the transcriptional regulatory expression element group, or promoter, or leader, or intron regulates the expression of a gene. The transgenic plant cell can be a monocotyledonous or dicotyledonous plant cell.

Further provided by the invention is a transgenic plant, or part of the transgenic plant containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, the transgenic plant may be a progeny plant of any generation that contains the transcriptional regulatory expression element group, or promoter, or leader, or intron.

Still further provided is a transgenic seed containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In yet another aspect, the invention provides a method of producing a commodity product from the transgenic plant, transgenic plant part or transgenic seed which contains a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In one embodiment, the commodity product is protein concentrate, protein isolate, grain, starch, seeds, meal, flour, biomass, or seed oil.

In another aspect, the invention provides a commodity product comprising a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In still yet another aspect, the invention provides a method of expressing a transcribable polynucleotide molecule in a transgenic plant using a DNA molecule such as a transcriptional regulatory expression element group, or promoter, or leader, or intron which has a DNA sequence which is at least 85 percent identical to that of any of SEQ ID NOs: 1-199, 211 and 212, or contains any of SEQ ID NOs: 1-199, 211 and 212, or consists of a fragment of any of SEQ ID NOs: 1-199, 211 and 212; and cultivating the transgenic plant.

BRIEF DESCRIPTION OF THE SEQUENCES

SEQ ID NOs: 1, 5, 7, 9, 11, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 are *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element.

SEQ ID NOs: 2, 6, 8, 10, 12, 163 and 169 are promoter elements.

SEQ ID NOs: 3, 164, 166 and 170 are leader sequences.

SEQ ID NOs: 4, 165 and 171are intron sequences.

SEQ ID NOs: 157, 160, 173, 179 and 186 are sequences wherein a promoter is operably linked to a leader element.

SEQ ID NOs: 158, 161, 174, 180 and 187 are sequences wherein an intron is operably linked to a leader element.

BRIEF DESCRIPTION OF THE DRAWINGS

FIGS. 1*a*-1*f* depict alignment of promoter variant segments corresponding to promoter elements isolated from the Cucumis melo. In particular, FIGS. 1*a*-1*f* show alignment of the 2068 bp promoter sequence P-CUCme.Ubq1-1:1:15 (SEQ ID NO: 2), found in the transcriptional regulatory expression element group EXP-CUCme.Ubq1:1:1 (SEQ ID NO: 1), vs. promoter sequences derived via 5' deletions of the promoter, P-CUCme.Ubq1-1:1:15. Deletion, for instance of the 5' end of P-CUCme.Ubq1-1:1:15, produced the promoters, P-CUCme.Ubq1-1:1:16 (SEQ ID NO: 6) a 1459 bp promoter which is found within EXP-CUCme.Ubq1:1:2 (SEQ ID NO: 5); P-CUCme.Ubq1-1:1:17 (SEQ ID NO: 8), a 964 bp sequence comprised within EXP-CUCme.Ubq1:1:3 (SEQ ID NO: 7); P-CUCme.Ubq 1-1:1:18 (SEQ ID NO: 10), a 479 bp sequence comprised within EXP-CUCme.Ubq1:1:4 (SEQ ID NO: 9); and P-CUCme.Ubq1-1:1:19 (SEQ ID NO: 12), a 173 bp sequence comprised within EXP-CUCme.Ubq1:1:5 (SEQ ID NO: 11).

DETAILED DESCRIPTION OF THE INVENTION

Figure 1A:
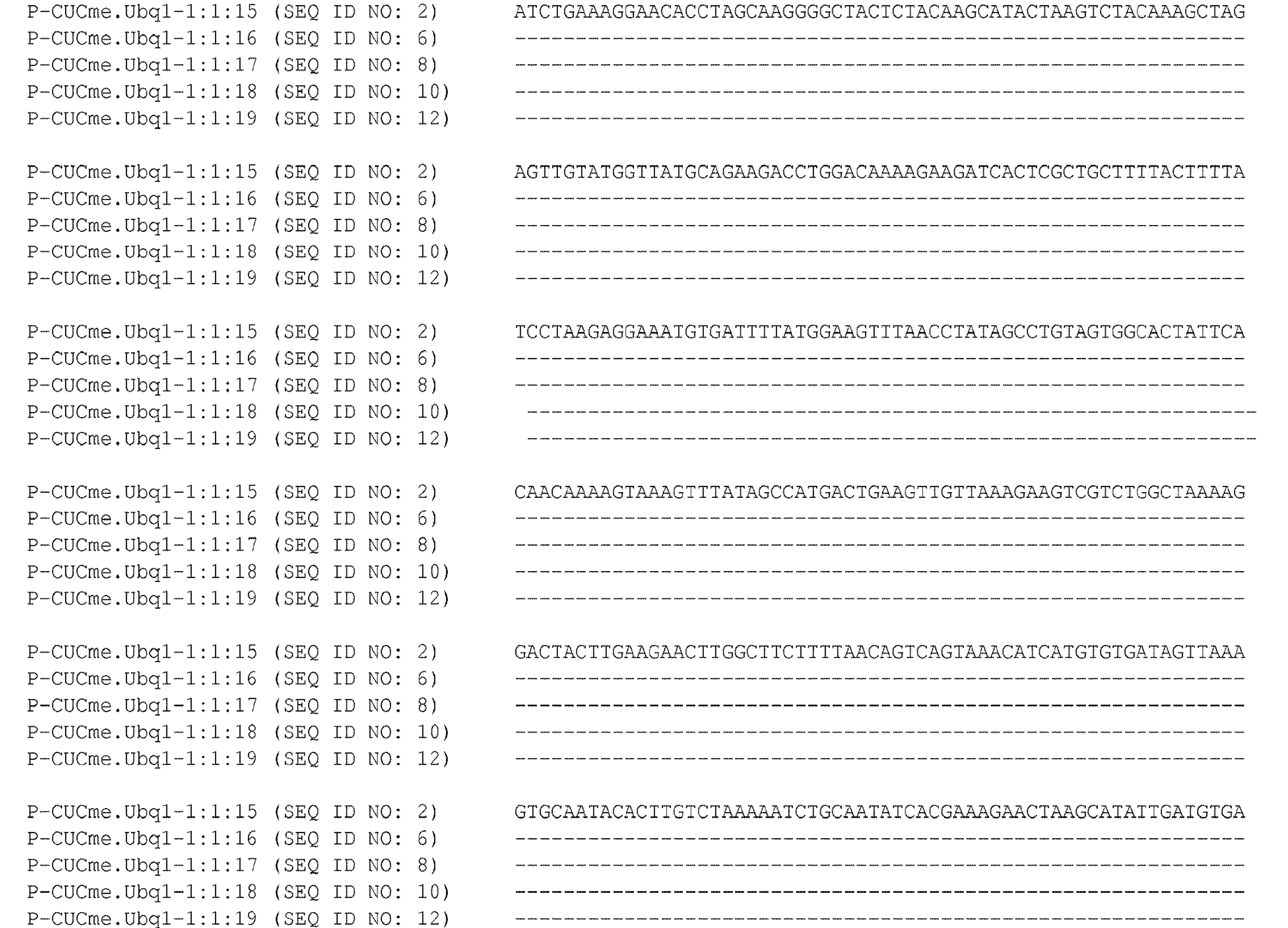

The invention disclosed herein provides polynucleotide molecules obtained from *Cucumis melo* having beneficial gene regulatory activity. The design, construction, and use of these polynucleotide molecules are described. The nucleotide sequences of these polynucleotide molecules are provided among SEQ ID NOs: 1-199, 211 and 212. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods are known in the to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-199, 211 and 212.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-199, 211 and 212, has at least about 85 percent identity at least about 90 percent identity at least about 95 percent identity, at least about 96 percent identity, at least about 97 percent identity, at least about 98 percent identity, or at least about 99 percent identity to the reference sequence. In particular embodiments such sequences may be defined as having gene-regulatory activity or encoding a peptide that functions to localize an operably linked polypeptide within a cell.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group (EXP) may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include any of SEQ ID NOs: 2, 6, 8, 10, 12, 163 and 169, or the promoter elements comprised within any of SEQ ID NOs: 13 through 199, 211 and 212, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for intiation of transcription.

In one embodiment, fragments of a promoter molecule are provided. Promoter fragments provide promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOs: 2, 6, 8, 10, 12, 163 and 169, or the promoter elements comprised within SEQ ID NOs: 13 through 199, 211 and 212, such as internal or 5' deletions, for example, can be produced to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOs: 2, 6, 8, 10, 12, 163 and 169, or the promoter elements comprised within SEQ ID NOs: 13 through 199, 211 and 212 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOs: 2, 6, 8, 10, 12, 163 and 169, or the promoter elements comprised within SEQ ID NOs: 13 through 199, 211 and 212, and fragments or enhancers derived there from can be used to make chimeric transcriptional regulatory element compositions comprised of any of the promoters presented as SEQ ID NOs: 2, 6, 8, 10, 12, 163 and 169, or the promoter elements comprised within SEQ ID NOs: 13 through 199, 211 and 212, and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOs: 3, 164, 166 and 170, or the leader element comprised within SEQ ID NOs: 13 through 199, 211 and 212, or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOs: 3, 164, 166 and 170, or the leader element comprised within any of SEQ ID NOs: 13 through 199, 211 and 212 may be comprised of regulatory elements or may adopt secondary structures that can have an effect on transcription or translation of a transgene. The leader sequences presented as SEQ ID NOs: 3, 164, 166 and 170, or the leader element comprised within SEQ ID NOs: 13 through 199, 211 and 212 can be used in accordance with the invention to make chimeric regulatory elements that affect transcription or translation of a transgene. In addition, the leader sequences presented as SEQ ID NOs: 3, 164, 166 and 170, or the leader element comprised within any of SEQ ID NOs: 13 through 199, 211 and 212 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However, multiple use of the same intron in one transgenic plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOs: 4, 165 and 171 or the intron element comprised within SEQ ID NOs: 13 through 199, 211 and 212 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter.cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from petunia (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.*11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pati gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adla gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In W E Cohn, K Moldave, eds, *Progress in Nucleic Acid Research and Molecular Biology,* Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause IME.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/or insertion of one or more nucleotides of a reference sequence, wherein the derivative regulatory element has more or less or equivalent transcriptional or translational activity than the corresponding parent regulatory molecule. The regulatory element "variants" may also encompass variants arising from mutations that naturally occur in bacterial and plant cell transformation. In the present invention, a polynucleotide sequence provided as SEQ ID NOs: 1-199, 211 and 212 may be used to create variants similar in composition, but not identical to, the polynucleotide sequence of the original regulatory element, while still maintaining the general functionality of, i.e. same or similar expression pattern, the original regulatory element. Production of such variants of the present invention is well within the ordinary skill of the art in light of the disclosure and is encompassed within the scope of the present invention. "Varients" of chimeric regulatory element comprise the same constituent elements as a reference chimeric regulatory element sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the chimeric regulatory element as well as other methods known in the art. The resulting "variant" chimeric regulatory element is comprised of the same, or variants of the same, constituent elements as the reference sequence but differ in the sequence or sequences that are used to operably link the constituent elements. In the present invention, the polynucleotide sequences provided as SEQ ID NOs: 1-199, 211 and 212 each provide a reference sequence wherein the constituent elements of the reference sequence may be joined by methods known in the art and may consist of substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known in the art of plant transformation can function in the present invention.

Methods are available for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells can be found in, for example, Molecular Cloning: *A Laboratory Manual, 3rd edition Volumes* 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses,* Butterworths, Boston, (1988) and Glick, et al., *Methods in Plant Molecular Biology and Biotechnology,* CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605). The expression properties imparted by such operable linkages of heterologous elements is not necessarily additive of the elucidated properties of each promoter and leader, but rather is determined through empirical analysis of expression driven by the operably linked heterologous promoter and leader.

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOs: 4, 165 and 171 or the intron element comprised within any of SEQ ID NOs: 13 through 199, 211 and 212.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules are the nopaline synthase 3' region (see, Fraley, el al., *Proc. NaCl. Acad. Sci. USA,* 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *Bio-Techniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Foxtail millet (*Setaria italica* (L.) Beauv). Libraries of cDNA are made from tissues isolated from selected plant species using flower tissue, seed, leaf and root. The resulting cDNAs are sequenced using various sequencing methods. The resulting ESTs are assembled into clusters using bioinformatics software such as clc_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-199, 211 and 212, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding ß-glucuronidase (GUS described in U.S. Pat. No. 5,599,670), green fluorescent protein and variants thereof (GFP described in U.S. Pat. No. 5,491,084 and 6,146,826), proteins that confer antibiotic resistance, or proteins that confer herbicide tolerance. Useful antibiotic resistance markers include those encoding proteins conferring resistance to kanamycin (nptII), hygromycin B (aph IV), streptomycin or spectinomycin (aad, spec/strep) and gentamycin (aac3 and aacC4). Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, delapon, dicamba, cyclohezanedione, protoporphyrinogen oxidase inhibitors, and isoxasflutole herbicides. Transcribable polynucleotide molecules encoding proteins involved in herbicide tolerance include, but are not limited to, a transcribable polynucleotide molecule encoding 5-enolpyruvylshikimate-3-phosphate synthase (EPSPS for glyphosate tolerance described in U.S. Pat. No. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtII described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glypho sate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Any transformation methods may be utilized to transform a host cell with one or more promoters and/or constructs of the present invention. Host cells may be any cell or organism such as a plant cell, algae cell, algae, fungal cell, fungi, bacterial cell, or insect cell. Preferred hosts and transformed cells include cells from: plants, *Aspergillus,* yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding,* John Wiley & Sons, NY, U. of CA, Davis, Calif., 50-98 (1960); Simmonds, *Principles of crop improvement,* Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique,* (Vol. 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Novel transcriptional regulatory elements, or transcriptional regulatory expression element group (EXP) sequences were identified and isolated from genomic DNA of the dicot species *Cucumis melo* WSH-39-1070AN.

Transcriptional regulatory elements were selected based upon proprietary and public microarray data derived from transcriptional profiling experiments conducted in soybean (*Glycine max*) and Arabidopsis as well as homology based searches using known dicot sequences as query against proprietary *Cucumis melo* sequences.

Using the identified sequences, a bioinformatic analysis was conducted to identify regulatory elements within the amplified DNA, followed by identification of the transcriptional start site (TSS) and any bi-directionality, introns, or upstream coding sequence present in the sequence. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *Cucumis melo.* The resulting DNA fragments were ligated into base plant expression vectors using standard restriction enzyme digestion of compatible restriction sites and DNA ligation methods.

Analysis of the regulatory element TSS and intron/exon splice junctions can be performed using transformed plant protoplasts. Briefly, the protoplasts are transformed with the plant expression vectors comprising the cloned DNA fragments operably linked to a heterologous transcribable polynucleotide molecule and the 5' RACE System for Rapid Amplification of cDNA Ends, Version 2.0 (Invtrogen, Carlsbad, Calif. 92008) is used to confirm the regulatory element TSS and intron/exon splice junctions by analyzing the sequence of the mRNA transcripts produced thereby.

Sequences encoding ubiquitin 1 transcriptional regulatory expression element groups (EXP) were analyzed as described above and each transcriptional regulatory expression element groups ("EXP's") was also broken down into the corresponding promoters, leaders and introns comprising each transcriptional regulatory expression element group. Sequences of the identified ubiquitin 1 transcriptional regulatory expression element groups ("EXP's") are provided herein as SEQ ID NOs: 1, 5, 7, 9 and 11 and is listed in Table 1 below. The corresponding ubiquitin 1 promoters are provided herein as SEQ ID NOs: 2, 6, 8, 10 and 12. The ubiquitin 1leader and intron are herein provided as SEQ ID NOs: 3 and 4, respectively.

Sequences encoding other Cucumis transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element are provided as SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 and are also listed in Table 1 below. Additional promoter elements are provided as SEQ ID NOs: 163 and 169. Additional leader elements are provided as SEQ ID NOs: 164, 166 and 170. Additional intron elements are provided as SEQ ID NOs: 165 and 171. Elements wherein a promoter is operably linked to a leader element are provided as SEQ ID NOs: 157, 160, 173, 179 and 186. Elements wherein an intron is operably linked to a leader element are provided as SEQ ID NOs: 158, 161, 174, 180 and 187. With respect to the subset of sequences provided as SEQ ID NOs: 13 through 199, 211 and 212, these sequences were selected and cloned based upon the results of experiments such as transcript profiling or expression driven by promoters from homologous genes of a different species suggesting desirable patterns of expression such as constitutive expression, root expression, above ground expression or seed expression. The actual activity imparted by the *Cucumis* sequences is determined empirically and is not necessarily the same as that of a regulatory element derived from a homologous gene from a species other than *Cucumis melo* when used in a transformed plant host cell and whole transgenic plant.

TABLE 1

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| EXP-CUCme.Ubq1:1:1 | 1 | Ubiquitin 1 | EXP | 2611 | Promoter; Leader; Intron | 1-2068; 2069-2150; 2151-2608 |
| P-CUCme.Ubq1-1:1:15 | 2 | Ubiquitin 1 | P | 2068 | Promoter | |
| L-CUCme.Ubq1-1:1:1 | 3 | Ubiquitin 1 | L | 82 | Leader | |
| I-CUCme.Ubq1-1:1:1 | 4 | Ubiquitin 1 | I | 461 | Intron | |
| EXP-CUCme.Ubq1:1:2 | 5 | Ubiquitin 1 | EXP | 2002 | Promoter; Leader; Intron | 1-1459; 1460-1541; 1542-1999 |
| P-CUCme.Ubq1-1:1:16 | 6 | Ubiquitin 1 | P | 1459 | Promoter | |
| EXP-CUCme.Ubq1:1:3 | 7 | Ubiquitin 1 | EXP | 1507 | Promoter; Leader; Intron | 1-964; 965-1046; 1047-1504 |
| P-CUCme.Ubq1-1:1:17 | 8 | Ubiquitin 1 | P | 964 | Promoter | |
| EXP-CUCme.Ubq1:1:4 | 9 | Ubiquitin 1 | EXP | 1022 | Promoter; Leader; Intron | 1-479; 480-561; 562-1019 |
| P-CUCme.Ubq1-1:1:18 | 10 | Ubiquitin 1 | P | 479 | Promoter | |
| EXP-CUCme.Ubq1:1:5 | 11 | Ubiquitin 1 | EXP | 716 | Promoter; Leader; Intron | 1-173; 174-255; 256-713 |
| P-CUCme.Ubq1-1:1:19 | 12 | Ubiquitin 1 | P | 173 | Promoter | |
| P-CUCme.1-1:1:1 | 13 | Phosphatase 2A | EXP | 2000 | Promoter; Leader; Intron; Leader | Reverse compliment; see SEQ ID NO: 155 |
| P-CUCme.2-1:1:1 | 14 | Actin 1 | EXP | 2000 | Promoter; Leader; Intron; Leader | 1-964; 965-1028; 1029-1991; 1992-2003 |
| P-CUCme.3-1:1:3 | 15 | Actin 2 | EXP | 1990 | Promoter; Leader; Intron; Leader | 1-1243; 1244-1319; 1320-1982; 1983-1990 |
| P-CUCme.4-1:1:2 | 16 | Ubiquitin 2 | EXP | 2005 | Promoter; Leader; Intron; Leader | 1-1646; 1647-1704; 1705-2005; 2006-2008 |
| P-CUCme.5-1:1:2 | 17 | Ubiquitin 3 | EXP | 2004 | Promoter; Leader; Intron | 1-748; 749-819; 820-2004 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.6-1:1:1 | 18 | Tubulin beta chain | EXP | 1935 | Promoter; Leader; Intron; Leader | 1-1436; 1437-1482; 1483-1919; 1920-1935 |
| P-CUCme.8-1:1:2 | 19 | Tubulin beta chain | EXP | 1606 | Promoter; Leader | 1-1527; 1528-1606 |
| P-CUCme.9-1:1:2 | 20 | Tubulin beta chain | EXP | 1487 | Promoter; Leader | 1-1384; 1385-1487 |
| P-CUCme.10-1:1:1 | 21 | Tubulin beta chain | EXP | 1448 | Promoter; Leader | 1-1363; 1364-1448 |
| P-CUCme.11-1:1:2 | 22 | Elongation Factor 1 alpha | EXP | 1235 | Promoter; Leader; Intron | 1-617; 618-677; 678-1213; 1214-1235 |
| P-CUCme.15-1:1:2 | 23 | Elongation Factor 1 alpha | EXP | 2003 | Promoter; Leader; Intron; Leader | 1-1330; 1331-1435; 1430-1975; 1976-2002 |
| P-CUCme.16a-1:1:2 | 24 | Ubiquitin 7 | EXP | 2015 | Promoter; Leader | |
| P-CUCme.16b-1:1:1 | 25 | Ubiquitin 6 | EXP | 2006 | Promoter; Leader | |
| P-CUCme.17-1:1:2 | 26 | ubiquitin-40S ribosomal protein S27a | EXP | 2017 | Promoter; Leader | 1-1969; 1970-2017 |
| P-CUCme.18-1:1:2 | 27 | ubiquitin-40S ribosomal protein S27a | EXP | 1353 | Promoter; Leader | 1-1308; 1309-1353 |
| P-CUCme.19-1:1:2 | 28 | Chloropyll a/b binding protein | EXP | 2005 | Promoter; Leader | 1-1960; 1961-2005 |
| P-CUCme.20-1:1:2 | 29 | Chloropyll a/b binding protein | EXP | 1445 | Promoter; Leader | 1-1390; 1391-1445 |
| P-CUCme.21-1:1:1 | 30 | Chloropyll a/b binding protein | EXP | 1282 | Promoter; Leader | 1-1233; 1234-1282 |
| P-CUCme.22-1:1:3 | 31 | Elongation Factor 4 alpha | EXP | 2002 | | |
| P-CUCme.24-1:1:2 | 32 | S-Adenosylmethionine Synthetase | EXP | 2003 | Promoter; Leader; Intron; Leader | 1-1067; 1068-1165; 1166-2001; 2002-2003 |
| P-CUCme.26-1:1:2 | 33 | Stress responsive protein | EXP | 1372 | Promoter; Leader; Intron; Leader | 1-577; 578-654; 655-1366; 1367-1372 |
| P-CUCme.28-1:1:2 | 34 | Ribosomal protein S5a | EXP | 1122 | | |
| P-CUCme.29-1:1:2 | 35 | Ribosomal protein S5a | EXP | 2017 | Promoter; Leader; Intron; Leader | 1-490; 491-571; 572-2012; 2013-2017 |
| CumMe_WSM_ SF143981.G5150 | 36 | LHCB6 (LIGHT HARVESTING COMPLEX PSII SUBUNIT 6) | EXP | 2000 | | |
| CumMe_WSM_ SF144839.G5080 | 37 | EIF2 GAMMA translation initiation factor | EXP | 1760 | | |
| CumMe_WSM_ SF146040.G5050 | 38 | EIF2 translation initiation factor | EXP | 1767 | | |
| CumMe_WSM_ SF16408.G5350 | 39 | elongation factor Tu | EXP | 2000 | | |
| CumMe_WSM_ SF16429.G5670 | 40 | unknown protein | EXP | 2000 | | |
| CumMe_WSM_ SF16444.G5140 | 41 | histone H4 | EXP | 2000 | Promoter; Leader | 1-1947; 1948-2000 |
| CumMe_WSM_ SF16530.G6000 | 42 | HMGB2 (HIGH MOBILITY GROUP B 2) transcription factor | EXP | 2000 | | |
| CumMe_WSM_ SF16553.G5090 | 43 | PBG1; threonine-type endopeptidase | EXP | 1115 | | |
| CumMe_WSM_ SF16563.G5560 | 44 | ATARFB1A (ADP-ribosylation factor B1A) | EXP | 2000 | Promoter; Leader; Intron; Leader | 1-1329; 1330-1427; 1428-1988; 1989-2000 |
| CumMe_WSM_ SF16675.G5720 | 45 | chromatin protein family | EXP | 2000 | | |
| CumMe_WSM_ SF16920.G5650 | 46 | CSD1 (COPPER/ZINC SUPEROXIDE DISMUTASE 1) | EXP | 2000 | | |
| CumMe_WSM_ SF16953.G5180 | 47 | SCE1 (SUMO CONJUGATION ENZYME 1); SUMO ligase | EXP | 2000 | | |
| CumMe_WSM_ SF17051.G5470 | 48 | 60S ribosomal protein L9 (RPL90D) | EXP | 2000 | | |
| CumMe_WSM_ SF17111.G5790 | 49 | ubiquinol-cytochrome C reductase complex ubiquinone-binding protein | EXP | 2000 | Promoter; Leader | 1-1895; 1896-2000 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF17142.G5920 | 50 | peptidyl-prolyl cis-trans isomerase, chloroplast | EXP | 2000 | | |
| CumMe_WSM_SF17190.G6200 | 51 | PRK (PHOSPHORIBULOKINASE) | EXP | 2000 | | |
| CumMe_WSM_SF17250.G5910 | 52 | LHCB5 (LIGHT HARVESTING COMPLEX OF PHOTOSYSTEM II 5) | EXP | 2000 | | |
| CumMe_WSM_SF17252.G7330 | 53 | nascent polypeptide-associated complex (NAC) domain-containing protein | EXP | 2000 | Promoter; Leader; Intron | 1-1195; 1196-1297; 1298-2000 |
| CumMe_WSM_SF17253.G5150 | 54 | RPS9 (RIBOSOMAL PROTEIN S9) | EXP | 1547 | | |
| CumMe_WSM_SF17322.G5110 | 55 | 60S ribosomal protein L22 (RPL22A) | EXP | 2000 | | |
| CumMe_WSM_SF17349.G5770 | 56 | PGRL1B (PGR5-Like B) | EXP | 2000 | | |
| CumMe_WSM_SF17357.G5630 | 57 | 40S ribosomal protein S10 (RPS10B) | EXP | 2000 | | |
| CumMe_WSM_SF17494.G5140 | 58 | MEE34 (maternal effect embryo arrest 34) | EXP | 1591 | | |
| CumMe_WSM_SF17524.G6410 | 59 | SUS2 (ABNORMAL SUSPENSOR 2) | EXP | 2000 | | |
| CumMe_WSM_SF17672.G5610 | 60 | PSAK (photosystem I subunit K) | EXP | 2000 | | |
| CumMe_WSM_SF17773.G6620 | 61 | aconitase C-terminal domain-containing protein | EXP | 2000 | | |
| CumMe_WSM_SF17866.G6050 | 62 | ATPDIL5-1 (PDI-like 5-1) | EXP | 2000 | | |
| CumMe_WSM_SF18004.G6600 | 63 | hydroxyproline-rich glycoprotein family protein | EXP | 2000 | | |
| CumMe_WSM_SF18045.G6670 | 64 | | EXP | 2000 | | |
| CumMe_WSM_SF18053.G5410 | 65 | endomembrane protein 70 | EXP | 2000 | | |
| CumMe_WSM_SF18287.G5380 | 66 | CP12-1 | EXP | 2000 | | |
| CumMe_WSM_SF18488.G5340 | 67 | caffeoyl-CoA 3-O-methyltransferase | EXP | 2000 | Promoter; Leader | 1-1923; 1924-2000 |
| CumMe_WSM_SF18504.G5090 | 68 | vacuolar ATP synthase subunit H family protein | EXP | 2000 | | |
| CumMe_WSM_SF18530.G5750 | 69 | GUN5 (GENOMES UNCOUPLED 5); magnesium chelatase | EXP | 2000 | | |
| CumMe_WSM_SF18536.G6480 | 70 | MBF1A (MULTIPROTEIN BRIDGING FACTOR 1A) transcription coactivator | EXP | 2000 | | |
| CumMe_WSM_SF18575.G6410 | 71 | unknown protein | EXP | 2000 | | |
| CumMe_WSM_SF18634.G5190 | 72 | 60S ribosomal protein L23 (RPL23A) | EXP | 2000 | Promoter; Leader | 1-1971; 1972-2000 |
| CumMe_WSM_SF18645.G5380 | 73 | GS2 (GLUTAMINE SYNTHETASE 2) | EXP | 2000 | | |
| CumMe_WSM_SF18716.G5860 | 74 | 40S ribosomal protein S12 (RPS12A); reverse compliment: Auxin-induced protein x10A-like | EXP | 2000 | Promoter; Leader | Reverse compliment; see SEQ ID NO: 184 |
| CumMe_WSM_SF18801.G5040 | 75 | | EXP | 2000 | | |
| CumMe_WSM_SF18806.G6220 | 76 | unknown protein | EXP | 2000 | | |
| CumMe_WSM_SF18850.G5630 | 77 | PAC1; threonine-type endopeptidase | EXP | 2000 | | |
| CumMe_WSM_SF18863.G7550 | 78 | ATP synthase gamma chain, mitochondrial (ATPC) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF18986.G6110 | 79 | GER1 (GERMIN-LIKE PROTEIN 1); oxalate oxidase | EXP | 2000 | | |
| CumMe_WSM_SF19064.G5690 | 80 | histone H3.2 | EXP | 2000 | Promoter; Leader; Intron | 1-1581; 1582-1670; 1671-2000 |
| CumMe_WSM_SF19323.G5120 | 81 | chloroplast outer envelope GTP-binding protein, putative | EXP | 2000 | | |
| CumMe_WSM_SF19452.G5090 | 82 | glucan phosphorylase, putative | EXP | 1072 | | |
| CumMe_WSM_SF19631.G5170 | 83 | RuBisCO activase, putative | EXP | 1730 | | |
| CumMe_WSM_SF19647.G5760 | 84 | 6-phosphogluconate dehydrogenase family protein | EXP | 2000 | Promoter; Leader; Intron; Leader | 1-936; 937-1021; 1022-1992; 1993-2000 |
| CumMe_WSM_SF19839.G5090 | 85 | ATPDX1.1 (pyridoxine biosynthesis 1.1) | EXP | 1020 | Promoter; Leader | 1-928; 929-1020 |
| CumMe_WSM_SF19850.G5130 | 86 | HMGB2 (HIGH MOBILITY GROUP B 2) transcription factor | EXP | 2000 | | |
| CumMe_WSM_SF19902.G5260 | 87 | universal stress protein (USP) family protein/ early nodulin ENOD18 family protein | EXP | 2000 | | |
| CumMe_WSM_SF19992.G6100 | 88 | unknown protein | EXP | 2000 | | |
| CumMe_WSM_SF20132.G5560 | 89 | peroxidase 21 | EXP | 2000 | Promoter; Leader | 1-1962; 1963-2000 |
| CumMe_WSM_SF20147.G7910 | 90 | CSD1 (COPPER/ZINC SUPEROXIDE DISMUTASE 1) | EXP | 2000 | | |
| CumMe_WSM_SF20355.G5130 | 91 | ATP synthase family | EXP | 2000 | | |
| CumMe_WSM_SF20359.G5870 | 92 | NADH-ubiquinone oxidoreductase 20 kDa subunit, mitochondrial | EXP | 2000 | | |
| CumMe_WSM_SF20368.G5700 | 93 | PGR5 (proton gradient regulation 5) | EXP | 2000 | | |
| CumMe_WSM_SF20409.G5240 | 94 | elongation factor 1B alpha-subunit 1 (eEF1Balpha1) | EXP | 2000 | | |
| CumMe_WSM_SF20431.G6340 | 95 | DHS2 (3-deoxy-d-arabino-heptulosonate 7-phosphate synthase) | EXP | 2000 | | |
| CumMe_WSM_SF20505.G5440 | 96 | THIC (ThiaminC); ADP-ribose pyrophosphohydrolase | EXP | 1373 | | |
| CumMe_WSM_SF20509.G5920 | 97 | Y14; RNA binding/ protein binding | EXP | 2000 | | |
| CumMe_WSM_SF206458.G5970 | 98 | FAD2 (FATTY ACID DESATURASE 2) | EXP | 2000 | Promoter | 1-2000 |
| CumMe_WSM_SF206534.G5200 | 99 | unknown protein | EXP | 2000 | | |
| CumMe_WSM_SF20997.G6990 | 100 | ALD1 (AGD2-LIKE DEFENSE RESPONSE PROTEIN1) | EXP | 2000 | | |
| CumMe_WSM_SF21035.G5090 | 101 | sodium/calcium exchanger family protein | EXP | 1078 | | |
| CumMe_WSM_SF21117.G5370 | 102 | 30S ribosomal protein, putative | EXP | 2000 | | |
| CumMe_WSM_SF21141.G5630 | 103 | 40S ribosomal protein S24 (RPS24A) | EXP | 2000 | | |
| CumMe_WSM_SF21198.G5180 | 104 | | EXP | 1974 | | |
| CumMe_WSM_SF21366.G5980 | 105 | GRF12 (GENERAL REGULATORY FACTOR 12) | EXP | 2000 | | |
| CumMe_WSM_SF21828.G5150 | 106 | cpHsc70-1 (chloroplast heat shock protein 70-1) | EXP | 1643 | | |
| CumMe_WSM_SF21886.G5080 | 107 | NPQ4 (NONPHOTOCHEMICAL QUENCHING) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF22008.G5670 | 108 | NAP1; 2 (NUCLEOSOME ASSEMBLY PROTEIN 1; 2) | EXP | 2000 | | |
| CumMe_WSM_SF22070.G5280 | 109 | fructose-bisphosphate aldolase, putative | EXP | 2000 | | |
| CumMe_WSM_SF22097.G5540 | 110 | APX3 (ASCORBATE PEROXIDASE 3) | EXP | 2000 | | |
| CumMe_WSM_SF22254.G5760 | 111 | 40S ribosomal protein S7 (RPS7B) | EXP | 2000 | | |
| CumMe_WSM_SF22275.G5780 | 112 | ribosomal protein L17 family protein | EXP | 1027 | | |
| CumMe_WSM_SF22355.G5310 | 113 | | EXP | 2000 | | |
| CumMe_WSM_SF22531.G5120 | 114 | eukaryotic translation initiation factor 1A, putative | EXP | 2000 | Promoter; Leader; Intron; Leader | 1-759; 760-858; 859-1979; 1980-2000 |
| CumMe_WSM_SF229870.G5370 | 115 | ATSARA1A (*ARABIDOPSIS THALIANA* SECRETION-ASSOCIATED RAS SUPER FAMILY 1) | EXP | 2000 | | |
| CumMe_WSM_SF22934.G5290 | 116 | T-complex protein 1 epsilon subunit, putative | EXP | 2000 | | |
| CumMe_WSM_SF23181.G5100 | 117 | CEV1 (CONSTITUTIVE EXPRESSION OF VSP 1) | EXP | 1025 | | |
| CumMe_WSM_SF23186.G6160 | 118 | ubiquinol-cytochrome C reductase complex 14 kDa protein, putative | EXP | 2000 | | |
| CumMe_WSM_SF23397.G5210 | 119 | RPL27 (RIBOSOMAL PROTEIN LARGE SUBUNIT 27) | EXP | 2000 | | |
| CumMe_WSM_SF23760.G5200 | 120 | NDPK1; ATP binding/nucleoside diphosphate kinase | EXP | 2000 | Promoter; Leader | 1-1901; 1902-2000 |
| CumMe_WSM_SF23906.G6180 | 121 | PSBX (photosystem II subunit X) | EXP | 2000 | | |
| CumMe_WSM_SF24040.G5450 | 122 | RPS17 (RIBOSOMAL PROTEIN S17) | EXP | 2000 | | |
| CumMe_WSM_SF24045.G5400 | 123 | EXL3 (EXORDIUM LIKE 3) | EXP | 2000 | | |
| CumMe_WSM_SF24117.G5600 | 124 | 60S ribosomal protein L26 (RPL26A) | EXP | 2000 | | |
| CumMe_WSM_SF25084.G5580 | 125 | | EXP | 2000 | | |
| CumMe_WSM_SF25141.G5160 | 126 | isocitrate dehydrogenase, putative | EXP | 1397 | Promoter; Leader | 1-1322; 1323-1397 |
| CumMe_WSM_SF25355.G5000 | 127 | LOS1; copper ion binding translation elongation factor | EXP | 2000 | Promoter; Leader; Intron; Leader; CDS | 1-734; 735-811; 812-1340; 1341-1360; 1361-2000 |
| CumMe_WSM_SF25370.G5000 | 128 | PSBP-1 (PHOTOSYSTEM II SUBUNIT P-1) | EXP | 1657 | | |
| CumMe_WSM_SF25455.G5370 | 129 | GLY3 (GLYOXALASE II 3) | EXP | 2000 | | |
| CumMe_WSM_SF25936.G5450 | 130 | mitochondrial substrate carrier family protein | EXP | 2000 | Promoter; Leader | 1-1878; 1879-2000 |
| CumMe_WSM_SF27080.G5510 | 131 | LIP1 (LIPOIC ACID SYNTHASE 1) | EXP | 2000 | | |
| CumMe_WSM_SF27222.G5150 | 132 | DRT112; copper ion binding/electron carrier | EXP | 2000 | | |
| CumMe_WSM_SF27957.G5450 | 133 | SMAP1 (SMALL ACIDIC PROTEIN 1) | EXP | 2000 | | |
| CumMe_WSM_SF28729.G5340 | 134 | RNA-binding protein cp29, putative | EXP | 1696 | | |
| CumMe_WSM_SF28805.G6200 | 135 | unknown protein | EXP | 2000 | | |
| CumMe_WSM_SF31264.G5380 | 136 | ATPH1 (*ARABIDOPSIS THALIANA* PLECKSTRIN HOMOLOGUE 1) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_ SF35856.G5150 | 137 | TIP4; 1 (tonoplast intrinsic protein 4; 1) | EXP | 1575 | | |
| CumMe_WSM_ SF40859.G5250 | 138 | SMT2 (STEROL METHYLTRANSFERASE 2) | EXP | 2000 | | |
| CumMe_WSM_ SF41124.G5080 | 139 | 40S ribosomal protein S2 (RPS2C) | EXP | 1006 | Promoter; Leader | 1-883; 884-1006 |
| CumMe_WSM_ SF41128.G5410 | 140 | CRY2 (CRYPTOCHROME 2) | EXP | 2000 | | |
| CumMe_WSM_ SF41254.G5160 | 141 | GDP-D-glucose phosphorylase | EXP | 1556 | | |
| CumMe_WSM_ SF41588.G5470 | 142 | PRPL11 (PLASTID RIBOSOMAL PROTEIN L11) | EXP | 2000 | | |
| CumMe_WSM_ SF41644.G6400 | 143 | SHD (SHEPHERD) | EXP | 2000 | | |
| CumMe_WSM_ SF41983.G5000 | 144 | catalytic/coenzyme binding | EXP | 1337 | | |
| CumMe_WSM_ SF42075.G5100 | 145 | CPN60B (CHAPERONIN 60 BETA) | EXP | 2000 | | |
| CumMe_WSM_ SF42141.G5110 | 146 | cathepsin B-like cysteine protease, putative | EXP | 1212 | | |
| CumMe_WSM_ SF44933.G5290 | 147 | EBF1 (EIN3-BINDING F BOX PROTEIN 1) ubiquitin-protein ligase | EXP | 2000 | | |
| CumMe_WSM_ SF44977.G5000 | 148 | PAP26 (PURPLE ACID PHOSPHATASE 26) | EXP | 1254 | | |
| CumMe_WSM_ SF45441.G5510 | 149 | GAPA-2 (GLYCERALDEHYDE 3-PHOSPHATE DEHYDROGENASE A SUBUNIT 2) | EXP | 2000 | | |
| CumMe_WSM_ SF45882.G5120 | 150 | fructose-1,6-bisphosphatase, putative | EXP | 1680 | | |
| CumMe_WSM_ SF47806.G5070 | 151 | ATP synthase epsilon chain, mitochondrial | EXP | 1524 | | |
| CumMe_WSM_ SF53106.G5190 | 152 | CPN60A (CHAPERONIN-60ALPHA) | EXP | 1851 | | |
| CumMe_WSM_ SF65588.G5230 | 153 | vacuolar calcium-binding protein-related | EXP | 2000 | | |
| CumMe_WSM_ SF9060.G5120 | 154 | APE2 (ACCLIMATION OF PHOTOSYNTHESIS TO ENVIRONMENT 2) | EXP | 1288 | | |
| P-CUCme.1-1:1:1rc | 155 | Phosphatase 2A | EXP | 2000 | Promoter; Leader; Intron; Leader | 1-1135; 1136-1249; 1250-1990; 1991-2000 |
| EXP-CUCme.4:1:1 | 156 | Ubiquitin 2 | EXP | 2011 | Promoter; Leader; Intron; Leader | 1-1646; 1647-1704; 1705-2005; 2006-2008 |
| P-CUCme.4-1:1:4 | 157 | Ubiquitin 2 | P; L | 1698 | Promoter; Leader | |
| I-CUCme.4-1:1:1 | 158 | Ubiquitin 2 | I; L | 313 | Intron; Leader | |
| EXP-CUCme.5:1:1 | 159 | Ubiquitin 3 | EXP | 2010 | Promoter; Leader; Intron; Leader | 1-748; 749-819; 820-2004; 2005-2007 |
| P-CUCme.5-1:1:3 | 160 | Ubiquitin 3 | P; L | 1107 | Promoter; Leader | |
| I-CUCme.5-1:1:1 | 161 | Ubiquitin 3 | I; L | 903 | Intron; Leader | |
| EXP-CUCme.eEF1a:1:1 | 162 | Elongation Factor 1 alpha | EXP | 1235 | Promoter; Leader; Intron; Leader | 1-617; 618-677; 678-1213; 1214-1235 |
| P-CUCme.eEF1a-1:1:1 | 163 | Elongation Factor 1 alpha | P | 617 | Promoter | |
| L-CUCme.eEF1a-1:1:1 | 164 | Elongation Factor 1 alpha | L | 54 | Leader | |
| I-CUCme.eEF1a-1:1:1 | 165 | Elongation Factor 1 alpha | I | 545 | Intron | |
| L-CUCme.eEF1a-1:1:2 | 166 | Elongation Factor 1 alpha | L | 19 | Leader | |
| P-CUCme.19-1:1:3 | 167 | Chloropyll a/b binding protein | EXP | 2003 | Promoter; Leader | 1-1958; 1959-2003 |
| EXP-CUCme.SAMS2:1:1 | 168 | S-Adenosylmethionine Synthetase | EXP | 2004 | Promoter; Leader; Intron | 1-1067; 1068-1165; 1166-2003 |
| P-CUCme.SAMS2-1:1:1 | 169 | S-Adenosylmethionine Synthetase | P | 1067 | Promoter | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| L-CUCme.SAMS2-1:1:1 | 170 | S-Adenosylmethionine Synthetase | L | 92 | Leader | |
| I-CUCme.SAMS2-1:1:1 | 171 | S-Adenosylmethionine Synthetase | I | 845 | Intron | |
| EXP-CUCme.29:1:1 | 172 | Ribosomal protein S5a | EXP | 2018 | Promoter; Leader; Intron; Leader | 1-490; 491-571; 572-2012; 2013-2018 |
| P-CUCme.29-1:1:4 | 173 | Ribosomal protein S5a | P; L | 565 | Promoter; Leader | |
| I-CUCme.29-1:1:1 | 174 | Ribosomal protein S5a | I; L | 1453 | Intron; Leader | |
| P-CUCme.CumMe_WSM_SF16444.G5140-1:1:1 | 175 | histone H4 | EXP | 1999 | Promoter; Leader; Intron | 1-1946; 947-1999 |
| P-CUCme.CumMe_WSM_SF16563.G5560-1:1:1 | 176 | ATARFB1A (ADP-ribosylation factor B1A) | EXP | 2004 | Promoter; Leader; Intron; Leader | 1-1331; 1332-1429; 1430-1992; 1993-2004 |
| P-CUCme.CumMe_WSM_SF1711 1.G5790-1:1:1 | 177 | ubiquinol-cytochrome C reductase complex ubiquinone-binding protein | EXP | 2005 | Promoter; Leader | 1-1901; 1902-2005 |
| EXP-CumMe.WSM_SF17252.G7330:1:1 | 178 | nascent polypeptide-associated complex (NAC) domain-containing protein | EXP | 1978 | Promoter; Leader; Intron; Leader | 1-1167; 1168-1269; 1270-1972; 1973-1975 |
| P-CUCme.WSM_SF17252.G7330-1:1:1 | 179 | nascent polypeptide-associated complex (NAC) domain-containing protein | P; L | 1263 | Promoter; Leader | |
| I-CUCme.WSM_SF17252.G7330-1:1:1 | 180 | nascent polypeptide-associated complex (NAC) domain-containing protein | I; L | 715 | Intron; Leader | |
| P-CUCme.CumMe_WSM_SF18488.G5340-1:1:1 | 181 | caffeoyl-CoA 3-O-methyltransferase | EXP | 2000 | Promoter; Leader | 1-923; 1924-2000 |
| P-CUCme.CumMe_WSM_SF18536.G6480-1:1:1 | 182 | MBF1A (MULTIPROTEIN BRIDGING FACTOR 1A) transcription coactivator | EXP | 2000 | Promoter; Leader; Intron | |
| P-CUCme.CumMe_WSM_SF18634.G5190-1:1:1 | 183 | 60S ribosomal protein L23 (RPL23A) | EXP | 1989 | Promoter; Leader | 1-1960; 1961-1989 |
| P-CUCme.CumMe_WSM_SF18716.G5860-1:1:1 | 184 | Auxin-induced prtoein X10A-like | EXP | 1463 | Promoter; Leader | 1-1392; 1393-1463 |
| EXP-CUCme.WSM_SF19064.G5690:1:1 | 185 | histone H3.2 | EXP | 2006 | Promoter; Leader; Intron; Leader | 1-1581; 1582-1670; 1671-2000; 2001-2003 |
| P-CUCme.WSM_SF19064.G5690-1:1:1 | 186 | histone H3.2 | P; L | 1664 | Promoter; Leader | |
| I-CUCme.WSM_SF19064.G5690-1:1:1 | 187 | histone H3.2 | I; L | 342 | Intron; Leader | |
| P-CUCme.CumMe_WSM_SF19647.G5760-1:1:1 | 188 | 6-phosphogluconate dehydrogenase family protein | EXP | 2003 | Promoter; Leader; Intron; Leader | 1-939; 940-1024; 1025-1995; 1996-2003 |
| P-CUCme.CumMe_WSM_SF19839.G5090-1:1:1 | 189 | ATPDX1.1 (pyridoxine biosynthesis 1.1) | EXP | 1024 | Promoter; Leader | 1-904; 905-1024 |
| P-CUCme.CumMe_WSM_SF20132.G5560-1:1:1 | 190 | peroxidase 21 | EXP | 2001 | Promoter; Leader | 1-1962; 1963-2001 |
| P-CUCme.CumMe_WSM_SF206458.G5970-1:1:1 | 191 | FAD2 (FATTY ACID DESATURASE 2) | EXP | 4175 | Promoter; Leader; Intron; Leader | 1-2171; 2172-2325; 2326-4155; 4156-4175 |
| P-CUCme.CumMe_WSM_SF22531.G5120-1:1:1 | 192 | eukaryotic translation initiation factor 1A, putative | EXP | 1999 | Promoter; Leader; Intron; Leader | 1-759; 760-858; 859-1978; 1979-1999 |
| P-CUCme.CumMe_WSM_SF23760.G5200-1:1:1 | 193 | NDPK1; ATP binding/nucleoside diphosphate kinase | EXP | 2000 | Promoter; Leader | 1-1901; 1902-2000 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.CumMe_WSM_SF23906.G6180-1:1:1 | 194 | PSBX (photosystem II subunit X) | EXP | 2000 | Promoter; Leader | |
| P-CUCme.CumMe_WSM_SF25141.G5160-1:1:2 | 195 | isocitrate dehydrogenase, putative | EXP | 1400 | Promoter; Leader | 1-1325; 1326-1400 |
| P-CUCme.CumMe_WSM_SF25355.G5000-1:1:1 | 196 | LOS1; copper ion binding translation elongation factor | EXP | 2019 | Promoter; Leader; Intron; Leader; CDS | 1-734; 735-811; 812-1340; 1341-1360; 1361-2019 |
| P-CUCme.CumMe_WSM_SF25936.G5450-1:1:1 | 197 | mitochondrial substrate carrier family protein | EXP | 1999 | Promoter; Leader | 1-1877; 1878-1999 |
| P-CUCme.CumMe_WSM_SF35856.G5150-1:1:1 | 198 | TIP4; 1 (tonoplast intrinsic protein 4; 1) | EXP | 1578 | | |
| P-CUCme.CumMe_WSM_SF41124.G5080-1:1:1 | 199 | 40S ribosomal protein S2 (RPS2C) | EXP | 1023 | Promoter; Leader | 1-945; 946-1023 |
| P-CUCme.20-1:3 | 211 | Chloropyll a/b binding protein | EXP | 1446 | Promoter; Leader | 1-1390; 1391-1446 |
| EXP-CUCme.29:1:2 | 212 | Ribosomal protein S5a | EXP | 2018 | Promoter; Leader; Intron; Leader | 1-490; 491-571; 572-2011; 2013-2018 |

As shown in Table 1, for example, the transcriptional regulatory expression element group (EXP) designated EXP-CUCme.Ubq1:1:1 (SEQ ID NO: 1), with components isolated from *C. melo,* comprises a 2068 base pair sized (bp) promoter element, P-CUCme.Ubq1-1:1:15 (SEQ ID NO: 2), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:2 (SEQ ID NO: 5), with components isolated from *C. melo*, comprises a 1459 bp promoter element, P-CUCme.Ubq1-1:1:16 (SEQ ID NO: 6), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:3 (SEQ ID NO: 7), with components isolated from *C. melo,* comprises a 964 bp promoter element, P-CUCme.Ubq1-1:1:17 (SEQ ID NO: 8), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:4 (SEQ ID NO: 9), with components isolated from *C. melo,* comprises a 479 bp promoter element, P-CUCme.Ubq 1-1:1:18 (SEQ ID NO: 10), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:5 (SEQ ID NO: 11), with components isolated from *C. melo,* comprises a 173 bp promoter element, P-CUCme.Ubq1-1:1:19 (SEQ ID NO: 12), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4).

An alignment of the ubiquitin 1 promoter sequences is provided in FIGS. 1*a*-1*f*. The promoter elements, P-CUCme.Ubq1-1:1:16 (SEQ ID NO: 6), P-CUCme.Ubq1-1:1:17 (SEQ ID NO: 8), P-CUCme.Ubq1-1:1:18 (SEQ ID NO: 10) and P-CUCme.Ubq1-1:1:19 (SEQ ID NO: 12) were built by introducing varying lengths of deletions from the 5' end of the promoter, P-CUCme.Ubq1-1:1:15 (SEQ ID NO: 2).

Example 2

Analysis of Regulatory Elements Driving GUS in Soy Cotyledon Protoplasts

Soybean cotyledon protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters. Each plant expression vector was comprised of a right border region from *Agrobacterium tumefaciens,* a first transgene cassette comprised of an EXP sequence or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the Arabidopsis Actin 7 promoter) or the antibiotic, kanamycin and a left border region from *A. tumefaciens.* A promoterless control plant expression vector (pMON124912) served as a negative control for expression. The foregoing test and constitutive expression element groups were cloned into plant expression vectors as shown in Table 2 below.

TABLE 2

Plant expression vectors and corresponding expression element group and 3' UTR.

| Expression Vector | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | No promoter | | T-Gb.FbL2-1:1:1 |
| pMON138776 | EXP-CUCme.Ubq1:1:1 | 1 | T-Gb.FbL2-1:1:1 |
| pMON138777 | EXP-CUCme.Ubq1:1:2 | 5 | T-Gb.FbL2-1:1:1 |
| pMON138778 | EXP-CUCme.Ubq1:1:3 | 7 | T-Gb.FbL2-1:1:1 |
| pMON138779 | EXP-CUCme.Ubq1:1:4 | 9 | T-Gb.FbL2-1:1:1 |
| pMON138780 | EXP-CUCme.Ubq1:1:5 | 11 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON138776, pMON138777, pMON138778, pMON138779 and pMON138780 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p.02). Sample measurements were made using 3 or 4 replicates per transformation. The average GUS and luciferase values are presented in Table 3 below.

TABLE 3

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON80585 | EXP-At.Atntt1:1:2 | 200 | 55173 | 6498 | 30503 | 8.49 | 1.81 |
| pMON109584 | EXP-CaMV.35S-enh + Ph.DnaK:1:3 | 200 | 24940 | 5050.75 | 35495 | 4.94 | 0.70 |
| pMON118756 | EXP-At.Act7:1:11 | 201 | 9871 | 6880 | 40850 | 1.43 | 0.24 |
| pMON124912 | No promoter | | 2000 | 11670 | 73187 | 0.17 | 0.03 |
| pMON138776 | EXP-CUCme.Ubq1:1:1 | 1 | 26972 | 6467.25 | 37200 | 4.17 | 0.73 |
| pMON138777 | EXP-CUCme.Ubq1:1:2 | 5 | 41307 | 5902.5 | 24396 | 7.00 | 1.69 |
| pMON138778 | EXP-CUCme.Ubq1:1:3 | 7 | 90140 | 10710.5 | 60983 | 8.42 | 1.48 |
| pMON138779 | EXP-CUCme.Ubq1:1:4 | 9 | 35526 | 5590 | 28001 | 6.36 | 1.27 |
| pMON138780 | EXP-CUCme.Ubq1:1:5 | 11 | 23298 | 4483.25 | 19075 | 5.20 | 1.22 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 4 below shows the GUS to firefly luciferase (FLuc) ratios normalized with respect to EXP-At.Act7:1:11 and EXP-CaMV.35S-enh+Ph.DnaK:1:3. Table 5 below shows the GUS to *renilla* luciferase (RLuc) ratios normalized with respect to EXP-At.Act7:1:11 and EXP-CaMV.35S-enh+Ph.DnaK:1:3.

TABLE 4

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON80585 | EXP-At.Atntt1:1:2 | 200 | 5.92 | 1.72 |
| pMON109584 | EXP-CaMV.35S-enh + Ph.DnaK:1:3 | 201 | 3.44 | 1.00 |
| pMON118756 | EXP-At.Act7:1:11 | 202 | 1.00 | 0.29 |
| pMON124912 | No promoter | | 0.12 | 0.03 |
| pMON138776 | EXP-CUCme.Ubq1:1:1 | 1 | 2.91 | 0.84 |
| pMON138777 | EXP-CUCme.Ubq1:1:2 | 5 | 4.88 | 1.42 |
| pMON138778 | EXP-CUCme.Ubq1:1:3 | 7 | 5.87 | 1.70 |
| pMON138779 | EXP-CUCme.Ubq1:1:4 | 9 | 4.43 | 1.29 |
| pMON138780 | EXP-CUCme.Ubq1:1:5 | 11 | 3.62 | 1.05 |

TABLE 5

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON80585 | EXP-At.Atntt1:1:2 | 200 | 7.49 | 2.57 |
| pMON109584 | EXP-CaMV.35S-enh + Ph.DnaK:1:3 | 201 | 2.91 | 1.00 |
| pMON118756 | EXP-At.Act7:1:11 | 202 | 1.00 | 0.34 |
| pMON124912 | No promoter | | 0.11 | 0.04 |
| pMON138776 | EXP-CUCme.Ubq1:1:1 | 1 | 3.00 | 1.03 |
| pMON138777 | EXP-CUCme.Ubq1:1:2 | 5 | 7.01 | 2.41 |
| pMON138778 | EXP-CUCme.Ubq1:1:3 | 7 | 6.12 | 2.10 |
| pMON138779 | EXP-CUCme.Ubq1:1:4 | 9 | 5.25 | 1.81 |
| pMON138780 | EXP-CUCme.Ubq1:1:5 | 11 | 5.05 | 1.74 |

As can be seen in Tables 4 and 5 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1: 1:5 (SEQ ID NO: 11) demonstrated the ability of driving transgene expression in soybean cotyledon protoplasts. Expression levels were greater than that of EXP-At.Act7:1:11 and was 2.9 to 5.8 (FLuc) or 3 to 7 (RLuc) fold higher than EXP-At.Act7:1:11 in this assay. Expression was equivalent or higher than expression observed for EXP-CaMV.35S-enh+Ph.DnaK:1:3. Expression levels were 0.8 to 1.7 (FLuc) or 1 to 2.4 (RLuc) fold higher than expression observed for EXP-CaMV.35S-enh+Ph.DnaK:1:3.

Example 3

Analysis of Regulatory Elements Driving GUS in Bombarded Soybean Leaves and Roots Soybean leaves and roots were transformed with plant expression vectors containing a test transcriptional regulatory expression element group driving expression of the ß-glucuronidase (GUS) transgene and compared to GUS expression in roots and leaves in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters in particle bombarded soybean leaves and roots. The plant expression vectors used for transformation of leaves and roots was the same as those presented in Table 2 of Example 2 above.

The plant expression vectors, pMON80585, pMON109584, pMON118756, pMON124912, pMON138776, pMON138777, pMON138778, pMON138779 and pMON138780 were used to transform soybean leaves and roots using particle bombardment transformationmethods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules Calif.). A PDS 1000/He biolistic gun was used for transformation (Catalog #165-2257 Bio-Rad, Hercules Calif.). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0","+" to "++++++" reflecting the level of GUS expression is assigned to each construct (0—no expression,+to ++++++—low to high, respectively).

Expression of the GUS transgene demonstrated in each tissue is used to infer the relative potential level and specificity of each element's capacity to drive transgene expression in stably transformed corn plants. Average GUS expression ratings are provided in Table 6 below.

TABLE 6

GUS expression ratings for particle bombarded leaf and root.

| Construct | Regulatory Element | SEQ ID NO: | Leaf Expression Rating | Root Expression Rating |
|---|---|---|---|---|
| pMON80585 | EXP-At.Atntt1:1:2 | 200 | ++++ | ++ |
| pMON109584 | EXP-CaMV.35S-enh + Ph.DnaK:1:3 | 201 | +++++ | +++ |
| pMON118756 | EXP-At.Act7:1:11 | 202 | ++++ | ++ |
| pMON124912 | No promoter | | 0 | 0 |
| pMON138776 | EXP-CUCme.Ubq1:1:1 | 1 | ++++ | +++ |
| pMON138777 | EXP-CUCme.Ubq1:1:2 | 5 | +++ | ++ |
| pMON138778 | EXP-CUCme.Ubq1:1:3 | 7 | +++ | ++ |
| pMON138779 | EXP-CUCme.Ubq1:1:4 | 9 | +++ | ++ |
| pMON138780 | EXP-CUCme.Ubq1:1:5 | 11 | ++ | + |

As can be seen in Table 6 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in particle bombarded transformed leaf and root tissues.

Example 4

Analysis of Regulatory Elements Driving GUS in Soy Cotyledon Protoplasts

Soybean cotyledon protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens,* a first transgene cassette comprised of a test promoter or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum salivum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the Arabidopsis Actin 7 promoter) or the antibiotic, kanamycin and a left border region from *A. tumefaciens.* A promoterless control plant expression vector (pMON124912) served as a negative control for expression. The foregoing test and constitutive expression element groups were cloned into plant expression vectors as shown in Table 7 below.

TABLE 7

Plant expression vectors and corresponding expression element group and 3' UTR.

| Construct | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140822 | EXP-CUCme.5:1:1 | 159 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |

TABLE 7-continued

| Plant expression vectors and corresponding expression element group and 3' UTR. | | | |
|---|---|---|---|
| Construct | Regulatory Element | SEQ ID NO: | 3' UTR |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON 140829, pMON 140830, pMON 140831, pMON 140832, pMON 140833, pMON 140834, pMON140835, pMON140836, pMON140837, pMON140838 and pMON140839 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p.02). Sample measurements were made using 3 or 4 replicates per transformation. The average GUS and luciferase values are presented in Table 8 below.

TABLE 8

| Average GUS and luciferase expression values and GUS/luciferase ratios. | | | | | | | |
|---|---|---|---|---|---|---|---|
| Construct | Regulatory Element | SEQ ID NO: | Average GUS | Average FLuc | Average RLuc | GUS/ FLuc | GUS/ RLuc |
| pMON80585 | EXP-At.Atntt1:1:2 | 200 | 586 | 5220.7 | 8323 | 0.1100 | 0.0700 |
| pMON109584 | EXP-CaMV.35S-enh + Ph.DnaK:1:3 | 201 | 5768 | 4275 | 15098 | 1.3500 | 0.3800 |
| pMON118756 | EXP-At.Act7:1:11 | 202 | 773 | 7722 | 10545 | 0.1000 | 0.0700 |
| pMON124912 | Promoterless | | 48 | 9746.5 | 13905 | 0.0000 | 0.0000 |
| pMON140818 | P-CUCme.1-1:1:1rc | 155 | 194 | 4772 | 6363 | 0.0400 | 0.0300 |
| pMON140819 | P-CUCme.2-1:1:1 | 14 | 171 | 6855 | 10123 | 0.0200 | 0.0200 |
| pMON140820 | P-CUCme.3-1:1:3 | 15 | 37 | 7089.3 | 9593 | 0.0100 | 0.0000 |
| pMON140821 | EXP-CUCme.4:1:1 | 156 | 4211 | 7626.8 | 13935 | 0.5500 | 0.3000 |
| pMON140822 | EXP-CUCme.5:1:1 | 159 | 626 | 15609.3 | 21140 | 0.0400 | 0.0300 |
| pMON140823 | P-CUCme.6-1:1:1 | 18 | 331 | 15178.5 | 22818 | 0.0200 | 0.0100 |
| pMON140824 | P-CUCme.8-1:1:2 | 19 | 238 | 17514.5 | 28429 | 0.0100 | 0.0100 |
| pMON140825 | P-CUCme.9-1:1:2 | 20 | 510 | 13208 | 19567 | 0.0400 | 0.0300 |
| pMON140826 | P-CUCme.10-1:1:1 | 21 | 352 | 14805.3 | 22200 | 0.0200 | 0.0200 |
| pMON140827 | EXP-CUCme.eEF1a:1:1 | 162 | 724 | 9326.8 | 14476 | 0.0800 | 0.0500 |
| pMON140828 | P-CUCme.15-1:1:2 | 23 | 304 | 11798 | 17486 | 0.0300 | 0.0200 |
| pMON140829 | P-CUCme.16a-1:1:2 | 24 | 88 | 5429 | 9596 | 0.0200 | 0.0100 |
| pMON140830 | P-CUCme.17-1:1:2 | 26 | 180 | 10477.8 | 15291 | 0.0200 | 0.0100 |
| pMON140831 | P-CUCme.18-1:1:2 | 27 | 111 | 5059.3 | 6778 | 0.0200 | 0.0200 |
| pMON140832 | P-CUCme.19-1:1:3 | 167 | 121 | 3765 | 6032 | 0.0300 | 0.0200 |
| pMON140833 | P-CUCme.20-1:3 | 211 | 155 | 10458.8 | 14748 | 0.0100 | 0.0100 |
| pMON140834 | P-CUCme.21-1:1:1 | 30 | 582 | 7760 | 11440 | 0.0800 | 0.0500 |
| pMON140835 | P-CUCme.22-1:1:3 | 31 | 400 | 11393.8 | 18654 | 0.0400 | 0.0200 |
| pMON140836 | EXP-CUCme.SAMS2:1:1 | 168 | 568 | 9466.3 | 13962 | 0.0600 | 0.0400 |
| pMON140837 | P-CUCme.26-1:1:2 | 33 | 87 | 6683 | 8494 | 0.0100 | 0.0100 |
| pMON140838 | P-CUCme.28-1:1:2 | 34 | 171 | 19104.8 | 29619 | 0.0100 | 0.0100 |
| pMON140839 | EXP-CUCme.29:1:2 | 212 | 90 | 11247.3 | 15919 | 0.0100 | 0.0057 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 9 below shows the GUS to firefly luciferase (FLuc) ratios normalized with respect to EXP-At.Act7:1:11 and EXP-CaMV.35S-enh+Ph.DnaK:1:3. Table 10 below shows the GUS to *renilla* luciferase (RLuc) ratios normalized with respect to EXP-At.Act7:1:11 and EXP-CaMV.35S-enh+Ph.DnaK:1:3.

TABLE 9

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON80585 | EXP-At.Atntt1:1:2 | 200 | 1.12 | 0.08 |
| pMON109584 | EXP-CaMV.35S-enh + Ph.DnaK:1:3 | 201 | 13.48 | 1.00 |
| pMON118756 | EXP-At.Act7:1:11 | 202 | 1.00 | 0.07 |
| pMON124912 | Promoterless | | 0.05 | 0.00 |
| pMON140818 | P-CUCme.1-1:1:1rc | 155 | 0.41 | 0.03 |
| pMON140819 | P-CUCme.2-1:1:1 | 14 | 0.25 | 0.02 |
| pMON140820 | P-CUCme.3-1:1:3 | 15 | 0.05 | 0.00 |
| pMON140821 | EXP-CUCme.4:1:1 | 156 | 5.52 | 0.41 |
| pMON140822 | EXP-CUCme.5:1:1 | 159 | 0.40 | 0.03 |
| pMON140823 | P-CUCme.6-1:1:1 | 18 | 0.22 | 0.02 |
| pMON140824 | P-CUCme.8-1:1:2 | 19 | 0.14 | 0.01 |
| pMON140825 | P-CUCme.9-1:1:2 | 20 | 0.39 | 0.03 |
| pMON140826 | P-CUCme.10-1:1:1 | 21 | 0.24 | 0.02 |
| pMON140827 | EXP-CUCme.eEF1a:1:1 | 162 | 0.78 | 0.06 |
| pMON140828 | P-CUCme.15-1:1:2 | 23 | 0.26 | 0.02 |
| pMON140829 | P-CUCme.16a-1:1:2 | 24 | 0.16 | 0.01 |
| pMON140830 | P-CUCme.17-1:1:2 | 26 | 0.17 | 0.01 |
| pMON140831 | P-CUCme.18-1:1:2 | 27 | 0.22 | 0.02 |
| pMON140832 | P-CUCme.19-1:1:3 | 167 | 0.32 | 0.02 |
| pMON140833 | P-CUCme.20-1:3 | 211 | 0.15 | 0.01 |
| pMON140834 | P-CUCme.21-1:1:1 | 30 | 0.75 | 0.06 |
| pMON140835 | P-CUCme.22-1:1:3 | 31 | 0.35 | 0.03 |
| pMON140836 | EXP-CUCme.SAMS2:1:1 | 168 | 0.60 | 0.04 |
| pMON140837 | P-CUCme.26-1:1:2 | 33 | 0.13 | 0.01 |
| pMON140838 | P-CUCme.28-1:1:2 | 34 | 0.09 | 0.01 |
| pMON140839 | EXP-CUCme.29:1:2 | 212 | 0.08 | 0.01 |

TABLE 10

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At. Act7:1:11 | GUS/RLuc normalized with respect to EXP-CaMV. 35S-enh + Ph.DnaK:1:3 |
|---|---|---|---|---|
| pMON80585 | EXP-At.Atntt1:1:2 | 200 | 0.96 | 0.18 |
| pMON109584 | EXP-CaMV.35S-enh + Ph.DnaK:1:3 | 201 | 5.21 | 1.00 |
| pMON118756 | EXP-At.Act7:1:11 | 202 | 1.00 | 0.19 |
| pMON124912 | Promoterless | | 0.05 | 0.01 |
| pMON140818 | P-CUCme.1-1:1:1rc | 155 | 0.42 | 0.08 |
| pMON140819 | P-CUCme.2-1:1:1 | 14 | 0.23 | 0.04 |
| pMON140820 | P-CUCme.3-1:1:3 | 15 | 0.05 | 0.01 |
| pMON140821 | EXP-CUCme.4:1:1 | 156 | 4.12 | 0.79 |
| pMON140822 | EXP-CUCme.5:1:1 | 159 | 0.40 | 0.08 |
| pMON140823 | P-CUCme.6-1:1:1 | 18 | 0.20 | 0.04 |

TABLE 10-continued

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At. Act7:1:11 | GUS/RLuc normalized with respect to EXP-CaMV. 35S-enh + Ph.DnaK:1:3 |
|---|---|---|---|---|
| pMON140824 | P-CUCme.8-1:1:2 | 19 | 0.11 | 0.02 |
| pMON140825 | P-CUCme.9-1:1:2 | 20 | 0.36 | 0.07 |
| pMON140826 | P-CUCme.10-1:1:1 | 21 | 0.22 | 0.04 |
| pMON140827 | EXP-CUCme.eEF1a:1:1 | 162 | 0.68 | 0.13 |
| pMON140828 | P-CUCme.15-1:1:2 | 23 | 0.24 | 0.05 |
| pMON140829 | P-CUCme.16a-1:1:2 | 24 | 0.13 | 0.02 |
| pMON140830 | P-CUCme.17-1:1:2 | 26 | 0.16 | 0.03 |
| pMON140831 | P-CUCme.18-1:1:2 | 27 | 0.22 | 0.04 |
| pMON140832 | P-CUCme.19-1:1:3 | 167 | 0.27 | 0.05 |

TABLE 10-continued

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At. Act7:1:11 | GUS/RLuc normalized with respect to EXP-CaMV. 35S-enh + Ph.DnaK:1:3 |
|---|---|---|---|---|
| pMON140833 | P-CUCme.20-1:3 | 211 | 0.14 | 0.03 |
| pMON140834 | P-CUCme.21-1:1:1 | 30 | 0.69 | 0.13 |
| pMON140835 | P-CUCme.22-1:1:3 | 31 | 0.29 | 0.06 |
| pMON140836 | EXP-CUCme. SAMS2:1:1 | 168 | 0.55 | 0.11 |
| pMON140837 | P-CUCme.26-1:1:2 | 33 | 0.14 | 0.03 |
| pMON140838 | P-CUCme.28-1:1:2 | 34 | 0.08 | 0.02 |
| pMON140839 | EXP-CUCme.29: 1:2 | 212 | 0.08 | 0.01 |

As can be seen in Tables 9 and 10, most of the expression element groups tested, demonstrated the ability to drive transgene expression in soybean cotyledon protoplast cells. One expression element group, EXP-CUCme.4:1:1 (SEQ ID NO: 156) demonstrated levels of transgene expression higher than that of EXP-At.Act7:1:11 in this assay.

Example 5

Analysis of Regulatory Elements Driving GUS in Bombarded Soybean Leaves and Roots.

Soybean leaves and roots were transformed with plant expression vectors containing a test transcriptional regulatory expression element group driving expression of the ß-glucuronidase (GUS) transgene and compared to GUS expression in roots and leaves in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme-.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups in particle bombarded soybean leaves and roots. The plant expression vectors used for transformation of leaves and roots was the same as those presented in Table 7 of Example 4 above.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules CA). A PDS 1000/He biolistic gun was used for transformation (Catalog #165-2257 Bio-Rad, Hercules Calif.). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0—no expression,+to ++++++—low to high, respectively).

Expression of the GUS transgene demonstrated in each tissue is used to infer the relative potential level and specificity of each element's capacity to drive transgene expression in stably transformed corn plants. Average GUS expression ratings are provided in Table 11 below.

TABLE 11

GUS expression ratings for particle bombarded leaf and root.

| Construct | Regulatory Element | SEQ ID NO: | Leaf Expression | Root Expression |
|---|---|---|---|---|
| pMON80585 | EXP-At.Atntt1:1:2 | 200 | +++ | +++ |
| pMON109584 | EXP-CaMV.35S-enh + Ph.DnaK:1:3 | 201 | +++++ | ++ |
| pMON118756 | EXP-At.Act7:1:11 | 202 | ++++ | +++ |
| pMON124912 | Promoterless | | 0 | 0 |
| pMON140818 | P-CUCme.1-1:1:1rc | 155 | +++ | + |
| pMON140819 | P-CUCme.2-1:1:1 | 14 | ++ | + |
| pMON140820 | P-CUCme.3-1:1:3 | 15 | 0 | 0 |
| pMON140821 | EXP-CUCme.4:1:1 | 156 | ++++++ | +++ |
| pMON140822 | EXP-CUCme.5:1:1 | 159 | ++ | + |
| pMON140823 | P-CUCme.6-1:1:1 | 18 | ++ | + |
| pMON140824 | P-CUCme.8-1:1:2 | 19 | + | + |
| pMON140825 | P-CUCme.9-1:1:2 | 20 | ++ | + |
| pMON140826 | P-CUCme.10-1:1:1 | 21 | +++ | +++ |
| pMON140827 | EXP-CUCme. eEF1a:1:1 | 162 | ++++ | +++ |
| pMON140828 | P-CUCme.15-1:1:2 | 23 | + | + |
| pMON140829 | P-CUCme.16a-1:1:2 | 24 | + | |
| pMON140830 | P-CUCme.17-1:1:2 | 26 | ++++ | + |
| pMON140831 | P-CUCme.18-1:1:2 | 27 | +++ | + |
| pMON140832 | P-CUCme.19-1:1:3 | 167 | + | + |
| pMON140833 | P-CUCme.20-1:3 | 211 | + | + |
| pMON140834 | P-CUCme.21-1:1:1 | 30 | + | + |
| pMON140835 | P-CUCme.22-1:1:3 | 31 | ++++ | + |
| pMON140836 | EXP-CUCme. SAMS2:1:1 | 168 | +++++ | +++ |
| pMON140837 | P-CUCme.26-1:1:2 | 33 | + | + |
| pMON140838 | P-CUCme.28-1:1:2 | 34 | + | + |
| pMON140839 | EXP-CUCme.29:1:2 | 212 | + | + |

As can be seen in Table 11 above, all but one of the expression element groups demonstrated the ability to drive transgene expression in particle bombarded soybean leaf and root tissue. Two expression element groups, P-CUCme.28-

1:1:2 (SEQ ID NO: 34) and EXP-CUCme.4:1:1 (SEQ ID NO: 156) demonstrated similar or higher levels of expression relative to expression driven by EXP-CaMV.35S-enh+Ph.DnaK:1:3 in this assay.

Example 6

Analysis of Regulatory Elements Driving GUS in Soy Cotyledon Protoplast using Transgene Cassette Amplicons Soybean cotyledon protoplasts were transformed with transgene cassette amplicons containing a transcriptional regulatory expression element group driving expression of the ß-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 12 below shows the mean GUS expression values conferred by each transgene amplicon. Table 13 below shows the GUS to firefly luciferase (FLuc) ratios normalized with respect to EXP-At.Atntt1:1:2 and P-CaMV.35S-enh-1:1:102/L-CaMV.35S -1:1:2

TABLE 12

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| No DNA | | | 0.00 | 0.00 | 0.00 |
| pMON124912 | No promoter | | 54.67 | 34905.00 | 0.00 |
| pMON33449 | P-CaMV.35S-enh-1:1:102/L-CaMV.35S-1:1:2 | 210 | 107064.67 | 21757.67 | 4.92 |
| pMON80585 | EXP-At.Atntt1:1:2 | 200 | 4962.33 | 40778.67 | 0.12 |
| 56969 | CumMe_WSM_SF16429.G5670 | 40 | 283.67 | 53452.00 | 0.01 |
| 56877 | P-CUCme.CumMe_WSM_SF16444.G5140-1:1:1 | 175 | 5297.67 | 46576.67 | 0.11 |
| 56749 | P-CUCme.CumMe_WSM_SF16563.G5560-1:1:1 | 176 | 280.67 | 41958.33 | 0.01 |
| 56918 | CumMe_WSM_SF17051.G5470 | 48 | 1088.00 | 36321.00 | 0.03 |
| 56849 | P-CUCme.CumMe_WSM_SF17111.G5790-1:1:1 | 177 | 196.00 | 48128.00 | 0.00 |
| 56754 | P-CUCme.WSM_SF17252.G7330-1:1:1 | 179 | 175.67 | 45427.00 | 0.00 |
| 56892 | CumMe_WSM_SF17349.G5770 | 56 | 34.00 | 38016.00 | 0.00 |
| 56477 | CumMe_WSM_SF17866.G6050 | 62 | 862.00 | 52203.33 | 0.02 |
| 56842 | P-CUCme.CumMe_WSM_SF18488.G5340-1:1:1 | 181 | 2892.67 | 49144.33 | 0.06 |
| 56852 | P-CUCme.CumMe_WSM_SF18536.G6480-1:1:1 | 182 | 3462.67 | 46549.33 | 0.07 |
| 56497 | CumMe_WSM_SF18575.G6410 | 71 | 92.67 | 47628.33 | 0.00 |
| 56847 | P-CUCme.CumMe_WSM_SF18634.G5190-1:1:1 | 183 | 122.33 | 36815.33 | 0.00 |
| 56746 | P-CUCme.CumMe_WSM_SF18716.G5860-1:1:1 | 184 | 14.33 | 62483.33 | 0.00 |
| 56883 | CumMe_WSM_SF18986.G6110 | 79 | 863.33 | 54379.33 | 0.02 |
| 56734 | EXP-CUCme.WSM_SF19064.G5690:1:1 | 185 | 142.00 | 46962.67 | 0.00 |
| 56912 | P-CUCme.CumMe_WSM_SF19647.G5760-1:1:1 | 188 | 7659.00 | 46935.67 | 0.16 |
| 56482 | P-CUCme.CumMe_WSM_SF19839.G5090-1:1:1 | 189 | 3279.00 | 37070.67 | 0.09 |
| 56963 | CumMe_WSM_SF19902.G5260 | 87 | 1629.00 | 55649.00 | 0.03 |
| 56747 | P-CUCme.CumMe_WSM_SF20132.G5560-1:1:1 | 190 | 340.33 | 40577.00 | 0.01 |
| 56479 | CumMe_WSM_SF20359.G5870 | 92 | 192.00 | 61341.67 | 0.00 |
| 56744 | CumMe_WSM_SF206458.G5970 | 98 | 154.67 | 33139.33 | 0.00 |
| 56948 | CumMe_WSM_SF206534.G5200 | 99 | 62.00 | 52118.00 | 0.00 |
| 56896 | CumMe_WSM_SF22008.G5670 | 108 | 1585.00 | 53540.00 | 0.03 |
| 56919 | CumMe_WSM_SF22275.G5780 | 112 | 8.33 | 48546.33 | 0.00 |
| 56967 | CumMe_WSM_SF22355.G5310 | 113 | 74.33 | 36202.67 | 0.00 |
| 56837 | P-CUCme.CumMe_WSM_SF22531.G5120-1:1:1 | 192 | 1526.67 | 52799.33 | 0.03 |
| 56940 | CumMe_WSM_SF22870.G5370 | 115 | 14.67 | 53663.33 | 0.00 |
| 56495 | P-CUCme.CumMe_WSM_SF23760.G5200-1:1:1 | 193 | 196.33 | 49870.67 | 0.00 |
| 56868 | P-CUCme.CumMe_WSM_SF23906.G6180-1:1:1 | 194 | 1584.33 | 42532.33 | 0.04 |
| 56998 | CumMe_WSM_SF24045.G5400 | 123 | 80.67 | 47553.00 | 0.00 |
| 56976 | P-CUCme.CumMe_WSM_SF25141.G5160-1:1:2 | 195 | 4506.00 | 57213.00 | 0.08 |
| 56742 | P-CUCme.CumMe_WSM_SF25355.G5000-1:1:1 | 196 | 4.00 | 41114.33 | 0.00 |
| 56915 | P-CUCme.CumMe_WSM_SF25936.G5450-1:1:1 | 197 | 965.33 | 34494.67 | 0.03 |
| 56854 | CumMe_WSM_SF28729.G5340 | 134 | 208.33 | 53956.00 | 0.00 |
| 56936 | CumMe_WSM_SF31264.G5380 | 136 | 292.67 | 42320.67 | 0.01 |
| 56863 | P-CUCme.CumMe_WSM_SF35856.G5150-1:1:1 | 198 | 125.00 | 48705.33 | 0.00 |
| 56751 | P-CUCme.CumMe_WSM_SF41124.G5080-1:1:1 | 199 | 31.33 | 53595.00 | 0.00 |
| 56921 | CumMe_WSM_SF41254.G5160 | 141 | 11.67 | 52643.67 | 0.00 |
| 56884 | CumMe_WSM_SF42141.G5110 | 146 | 48.33 | 40556.67 | 0.00 |

TABLE 13

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| No DNA | | | 0.00 | 0.00 |
| pMON124912 | No promoter | | 0.01 | 0.00 |
| pMON33449 | P-CaMV.35S-enh-1:1:102/L-CaMV.35S-1:1:2 | 210 | 40.44 | 1.00 |
| pMON80585 | EXP-At.Atntt1:1:2 | 200 | 1.00 | 0.02 |
| 56969 | CumMe_WSM_SF16429.G5670 | 40 | 0.04 | 0.00 |
| 56877 | P-CUCme.CumMe_WSM_SF16444.G5140-1:1:1 | 175 | 0.93 | 0.02 |
| 56749 | P-CUCme.CumMe_WSM_SF16563.G5560-1:1:1 | 176 | 0.05 | 0.00 |
| 56918 | CumMe_WSM_SF17051.G5470 | 48 | 0.25 | 0.01 |
| 56849 | P-CUCme.CumMe_WSM_SF17111.G5790-1:1:1 | 177 | 0.03 | 0.00 |
| 56754 | P-CUCme.WSM_SF17252.G7330-1:1:1 | 179 | 0.03 | 0.00 |
| 56892 | CumMe_WSM_SF17349.G5770 | 56 | 0.01 | 0.00 |
| 56477 | CumMe_WSM_SF17866.G6050 | 62 | 0.14 | 0.00 |
| 56842 | P-CUCme.CumMe_WSM_SF18488.G5340-1:1:1 | 181 | 0.48 | 0.01 |
| 56852 | P-CUCme.CumMe_WSM_SF18536.G6480-1:1:1 | 182 | 0.61 | 0.02 |
| 56497 | CumMe_WSM_SF18575.G6410 | 71 | 0.02 | 0.00 |
| 56847 | P-CUCme.CumMe_WSM_SF18634.G5190-1:1:1 | 183 | 0.03 | 0.00 |
| 56746 | P-CUCme.CumMe_WSM_SF18716.G5860-1:1:1 | 184 | 0.00 | 0.00 |
| 56883 | CumMe_WSM_SF18986.G6110 | 79 | 0.13 | 0.00 |
| 56734 | EXP-CUCme.WSM_SF19064.G5690:1:1 | 185 | 0.02 | 0.00 |
| 56912 | P-CUCme.CumMe_WSM_SF19647.G5760-1:1:1 | 188 | 1.34 | 0.03 |
| 56482 | P-CUCme.CumMe_WSM_SF19839.G5090-1:1:1 | 189 | 0.73 | 0.02 |
| 56963 | CumMe_WSM_SF19902.G5260 | 87 | 0.24 | 0.01 |
| 56747 | P-CUCme.CumMe_WSM_SF20132.G5560-1:1:1 | 190 | 0.07 | 0.00 |
| 56479 | CumMe_WSM_SF20359.G5870 | 92 | 0.03 | 0.00 |
| 56744 | CumMe_WSM_SF206458.G5970 | 98 | 0.04 | 0.00 |
| 56948 | CumMe_WSM_SF206534.G5200 | 99 | 0.01 | 0.00 |
| 56896 | CumMe_WSM_SF22008.G5670 | 108 | 0.24 | 0.01 |
| 56919 | CumMe_WSM_SF22275.G5780 | 112 | 0.00 | 0.00 |
| 56967 | CumMe_WSM_SF22355.G5310 | 113 | 0.02 | 0.00 |
| 56837 | P-CUCme.CumMe_WSM_SF22531.G5120-1:1:1 | 192 | 0.24 | 0.01 |
| 56940 | CumMe_WSM_SF22870.G5370 | 115 | 0.00 | 0.00 |
| 56495 | P-CUCme.CumMe_WSM_SF23760.G5200-1:1:1 | 193 | 0.03 | 0.00 |
| 56868 | P-CUCme.CumMe_WSM_SF23906.G6180-1:1:1 | 194 | 0.31 | 0.01 |
| 56998 | CumMe_WSM_SF24045.G5400 | 123 | 0.01 | 0.00 |
| 56976 | P-CUCme.CumMe_WSM_SF25141.G5160-1:1:2 | 195 | 0.65 | 0.02 |
| 56742 | P-CUCme.CumMe_WSM_SF25355.G5000-1:1:1 | 196 | 0.00 | 0.00 |
| 56915 | P-CUCme.CumMe_WSM_SF25936.G5450-1:1:1 | 197 | 0.23 | 0.01 |
| 56854 | CumMe_WSM_SF28729.G5340 | 134 | 0.03 | 0.00 |
| 56936 | CumMe_WSM_SF31264.G5380 | 136 | 0.06 | 0.00 |
| 56863 | P-CUCme.CumMe_WSM_SF35856.G5150-1:1:1 | 198 | 0.02 | 0.00 |
| 56751 | P-CUCme.CumMe_WSM_SF41124.G5080-1:1:1 | 199 | 0.00 | 0.00 |
| 56921 | CumMe_WSM_SF41254.G5160 | 141 | 0.00 | 0.00 |
| 56884 | CumMe_WSM_SF42141.G5110 | 146 | 0.01 | 0.00 |

As can be seen in Table 12 above, not all EXP sequences demonstrated the ability to drive transgene expression when compared to the promoterless control. However, the EXP sequences, CumMe_WSM_SF16429.G5670 (SEQ ID NO: 40), P-CUCme.CumMe_WSM SF16444.G5140-1:1:1 (SEQ ID NO: 175), P-CUCme.CumMe_WSM_SF16563.G5560-1: 1: 1 (SEQ ID NO: 176), CumMe_WSM_SF17051.G5470 (SEQ ID NO: 48), P-CUCme.CumMe_WSM_SF17111.65790-1:1:1 (SEQ ID NO: 177), P-CUCme.WSM_SF17252.G7330-1:1:1 (SEQ ID NO: 179), CumMe_WSM_SF17866.G6050 (SEQ ID NO: 62), P-CUCme.CumMe_WSM_SF18488.G5340-1:1:1 (SEQ ID NO: 181), P-CUCme.CumMe_WSM_SF18536.G6480-1:1:1 (SEQ ID NO: 182), CumMe_WSM_SF18575.G6410 (SEQ ID NO: 71), P-CUCme.CumMe_WSM_SF18634.G5190-1:1:1 (SEQ ID NO: 183), CumMe_WSM_SF18986.G6110 (SEQ ID NO: 79), EXP-CUCme.WSM_SF19064.G5690:1:1 (SEQ ID NO: 185), P-CUCme.CumMe_WSM_SF19647.G5760-1:1:1 (SEQ ID NO: 188), P-CUCme.CumMe_WSM_SF19839.G5090-1:1:1 (SEQ ID NO: 189), CumMe_WSM_SF19902.G5260 (SEQ ID NO: 87), P-CUCme.CumMe_WSM_SF20132.G5560-1:1:1 (SEQ ID NO: 190), CumMe_WSM_SF20359.G5870 (SEQ ID NO: 92), CumMe_WSM_SF206458.G5970 (SEQ ID NO: 98), CumMe_WSM_SF206534.G5200 (SEQ ID NO: 99), CumMe_WSM_SF22008.G5670 (SEQ ID NO: 108), CumMe_WSM_SF22355.G5310 (SEQ ID NO: 113), P-CUCme.CumMe_WSM_SF22531.G5120-1:1:1 (SEQ ID NO: 192), EXP-CUCme.WSM_SF19064.G5690:1:1 (SEQ ID NO: 193), P-CUCme.CumMe_WSM_SF23906.G6180-1:1:1 (SEQ ID NO: 194), CumMe_WSM_SF24045.G5400 (SEQ ID NO: 123), P-CUCme.CumMe_WSM_SF25141.G5160-1:1:2 (SEQ ID NO: 195), P-CUCme.CumMe_WSM_SF25936.G5450-1:1:1 (SEQ ID NO: 197), CumMe_WSM_SF28729.G5340 (SEQ ID NO: 134), CumMe_WSM_SF31264.G5380 (SEQ ID NO: 136) and P-CUCme.CumMe_WSM_SF35856.G5150-1:1:1 (SEQ ID NO: 198) demonstrated the ability to drive trangene expression in soybean cotyledon protoplasts at a level similar or greater than EXP-At.Atntt1:1:2. As shown in Table 13 above, the EXP sequence P-CUCme.CumMe_WSM_SF19647.G5760-1:1:1 (SEQ ID NO: 188) demonstrated the ability to drive transgene expression in this assay at a level greater than EXP-At.Atntt1:1:2.

Example 7

Analysis of Regulatory Elements Driving GUS in Cotton Leaf Protoplasts

Cotton leaf protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens,* a first transgene cassette comprised of a test promoter or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the Arabidopsis Actin 7 promoter) or the antibiotic, kanamycin and a left border region from *A. tumefaciens.* A promoterless control plant expression vector (pMON124912) served as a negative control for expression. The foregoing test and constitutive expression element groups were cloned into plant expression vectors as shown in Table 14 below.

TABLE 14

Plant expression vectors and corresponding expression element group and 3' UTR.

| Construct | Regulatory Element | SEQ ID NO: | 3' UTR |
|---|---|---|---|
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 206), operably linked 5' to a 3' termination region from the *Agrobacterium lumefaciens* nopaline synthase gene.

The plant expression vectors, pMON80585, pMON109584, pMON118756, pMON124912, pMON140818, pMON140819, pMON140820, pMON140821, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform cotton leaf protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p.02). Sample measurements were made using 4 replicates per transformation. The average GUS and luciferase values are presented in Table 15 below.

TABLE 15

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON109584 | EXP-C.aMV.35S-enh + Ph.DnaK:1:3 | 201 | 5322.8 | 14842.8 | 27990.5 | 0.3586 | 0.1902 |
| pMON118756 | EXP-At.Act7:1:11 | 202 | 1006.3 | 19746.8 | 25582.3 | 0.0510 | 0.0393 |
| pMON124912 | Promoterless | | 21 | 19248.5 | 25012 | 0.0011 | 0.0008 |
| pMON140818 | P-CUCme.1-1:1:1rc | 155 | 170.3 | 17796.8 | 22026.3 | 0.0096 | 0.0077 |
| pMON140819 | P-CUCme.2-1:1:1 | 14 | 34.8 | 16326.3 | 21407.5 | 0.0021 | 0.0016 |
| pMON140820 | P-CUCme.3-1:1:3 | 15 | 51.5 | 17356.8 | 21523.8 | 0.0030 | 0.0024 |
| pMON140821 | EXP-CUCme.4:1:1 | 156 | 3497.8 | 18745.3 | 26065.3 | 0.1866 | 0.1342 |
| pMON140823 | P-CUCme.6-1:1:1 | 18 | 40.8 | 19533.8 | 26361.5 | 0.0021 | 0.0015 |
| pMON140824 | P-CUCme.8-1:1:2 | 19 | 22 | 19701 | 26278 | 0.0011 | 0.0008 |
| pMON140825 | P-CUCme.9-1:1:2 | 20 | 372.5 | 21972.3 | 28755 | 0.0170 | 0.0130 |
| pMON140826 | P-CUCme.10-1:1:1 | 21 | 198 | 21362.8 | 28902 | 0.0093 | 0.0069 |
| pMON140827 | EχP-CUCme.eEF1a:1:1 | 162 | 725 | 21589 | 27635.3 | 0.0336 | 0.0262 |
| pMON140828 | P-CUCme.15-1:1:2 | 23 | 55.3 | 17706 | 28846 | 0.0031 | 0.0019 |
| pMON140829 | P-CUCme.16a-1:1:2 | 24 | 14 | 23289.5 | 30190 | 0.0006 | 0.0005 |
| pMON140830 | P-CUCme.17-1:1:2 | 26 | 155.5 | 23178.3 | 31602.8 | 0.0067 | 0.0049 |
| pMON140831 | P-CUCme.18-1:1:2 | 27 | 86.8 | 19085.8 | 22396.5 | 0.0045 | 0.0039 |
| pMON140832 | P-CUCme.19-1:1:3 | 167 | 130 | 21520.3 | 27270.5 | 0.0060 | 0.0048 |
| pMON140833 | P-CUCme.20-1:3 | 211 | 88.5 | 22223.8 | 30786 | 0.0040 | 0.0029 |
| pMON140834 | P-CUCme.21-1:1:1 | 30 | 98.5 | 18579 | 20506.3 | 0.0053 | 0.0048 |
| pMON140835 | P-CUCme.22-1:1:3 | 31 | 363 | 21780.3 | 28816.3 | 0.0167 | 0.0126 |
| pMON140836 | EXP-CUCme.SAMS2:1:1 | 168 | 515 | 17906 | 23031 | 0.0288 | 0.0224 |
| pMON140837 | P-CUCme.26-1:1:2 | 33 | 125 | 15529.3 | 15169.3 | 0.0080 | 0.0082 |
| pMON140838 | P-CUCme.28-1:1:2 | 34 | 115.8 | 17013.5 | 22236.5 | 0.0068 | 0.0052 |
| pMON140839 | EXP-CUCme.29:1:2 | 212 | 15.5 | 16370.3 | 20409 | 0.0009 | 0.0008 |

To compare the relative activity of each promoter in cotton leaf protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 16 below shows the GUS to firefly luciferase (FLuc) ratios normalized with respect to EXP-At.Act7:1:11 and EXP-CaMV.35S-enh+Ph.DnaK:1:3. Table 17 below shows the GUS to *renilla* luciferase (RLuc) ratios normalized with respect to EXP-At.Act7:1:11 and EXP-CaMV.35S-enh+Ph.DnaK:1:3.

TABLE 16

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At. Act7:1:11 | GUS/FLuc normalized with respect to EXP-CaMV. 35S-enh + Ph.DnaK:1:3 |
|---|---|---|---|---|
| pMON109584 | EXP-CaMV.35S-enh + Ph.DnaK:1:3 | 201 | 7.037 | 1.000 |
| pMON118756 | EXP-At.Act7:1:11 | 202 | 1.000 | 0.142 |
| pMON124912 | Promoterless | | 0.021 | 0.003 |
| pMON140818 | P-CUCme.1-1:1:1rc | 155 | 0.188 | 0.027 |
| pMON140819 | P-CUCme.2-1:1:1 | 14 | 0.042 | 0.006 |
| pMON140820 | P-CUCme.3-1:1:3 | 15 | 0.058 | 0.008 |
| pMON140821 | EXP-CUCme.4:1:1 | 156 | 3.662 | 0.520 |
| pMON140823 | P-CUCme.6-1:1:1 | 18 | 0.041 | 0.006 |
| pMON140824 | P-CUCme.8-1:1:2 | 19 | 0.022 | 0.003 |
| pMON140825 | P-CUCme.9-1:1:2 | 20 | 0.333 | 0.047 |
| pMON140826 | P-CUCme.10-1:1:1 | 21 | 0.182 | 0.026 |
| pMON140827 | EXP-CUCme. eEF1a:1:1 | 162 | 0.659 | 0.094 |
| pMON140828 | P-CUCme.15-1:1:2 | 23 | 0.061 | 0.009 |
| pMON140829 | P-CUCme.16a-1:1:2 | 24 | 0.012 | 0.002 |
| pMON140830 | P-CUCme.17-1:1:2 | 26 | 0.132 | 0.019 |
| pMON140831 | P-CUCme.18-1:1:2 | 27 | 0.089 | 0.013 |

TABLE 16-continued

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At. Act7:1:11 | GUS/FLuc normalized with respect to EXP-CaMV. 35S-enh + Ph.DnaK:1:3 |
|---|---|---|---|---|
| pMON140832 | P-CUCme.19-1:1:3 | 167 | 0.119 | 0.017 |
| pMON140833 | P-CUCme.20-1:3 | 211 | 0.078 | 0.011 |
| pMON140834 | P-CUCme.21-1:1:1 | 30 | 0.104 | 0.015 |
| pMON140835 | P-CUCme.22-1:1:3 | 31 | 0.327 | 0.046 |
| pMON140836 | EXP-CUCme. SAMS2:1:1 | 168 | 0.564 | 0.080 |
| pMON140837 | P-CUCme.26-1:1:2 | 33 | 0.158 | 0.022 |
| pMON140838 | P-CUCme.28-1:1:2 | 34 | 0.134 | 0.019 |
| pMON140839 | EXP-CUCme.29:1:2 | 212 | 0.019 | 0.003 |

TABLE 17

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At. Act7:1:11 | GUS/RLuc normalized with respect to EXP-CaMV. 35S-enh + Ph.DnaK:1:3 |
|---|---|---|---|---|
| pMON109584 | EXP-CaMV.35S-enh + Ph.DnaK:1:3 | 201 | 4.83 | 1.00 |
| pMON118756 | EXP-At.Act7:1:11 | 202 | 1.00 | 0.21 |
| pMON124912 | Promoterless | | 0.02 | 0.00 |
| pMON140818 | P-CUCme.1-1:1:1rc | 155 | 0.20 | 0.04 |
| pMON140819 | P-CUCme.2-1:1:1 | 14 | 0.04 | 0.01 |
| pMON140820 | P-CUCme.3-1:1:3 | 15 | 0.06 | 0.01 |
| pMON140821 | EXP-CUCme.4:1:1 | 156 | 3.41 | 0.71 |

TABLE 17-continued

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At. Act7:1:11 | GUS/RLuc normalized with respect to EXP-CaMV. 35S-enh + Ph.DnaK:1:3 |
|---|---|---|---|---|
| pMON140823 | P-CUCme.6-1:1:1 | 18 | 0.04 | 0.01 |
| pMON140824 | P-CUCme.8-1:1:2 | 19 | 0.02 | 0.00 |
| pMON140825 | P-CUCme.9-1:1:2 | 20 | 0.33 | 0.07 |
| pMON140826 | P-CUCme.10-1:1:1 | 21 | 0.17 | 0.04 |
| pMON140827 | EXP-CUCme.eEF1a:1:1 | 162 | 0.67 | 0.14 |
| pMON140828 | P-CUCme.15-1:1:2 | 23 | 0.05 | 0.01 |
| pMON140829 | P-CUCme.16a-1:1:2 | 24 | 0.01 | 0.00 |
| pMON140830 | P-CUCme.17-1:1:2 | 26 | 0.13 | 0.03 |
| pMON140831 | P-CUCme.18-1:1:2 | 27 | 0.10 | 0.02 |
| pMON140832 | P-CUCme.19-1:1:3 | 167 | 0.12 | 0.03 |
| pMON140833 | P-CUCme.20-1:3 | 211 | 0.07 | 0.02 |
| pMON140834 | P-CUCme.21-1:1:1 | 30 | 0.12 | 0.03 |
| pMON140835 | P-CUCme.22-1:1:3 | 31 | 0.32 | 0.07 |
| pMON140836 | EXP-CUCme.SAMS2:1:1 | 168 | 0.57 | 0.12 |
| pMON140837 | P-CUCme.26-1:1:2 | 33 | 0.21 | 0.04 |
| pMON140838 | P-CUCme.28-1:1:2 | 34 | 0.13 | 0.03 |
| pMON140839 | EXP-CUCme.29:1:2 | 212 | 0.02 | 0.00 |

As can be seen in Tables 16 and 17, most of the expression element groups tested, demonstrated the ability to drive transgene expression in cotton leaf protoplast cells. One expression element group, EXP-CUCme.4:1:1 (SEQ ID NO: 156) demonstrated levels of transgene expression higher than that of EXP-At.Act7:1:11 in this assay.

Example 8

Analysis of Regulatory Elements Driving GUS in Cotton Leaf Protoplasts using Transgene Cassette Amplicons Cotton leaf protoplasts were transformed with transgene cassette amplicons containing a transcriptional regulatory expression element group driving expression of the ß-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 18 below shows the mean GUS expression values conferred by each transgene amplicon. Table 19 below shows the GUS to firefly luciferase (FLuc) ratios normalized with respect to EXP-At.Atntt1:1:2 and P-CaMV.35S-enh-1:1:102/L-CaMV.35S -1:1:2.

TABLE 18

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| Empty Vector | No DNA | | 32.8 | 14087.5 | 0.002 |
| pMON124912 | No promoter | | 12 | 20486.3 | 0.001 |
| pMON80585 | EXP-At.Atntt1:1:2 | 200 | 55.5 | 18811 | 0.003 |
| pMON33449 | P-CaMV.35S-enh-1:1:102/L-CaMV.35S-1:1:2 | 210 | 12472.5 | 19126.3 | 0.652 |
| 56741 | CumMe_WSM_SF143981.G5150 | 36 | 5.8 | 17449.5 | 0.000 |
| 56492 | CumMe_WSM_SF144839.G5080 | 37 | 27.5 | 16674 | 0.002 |
| 56877 | P-CUCme.CumMe_WSM_SF16444.G5140-1:1:1 | 175 | 96.3 | 17237.8 | 0.006 |
| 56485 | CumMe_WSM_SF16530.G6000 | 42 | 27.3 | 17858.5 | 0.002 |
| 56844 | CumMe_WSM_SF16953.G5180 | 47 | 22.3 | 19398.5 | 0.001 |
| 56500 | CumMe_WSM_SF17250.G5910 | 52 | 12.3 | 23980.3 | 0.001 |
| 56754 | P-CUCme.WSM_SF17252.G7330-1:1:1 | 179 | 16 | 13848.8 | 0.001 |
| 56740 | CumMe_WSM_SF17672.G5610 | 60 | 12 | 16646.8 | 0.001 |
| 56870 | CumMe_WSM_SF18287.G5380 | 66 | 39.3 | 13930.5 | 0.003 |
| 56478 | CumMe_WSM_SF18504.G5090 | 68 | 11.8 | 15830.5 | 0.001 |
| 56481 | CumMe_WSM_SF18530.G5750 | 69 | 6.5 | 15211.3 | 0.000 |
| 56498 | CumMe_WSM_SF18645.G5380 | 73 | 36 | 14569.8 | 0.002 |
| 56746 | P-CUCme.CumMe_WSM_SF18716.G5860-1:1:1 | 184 | 11 | 18054.5 | 0.001 |
| 56490 | CumMe_WSM_SF18801.G5040 | 75 | 21.5 | 14147.3 | 0.002 |
| 56488 | CumMe_WSM_SF19323.G5120 | 81 | 15.3 | 11985.3 | 0.001 |
| 56499 | CumMe_WSM_SF19631.G5170 | 83 | 12.5 | 20140.5 | 0.001 |
| 56482 | P-CUCme.CumMe_WSM_SF19839.G5090-1:1:1 | 189 | 75 | 18690.5 | 0.004 |
| 56489 | CumMe_WSM_SF19850.G5130 | 86 | 38.3 | 19756.5 | 0.002 |
| 56476 | CumMe_WSM_SF20355.G5130 | 91 | 10.5 | 27901.8 | 0.000 |
| 56895 | CumMe_WSM_SF20431.G6340 | 95 | 34.8 | 16283.8 | 0.002 |
| 56744 | CumMe_WSM_SF206458.G5970 | 98 | 11 | 19659 | 0.001 |

TABLE 18-continued

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| 56480 | CumMe_WSM_SF21366.G5980 | 105 | 10.8 | 17367 | 0.001 |
| 56930 | CumMe_WSM_SF22070.G5280 | 109 | 25.3 | 14210.5 | 0.002 |
| 56484 | CumMe_WSM_SF23181.G5100 | 117 | 20.3 | 13506 | 0.002 |
| 56495 | P-CUCme.CumMe_WSM_SF23760.G5200-1:1:1 | 193 | 7.8 | 15138.5 | 0.001 |
| 56971 | CumMe_WSM_SF25084.G5580 | 125 | 16 | 16135.3 | 0.001 |
| 56742 | P-CUCme.CumMe_WSM_SF25355.G5000-1:1:1 | 196 | 18 | 13782.8 | 0.001 |
| 56494 | CumMe_WSM_SF25455.G5370 | 129 | 10.5 | 16089.8 | 0.001 |
| 56751 | P-CUCme.CumMe_WSM_SF41124.G5080-1:1:1 | 199 | 24.3 | 17884.3 | 0.001 |
| 56483 | CumMe_WSM_SF41644.G6400 | 143 | 14.5 | 13130.5 | 0.001 |
| 56904 | CumMe_WSM_SF44933.G5290 | 147 | 33 | 13369 | 0.002 |
| 56743 | CumMe_WSM_SF9060.G5120 | 154 | 11.3 | 15230.8 | 0.001 |

TABLE 19

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| Empty Vector | No DNA | | | |
| pMON124912 | No promoter | | | |
| pMON80585 | EXP-At.Atntt1:1:2 | 200 | 1.000 | 0.005 |
| pMON33449 | P-CaMV.35S-enh-1:1:102/L-CaMV.35S-1:1:2 | 210 | 221.025 | 1.000 |
| 56741 | CumMe_WSM_SF143981.G5150 | 36 | 0.113 | 0.001 |
| 56492 | CumMe_WSM_SF144839.G5080 | 37 | 0.559 | 0.003 |
| 56877 | P-CUCme.CumMe_WSM_SF16444.G5140-1:1:1 | 175 | 1.893 | 0.009 |
| 56485 | CumMe_WSM_SF16530.G6000 | 42 | 0.518 | 0.002 |
| 56844 | CumMe_WSM_SF16953.G5180 | 47 | 0.390 | 0.002 |
| 56500 | CumMe_WSM_SF17250.G5910 | 52 | 0.174 | 0.001 |
| 56754 | P-CUCme.WSM_SF17252.G7330-1:1:1 | 179 | 0.392 | 0.002 |
| 56740 | CumMe_WSM_SF17672.G5610 | 60 | 0.244 | 0.001 |
| 56870 | CumMe_WSM_SF18287.G5380 | 66 | 0.956 | 0.004 |
| 56478 | CumMe_WSM_SF18504.65090 | 68 | 0.253 | 0.001 |
| 56481 | CumMe_WSM_SF18530.G5750 | 69 | 0.145 | 0.001 |
| 56498 | CumMe_WSM_SF18645.G5380 | 73 | 0.837 | 0.004 |
| 56746 | P-CUCme.CumMe_WSM_SF18716.G5860-1:1:1 | 184 | 0.207 | 0.001 |
| 56490 | CumMe_WSM_SF18801.G5040 | 75 | 0.515 | 0.002 |
| 56488 | CumMe_WSM_SF19323.G5120 | 81 | 0.433 | 0.002 |
| 56499 | CumMe_WSM_SF19631.G5170 | 83 | 0.210 | 0.001 |
| 56482 | P-CUCme.CumMe_WSM_SF19839.G5090-1:1:1 | 189 | 1.360 | 0.006 |
| 56489 | CumMe_WSM_SF19850.G5130 | 86 | 0.657 | 0.003 |
| 56476 | CumMe_WSM_SF20355.G5130 | 91 | 0.128 | 0.001 |
| 56895 | CumMe_WSM_SF20431.G6340 | 95 | 0.724 | 0.003 |
| 56744 | CumMe_WSM_SF206458.G5970 | 98 | 0.190 | 0.001 |
| 56480 | CumMe_WSM_SF21366.G5980 | 105 | 0.211 | 0.001 |
| 56930 | CumMe_WSM_SF22070.G5280 | 109 | 0.603 | 0.003 |
| 56484 | CumMe_WSM_SF23181.G5100 | 117 | 0.509 | 0.002 |
| 56495 | P-CUCme.CumMe_WSM_SF23760.G5200-1:1:1 | 193 | 0.175 | 0.001 |

TABLE 19-continued

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56971 | CumMe_WSM_SF25084.G5580 | 125 | 0.336 | 0.002 |
| 56742 | P-CUCme.CumMe_WSM_SF25355.G5000-1:1:1 | 196 | 0.443 | 0.002 |
| 56494 | CumMe_WSM_SF25455.G5370 | 129 | 0.221 | 0.001 |
| 56751 | P-CUCme.CumMe_WSM_SF41124.G5080-1:1:1 | 199 | 0.461 | 0.002 |
| 56483 | CumMe_WSM_SF41644.G6400 | 143 | 0.374 | 0.002 |
| 56904 | CumMe_WSM_SF44933.G5290 | 147 | 0.837 | 0.004 |
| 56743 | CumMe_WSM_SF9060.G5120 | 154 | 0.251 | 0.001 |

As can be seen in Table 18 above, not all EXP sequences demonstrated the ability to drive transgene expression when compared to the promoterless control. However, the EXP sequences, P-CUCme.CumMe_WSM_SF16444.G5140-1:1:1 (SEQ ID NO: 175) and P-CUCme.CumMe_WSM_SF19839.G5090-1:1:1 (SEQ ID NO: 189) demonstrated the ability to drive trangene expression in soybean cotyledon protoplasts at a level similar or greater than EXP-At.Atntt1:1:2. As shown in Table 19 above, the EXP sequence, P-CUCme.CumMe_WSM_SF19839.G5090-1:1:1 (SEQ ID NO: 189) demonstrated the ability to drive transgene expression in this assay at a level greater than EXP-At.Atntt1:1:2.

Example 9

Analysis of Regulatory Elements Driving GUS in Stably Transformed Soybean

Soybean plants were transformed with plant expression vectors containing an EXP sequence driving expression of the ß-glucuronidase (GUS) transgene.

Expression of the GUS transgene driven by EXP-CUCme.Ubq1:1:1 (SEQ ID NO: 1), EXP-CUCme.Ubq1:1:3 (SEQ ID NO: 7), P-CUCme.1-1:1: lrc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe WSM SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) assayed both qualitatively through inspection of stained tissue sections and quantitatively. Each plant expression vector was comprised of a right border region from *Agrobacterium tumefaciens,* a first transgene cassette comprised of an EXP sequence operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the the *Gossypium barbadense* FbLate-2 gene (T-Gb.FbL2-1:1:1, SEQ ID NO: 205); a second transgene selection cassette used for selection of transformed plant cells that confered resistance to the herbicide glyphosate (driven by the Arabidopsis Actin 7 promoter) and a left border region from *A. tumefaciens.*

The foregoing EXP sequences were cloned into plant expression constructs as shown in Tables 20 through 23 below and used to transform soybean plants using an *agrobacterium* mediated transformation method. Expression of GUS was assayed qualitatively using histological sections of selected tissues and quantitatively.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ generation plants were inspected for expression in Vn5 Root, R1 Root, Vn5 Sink Leaf, Vn5 Source Leaf, R1 Source Leaf, R1 Petiole, Yellow Pod Embryo, Yellow Pod Cotyledon, R3 Immature Seed, R3 Pod, R5 Cotyledon and R1 Flower.

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3nm.

Tables 20 and 21 below show the mean quantitative expression levels measured in the $R_0$ generation plant tissues. Those tissued not assayed are shown as blank cells in both tables.

TABLE 20

Mean GUS expression in Vn5 Root, R1 Root, Vn5 Sink Leaf, Vn5 Source Leaf, R1 Source Leaf and R1 Petiole of $R_0$ generation transformed soybean plants

| Construct | Regulatory Element | SEQ ID NO: | Vn5_ Root | R1_ Root | Vn5_ Sink_Leaf | Vn5_Source Leaf | R1_ Source_Leaf | R1_ Petiole |
|---|---|---|---|---|---|---|---|---|
| pMON138776 | EXP-CUCme.Ubq1:1:1 | 1 | 4 | | | | 4 | 4 |
| pMON138778 | EXP-CUCme.Ubq1:1:3 | 7 | 16 | | 1 | 2 | 13 | 23 |
| pMON140818 | P-CUCme.1-1:1:1rc | 155 | 48.21 | | 22.35 | 20.24 | 33.01 | 78.17 |
| pMON140819 | P-CUCme.2-1:1:1 | 14 | | | | | | |
| pMON140820 | P-CUCme.3-1:1:3 | 15 | | | | | | |
| pMON140821 | EXP-CUCme.4:1:1 | 156 | 96.82 | | 28.32 | 39.17 | 322.98 | 280.03 |
| pMON140822 | EXP-CUCme.5:1:1 | 159 | 28.88 | | | | 41.11 | |
| pMON140823 | P-CUCme.6-1:1:1 | 18 | 23.94 | | | | 32.14 | 30.22 |
| pMON140824 | P-CUCme.8-1:1:2 | 19 | | | | | | |
| pMON140825 | P-CUCme.9-1:1:2 | 20 | 22.06 | | | | 21.22 | 23.08 |
| pMON140826 | P-CUCme.10-1:1:1 | 21 | | | | | | |
| pMON140827 | EXP-CUCme.eEF1a:1:1 | 162 | 189.24 | 153.52 | 59.6 | 37.44 | 103.01 | 130.6 |
| pMON140828 | P-CUCme.15-1:1:2 | 23 | 30.53 | | | | | |
| pMON140830 | P-CUCme.17-1:1:2 | 26 | 51.62 | | 30.07 | 31.08 | 30.49 | 60.14 |
| pMON140831 | P-CUCme.18-1:1:2 | 27 | 57.38 | | | | | 30.03 |
| pMON140832 | P-CUCme.19-1:1:3 | 167 | 23.07 | | 50.21 | 59.73 | 65.58 | 137.42 |
| pMON140833 | P-CUCme.20-1:3 | 211 | 23.15 | | 61.6 | 118.76 | 502.55 | 119.46 |
| pMON140834 | P-CUCme.21-1:1:1 | 30 | | | | | 25.49 | |
| pMON140836 | EXP-CUCme.SAMS2:1:1 | 168 | 230.89 | 184.88 | 65.44 | 53.36 | 118.82 | 351.49 |
| pMON140837 | P-CUCme.26-1:1:2 | 33 | 56.21 | | 26.81 | 45.07 | 51.61 | 47.42 |
| pMON140839 | EXP-CUCme.29:1:2 | 212 | 82.17 | | 45.2 | 28.27 | 64.96 | 109.9 |
| pMON144926 | P-CUCme.CumMe_WSM_SF25355.G5000-1:1:1 | 196 | 28.53 | | | | | |
| pMON144927 | P-CUCme.CumMe_WSM_SF17111.G5790-1:1:1 | 177 | 23.62 | | | | | |
| pMON144928 | P-CUCme.CumMe_WSM_SF22531.G5120-1:1:1 | 192 | 75.62 | | 23 | 20.46 | 21.78 | 39.77 |
| pMON144931 | P-CUCme.CumMe_WSM_SF18488.G5340-1:1:1 | 181 | 43.2 | | | | | 52.55 |
| pMON144933 | P-CUCme.CumMe_WSM_SF23760.G5200-1:1:1 | 193 | 25.61 | | 20.45 | 0 | 0 | 28.69 |
| pMON146941 | EXP-CUCme.WSM_SF19064.G5690:1:1 | 185 | 33.5 | | 0 | 0 | 24.27 | 47.82 |
| pMON144932 | P-CUCme.WSM_SF17252.G7330-1:1:1 | 179 | 32.54 | | 23.76 | 21.5 | 0 | 22.21 |
| pMON146940 | P-CUCme.CumMe_WSM_SF18634.G5190-1:1:1 | 183 | 0 | | 0 | 0 | 0 | 0 |
| pMON147340 | P-CUCme.CumMe_WSM_SF19647.G5760-1:1:1 | 188 | 28.9 | | 0 | 0 | 29.77 | 25.82 |
| pMON147342 | P-CUCme.CumMe_WSM_SF25936.G5450-1:1:1 | 197 | 50.15 | | 24.26 | 0 | 29.38 | 29.91 |
| pMON147343 | P-CUCme.CumMe_WSM_SF19839.G5090-1:1:1 | 189 | 36.05 | | 25.7 | 27.54 | 22.85 | 37.15 |
| pMON144929 | CumMe_WSM_SF206458.G5970 | 98 | | | | | | |
| pMON147304 | P-CUCme.CumMe_WSM_SF18716.G5860-1:1:1 | 184 | 35.01 | | 21.17 | 21.23 | 22 | 44.57 |

TABLE 21

Mean GUS expression in Yellow Pod Embryo, Yellow Pod Cotyledon, R3 Immature Seed, R3 Pod, R5 Cotyledon and R1 Flower of $R_0$ generation transformed soybean plants

| Construct | Regulatory Element | SEQ ID NO: | Yellow_Pod_Embryo | Yellow_Pod_Cotyledon | R3_Immature_Seed | R3_Pod | R5_Cotyledon | R1_Flower |
|---|---|---|---|---|---|---|---|---|
| pMON138776 | EXP-CUCme.Ubq1:1:1 | 1 | 12 | 9 | 13 | 11 | 10 | 7 |
| pMON138778 | EXP-CUCme.Ubq1:1:3 | 7 | 3 | 1 | 13 | 9 | 13 | 27 |
| pMON140818 | P-CUCme.1-1:1:1rc | 155 | 100.79 | 117.5 | 38.31 | 84.72 | 132.27 | 66.8 |
| pMON140819 | P-CUCme.2-1:1:1 | 14 | | | | | 20.35 | 36.18 |
| pMON140820 | P-CUCme.3-1:1:3 | 15 | | | | | | |
| pMON140821 | EXP-CUCme.4:1:1 | 156 | 86.68 | 225.53 | 105.62 | 342.07 | 119.08 | 184.92 |
| pMON140822 | EXP-CUCme.5:1:1 | 159 | 21.48 | 32.27 | 21.47 | 21.66 | | 36.88 |
| pMON140823 | P-CUCme.6-1:1:1 | 18 | 38.75 | | 23.03 | | 25.32 | 58.7 |
| pMON140824 | P-CUCme.8-1:1:2 | 19 | | | | | 90.33 | 25.77 |
| pMON140825 | P-CUCme.9-1:1:2 | 20 | 132.04 | | | 20.56 | 34.78 | |
| pMON140826 | P-CUCme.10-1:1:1 | 21 | | | | | 22.34 | |
| pMON140827 | EXP-CUCme.eEF1a:1:1 | 162 | 200.28 | 291.26 | 58.21 | 131.17 | 114.29 | 130.38 |
| pMON140828 | P-CUCme.15-1:1:2 | 23 | | | 142.24 | 26.2 | | |
| pMON140830 | P-CUCme.17-1:1:2 | 26 | 343.34 | 302.94 | 65.55 | 80.94 | 137.02 | 62.7 |
| pMON140831 | P-CUCme.18-1:1:2 | 27 | 103.17 | 135.97 | 30 | 34.62 | 88.14 | 23.73 |
| pMON140832 | P-CUCme.19-1:1:3 | 167 | 30.96 | 64.46 | | 316.66 | | 53.46 |
| pMON140833 | P-CUCme.20-1:3 | 211 | 174.62 | 524.88 | | 222.04 | 59.43 | 124.68 |
| pMON140834 | P-CUCme.21-1:1:1 | 30 | | | 28.15 | 20.52 | 23.89 | |
| pMON140836 | EXP-CUCme.SAMS2:1:1 | 168 | 110.23 | 159.43 | 61.99 | 248.96 | 49.17 | 224.24 |
| pMON140837 | P-CUCme.26-1:1:2 | 33 | 56.73 | 50.06 | 70 | 143.05 | 25.06 | 49.92 |
| pMON140839 | EXP-CUCme.29:1:2 | 212 | 251.76 | 237.2 | 49.16 | 89.28 | 114.92 | 57.84 |
| pMON144926 | P-CUCme.CumMe_WSM_SF25355.G5000-1:1:1 | 196 | | | 21.41 | | 22.23 | |
| pMON144927 | P-CUCme.CumMe_WSM_SF17111.G5790-1:1:1 | 177 | 58.84 | 28.94 | | | 20.97 | |
| pMON144928 | P-CUCme.CumMe_WSM_SF22531.G5120-1:1:1 | 192 | 135.62 | 152.48 | 30.45 | 51.71 | 129.72 | 42.2 |
| pMON144931 | P-CUCme.CumMe_WSM_SF18488.G5340-1:1:1 | 181 | 866.94 | | 23.26 | 21.49 | | |
| pMON144933 | P-CUCme.CumMe_WSM_SF23760.G5200-1:1:1 | 193 | | | 29.03 | 34.9 | 69.63 | 24.42 |
| pMON146941 | EXP-CUCme.WSM_SF19064.G5690:1:1 | 185 | | | 36.69 | 83.08 | 89.81 | 33.99 |
| pMON144932 | P-CUCme.WSM_SF17252.G7330-1:1:1 | 179 | | | 34.29 | 39.89 | 113.83 | 0 |
| pMON146940 | P-CUCme.CumMe_WSM_SF18634.G5190-1:1:1 | 183 | | | 30.25 | 0 | 0 | 0 |
| pMON147340 | P-CUCme.CumMe_WSM_SF19647.G5760-1:1:1 | 188 | | | 25.73 | 28.28 | 24.04 | 23.35 |
| pMON147342 | P-CUCme.CumMe_WSM_SF25936.G5450-1:1:1 | 197 | | | 104.02 | 80.27 | 31.06 | 26.8 |
| pMON147343 | P-CUCme.CumMe_WSM_SF19839.G5090-1:1:1 | 189 | | | | | | 29.09 |
| pMON144929 | CumMe_WSM_SF206458.G5970 | 98 | | | 24.42 | 25.33 | | |
| pMON147304 | P-CUCme.CumMe_WSM_SF18716.G5860-1:1:1 | 184 | | | | 283.49 | | 61.43 |

As can be seen in Tables 20 and 21, the EXP sequences, EXP-CUCme.Ubq1:1:1 (SEQ ID NO: 1), EXP-CUCme.Ubq1:1:3 (SEQ ID NO: 7), P-CUCme.1-1:1:1 rc (SEQ ID NO: 155), P-CUCme.2-1:1:1 (SEQ ID NO: 14), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) demonstrated quantitatively the capacity to drive transgene expression in some or all tissues assayed, depending upon the EXP sequence used to drive expression.

Histological analysis of selected tissue sections provided further evidence of expression for many of the EXP sequences. EXP-CUCme.Ubq 1:1:1 (SEQ ID NO: 1) and EXP-CUCme.Ubq1:1:3 (SEQ ID NO: 7) demonstrated a constitutive expression pattern with staining observed in all tissues, even though quantitative analysis showed fairly low levels of expression. This type of expression pattern can be most adventitious to driving expression of transgenes that require a low level of constitutive expression. Expression driven by P-CUCme.1-1:1:1rc (SEQ ID NO: 155) demonstrated expression in sink and source leaf vascular bundles and xylem and in the root cortex, phloem, xylem, endodermis, stele and tip. Expression driven by EXP-CUCme.4:1:1 (SEQ ID NO: 156) was observed in all tissues with the highest expression observed in the reproductive phase of the plant. Expression driven by P-CUCme.10-1:1:1 (SEQ ID NO: 21) was observed only in in V5 Sink Leaf and R1 Flower anthers. Expression driven by EXP-CUCme.eEF1a:1:1 (SEQ ID NO: 162) demonstrated a consititutive expression pattern with highest expression being observed in yellow pod embryo and cotyledon. The yellow pod embryo activity was 5fold higher in the Rlgeneration than in the RO generation (see Table 23 below). Expression driven by P-CUCme.15-1:1:2 (SEQ ID NO: 23), P-CUCme.17-1:1:2 (SEQ ID NO: 26) and P-CUCme.18-1:1:2 (SEQ ID NO: 27) demonstrated a constitutive level of expression histologically. Expression driven by P-CUCme.19-1:1:3 (SEQ ID NO: 167) demonstrated a constitutive pattern of expression histologically with the exception of the V5 root and R1 petiole. R3 pod showed the highest expression.

Expression driven by P-CUCme.20-1:3 (SEQ ID NO: 211) demonstrated a constitutive expression pattern histologically with the exception of expression in V5 root. Expression was highest in the R8 stage cotyledon. Expression driven by EXP-CUCme.SAMS2:1:1 (SEQ ID NO: 168) demonstrated a constitutive pattern of expression with expression observed histologically in all tissues. GUS expression was observed to increase in the R1 generation (see Tables 22 and 23 below). The R1 stage flowers and petioles demonstrated the highest levels of expression in soybean. Expression driven by P-CUCme.CumMe_WSM_SF22531.G5120-1:1:1 (SEQ ID NO: 192) demonstrated a constitutive pattern of expression histologically with highest expression in the R8 stage cotyledon and embryo. Expression driven by P-CUCme.CumMe_WSM_SF18488.G5340-1:1:1 (SEQ ID NO: 181) demonstrated a constitutive level of expression while quantitatively high expression was observed in the yellow pod embryo.

$R_0$ generation plants transformed with the plasmid constructs comprising EXP-CUCme.eEF1a:1:1 (SEQ ID NO: 162) and EXP-CUCme.SAMS2:1:1 (SEQ ID NO: 168) were allowed to set seed and the $R_1$ generation plants analyzed for GUS expression. The $R_1$ generation plants were analyzed for expression in Vn5 Root, Vn5 Sink Leaf, Vn5 Source Leaf, R1 Source Leaf, R1 Petiole Yellow Pod Embryo, Yellow Pod Cotyledon, R3 Immature Seed, R3 Pod, R5 Cotyledon and R1 Flower. Tables 22 and 23 show the mean GUS expression measured in each tissue of the $R_1$ generation transformed plants.

TABLE 22

Mean GUS expression in Vn5 Root, Vn5 Sink Leaf, Vn5 Source Leaf, R1 Source Leaf, R1 Petiole of $R_1$ generation transformed soybean plants

| Construct | Regulatory Element | SEQ ID NO: | Vn5_Root | Vn5_Sink_Leaf | Vn5_Source Leaf | R1_Source_Leaf | R1_Petiole |
|---|---|---|---|---|---|---|---|
| pMON140827 | EXP-CUCme.eEF1a:1:1 | 162 | 145.84 | 50.24 | 43.73 | 107.98 | 357.67 |
| pMON140836 | EXP-CUCme.SAMS2:1:1 | 168 | 260.41 | 65.52 | 51.12 | 129.86 | 623.42 |

TABLE 23

Mean GUS expression in Yellow Pod Embryo, Yellow Pod Cotyledon, R3 Immature Seed, R3 Pod, R5 Cotyledon, R1 Flower of $R_1$ generation transformed soybean plants

| Construct | Regulatory Element | SEQ ID NO: | Yellow_Pod_Embryo | Yellow_Pod_Cotyledon | R3_Immature_Seed | R3_Pod | R5_Cotyledon | R1_Flower |
|---|---|---|---|---|---|---|---|---|
| pMON140827 | EXP-CUCme.eEF1a:1:1 | 162 | 1098.51 | 764.83 | 288.77 | 214.6 | 459.62 | 394.77 |
| pMON140836 | EXP-CUCme.SAMS2:1:1 | 168 | 219.04 | 291.58 | 241.48 | 382.73 | 397.91 | 653.23 |

As can be seen in Tables 22 and 23 above expression driven in $R_1$ generation by EXP-CUCme.eEF1a:1:1 (SEQ ID NO: 162) and EXP-CUCme.SAMS2:1:1 (SEQ ID NO: 168) shows a constitutive level of expression with increase in expression observed in many tissues at $R_1$ generation relative to $R_0$ generation.

Having illustrated and described the principles of the present invention, it should be apparent to persons skilled in the art that the invention can be modified in arrangement and detail without departing from such principles. All modifications that are within the spirit and scope of the claims are intended to be included within the scope of the present invention. All publications and published patent documents cited herein are hereby incorporated by reference to the same extent as if each individual publication or patent application is specifically and individually indicated to be incorporated by reference.

What is claimed is:

1. A DNA molecule exhibiting a gene regulatory functional activity comprising a polynucleotide sequence selected from the group consisting of:

a) a sequence with at least 95 percent sequence identity to SEQ ID NO: 156, and exhibiting promoter activity;

b) a sequence comprising SEQ ID NO: 156; and c) a fragment comprising at least 250 contiguous nucleotides of SEQ ID NO: 156 exhibiting promoter activity;

wherein said DNA molecule is operably linked to a heterologous transcribable polynucleotide molecule.

2. The DNA molecule of claim 1, wherein said polynucleotide sequence has at least 97 percent sequence identity to the polynucleotide sequence as set forth in SEQ ID NO: 156.

3. The DNA molecule of claim 1, wherein said polynucleotide sequence has at least 99 percent sequence identity to the polynucleotide sequence as set forth in SEQ ID NO: 156.

4. The DNA molecule of claim 1, wherein the heterologous transcribable polynucleotide molecule comprises a gene of agronomic interest.

5. The DNA molecule of claim 4, wherein the gene of agronomic interest confers herbicide tolerance in plants.

6. The DNA molecule of claim 4, wherein the gene of agronomic interest confers pest resistance in plants.

7. A transgenic plant cell comprising the DNA molecule of claim 1.

8. The transgenic plant cell of claim 7, wherein said transgenic plant cell is a monocotyledonous plant cell.

9. The transgenic plant cell of claim 7, wherein said transgenic plant cell is a dicotyledonous plant cell.

10. A transgenic plant, or part thereof, comprising the DNA molecule of claim 1.

11. A progeny plant of the transgenic plant of claim 10, or part thereof, wherein the progeny plant or part thereof comprises said DNA molecule exhibiting a gene-regulatory functional activity.

12. A transgenic seed comprising the DNA molecule of claim 1.

13. A method of producing a commodity product comprising:

a) obtaining a transgenic plant or part thereof comprising the DNA molecule of claim 1; and b) producing the commodity product from the transgenic plant or part thereof.

14. The method of claim 13, wherein the commodity product is protein concentrate, protein isolate, grain, starch, seeds, meal, flour, biomass, or seed oil.

15. A commodity product comprising the DNA molecule of claim 1.

16. A method of expressing a transcribable polynucleotide molecule comprising:

a) obtaining a transgenic plant comprising a DNA molecule exhibiting a gene regulatory functional activity comprising a polynucleotide sequence selected from the group consisting of:

1) a sequence with at least 95 percent sequence identity to SEQ ID NO: 156, and exhibiting promoter activity;

2) a sequence comprising SEQ ID NO: 156; and 3) a fragment comprising at least 250 contiguous nucleotides of SEQ ID NO: 156 exhibiting promoter activity;

wherein said DNA molecule is operably linked to a heterologous transcribable polynucleotide molecule; and b) cultivating said transgenic plant, wherein the transcribable polynucleotide is expressed.

* * * * *